(12) United States Patent
Villani et al.

(10) Patent No.: US 11,630,103 B2
(45) Date of Patent: Apr. 18, 2023

(54) PRODUCT AND METHODS USEFUL FOR MODULATING AND EVALUATING IMMUNE RESPONSES

(71) Applicants: The Broad Institute, Inc., Cambridge, MA (US); Massachusetts Institute of Technology, Cambridge, MA (US); The General Hospital Corporation, Boston, MA (US)

(72) Inventors: Alexandra-Chloé Villani, Boston, MA (US); Rahul Satija, Cambridge, MA (US); Aviv Regev, Cambridge, MA (US); Nir Hacohen, Boston, MA (US)

(73) Assignees: The Broad Institute, Inc., Cambridge, MA (US); Massachusetts Institute of Technology, Cambridge, MA (US); The General Hospital Corporation, Boston, MA (US)

( * ) Notice: Subject to any disclaimer, the term of this patent is extended or adjusted under 35 U.S.C. 154(b) by 660 days.

(21) Appl. No.: 16/325,807

(22) PCT Filed: Aug. 17, 2017

(86) PCT No.: PCT/US2017/047422
§ 371 (c)(1),
(2) Date: Feb. 15, 2019

(87) PCT Pub. No.: WO2018/035364
PCT Pub. Date: Feb. 22, 2018

(65) Prior Publication Data
US 2022/0397568 A1    Dec. 15, 2022

Related U.S. Application Data
(60) Provisional application No. 62/376,007, filed on Aug. 17, 2016.

(51) Int. Cl.
*G01N 33/50* (2006.01)
*G01N 33/68* (2006.01)
*C12N 5/078* (2010.01)

(52) U.S. Cl.
CPC ....... *G01N 33/5047* (2013.01); *C12N 5/0634* (2013.01); *G01N 33/6893* (2013.01); *G01N 2800/24* (2013.01)

(58) Field of Classification Search
None
See application file for complete search history.

(56) References Cited

U.S. PATENT DOCUMENTS

| | | |
|---|---|---|
| 4,751,180 A | 6/1988 | Cousens et al. |
| 4,816,567 A | 3/1989 | Cabilly et al. |
| 4,935,233 A | 6/1990 | Bell et al. |
| 5,270,163 A | 12/1993 | Gold et al. |
| 5,686,281 A | 11/1997 | Roberts |
| 5,843,728 A | 12/1998 | Seed et al. |
| 5,851,828 A | 12/1998 | Seed et al. |
| 5,858,358 A | 1/1999 | June et al. |
| 5,883,223 A | 3/1999 | Gray |
| 5,906,936 A | 5/1999 | Eshhar et al. |
| 5,912,170 A | 6/1999 | Seed et al. |
| 5,912,172 A | 6/1999 | Eshhar et al. |
| 6,004,811 A | 12/1999 | Seed et al. |
| 6,284,240 B1 | 9/2001 | Seed et al. |
| 6,352,694 B1 | 3/2002 | June et al. |
| 6,392,013 B1 | 5/2002 | Seed et al. |
| 6,410,014 B1 | 6/2002 | Seed et al. |
| 6,489,458 B2 | 12/2002 | Hackett et al. |
| 6,534,055 B1 | 3/2003 | June et al. |
| 6,753,162 B1 | 6/2004 | Seed et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,144,575 B2 | 12/2006 | June et al. |
| 7,148,203 B2 | 12/2006 | Hackett et al. |
| 7,160,682 B2 | 1/2007 | Hackett et al. |
| 7,175,843 B2 | 2/2007 | June et al. |
| 7,232,566 B2 | 6/2007 | June et al. |

(Continued)

FOREIGN PATENT DOCUMENTS

| | | | |
|---|---|---|---|
| EP | 2 771 468 B1 | 2/2015 | |
| EP | 2 784 162 B1 | 4/2015 | |

(Continued)

OTHER PUBLICATIONS

The Broad Institute, Inc., "International Preliminary Report on Patentability issued in International Application No. PCT/US2017/047422", dated Feb. 28, 2019, 13 pages.

(Continued)

*Primary Examiner* — Changhwa J Cheu
(74) *Attorney, Agent, or Firm* — F. Brent Nix, Esq.; Johnson, Marcou, Isaacs & Nix, LL; Michael B. Scher, Esq.

(57) ABSTRACT

The present invention provides isolated immune cells, immune cell populations and compositions, as well as markers, marker signatures and molecular targets characterising the immune cells. The cell products, substances, compositions, markers, marker signatures, molecular targets, kits of parts and methods of the present invention provide for new ways to characterise, evaluate and modulate the immune system and immune responses.

10 Claims, 60 Drawing Sheets
Specification includes a Sequence Listing.

(56) References Cited

U.S. PATENT DOCUMENTS

| | | |
|---|---|---|
| 7,572,631 B2 | 8/2009 | Berenson et al. |
| 7,741,465 B1 | 6/2010 | Eshhar et al. |
| 7,985,739 B2 | 7/2011 | Kay et al. |
| 8,088,379 B2 | 1/2012 | Robbins et al. |
| 8,211,422 B2 | 7/2012 | Eshhar et al. |
| 8,227,432 B2 | 7/2012 | Hackett et al. |
| 8,399,645 B2 | 3/2013 | Campana et al. |
| 8,697,359 B1 | 4/2014 | Zhang |
| 8,697,854 B2 | 4/2014 | Schendel et al. |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,906,682 B2 | 12/2014 | June et al. |
| 8,911,993 B2 | 12/2014 | June et al. |
| 8,916,381 B1 | 12/2014 | June et al. |
| 8,932,814 B2 | 1/2015 | Cong et al. |
| 8,945,839 B2 | 2/2015 | Zhang |
| 8,975,071 B1 | 3/2015 | June et al. |
| 8,993,233 B2 | 3/2015 | Zhang et al. |
| 8,999,641 B2 | 4/2015 | Zhang et al. |
| 9,101,584 B2 | 8/2015 | June et al. |
| 9,102,760 B2 | 8/2015 | June et al. |
| 9,102,761 B2 | 8/2015 | June et al. |
| 2006/0013842 A1 | 1/2006 | Matkin et al. |
| 2011/0265198 A1 | 10/2011 | Gregory et al. |
| 2012/0017290 A1 | 1/2012 | Cui et al. |
| 2013/0071414 A1 | 3/2013 | Dotti et al. |
| 2013/0236946 A1 | 9/2013 | Gouble |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |
| 2014/0310830 A1 | 10/2014 | Zhang et al. |
| 2015/0232883 A1 | 8/2015 | Dahlman et al. |
| 2016/0251648 A1 | 9/2016 | Wang et al. |
| 2017/0166903 A1 | 6/2017 | Zhang et al. |
| 2017/0306335 A1 | 10/2017 | Zhang et al. |
| 2019/0144942 A1* | 5/2019 | Shalek .............. A61K 35/15 424/93.7 |

FOREIGN PATENT DOCUMENTS

| | | |
|---|---|---|
| EP | 2 764 103 B1 | 8/2015 |
| WO | 92/15322 A1 | 9/1992 |
| WO | 03/020763 A2 | 3/2003 |
| WO | 2004/033685 A1 | 4/2004 |
| WO | 2004/044004 A2 | 5/2004 |
| WO | 2004/074322 A1 | 9/2004 |
| WO | 2005/113595 A2 | 12/2005 |
| WO | 2005/114215 A2 | 12/2005 |
| WO | 2006/000830 A2 | 1/2006 |
| WO | 2006/125962 A2 | 11/2006 |
| WO | 2008/038002 A2 | 4/2008 |
| WO | 2008/039818 A2 | 4/2008 |
| WO | 2009/013484 A1 | 1/2009 |
| WO | 2011/146862 A1 | 11/2011 |
| WO | 2012/079000 A1 | 6/2012 |
| WO | 2013/039889 A1 | 3/2013 |
| WO | 2013/040371 A2 | 3/2013 |
| WO | 2013/166321 A1 | 11/2013 |
| WO | 2013/176915 A1 | 11/2013 |
| WO | 2014/011987 A1 | 1/2014 |
| WO | 2014/018423 A2 | 1/2014 |
| WO | 2014/018863 A1 | 1/2014 |
| WO | 2014/059173 A2 | 4/2014 |
| WO | 2014/083173 A1 | 6/2014 |
| WO | 2014/093595 A1 | 6/2014 |
| WO | 2014/093622 A2 | 6/2014 |
| WO | 2014/093635 A1 | 6/2014 |
| WO | 2014/093655 A2 | 6/2014 |
| WO | 2014/093661 A2 | 6/2014 |
| WO | 2014/093694 A1 | 6/2014 |
| WO | 2014/093701 A1 | 6/2014 |
| WO | 2014/093709 A1 | 6/2014 |
| WO | 2014/093712 A1 | 6/2014 |
| WO | 2014/093718 A1 | 6/2014 |
| WO | 2014/134165 A1 | 9/2014 |
| WO | 2014/145631 A1 | 9/2014 |
| WO | 2014/172606 A1 | 10/2014 |
| WO | 2014/184744 A1 | 11/2014 |
| WO | 2014/191128 A1 | 12/2014 |
| WO | 2014/204723 A1 | 12/2014 |
| WO | 2014/204724 A1 | 12/2014 |
| WO | 2014/204725 A1 | 12/2014 |
| WO | 2014/204726 A1 | 12/2014 |
| WO | 2014/204727 A1 | 12/2014 |
| WO | 2014/204728 A1 | 12/2014 |
| WO | 2014/204729 A1 | 12/2014 |
| WO | 2015/065964 A1 | 5/2015 |
| WO | 2015/089351 A1 | 6/2015 |
| WO | 2015/089419 A2 | 6/2015 |
| WO | 2015/089486 A2 | 6/2015 |
| WO | 2016/069591 A2 | 5/2016 |
| WO | 2018/035250 A1 | 2/2018 |

OTHER PUBLICATIONS

Breton et al., "Circulating Precursors of Human CD1c+ and CD141+ Dendritic Cells", Journal of Experimental Medicine, vol. 212, No. 3, Mar. 9, 2015, 401-413.

Breton et al., "Defining Human Dendritic Cell Progenitors by Multiparametric Flow Cytometry", Nature Protocols, vol. 10, No. 9, Sep. 2015, 1407-1422.

Bryant et al., "A CD2 High-Expressing Stress-Resistant Human Plasmacytoid Dendritic-Cell Subset", Immunology and Cell Biology, vol. 94, No. 5, Jan. 21, 2016, 45 pages.

Cella et al., "Plasmacytoid Monocytes Migrate to Inflamed Lymph Nodes and Produce Large Amounts of Type I Interferon", Nature Medicine, vol. 5, No. 8, Aug. 1999, 919-923.

Cheng et al., "Characterization of Species-Specific Genes Regulated by E2-2 in Human Plasmacytoid Dendritic Cells", Scientific Reports, vol. 5, No. 10752, Jul. 17, 2015, 11 pages.

Crozat et al., "The XC Chemokine Receptor 1 Is a Conserved Selective Marker of Mammalian Cells Homologous to Mouse CD8alpha+ Dendritic Cells", Journal of Experimental Medicine, vol. 207, No. 6, Jun. 7, 2010, 1283-1292.

Doulatov et al., "Hematopoiesis: A Human Perspective", Cell Stem Cell, vol. 10, No. 2, Feb. 3, 2012, 120-136.

Du et al., "Preferential Depletion of CD2(low) Plasmacytoid Dendritic Cells in HIV-infected Subjects", Cellular and Molecular Immunology, vol. 8, No. 5, Apr. 25, 2011, 441-444.

Garnache-Ottou et al., "Plasmacytoid Dendritic Cell leukaemia/lymphoma: Towards a Well Defined Entity", British Journal of Haematology, vol. 136, No. 4, Jan. 8, 2007, 539-548.

Grouard et al., "The Enigmatic Plasmacytoid T Cells Develop into Dendritic Cells with Interleukin (IL)-3 and CD40-ligand", Journal of Experimental Medicine, vol. 185, No. 6, Mar. 17, 1997, 1101-1111.

Guilliams et al., "Dendritic Cells, Monocytes and Macrophages: a Unified Nomenclature based on Ontogeny", Nature Reviews, vol. 14, Aug. 2014, 571-578.

(56) References Cited

OTHER PUBLICATIONS

Haniffa et al., "Differential Rates of Replacement of Human Dermal Dendritic Cells and Macrophages During Hematopoietic Stem Cell Transplantation", Journal of Experimental Medicine, vol. 206, No. 2, Feb. 16, 2009, 371-385.

Haniffa et al., "Human Mononuclear Phagocyte System Reunited", Seminars in Cell and Developmental Biology, vol. 41, 2015, 11 pages.

Haniffa et al., "Human Tissues Contain CD141hi Cross-Presenting Dendritic Cells With Functional Homology to Mouse CD103+ Nonlymphoid Dendritic Cells", Immunity, vol. 37, No. 1, Jul. 27, 2012, 60-73.

Hildner et al., "Batf3 Deficiency Reveals a Critical Role for CD8alpha+ Dendritic Cells in Cytotoxic T Cell Immunity", Science, vol. 322, No. 5904, Nov. 14, 2008, 9 pages.

Jongbloed et al., "Human CD141+ (BDCA-3)+ Dendritic Cells (DCs) Represent a Unique Myeloid DC Subset that Cross-presents Necrotic Cell Antigens", Journal of Experimental Medicine, vol. 207, No. 6, Jun. 7, 2010, 1247-1260.

Lee et al., "Restricted Dendritic Cell and Monocyte Progenitors in Human Cord Blood and Bone Marrow", Journal of Experimental Medicine, vol. 212, No. 3, Mar. 9, 2015, 15 pages.

Matsui et al., "CD2 Distinguishes Two Subsets of Human Plasmacytoid Dendritic Cells With Distinct Phenotype and Functions", Journal of Immunology, vol. 182, No. 11, Jun. 1, 2009, 6815-6823.

Mildner et al., "Development and Function of Dendritic Cell Subsets", Immunity, vol. 40, No. 5, May 15, 2014, 542-656.

Miller et al., "Deciphering the Transcriptional Network of the Dendritic Cell Lineage", Nature Immunology, vol. 13, No. 9, Sep. 2012, 888-899.

Notta et al., "Distinct Routes of Lineage Development Reshape the Human Blood Hierarchy Across Ontogeny", Science, vol. 351, No. 6269, Jan. 8, 2016, 22 pages.

Osaki et al., "Characterization of CD56+ Dendritic-Like Cells: A Normal Counterpart of Blastic Plasmacytoid Dendritic Dell Neoplasm", PLoS One, vol. 8, No. 11, Nov. 2013, 10 pages.

Poulin et al., "Characterization of Human DNGR-1+ BDCA3+ Leukocytes as Putative Equivalents of Mouse CD8a+ Dendritic Cells", Journal of Experimental Medicine, vol. 207, No. 6, Jun. 7, 2010, 1261-1271.

Riaz et al., "Blastic Plasmacytoid Dendritic Cell Neoplasm: Update on Molecular Biology, Diagnosis, and Therapy", Dancer Control, vol. 21, No. 4, Oct. 2014, 279-289.

Sapienza et al., "Molecular Profiling of Blastic Plasmacytoid Dendritic Cell Neoplasm Reveals a Unique Pattern and Suggests Selective Sensitivity to NF-kB Pathway Inhibition", Leukemia, vol. 28, No. 8, Aug. 2014, 1606-1616.

Satpathy et al., "Re(de)fining the Dendritic Cell Lineage", Nature Immunology, vol. 13, No. 12, Dec. 2012, 22 pages.

Schraml et al., "Defining Dendritic Cells", Current Opinion in Immunology, vol. 32, pp. 13-20, Feb. 2015, 13-20.

Schwab et al., "An Imbalance of Two Functionally and Phenotypically Different Subsets of Plasmacytoid Dendritic Dells Characterizes the Dysfunctional Immune Regulation in Multiple Sclerosis", Journal of Immunology, vol. 184, No. 9, May 1, 2010, 5368-5374.

Swiecki et al., "The Multifaceted Biology of Plasmacytoid Dendritic Cells", Nature Reviews Immunology, vol. 15, No. 3, Aug. 2015, 36 pages.

Tel et al., "Human Plasmacytoid Dendritic Cells Are Equipped With Antigen-Presenting and Tumoricidal Capacities", Blood, vol. 120, No. 19, Nov. 8, 2012, 3936-3944.

Tel et al., "Natural Human Plasmacytoid Dendritic Cells Induce Antigen-Specific T-cell Responses in Melanoma Patients", Cancer Research, vol. 73, No. 3, Jan. 23, 2013, 1063-1075.

De Vries et al., "Immunotherapy: Cancer Vaccine Triggers Antiviral-Type Defences", Nature, vol. 534, No. 7607, Jun. 16, 2016, 329-331.

Wilhelm et al., "Siglec-1-positive Plasmacytoid Dendritic Cells (pDCs) in Human Peripheral Blood: A Semi-Mature and Myeloid-Like Subset Imbalanced During Protective and Autoimmune Responses", Journal of Clinical Immunology, vol. 163, Dec. 2015, 28 pages.

Yu et al., "Human BDCA2+CD123+CD56+ Dendritic Cells (DCs) Related to Blastic Plasmacytoid Dendritic Cell Neoplasm Represent a Unique Myeloid DC Subset", Protein Cell, vol. 6, No. 4, Apr. 2015, 297-306.

The Broad Institute, Inc., "International Search Report and Written Opinion of the International Searching Authority (PCT/US2017/047422)", dated Jan. 24, 2018, 1-18.

Collin, et al., "Human Dendritic Cell Subset", Immunology, vol. 140, No. 1,2013, pp. 22-30.

Dzionek, et al., "BDCA-2, BDCA-3, and BDCA-4: Three Markers for Distinct Subsets of Dendritic Cells in Human Peripheral Blood", J. Immunology, vol. 165, No. 11, 2000, pp. 6037-6046.

Shalek, et al., Single-cell RNA Seq reveals Dynamic Paracrine Control of Cellular Variation, Nature, 510(705), 2014, pp. 363-369.

Villani, et al., "Single-cell RNA-seq Reveals New Types of Human Blood Dendritic Cells, Monocytes and Progenitors", Science, vol. 356, No. 6335, 2017, 31 pages.

\* cited by examiner

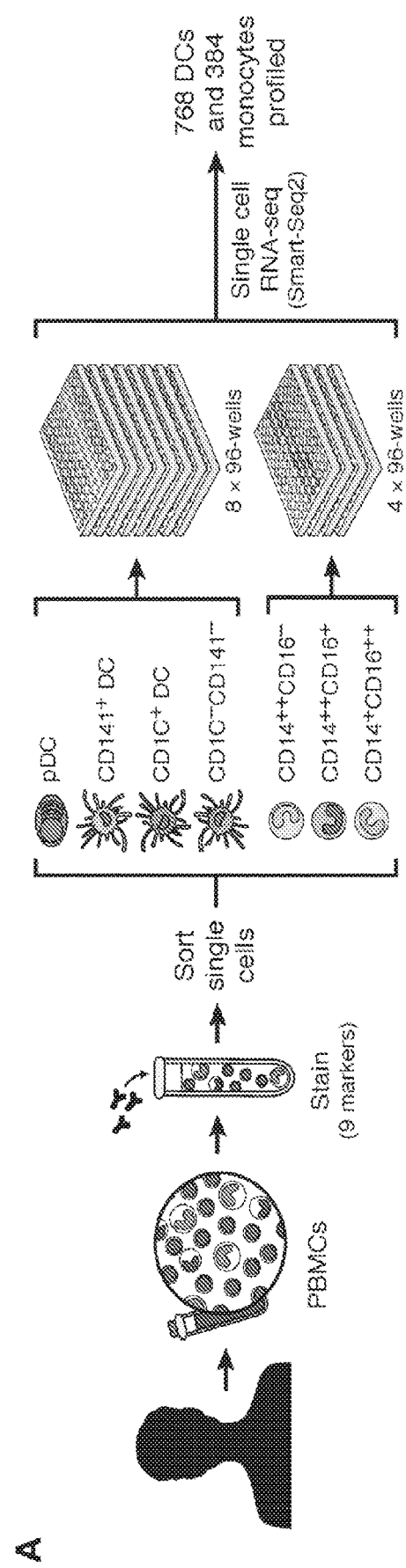

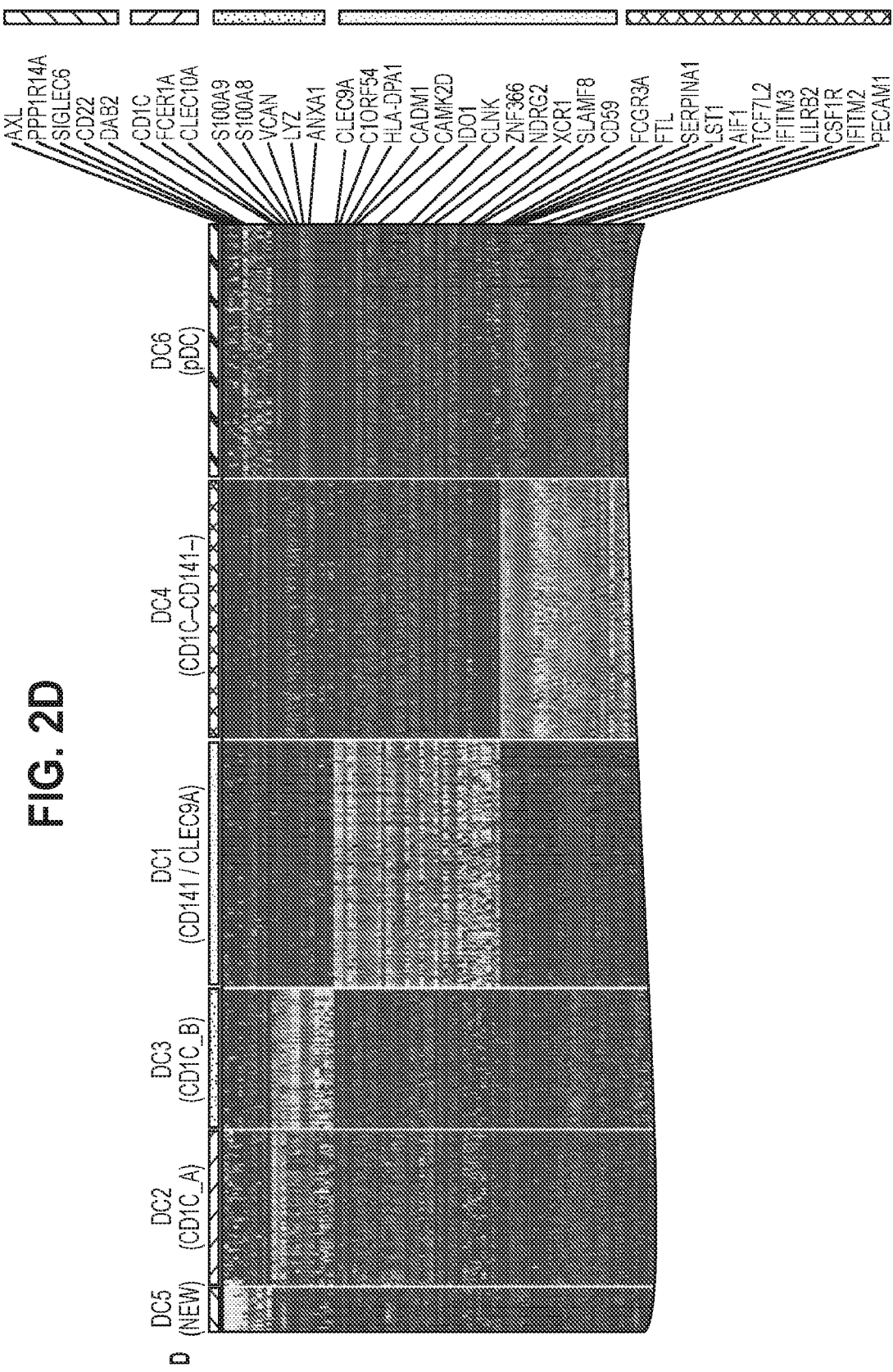

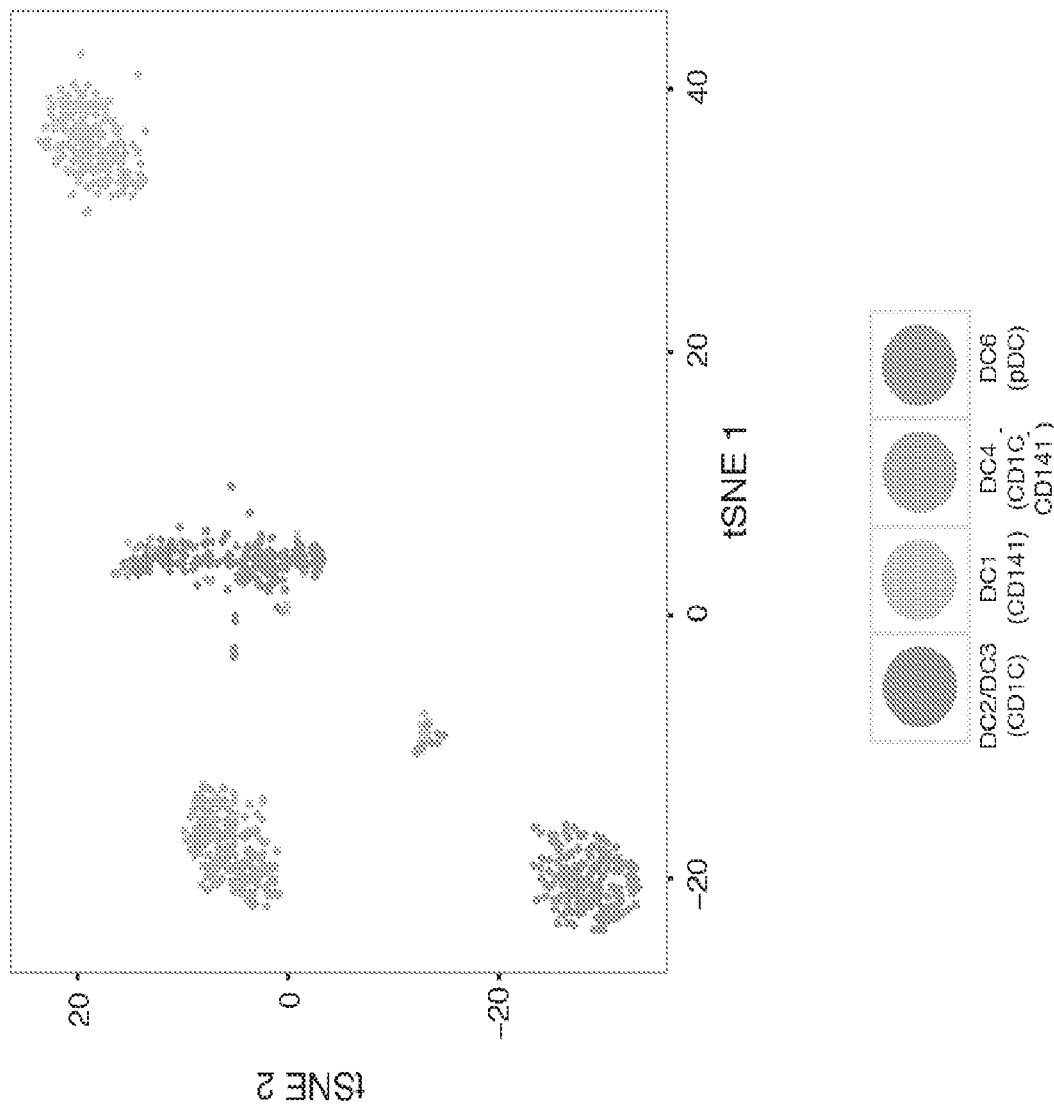

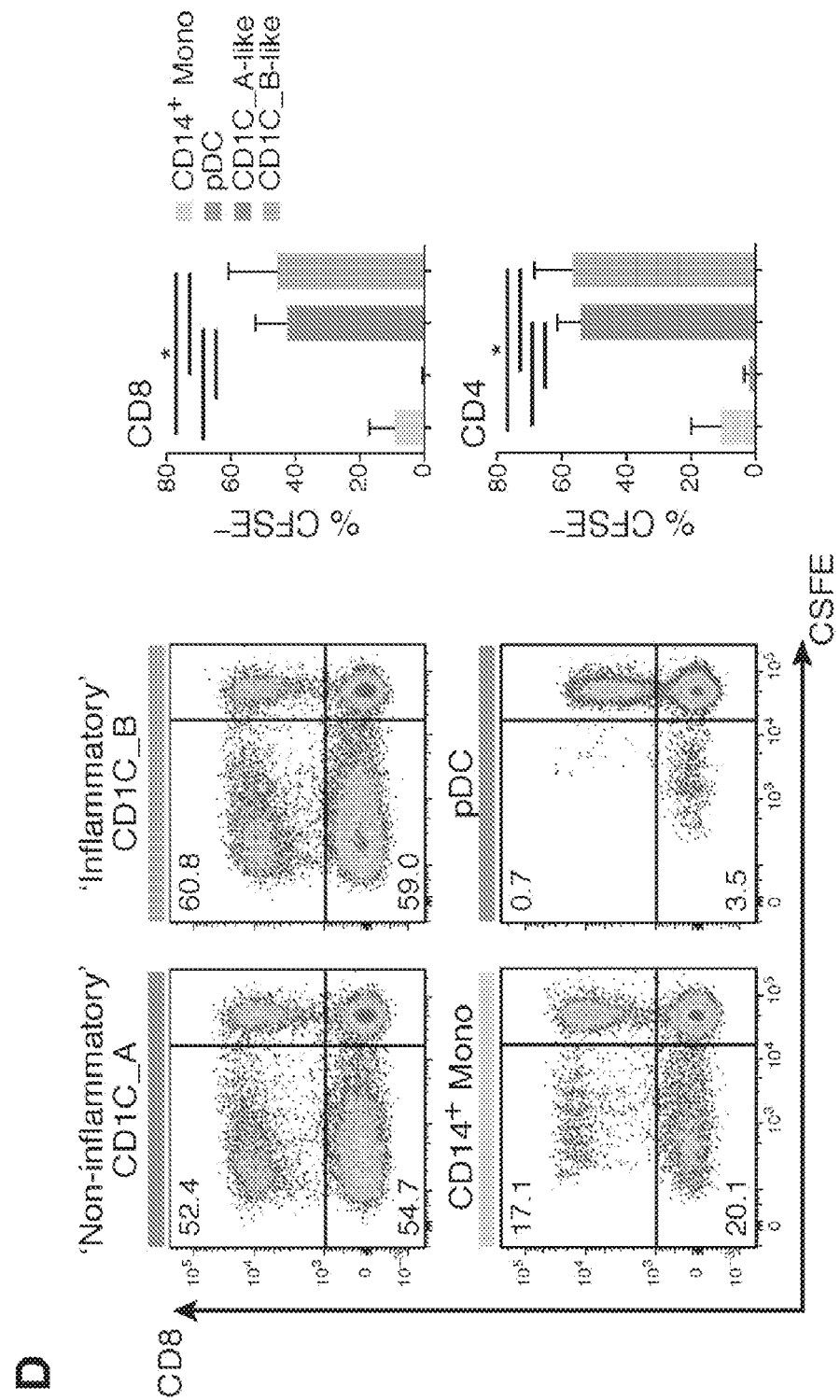

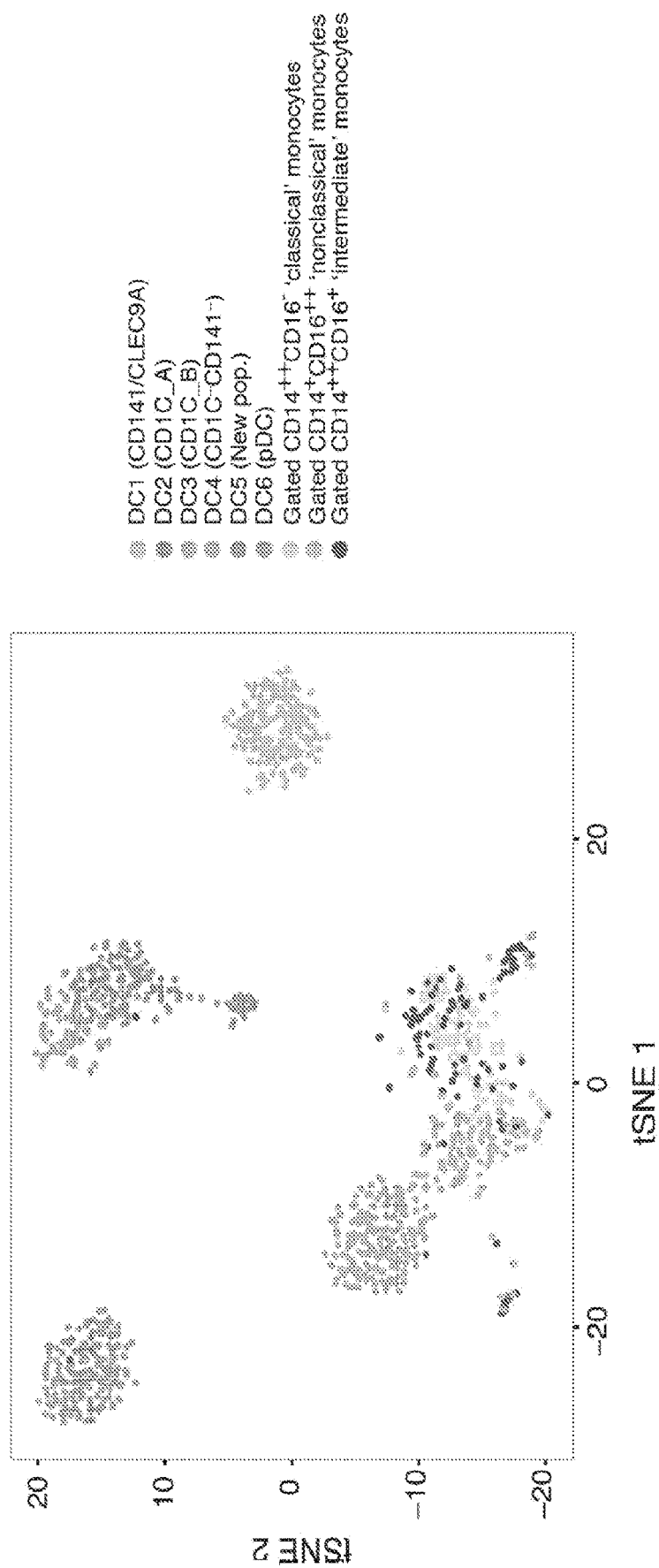

FIG. 5H-5I
H
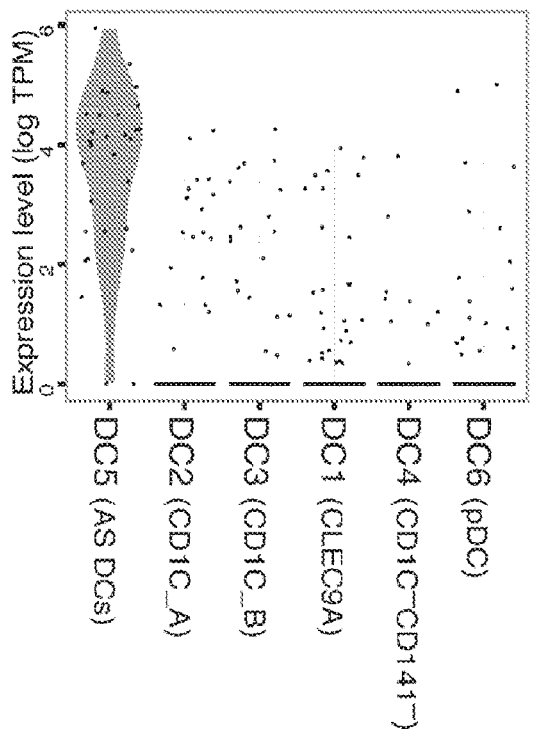
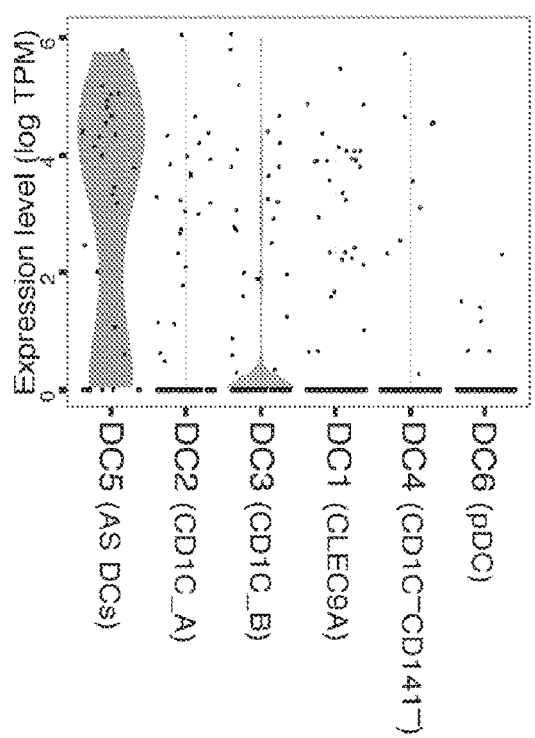
I
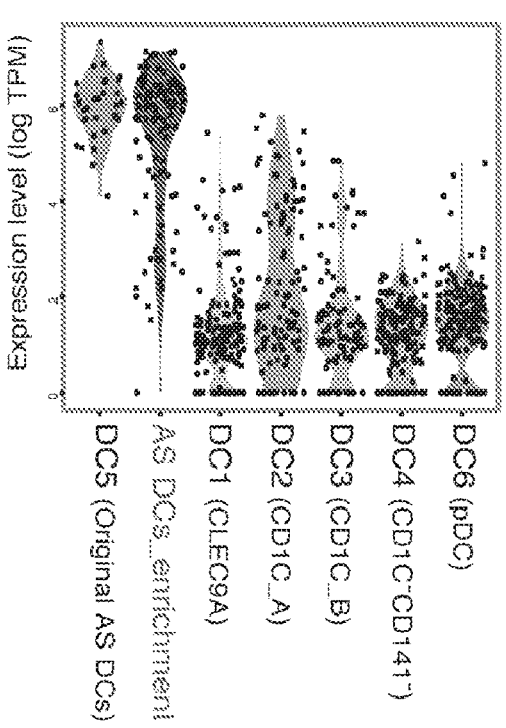
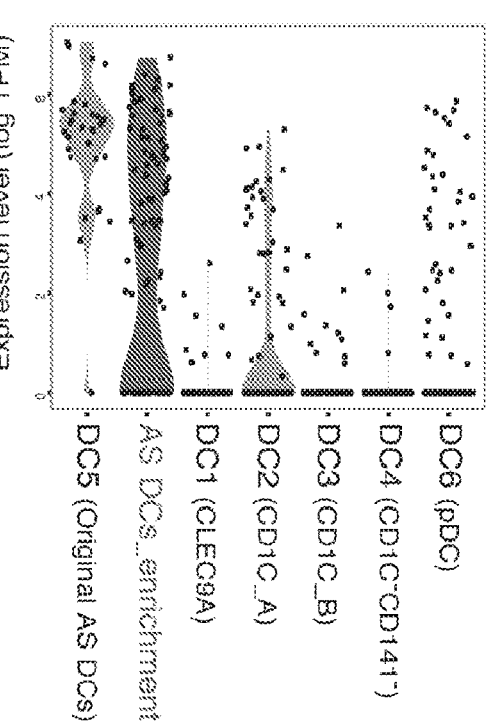

FIG. 5K-5N
K
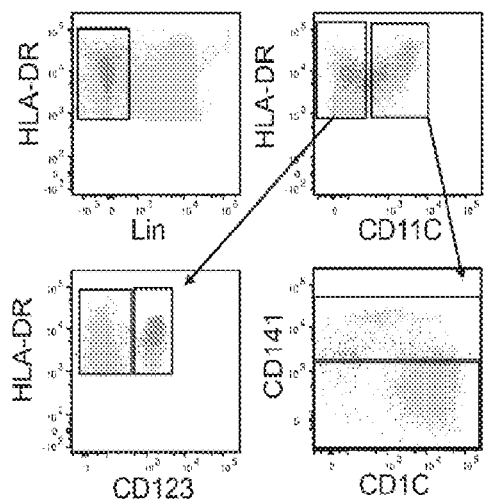
1: AXL⁺SIGLEC⁺CD123⁺CD11C⁻
2: AXL⁺SIGLEC6⁺CD123ⁱᵒCD11C⁺
M
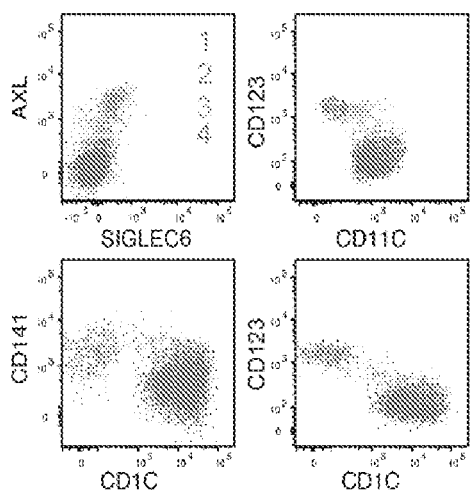
N
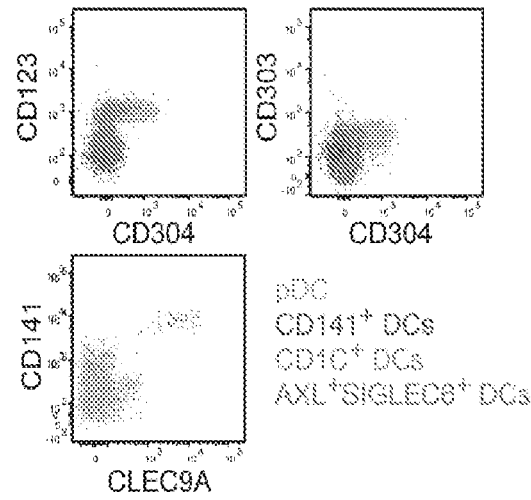
pDC
CD141⁺ DCs
CD1C⁺ DCs
AXL⁺SIGLEC6⁺ DCs

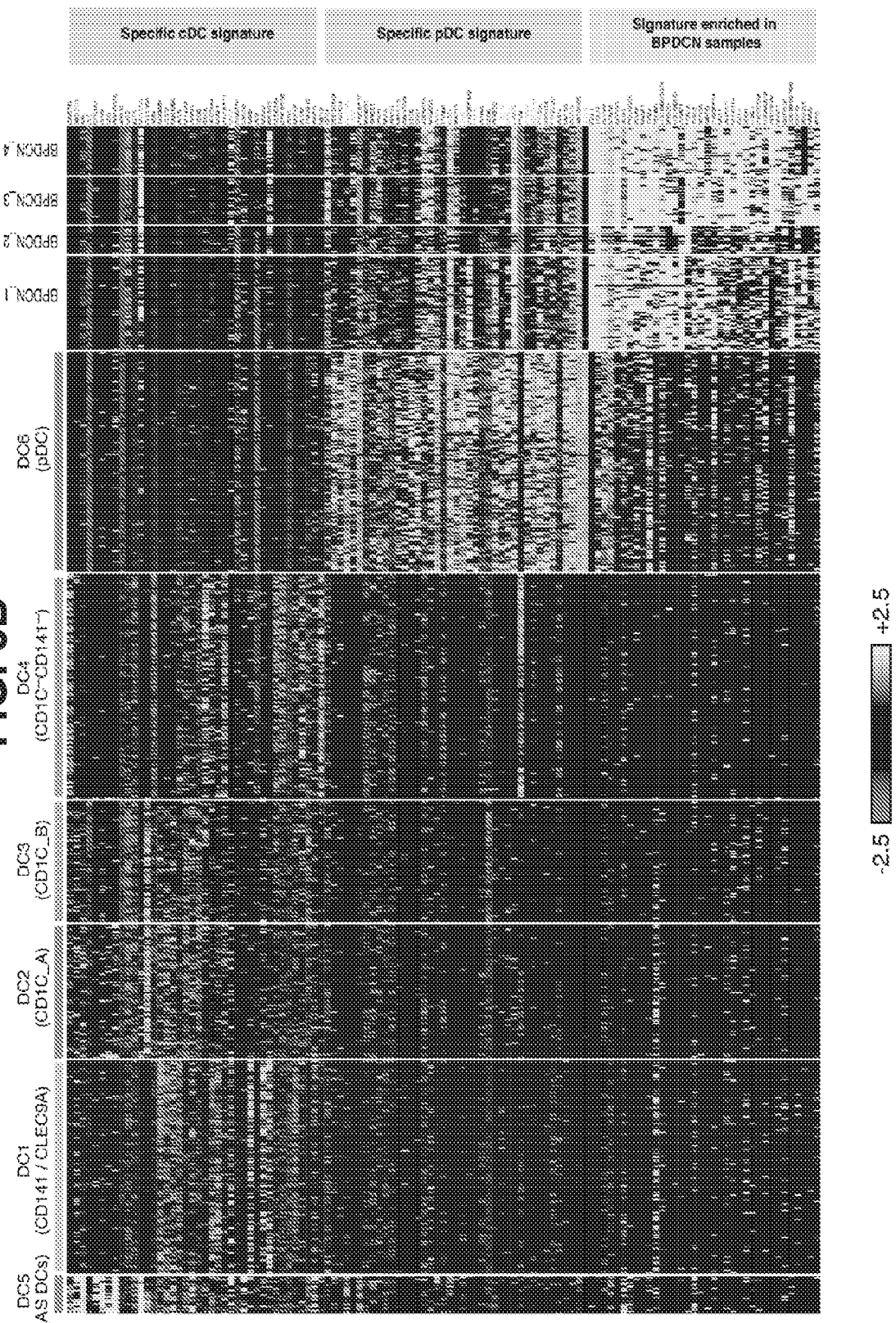

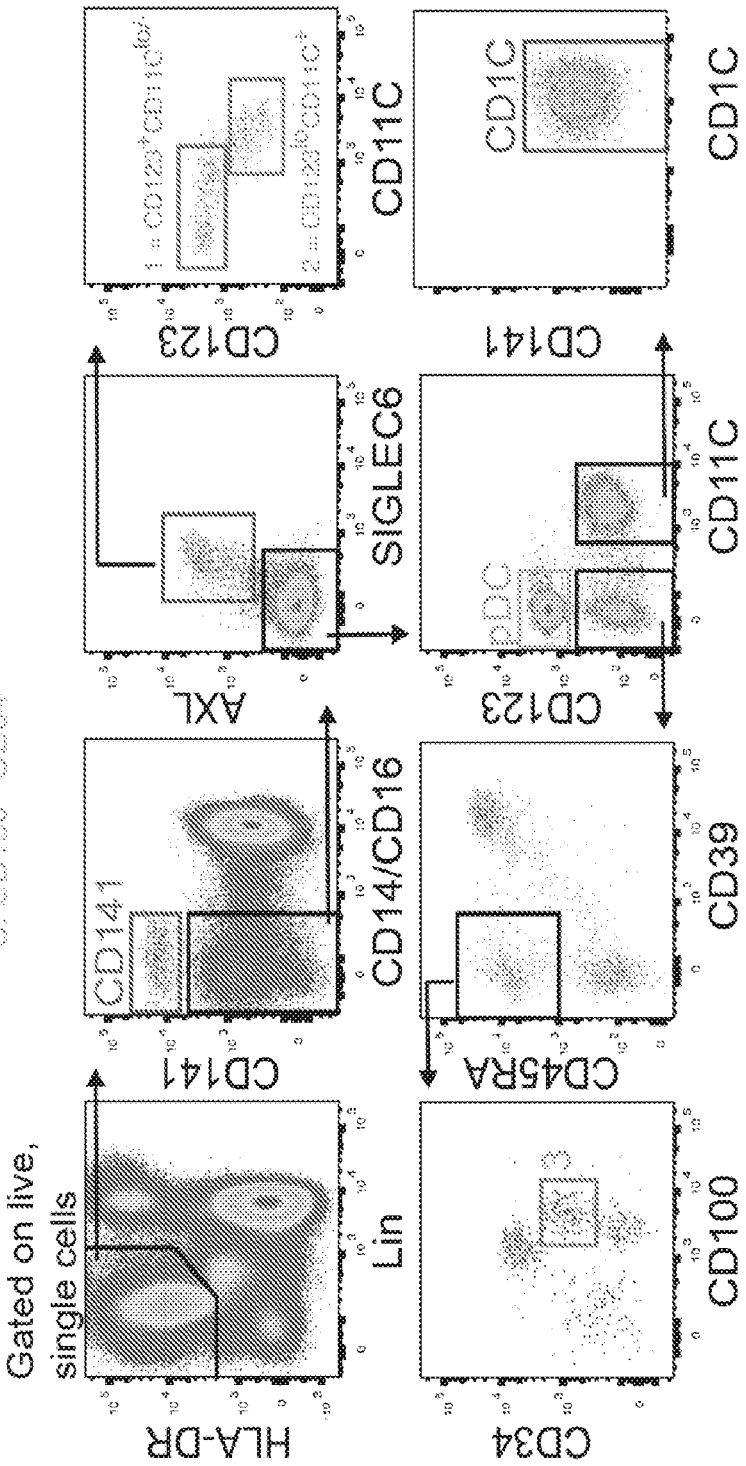

1: AXL+SIGLEC6+CD123+CD11C-/lo
2: AXL+SIGLEC6+CD123-CD11C+

SEQUENCE LISTING

```
<160> NUMBER OF SEQ ID NOS: 23

<210> SEQ ID NO 1
<211> LENGTH: 7
<212> TYPE: PRT
<213> ORGANISM: Simian virus 40

<400> SEQUENCE: 1

Pro Lys Lys Lys Arg Lys Val
1               5

<210> SEQ ID NO 2
<211> LENGTH: 16
<212> TYPE: PRT
<213> ORGANISM: Artificial Sequence
<220> FEATURE:
<223> OTHER INFORMATION: Synthetic

<400> SEQUENCE: 2

Lys Arg Pro Ala Ala Thr Lys Lys Ala Gly Gln Ala Lys Lys Lys Lys
1               5                   10                  15

<210> SEQ ID NO 3
<211> LENGTH: 9
<212> TYPE: PRT
<213> ORGANISM: Artificial Sequence
<220> FEATURE:
<223> OTHER INFORMATION: Synthetic

<400> SEQUENCE: 3

Pro Ala Ala Lys Arg Val Lys Leu Asp
1               5

<210> SEQ ID NO 4
<211> LENGTH: 11
<212> TYPE: PRT
```

```
-continued

<213> ORGANISM: Artificial Sequence
<220> FEATURE:
<223> OTHER INFORMATION: Synthetic

<400> SEQUENCE: 4

Arg Gln Arg Arg Asn Glu Leu Lys Arg Ser Pro
1               5                   10

<210> SEQ ID NO 5
<211> LENGTH: 38
<212> TYPE: PRT
<213> ORGANISM: Homo sapiens

<400> SEQUENCE: 5

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
        35

<210> SEQ ID NO 6
<211> LENGTH: 42
<212> TYPE: PRT
<213> ORGANISM: Artificial Sequence
<220> FEATURE:
<223> OTHER INFORMATION: Synthetic

<400> SEQUENCE: 6

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 7
<211> LENGTH: 8
<212> TYPE: PRT
<213> ORGANISM: Artificial Sequence
<220> FEATURE:
<223> OTHER INFORMATION: Synthetic

<400> SEQUENCE: 7

Val Ser Arg Lys Arg Pro Arg Pro
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic

<400> SEQUENCE: 8

Pro Pro Lys Lys Ala Arg Glu Asp
1               5

<210> SEQ ID NO 9
<211> LENGTH: 8
<212> TYPE: PRT
<213> ORGANISM: Homo sapiens
<220> FEATURE:
<221> NAME/KEY: MOD_RES
<222> LOCATION: (2)..(2)
```

<223> OTHER INFORMATION: "X" represents pyrrolysine

<400> SEQUENCE: 9

Pro Xaa Pro Lys Lys Pro Leu
1               5

<210> SEQ ID NO 10
<211> LENGTH: 12
<212> TYPE: PRT
<213> ORGANISM: Mus musculus

<400> SEQUENCE: 10

Ser Ala Leu Ile Lys Lys Lys Lys Lys Met Ala Pro
1               5                   10

<210> SEQ ID NO 11
<211> LENGTH: 5
<212> TYPE: PRT
<213> ORGANISM: Influenza virus

<400> SEQUENCE: 11

Asp Arg Leu Arg Arg
1               5

<210> SEQ ID NO 12
<211> LENGTH: 7
<212> TYPE: PRT
<213> ORGANISM: Influenza virus

<400> SEQUENCE: 12

Pro Lys Gln Lys Lys Arg Lys
1               5

<210> SEQ ID NO 13
<211> LENGTH: 10
<212> TYPE: PRT
<213> ORGANISM: Hepatitus delta virus

<400> SEQUENCE: 13

Arg Lys Leu Lys Lys Lys Ile Lys Lys Leu
1               5                   10

<210> SEQ ID NO 14
<211> LENGTH: 10
<212> TYPE: PRT
<213> ORGANISM: Mus musculus

<400> SEQUENCE: 14

Arg Glu Lys Lys Lys Phe Leu Lys Arg Arg
1               5                   10

<210> SEQ ID NO 15
<211> LENGTH: 20
<212> TYPE: PRT
<213> ORGANISM: Homo sapiens

<400> SEQUENCE: 15

Lys Arg Lys Gly Asp Glu Val Asp Gly Val Asp Glu Val Ala Lys Lys
1               5                   10                  15

Lys Ser Lys Lys
            20

<210> SEQ ID NO 16
<211> LENGTH: 17

```
<212> TYPE: PRT
<213> ORGANISM: Homo sapiens

<400> SEQUENCE: 16

Arg Lys Cys Leu Gln Ala Gly Met Asn Leu Glu Ala Arg Lys Thr Lys
1               5                   10                  15

Lys

<210> SEQ ID NO 17
<211> LENGTH: 288
<212> TYPE: PRT
<213> ORGANISM: Artificial Sequence
<220> FEATURE:
<223> OTHER INFORMATION: Synthetic

<400> SEQUENCE: 17

Met Asp Pro Ile Arg Ser Arg Thr Pro Ser Pro Ala Arg Glu Leu Leu
1               5                   10                  15

Ser Gly Pro Gln Pro Asp Gly Val Gln Pro Thr Ala Asp Arg Gly Val
            20                  25                  30

Ser Pro Pro Ala Gly Gly Pro Leu Asp Gly Leu Pro Ala Arg Arg Thr
        35                  40                  45

Met Ser Arg Thr Arg Leu Pro Ser Pro Ala Pro Ser Pro Ala Phe
    50                  55                  60

Ser Ala Asp Ser Phe Ser Asp Leu Leu Arg Gln Phe Asp Pro Ser Leu
65                  70                  75                  80

Phe Asn Thr Ser Leu Phe Asp Ser Leu Pro Pro Phe Gly Ala His His
                85                  90                  95

Thr Glu Ala Ala Thr Gly Glu Trp Asp Glu Val Gln Ser Gly Leu Arg
            100                 105                 110

Ala Ala Asp Ala Pro Pro Pro Thr Met Arg Val Ala Val Thr Ala Ala
        115                 120                 125

Arg Pro Pro Arg Ala Lys Pro Ala Pro Arg Arg Ala Ala Gln Pro
    130                 135                 140

Ser Asp Ala Ser Pro Ala Ala Gln Val Asp Leu Arg Thr Leu Gly Tyr
145                 150                 155                 160

Ser Gln Gln Gln Gln Glu Lys Ile Lys Pro Lys Val Arg Ser Thr Val
                165                 170                 175

Ala Gln His His Glu Ala Leu Val Gly His Gly Phe Thr His Ala His
            180                 185                 190

Ile Val Ala Leu Ser Gln His Pro Ala Ala Leu Gly Thr Val Ala Val
        195                 200                 205

Lys Tyr Gln Asp Met Ile Ala Ala Leu Pro Glu Ala Thr His Glu Ala
    210                 215                 220

Ile Val Gly Val Gly Lys Gln Trp Ser Gly Ala Arg Ala Leu Glu Ala
225                 230                 235                 240

Leu Leu Thr Val Ala Gly Glu Leu Arg Gly Pro Pro Leu Gln Leu Asp
                245                 250                 255

Thr Gly Gln Leu Leu Lys Ile Ala Lys Arg Gly Gly Val Thr Ala Val
            260                 265                 270

Glu Ala Val His Ala Trp Arg Asn Ala Leu Thr Gly Ala Pro Leu Asn
        275                 280                 285

<210> SEQ ID NO 18
<211> LENGTH: 183
<212> TYPE: PRT
<213> ORGANISM: Artificial Sequence
```

-continued

```
<220> FEATURE:
<223> OTHER INFORMATION: Synthetic

<400> SEQUENCE: 18

Arg Pro Ala Leu Glu Ser Ile Val Ala Gln Leu Ser Arg Pro Asp Pro
1               5                   10                  15

Ala Leu Ala Ala Leu Thr Asn Asp His Leu Val Ala Leu Ala Cys Leu
            20                  25                  30

Gly Gly Arg Pro Ala Leu Asp Ala Val Lys Lys Gly Leu Pro His Ala
        35                  40                  45

Pro Ala Leu Ile Lys Arg Thr Asn Arg Arg Ile Pro Glu Arg Thr Ser
    50                  55                  60

His Arg Val Ala Asp His Ala Gln Val Val Arg Val Leu Gly Phe Phe
65                  70                  75                  80

Gln Cys His Ser His Pro Ala Gln Ala Phe Asp Asp Ala Met Thr Gln
                85                  90                  95

Phe Gly Met Ser Arg His Gly Leu Leu Gln Leu Phe Arg Arg Val Gly
            100                 105                 110

Val Thr Glu Leu Glu Ala Arg Ser Gly Thr Leu Pro Pro Ala Ser Gln
        115                 120                 125

Arg Trp Asp Arg Ile Leu Gln Ala Ser Gly Met Lys Arg Ala Lys Pro
    130                 135                 140

Ser Pro Thr Ser Thr Gln Thr Pro Asp Gln Ala Ser Leu His Ala Phe
145                 150                 155                 160

Ala Asp Ser Leu Glu Arg Asp Leu Asp Ala Pro Ser Pro Met His Glu
                165                 170                 175

Gly Asp Gln Thr Arg Ala Ser
            180

<210> SEQ ID NO 19
<211> LENGTH: 53
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (52)..(52)
<223> OTHER INFORMATION: "v" represents A or C or G
<220> FEATURE:
<221> NAME/KEY: misc_feature
<222> LOCATION: (53)..(53)
<223> OTHER INFORMATION: "n" represents any nucleotide

<400> SEQUENCE: 19
agacgtgtgc tcttccgatc tttttttttt tttttttttt tttttttttt tvn         53

<210> SEQ ID NO 20
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(29)
<223> OTHER INFORMATION: any "n" represents any nucleotide

<400> SEQUENCE: 20
agacgtgtgc tcttccgatc tnnnnnggg                                    29

<210> SEQ ID NO 21
```

```
<211> LENGTH: 21
<212> TYPE: DNA
<213> ORGANISM: Artificial Sequence
<220> FEATURE:
<223> OTHER INFORMATION: Synthetic

<400> SEQUENCE: 21
agacgtgtgc tcttccgatc t                                          21

<210> SEQ ID NO 22
<211> LENGTH: 51
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(51)
<223> OTHER INFORMATION: any "n" represents any nucleotide

<400> SEQUENCE: 22
aatgatacgg cgaccaccga gatctacacn nnnnnnntcg tcggcagcgt c          51

<210> SEQ ID NO 23
<211> LENGTH: 69
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(69)
<223> OTHER INFORMATION: Any "n" represents any nucleotide

<400> SEQUENCE: 23
caagcagaag acggcatacg agatnnnnnn nngtgactgg agttcagacg tgtgctcttc  60
cgatctggg                                                         69
```

PRODUCT AND METHODS USEFUL FOR MODULATING AND EVALUATING IMMUNE RESPONSES

RELATED APPLICATIONS AND INCORPORATION BY REFERENCE

This application is the U.S. National Stage of International Application No. PCT/US2017/047422, filed Aug. 17, 2017 published in English under PCT Article 21(2), which claims the benefit of U.S. Provisional Application No. 62/376,007, filed Aug. 17, 2016.

All documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FEDERAL FUNDING LEGEND

This invention was made with government support under Grant No. HG006193 awarded by the National Institutes of Health. The government has certain rights in the invention.

REFERENCE TO AN ELECTRONIC SEQUENCE LISTING

The contents of the electronic sequence listing (BROD-2700US_ST25.txt; Size is 12 KB) was created on Feb. 25, 2019. Applicants respectfully request that the reference Sequence Listing is incorporated by reference in its entirety.

FIELD OF THE INVENTION

The invention relates broadly to cell products, substances, compositions, markers, marker signatures, molecular targets, kits of parts and methods useful in characterising, evaluating and modulating the immune system and immune responses.

BACKGROUND OF THE INVENTION

A fundamental challenge in immunology is to accurately assign identity and function to immune cells, which are responsible for the delicate balance between tolerance and immunity. Leukocyte populations have historically been defined by the expression of a restricted set of surface markers, a strategy that tends to be inherently biased.

The ability to analyse the function and dysfunction of individual immune cell types and their contribution to physiological and pathophysiological processes is, however, critical for characterising and understanding the operation of the immune system in health and disease, and consequently for provision of tools and methods useful for evaluating and modulating the immune system and immune responses.

Among the various cells of the immune system, dendritic cells (DCs) are mononuclear phagocytes found in blood, lymphoid organs and all tissues (Haniffa et al. 2015, Mildner and Jung; Schraml and Reis e Sousa). One of their central functions is to ingest materials such as pathogens, present processed epitopes to T cells and regulate innate and adaptive immune responses. Hence, DCs participate inter alia in mounting the immune responses characterising cancer, inflammatory and infectious diseases. DCs are heterogeneous and consist of multiple subtypes with unique functions that have been defined over the past decade in mice and humans. However, it is not clear how many DC subtypes exist, how they are related to each other and how they differ from other mononuclear phagocytes.

The results of numerous studies have shown that human dendritic cells express high levels of major histocompatibility complex class II (HLA-DR), a molecule essential for antigen presentation, and lack key markers of T, B, NK, granulocytes and monocytes. In the blood, DC subtypes include $CD11C^+$ conventional DCs (cDCs), including either $CD141^+$ or $CD1C^+$ cells, and plasmacytoid DCs (pDC), including $CD123^+$ cells. cDCs are effective at antigen-specific stimulation of $CD4^+$ and $CD8^+$ T cells, while pDCs specialize in producing type I interferons in response to viruses. pDCs and cDC subtypes differ in their expression of numerous sensors, pathways and effectors and play distinct roles in the immune response (Haniffa et al. 2015; Mildner and Jung; Schraml and Reis e Sousa). The different DC subtypes have historically been defined by a combination of morphology, physical properties, localization, molecular markers, functions and developmental origins, converging to the current model described above (Haniffa et al. 2015; Mildner and Jung; Schraml and Reis e Sousa). However, the definition of DCs is still likely to be biased by the limited markers available to identify, isolate and manipulate the cells. Such biases, in turn, would alter the assignment of function and ontogeny to each DC subtype.

In view of the above, there exists a continuous need to provide for novel immune cells and immune cell populations, as well as for additional and preferably improved markers, marker signatures and molecular targets characterising such novel immune cells or existing immune cells. Likewise, there exists a continuous need to provide additional and preferably improved therapeutically useful products based on or impinging on such immune cells, immune cell populations or molecular targets to modulate immune responses.

SUMMARY OF THE INVENTION

The various aspects of the invention as disclosed in this specification are based, at least in part, on the discovery of novel immune cells and immune cell populations, as well as markers, marker signatures and molecular targets characterising such novel immune cells. Further aspects of the invention are based, at least in part, on the discovery of novel markers, marker signatures and molecular targets characterising existing immune cells. The present cell products, substances, compositions, markers, marker signatures, molecular targets, kits of parts and methods provide for new ways to characterise, evaluate and modulate the immune system and immune responses.

Accordingly, an aspect of the invention provides an isolated immune cell selected from the group consisting of:
a1) an immune cell characterised in that the immune cell comprises expression of HLA-DR, does not express CD3, CD56, CD19 and CD14, and comprises expression of CLEC9A;
a2) an immune cell which is HLA-DR positive, CD3 negative, CD56 negative, CD19 negative, CD14 negative, and CLEC9A positive;

a3) an immune cell characterised in that the immune cell comprises expression of HLA-DR, does not express CD3, CD56, CD19 and CD14, and comprises a gene or gene product signature, the signature comprising or consisting of one or more genes or gene products as set forth in Table E1 part a or in Table E2 part a or in FIG. 2C cluster 'DC1' or in FIG. 2D cluster 'DC.' or in FIG. 2G cluster 'DC1';

b1) an immune cell characterised in that the immune cell comprises expression of HLA-DR, does not express CD3, CD56, CD19 and CD14, and comprises expression of FCGR2B;

b2) an immune cell which is HLA-DR positive, CD3 negative, CD56 negative, CD19 negative and CD14 negative, and FCGR2B positive;

b3) an immune cell characterised in that the immune cell comprises expression of HLA-DR, does not express CD3, CD56, CD19 and CD14, and comprises a gene or gene product signature, the signature comprising or consisting of one or more genes or gene products as set forth in Table E1 part b or in Table E2 part b or in Table E3 part a or in FIG. 2C cluster 'DC2' or in FIG. 2D cluster 'DC2' or in FIG. 2G cluster 'DC2';

c1) an immune cell characterised in that the immune cell comprises expression of HLA-DR, does not express CD3, CD56 and CD19, and comprises expression of one or more genes or gene products selected from the group consisting of CD163, CD36, CD14, LYZ, S100A8, S100A9, and S100A12;

c2) an immune cell which is HLA-DR positive, CD3 negative, CD56 negative and CD19 negative, and positive for one or more genes or gene products selected from the group consisting of CD163, CD36, CD14, LYZ, S100A8, S100A9, and S100A12:

c3) an immune cell characterised in that the immune cell comprises expression of HLA-DR, does not express CD3, CD56 and CD19, and comprises a gene or gene product signature, the signature comprising or consisting of one or more genes or gene products as set forth in Table E1 part c or in Table E2 part c or in Table E3 part b or in FIG. 2C cluster 'DC3' or in FIG. 2D cluster 'DC3' or in FIG. 2G cluster 'DC3';

d1) an immune cell characterised in that the immune cell comprises expression of HLA-DR, does not express CD3, CD56, CD19 and CD14, and comprises expression of FCGR3A;

d2) an immune cell which is HLA-DR positive, CD3 negative, CD56 negative, CD19 negative and CD14 negative, and FCGR3A positive;

d3) an immune cell characterised in that the immune cell comprises expression of HLA-DR, does not express CD3, CD56, CD19 and CD14, and comprises a gene or gene product signature, the signature comprising or consisting of one or more genes or gene products as set forth in Table E1 part d or in Table E2 part d or in FIG. 2C cluster 'DC4' or in FIG. 2D cluster 'DC4' or in FIG. 2G cluster 'DC4';

e1) an immune cell characterised in that the immune cell comprises expression of HLA-DR, does not express CD3, CD56, CD19 and CD14, and comprises expression of one or more genes or gene products selected from the group consisting of AXL, SIGLEC6, SIGLEC1, PPP1R14A, CD22, CD5, and GPR146;

e2) an immune cell which is HLA-DR positive, CD3 negative, CD56 negative, CD19 negative and CD14 negative, and positive for one or more genes or gene products selected from the group consisting of AXL, SIGLEC6, SIGLEC1, PPP1R14A, CD22, CD5, and GPR146;

e3) an immune cell characterised in that the immune cell comprises expression of HLA-DR, does not express CD3, CD56, CD19 and CD14, and comprises a gene or gene product signature, the signature comprising or consisting of one or more genes or gene products as set forth in Table E1 part e or in Table E2 part e or in FIG. 2C cluster 'DC5' or in FIG. 2D cluster 'DC5' or in FIG. 2G cluster 'DC5';

f1) an immune cell characterised in that the immune cell comprises expression of HLA-DR, does not express CD3, CD56, CD19 and CD14, and comprises expression of one or more genes or gene products selected from the group consisting of GZMB, SELPLG, DERL3, PTPRCAP, BCL11A, LAMP5, SLA2, SELS, NRP1, SIDT1, TCF4, SLC15A4, PTCRA, IRF7, and TRAF4;

f2) an immune cell which is HLA-DR positive, CD3 negative, CD56 negative, CD19 negative and CD14 negative, and positive for one or more genes or gene products selected from the group consisting of GZMB, SELPLG, DERL3, PTPRCAP, BCL11A, LAMP5, SLA2, SELS, NRP1, SIDT1, TCF4, SLC15A4, PTCRA, IRF7, and TRAF4;

f3) an immune cell characterised in that the immune cell comprises expression of HLA-DR, does not express CD3, CD56, CD19 and CD14, and comprises a gene or gene product signature, the signature comprising or consisting of one or more genes or gene products as set forth in Table E1 part f or in Table E2 part f or in FIG. 2C cluster 'DC6' or in FIG. 2D cluster 'DC6' or in FIG. 2G cluster 'DC6' or in FIG. 6A cluster 'DC6';

g1) an immune cell characterised in that the immune cell comprises expression of HLA-DR, does not express CD3, CD56, CD19 and CD14, does not express CD11C, CD123 and CD39, and comprises expression of CD45RA, high expression of CD100, and intermediate expression of CD34;

g2) an immune cell which is HLA-DR positive, CD3 negative, CD56 negative, CD19 negative, CD14 negative, CD11C negative, CD123 negative, CD39 negative, CD45RA positive, CD100 high, CD34 intermediate;

g3) an immune cell characterised in that the immune cell comprises expression of HLA-DR, does not express CD3, CD56, CD19 and CD14, does not express CD11C, CD123 and CD39, and comprises expression of one or more genes or gene products selected from the group consisting of RUNX2, TNFRSF18, ID2, ACY3, RORC, SEMA4D, SATB1, KIT, AHR, HLX, and CCR7;

g4) an immune cell which is HLA-DR positive, CD3 negative, CD56 negative, CD19 negative, CD14 negative, CD11C negative, CD123 negative, CD39 negative, and positive for one or more genes or gene products selected from the group consisting of RUNX2, TNFRSF18, ID2, ACY3, RORC, SEMA4D, SATB1, KIT, AHR, HLX, and CCR7;

g5) an immune cell characterised in that the immune cell comprises expression of HLA-DR, does not express CD3, CD56, CD19 and CD14, does not express CD11C, CD123 an CD39, and is capable of differentiation to: the immune cell as defined in any one of a1), a2), or a3), the immune cell as defined in any one of b1), b2), or b3), and the immune cell as defined in any one of c1), c2), or c3);

g6) an immune cell which is HLA-DR positive, CD3 negative, CD56 negative, CD19 negative, CD14 negative, CD11C negative, CD123 negative, CD39 negative, and is capable of differentiation to: the immune cell as defined in any one of a1), a2), or a3), the immune cell as defined in any one of b1), b2), or b3), and the immune cell as defined in any one of c1), c2), or c3); or h1) an immune cell characterised in that the immune cell comprises expression of HLA-DR, CD45 and CD123, and comprises a gene or gene product signature, the signature comprising or consisting of one or more genes or gene products as set forth in Table E8 or in FIG. 8B clusters BPDCN_1 to 4.

A further aspect of the invention relates to an immune cell gene or gene product signature selected from the group consisting of:

a) a signature comprising or consisting of one or more genes or gene products as set forth in Table E1 part a or in Table E2 part a or in FIG. 2C cluster 'DC1' or in FIG. 2D cluster 'DC1' or in FIG. 2G cluster 'DC1';

b) a signature comprising or consisting of one or more genes or gene products as set forth in Table E1 part b or in Table E2 part b or in Table E3 part a or in FIG. 2C cluster 'DC2' or in FIG. 2D cluster 'DC2' or in FIG. 2G cluster 'DC2';

c) a signature comprising or consisting of one or more genes or gene products as set forth in Table E1 part c or in Table E2 part c or in Table E3 part b or in FIG. 2C cluster 'DC3' or in FIG. 2D cluster 'DC3' or in FIG. 2G cluster 'DC3';

d) a signature comprising or consisting of one or more genes or gene products as set forth in Table E1 part d or in Table E2 part d or in FIG. 2C cluster 'DC4' or in FIG. 2D cluster 'DC4' or in FIG. 2G cluster 'DC4';

e) a signature comprising or consisting of one or more genes or gene products as set forth in Table E1 part e or in Table E2 part e or in FIG. 2C cluster 'DC5' or in FIG. 2D cluster 'DC5' or in FIG. 2G cluster 'DC5';

f) a signature comprising or consisting of one or more genes or gene products as set forth in Table E1 part f or in Table E2 part f or in FIG. 2C cluster 'DC6' or in FIG. 2D cluster 'DC6' or in FIG. 2G cluster 'DC6' or in FIG. 6A cluster 'DC6';

g) a signature comprising or consisting of one or more genes or gene products selected from the group consisting of PROC, IRF8, FMNL3, APP, SERPINF1, C1ORF186, CYBASC3, PLAC8, NRP1, CCDC50, TSPAN13, UGCG, LILRA4, MZB1, PTPRS, AK128525, IGJ, and IL3RA;

h) a signature comprising or consisting of one or more genes or gene products selected from the group consisting of ITGAX, IFI30, LGALS2, FGR, LY86, GLIPR2, TIMP1, LST1, AGPAT9, IFITM3, DUSP23, ENTPD1, LOC645638, and IL1RN; or i) a signature comprising or consisting of one or more genes or gene products as set forth in Table E8 or in FIG. 8B clusters BPDCN_1 to 4.

A further aspect of the invention provides a kit of parts or an article of manufacture for detecting, quantifying or isolating immune cells, the kit of parts or article of manufacture comprising:

a') one or more agents capable of specifically binding to CLEC9A, optionally further comprising one or more agents capable of specifically binding to one or more gene products selected from the group consisting of HLA-DR, CD3, CD56, CD19 and CD14;

a") one or more agents capable of specifically binding to one or more gene products comprised by or constituting the signature as defined in a) above, optionally further comprising one or more agents capable of specifically binding to one or more gene products selected from the group consisting of HLA-DR, CD3, CD56, CD19 and CD14;

b') one or more agents capable of specifically binding to FCGR2B, optionally further comprising one or more agents capable of specifically binding to one or more gene products selected from the group consisting of HLA-DR, CD3, CD56, CD19 and CD14;

b") one or more agents capable of specifically binding to one or more gene products comprised by or constituting the signature as defined in b) above, optionally further comprising one or more agents capable of specifically binding to one or more gene products selected from the group consisting of HLA-DR, CD3, CD56, CD19 and CD14;

c') one or more agents capable of specifically binding to one or more gene products selected from the group consisting of CD163, CD36, CD14, LYZ, S100A8, S100A9, and S100A12, optionally further comprising one or more agents capable of specifically binding to one or more gene products selected from the group consisting of HLA-DR, CD3, CD56 and CD19;

c") one or more agents capable of specifically binding to one or more gene products comprised by or constituting the signature as defined in c) above, optionally further comprising one or more agents capable of specifically binding to one or more gene products selected from the group consisting of HLA-DR, CD3, CD56 and CD19;

d') one or more agents capable of specifically binding to FCGR3A, optionally further comprising one or more agents capable of specifically binding to one or more gene products selected from the group consisting of HLA-DR, CD3, CD56, CD19 and CD14;

d") one or more agents capable of specifically binding to one or more gene products comprised by or constituting the signature as defined in d) above, optionally further comprising one or more agents capable of specifically binding to one or more gene products selected from the group consisting of HLA-DR, CD3, CD56, CD19 and CD14;

e') one or more agents capable of specifically binding to one or more gene products selected from the group consisting of AXL, SIGLEC6, SIGLEC1, PPP1R14A, CD22, CD5, and GPR146, optionally further comprising one or more agents capable of specifically binding to one or more gene products selected from the group consisting of HLA-DR, CD3, CD56, CD19 and CD14;

e") one or more agents capable of specifically binding to one or more gene products comprised by or constituting the signature as defined in e) above, optionally further comprising one or more agents capable of specifically binding to one or more gene products selected from the group consisting of HLA-DR, CD3, CD56, CD19 and CD14;

f') one or more agents capable of specifically binding to one or more gene products selected from the group consisting of GZMB, SELPLG, DERL3, PTPRCAP, BCL11A, LAMP5, SLA2, SELS, NRP1, SIDT1, TCF4, SLC15A4, PTCRA, IRF7, and TRAF4, optionally further comprising one or more agents capable of specifically binding to one or more gene products selected from the group consisting of HLA-DR, CD3, CD56, CD19 and CD14;

f") one or more agents capable of specifically binding to one or more gene products comprised by or constituting the signature as defined in f) above, optionally further comprising one or more agents capable of specifically binding to one or more gene products selected from the group consisting of HLA-DR, CD3, CD56, CD19 and CD14;

g') one or more agents capable of specifically binding to CD45RA, CD100, and CD34, optionally further comprising one or more agents capable of specifically binding to one or more gene products selected from the group consisting of HLA-DR, CD3, CD56, CD19, CD14, CD11C, CD123 and CD39.

g") one or more agents capable of specifically binding to one or more gene products selected from the group consisting of RUNX2, TNFRSF18, ID2, ACY3, RORC, SEMA4D, SATB1, KIT, AHR, HLX, and CCR7, optionally further comprising one or more agents capable of specifically binding to one or more gene products selected from the group consisting of HLA-DR, CD3, CD56, CD19, CD14, CD11C, CD123 and CD39; and/or h') one or more agents capable of specifically binding to one or more gene products comprised by or constituting the signature as defined in i) above, optionally further comprising one or more agents capable of specifically binding to one or more gene products selected from the group consisting of HLA-DR, CD45 and CD123.

A further aspect of the invention provides an isolated immune cell selected from the group consisting of:

x) an immune cell characterised in that the immune cell does not express CD3, CD56, CD19, comprises expression of CD14, and comprises a gene or gene product signature, the signature comprising or consisting of one or more genes or gene products as set forth in Table E4 part a or in FIG. 4B cluster 'Mono1' or in FIG. 4D cluster 'Mono1' or in FIG. 4E cluster 'Mono1';

y) an immune cell characterised in that the immune cell does not express CD3, CD56, CD19, comprises expression of CD14, and comprises a gene or gene product signature, the signature comprising or consisting of one or more genes or gene products as set forth in Table E4 part b or in FIG. 4B cluster 'Mono2' or in FIG. 4D cluster 'Mono2' or in FIG. 4E cluster 'Mono2';

w) an immune cell characterised in that the immune cell does not express CD3, CD56, CD19, comprises expression of CD14, and comprises a gene or gene product signature, the signature comprising or consisting of one or more genes or gene products as set forth in Table E4 part c or in FIG. 4B cluster 'Mono3' or in FIG. 4D cluster 'Mono3' or in FIG. 4E cluster 'Mono3';

z) an immune cell characterised in that the immune cell does not express CD3, CD56, CD19, comprises expression of CD14, and comprises a gene or gene product signature, the signature comprising or consisting of one or more genes or gene products as set forth in Table E4 part d or in FIG. 4B cluster 'Mono4' or in FIG. 4D cluster 'Mono4' or in FIG. 4E cluster 'Mono4'.

A further aspect of the invention relates to an immune cell gene or gene product signature selected from the group consisting of:

x) a signature comprising or consisting of one or more genes or gene products as set forth in as set forth in Table E4 part a or in FIG. 4B cluster 'Mono1' or in FIG. 4D cluster 'Mono1' or in FIG. 4E cluster 'Mono1';

y) a signature comprising or consisting of one or more genes or gene products as set forth in as set forth in Table E4 part b or in FIG. 4B cluster 'Mono2' or in FIG. 4D cluster 'Mono2' or in FIG. 4E cluster 'Mono2';

w) a signature comprising or consisting of one or more genes or gene products as set forth in as set forth in Table E4 part c or in FIG. 4B cluster 'Mono3' or in FIG. 4D cluster 'Mono3' or in FIG. 4E cluster 'Mono3'; or z) a signature comprising or consisting of one or more genes or gene products as set forth in as set forth in Table E4 part d or in FIG. 4B cluster 'Mono4' or in FIG. 4D cluster 'Mono4' or in FIG. 4E cluster 'Mono4'.

Another aspect of the invention provides a kit of parts or an article of manufacture for detecting, quantifying or isolating immune cells, the kit of parts or article of manufacture comprising:

x) one or more agents capable of specifically binding to one or more gene products comprised by or constituting the signature as defined in x) above, optionally further comprising one or more agents capable of specifically binding to one or more gene products selected from the group consisting of CD3, CD56, CD19, and CD14;

y) one or more agents capable of specifically binding to one or more gene products comprised by or constituting the signature as defined in y) above, optionally further comprising one or more agents capable of specifically binding to one or more gene products selected from the group consisting of CD3, CD56, CD19, and CD14;

w) one or more agents capable of specifically binding to one or more gene products comprised by or constituting the signature as defined in w) above, optionally further comprising one or more agents capable of specifically binding to one or more gene products selected from the group consisting of CD3, CD56, CD19, and CD14; and/or z) one or more agents capable of specifically binding to one or more gene products comprised by or constituting the signature as defined in z) above, optionally further comprising one or more agents capable of specifically binding to one or more gene products selected from the group consisting of CD3, CD56, CD19, and CD14.

Another aspect of the invention provides a method for detecting or quantifying immune cells in a biological sample of a subject, or for isolating immune cells from a biological sample of a subject, the method comprising:

a) providing a biological sample of a subject; and b) detecting or quantifying in the biological sample immune cells as defined above, or isolating from the biological sample immune cells as defined above.

A further aspect of the invention provides a population of immune cells as defined above.

A further aspect of the invention provides a composition, pharmaceutical composition or vaccine comprising the immune cell or the immune cell population as defined above.

A further aspect of the invention provides a method for preparing an immune cell vaccine comprising:

a) isolating from a biological sample of a subject an immune cell or an immune cell population as defined above;

b) optionally in vitro expanding the immune cell or immune cell population of a);

c) loading said immune cell or immune cell population with an antigen; and d) isolating the antigen-loaded immune cell or immune cell population.

A further aspect of the invention provides a method for eliciting an immune response or immune tolerance to an antigen in a subject comprising administering to the subject the immune cell or the immune cell population or the pharmaceutical composition or vaccine as defined above, wherein the immune cell or immune cell population has been loaded with said antigen.

A related aspect of the invention provides the immune cell or the immune cell population or the pharmaceutical composition or vaccine as defined above, wherein the immune cell or immune cell population has been loaded with an antigen for use in a method for eliciting an immune response or immune tolerance to said antigen.

A further aspect of the invention provides a method for eliciting an immune response or immune tolerance to an antigen in a subject comprising:

a) isolating from a biological sample of the subject an immune cell or an immune cell population as defined above;

b) in vitro differentiating the immune cell or immune cell population of a) into a comparatively more mature immune cell or immune cell population;

c) loading said in vitro differentiated immune cell or immune cell population of b) with said antigen;

d) administering the in vitro differentiated antigen loaded immune cell or immune cell population of c) to the subject.

A related aspect of the invention provides an in vitro differentiated antigen loaded immune cell or immune cell population for use in a method for eliciting an immune response or immune tolerance to an antigen in a subject, the method comprising:

a) isolating from a biological sample of the subject an immune cell or an immune cell population as defined above;

b) in vitro differentiating the immune cell or immune cell population of a) into a comparatively more mature immune cell or immune cell population;

c) loading said in vitro differentiated immune cell or immune cell population of b) with said antigen;

d) administering the in vitro differentiated antigen loaded immune cell or immune cell population of c) to the subject.

A further aspect of the invention provides a method for treating or preventing a pathological condition comprising administering to a subject in need thereof the immune cell or the immune cell population or the pharmaceutical composition or vaccine as defined above.

A related aspect of the invention provides the immune cell or the immune cell population or the pharmaceutical composition or vaccine as defined above for use in a method for treating or preventing a pathological condition.

A further aspect of the invention provides an in vitro method for differentiating the immune cell as defined above into a comparatively more mature immune cell, comprising exposing the immune cell to one or more conditions and/or substances conducive to the differentiation.

A further aspect of the invention provides a method for treating or preventing a pathological condition in a subject in need thereof, the method comprising:

a) isolating from a biological sample of the subject an immune cell or the immune cell population as defined above;

b) in vitro differentiating the immune cell of a) into a comparatively more mature immune cell or immune cell population;

c) administering the in vitro differentiated immune cell or immune cell population of b) to the subject.

A related aspect of the invention provides in vitro differentiated immune cell or immune cell population for use in a method for treating or preventing a pathological condition in a subject, the method comprising:

a) isolating from a biological sample of the subject an immune cell or the immune cell population as defined above;

b) in vitro differentiating the immune cell of a) into a comparatively more mature immune cell or immune cell population;

c) administering the in vitro differentiated immune cell or immune cell population of b) to the subject.

A further aspect of the invention provides a method for preparing a composition comprising activated T cells, the method comprising isolating T cells from a biological sample of a subject and contacting said T cells in vitro with an immune cell or an immune cell population as defined above, wherein the immune cell or immune cell population has been loaded with an antigen.

A further aspect of the invention provides a method for adoptive immunotherapy in a subject in need thereof comprising administering to said subject a composition comprising activated T cells prepared with the method as set forth above.

A related aspect of the invention provides a composition comprising activated T cells prepared with the method as set forth above for use in a method for adoptive immunotherapy in a subject.

A further aspect of the invention provides a method for identifying an immunomodulant capable of modulating one or more phenotypic aspects of the immune cell or the immune cell population as defined above, comprising:

a) applying a candidate immunomodulant to the immune cell or immune cell population;

b) detecting modulation of one or more phenotypic aspects of the immune cell or immune cell population by the candidate immunomodulant;

thereby identifying the immunomodulant.

A further aspect of the invention provides an immunomodulant capable of modulating one or more phenotypic aspects of the immune cell or the immune cell population as defined above, such as an immunomodulant identified using the method set forth above.

A further aspect of the invention provides a composition, pharmaceutical composition or vaccine comprising the immunomodulant as defined above.

A further aspect of the invention provides a method for treating or preventing a pathological condition comprising administering to a subject in need thereof the immunomodulant, pharmaceutical composition or vaccine comprising such as defined above.

A related aspect of the invention provides the immunomodulant, pharmaceutical composition or vaccine comprising such as defined above for use in a method for treating or preventing a pathological condition.

A further aspect of the invention provides a method for treating or preventing a pathological condition in a subject in need thereof comprising:

a) applying to the immune cell or the immune cell population as defined above the immunomodulant, or the pharmaceutical composition or vaccine comprising such as defined above; and b) administering the immune cell or immune cell population of a) to the subject.

A related aspect of the invention provides an immune cell or immune cell population for use in a method for treating or preventing a pathological condition in a subject, the method comprising:

a) applying to the immune cell or the immune cell population as defined above the immunomodulant, or the pharmaceutical composition or vaccine comprising such as defined above; and b) administering the immune cell or immune cell population of a) to the subject.

A further aspect of the invention provides a method for determining the immune status of a subject, or for diagnosing, prognosing or monitoring a disease comprising an immune component in a subject, the method comprising detecting or quantifying in a biological sample of the subject immune cells as defined above.

A related aspect of the invention provides a method for detecting or quantifying immune cells as defined above in a biological sample of a subject, wherein the subject is suspected of having or is at risk of developing an altered immune status, or is suspected of having or is at risk of developing a disease comprising an immune component.

A related aspect of the invention provides a method for diagnosing and treating an altered immune status of a subject, or for diagnosing and treating a disease comprising an immune component in a subject, the method comprising:
obtaining a biological sample from the subject;
detecting or quantifying the immune cells as defined above in the biological sample of the subject;
diagnosing the subject as in need of treatment for the altered immune status or for the disease comprising an immune component when said immune cells are detected in the sample and/or when the quantity of said immune cells differs from a reference value; and
administering an effective amount of a treatment to the diagnosed subject.

A further aspect of the invention provides a method for determining whether immune cells as defined above contribute to pathology of a disease, such as a disease comprising an immune component, the method comprising detecting or quantifying immune cells as defined above in a biological sample of a subject having the disease and a subject not having the disease, whereby altered quantity or phenotype of the immune cells between the subjects indicates that the immune cells contribute to pathology of the disease.

A further aspect of the invention provides a method for diagnosing, prognosing or monitoring blastic plasmacytoid dendritic cell neoplasm (BPDCN) in a subject, the method comprising detecting or quantifying immune cells as defined in h1) above in a biological sample of the subject.

A further aspect of the invention provides a method for detecting or quantifying immune cells as defined in h1) above in a biological sample of a subject, wherein the subject is suspected of having or is at risk of developing BPDCN.

A further aspect of the invention provides a method for diagnosing and treating BPDCN in a subject, the method comprising:
obtaining a biological sample from the subject;
detecting or quantifying immune cells as defined in h1) in the biological sample of the subject;
diagnosing the subject as in need of treatment for BPDCN when said immune cells are detected in the sample and/or when the quantity of said immune cells differs from a reference value; and
administering an effective amount of a treatment to the diagnosed subject.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention. |Normal|ZZMPTAG|

These and other embodiments are disclosed or are obvious from and encompassed by, the following Detailed Description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings.

FIG. 2A-2H illustrates human blood DC heterogeneity delineated by single-cell RNA-sequencing. (A) Workflow of experimental strategy: isolation of human peripheral blood mononuclear cells (PBMC) from blood by ficoll gradient centrifugation; sorting single DC (8×96-well plates) and monocytes (4×96-well plates) into single wells containing lysis buffer using an antibody cocktail to enrich for these cell types: single cell transcriptome profiling using a modified version of the Smart-Seq2 protocol. (B) Gating strategy for single cell sort: DCs were defined as live, lineage (LIN: CD3, CD19, CD56)$^-$CD14$^-$HLA-DR$^+$ cells. cDCs were further defined as CD11C$^+$ and 3 loose overlapping gates were drawn as an enrichment strategy to ensure a comprehensive and even sampling of both rare and common DC populations: CD11C$^+$CD141$^+$ (CD141; turquoise), CD11C$^+$CD1C$^+$ (CD1C; orange), CD11C$^+$CD141$^-$CD1C$^-$ ('Double Negative'; blue). Plasmacytoid DCs (pDCs) were defined as CD11C$^-$CD123$^+$ (pDC; purple). 24 single cells from these 4 loosely gated populations were sorted per 96-well plate and eight plates were analysed by single-cell RNA-sequencing. A fifth gate defined as CD11C$^-$ CD123$^-$ (red dashed gate), likely comprising other populations not captured by our lineage cocktail, was subsequently investigated (see FIG. 9). SSC: side scatter; FSC: forward scatter. (C) t-SNE analysis of DCs (n=742). Number of successfully profiled single cells per cluster include: DC1 (single cells mapping mostly to cells from CD141$^+$ DC gate, n=166); DC2 (named CD1C_A, n=105); DC3 (named CD1C_B, n=95); DC4 (mapping mostly to cells from CD1C$^-$CD141$^-$ gate, in =175); DC5 (new population, n=30); DC6 cluster (mapping mostly to cells from pDCs gate, n=171). Number in bracket, next to population ID in the legend, refers to the number of discriminative genes with AUC cutoff≥0.85. Up to 5 top discriminators are listed next to each cluster; number in bracket next to gene refers to AUC value (Table E2 for list of discriminative markers). Colors indicate unbiased DC classification via graph-based clustering (FIG. 2F for t-SNE analysis output colored by location within FACS-sorting gates). Each dot represents an individual cell. (D) Heatmap reports scaled expression (log TPM (Transcripts Per Million) values) of discriminative gene sets for each subset defined in FIG. 2C with AUC cutoff≥0.85. Number of genes per cluster within that AUC cutoff include: DC5 ('New pop.'), n=11; DC2 (CD1C_A), n=3: DC3 (CD1C_B), n=11; DC1 (CD141), in =36; DC4 (CD1C⁻CD141⁻), n=86; DC5 (pDC), n=92. Heatmap color scheme is based on z-score distribution from −2.5 (yellow) to 2.5 (purple). Right margin color bars highlight gene sets specific to the respective DCsubset. (E) Gene expression level distribution of surface markers commonly used to isolate particular DC subsets. Expression distribution (violin plots) for each population according to the clusters defined in FIG. 2 (horizontal axes) is shown. Each dot represents an individual cell. (F) Single cells color-labeled according to the loosely defined gates cells were sorted from t-SNE analysis of DCs (n=742) from the R software package Seurat. Colors indicate location of each transcriptionally profiled single DC within the FACS-sorting gate shown in FIG. 2B. Each dot represents an individual cell. (G) Heatmap reports scaled expression (log TPM values) of discriminative gene sets for each subset defined in panel D with AUC cutoff≥0.85. Heatmap color scheme is based on z-score distribution from −2.5 (yellow) to 2.5 (purple). See Table E2 for detailed information on discriminative markers. (H) Gating on pDC population highlights that some pDC express CD141 at the protein level. Left panel: relative protein expression level of CD141 and CD123 by cells characterized by cluster DC1 (red) and pDCs (green; cluster DC6). Right panel: shows the corresponding single cell gene expression distribution (violin plots), highlighting that pDC (DC6) express some level of THBD/CD141 (consistent with protein level detected), and thus confirming that THBD/CD141 is not a perfect classifier for DC1 cells (see FIG. 5N for additional characterization).

FIG. 3A-3D illustrates definition and validation of CD1C⁺ DC subsets. (A) Gene sets defining the two subsets of CD1C⁺ DCs identified in FIG. 2D (i.e. DC2 (CD1C_A) and DC3 (CD1C_B)). Heatmap showing scaled expression (log TPM values) of discriminative gene sets for each CD1C⁺ DC subset with AUC cutoff≥0.75 (extended list of discriminative markers can be found in Table E3). Heatmap color scheme is based on z-score distribution, from −2.5 (yellow) to 2.5 (purple). Violin plots on the right side illustrate gene expression distribution of candidate genes across both CD1C subsets on the x-axis (orange for CD1C_A, 'non-inflammatory'; green for CD1C_B, 'inflammatory' subset). FCGR2B/CD32B (AUC=0.63) is included in this heatmap as a reference, since this was the surface marker with the highest discriminative value that was overexpressed in 'non-inflammatory' CD1C_A (cluster DC2) and enabled subsequent enrichment experiments. CD163, CD36 and FCGR2B, labeled in red, were markers used to develop enrichment sorting panel described in (B). (B) Gating strategy to enrich for the two CD1C⁺ DC subsets. CD1C⁺ DCs were enriched by selecting on LIN(CD3, CD19, CD56)⁻HLA-DR⁺CD14⁻CD1C⁺CD11C⁺ cells. 'Non-inflammatory' CD1C_A subset was enriched by sorting on the 10% brightest of CD32B⁺ cells (orange gate). 'Inflammatory' CD1C_B subset was enriched by sorting on CD32B⁻CD163⁺CD36⁺ cells (green gate), or on CD32B⁻CD163⁺. Overlay of the two CD1C⁺ DC populations by CD1C versus CD11C expression demonstrated lower CD1C and CD11C expression by the CD1C_B 'inflammatory' subset (green), in contrast to the CD1C_A 'non-inflammatory' subset. 48 single cells were sorted from the green and orange gates in a 96-well plate for subsequent scRNA-seq profiling. SSC, side scatter; FSC, forward scatter. (C) Heatmap reporting scaled expression (log TPM values) of scRNAseq data from profiling three groups of CD1C⁺ DC subsets (CD1C⁺CD32B⁺, CD1C⁺CD36⁺CD163⁺, CD1C⁺ CD163⁺) isolated using the gating strategy in panel B. Results show enrichment for key gene signatures defining CD1C⁺ DC heterogeneity from previous unbiased analysis in panel A. Note that using either the combination of CD1C⁺ CD36⁺CD163⁺ or just CD1C⁺CD163⁺ recapitulated the CD1C_B 'inflammatory' signature. (D) Proliferation of allogeneic CD4⁺ and CD8⁺ T cells five days after co-culture with CD14⁺ monocytes, pDCs, CD1C_A 'non-inflammatory' DCs (i.e. CD1C⁺CD32B⁺), CD1C_B 'inflammatory' DCs (i.e. CD1C⁺CD163⁺). Left panel depicts representative pseudocolor dot plot and right panel bar graphs of composite data (n=3, mean±SEM, *p<0.05, paired t-test).

FIG. 4A-4E illustrates human blood monocyte heterogeneity defined by single-cell RNA-sequencing. (A) Gating strategy for monocyte single cell sorting. Monocytes were enriched by gating on LIN(CD3, CD19, CD56)⁻CD14$^{+/lo}$ and further defined by relative expression of CD14 and CD16 to delineate three loose overlapping sorting gates for comprehensive and even sampling of both rare and common populations: CD14⁺CD16⁻ (yellow gate; 'classical monocyte'), CD14⁺⁺CD16⁺ (purple; 'intermediate monocytes'), CD14⁺CD16⁺⁺ (blue; 'non-classical monocytes'). 32 cells from each of these 3 gates were sorted per 96-well plate and a total of 384 cells were profiled. Bottom right dot plot shows overlay of the 3 population sorted by CD14 and lineage markers expression. SSC: side scatter; FSC: forward scatter. (B) t-SNE analysis incorporating monocytes (n=337 successfully profiled) and DCs (n=742; see FIG. 2C). Number of successfully profiled single monocytes per transcriptionally defined clusters includes: Mono1, n=148; Mono2, n=137: Mono3, n=31; Mono4, n=21). Number in bracket next to cluster ID in the legend refers to the number of discriminative genes with AUC cutoff≥0.85 upon reanalyzing the DC and monocyte datasets together (extended list of discriminative markers can be found in Table E4). Up to 5 top discriminators are listed next to each cluster; number in bracket next to gene refers to AUC value. Colors indicate unbiased DC and monocyte clustering from unbiased graph-based clustering (see FIG. 4C for t-SNE analysis output colored by sorting gate identities). Each dot represents an individual cell. (C) Heatmap reporting scaled expression (log TPM values) of discriminative gene sets for each monocyte subsets with AUC cutoff≥0.85 (see FIG. 4E for detailed heatmap). Heatmap color scheme is based on z-score distribution, from −2.5 (yellow) to 2.5 (purple). Right margin color bars highlight gene sets of interest. (D) Monocyte single cells color-labeled according to one of the three loosely defined gates from which cells were sorted from (FIG. 4A). DCs are colored by unbiased classification as shown in FIG. 2C. t-SNE analysis incorporating successfully profiled monocytes (n=337) and DCs (n=742) using the R software package Seurat. The break-down of profiled monocytes from the original gating strategy in each transcriptionally defined cluster is as follow. Mono1 cluster is composed of: 90 cells sorted from 'classical' CD14⁺⁺CD16⁻ monocyte (yellow gate), 54 cells from the 'intermediate' CD14⁺⁺CD16⁺ monocyte (purple gate), and 4 cells from the and 'nonclassical' CD14⁺CD16⁺⁺ monocytes (blue gate). Mono2 cluster is composed of: 25 'classical', 13 'intermediate', 97 'nonclassical' cells. Mono3 cluster includes: 1 'classical', 23 'intermediate', 7 'nonclassical' cells. Mono4 includes: 17 'intermediate', 4 'nonclassical' cells. Each dot represents an individual cell. (E) Heatmap reporting scaled expression (log TPM values) of discriminative gene sets for each monocyte subset with AUC cutoff≥0.85. Gene sets of DC clusters are defined in FIG. 2. See Table E4 for more extensive list of markers. Heatmap color scheme is based on z-score distribution, from −2.5 (yellow) to 2.5 (purple).

FIG. 8A-8B illustrates leveraging human blood DC atlas to map the ontogeny of BPDCN. (A) Heatmap of scaled expression (log TPM values) of discriminative gene sets for each DC subset defined in FIG. 2D (AUC cutoff≥20.85; n=742) with the additional mapping of the 4 BPDCN patient samples (n=174) to evaluate overlap between DC subset signatures and BPDCN samples (Methods). Genes labeled in blue are expressed in healthy pDCs but not in BPDCN patient samples. Genes in red are co-expressed by healthy pDCs and BPDCN patient samples. Red box on the right indicates gene set common to BPDCN, pDC, and AXL$^+$ SIGLEC6$^+$. Heatmap color scheme is based on z-score distribution from −2.5 (yellow) to 2.5 (purple). (B) Heatmap of scaled expression (log TPM values) of distinct BPDCN signature (red side-bar; AUC cutoff≥0.75; see Table S8 for extended list), shared signature with 'pure' pDC gene sets (excluding common signature with AXL$^+$SIGLEC6$^+$ cells; blue side bar) and shared signature with cDC-gene sets (green side-bar). Samples include successfully profiled DCs (n=742) and four BPDCN samples (n=174). Genes labeled in blue are expressed in healthy pDCs but not in BPDCN patient samples. Genes labeled in red are commonly expressed in healthy pDCs and BPDCN patient samples. Heatmap color scheme is based on z-score distribution from −2.5 (yellow) to 2.5 (purple).

DETAILED DESCRIPTION OF THE INVENTION

Figure 1:
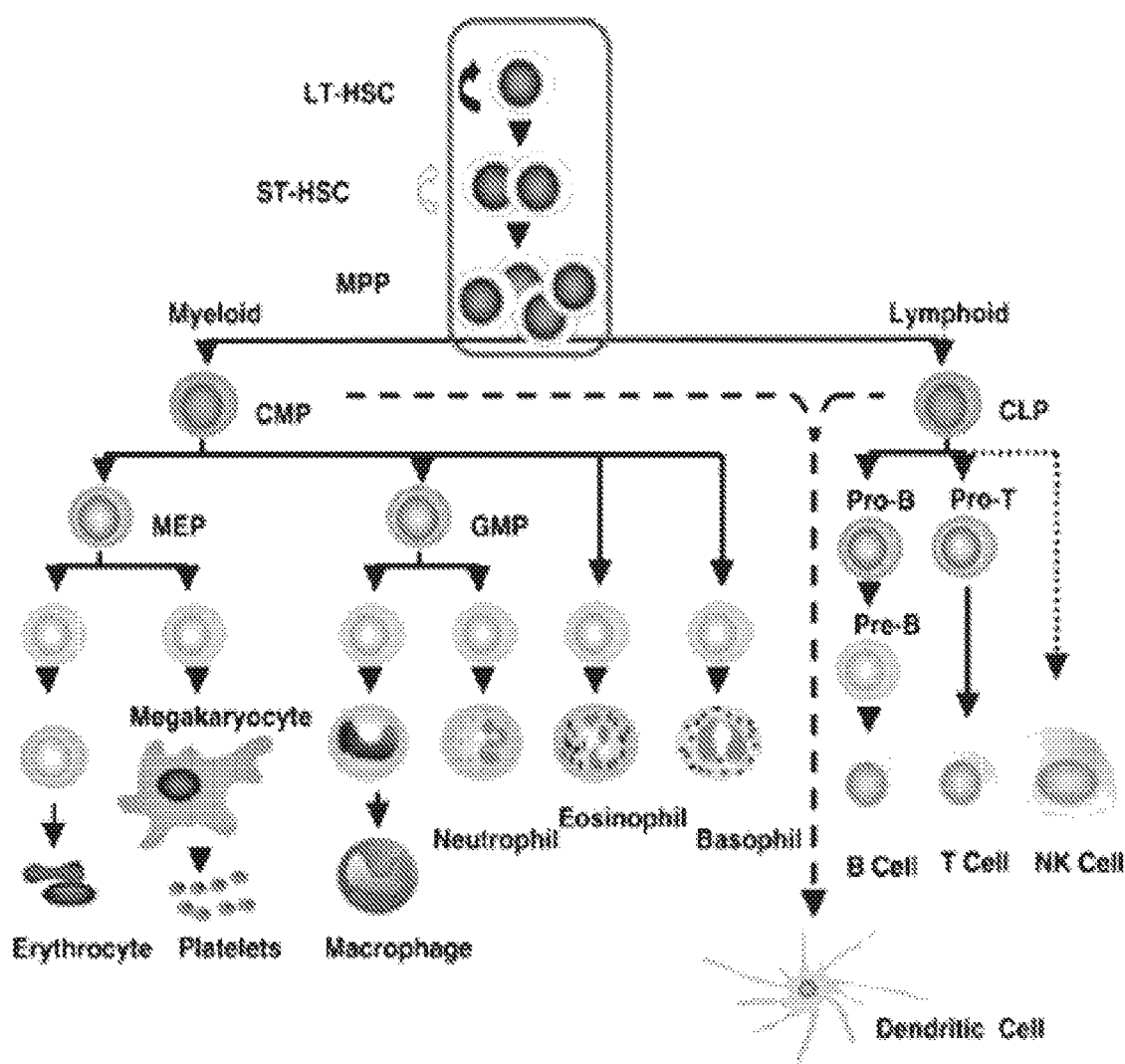
FIG. 1 illustrates a schematic overview of major immune cell types constituting a mammalian, such as human, immune system and their ontogeny.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the invention. When specific terms are defined in connection with a particular aspect of the invention or a particular embodiment of the invention, such connotation is meant to apply throughout this specification, i.e., also in the context of other aspects or embodiments of the invention, unless otherwise defined.

General Definitions

As used herein, the singular forms "a", "an", and "the" include both singular and plural referents unless the context clearly dictates otherwise.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one", such as one or more members or at least one member of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members. In another example, "one or more" or "at least one" may refer to 1, 2, 3, 4, 5, 6, 7 or more.

The term "optional" or "optionally" means that the subsequent described event, circumstance or substituent may or may not occur, and that the description includes instances where the event or circumstance occurs and instances where it does not.

In the following passages, different aspects or embodiments of the invention are defined in more detail. Each aspect or embodiment so defined may be combined with any other aspect(s) or embodiment(s) unless clearly indicated to the contrary. In particular, any feature indicated as being preferred or advantageous may be combined with any other feature or features indicated as being preferred or advantageous.

Reference throughout this specification to "one embodiment", "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

Invention Statement

The present invention relates to cell products, substances, compositions, markers, marker signatures, molecular targets, kits of parts and methods useful in characterising, evaluating and modulating the immune system and immune responses.

Figure 2B:
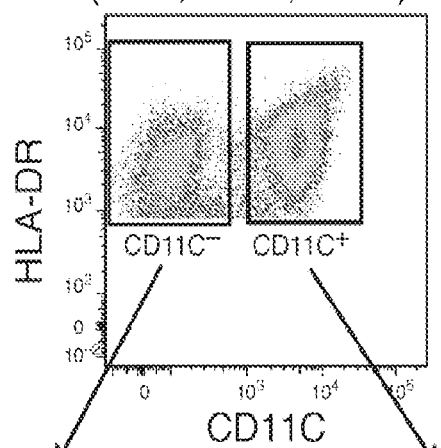
Figure 2B:
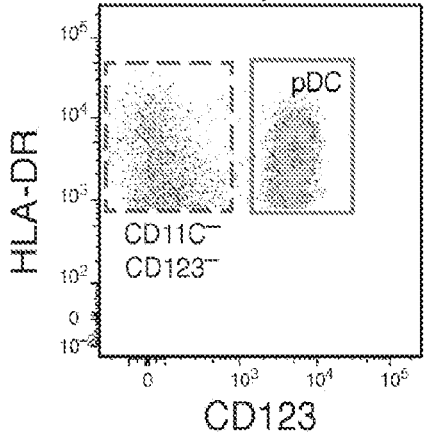
Figure 2B:
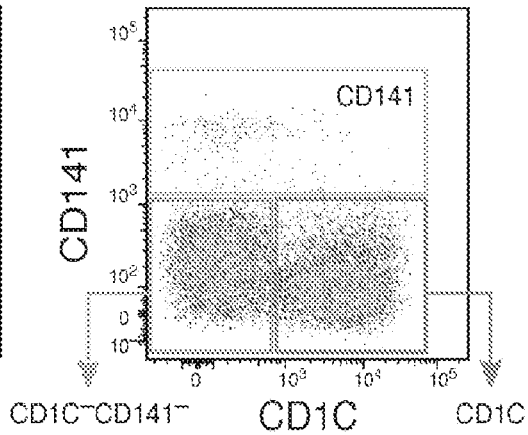
Figure 2C:
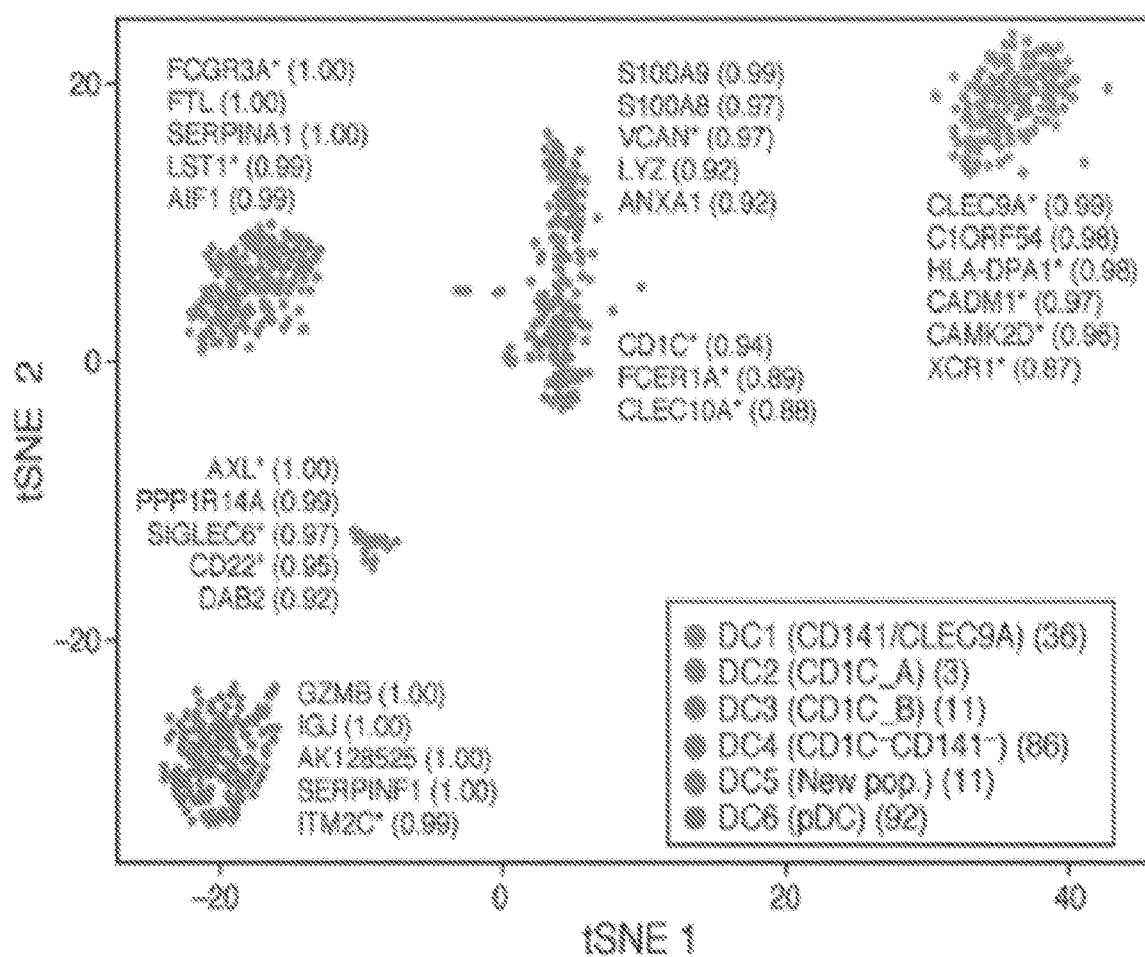
Figure 2D:
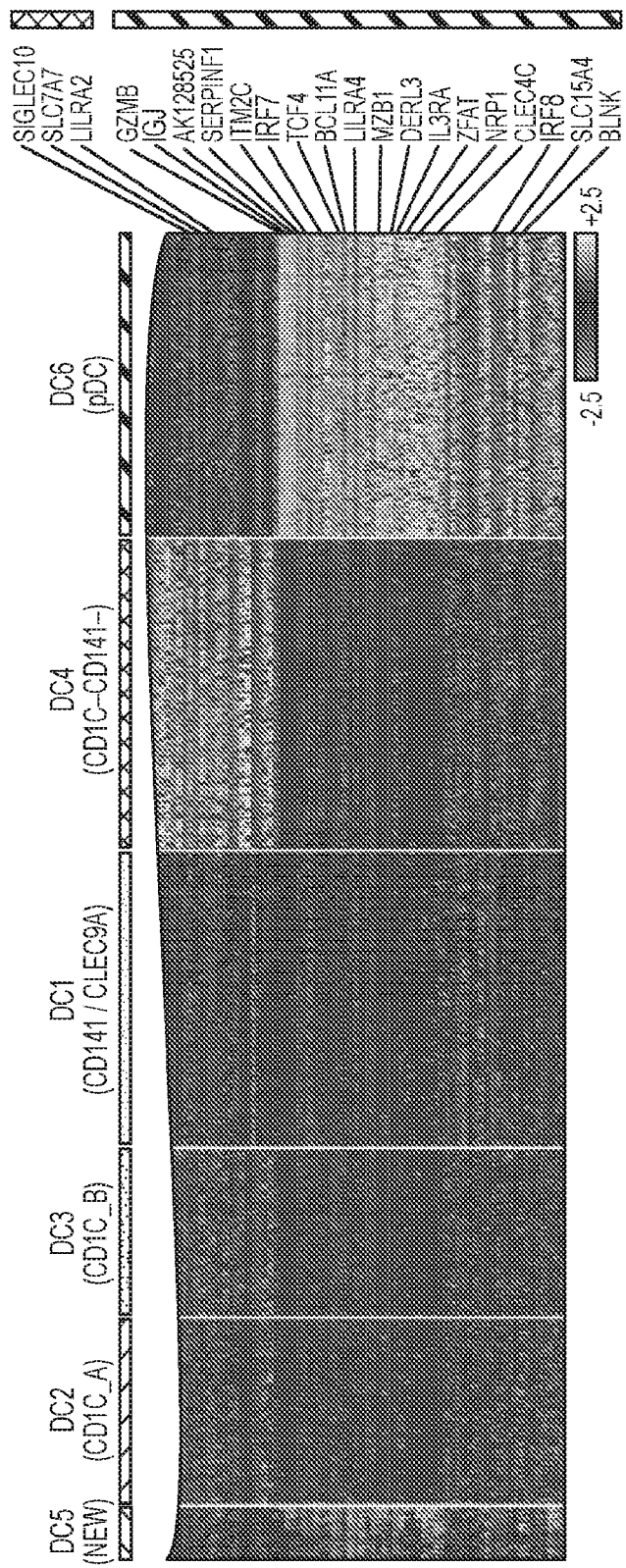
Figure 2E:
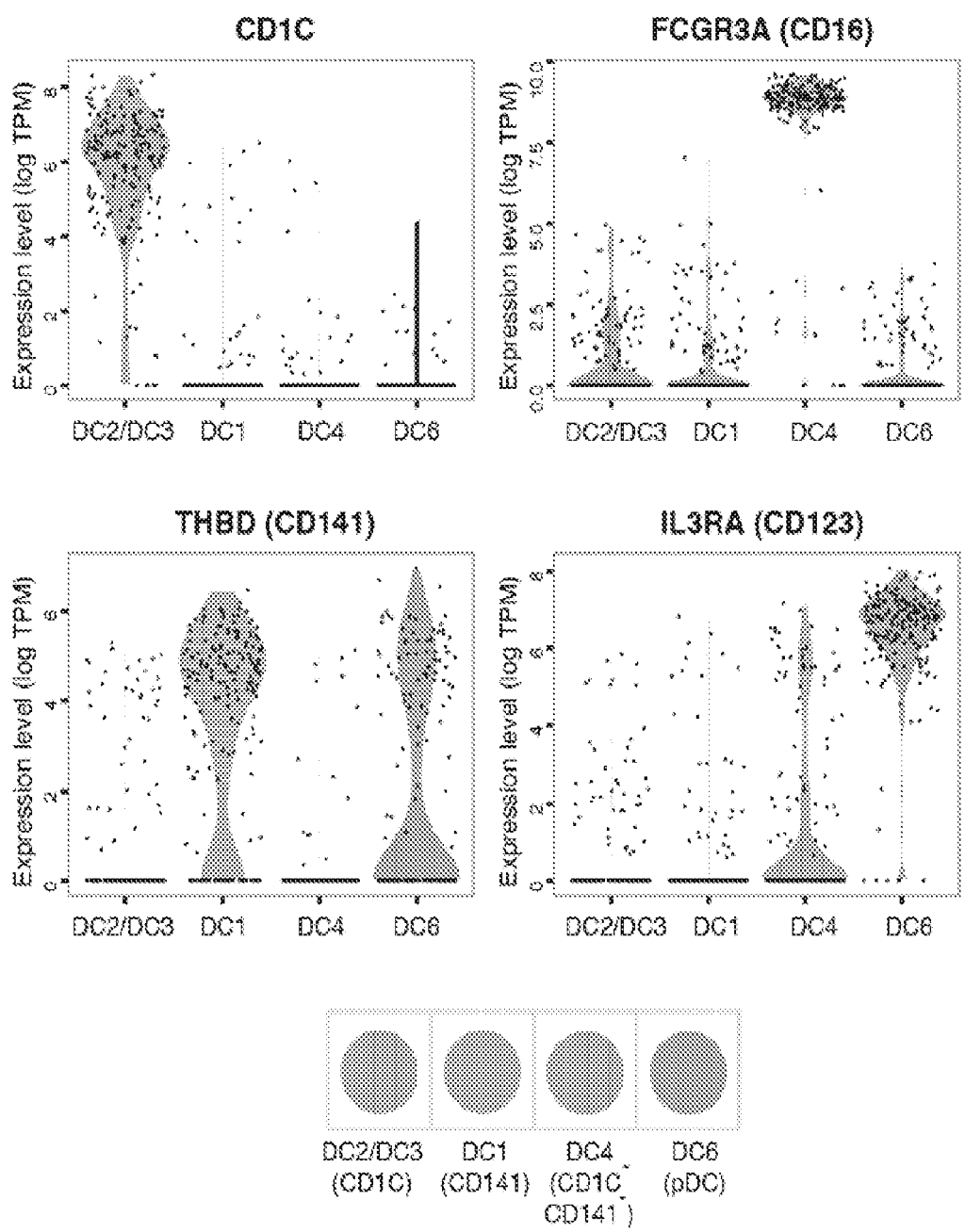
Figure 2G:
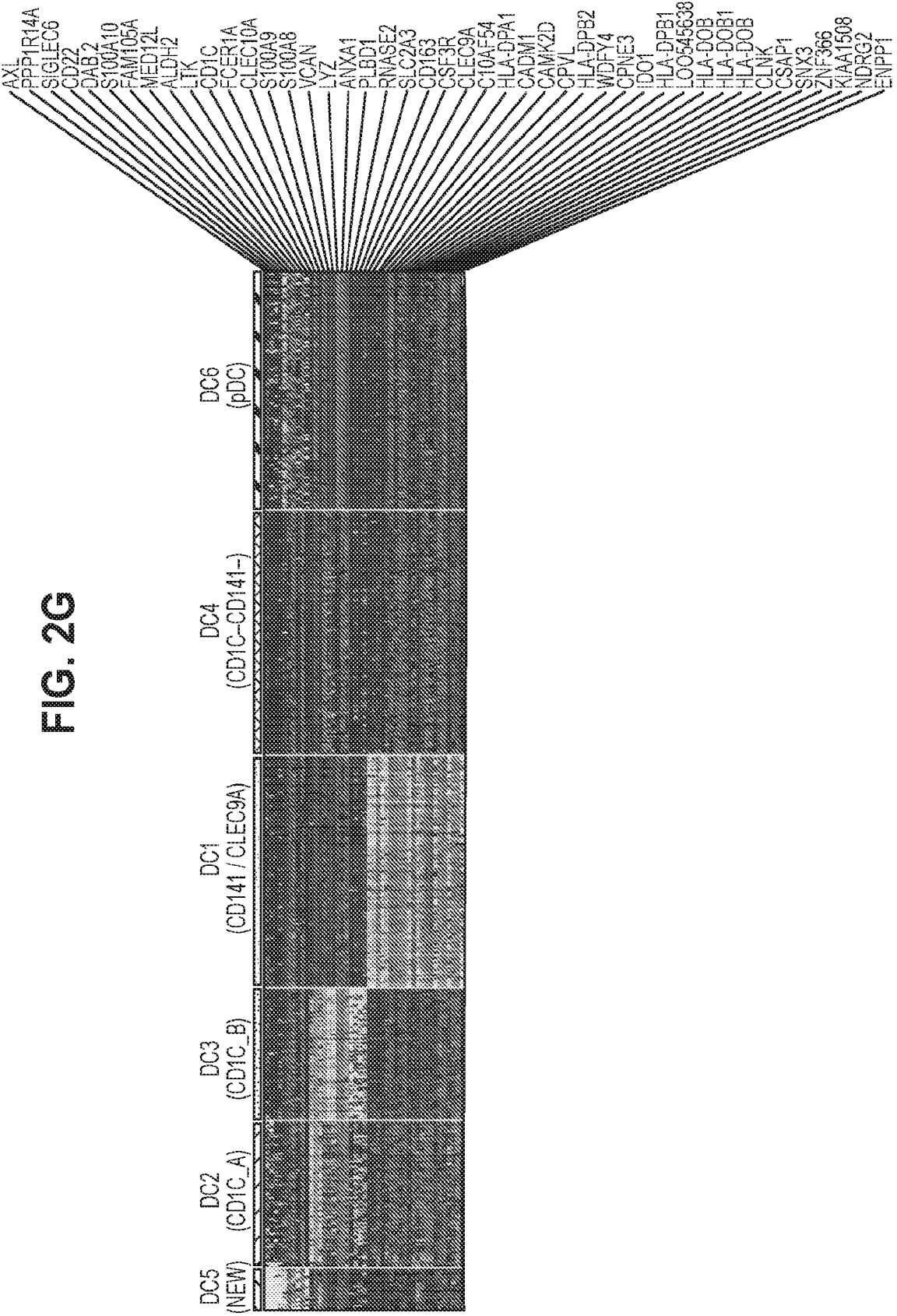
Figure 2G:
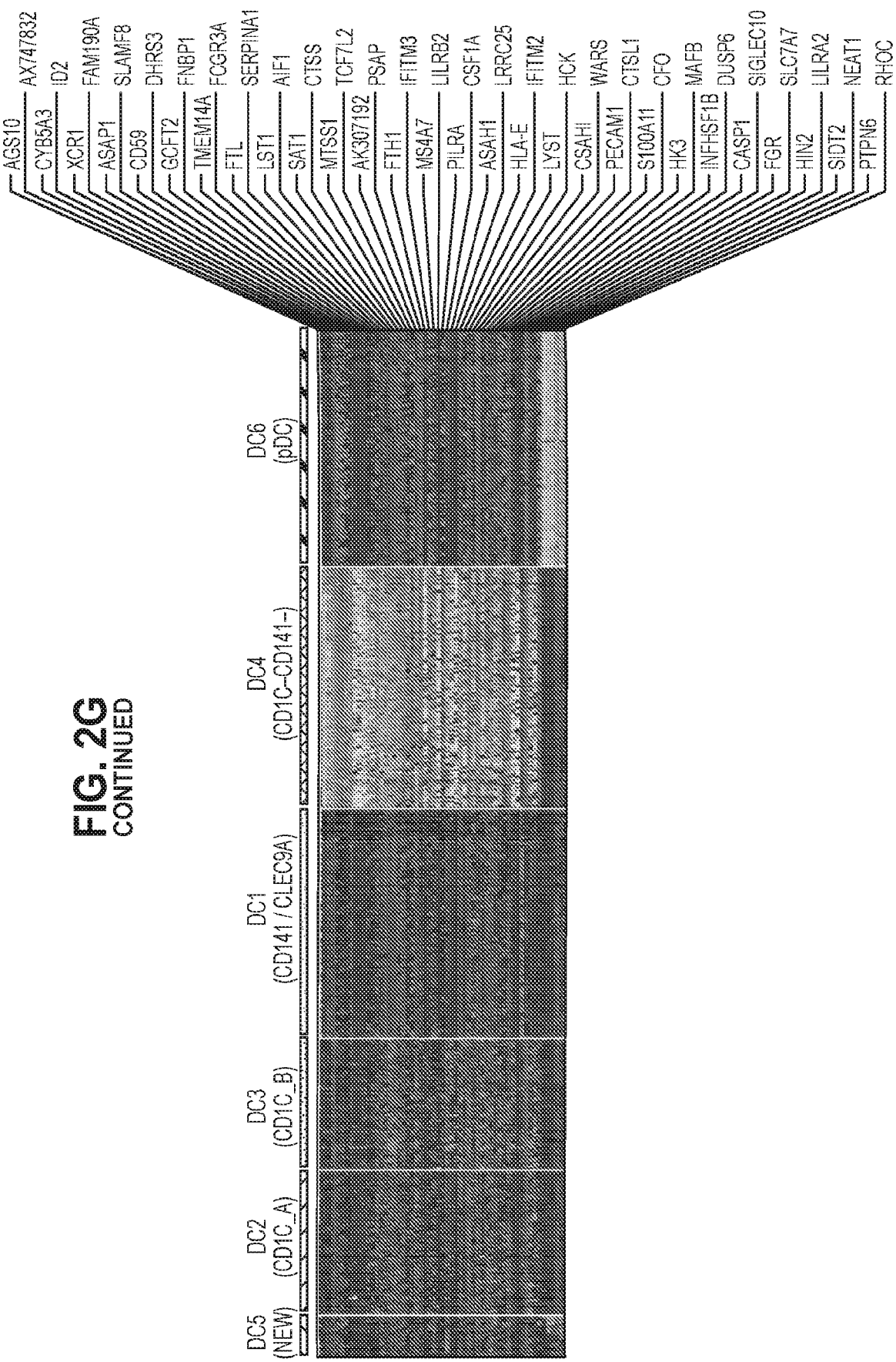
Figure 2G:
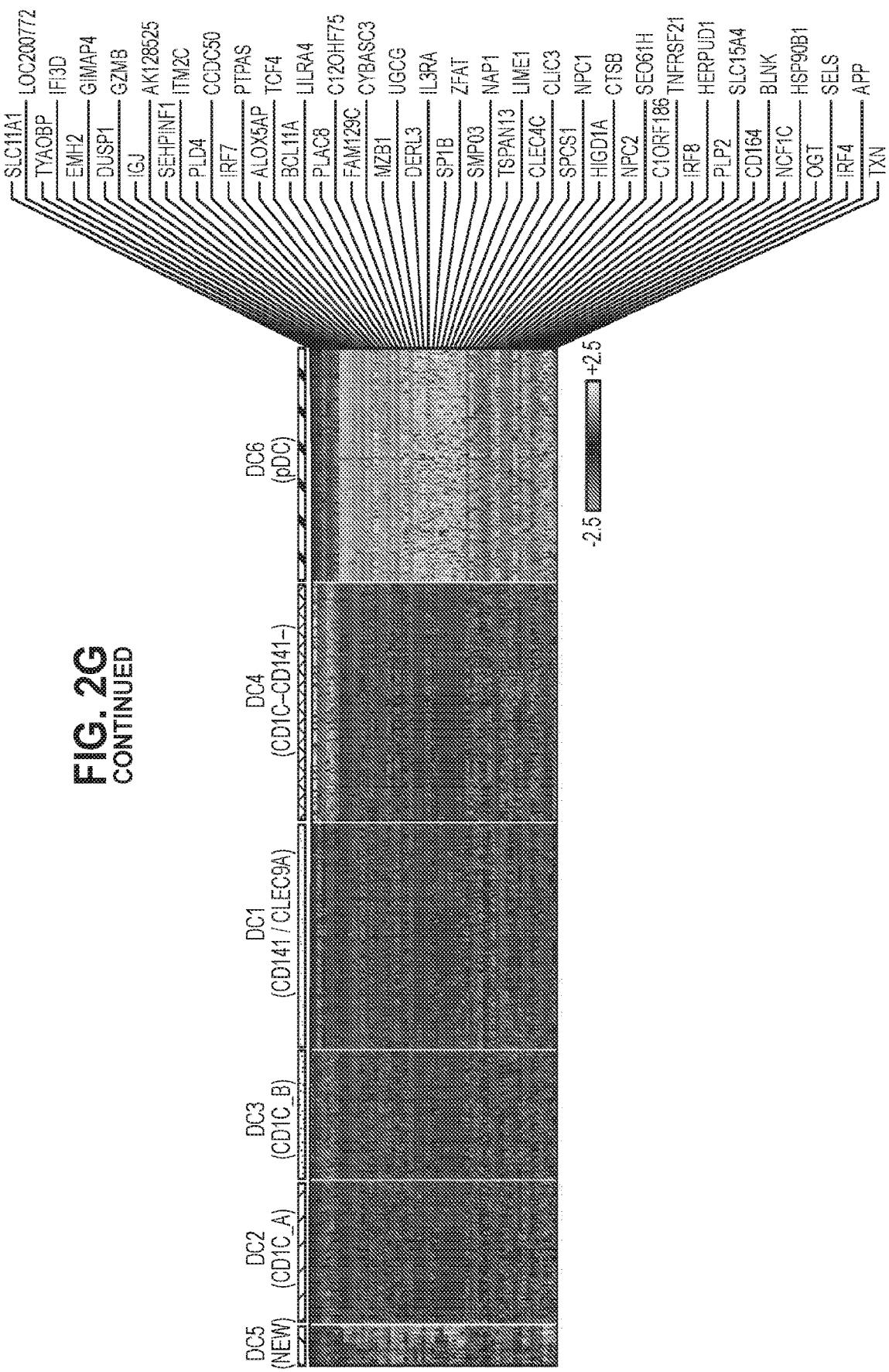
Figure 2H:
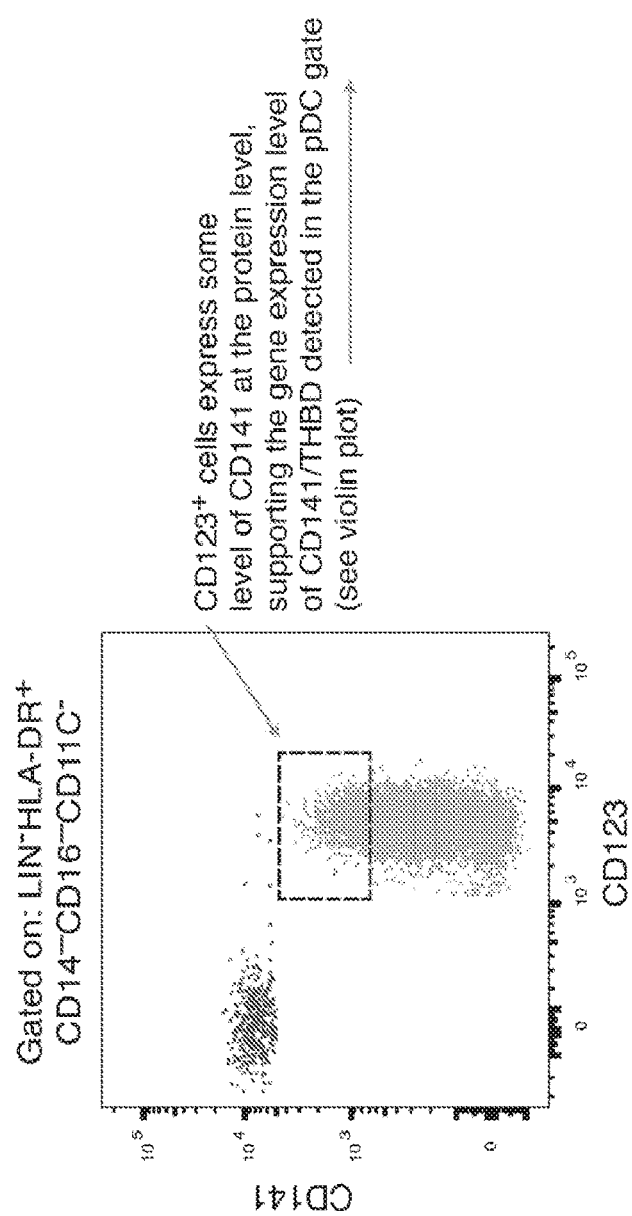
Figure 6A:
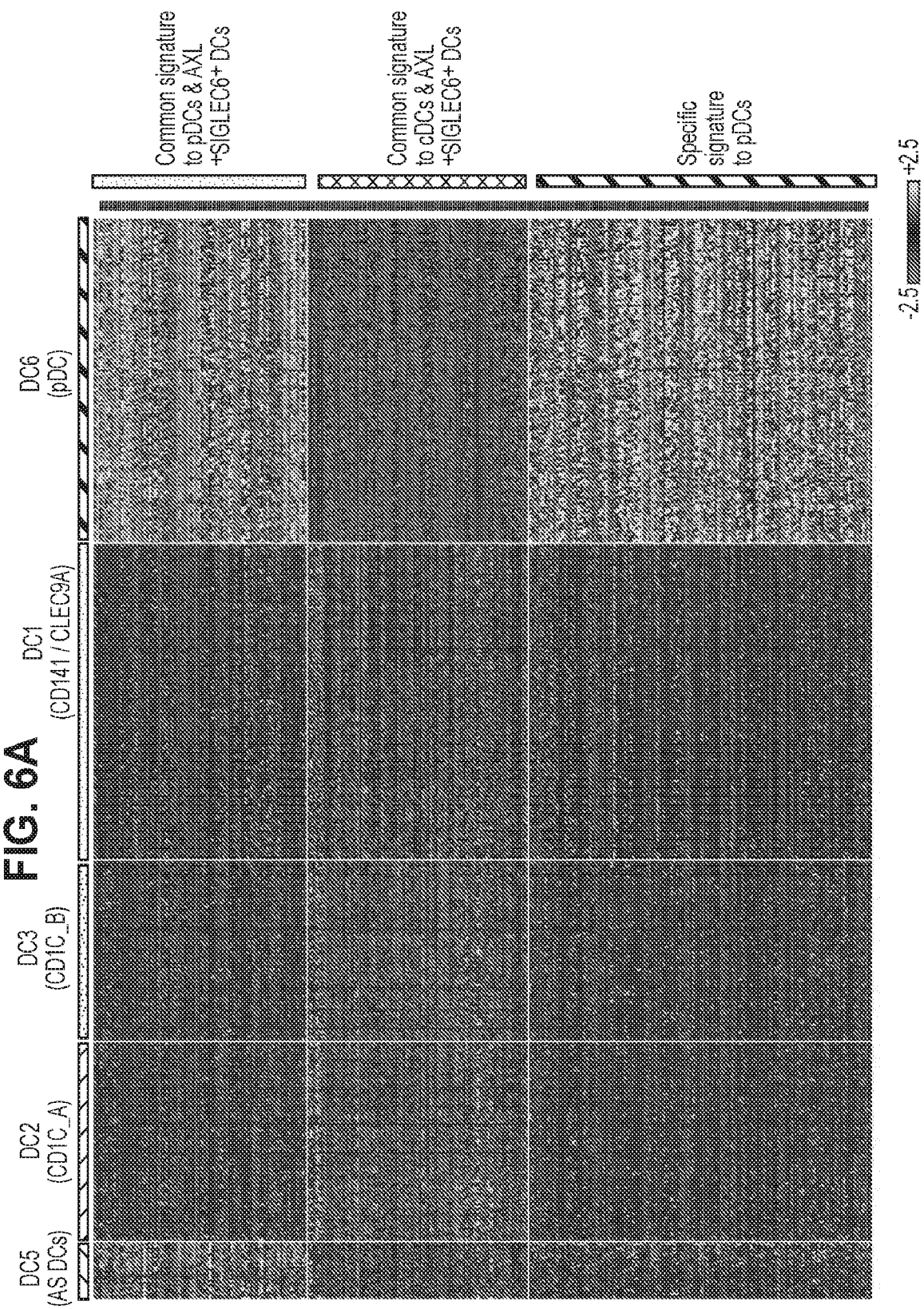
FIG. 6A-6D illustrates phenotypic characterization of novel AXL and SIGLEC6 expressing blood DCs. (A) Heatmap reporting scaled expression (log TPM values) of gene signatures common between AXL$^+$SIGLEC6$^+$ and pDC, common between AXL$^+$SIGLEC6$^+$ and conventional DCs (cDC), and those unique to pDCs. Gene sets were generated through K-means clustering using the doK means function in the Seurat package. Heatmap color scheme is based on z-score distribution, from −2.5 (yellow) to 2.5 (purple). Note that the ability of AXL$^+$SIGLEC6$^+$ cells to activate T cell proliferation (FIG. 7E) aligns with their expression of genes related to T cell proliferation induction that are commonly expressed in conventional DCs, but not pDC, such as IF130 (enzyme involved in MHC class II-restricted antigen processing), LAT2 (needed for FcR signaling), and CST3 (inhibits cathepsin S activity). (B-D) Relative expression of selected antigens (B); co-stimulatory and activation markers (C) and skin and lymph node homing markers (D) represented as overlay histograms comparing AXL$^+$SIGLEC6$^+$ CD123$^+$CD11C$^{-/lo}$ (pink), AXL$^+$SIGLEC6$^+$ CD123$^{lo}$CD11C$^+$ (blue), CD100$^+$CD34$^{int.}$ (beige) cells (refer to FIG. 9 for characterization of this population), CLEC9A$^+$ DCs (red), CD1C$^+$ (dark blue) and pDCs (green) and isotype control (grey). Representative data from at least three donors is shown.

An aspect of the invention relates to an isolated immune cell selected from the group consisting of:

a1) an immune cell characterised in that the immune cell comprises expression of HLA-DR, does not express CD3, CD56, CD19 and CD14, and comprises expression of CLEC9A;

a2) an immune cell which is HLA-DR positive, CD3 negative, CD56 negative, CD19 negative, CD14 negative, and CLEC9A positive;

a3) an immune cell characterised in that the immune cell comprises expression of HLA-DR, does not express CD3, CD56, CD19 and CD14, and comprises a gene or gene product signature, the signature comprising or consisting of one or more genes or gene products as set forth in Table E1 part a or in Table E2 part a or in FIG. 2C cluster 'DC1' or in FIG. 2D cluster 'DC1' or in FIG. 2G cluster 'DC1';

b1) an immune cell characterised in that the immune cell comprises expression of HLA-DR, does not express CD3, CD56, CD19 and CD14, and comprises expression of FCGR2B;

b2) an immune cell which is HLA-DR positive, CD3 negative, CD56 negative, CD19 negative and CD14 negative, and FCGR2B positive;

b3) an immune cell characterised in that the immune cell comprises expression of HLA-DR, does not express CD3, CD56, CD19 and CD14, and comprises a gene or gene product signature, the signature comprising or consisting of one or more genes or gene products as set forth in Table E1 part b or in Table E2 part b or in Table E3 part a or in FIG. 2C cluster 'DC2' or in FIG. 2D cluster 'DC2' or in FIG. 2G cluster 'DC2';

c1) an immune cell characterised in that the immune cell comprises expression of HLA-DR, does not express CD3, CD56 and CD19, and comprises expression of one or more genes or gene products selected from the group consisting of CD163, CD36, CD14, LYZ, S100A8, S100A9, and S100A12;

c2) an immune cell which is HLA-DR positive, CD3 negative, CD56 negative and CD19 negative, and positive for one or more genes or gene products selected from the group consisting of CD163, CD36, CD14, LYZ, S100A8, S100A9, and S100A12;

c3) an immune cell characterised in that the immune cell comprises expression of HLA-DR, does not express CD3, CD56 and CD19, and comprises a gene or gene product signature, the signature comprising or consisting of one or more genes or gene products as set forth in Table E1 part c or in Table E2 part c or in Table E3 part b or in FIG. 2C cluster 'DC3' or in FIG. 2D cluster 'DC3' or in FIG. 2G cluster 'DC3';

d1) an immune cell characterised in that the immune cell comprises expression of HLA-DR, does not express CD3, CD56, CD19 and CD14, and comprises expression of FCGR3A;

d2) an immune cell which is HLA-DR positive, CD3 negative, CD56 negative, CD19 negative and CD14 negative, and FCGR3A positive;

d3) an immune cell characterised in that the immune cell comprises expression of HLA-DR, does not express CD3, CD56, CD19 and CD14, and comprises a gene or gene product signature, the signature comprising or consisting of one or more genes or gene products as set forth in Table E1 part d or in Table E2 part d or in FIG. 2C cluster 'DC4' or in FIG. 2D cluster 'DC4' or in FIG. 2G cluster 'DC4';

e1) an immune cell characterised in that the immune cell comprises expression of HLA-DR, does not express CD3, CD56, CD19 and CD14, and comprises expression of one or more genes or gene products selected from the group consisting of AXL, SIGLEC6, SIGLEC1, PPP1R14A, CD22, CD5, and GPR146;

e2) an immune cell which is HLA-DR positive, CD3 negative, CD56 negative, CD19 negative and CD14 negative, and positive for one or more genes or gene products selected from the group consisting of AXL, SIGLEC6, SIGLEC1, PPP1R14A, CD22, CD5, and GPR146;

e3) an immune cell characterised in that the immune cell comprises expression of HLA-DR, does not express CD3, CD56, CD19 and CD14, and comprises a gene or gene product signature, the signature comprising or consisting of one or more genes or gene products as set forth in Table E1 part e or in Table E2 part e or in FIG. 2C cluster 'DC5' or in FIG. 2D cluster 'DC5' or in FIG. 2G cluster 'DC5';

f1) an immune cell characterised in that the immune cell comprises expression of HLA-DR, does not express CD3, CD56, CD19 and CD14, and comprises expression of one or more genes or gene products selected from the group consisting of GZMB, SELPLG, DERL3, PTPRCAP, BCL11A, LAMP5, SLA2, SELS, NRP1, SIDT1, TCF4, SLC15A4, PTCRA, IRF7, and TRAF4;

f2) an immune cell which is HLA-DR positive, CD3 negative, CD56 negative, CD19 negative and CD14 negative, and positive for one or more genes or gene products selected from the group consisting of GZMB, SELPLG, DERL3, PTPRCAP, BCL11A, LAMP5, SLA2, SELS, NRP1, SIDT1, TCF4, SLC15A4, PTCRA, IRF7, and TRAF4;

f3) an immune cell characterised in that the immune cell comprises expression of HLA-DR, does not express CD3, CD56, CD19 and CD14, and comprises a gene or gene product signature, the signature comprising or consisting of one or more genes or gene products as set forth in Table E1 part f or in Table E2 part f or in FIG. 2C cluster 'DC6' or in FIG. 2D cluster 'DC6' or in FIG. 2G cluster 'DC6' or in FIG. 6A cluster 'DC6';

g1) an immune cell characterised in that the immune cell comprises expression of HLA-DR, does not express CD3, CD56, CD19 and CD14, does not express CD11C, CD123 and CD39, and comprises expression of CD45RA, high expression of CD100, and intermediate expression of CD34;

g2) an immune cell which is HLA-DR positive, CD3 negative, CD56 negative, CD19 negative, CD14 negative, CD11C negative, CD123 negative, CD39 negative, CD45RA positive, CD100 high, CD34 intermediate;

g3) an immune cell characterised in that the immune cell comprises expression of HLA-DR, does not express CD3, CD56, CD19 and CD14, does not express CD11C, CD123 and CD39, and comprises expression of one or more genes or gene products selected from the group consisting of RUNX2, TNFRSF18, ID2, ACY3, RORC, SEMA4D, SATB1, KIT, AHR, HLX, and CCR7;

g4) an immune cell which is HLA-DR positive, CD3 negative, CD56 negative, CD19 negative, CD14 negative, CD11C negative, CD123 negative, CD39 negative, and positive for one or more genes or gene products selected from the group consisting of RUNX2, TNFRSF18, ID2, ACY3, RORC, SEMA4D, SATB1, KIT, AHR, HLX, and CCR7;

g5) an immune cell characterised in that the immune cell comprises expression of HLA-DR, does not express CD3, CD56, CD19 and CD14, does not express CD11C, CD123 an CD39, and is capable of differentiation to: the immune cell as defined in any one of a1), a2), or a3), the immune cell as defined in any one of b1), b2), or b3), and the immune cell as defined in any one of c1), c2), or c3);

g6) an immune cell which is HLA-DR positive, CD3 negative, CD56 negative, CD19 negative, CD14 negative, CD11C negative, CD123 negative, CD39 negative, and is capable of differentiation to: the immune cell as defined in any one of a1), a2), or a3), the immune cell as defined in any one of b1), b2), or b3), and the immune cell as defined in any one of c1), c2), or c3); or h1) an immune cell characterised in that the immune cell comprises expression of HLA-DR, CD45 and CD123, and comprises a gene or gene product signature, the signature comprising or consisting of one or more genes or gene products as set forth in Table E8 or in FIG. 8B clusters BPDCN_1 to 4.

In certain embodiments, the isolated immune cell is a dendritic cell or a progenitor or precursor of a dendritic cell. Preferably, the immune cell as defined in any one of a1) to a3), b1) to b3), c1) to c3), d1) to d3), f1) to f3), or h1) is a dendritic cell; or the immune cell as defined in any one of e1)-e3), or g1)-g6) is a progenitor or precursor of a dendritic cell.

In certain embodiments:
the immune cell as defined in any one of b1), b2), or b3) comprises expression of CD1C, or CD11C, or CD1C and CD11C;

the immune cell as defined in any one of b1), b2), or b3) is CD1C positive, or CD11C positive, or CD1C positive and CD11C positive;

the immune cell as defined in any one of c1), c2), or c3) comprises expression of CD1C, or CD11C, or CD1C and CD11C;

the immune cell as defined in any one of c1), c2), or c3) is CD1C positive, or CD11C positive, or CD1C positive and CD11C positive;

the immune cell as defined in c1) comprises expression of two or more, three or more, four or more, five or more, six or more, or all genes or gene products selected from the group consisting of CD163, CD36, CD14, LYZ, S100A8, S100A9, and S100A12;

the immune cell as defined in c1) comprises expression of CD163 and CD36;

the immune cell as defined in c2) is positive for two or more, three or more, four or more, five or more, six or more, or all genes or gene products selected from the group consisting of CD163, CD36, CD14, LYZ, S100A8, S100A9, and S100A12;

the immune cell as defined in c2) is CD163 positive and CD36 positive;

the immune cell as defined in any one of d1), d2), or d3) does not express CD1C, or CD141, or CD1C and CD141;

the immune cell as defined in any one of d1), d2), or d3) is CD1C negative, or CD141 negative, or CD1C negative and CD141 negative;

the immune cell as defined in e1) comprises expression of two or more, three or more, four or more, five or more, six or more, or all genes or gene products selected from the group consisting of AXL, SIGLEC6, SIGLEC1, PPP1R14A, CD22, CD5, and GPR146;

the immune cell as defined in e1) comprises expression of AXL and SIGLEC6;

the immune cell as defined in e2) is positive for two or more, three or more, four or more, five or more, six or more, or all genes or gene products selected from the group consisting of AXL, SIGLEC6, SIGLEC1, PPP1R14A, CD22, CD5, and GPR146;

the immune cell as defined in e2) is AXL positive and SIGLEC6 positive;

the immune cell as defined in any one of e1), e2), or e3) does not express CD141, or CD16, or CD141 and CD16;

the immune cell as defined in any one of e1), e2), or e3) is CD141 negative, or CD16 negative, or CD141 negative and CD16 negative;

the immune cell as defined in any one of e1), e2), or e3) comprises expression of CD123 and does not express or expresses low CD11C;

the immune cell as defined in any one of e1), e2), or e3) is CD123 positive and CD11C low or negative (CD123$^+$CD11C$^{lo}$);

the immune cell as defined in any one of e1), e2), or e3) comprises a gene or gene product signature, the signature comprising or consisting of one or more genes or gene products selected from the group consisting of PROC, IRF8, FMNL3, APP, SERPINF1, C1ORF186, CYBASC3, PLAC8, NRP1, CCDC50, TSPAN13, UGCG, LILRA4, MZB1, PTPRS, AK128525, IGJ, and IL3RA;

the immune cell as defined in any one of e1), e2), or e3) does not express ITGAX;

the immune cell as defined in any one of e1), e2), or e3) expresses low CD123 and comprises expression of CD11C;

the immune cell as defined in any one of e1), e2), or e3) is CD123 low and CD11C positive (CD123$^{lo}$CD11C$^+$);

the immune cell as defined in any one of e1), e2), or e3) comprises a gene or gene product signature, the signature comprising or consisting of one or more genes or gene products selected from the group consisting of ITGAX, IFI30, LGALS2, FGR, LY86, GLIPR2, TIMP1, LST1, AGPAT9, IFITM3, DUSP23, ENTPD1, LOC645638, and IL1RN;

the immune cell as defined in any one of e1), e2), or e3) comprises expression of ITGAX;

the immune cell as defined in f1) comprises expression of two or more, three or more, four or more, five or more, six or more, seven or more, eight or more, nine or more, ten or more, eleven or more, twelve or more, thirteen or more, fourteen or more, or all genes or gene products selected from the group consisting of GZMB, SELPLG, DERL3, PTPRCAP, BCL11A, LAMP5, SLA2, SELS, NRP1, SIDT1, TCF4, SLC15A4, PTCRA, IRF7, and TRAF4;

the immune cell as defined in f2) is positive for two or more, three or more, four or more, five or more, six or more, seven or more, eight or more, nine or more, ten or more, eleven or more, twelve or more, thirteen or more, fourteen or more, or all genes or gene products selected from the group consisting of GZMB, SELPLG, DERL3, PTPRCAP, BCL11A, LAMP5, SLA2, SELS, NRP1, SIDT1, TCF4, SLC15A4, PTCRA, IRF7, and TRAF4;

the immune cell as defined in any one of f1), f2), or f3) comprises expression of CD123, or does not express CD11C, or comprises expression of CD123 and does not express CD11C;

the immune cell as defined in any one of f1), f2), or f3) is CD123 positive, or CD11C negative, or CD123 positive and CD11C negative;

the immune cell as defined in any one of f1), f2), or f3) comprises expression of CD123, and does not express CD11C, CD141, AXL and SIGLE6;

the immune cell as defined in any one of f1), f2), or f3) is CD123 positive, CD11C negative, CD141 negative, AXL negative and SIGLE6 negative;

the immune cell as defined in g3) comprises expression of two or more, three or more, four or more, five or more, six or more, seven or more, eight or more, nine or more, ten or more, or all genes or gene products selected from the group consisting of RUNX2, TNFRSF18, ID2, ACY3, RORC, SEMA4D, SATB1, KIT, AHR, HLX, and CCR7; or the immune cell as defined in g4) is positive for two or more, three or more, four or more, five or more, six or more, seven or more, eight or more, nine or more, ten or more, or all genes or gene products selected from the group consisting of RUNX2, TNFRSF18, ID2, ACY3, RORC, SEMA4D, SATB1, KIT, AHR, HLX, and CCR7.

In certain embodiments:

the one or more genes or gene products comprised by or constituting the signature as defined in a3) are selected from the group consisting of genes or gene products as set forth in Table E2 part a which display AUC value of 0.70 or more, preferably 0.80 or more, more preferably 0.85 or more, even more preferably 0.90 or more, and still more preferably 0.95 or more;

the one or more genes or gene products comprised by or constituting the signature as defined in b3) are selected from the group consisting of genes or gene products as set forth in Table E2 part b which display AUC value of 0.70 or more, preferably 0.80 or more, more preferably 0.85 or more, even more preferably 0.90 or more, and still more preferably 0.95 or more;

the one or more genes or gene products comprised by or constituting the signature as defined in b3) are selected from the group consisting of genes or gene products as set forth in Table E3 part a which display AUC value of 0.70 or more, preferably 0.80 or more, more preferably 0.85 or more, even more preferably 0.90 or more, and still more preferably 0.95 or more;

the one or more genes or gene products comprised by or constituting the signature as defined in c3) are selected from the group consisting of genes or gene products as set forth in Table E2 part c which display AUC value of 0.70 or more, preferably 0.80 or more, more preferably 0.85 or more, even more preferably 0.90 or more, and still more preferably 0.95 or more;

the one or more genes or gene products comprised by or constituting the signature as defined in c3) are selected from the group consisting of genes or gene products as set forth in Table E3 part b which display AUC value of 0.30 or less, preferably 0.20 or less, more preferably 0.15 or less, even more preferably 0.10 or less, and still more preferably 0.05 or less;

the one or more genes or gene products comprised by or constituting the signature as defined in d3) are selected from the group consisting of genes or gene products as set forth in Table E2 part d which display AUC value of 0.70 or more, preferably 0.80 or more, more preferably 0.85 or more, even more preferably 0.90 or more, and still more preferably 0.95 or more;

the one or more genes or gene products comprised by or constituting the signature as defined in e3) are selected from the group consisting of genes or gene products as set forth in Table E2 part e which display AUC value of 0.70 or more, preferably 0.80 or more, more preferably 0.85 or more, even more preferably 0.90 or more, and still more preferably 0.95 or more;

the one or more genes or gene products comprised by or constituting the signature as defined in f3) are selected from the group consisting of genes or gene products as set forth in Table E2 part f which display AUC value of 0.70 or more, preferably 0.80 or more, more preferably 0.85 or more, even more preferably 0.90 or more, and still more preferably 0.95 or more; or the one or more genes or gene products comprised by or constituting the signature as defined in h1) are selected from the group consisting of genes or gene products as set forth in Table E8 which display AUC value of 0.80 or more, preferably 0.85 or more, more preferably 0.90 or more, and even more preferably 0.95 or more.

In certain embodiments:

the signature as defined in a3) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E2 part a; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E2 part a, which display AUC value of 0.70 or more, preferably 0.80 or more, more preferably 0.85 or more, even more preferably 0.90 or more, and still more preferably 0.95 or more;

the signature as defined in b3) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E2 part b; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E2 part b, which display AUC value of 0.70 or more, preferably 0.80 or more, more preferably 0.85 or more, even more preferably 0.90 or more, and still more preferably 0.95 or more;

the signature as defined in b3) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E3 part a; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E3 part a, which display AUC value of 0.70 or more, preferably 0.80 or more, more preferably 0.85 or more, even more preferably 0.90 or more, and still more preferably 0.95 or more;

the signature as defined in c3) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E2 part c; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E2 part c, which display AUC value of 0.70 or more, preferably 0.80 or more, more preferably 0.85 or more, even more preferably 0.90 or more, and still more preferably 0.95 or more;

the signature as defined in c3) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E3 part b; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E3 part b, which display AUC value of 0.30 or less, preferably 0.20 or less, more preferably 0.15 or less, even more preferably 0.10 or less, and still more preferably 0.05 or less;

the signature as defined in d3) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E2 part d; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E2 part d, which display AUC value of 0.70 or more, preferably 0.80 or more, more preferably 0.85 or more, even more preferably 0.90 or more, and still more preferably 0.95 or more;

the signature as defined in e3) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E2 part e; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E2 part e, which display AUC value of 0.70 or more, preferably 0.80 or more, more preferably 0.85 or more, even more preferably 0.90 or more, and still more preferably 0.95 or more;

the signature as defined in f3) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E2 part f; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E2 part f, which display AUC value of 0.70 or more, preferably 0.80 or more, more preferably 0.85 or more, even more preferably 0.90 or more, and still more preferably 0.95 or more; or the signature as defined in h1) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E8; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E8, which display AUC value of 0.70 or more, preferably 0.80 or more, more preferably 0.85 or more, even more preferably 0.90 or more, and still more preferably 0.95 or more.

Figure 4A:
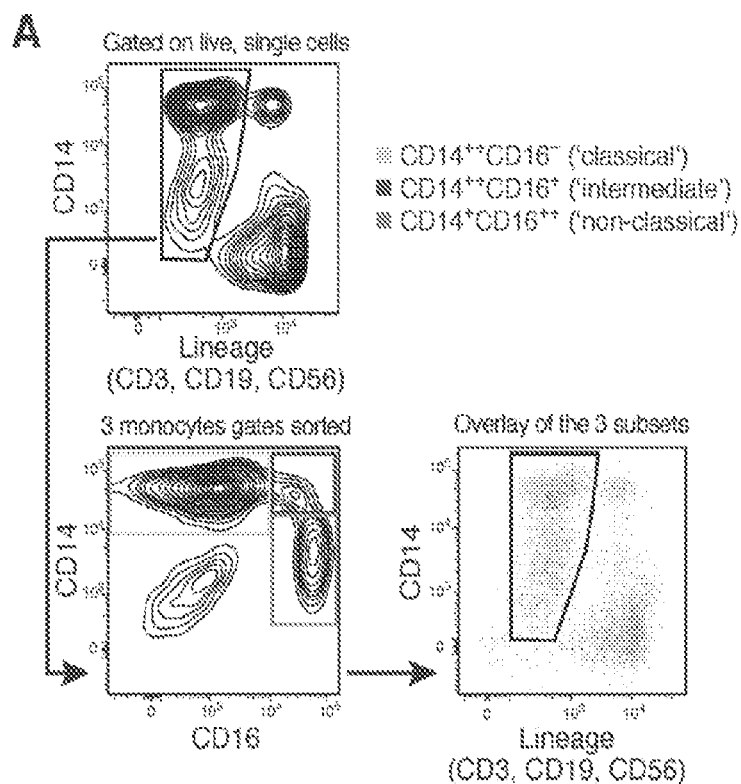
Figure 4B:
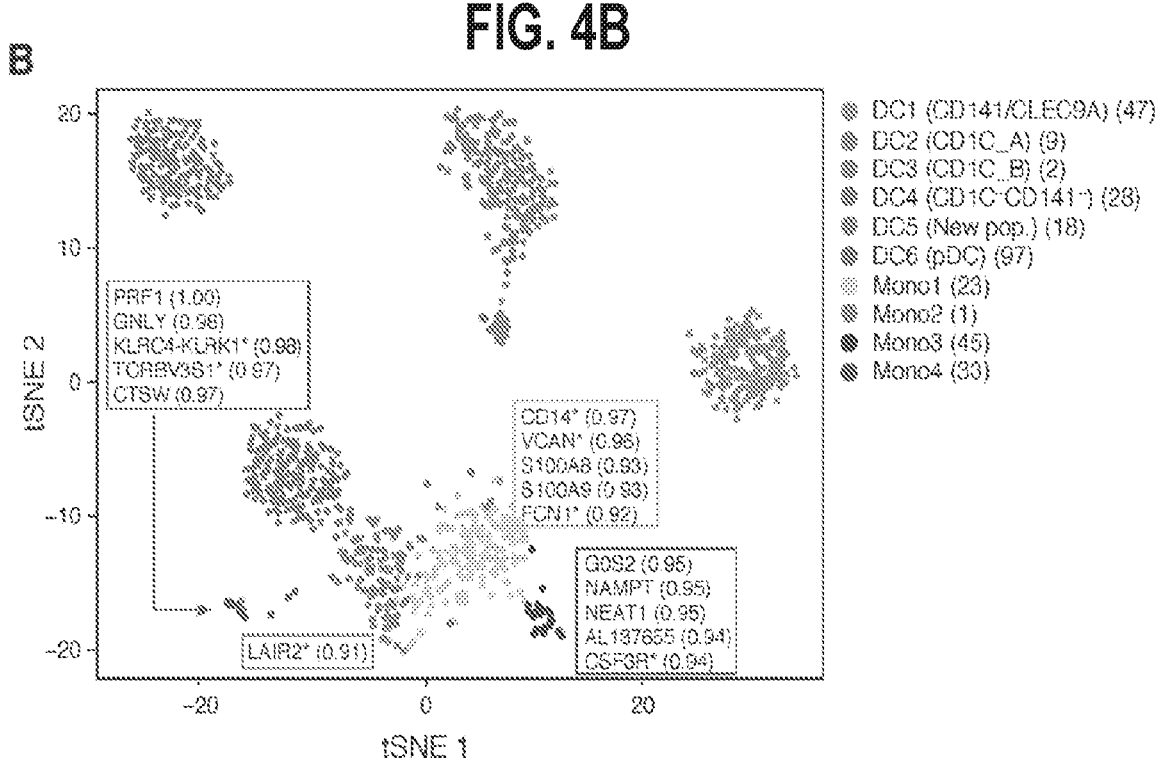
Figure 4C:
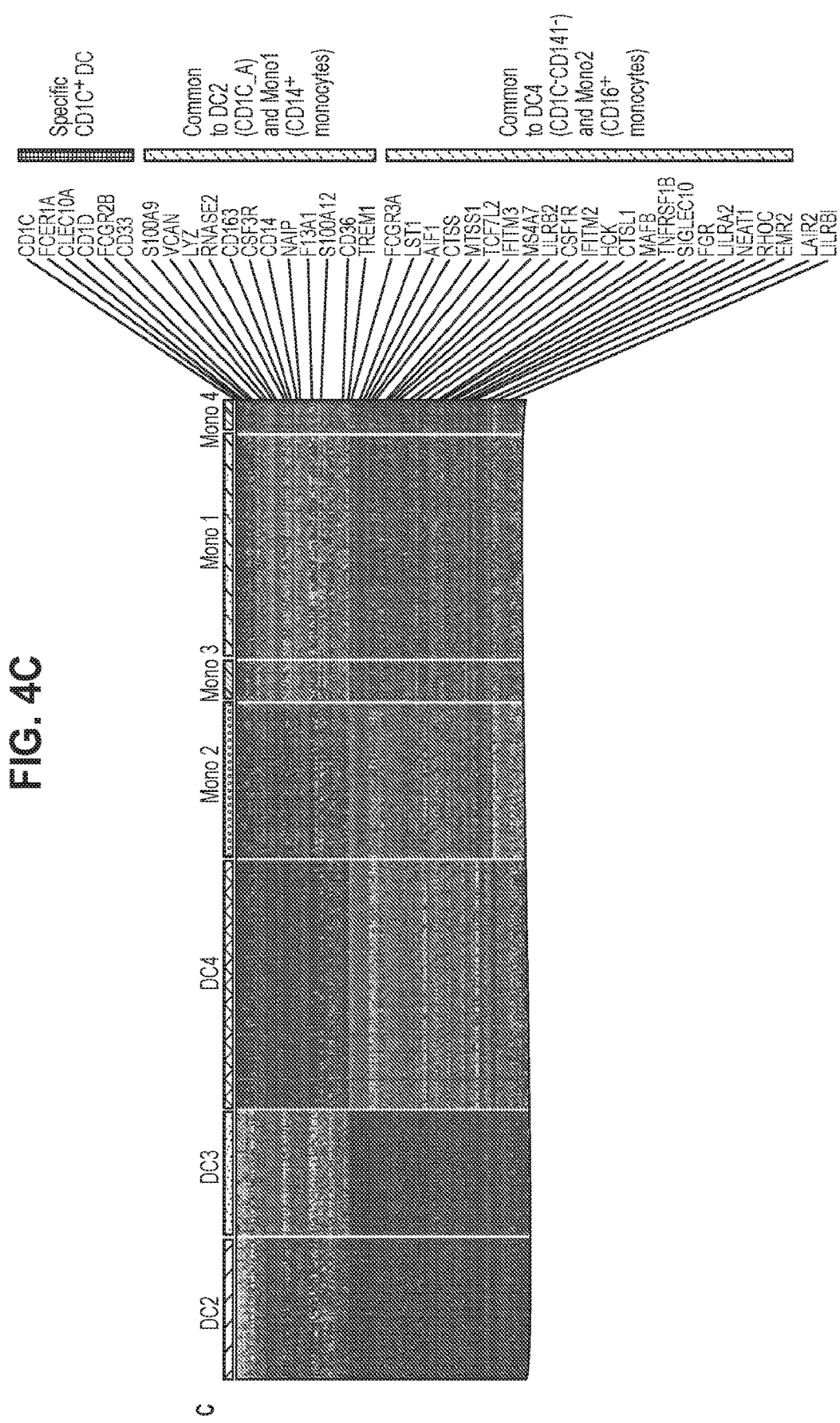
Figure 4C:
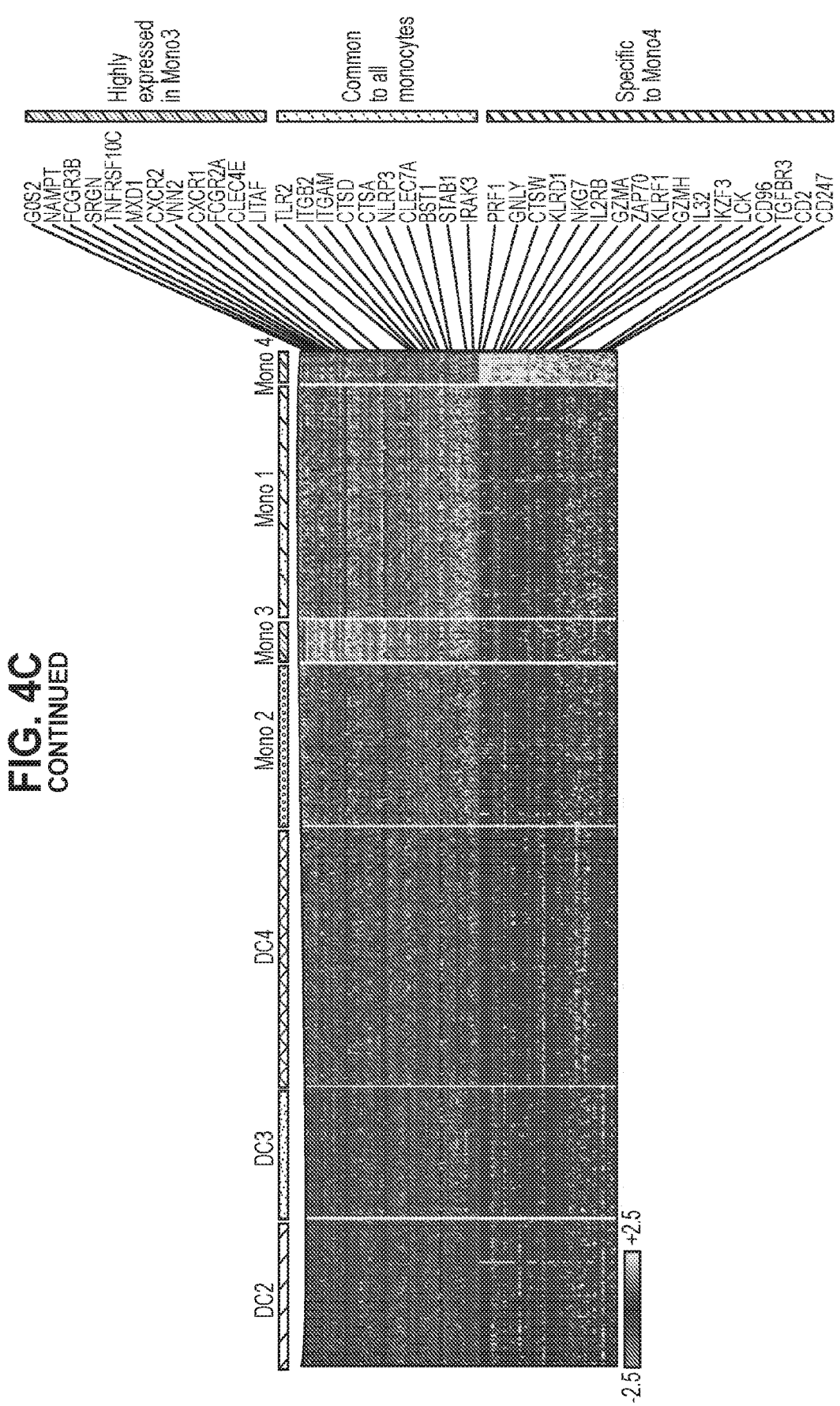
Figure 4E:
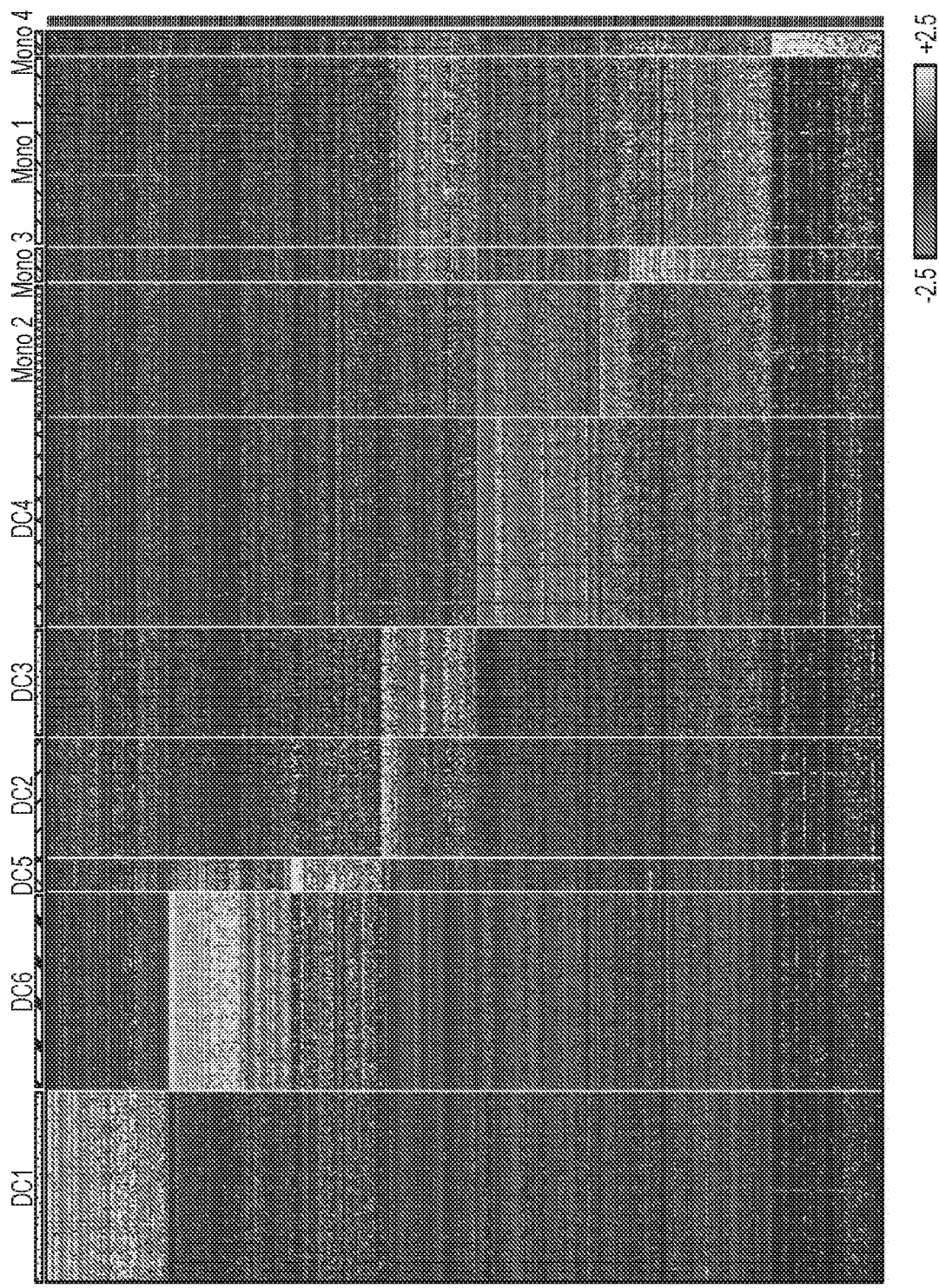

A further aspect of the invention relates to an isolated immune cell selected from the group consisting of:

x) an immune cell characterised in that the immune cell does not express CD3, CD56, CD19, comprises expression of CD14, and comprises a gene or gene product signature, the signature comprising or consisting of one or more genes or gene products as set forth in Table E4 part a or in FIG. 4B cluster 'Mono1' or in FIG. 4D cluster 'Mono1' or in FIG. 4E cluster 'Mono1';

y) an immune cell characterised in that the immune cell does not express CD3, CD56, CD19, comprises expression of CD14, and comprises a gene or gene product signature, the signature comprising or consisting of one or more genes or gene products as set forth in Table E4 part b or in FIG. 4B cluster 'Mono2' or in FIG. 4D cluster 'Mono2' or in FIG. 4E cluster 'Mono2';

w) an immune cell characterised in that the immune cell does not express CD3, CD56, CD19, comprises expression of CD14, and comprises a gene or gene product signature, the signature comprising or consisting of one or more genes or gene products as set forth in Table E4 part c or in FIG. 4B cluster 'Mono3' or in FIG. 4D cluster 'Mono3' or in FIG. 4E cluster 'Mono3';

z) an immune cell characterised in that the immune cell does not express CD3, CD56, CD19, comprises expression of CD14, and comprises a gene or gene product signature, the signature comprising or consisting of one or more genes or gene products as set forth in Table E4 part d or in FIG. 4B cluster 'Mono4' or in FIG. 4D cluster 'Mono4' or in FIG. 4E cluster 'Mono4'.

In certain embodiments, the immune cell is a monocyte or a progenitor or precursor of a monocyte.

In certain embodiments:

the one or more genes or gene products comprised by or constituting the signature as defined in x) are selected from the group consisting of genes or gene products as set forth in Table E4 part a which display AUC value of 0.70 or more, preferably 0.80 or more, more preferably 0.85 or more, even more preferably 0.90 or more, and still more preferably 0.95 or more;

the one or more genes or gene products comprised by or constituting the signature as defined in y) are selected from the group consisting of genes or gene products as set forth in Table E4 part b which display AUC value of 0.70 or more, preferably 0.80 or more, more preferably 0.85 or more, even more preferably 0.90 or more, and still more preferably 0.95 or more;

the one or more genes or gene products comprised by or constituting the signature as defined in w) are selected from the group consisting of genes or gene products as set forth in Table E4 part c which display AUC value of 0.70 or more, preferably 0.80 or more, more preferably 0.85 or more, even more preferably 0.90 or more, and still more preferably 0.95 or more; or the one or more genes or gene products comprised by or constituting the signature as defined in z) are selected from the group consisting of genes or gene products as set forth in Table E4 part d which display AUC value of 0.70 or more, preferably 0.80 or more, more preferably 0.85 or more, even more preferably 0.90 or more, and still more preferably 0.95 or more.

In certain embodiments:

the signature as defined in x) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E4 part a; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E4 part a, which display AUC value of 0.70 or more, preferably 0.80 or more, more preferably 0.85 or more, even more preferably 0.90 or more, and still more preferably 0.95 or more;

the signature as defined in y) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E4 part b; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E4 part b, which display AUC value of 0.70 or more, preferably 0.80 or more, more preferably 0.85 or more, even more preferably 0.90 or more, and still more preferably 0.95 or more;

the signature as defined in w) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E4 part c; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E4 part c, which display AUC value of 0.70 or more, preferably 0.80 or more, more preferably 0.85 or more, even more preferably 0.90 or more, and still more preferably 0.95 or more; or the signature as defined in z) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E4 part d; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E4 part d, which display AUC value of 0.70 or more, preferably 0.80 or more, more preferably 0.85 or more, even more preferably 0.90 or more, and still more preferably 0.95 or more.

The term "isolated" as used throughout this specification with reference to a particular component generally denotes that such component exists in separation from—for example, has been separated from or prepared and/or maintained in separation from—one or more other components of its natural environment. More particularly, the term "isolated" as used herein in relation to a cell or cell population denotes that such cell or cell population does not form part of an animal or human body.

The term "immune cell" as used throughout this specification generally encompasses any cell derived from a hematopoietic stem cell that plays a role in the immune response. The term is intended to encompass immune cells both of the innate or adaptive immune system. The immune cell as referred to herein may be a leukocyte, at any stage of differentiation (e.g., a stem cell, a progenitor cell, a mature cell) or any activation stage. Immune cells include lymphocytes (such as natural killer cells, T-cells (including, e.g., thymocytes, Th or Tc; Th1, Th2, Th17, Thαβ, CD4+, CD8+, effector Th, memory Th, regulatory Th, CD4+/CD8+ thymocytes, CD4-/CD8-thymocytes, γδ T cells, etc.) or B-cells (including, e.g., pro-B cells, early pro-B cells, late pro-B cells, pre-B cells, large pre-B cells, small pre-B cells, immature or mature B-cells, producing antibodies of any isotype, T1 B-cells, T2, B-cells, naïve B-cells, GC B-cells, plasmablasts, memory B-cells, plasma cells, follicular B-cells, marginal zone B-cells, B-1 cells, B-2 cells, regulatory B cells, etc.), such as for instance, monocytes (including, e.g., classical, non-classical, or intermediate monocytes), (segmented or banded) neutrophils, eosinophils, basophils, mast cells, histiocytes, microglia, including various subtypes, maturation, differentiation, or activation stages, such as for instance hematopoietic stem cells, myeloid progenitors, lymphoid progenitors, myeloblasts, promyelocytes, myelocytes, metamyelocytes, monoblasts, promonocytes, lymphoblasts, prolymphocytes, small lymphocytes, macrophages (including, e.g., Kupffer cells, stellate macrophages, M1 or M2 macrophages), (myeloid or lymphoid) dendritic cells (including, e.g., Langerhans cells, conventional or myeloid dendritic cells, plasmacytoid dendritic cells, mDC-1, mDC-2, Mo-DC, HP-DC, veiled cells), granulocytes, polymorphonuclear cells, antigen-presenting cells (APC), etc.

In certain embodiments, the immune cell may be an antigen presenting cell (APC), e.g., at any stage of differentiation or any activation stage. The term "antigen-presenting cell" as used throughout this specification denotes any of a variety of cells capable of acquiring, processing, presenting, or displaying at least one antigen or antigenic fragment on (or at) its cell surface. In general, the term "antigen-presenting cell" can be any cell that aids the enhancement of an immune response or immune tolerance (e.g., from the T-cell or B-cell arms of the immune system) to an antigen or antigenic composition. By means of further guidance, a cell that displays or presents an antigen normally or preferentially with a class II major histocompatibility molecule or complex to an immune cell may be denoted as an "antigen-presenting cell". APC may for example refer to professional APC, such as macrophages, B cells, or dendritic cells.

In certain embodiments, the immune cell is a dendritic cell, e.g., at any stage of differentiation (e.g., a stem cell, a progenitor cell, a mature cell) or any activation stage. As used throughout this specification, "dendritic cell" (DC) may refer to any member of a diverse population of morphologically similar cell types found in lymphoid or non-lymphoid tissues. DC may include, for example, "professional" antigen presenting cells, and have a high capacity for sensitising MHC-restricted T cells. DCs may be recognised, for example, by function, by phenotype and/or by gene expression pattern, particularly by cell surface phenotype. These cells can be characterised by their distinctive morphology, high levels of surface MHC-class II expression and ability to present antigen to CD4+ and/or CD8+ T cells, particularly to naive T cells. Functionally, DCs may be identified by any suitable assay, known to one of skilled in the art, for determination of antigen presentation. Such assays may include, for example, testing the ability to stimulate antigen-primed and/or naive T cells by presentation of a test antigen, followed by determination of T cell proliferation, release of cytokines such as IL-2, and the like. Dendritic cells can be isolated or generated from a biological sample by methods well known in the art. Suitable biological samples for isolation or generation of DC include without limitation a peripheral blood sample, bone marrow sample, umbilical cord blood sample or the like. By means of an example but without limitation, DC present in a biological sample may be isolated by immunofluorescent or immunomagnetic labelling of select surface markers known to be expressed or not expressed by DC, coupled with a corresponding fluorescence activated cell sorting (FACS) gating strategy or immunomagnetic separation, respectively. Alternatively, DC can be generated from CD14+ monocytes by incubating them with suitable cytokines (Zhou & Tedder, Proc Natl Acad Sci USA. 1996, vol. 93, 2588-92).

In certain embodiments, the immune cell may be a progenitor or precursor of a dendritic cell. The terms "progenitor" or "precursor" as used throughout this specification are synonymous and generally refer to an unspecialised or relatively less specialised and proliferation-competent cell, which or the progeny of which can under appropriate conditions give rise to at least one relatively more specialised cell type, such as inter alia to relatively more specialised progenitor or precursor cells or to terminally differentiated cells. A progenitor or precursor cell may "give rise" to another, relatively more specialised cell when, for example, the progenitor or precursor cell differentiates to become said other cell without previously undergoing cell division, or if said other cell is produced after one or more rounds of cell division and/or differentiation of the progenitor or precursor cell. Progenitors or precursors of dendritic cells as intended herein may be capable of also differentiating to other immune cell type(s), or else may be committed to differentiate to dendritic cells and not capable of differentiating to other immune cell types.

In certain embodiments, the immune cell is a monocyte, e.g., at any stage of differentiation (e.g., a stem cell, a progenitor cell, a mature cell) or any activation stage. As used throughout this specification, "monocyte" may refer to a type of white blood cells capable of dividing and differentiating into and hence replenishing or producing macrophages and dendritic cells, e.g., under normal states or in response to inflammation signals. Monocytes are typically identified in stained smears by their large bilobate nucleus. Monocytes are further typified by expression of CD14, and can also show expression of one or more of following surface markers such as 125I-WVH-1, Adipophilin, CB12, CD11a, CD11b, CD15, CD54, CD163, cytidine deaminase, or FLT1. Monocytes encompass previously known subtypes, such as the 'classical' monocyte, the 'non-classical' monocyte and the 'intermediate' monocyte, which are present in human tissues such as blood. 'Classical' monocytes are typified by high level expression of CD14 ($CD14^{++}$ monocyte) and 'non-classical' monocytes display low level expression of CD14 and additional co-expression of CD16 ($CD14^+CD16^{++}$ monocyte). 'Intermediate' monocytes show a phenotype intermediate between the aforementioned types in terms of CD14 and CD16 expression ($CD14^{++}$ $CD16^+$ monocyte).

In certain embodiments, the isolated immune cell is an animal cell, preferably a warm-blooded animal cell, more preferably a vertebrate cell, yet more preferably a mammalian cell, including humans and non-human mammals. In certain particularly preferred embodiments, the isolated immune cell is a human cell.

Cells such as immune cells as disclosed herein may in the context of the present specification be said to "comprise the expression" or conversely to "not express" one or more markers, such as one or more genes or gene products; or be described as "positive" or conversely as "negative" for one or more markers, such as one or more genes or gene products; or be said to "comprise" a defined "gene or gene product signature".

Such terms are commonplace and well-understood by the skilled person when characterising cell phenotypes. By means of additional guidance, when a cell is said to be positive for or to express or comprise expression of a given marker, such as a given gene or gene product, a skilled person would conclude the presence or evidence of a distinct signal for the marker when carrying out a measurement capable of detecting or quantifying the marker in or on the cell. Suitably, the presence or evidence of the distinct signal for the marker would be concluded based on a comparison of the measurement result obtained for the cell to a result of the same measurement carried out for a negative control (for example, a cell known to not express the marker) and/or a positive control (for example, a cell known to express the marker). Where the measurement method allows for a quantitative assessment of the marker, a positive cell may generate a signal for the marker that is at least 1.5-fold higher than a signal generated for the marker by a negative control cell or than an average signal generated for the marker by a population of negative control cells, e.g., at least 2-fold, at least 4-fold, at least 10-fold, at least 20-fold, at least 30-fold, at least 40-fold, at least 50-fold higher or even higher. Further, a positive cell may generate a signal for the marker that is 3.0 or more standard deviations, e.g., 3.5 or more, 4.0 or more, 4.5 or more, or 5.0 or more standard deviations, higher than an average signal generated for the marker by a population of negative control cells.

The term "marker" is widespread in the art and commonly broadly denotes a biological molecule, more particularly an endogenous biological molecule, and/or a detectable portion thereof, whose qualitative and/or quantitative evaluation in a tested object (e.g., in or on a cell, cell population, tissue, organ, or organism, e.g., in a biological sample of a subject) is predictive or informative with respect to one or more aspects of the tested object's phenotype and/or genotype. The terms "marker" and "biomarker" may be used interchangeably throughout this specification.

Preferably, markers as intended herein may be peptide-, polypeptide- and/or protein-based, or may be nucleic acid-based. For example, a marker may be comprised of peptide(s), polypeptide(s) and/or protein(s) encoded by a given gene, or of detectable portions thereof. Further, whereas the term "nucleic acid" generally encompasses DNA, RNA and DNA/RNA hybrid molecules, in the context of markers the term may typically refer to heterogeneous nuclear RNA (hnRNA), pre-mRNA, messenger RNA (mRNA), or copy DNA (cDNA), or detectable portions thereof. Such nucleic acid species are particularly useful as markers, since they contain qualitative and/or quantitative information about the expression of the gene. Particularly preferably, a nucleic acid-based marker may encompass mRNA of a given gene, or cDNA made of the mRNA, or detectable portions thereof. Any such nucleic acid(s), peptide(s), polypeptide(s) and/or protein(s) encoded by or produced from a given gene are encompassed by the term "gene product(s)".

Preferably, markers as intended herein may be extracellular or cell surface markers, as methods to measure extracellular or cell surface marker(s) need not disturb the integrity of the cell membrane and may not require fixation/permeabilisation of the cells.

The term "protein" as used throughout this specification generally encompasses macromolecules comprising one or more polypeptide chains, i.e., polymeric chains of amino acid residues linked by peptide bonds. The term may encompass naturally, recombinantly, semi-synthetically or synthetically produced proteins. The term also encompasses proteins that carry one or more co- or post-expression-type modifications of the polypeptide chain(s), such as, without limitation, glycosylation, acetylation, phosphorylation, sulfonation, methylation, ubiquitination, signal peptide removal, N-terminal Met removal, conversion of pro-enzymes or pre-hormones into active forms, etc. The term further also includes protein variants or mutants which carry amino acid sequence variations vis-à-vis a corresponding native proteins, such as, e.g., amino acid deletions, additions and/or substitutions. The term contemplates both full-length proteins and protein parts or fragments, e.g., naturally-occurring protein parts that ensue from processing of such full-length proteins.

The term "polypeptide" as used throughout this specification generally encompasses polymeric chains of amino acid residues linked by peptide bonds. Hence, insofar a protein is only composed of a single polypeptide chain, the terms "protein" and "polypeptide" may be used interchangeably herein to denote such a protein. The term is not limited to any minimum length of the polypeptide chain. The term may encompass naturally, recombinantly, semi-synthetically or synthetically produced polypeptides. The term also encompasses polypeptides that carry one or more co- or post-expression-type modifications of the polypeptide chain, such as, without limitation, glycosylation, acetylation, phosphorylation, sulfonation, methylation, ubiquitination, signal peptide removal, N-terminal Met removal, conversion of pro-enzymes or pre-hormones into active forms, etc. The term further also includes polypeptide variants or mutants which carry amino acid sequence variations vis-à-vis a corresponding native polypeptide, such as, e.g., amino acid deletions, additions and/or substitutions. The term contemplates both full-length polypeptides and polypeptide parts or fragments, e.g., naturally-occurring polypeptide parts that ensue from processing of such full-length polypeptides.

The term "peptide" as used throughout this specification preferably refers to a polypeptide as used herein consisting essentially of 50 amino acids or less, e.g., 45 amino acids or less, preferably 40 amino acids or less, e.g., 35 amino acids or less, more preferably 30 amino acids or less, e.g., 25 or less, 20 or less, 15 or less, 10 or less or 5 or less amino acids.

The term "nucleic acid" as used throughout this specification typically refers to a polymer (preferably a linear polymer) of any length composed essentially of nucleoside units. A nucleoside unit commonly includes a heterocyclic base and a sugar group. Heterocyclic bases may include inter alia purine and pyrimidine bases such as adenine (A), guanine (G), cytosine (C), thymine (T) and uracil (U) which are widespread in naturally-occurring nucleic acids, other naturally-occurring bases (e.g., xanthine, inosine, hypoxanthine) as well as chemically or biochemically modified (e.g., methylated), non-natural or derivatised bases. Exemplary modified nucleobases include without limitation 5-substituted pyrimidines, 6-azapyrimidines and N-2, N-6 and O-6 substituted purines, including 2-aminopropyladenine, 5-propynyluracil and 5-propynylcytosine. In particular, 5-methylcytosine substitutions have been shown to increase nucleic acid duplex stability and may be preferred base substitutions in for example antisense agents, even more particularly when combined with 2'-O-methoxyethyl sugar modifications. Sugar groups may include inter alia pentose (pentofuranose) groups such as preferably ribose and/or 2-deoxyribose common in naturally-occurring nucleic acids, or arabinose, 2-deoxyarabinose, threose or hexose sugar groups, as well as modified or substituted sugar groups (such as without limitation 2'-O-alkylated, e.g., 2'-O-methylated or 2'-O-ethylated sugars such as ribose; 2'-O-alkyloxyalkylated, e.g., 2'-O-methoxyethylated sugars such as ribose; or 2'-0,4'-C-alkylene-linked, e.g., 2'-0,4'-C-methylene-linked or 2'-0,4'-C-ethylene-linked sugars such as ribose; 2'-fluoro-arabinose, etc.). Nucleoside units may be linked to one another by any one of numerous known inter-nucleoside linkages, including inter alia phosphodiester linkages common in naturally-occurring nucleic acids, and further modified phosphate- or phosphonate-based linkages such as phosphorothioate, alkyl phosphorothioate such as methyl phosphorothioate, phosphorodithioate, alkylphosphonate such as methylphosphonate, alkylphosphonothioate, phosphotriester such as alkylphosphotriester, phosphoramidate, phosphoropiperazidate, phosphoromorpholidate, bridged phosphoramidate, bridged methylene phosphonate, bridged phosphorothioate; and further siloxane, carbonate, sulfamate, carboalkoxy, acetamidate, carbamate such as 3'-N-carbamate, morpholino, borano, thioether, 3'-thioacetal, and sulfone internucleoside linkages. Preferably, internucleoside linkages may be phosphate-based linkages including modified phosphate-based linkages, such as more preferably phosphodiester, phosphorothioate or phosphorodithioate linkages or combinations thereof. The term "nucleic acid" also encompasses any other nucleobase containing polymers such as nucleic acid mimetics, including, without limitation, peptide nucleic acids (PNA), peptide nucleic acids with phosphate groups (PHONA), locked nucleic acids (LNA), morpholino phosphorodiamidate-backbone nucleic acids (PMO), cyclohexene nucleic acids (CeNA), tricyclo-DNA (tcDNA), and nucleic acids having backbone sections with alkyl linkers or amino linkers (see, e.g., Kurreck 2003 (Eur J Biochem 270: 1628-1644)). "Alkyl" as used herein particularly encompasses lower hydrocarbon moieties, e.g., C1-C4 linear or branched, saturated or unsaturated hydrocarbon, such as methyl, ethyl, ethenyl, propyl, 1-propenyl, 2-propenyl, and isopropyl. Nucleic acids as intended herein may include naturally occurring nucleosides, modified nucleosides or mixtures thereof. A modified nucleoside may include a modified heterocyclic base, a modified sugar moiety, a modified inter-nucleoside linkage or a combination thereof. The term "nucleic acid" further preferably encompasses DNA, RNA and DNA/RNA hybrid molecules, specifically including hnRNA, pre-mRNA, mRNA, cDNA, genomic DNA, amplification products, oligonucleotides, and synthetic (e.g., chemically synthesised) DNA, RNA or DNA/RNA hybrids. A nucleic acid can be naturally occurring, e.g., present in or isolated from nature, can be recombinant, i.e., produced by recombinant DNA technology, and/or can be, partly or entirely, chemically or biochemically synthesised. A "nucleic acid" can be double-stranded, partly double stranded, or single-stranded. Where single-stranded, the nucleic acid can be the sense strand or the antisense strand. In addition, nucleic acid can be circular or linear.

Unless otherwise apparent from the context, reference herein to any marker, such as a peptide, polypeptide, protein, or nucleic acid, may generally also encompass modified forms of said marker, such as bearing post-expression modifications including, for example, phosphorylation, glycosylation, lipidation, methylation, cysteinylation, sulphonation, glutathionylation, acetylation, oxidation of methionine to methionine sulphoxide or methionine sulphone, and the like.

The reference to any marker, including any peptide, polypeptide, protein, or nucleic acid, corresponds to the marker commonly known under the respective designations in the art. The terms encompass such markers of any organism where found, and particularly of animals, preferably warm-blooded animals, more preferably vertebrates, yet more preferably mammals, including humans and non-human mammals, still more preferably of humans.

The terms particularly encompass such markers, including any peptides, polypeptides, proteins, or nucleic acids, with a native sequence, i.e., ones of which the primary sequence is the same as that of the markers found in or derived from nature. A skilled person understands that native sequences may differ between different species due to genetic divergence between such species. Moreover, native sequences may differ between or within different individuals of the same species due to normal genetic diversity (variation) within a given species. Also, native sequences may differ between or even within different individuals of the same species due to somatic mutations, or post-transcriptional or post-translational modifications. Any such variants or isoforms of markers are intended herein. Accordingly, all sequences of markers found in or derived from nature are considered "native". The terms encompass the markers when forming a part of a living organism, organ, tissue or cell, when forming a part of a biological sample, as well as when at least partly isolated from such sources. The terms also encompass markers when produced by recombinant or synthetic means.

In certain embodiments, markers, including any peptides, polypeptides, proteins, or nucleic acids, may be human, i.e., their primary sequence may be the same as a corresponding primary sequence of or present in a naturally occurring human markers. Hence, the qualifier "human" in this connection relates to the primary sequence of the respective markers, rather than to their origin or source. For example, such markers may be present in or isolated from samples of human subjects or may be obtained by other means (e.g., by recombinant expression, cell-free transcription or translation, or non-biological nucleic acid or peptide synthesis).

The reference herein to any marker, including any peptide, polypeptide, protein, or nucleic acid, also encompasses fragments thereof. Hence, the reference herein to measuring (or measuring the quantity of) any one marker may encompass measuring the marker and/or measuring one or more fragments thereof.

For example, any marker and/or one or more fragments thereof may be measured collectively, such that the measured quantity corresponds to the sum amounts of the collectively measured species. In another example, any marker and/or one or more fragments thereof may be measured each individually.

The term "fragment" as used throughout this specification with reference to a peptide, polypeptide, or protein generally denotes a portion of the peptide, polypeptide, or protein, such as typically an N- and/or C-terminally truncated form of the peptide, polypeptide, or protein. Preferably, a fragment may comprise at least about 30%, e.g., at least about 50% or at least about 70%, preferably at least about 80%, e.g., at least about 85%, more preferably at least about 90%, and yet more preferably at least about 95% or even about 99% of the amino acid sequence length of said peptide, polypeptide, or protein. For example, insofar not exceeding the length of the full-length peptide, polypeptide, or protein, a fragment may include a sequence of ≥5 consecutive amino acids, or ≥10 consecutive amino acids, or ≥20 consecutive amino acids, or ≥30 consecutive amino acids, e.g., ≥40 consecutive amino acids, such as for example ≥50 consecutive amino acids, e.g., ≥60, ≥70, ≥80, ≥90, ≥100, ≥200, ≥300, ≥400, ≥500 ≥600 consecutive amino acids of the corresponding full-length peptide, polypeptide, or protein.

The term "fragment" with reference to a nucleic acid (polynucleotide) generally denotes a 5'- and/or 3'-truncated form of a nucleic acid. Preferably, a fragment may comprise at least about 30%, e.g., at least about 50% or at least about 70%, preferably at least about 80%, e.g., at least about 85%, more preferably at least about 90%, and yet more preferably at least about 95% or even about 99% of the nucleic acid sequence length of said nucleic acid. For example, insofar not exceeding the length of the full-length nucleic acid, a fragment may include a sequence of ≥5 consecutive nucleotides, or ≥10 consecutive nucleotides, or ≥20 consecutive nucleotides, or ≥30 consecutive nucleotides, e.g., ≥40 consecutive nucleotides, such as for example ≥50 consecutive nucleotides, e.g., ≥60, ≥70, ≥80, ≥90, ≥100, ≥200, ≥300, ≥400, ≥500 or ≥600 consecutive nucleotides of the corresponding full-length nucleic acid.

The terms encompass fragments arising by any mechanism, in vivo and/or in vitro, such as, without limitation, by alternative transcription or translation, exo- and/or endo-proteolysis, exo- and/or endo-nucleolysis, or degradation of the peptide, polypeptide, protein, or nucleic acid, such as, for example, by physical, chemical and/or enzymatic proteolysis or nucleolysis.

A further aspect of the invention relates to an immune cell gene or gene product signature selected from the group consisting of:

a) a signature comprising or consisting of one or more genes or gene products as set forth in Table E1 part a or in Table E2 part a or in FIG. 2C cluster 'DC1' or in FIG. 2D cluster 'DC1' or in FIG. 2G cluster 'DC1';

b) a signature comprising or consisting of one or more genes or gene products as set forth in Table E1 part b or in Table E2 part b or in Table E3 part a or in FIG. 2C cluster 'DC2' or in FIG. 2D cluster 'DC2' or in FIG. 2G cluster 'DC2';

c) a signature comprising or consisting of one or more genes or gene products as set forth in Table E1 part c or in Table E2 part c or in Table E3 part b or in FIG. 2C cluster 'DC3' or in FIG. 2D cluster 'DC3' or in FIG. 2G cluster 'DC3';

d) a signature comprising or consisting of one or more genes or gene products as set forth in Table E1 part d or in Table E2 part d or in FIG. 2C cluster 'DC4' or in FIG. 2D cluster 'DC4' or in FIG. 2G cluster 'DC4';

e) a signature comprising or consisting of one or more genes or gene products as set forth in Table E1 part e or in Table E2 part e or in FIG. 2C cluster 'DC5' or in FIG. 2D cluster 'DC5' or in FIG. 2G cluster 'DC5';

f) a signature comprising or consisting of one or more genes or gene products as set forth in Table E1 part f or in Table E2 part f or in FIG. 2C cluster 'DC6' or in FIG. 2D cluster 'DC6' or in FIG. 2G cluster 'DC6' or in FIG. 6A cluster 'DC6';

g) a signature comprising or consisting of one or more genes or gene products selected from the group consisting of PROC, IRF8, FMNL3, APP, SERPINF1, C1ORF186, CYBASC3, PLAC8, NRP1, CCDC50, TSPAN13, UGCG, LILRA4, MZB1, PTPRS, AK128525, IGJ, and IL3RA;

h) a signature comprising or consisting of one or more genes or gene products selected from the group consisting of ITGAX, IFI30, LGALS2, FGR, LY86, GLIPR2, TIMP1, LST1, AGPAT9, IFITM3, DUSP23, ENTPD1, LOC645638, and IL1RN; or i) a signature comprising or consisting of one or more genes or gene products as set forth in Table E8 or in FIG. 8B clusters BPDCN_1 to 4.

In certain embodiments:
the one or more genes or gene products comprised by or constituting the signature as defined in a) are selected from the group consisting of genes or gene products as set forth in Table E2 part a which display AUC value of 0.70 or more, preferably 0.80 or more, more preferably 0.85 or more, even more preferably 0.90 or more, and still more preferably 0.95 or more;
the one or more genes or gene products comprised by or constituting the signature as defined in b) are selected from the group consisting of genes or gene products as set forth in Table E2 part b which display AUC value of 0.70 or more, preferably 0.80 or more, more preferably 0.85 or more, even more preferably 0.90 or more, and still more preferably 0.95 or more;
the one or more genes or gene products comprised by or constituting the signature as defined in b) are selected from the group consisting of genes or gene products as set forth in Table E3 part a which display AUC value of 0.70 or more, preferably 0.80 or more, more preferably 0.85 or more, even more preferably 0.90 or more, and still more preferably 0.95 or more;
the one or more genes or gene products comprised by or constituting the signature as defined in c) are selected from the group consisting of genes or gene products as set forth in Table E2 part c which display AUC value of 0.70 or more, preferably 0.80 or more, more preferably 0.85 or more, even more preferably 0.90 or more, and still more preferably 0.95 or more;
the one or more genes or gene products comprised by or constituting the signature as defined in c) are selected from the group consisting of genes or gene products as set forth in Table E3 part b which display AUC value of 0.30 or less, preferably 0.20 or less, more preferably 0.15 or less, even more preferably 0.10 or less, and still more preferably 0.05 or less;
the one or more genes or gene products comprised by or constituting the signature as defined in d) are selected from the group consisting of genes or gene products as set forth in Table E2 part d which display AUC value of 0.70 or more, preferably 0.80 or more, more preferably 0.85 or more, even more preferably 0.90 or more, and still more preferably 0.95 or more;
the one or more genes or gene products comprised by or constituting the signature as defined in e) are selected from the group consisting of genes or gene products as set forth in Table E2 part e which display AUC value of 0.70 or more, preferably 0.80 or more, more preferably 0.85 or more, even more preferably 0.90 or more, and still more preferably 0.95 or more;
the one or more genes or gene products comprised by or constituting the signature as defined in f) are selected from the group consisting of genes or gene products as set forth in Table E2 part f which display AUC value of 0.70 or more, preferably 0.80 or more, more preferably 0.85 or more, even more preferably 0.90 or more, and still more preferably 0.95 or more; or
the one or more genes or gene products comprised by or constituting the signature as defined in i) are selected from the group consisting of genes or gene products as set forth in Table E8 which display AUC value of 0.80 or more, preferably 0.85 or more, more preferably 0.90 or more, and even more preferably 0.95 or more.

In certain embodiments:
the signature as defined in a) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E2 part a; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E2 part a, which display AUC value of 0.70 or more, preferably 0.80 or more, more preferably 0.85 or more, even more preferably 0.90 or more, and still more preferably 0.95 or more;
the signature as defined in b) comprises or consists of at least 1%, at least 2%, at least 3%, at least 4%, at least 5%, at least 6%, at least 7%, at least 8%, at least 9%, at least 10%, at least 15%, at least 200%, at least 25%, at least 30%, at least 40%, at least 50%, at least 60%, at least 70%, at least 80%, or at least 90%, or up to 100% (by number) of the genes or gene products as set forth in Table E2 part b; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E2 part b, which display AUC value of 0.70 or more, preferably 0.80 or more, more preferably 0.85 or more, even more preferably 0.90 or more, and still more preferably 0.95 or more;

the signature as defined in b) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E3 part a; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E3 part a, which display AUC value of 0.70 or more, preferably 0.80 or more, more preferably 0.85 or more, even more preferably 0.90 or more, and still more preferably 0.95 or more;

the signature as defined in c) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E2 part c; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E2 part c, which display AUC value of 0.70 or more, preferably 0.80 or more, more preferably 0.85 or more, even more preferably 0.90 or more, and still more preferably 0.95 or more;

the signature as defined in c) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E3 part b; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E3 part b, which display AUC value of 0.30 or less, preferably 0.20 or less, more preferably 0.15 or less, even more preferably 0.10 or less, and still more preferably 0.05 or less;

the signature as defined in d) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 600%, at least 70%, at least 80%, or at least 90%, or up to 100% (by number) of the genes or gene products as set forth in Table E2 part d; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E2 part d, which display AUC value of 0.70 or more, preferably 0.80 or more, more preferably 0.85 or more, even more preferably 0.90 or more, and still more preferably 0.95 or more;

the signature as defined in e) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E2 part e; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E2 part e, which display AUC value of 0.70 or more, preferably 0.80 or more, more preferably 0.85 or more, even more preferably 0.90 or more, and still more preferably 0.95 or more;

the signature as defined in f) comprises or consists of at least 1%, at least 2%, at least 3%, at least 4%, at least 5%, at least 6%, at least 7%, at least 8%, at least 9%, at least 10%, at least 15%, at least 200%, at least 25%, at least 30%, at least 40%, at least 50%, at least 60%, at least 70%, at least 80%, or at least 90%, or up to 100% (by number) of the genes or gene products as set forth in Table E2 part f; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E2 part f, which display AUC value of 0.70 or more, preferably 0.80 or more, more preferably 0.85 or more, even more preferably 0.90 or more, and still more preferably 0.95 or more; or the signature as defined in i) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E8; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E8, which display AUC value of 0.70 or more, preferably 0.80 or more, more preferably 0.85 or more, even more preferably 0.90 or more, and still more preferably 0.95 or more.

A further aspect of the invention relates to an immune cell gene or gene product signature selected from the group consisting of:

x) a signature comprising or consisting of one or more genes or gene products as set forth in as set forth in Table E4 part a or in FIG. 4B cluster 'Mono1' or in FIG. 4D cluster 'Mono1' or in FIG. 4E cluster 'Mono1';

y) a signature comprising or consisting of one or more genes or gene products as set forth in as set forth in Table E4 part b or in FIG. 4B cluster 'Mono2' or in FIG. 4D cluster 'Mono2' or in FIG. 4E cluster 'Mono2';

w) a signature comprising or consisting of one or more genes or gene products as set forth in as set forth in Table E4 part c or in FIG. 4B cluster 'Mono3' or in FIG. 4D cluster 'Mono3' or in FIG. 4E cluster 'Mono3'; or z) a signature comprising or consisting of one or more genes or gene products as set forth in as set forth in Table E4 part d or in FIG. 4B cluster 'Mono4' or in FIG. 4D cluster 'Mono4' or in FIG. 4E cluster 'Mono4'.

In certain embodiments:
the one or more genes or gene products comprised by or constituting the signature as defined in x) are selected from the group consisting of genes or gene products as set forth in Table E4 part a which display AUC value of 0.70 or more, preferably 0.80 or more, more preferably 0.85 or more, even more preferably 0.90 or more, and still more preferably 0.95 or more;
the one or more genes or gene products comprised by or constituting the signature as defined in y) are selected from the group consisting of genes or gene products as set forth in Table E4 part b which display AUC value of 0.70 or more, preferably 0.80 or more, more preferably 0.85 or more, even more preferably 0.90 or more, and still more preferably 0.95 or more;
the one or more genes or gene products comprised by or constituting the signature as defined in w) are selected from the group consisting of genes or gene products as set forth in Table E4 part c which display AUC value of 0.70 or more, preferably 0.80 or more, more preferably 0.85 or more, even more preferably 0.90 or more, and still more preferably 0.95 or more; or
the one or more genes or gene products comprised by or constituting the signature as defined in z) are selected from the group consisting of genes or gene products as set forth in Table E4 part d which display AUC value of 0.70 or more, preferably 0.80 or more, more preferably 0.85 or more, even more preferably 0.90 or more, and still more preferably 0.95 or more.

In certain embodiments:
the signature as defined in x) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E4 part a; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E4 part a, which display AUC value of 0.70 or more, preferably 0.80 or more, more preferably 0.85 or more, even more preferably 0.90 or more, and still more preferably 0.95 or more;
the signature as defined in y) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E4 part b; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E4 part b, which display AUC value of 0.70 or more, preferably 0.80 or more, more preferably 0.85 or more, even more preferably 0.90 or more, and still more preferably 0.95 or more;
the signature as defined in w) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E4 part c; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E4 part c, which display AUC value of 0.70 or more, preferably 0.80 or more, more preferably 0.85 or more, even more preferably 0.90 or more, and still more preferably 0.95 or more; or
the signature as defined in z) comprises or consists of at least 1%, at least 2%, at least 3%, at least 4%, at least 5%, at least 6%, at least 7%, at least 8%, at least 9/c, at least 10%, at least 15%, at least 20%, at least 25%, at least 30%, at least 400%, at least 50%, at least 60%, at least 70%, at least 80%, or at least 90%, or up to 100% (by number) of the genes or gene products as set forth in Table E4 part d; preferably comprises or consists of at least 1%, at least 2%, at least 3%, at least 4%, at least 5%, at least 6%, at least 7%, at least 8%, at least 9%, at least 10%/c, at least 15%, at least 20%, at least 25%, at least 30%, at least 40%, at least 50%, at least 60%, at least 70%, at least 80%, or at least 90%, and up to 100% (by number) of the genes or gene products as set forth in Table E4 part d, which display AUC value of 0.70 or more, preferably 0.80 or more, more preferably 0.85 or more, even more preferably 0.90 or more, and still more preferably 0.95 or more.

The phrase "gene or gene product signature" as intended throughout this specification refers to a set, group or collection of one or more, preferably two or more markers, such as genes or gene products, the expression status or profile of which is associated with or identifies a specific cell type, cell subtype, or cell state of a specific cell type or subtype. Such gene or gene product signatures can be used for example to indicate the presence of a specific cell type, cell subtype, or cell state of a specific cell type or subtype in a population of cells, and/or the overall cell type composition or status of an entire cell population. Such gene or gene product signatures may be indicative of cells within a population of cells in vivo. Preferably, a reference herein to a gene or gene product signature comprising or consisting of one or more genes or gene products from a discrete list of genes or gene products may denote that the genes or gene products said to be comprised by or constituting the signature are expressed in a specific cell type, cell subtype, or cell state of a specific cell type or subtype, i.e., that cells of the specific cell type, cell subtype, or cell state of the specific cell type or subtype are positive for the genes or gene products comprised by the signature. Typically, a signature may comprise or consist of two or more, three or more, four or more, five or more, six or more, seven or more, eight or more, nine or more, ten or more, 15 or more, 20 or more, 25 or more, 30 or more, 35 or more, 40 or more, 45 or more, 50 or more, 60 or more, 70 or more, 80 or more, 90 or more, or 100 or more, or 200 or more, or 300 or more, or 400 or more, or 500 or more genes or gene products. Where the present specification refers to a signature as comprising or consisting of one or more genes set forth in a given Table, the signature may comprise of consist of, by means of example and without limitation, one, or two or more, three or more, four or more, five or more, six or more, seven or more, eight or more, nine or more, ten or more, 15 or more, 20 or more, 25 or more, 30 or more, 35 or more, 40 or more, 45 or more, 50 or more, 60 or more, 70 or more, 80 or more, 90 or more, or 100 or more (provided that the recited number does not exceed the number of genes or gene products listed in the Table) or substantially all or all genes or gene products as set forth in the Table. In certain embodiments, the signature may comprise or consist of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or at least 95%, e.g., 96%, 97%, 98%, 99%, or up to 100% (by number) of the genes or gene products set forth in the Table (rounded up or down as conventional to the closest integer).

As used herein a signature may encompass any gene or genes, or protein or proteins, whose expression profile or whose occurrence is associated with a specific cell type, subtype, or cell state of a specific cell type or subtype within a population of cells. Increased or decreased expression or activity or prevalence may be compared between different cells in order to characterize or identify for instance specific cell (sub)populations. A gene signature as used herein, may thus refer to any set of up- and down-regulated genes between different cells or cell (sub)populations derived from a gene-expression profile. For example, a gene signature may comprise a list of genes differentially expressed in a distinction of interest. It is to be understood that also when referring to proteins (e.g. differentially expressed proteins), such may fall within the definition of "gene" signature.

The signatures as defined herein (being it a gene signature, protein signature or other genetic signature) can be used to indicate the presence of a cell type, a subtype of the cell type, the state of the microenvironment of a population of cells, a particular cell type population or subpopulation, and/or the overall status of the entire cell (sub)population. Furthermore, the signature may be indicative of cells within a population of cells in vivo. The signature may also be used to suggest for instance particular therapies, or to follow up treatment, or to suggest ways to modulate immune systems. The signatures of the present invention may be discovered by analysis of expression profiles of single-cells within a population of cells from isolated samples (e.g. blood samples), thus allowing the discovery of novel cell subtypes or cell states that were previously invisible or unrecognized. The presence of subtypes or cell states may be determined by subtype specific or cell state specific signatures. The presence of these specific cell (sub)types or cell states may be determined by applying the signature genes to bulk sequencing data in a sample. Not being bound by a theory, a combination of cell subtypes having a particular signature may indicate an outcome. Not being bound by a theory, the signatures can be used to deconvolute the network of cells present in a particular pathological condition. Not being bound by a theory the presence of specific cells and cell subtypes are indicative of a particular response to treatment, such as including increased or decreased susceptibility to treatment. The signature may indicate the presence of one particular cell type. In one embodiment, the novel signatures are used to detect multiple cell states or hierarchies that occur in subpopulations of immune cells that are linked to particular pathological condition (e.g. cancer), or linked to a particular outcome or progression of the disease, or linked to a particular response to treatment of the disease.

The signature according to certain embodiments of the present invention may comprise or consist of one or more genes and/or proteins, such as for instance 1, 2, 3, 4, 5, 6, 7, 8, 9, 10 or more. In certain embodiments, the signature may comprise or consist of two or more genes and/or proteins, such as for instance 2, 3, 4, 5, 6, 7, 8, 9, 10 or more. In certain embodiments, the signature may comprise or consist of three or more genes and/or proteins, such as for instance 3, 4, 5, 6, 7, 8, 9, 10 or more. In certain embodiments, the signature may comprise or consist of four or more genes and/or proteins, such as for instance 4, 5, 6, 7, 8, 9, 10 or more. In certain embodiments, the signature may comprise or consist of five or more genes and/or proteins, such as for instance 5, 6, 7, 8, 9, 10 or more. In certain embodiments, the signature may comprise or consist of six or more genes and/or proteins, such as for instance 6, 7, 8, 9, 10 or more. In certain embodiments, the signature may comprise or consist of seven or more genes and/or proteins, such as for instance 7, 8, 9, 10 or more. In certain embodiments, the signature may comprise or consist of eight or more genes and/or proteins, such as for instance 8, 9, 10 or more. In certain embodiments, the signature may comprise or consist of nine or more genes and/or proteins, such as for instance 9, 10 or more. In certain embodiments, the signature may comprise or consist of ten or more genes and/or proteins, such as for instance 10, 11, 12, 13, 14, 15, or more. It is to be understood that a signature according to the invention may for instance also include a combination of genes or proteins.

It is to be understood that "differentially expressed" genes/proteins include genes/proteins which are up- or down-regulated as well as genes/proteins which are turned on or off. When referring to up- or down-regulation, in certain embodiments, such up- or down-regulation is preferably at least two-fold, such as two-fold, three-fold, four-fold, five-fold, or more, such as for instance at least ten-fold, at least 20-fold, at least 30-fold, at least 40-fold, at least 50-fold, or more. Alternatively, or in addition, differential expression may be determined based on common statistical tests, as is known in the art.

As discussed herein, differentially expressed genes/proteins may be differentially expressed on a single cell level, or may be differentially expressed on a cell population level. Preferably, the differentially expressed genes/proteins as discussed herein, such as constituting the gene signatures as discussed herein, when as to the cell population level, refer to genes that are differentially expressed in all or substantially all cells of the population (such as at least 80%, preferably at least 90%, such as at least 95% of the individual cells). This allows one to define a particular subpopulation of cells. As referred to herein, a "subpopulation" of cells preferably refers to a particular subset of cells of a particular cell type which can be distinguished or are uniquely identifiable and set apart from other cells of this cell type. The cell subpopulation may be phenotypically characterized, and is preferably characterized by the signature as discussed herein. A cell (sub)population as referred to herein may constitute of a (sub)population of cells of a particular cell type characterized by a specific cell state.

When referring to induction, or alternatively suppression of a particular signature, preferable is meant induction or alternatively suppression (or upregulation or downregulation) of at least one gene/protein of the signature, such as for instance at least to, at least three, at least four, at least five, at least six, or all genes/proteins of the signature.

Signatures may be functionally validated as being uniquely associated with a particular immune phenotype. Induction or suppression of a particular signature may consequentially be associated with or causally drive a particular immune phenotype.

Various aspects and embodiments of the invention may involve analyzing gene signatures, protein signature, and/or other genetic signature based on single cell analyses (e.g. single cell RNA sequencing) or alternatively based on cell population analyses, as is defined herein elsewhere.

In further aspects, the invention relates to gene signatures, protein signature, and/or other genetic signature of particular immune cell subpopulations, as defined herein. The invention hereto also further relates to particular immune cell subpopulations, which may be identified based on the methods according to the invention as discussed herein; as well as methods to obtain such cell (sub)populations and screening methods to identify agents capable of inducing or suppressing particular immune cell (sub)populations.

The invention further relates to various uses of the gene signatures, protein signature, and/or other genetic signature as defined herein, as well as various uses of the immune cells or immune cell (sub)populations as defined herein. Particular advantageous uses include methods for identifying agents capable of inducing or suppressing particular immune cell (sub)populations based on the gene signatures, protein signature, and/or other genetic as defined herein. The invention further relates to agents capable of inducing or suppressing particular immune cell (sub)populations based on the gene signatures, protein signature, and/or other genetic signature as defined herein, as well as their use for modulating, such as inducing or repressing, a particular gene signature, protein signature, and/or other genetic signature. In related aspects, modulating, such as inducing or repressing, a particular gene signature, protein signature, and/or other genetic signature may modify overall immune cells composition, such as activated or dysfunctional immune cell composition, or distribution, or functionality.

As used herein the term "signature gene" means any gene or genes whose expression profile is associated with a specific cell type, subtype, or cell state of a specific cell type or subtype within a population of cells. The signature gene can be used to indicate the presence of a cell type, a subtype of the cell type, the state of the microenvironment of a population of cells, and/or the overall status of the entire cell population. Furthermore, the signature genes may be indicative of cells within a population of cells in vivo. Not being bound by a theory, the signature genes can be used to deconvolute the cells present in a tumor based on comparing them to data from bulk analysis of a tumor sample. The signature gene may indicate the presence of one particular cell type. In one embodiment, the signature genes may indicate that dysfunctional or activated tumor infiltrating T-cells are present. The presence of cell types within a tumor may indicate that the tumor will be resistant to a treatment. In one embodiment the signature genes of the present invention are applied to bulk sequencing data from a tumor sample to transform the data into information relating to disease outcome and personalized treatments. In one embodiment, the novel signature genes are used to detect multiple cell states that occur in a subpopulation of tumor cells that are linked to resistance to targeted therapies and progressive tumor growth. In preferred embodiments, immune cell states of tumor infiltrating lymphocytes are detected.

In certain embodiments, markers as taught herein or genes or gene products comprised by or constituting gene or gene product signatures as taught herein, or the gene or gene product signatures as taught herein, may display AUC (area under the receiver-operating curve (ROC) as well-established in the art) value of 0.70 or more, e.g., 0.75 or more, preferably 0.80 or more, more preferably 0.85 or more, even more preferably 0.90 or more, and still more preferably 0.95 or more, e.g., 0.96, 0.97, 0.98, 0.99, or 1.00. An AUC value of 1 implies that the marker, gene, gene product or signature is a perfect classifier for a given outcome (e.g., a cell type or cluster). An AUC value of 0.50 implies no predictive value for the outcome.

A marker, for example a gene or gene product, for example a peptide, polypeptide, protein, or nucleic acid, or a group of two or more markers, is "measured" in a tested object (e.g., in or on a cell, cell population, tissue, organ, or organism, e.g., in a biological sample of a subject) when the presence or absence and/or quantity of said marker or said group of markers is detected or determined in the tested object, preferably substantially to the exclusion of other molecules and analytes, e.g., other genes or gene products.

Depending on factors that can be evaluated and decided on by a skilled person, such as inter alia the type of a marker (e.g., peptide, polypeptide, protein, or nucleic acid), the type of the tested object (e.g., a cell, cell population, tissue, organ, or organism, e.g., the type of biological sample of a subject, e.g., whole blood, plasma, serum, tissue biopsy), the expected abundance of the marker in the tested object, the type, robustness, sensitivity and/or specificity of the detection method used to detect the marker, etc., the marker may be measured directly in the tested object, or the tested object may be subjected to one or more processing steps aimed at achieving an adequate measurement of the marker.

The terms "quantity", "amount" and "level" are synonymous and generally well-understood in the art. The terms as used throughout this specification may particularly refer to an absolute quantification of a marker in a tested object (e.g., in or on a cell, cell population, tissue, organ, or organism, e.g., in a biological sample of a subject), or to a relative quantification of a marker in a tested object, i.e., relative to another value such as relative to a reference value, or to a range of values indicating a base-line of the marker. Such values or ranges may be obtained as conventionally known.

An absolute quantity of a marker may be advantageously expressed as weight or as molar amount, or more commonly as a concentration, e.g., weight per volume or mol per volume. A relative quantity of a marker may be advantageously expressed as an increase or decrease or as a fold-increase or fold-decrease relative to said another value, such as relative to a reference value. Performing a relative comparison between first and second variables (e.g., first and second quantities) may but need not require determining first the absolute values of said first and second variables. For example, a measurement method may produce quantifiable readouts (such as, e.g., signal intensities) for said first and second variables, wherein said readouts are a function of the value of said variables, and wherein said readouts may be directly compared to produce a relative value for the first variable vs. the second variable, without the actual need to first convert the readouts to absolute values of the respective variables.

Where a marker is detected in or on a cell, the cell may be conventionally denoted as positive (+) or negative (−) for the marker. Semi-quantitative denotations of marker expression in cells are also commonplace in the art, such as particularly in flow cytometry quantifications, for example, "dim" vs. "bright", or "low" vs. "medium"/"intermediate" vs. "high", or"−" vs. "+" vs. "++", commonly controlled in flow cytometry quantifications by setting of the gates. Where a marker is quantified in or on a cell, absolute quantity of the marker may also be expressed for example as the number of molecules of the marker comprised by the cell.

Where a marker is detected and/or quantified on a single cell level in a cell population, the quantity of the marker may also be expressed for example as a percentage or fraction (by number) of cells comprised in said population that are positive for said marker, or as percentages or fractions (by number) of cells comprised in said population that are "dim" or "bright", or that are "low" or "medium"/"intermediate" or "high", or that are "−" or "+" or "++". By means of an example, a sizeable proportion of the tested cells of the cell population may be positive for the marker, e.g., at least about 20%, at least about 40%, at least about 50%, at least about 60%, at least about 70%, at least about 80%, at least about 90%, at least about 95%, or up to 100%.

Any existing, available or conventional separation, detection and/or quantification methods may be used to measure the presence or absence (e.g., readout being present vs. absent; or detectable amount vs. undetectable amount) and/or quantity (e.g., readout being an absolute or relative quantity) of markers in a tested object (e.g., in or on a cell, cell population, tissue, organ, or organism, e.g., in a biological sample of a subject).

In certain examples, such methods may include biochemical assay methods, including inter alia assays of enzymatic activity, membrane channel activity, substance-binding activity, gene regulatory activity, or cell signalling activity of a marker, e.g., peptide, polypeptide, protein, or nucleic acid.

In other examples, such methods may include immunological assay methods, wherein the ability of an assay to separate, detect and/or quantify a marker (such as, preferably, peptide, polypeptide, or protein) is conferred by specific binding between a separable, detectable and/or quantifiable immunological binding agent (antibody) and the marker. Immunological assay methods include without limitation immunohistochemistry, immunocytochemistry, flow cytometry, mass cytometry, fluorescence activated cell sorting (FACS), fluorescence microscopy, fluorescence based cell sorting using microfluidic systems, immunoaffinity adsorption based techniques such as affinity chromatography, magnetic particle separation, magnetic activated cell sorting or bead based cell sorting using microfluidic systems, enzyme-linked immunosorbent assay (ELISA) and ELISPOT based techniques, radioimmunoassay (RIA), Western blot, etc.

In further examples, such methods may include mass spectrometry analysis methods. Generally, any mass spectrometric (MS) techniques that are capable of obtaining precise information on the mass of peptides, and preferably also on fragmentation and/or (partial) amino acid sequence of selected peptides (e.g., in tandem mass spectrometry, MS/MS; or in post source decay, TOF MS), may be useful herein for separation, detection and/or quantification of markers (such as, preferably, peptides, polypeptides, or proteins). Suitable peptide MS and MS/MS techniques and systems are well-known per se (see, e.g., Methods in Molecular Biology, vol. 146: "Mass Spectrometry of Proteins and Peptides", by Chapman, ed., Humana Press 2000, ISBN 089603609x; Biemann 1990. Methods Enzymol 193: 455-79; or Methods in Enzymology, vol. 402: "Biological Mass Spectrometry", by Burlingame, ed., Academic Press 2005, ISBN 9780121828073) and may be used herein. MS arrangements, instruments and systems suitable for biomarker peptide analysis may include, without limitation, matrix-assisted laser desorption/ionisation time-of-flight (MALDI-TOF) MS; MALDI-TOF post-source-decay (PSD); MALDI-TOF/TOF; surface-enhanced laser desorption/ionization time-of-flight mass spectrometry (SELDI-TOF) MS; electrospray ionization mass spectrometry (ESI-MS); ESI-MS/MS; ESI-MS/(MS)$^n$ (n is an integer greater than zero); ESI 3D or linear (2D) ion trap MS; ESI triple quadrupole MS; ESI quadrupole orthogonal TOF (Q-TOF); ESI Fourier transform MS systems; desorption/ionization on silicon (DIOS); secondary ion mass spectrometry (SIMS); atmospheric pressure chemical ionization mass spectrometry (APCI-MS); APCI-MS/MS; APCI-(MS)$^n$; atmospheric pressure photoionization mass spectrometry (APPI-MS); APPI-MS/MS; and APPI-(MS)$^n$. Peptide ion fragmentation in tandem MS (MS/MS) arrangements may be achieved using manners established in the art, such as, e.g., collision induced dissociation (CID). Detection and quantification of markers by mass spectrometry may involve multiple reaction monitoring (MRM), such as described among others by Kuhn et al. 2004 (Proteomics 4: 1175-86). MS peptide analysis methods may be advantageously combined with upstream peptide or protein separation or fractionation methods, such as for example with the chromatographic and other methods.

In other examples, such methods may include chromatography methods. The term "chromatography" encompasses methods for separating substances, such as chemical or biological substances, e.g., markers, such as preferably peptides, polypeptides, or proteins, referred to as such and vastly available in the art. In a preferred approach, chromatography refers to a process in which a mixture of substances (analytes) carried by a moving stream of liquid or gas ("mobile phase") is separated into components as a result of differential distribution of the analytes, as they flow around or over a stationary liquid or solid phase ("stationary phase"), between said mobile phase and said stationary phase. The stationary phase may be usually a finely divided solid, a sheet of filter material, or a thin film of a liquid on the surface of a solid, or the like. Chromatography is also widely applicable for the separation of chemical compounds of biological origin, such as, e.g., amino acids, proteins, fragments of proteins or peptides, etc.

Chromatography may be preferably columnar (i.e., wherein the stationary phase is deposited or packed in a column), preferably liquid chromatography, and yet more preferably HPLC. While particulars of chromatography are well known in the art, for further guidance see, e.g., Meyer M., 1998, ISBN: 047198373X, and "Practical HPLC Methodology and Applications", Bidlingmeyer, B. A., John Wiley & Sons Inc., 1993. Exemplary types of chromatography include, without limitation, high-performance liquid chromatography (HPLC), normal phase HPLC (NP-HPLC), reversed phase HPLC (RP-HPLC), ion exchange chromatography (IEC), such as cation or anion exchange chromatography, hydrophilic interaction chromatography (HILIC), hydrophobic interaction chromatography (HIC), size exclusion chromatography (SEC) including gel filtration chromatography or gel permeation chromatography, chromatofocusing, affinity chromatography such as immunoaffinity, immobilised metal affinity chromatography, and the like.

Further techniques for separating, detecting and/or quantifying markers, such as preferably peptides, polypeptides, or proteins, may be used, optionally in conjunction with any of the above described analysis methods. Such methods include, without limitation, chemical extraction partitioning, isoelectric focusing (IEF) including capillary isoelectric focusing (CIEF), capillary isotachophoresis (CITP), capillary electrochromatography (CEC), and the like, one-dimensional polyacrylamide gel electrophoresis (PAGE), two-dimensional polyacrylamide gel electrophoresis (2D-PAGE), capillary gel electrophoresis (CGE), capillary zone electrophoresis (CZE), micellar electrokinetic chromatography (MEKC), free flow electrophoresis (FFE), etc.

In certain examples, such methods may include separating, detecting and/or quantifying markers at the nucleic acid level, more particularly RNA level, e.g., at the level of hnRNA, pre-mRNA, mRNA, or cDNA. Standard quantitative RNA or cDNA measurement tools known in the art may be used. Non-limiting examples include hybridisation-based analysis, microarray expression analysis, digital gene expression profiling (DGE), RNA-in-situ hybridisation (RISH), Northern-blot analysis and the like; PCR, RT-PCR, RT-qPCR, end-point PCR, digital PCR or the like; supported oligonucleotide detection, pyrosequencing, polony cyclic sequencing by synthesis, simultaneous bi-directional sequencing, single-molecule sequencing, single molecule real time sequencing, true single molecule sequencing, hybridization-assisted nanopore sequencing, sequencing by synthesis, single-cell RNA sequencing (sc-RNA seq), or the like. By means of an example, methods to profile the RNA content of large numbers of individual cells have been recently developed. To do so, special microfluidic devices have been developed to encapsulate each cell in an individual drop, associate the RNA of each cell with a 'cell barcode' unique to that cell/drop, measure the expression level of each RNA with sequencing, and then use the cell barcodes to determine which cell each RNA molecule came from. In particular, methods of Macosko et al. (Cell. 2015, vol. 161, 1202-1214) and Klein et al. (Cell. 2015, vol. 161, 1187-1201) are contemplated for the present invention.

In further examples, any combinations of methods such as discussed herein may be employed.

A further aspect of the invention thus relates to a method for detecting or quantifying immune cells in a biological sample of a subject, or for isolating immune cells from a biological sample of a subject, the method comprising: a) providing a biological sample of a subject; and b) detecting or quantifying in the biological sample immune cells as disclosed herein, or isolating from the biological sample immune cells as disclosed herein.

The terms "subject", "individual" or "patient" are used interchangeably throughout this specification, and typically and preferably denote humans, but may also encompass reference to non-human animals, preferably warm-blooded animals, even more preferably mammals, such as, e.g., non-human primates, rodents, canines, felines, equines, ovines, porcines, and the like. The term "non-human animals" includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is a non-human mammal. In another embodiment, the subject is human. In another embodiment, the subject is an experimental animal or animal substitute as a disease model. The term does not denote a particular age or sex. Thus, adult and newborn subjects, as well as fetuses, whether male or female, are intended to be covered. Examples of subjects include humans, dogs, cats, cows, goats, and mice. The term subject is further intended to include transgenic species.

The terms "sample" or "biological sample" as used throughout this specification include any biological specimen obtained from a subject. Particularly useful samples are those known to comprise, or expected or predicted to comprise immune cells as taught herein. Preferably, a sample may be readily obtainable by minimally invasive methods, such as blood collection or tissue biopsy, allowing the removal/isolation/provision of the sample from the subject. Examples of particularly useful samples include without limitation whole blood or a cell-containing fraction of whole blood, such as serum, white blood cells, or peripheral blood mononuclear cells (PBMC), lymph, lymphatic tissue, inflammation fluid, tissue specimens, or tissue biopsies. The term "tissue" as used throughout this specification refers to any animal tissue types including, but not limited to, bone, bone marrow, neural tissue, fibrous connective tissue, cartilage, muscle, vasculature, skin, adipose tissue, blood and glandular tissue or other non-bone tissue. The tissue may be healthy or affected by pathological alterations, e.g., tumor tissue or tissue affected by a disease comprising an immune component. The tissue may be from a living subject or may be cadaveric tissue. The tissue may be autologous tissue or syngeneic tissue or may be allograft or xenograft tissue.

The method may allow to detect or conclude the presence or absence of the specified immune cells in a tested object (e.g., in a cell population, tissue, organ, organism, or in a biological sample of a subject). The method may also allow to quantify the specified immune cells in a tested object (e.g., in a cell population, tissue, organ, organism, or in a biological sample of a subject). The quantity of the specified immune cells in the tested object such as the biological sample may be suitably expressed for example as the number (count) of the specified immune cells per standard unit of volume (e.g., ml, µl or nl) or weight (e.g., g or mg or ng) of the tested object such as the biological sample. The quantity of the specified immune cells in the tested object such as the biological sample may also be suitably expressed as a percentage or fraction (by number) of all cells comprised in the tested object such as the biological sample, or as a percentage or fraction (by number) of a select subset of the cells comprised in the tested object such as the biological sample, e.g., as a percentage or fraction (by number) of white blood cells, peripheral blood mononuclear cells, immune cells, antigen presenting cells, or dendritic cells comprised in the tested object such as the biological sample. The quantity of the specified immune cells in the tested object such as the biological sample may also be suitably represented by an absolute or relative quantity of a suitable surrogate analyte, such as a peptide, polypeptide, protein, or nucleic acid expressed or comprised by the specified immune cells.

The method may allow to isolate or purify the specified immune cells from the tested object such as the biological sample. The terms "isolating" or "purifying" as used throughout this specification with reference to a particular component of a composition or mixture (e.g., the tested object such as the biological sample) encompass processes or techniques whereby such component is separated from one or more or (substantially) all other components of the composition or mixture (e.g., the tested object such as the biological sample). The terms do not require absolute purity.

Instead, isolating or purifying the component will produce a discrete environment in which the abundance of the component relative to one or more or all other components is greater than in the starting composition or mixture (e.g., the tested object such as the biological sample). A discrete environment may denote a single medium, such as for example a single solution, dispersion, gel, precipitate, etc. Isolating or purifying the specified immune cells from the tested object such as the biological sample may increase the abundance of the specified immune cells relative to all other cells comprised in the tested object such as the biological sample, or relative to other cells of a select subset of the cells comprised in the tested object such as the biological sample, e.g., relative to other white blood cells, peripheral blood mononuclear cells, immune cells, antigen presenting cells, or dendritic cells comprised in the tested object such as the biological sample. By means of example, isolating or purifying the specified immune cells from the tested object such as the biological sample may yield a cell population, in which the specified immune cells constitute at least 40% (by number) of all cells of said cell population, for example, at least 45%, preferably at least 50%, at least 55%, more preferably at least 60%, at least 65%, still more preferably at least 70%, at least 75%, even more preferably at least 80%, at least 85%, and yet more preferably at least 90%, at least 95%, at least 96%, at least 97%, at least 98%, at least 99%, or even 100% of all cells of said cell population.

The immune cells disclosed herein are generally described or characterised with reference to certain marker(s) or combination(s) of markers (such as genes or gene products, e.g., peptides, polypeptides, proteins, or nucleic acids) expressed or not expressed by the immune cells, or with reference to certain gene or gene product signature(s) comprised by the immune cells. Accordingly, the present methods for detecting, quantifying or isolating the specified immune cells may be marker-based or gene or gene product signature-based, i.e., may involve detection, quantification or isolation of cells expressing or not expressing marker(s) or combination(s) of markers the expression or lack of expression of which is taught herein as typifying or characterising the specified immune cells, or may involve detection, quantification or isolation of cells comprising gene or gene product signature(s) taught herein as typifying or characterising the specified immune cells.

Any existing, available or conventional separation, detection and/or quantification methods may be used to measure the presence or absence (e.g., readout being present vs. absent; or detectable amount vs. undetectable amount) and/or quantity (e.g., readout being an absolute or relative quantity) of the specified immune cells in, or to isolate the specified immune cells from, a tested object (e.g., a cell population, tissue, organ, organism, or a biological sample of a subject). Such methods allow to detect, quantify or isolate the specified immune cells in or from the tested object (e.g., a cell population, tissue, organ, organism, or a biological sample of a subject) substantially to the exclusion of other cells comprised in the tested object. Such methods may allow to detect, quantify or isolate the specified immune cells with sensitivity of at least 50%, at least 55%, at least 60%6, at least 65%, preferably at least 70%, at least 75%, more preferably at least 80%, at least 85%, even more preferably at least 90%, at least 95%, at least 96%, at least 97%, at least 98%, at least 99%, or even 100%, and/or with specificity of at least 50%, at least 55%, at least 60%, at least 65%, preferably at least 70%, at least 75%, more preferably at least 80%, at least 85%, even more preferably at least 90%, at least 95%, at least 96%, at least 97%, at least 98%, at least 99%, or even 100%. By means of example, at least 40% (by number), for example at least 45%, preferably at least 50%, at least 55%, more preferably at least 60%, at least 65%, still more preferably at least 70%, at least 75%, even more preferably at least 80%, at least 85%, and yet more preferably at least 90%, at least 95%, at least 96%, at least 97%, at least 98%, at least 99%, or even 100% of all cells detected, quantified or isolated by such methods may correspond to the specified immune cells.

In certain embodiments, methods for detecting, quantifying or isolating the specified immune cells may comprise treatment(s) or step(s) which diminish or eliminate the viability of the cells. For example, methods which comprise measuring intracellular marker(s) typically necessitate permeabilisation of the cell membrane and possibly fixation of the cells; and methods which comprise measuring nucleic acid marker(s) may typically necessitate obtaining nucleic acids (such as particularly RNA, more particularly mRNA) from the cells. In certain other embodiments, methods for detecting, quantifying or isolating the specified immune cells may substantially preserve the viability of the cells. For example, methods which comprise measuring extracellular or cell surface marker(s) need not disturb the integrity of the cell membrane and may not require fixation/permeabilisation of the cells. By means of an example, methods for detecting, quantifying or isolating the specified immune cells may be configured such that at least 40% (by number), for example, at least 45%, preferably at least 50%, at least 55%, more preferably at least 60%, at least 65%, still more preferably at least 70%, at least 75%, even more preferably at least 80%, at least 85%, and yet more preferably at least 90%, at least 95%, at least 96%, at least 97%, at least 98%, at least 99%, or even 100% of the detected, quantified or isolated cells remain viable. The term "viable cells" as used throughout this specification refers to cells that can be qualified as viable by tests and assays known per se. For instance, the viability of cells may be measured using conventional dye exclusion assays, such as Trypan Blue exclusion assay or propidium iodide exclusion assay. In such assays, viable cells exclude the dye and hence remain unstained, while non-viable cells take up the dye and are stained. The cells and their uptake of the dye can be visualised and revealed by suitable techniques (e.g., conventional light microscopy, fluorescence microscopy, or flow cytometry), and viable (unstained) and non-viable (stained) cells in the tested sample can be counted.

In certain embodiments, methods for detecting, quantifying or isolating the specified immune cells may be single-cell-based, i.e., may allow to discretely detect, quantify or isolate the specified immune cells as individual cells. In other embodiments, methods for detecting, quantifying or isolating the specified immune cells may be cell population-based, i.e., may only allow to detect, quantify or isolate the specified immune cells as a group or collection of cells, without providing information on or allowing to isolate individual cells.

Methods for detecting, quantifying or isolating the specified immune cells may employ any of the above-described techniques for measuring markers, insofar the separation or the qualitative and/or quantitative measurement of the marker(s) can be correlated with or translated into detection, quantification or isolation of the specified immune cells. For example, any of the above-described biochemical assay methods, immunological assay methods, mass spectrometry analysis methods, chromatography methods, or nucleic acid analysis method, or combinations thereof for measuring markers, may be employed for detecting, quantifying or isolating the specified immune cells.

In certain embodiments, the immune cells are detected, quantified or isolated using a technique selected from the group consisting of flow cytometry, fluorescence activated cell sorting, mass cytometry, fluorescence microscopy, affinity separation, magnetic cell separation, microfluidic separation, and combinations thereof.

Flow cytometry encompasses methods by which individual cells of a cell population are analysed by their optical properties (e.g., light absorbance, light scattering and fluorescence properties, etc.) as they pass in a narrow stream in single file through a laser beam. Flow cytometry methods include fluorescence activated cell sorting (FACS) methods by which a population of cells having particular optical properties are separated from other cells.

Elemental mass spectrometry-based flow cytometry, or mass cytometry, offers an approach to analyse cells by replacing fluorochrome-labelled binding reagents with mass tagged binding reagents, i.e., tagged with an element or isotope having a defined mass. In these methods, labelled particles are introduced into a mass cytometer, where they are individually atomised and ionised. The individual particles are then subjected to elemental analysis, which identifies and measures the abundance of the mass tags used. The identities and the amounts of the isotopic elements associated with each particle are then stored and analysed. Due to the resolution of elemental analysis and the number of elemental isotopes that can be used, it is possible to simultaneously measure up to 100 or more parameters on a single particle.

Fluorescence microscopy broadly encompasses methods by which individual cells of a cell population are microscopically analysed by their fluorescence properties. Fluorescence microscopy approaches may be manual or preferably automated.

Affinity separation also referred to as affinity chromatography broadly encompasses techniques involving specific interactions of cells present in a mobile phase, such as a suitable liquid phase (e.g., cell population in an aqueous suspension) with, and thereby adsorption of the cells to, a stationary phase, such as a suitable solid phase; followed by separation of the stationary phase from the remainder of the mobile phase; and recovery (e.g., elution) of the adsorbed cells from the stationary phase. Affinity separation may be columnar, or alternatively, may entail batch treatment, wherein the stationary phase is collected/separated from the liquid phases by suitable techniques, such as centrifugation or application of magnetic field (e.g., where the stationary phase comprises magnetic substrate, such as magnetic particles or beads). Accordingly, magnetic cell separation is also envisaged herein.

Microfluidic systems allow for accurate and high throughput cell detection, quantification and/or sorting, exploiting a variety of physical principles. Cell sorting on microchips provides numerous advantages by reducing the size of necessary equipment, eliminating potentially biohazardous aerosols, and simplifying the complex protocols commonly associated with cell sorting. The term "microfluidic system" as used throughout this specification broadly refers to systems having one or more fluid microchannels. Microchannels denote fluid channels having cross-sectional dimensions the largest of which are typically less than 1 mm, preferably less than 500 µm, more preferably less than 400 µm, more preferably less than 300 µm, more preferably less than 200 µm, e.g., 100 µm or smaller. Such microfluidic systems can be used for manipulating fluid and/or objects such as droplets, bubbles, capsules, particles, cells and the like. Microfluidic systems may allow for example for fluorescent label-based (e.g., employing fluorophore-conjugated binding agent(s), such as fluorophore-conjugated antibody(ies)), bead-based (e.g., bead-conjugated binding agent(s), such as bead-conjugated antibody(ies)), or label-free cell sorting (reviewed in Shields et al., Lab Chip. 2015, vol. 15: 1230-1249).

In certain embodiments, the aforementioned methods and techniques may employ agent(s) capable of specifically binding to one or more gene products, e.g., peptides, polypeptides, proteins, or nucleic acids, expressed or not expressed by the immune cells as taught herein. In certain preferred embodiments, such one or more gene products, e.g., peptides, polypeptides, or proteins, may be expressed on the cell surface of the immune cells (i.e., cell surface markers, e.g., transmembrane peptides, polypeptides or proteins, or secreted peptides, polypeptides or proteins which remain associated with the cell surface). Hence, further disclosed are binding agents capable of specifically binding to markers, such as genes or gene products, e.g., peptides, polypeptides, proteins, or nucleic acids as taught herein. Binding agents as intended throughout this specification may include inter alia antibodies, aptamers, spiegelmers (L-aptamers), photoaptamers, protein, peptides, peptidomimetics, nucleic acids such as oligonucleotides (e.g., hybridisation probes or amplification or sequencing primers and primer pairs), small molecules, or combinations thereof.

Binding agents may be in various forms, e.g., lyophilised, free in solution, or immobilised on a solid phase. They may be, e.g., provided in a multi-well plate or as an array or microarray, or they may be packaged separately, individually, or in combination. e term "specifically bind" as used throughout this specification means that an agent (denoted herein also as "specific-binding agent") binds to one or more desired molecules or analytes (e.g., peptides, polypeptides, proteins, or nucleic acids) substantially to the exclusion of other molecules which are random or unrelated, and optionally substantially to the exclusion of other molecules that are structurally related. The term "specifically bind" does not necessarily require that an agent binds exclusively to its intended target(s). For example, an agent may be said to specifically bind to target(s) of interest if its affinity for such intended target(s) under the conditions of binding is at least about 2-fold greater, preferably at least about 5-fold greater, more preferably at least about 10-fold greater, yet more preferably at least about 25-fold greater, still more preferably at least about 50-fold greater, and even more preferably at least about 100-fold, or at least about 1000-fold, or at least about $10^4$-fold, or at least about $10^5$-fold, or at least about $10^6$-fold or more greater, than its affinity for a non-target molecule, such as for a suitable control molecule (e.g., bovine serum albumin, casein).

Preferably, the specific binding agent may bind to its intended target(s) with affinity constant ($K_A$) of such binding $K_A \geq 1 \times 10^6$ $M^{-1}$, more preferably $K_A \geq 1 \times 10^7$ $M^{-1}$, yet more preferably $K_A \geq 1 \times 10^8$ $M^{-1}$, even more preferably $K_A \geq 1 \times 10^9$ $M^{-1}$, and still more preferably $K_A \geq 1 \times 10^{10}$ $M^{-1}$ or $K_A \geq 1 \times 10^{11}$ $M^{-1}$ or $K_A \geq 1 \times 10^{12}$ $M^{-1}$, wherein $K_A$=/[SBA][T], SBA denotes the specific-binding agent, T denotes the intended target. Determination of $K_A$ can be carried out by methods known in the art, such as for example, using equilibrium dialysis and Scatchard plot analysis.

As used herein, the term "antibody" is used in its broadest sense and generally refers to any immunologic binding agent. The term specifically encompasses intact monoclonal antibodies, polyclonal antibodies, multivalent (e.g., 2-, 3- or more-valent) and/or multi-specific antibodies (e.g., bi- or more-specific antibodies) formed from at least two intact antibodies, and antibody fragments insofar they exhibit the desired biological activity (particularly, ability to specifically bind an antigen of interest, i.e., antigen-binding fragments), as well as multivalent and/or multi-specific composites of such fragments. The term "antibody" is not only inclusive of antibodies generated by methods comprising immunisation, but also includes any polypeptide, e.g., a recombinantly expressed polypeptide, which is made to encompass at least one complementarity-determining region (CDR) capable of specifically binding to an epitope on an antigen of interest. Hence, the term applies to such molecules regardless whether they are produced in vitro or in vivo.

An antibody may be any of IgA, IgD, IgE, IgG and IgM classes, and preferably IgG class antibody. An antibody may be a polyclonal antibody, e.g., an antiserum or immunoglobulins purified there from (e.g., affinity-purified). An antibody may be a monoclonal antibody or a mixture of monoclonal antibodies. Monoclonal antibodies can target a particular antigen or a particular epitope within an antigen with greater selectivity and reproducibility. By means of example and not limitation, monoclonal antibodies may be made by the hybridoma method first described by Kohler et al. 1975 (Nature 256: 495), or may be made by recombinant DNA methods (e.g., as in U.S. Pat. No. 4,816,567). Monoclonal antibodies may also be isolated from phage antibody libraries using techniques as described by Clackson et al. 1991 (Nature 352: 624-628) and Marks et al. 1991 (J Mol Biol 222: 581-597), for example.

Antibody binding agents may be antibody fragments. "Antibody fragments" comprise a portion of an intact antibody, comprising the antigen-binding or variable region thereof. Examples of antibody fragments include Fab, Fab', F(ab')2, Fv and scFv fragments, single domain (sd) Fv, such as VH domains, VL domains and VHH domains; diabodies; linear antibodies; single-chain antibody molecules, in particular heavy-chain antibodies; and multivalent and/or multispecific antibodies formed from antibody fragment(s), e.g., dibodies, tribodies, and multibodies. The above designations Fab, Fab', F(ab')2, Fv, scFv etc. are intended to have their art-established meaning.

The term antibody includes antibodies originating from or comprising one or more portions derived from any animal species, preferably vertebrate species, including, e.g., birds and mammals. Without limitation, the antibodies may be chicken, turkey, goose, duck, guinea fowl, quail or pheasant. Also without limitation, the antibodies may be human, murine (e.g., mouse, rat, etc.), donkey, rabbit, goat, sheep, guinea pig, camel (e.g., *Camelus bactrianus* and *Camelus dromaderius*), llama (e.g., *Lama paccos, Lama glama* or *Lama vicugna*) or horse.

A skilled person will understand that an antibody can include one or more amino acid deletions, additions and/or substitutions (e.g., conservative substitutions), insofar such alterations preserve its binding of the respective antigen. An antibody may also include one or more native or artificial modifications of its constituent amino acid residues (e.g., glycosylation, etc.).

Methods of producing polyclonal and monoclonal antibodies as well as fragments thereof are well known in the art, as are methods to produce recombinant antibodies or fragments thereof (see for example, Harlow and Lane, "Antibodies: A Laboratory Manual", Cold Spring Harbour Laboratory, New York, 1988; Harlow and Lane, "Using Antibodies: A Laboratory Manual", Cold Spring Harbour Laboratory, New York, 1999, ISBN 0879695447; "Monoclonal Antibodies: A Manual of Techniques", by Zola, ed., CRC Press 1987, ISBN 0849364760; "Monoclonal Antibodies. A Practical Approach", by Dean & Shepherd, eds., Oxford University Press 2000, ISBN 0199637229; Methods in Molecular Biology, vol. 248: "Antibody Engineering: Methods and Protocols", Lo, ed., Humana Press 2004, ISBN 1588290921).

The term "aptamer" refers to single-stranded or double-stranded oligo-DNA, oligo-RNA or oligo-DNA/RNA or any analogue thereof that specifically binds to a target molecule such as a peptide. Advantageously, aptamers display fairly high specificity and affinity (e.g., $K_A$ in the order $1 \times 10^9 \, M^{-1}$) for their targets. Aptamer production is described inter alia in U.S. Pat. No. 5,270,163; Ellington & Szostak 1990 (Nature 346: 818-822); Tuerk & Gold 1990 (Science 249: 505-510); or "The Aptamer Handbook: Functional Oligonucleotides and Their Applications", by Klussmann, ed., Wiley-VCH 2006, ISBN 3527310592, incorporated by reference herein. The term "photoaptamer" refers to an aptamer that contains one or more photoreactive functional groups that can covalently bind to or crosslink with a target molecule. The term "spiegelmer" refers to an aptamer which includes L-DNA, L-RNA, or other left-handed nucleotide derivatives or nucleotide-like molecules. Aptamers containing left-handed nucleotides are resistant to degradation by naturally occurring enzymes, which normally act on substrates containing right-handed nucleotides. The term "peptidomimetic" refers to a non-peptide agent that is a topological analogue of a corresponding peptide. Methods of rationally designing peptidomimetics of peptides are known in the art. For example, the rational design of three peptidomimetics based on the sulphated 8-mer peptide CCK26-33, and of two peptidomimetics based on the 11-mer peptide Substance P, and related peptidomimetic design principles, are described in Horwell 1995 (Trends Biotechnol 13: 132-134).

The term "oligonucleotide" as used throughout this specification refers to a nucleic acid (including nucleic acid analogues and mimetics) oligomer or polymer as defined herein. Preferably, an oligonucleotide, such as more particularly an antisense oligonucleotide, is (substantially) single-stranded. Oligonucleotides as intended herein may be preferably between about 10 and about 100 nucleoside units (i.e., nucleotides or nucleotide analogues) in length, preferably between about 15 and about 50, more preferably between about 20 and about 40, also preferably between about 20 and about 30. Oligonucleotides as intended herein may comprise one or more or all non-naturally occurring heterocyclic bases and/or one or more or all non-naturally occurring sugar groups and/or one or more or all non-naturally occurring inter-nucleoside linkages, the inclusion of which may improve properties such as, for example, increased stability in the presence of nucleases and increased hybridization affinity, increased tolerance for mismatches, etc.

Nucleic acid binding agents, such as oligonucleotide binding agents, are typically at least partly antisense to a target nucleic acid of interest. The term "antisense" generally refers to an agent (e.g., an oligonucleotide) configured to specifically anneal with (hybridise to) a given sequence in a target nucleic acid, such as for example in a target DNA, hnRNA, pre-mRNA or mRNA, and typically comprises, consist essentially of or consist of a nucleic acid sequence that is complementary or substantially complementary to said target nucleic acid sequence. Antisense agents suitable for use herein, such as hybridisation probes or amplification or sequencing primers and primer pairs) may typically be capable of annealing with (hybridising to) the respective target nucleic acid sequences at high stringency conditions, and capable of hybridising specifically to the target under physiological conditions. The terms "complementary" or "complementarity" as used throughout this specification with reference to nucleic acids, refer to the normal binding of single-stranded nucleic acids under permissive salt (ionic strength) and temperature conditions by base pairing, preferably Watson-Crick base pairing. By means of example, complementary Watson-Crick base pairing occurs between the bases A and T, A and U or G and C. For example, the sequence 5'-A-G-U-3' is complementary to sequence 5'-A-C-U-3'.

The reference to oligonucleotides may in particular but without limitation include hybridisation probes and/or amplification primers and/or sequencing primers, etc., as commonly used in nucleic acid detection technologies.

The term "small molecule" refers to compounds, preferably organic compounds, with a size comparable to those organic molecules generally used in pharmaceuticals. The term excludes biological macromolecules (e.g., proteins, peptides, nucleic acids, etc.). Preferred small organic molecules range in size up to about 5000 Da, e.g., up to about 4000, preferably up to 3000 Da, more preferably up to 2000 Da, even more preferably up to about 1000 Da, e.g., up to about 900, 800, 700, 600 or up to about 500 Da.

In certain embodiments, the one or more binding agents may be one or more antibodies.

Binding agents as discussed herein may suitably comprise a detectable label. The term "label" refers to any atom, molecule, moiety or biomolecule that may be used to provide a detectable and preferably quantifiable read-out or property, and that may be attached to or made part of an entity of interest, such as a binding agent. Labels may be suitably detectable by for example mass spectrometric, spectroscopic, optical, colourimetric, magnetic, photochemical, biochemical, immunochemical or chemical means. Labels include without limitation dyes; radiolabels such as $^{32}P$, $^{33}P$, $^{35}S$, $^{125}I$, $^{131}I$; electron-dense reagents; enzymes (e.g., horse-radish peroxidase or alkaline phosphatase as commonly used in immunoassays); binding moieties such as biotin-streptavidin; haptens such as digoxigenin; luminogenic, phosphorescent or fluorogenic moieties; mass tags; and fluorescent dyes alone or in combination with moieties that may suppress or shift emission spectra by fluorescence resonance energy transfer (FRET).

In some embodiments, binding agents may be provided with a tag that permits detection with another agent (e.g., with a probe binding partner). Such tags may be, for example, biotin, streptavidin, his-tag, myc tag, maltose, maltose binding protein or any other kind of tag known in the art that has a binding partner. Example of associations which may be utilised in the probe:binding partner arrangement may be any, and includes, for example biotin:streptavidin, his-tag:metal ion (e.g., $Ni^{2+}$), maltose:maltose binding protein, etc.

The marker-binding agent conjugate may be associated with or attached to a detection agent to facilitate detection. Examples of detection agents include, but are not limited to, luminescent labels; colourimetric labels, such as dyes; fluorescent labels; or chemical labels, such as electroactive agents (e.g., ferrocyanide); enzymes; radioactive labels; or radiofrequency labels. The detection agent may be a particle. Examples of such particles include, but are not limited to, colloidal gold particles; colloidal sulphur particles; colloidal selenium particles; colloidal barium sulfate particles; colloidal iron sulfate particles; metal iodate particles; silver halide particles; silica particles; colloidal metal (hydrous) oxide particles; colloidal metal sulfide particles; colloidal lead selenide particles; colloidal cadmium selenide particles; colloidal metal phosphate particles; colloidal metal ferrite particles; any of the above-mentioned colloidal particles coated with organic or inorganic layers; protein or peptide molecules; liposomes; or organic polymer latex particles, such as polystyrene latex beads. Preferable particles may be colloidal gold particles.

In further aspects the invention provides kits of parts or articles of manufacture for detecting, quantifying or isolating immune cells as taught herein.

Hence, in an embodiment, the invention provides a kit of parts or an article of manufacture for detecting, quantifying or isolating immune cells, the kit of parts or article of manufacture comprising:

a') one or more agents capable of specifically binding to CLEC9A, optionally further comprising one or more agents capable of specifically binding to one or more gene products selected from the group consisting of HLA-DR, CD3, CD56, CD19 and CD14;

a") one or more agents capable of specifically binding to one or more gene products comprised by or constituting the signature as defined in a), optionally further comprising one or more agents capable of specifically binding to one or more gene products selected from the group consisting of HLA-DR, CD3, CD56, CD19 and CD14;

b') one or more agents capable of specifically binding to FCGR2B, optionally further comprising one or more agents capable of specifically binding to one or more gene products selected from the group consisting of HLA-DR, CD3, CD56, CD19 and CD14;

b") one or more agents capable of specifically binding to one or more gene products comprised by or constituting the signature as defined in b), optionally further comprising one or more agents capable of specifically binding to one or more gene products selected from the group consisting of HLA-DR, CD3, CD56, CD19 and CD14;

c') one or more agents capable of specifically binding to one or more gene products selected from the group consisting of CD163, CD36, CD14, LYZ, S100A8, S100A9, and S100A12, optionally further comprising one or more agents capable of specifically binding to one or more gene products selected from the group consisting of HLA-DR, CD3, CD56 and CD19;

c") one or more agents capable of specifically binding to one or more gene products comprised by or constituting the signature as defined in c), optionally further comprising one or more agents capable of specifically binding to one or more gene products selected from the group consisting of HLA-DR, CD3, CD56 and CD19;

d') one or more agents capable of specifically binding to FCGR3A, optionally further comprising one or more agents capable of specifically binding to one or more gene products selected from the group consisting of HLA-DR, CD3, CD56, CD19 and CD14;

d") one or more agents capable of specifically binding to one or more gene products comprised by or constituting the signature as defined in d), optionally further comprising one or more agents capable of specifically binding to one or more gene products selected from the group consisting of HLA-DR, CD3, CD56, CD19 and CD14;

e') one or more agents capable of specifically binding to one or more gene products selected from the group consisting of AXL, SIGLEC6, SIGLEC1, PPP1R14A, CD22, CD5, and GPR146, optionally further comprising one or more agents capable of specifically binding to one or more gene products selected from the group consisting of HLA-DR, CD3, CD56, CD19 and CD14;

e") one or more agents capable of specifically binding to one or more gene products comprised by or constituting the signature as defined in e), optionally further comprising one or more agents capable of specifically binding to one or more gene products selected from the group consisting of HLA-DR, CD3, CD56, CD19 and CD14;

f) one or more agents capable of specifically binding to one or more gene products selected from the group consisting of GZMB, SELPLG, DERL3, PTPRCAP, BCL11A, LAMP5, SLA2, SELS, NRP1, SIDT1, TCF4, SLC15A4, PTCRA, IRF7, and TRAF4, optionally further comprising one or more agents capable of specifically binding to one or more gene products selected from the group consisting of HLA-DR, CD3, CD56, CD19 and CD14;

f") one or more agents capable of specifically binding to one or more gene products comprised by or constituting the signature as defined in f), optionally further comprising one or more agents capable of specifically binding to one or more gene products selected from the group consisting of HLA-DR, CD3, CD56, CD19 and CD14;

g') one or more agents capable of specifically binding to CD45RA, CD100, and CD34, optionally further comprising one or more agents capable of specifically binding to one or more gene products selected from the group consisting of HLA-DR, CD3, CD56, CD19, CD14, CD11C, CD123 and CD39;

g") one or more agents capable of specifically binding to one or more gene products selected from the group consisting of RUNX2, TNFRSF18, ID2, ACY3, RORC, SEMA4D, SATB1, KIT, AHR, HLX, and CCR7, optionally further comprising one or more agents capable of specifically binding to one or more gene products selected from the group consisting of HLA-DR, CD3, CD56, CD19, CD14, CD11C, CD123 and CD39; and/or h') one or more agents capable of specifically binding to one or more gene products comprised by or constituting the signature as defined in i), optionally further comprising one or more agents capable of specifically binding to one or more gene products selected from the group consisting of HLA-DR, CD45 and CD123.

In certain embodiments:
the kit of parts or article of manufacture as defined in any one of b') or b") further comprises one or more agents capable of specifically binding to one or more gene products selected from the group consisting of CD1C and CD11C;
the kit of parts or article of manufacture as defined in any one of c') or c") further comprises one or more agents capable of specifically binding to one or more gene products selected from the group consisting of CD1C and CD11C;
the kit of parts or article of manufacture as defined in any one of c') or c") comprises agents capable of specifically binding to two or more, three or more, four or more, five or more, six or more, or all gene products selected from the group consisting of CD163, CD36, CD14, LYZ, S100A8, S100A9, and S100A12;
the kit of parts or article of manufacture as defined in any one of c') or c") comprises agents capable of specifically binding to CD163 and CD36;
the kit of parts or article of manufacture as defined in any one of d') or d") further comprises one or more agents capable of specifically binding to one or more gene products selected from the group consisting of CD1C and CD141;
the kit of parts or article of manufacture as defined in any one of e') or e") comprises agents capable of specifically binding to two or more, three or more, four or more, five or more, six or more, or all gene products selected from the group consisting of AXL, SIGLEC6, SIGLEC1, PPP1R14A, CD22, CD5, and GPR146;
the kit of parts or article of manufacture as defined in any one of e') or e") comprises agents capable of specifically binding to AXL and SIGLEC6;
the kit of parts or article of manufacture as defined in any one of e') or e") further comprises one or more agents capable of specifically binding to one or more gene products selected from the group consisting of CD141 and CD16;
the kit of parts or article of manufacture as defined in any one of e') or e") further comprises one or more agents capable of specifically binding to one or more gene products selected from the group consisting of CD123 and CD11C;
the kit of parts or article of manufacture as defined in any one of e') or e") comprises agents capable of specifically binding to one or more gene products selected from the group consisting of PROC, IRF8, FMNL3, APP, SERPINF1, C1ORF186, CYBASC3, PLAC8, NRP1, CCDC50, TSPAN13, UGCG, LILRA4, MZB1, PTPRS, AK128525, IGJ, and IL3RA;
the kit of parts or article of manufacture as defined in any one of e') or e") comprises agents capable of specifically binding to one or more gene products selected from the group consisting of ITGAX, IFI30, LGALS2, FGR, LY86, GLIPR2, TIMP1, LST1, AGPAT9, IFITM3, DUSP23, ENTPD1, LOC645638, and IL1RN;
the kit of parts or article of manufacture as defined in any one of e') or e") comprises agents capable of specifically binding to ITGAX;
the kit of parts or article of manufacture as defined in any one of f') or f") comprises agents capable of specifically binding to two or more, three or more, four or more, five or more, six or more, seven or more, eight or more, nine or more, ten or more, eleven or more, twelve or more, thirteen or more, fourteen or more, or all genes or gene products selected from the group consisting of GZMB, SELPLG, DERL3, PTPRCAP, BCL11A, LAMP5, SLA2, SELS, NRP1, SIDT1, TCF4, SLC15A4, PTCRA, IRF7, and TRAF4;
the kit of parts or article of manufacture as defined in any one of f') or f") further comprises one or more agents capable of specifically binding to one or more gene products selected from the group consisting of CD123 and CD11C;
the kit of parts or article of manufacture as defined in any one of f') or f") comprises agents capable of specifically binding to CD123, CD11C, CD141, AXL and SIGLE6; and/or
the kit of parts or article of manufacture as defined in any one of g') or g") comprises agents capable of specifically binding to two or more, three or more, four or more, five or more, six or more, seven or more, eight or more, nine or more, ten or more, or all genes or gene products selected from the group consisting of RUNX2, TNFRSF18, ID2, ACY3, RORC, SEMA4D, SATB1, KIT, AHR, HLX, and CCR7.

Further, in an embodiment, the invention provides a kit of parts or an article of manufacture for detecting, quantifying or isolating immune cells, the kit of parts or article of manufacture comprising:

x) one or more agents capable of specifically binding to one or more gene products comprised by or constituting the signature as defined in x), optionally further comprising one or more agents capable of specifically binding to one or more gene products selected from the group consisting of CD3, CD56, CD19, and CD14;

y) one or more agents capable of specifically binding to one or more gene products comprised by or constituting the signature as defined in y), optionally further comprising one or more agents capable of specifically binding to one or more gene products selected from the group consisting of CD3, CD56, CD19, and CD14;

w) one or more agents capable of specifically binding to one or more gene products comprised by or constituting the signature as defined in w), optionally further comprising one or more agents capable of specifically binding to one or more gene products selected from the group consisting of CD3, CD56, CD19, and CD14; and/or z) one or more agents capable of specifically binding to one or more gene products comprised by or constituting the signature as defined in z), optionally further comprising one or more agents capable of specifically binding to one or more gene products selected from the group consisting of CD3, CD56, CD19, and CD14.

The terms "kit of parts" and "kit" as used throughout this specification refer to a product containing components necessary for carrying out the specified methods (e.g., methods for detecting, quantifying or isolating immune cells as taught herein), packed so as to allow their transport and storage. Materials suitable for packing the components comprised in a kit include crystal, plastic (e.g., polyethylene, polypropylene, polycarbonate), bottles, flasks, vials, ampules, paper, envelopes, or other types of containers, carriers or supports. Where a kit comprises a plurality of components, at least a subset of the components (e.g., two or more of the plurality of components) or all of the components may be physically separated, e.g., comprised in or on separate containers, carriers or supports. The components comprised in a kit may be sufficient or may not be sufficient for carrying out the specified methods, such that external reagents or substances may not be necessary or may be necessary for performing the methods, respectively. Typically, kits are employed in conjunction with standard laboratory equipment, such as liquid handling equipment, environment (e.g., temperature) controlling equipment, analytical instruments, etc. In addition to the recited binding agents(s) as taught herein, such as for example, antibodies, hybridisation probes, amplification and/or sequencing primers, optionally provided on arrays or microarrays, the present kits may also include some or all of solvents, buffers (such as for example but without limitation histidine-buffers, citrate-buffers, succinate-buffers, acetate-buffers, phosphate-buffers, formate buffers, benzoate buffers, TRIS (Tris (hydroxymethyl)-aminomethan) buffers or maleate buffers, or mixtures thereof), enzymes (such as for example but without limitation thermostable DNA polymerase), detectable labels, detection reagents, and control formulations (positive and/or negative), useful in the specified methods. Typically, the kits may also include instructions for use thereof, such as on a printed insert or on a computer readable medium. The terms may be used interchangeably with the term "article of manufacture", which broadly encompasses any man-made tangible structural product, when used in the present context.

In certain embodiments, the one or more binding agents are configured for use in a technique selected from the group consisting of flow cytometry, fluorescence activated cell sorting, mass cytometry, fluorescence microscopy, affinity separation, magnetic cell separation, microfluidic separation, and combinations thereof.

In certain embodiments, the one or more binding agents are one or more antibodies.

In certain embodiments, the kit of parts or article of manufacture may comprise a microfluidic system.

The immune cells as taught herein may be comprised in a cell population. By means of example, the specified immune cells may constitute at least 40% (by number) of all cells of said cell population, for example, at least 45%, preferably at least 50%, at least 55%, more preferably at least 60%, at least 65%, still more preferably at least 70%, at least 75%, even more preferably at least 80%, at least 85%, and yet more preferably at least 90%, at least 95%, at least 96%, at least 97%, at least 98%, at least 99%, or even 100% of all cells of said cell population.

A further aspect of the invention provides a population of the immune cells as taught herein. The terms "cell population" or "population" denote a set of cells having characteristics in common. The characteristics may include in particular the one or more marker(s) or gene or gene product signature(s) as taught herein.

Another aspect of the invention provides a composition, pharmaceutical composition or vaccine comprising the immune cells or immune cell populations as taught herein.

A "pharmaceutical composition" refers to a composition that usually contains an excipient, such as a pharmaceutically acceptable carrier that is conventional in the art and that is suitable for administration to cells or to a subject.

The term "pharmaceutically acceptable" as used throughout this specification is consistent with the art and means compatible with the other ingredients of a pharmaceutical composition and not deleterious to the recipient thereof.

As used herein, "carrier" or "excipient" includes any and all solvents, diluents, buffers (such as, e.g., neutral buffered saline or phosphate buffered saline), solubilisers, colloids, dispersion media, vehicles, fillers, chelating agents (such as, e.g., EDTA or glutathione), amino acids (such as, e.g., glycine), proteins, disintegrants, binders, lubricants, wetting agents, emulsifiers, sweeteners, colorants, flavourings, aromatisers, thickeners, agents for achieving a depot effect, coatings, antifungal agents, preservatives, stabilisers, antioxidants, tonicity controlling agents, absorption delaying agents, and the like. The use of such media and agents for pharmaceutical active components is well known in the art. Such materials should be non-toxic and should not interfere with the activity of the cells or active components.

The precise nature of the carrier or excipient or other material will depend on the route of administration. For example, the composition may be in the form of a parenterally acceptable aqueous solution, which is pyrogen-free and has suitable pH, isotonicity and stability. For general principles in medicinal formulation, the reader is referred to Cell Therapy: Stem Cell Transplantation, Gene Therapy, and Cellular Immunotherapy, by G. Morstyn & W. Sheridan eds., Cambridge University Press, 1996; and Hematopoietic Stem Cell Therapy, E. D. Ball, J. Lister & P. Law, Churchill Livingstone, 2000.

The pharmaceutical composition can be applied parenterally, rectally, orally or topically. Preferably, the pharmaceutical composition may be used for intravenous, intramuscular, subcutaneous, peritoneal, peridural, rectal, nasal, pulmonary, mucosal, or oral application. In a preferred embodiment, the pharmaceutical composition according to the invention is intended to be used as an infuse. The skilled person will understand that compositions which are to be administered orally or topically will usually not comprise cells, although it may be envisioned for oral compositions to also comprise cells, for example when gastro-intestinal tract indications are treated. Each of the cells or active components (e.g., immunomodulants, antigens) as discussed herein may be administered by the same route or may be administered by a different route. By means of example, and without limitation, cells may be administered parenterally and other active components may be administered orally.

Liquid pharmaceutical compositions may generally include a liquid carrier such as water or a pharmaceutically acceptable aqueous solution. For example, physiological saline solution, tissue or cell culture media, dextrose or other saccharide solution or glycols such as ethylene glycol, propylene glycol or polyethylene glycol may be included.

The composition may include one or more cell protective molecules, cell regenerative molecules, growth factors, anti-apoptotic factors or factors that regulate gene expression in the cells. Such substances may render the cells independent of their environment.

Such pharmaceutical compositions may contain further components ensuring the viability of the cells therein. For example, the compositions may comprise a suitable buffer system (e.g., phosphate or carbonate buffer system) to achieve desirable pH, more usually near neutral pH, and may comprise sufficient salt to ensure isosmotic conditions for the cells to prevent osmotic stress. For example, suitable solution for these purposes may be phosphate-buffered saline (PBS), sodium chloride solution, Ringer's Injection or Lactated Ringer's Injection, as known in the art. Further, the composition may comprise a carrier protein, e.g., albumin (e.g., bovine or human albumin), which may increase the viability of the cells.

Further suitably pharmaceutically acceptable carriers or additives are well known to those skilled in the art and for instance may be selected from proteins such as collagen or gelatine, carbohydrates such as starch, polysaccharides, sugars (dextrose, glucose and sucrose), cellulose derivatives like sodium or calcium carboxymethylcellulose, hydroxypropyl cellulose or hydroxypropylmethyl cellulose, pregelatinized starches, pectin agar, carrageenan, clays, hydrophilic gums (acacia gum, guar gum, arabic gum and xanthan gum), alginic acid, alginates, hyaluronic acid, polyglycolic and polylactic acid, dextran, pectins, synthetic polymers such as water-soluble acrylic polymer or polyvinylpyrrolidone, proteoglycans, calcium phosphate and the like.

If desired, cell preparation can be administered on a support, scaffold, matrix or material to provide improved tissue regeneration. For example, the material can be a granular ceramic, or a biopolymer such as gelatine, collagen, or fibrinogen. Porous matrices can be synthesized according to standard techniques (e.g., Mikos et al., Biomaterials 14: 323, 1993; Mikos et al., Polymer 35:1068, 1994; Cook et al., J. Biomed. Mater. Res. 35:513, 1997). Such support, scaffold, matrix or material may be biodegradable or non-biodegradable. Hence, the cells may be transferred to and/or cultured on suitable substrate, such as porous or non-porous substrate, to provide for implants. For example, cells that have proliferated, or that are being differentiated in culture dishes, can be transferred onto three-dimensional solid supports in order to cause them to multiply and/or continue the differentiation process by incubating the solid support in a liquid nutrient medium of the invention, if necessary. Cells can be transferred onto a three-dimensional solid support, e.g. by impregnating said support with a liquid suspension containing said cells. The impregnated supports obtained in this way can be implanted in a human subject. Such impregnated supports can also be re-cultured by immersing them in a liquid culture medium, prior to being finally implanted. The three-dimensional solid support needs to be biocompatible so as to enable it to be implanted in a human. It may be biodegradable or non-biodegradable.

The cells or cell populations can be administered in a manner that permits them to survive, grow, propagate and/or differentiate towards desired cell types (e.g. differentiation) or cell states. The cells or cell populations may be grafted to or may migrate to and engraft within the intended organ.

In certain embodiments, a pharmaceutical cell preparation as taught herein may be administered in a form of liquid composition. In embodiments, the cells or pharmaceutical composition comprising such can be administered systemically, topically, within an organ or at a site of organ dysfunction or lesion.

Preferably, the pharmaceutical compositions may comprise a therapeutically effective amount of the specified immune cells and/or other active components (e.g., immunomodulants, antigens). The term "therapeutically effective amount" refers to an amount which can elicit a biological or medicinal response in a tissue, system, animal or human that is being sought by a researcher, veterinarian, medical doctor or other clinician, and in particular can prevent or alleviate one or more of the local or systemic symptoms or features of a disease or condition being treated.

The term "vaccine" generally refers to a therapeutic or prophylactic pharmaceutical composition for in vivo administration to a subject, comprising a component to which a vaccinated subject is induced to raise an immune response, preferably a protective immune response, or immune tolerance (tolerising vaccines).

Optionally, the vaccine may further comprise one or more adjuvants for enhancing the immune response. Suitable adjuvants include, for example, but without limitation, saponin, mineral gels such as aluminium hydroxide, surface active substances such as lysolecithin, pluronic polyols, polyanions, peptides, oil or hydrocarbon emulsions, bacilli Calmette-Guerin (BCG), keyhole limpet hemocyanin (KLH), monophosphoryl lipid A (MPL), *Corynebacterium parvum*, oligodeoxynucleotides containing unmethylated CpG motif, and QS-21.

Optionally, the vaccine may further comprise one or more immunostimulatory molecules, or one or more molecules promoting immune tolerance. Non-limiting examples of such molecules include various cytokines, lymphokines and chemokines. By means of example, non-limiting examples of molecules with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc.

In certain embodiments, the composition, pharmaceutical composition or vaccine may further comprise an antigen. The administration of the composition, pharmaceutical composition or vaccine to a subject can thus induce an immune response, preferably a protective immune response, or immune tolerance, to said antigen.

As used throughout this specification, "immune response" refers to a response by a cell of the immune system, such as a B cell, T cell (CD4+ or CD8+), regulatory T cell, antigen-presenting cell, dendritic cell, monocyte, macrophage, NKT cell, NK cell, basophil, eosinophil, or neutrophil, to a stimulus. In some embodiments, the response is specific for a particular antigen (an "antigen-specific response"), and refers to a response by a CD4 T cell, CD8 T cell, or B cell via their antigen-specific receptor. In some embodiments, an immune response is a T cell response, such as a CD4+ response or a CD8+ response. Such responses by these cells can include, for example, cytotoxicity, proliferation, cytokine or chemokine production, trafficking, or phagocytosis, and can be dependent on the nature of the immune cell undergoing the response.

T cell response refers more specifically to an immune response in which T cells directly or indirectly mediate or otherwise contribute to an immune response in a subject. T cell-mediated response may be associated with cell mediated effects, cytokine mediated effects, and even effects associated with B cells if the B cells are stimulated, for example, by cytokines secreted by T cells. By means of an example but without limitation, effector functions of MHC class I restricted Cytotoxic T lymphocytes (CTLs), may include cytokine and/or cytolytic capabilities, such as lysis of target cells presenting an antigen peptide recognised by the T cell receptor (naturally-occurring TCR or genetically engineered TCR, e.g., chimeric antigen receptor, CAR), secretion of cytokines, preferably IFN gamma, TNF alpha and/or or more immunostimulatory cytokines, such as IL-2, and/or antigen peptide-induced secretion of cytotoxic effector molecules, such as granzymes, perforins or granulysin. By means of example but without limitation, for MHC class II restricted T helper (Th) cells, effector functions may be antigen peptide-induced secretion of cytokines, preferably, IFN gamma, TNF alpha, IL-4, IL5, IL-10, and/or IL-2. By means of example but without limitation, for T regulatory (Treg) cells, effector functions may be antigen peptide-induced secretion of cytokines, preferably, IL-10, IL-35, and/or TGF-beta. B cell response refers more specifically to an immune response in which B cells directly or indirectly mediate or otherwise contribute to an immune response in a subject. Effector functions of B cells may include in particular production and secretion of antigen-specific antibodies by B cells (e.g., polyclonal B cell response to a plurality of the epitopes of an antigen (antigen-specific antibody response)), antigen presentation, and/or cytokine secretion.

The term "immune tolerance" as used throughout this specification refers to any mechanism by which a potentially injurious immune response is prevented, suppressed, delayed in the onset or progression, reduced in the risk of the onset or progression, or shifted to a non-injurious immune response. Specific immune tolerance occurs when immune tolerance is preferentially invoked against certain antigen(s) in comparison with others. Immune tolerance treatments may thus encompass antigen-specific therapies used to attenuate autoreactive T- and/or B-cell responses, while leaving global immune function intact (tolerising vaccines).

The term "antigen" as used throughout this specification refers to a molecule or a portion of a molecule capable of being bound by an antibody, or by a T cell receptor (TCR) when presented by MHC molecules. At the molecular level, an antigen is characterised by its ability to be bound at the antigen-binding site of an antibody. The specific binding denotes that the antigen will be bound in a highly selective manner by its cognate antibody and not by the multitude of other antibodies which may be evoked by other antigens. An antigen is additionally capable of being recognised by the immune system. In some instances, an antigen is capable of eliciting a humoral immune response in a subject. In some instances, an antigen is capable of eliciting a cellular immune response in a subject, leading to the activation of B- and/or T-lymphocytes. In some instances, an antigen is capable of eliciting a humoral and cellular immune response in a subject. Hence, an antigen may be preferably antigenic and immunogenic. Alternatively, an antigen may be antigenic and not immunogenic. Typically, an antigen may be a peptide, polypeptide, protein, nucleic acid, an oligo- or polysaccharide, or a lipid, or any combination thereof, a glycoprotein, proteoglycan, glycolipid, etc. In certain embodiments, an antigen may be a peptide, polypeptide, or protein. An antigen may have one or more than one epitope. The terms "antigenic determinant" or "epitope" generally refer to the region or part of an antigen that specifically reacts with or is recognised by the immune system, specifically by antibodies, B cells, or T cells. An antigen the administration of which results in the induction of immune tolerance toward the antigen may also be denoted as "tolerogen".

An antigens as contemplated throughout this specification may be obtained by any means available to a skilled person, e.g., may be isolated from a naturally-occurring material comprising the antigen, or may be produced recombinantly by a suitable host or host cell expression system and optionally isolated therefrom (e.g., a suitable bacterial, yeast, fungal, plant or animal host or host cell expression system), or may be produced recombinantly by cell-free transcription or translation, or non-biological nucleic acid or peptide synthesis.

In certain embodiments, the immune cell or immune cell population has been loaded with the antigen.

The term "antigen loading" as used throughout this specification refers to a method or process of delivering one or more antigens to immune cells, such as particularly to antigen-presenting cells, such as more particularly to dendritic cells or dendritic cell progenitor or precursor cells, such that the antigenic epitopes of the antigen(s) are presented on MHC, whether intracellular or on the immune cell surface. Typically, immune cells may be loaded with antigen(s) by a process comprising contacting or incubating the immune cells in vitro/ex vivo with a composition comprising the antigen(s) or a composition comprising nucleic acid(s) encoding the antigen(s) under conditions that permit the immune cells to contact, express (if needed), process and present the antigen(s) on MHC. The skilled person will know the incubation temperature and time periods sufficient to allow for effective loading of antigens. For example, incubation steps may be typically from between about 1 to about 2 or about 4 hours, at temperatures of between about 25° C. to about 37° C. and/or may be overnight at about 4° C., and the like. By means of an example, the immune cells may be contacted with a composition comprising an isolated antigen, for example, an antigen isolated from a naturally-occurring source of the antigen, or an antigen produced recombinantly by a suitable host or host cell expression system and isolated therefrom (e.g., a suitable bacterial, yeast, fungal, plant or animal host or host cell expression system), or produced recombinantly by cell-free transcription or translation, or non-biological nucleic acid or peptide synthesis. By means of another example, the immune cells may be contacted with a composition comprising a naturally-occurring source of the antigen, i.e., substantially without isolating the antigen from said naturally-occurring source. For instance, the immune cells may be contacted with a composition comprising cells which naturally express the antigen or cell debris of such cells, e.g., tumor cells expressing tumour antigen(s). Suitably, such cells may be rendered non-viable and preferably lysed, for example, killed and preferably lysed by a mechanical, chemical or physical treatment, such as heat killed, apoptotic, necrotic or otherwise processed. By means of a further example, the immune cells may be contacted with cells of a suitable host or host cell expression system which recombinantly produce the antigen, i.e., substantially without isolating the antigen from said cells. Suitably, such cells may be rendered non-viable and preferably lysed, for example, killed and preferably lysed by a mechanical, chemical or physical treatment, such as heat killed or otherwise processed.

Immune cells may also be loaded with an antigen by introducing into the immune cells a nucleic acid, commonly a recombinant nucleic acid, encoding the antigen, whereby the immune cells express the antigen.

The term "recombinant" is generally used to indicate that the material (e.g., a nucleic acid, a genetic construct or a protein) has been altered by technical means (i.e., non-naturally) through human intervention. The term "recombinant nucleic acid" can commonly refer nucleic acids comprised of segments joined together using recombinant DNA technology. The term "recombinant protein or polypeptide" refers to a protein or polypeptide that can result from the expression of recombinant nucleic acid such as recombinant DNA.

By "encoding" is particularly meant that a nucleic acid sequence or part(s) thereof corresponds to another nucleic acid sequence in a template—transcription product (e.g., RNA or RNA analogue) relationship, or corresponds, by virtue of the genetic code of an organism in question, to a particular amino acid sequence, e.g., the amino acid sequence of one or more desired proteins or polypeptides.

The (recombinant) nucleic acid may suitably comprise one or more regulatory sequences operably linked to and allowing for expression of a desired transcription or translation product, such as a desired polypeptide or protein, such as the antigen. For example, the (recombinant) nucleic acid may comprise an open reading frame encoding the antigen, operably linked to one or more such regulatory sequences.

The term "regulatory sequences" is used interchangeably with "regulatory elements" and as used throughout this specification refers to a segment of nucleic acid, typically but not limited to DNA or RNA or analogues thereof, that modulates the transcription of the nucleic acid sequence to which it is operatively linked, and thus act as transcriptional modulators. Regulatory sequences modulate the expression of gene and/or nucleic acid sequence to which they are operatively linked. Regulatory sequence often comprise "regulatory elements" which are nucleic acid sequences that are transcription binding domains and are recognised by the nucleic acid-binding domains of transcriptional proteins and/or transcription factors, repressors or enhancers etc. Typical regulatory sequences include, but are not limited to, a transcriptional promoter, such as a constitutive or inducible promoter, and transcriptional elements, such as an optional operator sequence to control transcription, a sequence encoding suitable mRNA ribosomal binding sites, and sequences to control the termination of transcription and/or translation. Regulatory sequences can be a single regulatory sequence or multiple regulatory sequences, or modified regulatory sequences or fragments thereof. Modified regulatory sequences are regulatory sequences where the nucleic acid sequence has been changed or modified by some means, for example, but not limited to, mutation, methylation etc.

As used throughout this specification, a "promoter" or "promoter region" or "promoter element" used interchangeably herein, refers to a segment of a nucleic acid sequence, typically but not limited to DNA or RNA or analogues thereof, that controls the transcription of the nucleic acid sequence to which it is operatively linked. The promoter region includes specific sequences that are sufficient for RNA polymerase recognition, binding and transcription initiation. This portion of the promoter region is referred to as the promoter. In addition, the promoter region includes sequences which modulate this recognition, binding and transcription initiation activity of RNA polymerase. These sequences may be cis-acting or may be responsive to trans-acting factors. Promoters, depending upon the nature of the regulation may be constitutive or regulated. The term "enhancer" refers to a cis-acting regulatory sequence involved in the transcriptional activation of a nucleic acid sequence. An enhancer can function in either orientation and may be upstream or downstream of the promoter.

An "operable linkage" is a linkage in which regulatory sequences and sequences sought to be expressed are connected in such a way as to permit said expression. Hence, the term generally refers to the functional relationship of the nucleic acid sequences with regulatory sequences of nucleotides, such as promoters, enhancers, transcriptional and translational stop sites, and other signal sequences. For example, operative linkage of nucleic acid sequences, typically DNA, to a regulatory sequence or promoter region refers to the physical and functional relationship between the DNA and the regulatory sequence or promoter such that the transcription of such DNA is initiated from the regulatory sequence or promoter, by an RNA polymerase that specifically recognises, binds and transcribes the DNA. In order to optimise expression and/or in vitro transcription, it may be necessary to modify the regulatory sequence for the expression of the nucleic acid or DNA in the cell type for which it is expressed. The desirability of, or need of, such modification may be empirically determined. Enhancers need not be located in close proximity to the coding sequences whose transcription they enhance. Furthermore, a gene transcribed from a promoter regulated in trans by a factor transcribed by a second promoter may be said to be operatively linked to the second promoter. In such a case, transcription of the first gene is said to be operatively linked to the first promoter and is also said to be operatively linked to the second promoter. By means of an example, sequences, such as, e.g., a promoter and an ORF, may be said to be operably linked if the nature of the linkage between said sequences does not: (1) result in the introduction of a frame-shift mutation, (2) interfere with the ability of the promoter to direct the transcription of the ORF, (3) interfere with the ability of the ORF to be transcribed from the promoter sequence. Hence, "operably linked" may mean incorporated into a genetic construct so that expression control sequences, such as a promoter, effectively control expression of a coding sequence of interest, such as the nucleic acid molecule as defined herein.

A (recombinant) nucleic acid encoding a desired transcription or translation product, such as a desired polypeptide or protein, such as the antigen, may be comprised in an expression cassette or an expression vector comprising suitable regulatory sequences.

The term "vector" generally denotes a tool that allows or facilitates the transfer of an entity from one environment to another. More particularly, the term "vector" as used throughout this specification refers to nucleic acid molecules to which nucleic acid fragments may be inserted and cloned, i.e., propagated. Hence, a vector is typically a replicon, into which another nucleic acid segment may be inserted, such as to bring about the replication of the inserted segment in a defined host cell or vehicle organism.

A vector thus typically contains an origin of replication and other entities necessary for replication and/or maintenance in a host cell. A vector may typically contain one or more unique restriction sites allowing for insertion of nucleic acid fragments. A vector may also preferably contain a selection marker, such as, e.g., an antibiotic resistance gene or auxotrophic gene (e.g., URA3, which encodes an enzyme necessary for uracil biosynthesis or TRP1, which encodes an enzyme required for tryptophan biosynthesis), to allow selection of recipient cells that contain the vector. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art.

Expression vectors are generally configured to allow for and/or effect the expression of nucleic acids introduced thereto in a desired expression system, e.g., in vitro, in a host cell, host organ and/or host organism. For example, expression vectors may advantageously comprise suitable regulatory sequences.

Vectors may include, without limitation, plasmids (which refer to circular double stranded DNA loops which, in their vector form are not bound to the chromosome), episomes, phagemids, bacteriophages, bacteriophage-derived vectors, bacterial artificial chromosomes (BAC), yeast artificial chromosomes (YAC), P1-derived artificial chromosomes (PAC), transposons, cosmids, linear nucleic acids, viral vectors, etc., as appropriate. A vector can be a DNA or RNA vector. A vectors can be a self-replicating extrachromosomal vector or a vector which integrates into a host genome, hence, vectors can be autonomous or integrative.

Integrative vectors can generally include a serially arranged sequence of at least a first insertable DNA fragment, a selectable marker gene, and a second insertable DNA fragment. The first and second insertable DNA fragments are each about 200 (e.g., about 250, about 300, about 350, about 400, about 450, about 500, or about 1000 or more) nucleotides in length and have nucleotide sequences which are homologous to portions of the genomic DNA of the host cell species to be transformed. A nucleotide sequence containing a gene of interest for expression is inserted in this vector between the first and second insertable DNA fragments, whether before or after the marker gene. Integrative vectors can be linearized prior to transformation to facilitate the integration of the nucleotide sequence of interest into the host cell genome.

Factors of importance in selecting a particular vector include inter alia: choice of recipient host cell, ease with which recipient cells that contain the vector may be recognised and selected from those recipient cells which do not contain the vector; the number of copies of the vector which are desired in particular recipient cells; whether it is desired for the vector to integrate into the chromosome or to remain extra-chromosomal in the recipient cells; and whether it is desirable to be able to "shuttle" the vector between recipient cells of different species.

The term "viral vectors" refers to the use as viruses, or virus-associated vectors as carriers of the nucleic acid construct into the cell. Constructs may be integrated and packaged into non-replicating, defective viral genomes like adenovirus, adeno-associated virus (AAV), or herpes simplex virus (HSV) or others, including retroviral and lentiviral vectors, for infection or transduction into cells. The vector may or may not be incorporated into the cells genome. The constructs may include viral sequences for transfection, if desired. Alternatively, the construct may be incorporated into vectors capable of episomal replication, e.g., EPV and EBV vectors.

Methods for introducing nucleic acids, including vectors, expression cassettes and expression vectors, into cells (transfection or transformation) are known to the person skilled in the art, and may include calcium phosphate co-precipitation, electroporation, micro-injection, protoplast fusion, lipofection, exosome-mediated transfection, transfection employing polyamine transfection reagents, bombardment of cells by nucleic acid-coated tungsten micro projectiles, viral particle delivery, etc.

In certain embodiments, the antigen is an allergen, autoimmune antigen, tumor antigen, or pathogen antigen.

The term "allergen" as used throughout this specification broadly encompasses any substance that is capable of producing an allergic reaction in a susceptible subject. The terms "allergic reaction" and "allergy" are used interchangeably to describe an abnormal reaction of the body to a previously encountered allergen introduced by inhalation, ingestion or skin contact. The use of these terms also includes clinically adverse reactions to environmental allergens which reflect the expression of acquired immunologic responsiveness involving allergen-specific antibodies and/or T cells. These terms also include adverse immunologic responses that are associated with the production of allergen-specific IgE. The term "allergic diseases" refers to a group of clinically manifested disorders in which immune responses, typically directed against otherwise innocuous environmental allergens, are thought to have a pathogenic role. Allergic diseases include, but are not limited to, hay fever, allergic asthma, allergic contact dermatitis, and clinical disorders in which IgE-associated immune responses are thought to play a role. The use of the term "allergen" encompasses without limitation any antigens that elicit a specific IgE response. Allergens may have little or no intrinsic toxicity by themselves, but cause a pathological condition due to their ability to elicit an IgE-associated immune response, and, upon subsequent exposure, due to their ability to elicit IgE- and/or T cell-dependent hypersensitivity reactions. Common allergens include but are not limited to pollen, grasses, dust, as well as foods, including, but not limited to, nuts, milk, eggs, shell fish, and venoms, and various drugs. Allergens include, without limitation, nanoparticles, metal or metal alloys, drug or medicine related antigens; various biological matters, e.g., proteins, which may be related to animals such as insects or arachnids. Other allergens may be related to humidifiers and air conditioners.

As used throughout this specification, the term "autoimmune antigen" refers to any self-component, i.e., a component own or native to a subject, e.g., a self-peptide, self-polypeptide, or self-protein, that serves either as a target or cause of an autoimmune condition or disease. Examples of autoimmune antigens include, but are not limited to, myelin basic protein, proteolipid protein, or myelin oligodendrocyte protein (multiple sclerosis); peripheral myelin proteins PO and P2 (Guillain-Barre syndrome); acetylcholine receptor (myasthenia gravis); cardiac myosin (rheumatic fever/myocarditis); proteins of the beta cells of the Islets of Langerhans—glutamic acid decarboxylase, insulin (Type I autoimmune diabetes mellitus); thyroid-stimulating hormone receptor (Grave's disease); platelet antigens (thrombocytopenic purpura); neuromuscular junctions (myasthenia gravis); red blood cell antigens (autoimmune haemolytic anaemia); intracellular antigens (spliceosomes, ribosomes, histones, nucleic acids, etc.) (systemic lupus erythematosus); rheumatoid factor IgG complexes, synovial joint antigens (rheumatoid arthritis); epidermal cadherin (Pemphigus vulgaris); and alpha-3 subunit of type IV collagen (Goodpasture's syndrome).

The term "tumor antigen" as used throughout this specification refers to an antigen that is uniquely or differentially expressed by a tumor cell, whether intracellular or on the tumor cell surface (preferably on the tumor cell surface), compared to a normal or non-neoplastic cell. By means of example, a tumor antigen may be present in or on a tumor cell and not typically in or on normal cells or non-neoplastic cells (e.g., only expressed by a restricted number of normal tissues, such as testis and/or placenta), or a tumor antigen may be present in or on a tumor cell in greater amounts than in or on normal or non-neoplastic cells, or a tumor antigen may be present in or on tumor cells in a different form than that found in or on normal or non-neoplastic cells. The term thus includes tumor-specific antigens (TSA), including tumor-specific membrane antigens, tumor-associated antigens (TAA), including tumor-associated membrane antigens, embryonic antigens on tumors, growth factor receptors, growth factor ligands, etc. The term further includes cancer/testis (CT) antigens. Examples of tumor antigens include, without limitation, β-human chorionic gonadotropin (βHCG), glycoprotein 100 (gp100/Pme117), carcinoembryonic antigen (CEA), tyrosinase, tyrosinase-related protein 1 (gp75/TRP1), tyrosinase-related protein 2 (TRP-2), NY-BR-1, NY-CO-58, NY-ESO-1, MN/gp250, idiotypes, telomerase, synovial sarcoma X breakpoint 2 (SSX2), mucin 1 (MUC-1), antigens of the melanoma-associated antigen (MAGE) family, high molecular weight-melanoma associated antigen (HMW-MAA), melanoma antigen recognized by T cells 1 (MART1), Wilms' tumor gene 1 (WT1), HER2/neu, mesothelin (MSLN), alphafetoprotein (AFP), cancer antigen 125 (CA-125), and abnormal forms of ras or p53.

The term "pathogen antigen" as used throughout this specification refers to an antigen of a biological entity that is pathogenic to a subject, hence, capable of causing a pathological condition or disease in the subject. Pathogens encompass pathogenic microorganisms, such as any pathogenic type of bacterium (including archaeabacteria and eubacteria), protozoum, fungus (including molds and yeasts), viroid and virus; as well as single-cell and multicellular parasites, e.g., helminths (e.g., cestodes, nematodes and trematodes). The term also encompasses biological entities, which display pathogenicity in immunocompromised hosts, but may not ordinarily be pathogenic in a non-immunocompromised host.

In certain embodiments, the pathogen is a bacterial, fungal, protozoal, parasitic, or viral pathogen.

Non-limiting examples of bacterial pathogens from which the pathogen antigen can be derived include any pathogenic bacterial species from a genus selected from the group comprising or consisting of *Bacillus, Bordetella, Borrelia, Brucella, Burkholderia, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio,* and *Yersinia.*

Non-limiting examples of fungal pathogens from which the pathogen antigen can be derived include any pathogenic fungal species from a genus selected from the group comprising or consisting of *Candida* (e.g., *Candida albicans*), *Aspergillus* (e.g., *Aspergillus fumigatus, Aspergillus flavus, Aspergillus clavatus*), *Cryptococcus* (e.g., *Cryptococcus neoformans, Cryptococcus gattii*), *Histoplasma* (e.g., *Histoplasma capsulatum*), *Microsporum* (e.g., *Microsporum gypseum*), *Pneumocystis* (e.g., *Pneumocystis jirovecii, Pneumocystis carinii*), *Stachybotrys* (e.g., *Stachybotrys chartarum*), and *Trichophyton* (e.g., *Trichophyton rubrum*).

Non-limiting examples of protozoal pathogens from which the pathogen antigen can be derived include, e.g., protists of the genus *Plasmodium*, such as *Plasmodium falciparum, Plasmodium vivax, Plasnodium ovale,* or *Plasmodium malariae,* and further pathogens, such as *Entamoeba histolytica, Giardia lambia,* or *Trypanosoma brucei.*

Non-limiting examples of parasitic pathogens from which the pathogen antigen can be derived include single-cell and multicellular parasites, such as *Acanthamoeba, Anisakis, Ascaris lumbricoides, Balantidium coli, Cestoda* (tapeworm), *Chiggers, Cochliomyia hominivorax, Entamoeba histolytica, Fasciola hepatica, Giardia lamblia,* Hookworm; *Leishmania, Linguatula serrata,* Liver fluke, *Loa loa, Paragonimus* (lung fluke), Pinworm, *Plasmodium falciparum, Schistosoma, Strongyloides stercoralis,* Tapeworm, *Toxoplasma gondii; Trypanosoma;* Whipworm; or *Wuchereria bancrofti.*

Non-limiting examples of viral pathogens from which the pathogen antigen can be derived include adenoviruses, papillomaviruses, hepadnaviruses (e.g., hepatitis B), parvoviruses, pox viruses (e.g., small pox virus, vaccinia virus), Epstein-Barr virus, cytomegalovirus (CMV), herpes simplex viruses, roseolovirus, varicella zoster virus, filoviruses (e.g., Ebola virus, Marburg virus), paramyxoviruses (e.g., measles virus, mumps virus, Nipah virus, Hendra virus, human respiratory syncytial virus (RSV), parainfluenza viruses, Newcastle disease virus, human metapneumovirus), orthomyxoviruses (e.g., influenza A, influenza B, influenza C), rhabdoviruses (e.g., Lyssavirus, also known as rabies virus), arenaviruses (e.g., Lassa virus), coronaviruses (severe acute respiratory syndrome (SARS), Middle East respiratory syndrome (MERS)), human enteroviruses, hepatitis A virus, human rhinoviruses, polio virus, retroviruses (e.g., human immunodeficiency virus 1 (HIV-1)), rotaviruses, flaviviruses (e.g., West Nile virus, dengue virus, yellow fever virus, Zika virus), hepaciviruses (e.g., hepatitis C virus), or rubella virus.

A further aspect of the invention relates to a method for preparing an immune cell vaccine comprising: a) isolating from a biological sample of a subject an immune cell as disclosed herein or an immune cell population as disclosed herein; b) optionally in vitro expanding the immune cell or immune cell population of a); c) loading said immune cell or immune cell population with an antigen; and d) isolating the antigen-loaded immune cell or immune cell population. In certain embodiments, the antigen is an allergen, autoimmune antigen, tumor antigen, or pathogen antigen. In certain further embodiments, the pathogen is a bacterial, fungal, protozoal, parasitic, or viral pathogen.

The term "in vitro" generally denotes outside, or external to, a body, e.g., an animal or human body. The term encompasses "ex vivo".

The isolated immune cells or immune cell populations as disclosed throughout this specification may be suitably cultured or cultivated in vitro. The terms "culturing" or "cell culture" are common in the art and broadly refer to maintenance of cells and potentially expansion (proliferation, propagation) of cells in vitro. Typically, animal cells, such as mammalian cells, such as human cells, are cultured by exposing them to (i.e., contacting them with) a suitable cell culture medium in a vessel or container adequate for the purpose (e.g., a 96-, 24-, or 6-well plate, a T-25, T-75, T-150 or T-225 flask, or a cell factory), at art-known conditions conducive to in vitro cell culture, such as temperature of 37° C., 5% v/v $CO_2$ and >95% humidity.

The term "medium" as used herein broadly encompasses any cell culture medium conducive to maintenance of cells, preferably conducive to proliferation of cells. Typically, the medium will be a liquid culture medium, which facilitates easy manipulation (e.g., decantation, pipetting, centrifugation, filtration, and such) thereof.

Typically, the medium will comprise a basal medium formulation as known in the art. Many basal media formulations (available, e.g., from the American Type Culture Collection, ATCC; or from Invitrogen, Carlsbad, Calif.) can be used, including but not limited to Eagle's Minimum Essential Medium (MEM), Dulbecco's Modified Eagle's Medium (DMEM), alpha modified Minimum Essential Medium (alpha-MEM), Basal Medium Essential (BME), Iscove's Modified Dulbecco's Medium (IMDM), BGJb medium, F-12 Nutrient Mixture (Ham), Liebovitz L-15, DMEM/F-12, Essential Modified Eagle's Medium (EMEM), RPMI-1640, Medium 199, Waymouth's MB 752/1 or Williams Medium E, and modifications and/or combinations thereof. Compositions of basal media are generally known in the art and it is within the skill of one in the art to modify or modulate concentrations of media and/or media supplements as necessary for the cells cultured.

Such basal media formulations contain ingredients necessary for mammalian cell development, which are known per se. By means of illustration and not limitation, these ingredients may include inorganic salts (in particular salts containing Na, K, Mg, Ca, Cl, P and possibly Cu, Fe, Se and Zn), physiological buffers (e.g., HEPES, bicarbonate), nucleotides, nucleosides and/or nucleic acid bases, ribose, deoxyribose, amino acids, vitamins, antioxidants (e.g., glutathione) and sources of carbon (e.g., glucose, sodium pyruvate, sodium acetate), etc.

For use in culture, basal media can be supplied with one or more further components. For example, additional supplements can be used to supply the cells with the necessary trace elements and substances for optimal growth and expansion. Furthermore, antioxidant supplements may be added, e.g., β-mercaptoethanol. While many basal media already contain amino acids, some amino acids may be supplemented later, e.g., L-glutamine, which is known to be less stable when in solution. A medium may be further supplied with antibiotic and/or antimycotic compounds, such as, typically, mixtures of penicillin and streptomycin, and/or other compounds, exemplified but not limited to, amphotericin, ampicillin, gentamicin, bleomycin, hygromycin, kanamycin, mitomycin, mycophenolic acid, nalidixic acid, neomycin, nystatin, paromomycin, polymyxin, puromycin, rifampicin, spectinomycin, tetracycline, tylosin, and zeocin.

Lipids and lipid carriers can also be used to supplement cell culture media. Such lipids and carriers can include, but are not limited to cyclodextrin, cholesterol, linoleic acid conjugated to albumin, linoleic acid and oleic acid conjugated to albumin, unconjugated linoleic acid, linoleic-oleic-arachidonic acid conjugated to albumin, oleic acid unconjugated and conjugated to albumin, among others. Albumin can similarly be used in fatty-acid free formulations.

Also contemplated is supplementation of cell culture media with mammalian plasma or sera. Plasma or sera often contain cellular factors and components that facilitate cell viability and expansion. Optionally, plasma or serum may be heat inactivated. Heat inactivation is used in the art mainly to remove the complement. Heat inactivation typically involves incubating the plasma or serum at 56° C. for 30 to 60 min, e.g., 30 min, with steady mixing, after which the plasma or serum is allowed to gradually cool to ambient temperature. A skilled person will be aware of any common modifications and requirements of the above procedure. Optionally, plasma or serum may be sterilised prior to storage or use. Usual means of sterilisation may involve, e.g., filtration through one or more filters with pore size smaller than 1 µm, preferably smaller than 0.5 µm, e.g., smaller than 0.45 µm, 0.40 µm, 0.35 µm, 0.30 µm or 0.25 µm, more preferably 0.2 µm or smaller, e.g., 0.15 µm or smaller, 0.10 µm or smaller. Suitable sera or plasmas for use in media as taught herein may include human serum or plasma, or serum or plasma from non-human animals, preferably non-human mammals, such as, e.g., non-human primates (e.g., lemurs, monkeys, apes), foetal or adult bovine, horse, porcine, lamb, goat, dog, rabbit, mouse or rat serum or plasma, etc., or any combination of such. In certain preferred embodiments, a medium as taught herein may comprise bovine serum or plasma, preferably foetal bovine (calf) serum or plasma, more preferably foetal bovine (calf) serum (FCS or FBS). When culturing human cells, media may preferably comprise human serum or plasma, such as autologous or allogeneic human serum or plasma, preferably human serum, such as autologous or allogeneic human serum, more preferably autologous human serum or plasma, even more preferably autologous human serum.

In certain preferred embodiments, serum or plasma can be substituted in media by serum replacements, such as to provide for serum-free media (i.e., chemically defined media). The provision of serum-free media may be advantageous particularly with view to administration of the media or fraction(s) thereof to subjects, especially to human subjects (e.g., improved bio-safety). By the term "serum replacement" it is broadly meant any a composition that may be used to replace the functions (e.g., cell maintenance and growth supportive function) of animal serum in a cell culture medium. A conventional serum replacement may typically comprise vitamins, albumin, lipids, amino acids, transferrin, antioxidants, insulin and trace elements. Many commercialized serum replacement additives, such as KnockOut Serum Replacement (KOSR), N2, B27, Insulin-Transferrin-Selenium Supplement (ITS), and G5 are well known and are readily available to those skilled in the art.

Plasma or serum or serum replacement may be comprised in media as taught herein at a proportion (volume of plasma or serum or serum replacement/volume of medium) between about 0.5% v/v and about 40.0% v/v, preferably between about 5.0% v/v and about 20.0% v/v, e.g., between about 5.0% v/v and about 15.0% v/v, more preferably between about 8.0% v/v and about 12.0% v/v, e.g., about 10.0% v/v.

A further aspect of the invention relates to a method for eliciting an immune response or immune tolerance to an antigen in a subject comprising administering to the subject an immune cell or immune cell population or a pharmaceutical composition or vaccine as disclosed herein, wherein the immune cell or immune cell population has been loaded with an antigen as disclosed herein.

In certain embodiments, the immune cell or immune cell population is autologous to said subject, i.e., the immune cell or immune cell population is isolated from the same subject as the subject to which/whom the immune cell or immune cell population is to be administered. In certain further embodiments, the immune cell or immune cell population is syngeneic to said subject, i.e., the immune cell or immune cell population is isolated from an identical twin of the subject to which/whom the immune cell or immune cell population is to be administered. In certain further embodiments, the immune cell or immune cell population is allogeneic to said subject, i.e., the immune cell or immune cell population is isolated from a different subject of the same species as the subject to which/whom the immune cell or immune cell population is to be administered. In certain embodiments, the immune cell or immune cell population may even be xenogeneic to said subject, i.e., the immune cell or immune cell population may be isolated from a subject of a different species than the subject to which/whom the immune cell or immune cell population is to be administered.

Preferably, non-autologous, such as allogeneic cells may be selected such as to maximise the tissue compatibility between the subject and the administered cells, thereby reducing the chance of rejection of the administered cells by patient's immune system or graft-vs.-host reaction. For example, advantageously the cells may be typically selected which have either identical HLA haplotypes (including one or preferably more HLA-A, HLA-B, HLA-C, HLA-D, HLA-DR, HLA-DP and HLA-DQ) to the subject, or which have the most HLA antigen alleles common to the subject and none or the least of HLA antigens to which the subject contains pre-existing anti-HLA antibodies.

The term "administer" encompasses any methods and routes of applying or delivering cells and/or active components as discussed herein to a subject, such as to result in an effective treatment in the subject, e.g., parenterally, rectally, orally or topically; e.g., intravenously, intramuscularly, subcutaneously, peritoneally, peridurally, rectally, nasally, pulmonarily, mucosally, or orally, etc. Such methods and routes, and tools, instruments and/or apparatus suitable therefore are well known to those skilled in the art.

In certain embodiments, the method may comprise: a) isolating from a biological sample of the subject an immune cell or immune cell population as disclosed herein; b) optionally in vitro expanding the immune cell or immune cell population of a); c) loading said in vitro expanded immune cell or immune cell population of b) with the antigen; and d) administering the in vitro expanded antigen loaded immune cell or immune cell population of c) to the subject.

A further aspect of the invention relates to a method for eliciting an immune response or immune tolerance to an antigen in a subject comprising: a) isolating from a biological sample of the subject an immune cell or immune cell population as disclosed herein; b) in vitro differentiating the immune cell or immune cell population of a) into a comparatively more mature immune cell or immune cell population: c) loading said in vitro differentiated immune cell or immune cell population of b) with the antigen; and d) administering the in vitro differentiated antigen loaded immune cell or immune cell population of c) to the subject.

Within the present specification, the terms "differentiation", "differentiating" or derivatives thereof, denote the process by which an unspecialised or relatively less specialised cell becomes relatively more specialised. In the context of cell ontogeny, the adjective "differentiated" is a relative term. Hence, a "differentiated cell" is a cell that has progressed further down a certain developmental pathway than the cell it is being compared with. The differentiated cell may, for example, be a terminally differentiated cell, i.e., a fully specialised cell capable of taking up specialised functions in various tissues or organs of an organism, which may but need not be post-mitotic; or the differentiated cell may itself be a progenitor cell within a particular differentiation lineage which can further proliferate and/or differentiate. A relatively more specialised cell may differ from an unspecialised or relatively less specialised cell in one or more demonstrable phenotypic characteristics, such as, for example, the presence, absence or level of expression of particular cellular components or products, e.g., RNA, proteins or other substances, activity of certain biochemical pathways, morphological appearance, proliferation capacity and/or kinetics, differentiation potential and/or response to differentiation signals, electrophysiological behaviour, etc., wherein such characteristics signify the progression of the relatively more specialised cell further along the said developmental pathway. Non-limiting examples of differentiation may include, e.g., the change of a pluripotent stem cell into a given type of multipotent progenitor or stem cell, the change of a multipotent progenitor or stem cell into a given type of unipotent progenitor or stem cell, or the change of a unipotent progenitor or stem cell to more specialised cell types or to terminally specialised cells within a given cell lineage. Differentiation of an unspecialised or less specialised cell to a more specialised cell may proceed through appearance of cells with an intermediate degree of specialisation. By means of an example, immune cell progenitor or precursor cells may differentiate into (more) mature immune cells, e.g., dendritic cell progenitor or precursor cells may differentiate into dendritic cells.

Suitably, the above methods may in certain embodiments further comprise formulating the in vitro expanded and/or differentiated immune cell or immune cell population into a pharmaceutical composition or vaccine, said pharmaceutical composition or vaccine optionally further comprising an antigen.

In any of the herein described methods, the immune response may comprise an antigen-specific T cell response and/or antigen-specific antibody response.

A further aspect of the invention relates to a method for treating or preventing a pathological condition, such as a disease or disorder, comprising administering to a subject in need thereof the an immune cell or the immune cell population or the pharmaceutical composition or vaccine as disclosed herein.

As used throughout this specification, the terms "treat", "treating" and "treatment" refer to the alleviation or measurable lessening of one or more symptoms or measurable markers of a pathological condition such as a disease or disorder. Measurable lessening includes any statistically significant decline in a measurable marker or symptom. Generally, the terms encompass both curative treatments and treatments directed to reduce symptoms and/or slow progression of the disease. The terms encompass both the therapeutic treatment of an already developed pathological condition, as well as prophylactic or preventative measures, wherein the aim is to prevent or lessen the chances of incidence of a pathological condition. In certain embodiments, the terms may relate to therapeutic treatments. In certain other embodiments, the terms may relate to preventative treatments. Treatment of a chronic pathological condition during the period of remission may also be deemed to constitute a therapeutic treatment. The term may encompass ex vivo or in vivo treatments as appropriate in the context of the present invention.

As used throughout this specification, the terms "prevent", "preventing" and "prevention" refer to the avoidance or delay in manifestation of one or more symptoms or measurable markers of a pathological condition, such as a disease or disorder. A delay in the manifestation of a symptom or marker is a delay relative to the time at which such symptom or marker manifests in a control or untreated subject with a similar likelihood or susceptibility of developing the pathological condition. The terms "prevent", "preventing" and "prevention" include not only the avoidance or prevention of a symptom or marker of the pathological condition, but also a reduced severity or degree of any one of the symptoms or markers of the pathological condition, relative to those symptoms or markers in a control or non-treated individual with a similar likelihood or susceptibility of developing the pathological condition, or relative to symptoms or markers likely to arise based on historical or statistical measures of populations affected by the disease or disorder. By "reduced severity" is meant at least a 10% reduction in the severity or degree of a symptom or measurable marker relative to a control or reference, e.g., at least 15%, 20%, 30%, 40%, 50%, 60%, 70%, 80%, 90%, 95%, 99% or even 100% (i.e., no symptoms or measurable markers).

The terms "disease" or "disorder" are used interchangeably throughout this specification, and refer to any alternation in state of the body or of some of the organs, interrupting or disturbing the performance of the functions and/or causing symptoms such as discomfort, dysfunction, distress, or even death to the person afflicted or those in contact with a person. A disease or disorder can also be related to a distemper, ailing, ailment, malady, disorder, sickness, illness, complaint, indisposition, or affliction.

In certain embodiments, the pathological condition may be an infection, inflammation, proliferative disease, autoimmune disease, or allergy.

The term "infection" as used herein refers to presence of an infective agent, such as a pathogen, e.g., a microorganism, in or on a subject, which, if its presence or growth were inhibited, would result in a benefit to the subject. Hence, the term refers to the state produced by the establishment, more particularly invasion and multiplication, of an infective agent, such as a pathogen, e.g., a microorganism, in or on a suitable host. An infection may produce tissue injury and progress to overt disease through a variety of cellular and toxic mechanisms.

The term "inflammation" generally refers to a response in vasculated tissues to cellular or tissue injury usually caused by physical, chemical and/or biological agents, that is marked in the acute form by the classical sequences of pain, heat, redness, swelling, and loss of function, and serves as a mechanism initiating the elimination, dilution or walling-off of noxious agents and/or of damaged tissue. Inflammation histologically involves a complex series of events, including dilation of the arterioles, capillaries, and venules with increased permeability and blood flow, exudation of fluids including plasma proteins, and leukocyte migration into the inflammatory focus.

Further, the term encompasses inflammation caused by extraneous physical or chemical injury or by biological agents, e.g., viruses, bacteria, fungi, protozoan or metazoan parasite infections, as well as inflammation which is seemingly unprovoked, e.g., which occurs in the absence of demonstrable injury or infection, inflammation responses to self-antigens (autoimmune inflammation), inflammation responses to engrafted xenogeneic or allogeneic cells, tissues or organs, inflammation responses to allergens, etc. The term covers both acute inflammation and chronic inflammation. Also, the term includes both local or localised inflammation, as well as systemic inflammation, i.e., where one or more inflammatory processes are not confined to a particular tissue but occur generally in the endothelium and/or other organ systems.

Systemic inflammatory conditions may particularly encompass systemic inflammatory response syndrome (SIRS) or sepsis. "SIRS" is a systemic inflammatory response syndrome with no signs of infection. It can be characterised by the presence of at least two of the four following clinical criteria: fever or hypothermia (temperature of 38.0° C.) or more, or temperature of 36.0° C. or less); tachycardia (at least 90 beats per minute); tachypnea (at least 20 breaths per minute or $PaCO_2$ less than 4.3 kPa (32.0 mm Hg) or the need for mechanical ventilation); and an altered white blood cell (WBC) count of $12 \times 10^6$ cells/mL or more, or an altered WBC count of $4 \times 10^6$ cells/mL or less, or the presence of more than 10% band forms. "Sepsis" can generally be defined as SIRS with a documented infection, such as for example a bacterial infection. Infection can be diagnosed by standard textbook criteria or, in case of uncertainty, by an infectious disease specialist. Bacteremia is defined as sepsis where bacteria can be cultured from blood. Sepsis may be characterised or staged as mild sepsis, severe sepsis (sepsis with acute organ dysfunction), septic shock (sepsis with refractory arterial hypotension), organ failure, multiple organ dysfunction syndrome and death.

The term "proliferative disease" generally refers to any disease or disorder characterised by neoplastic cell growth and proliferation, whether benign, pre-malignant, or malignant. The term proliferative disease generally includes all transformed cells and tissues and all cancerous cells and tissues. Proliferative diseases or disorders include, but are not limited to abnormal cell growth, benign tumours, pre-malignant or precancerous lesions, malignant tumors, and cancer.

The terms "tumor" or "tumor tissue" refer to an abnormal mass of tissue resulting from excessive cell division. A tumor or tumor tissue comprises "tumor cells" which are neoplastic cells with abnormal growth properties and no useful bodily function. Tumors, tumor tissue and tumor cells may be benign, pre-malignant or malignant, or may represent a lesion without any cancerous potential. A tumor or tumor tissue may also comprise "tumor-associated non-tumor cells", e.g., vascular cells which form blood vessels to supply the tumor or tumor tissue. Non-tumor cells may be induced to replicate and develop by tumor cells, for example, the induction of angiogenesis in a tumor or tumor tissue.

The term "cancer" refers to a malignant neoplasm characterised by deregulated or unregulated cell growth. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor. The term "metastatic" or "metastasis" generally refers to the spread of a cancer from one organ or tissue to another non-adjacent organ or tissue. The occurrence of the proliferative disease in the other non-adjacent organ or tissue is referred to as metastasis.

Examples of cancer include but are not limited to carcinoma, lymphoma, blastoma, sarcoma, and leukemia or lymphoid malignancies. More particular examples of such cancers include without limitation: squamous cell cancer (e.g., epithelial squamous cell cancer), lung cancer including small-cell lung cancer, non-small cell lung cancer, adenocarcinoma of the lung, squamous carcinoma of the lung and large cell carcinoma of the lung, cancer of the peritoneum, hepatocellular cancer, gastric or stomach cancer including gastrointestinal cancer, pancreatic cancer, glioma, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulval cancer, thyroid cancer, hepatic carcinoma, anal carcinoma, penile carcinoma, as well as CNS cancer, melanoma, head and neck cancer, bone cancer, bone marrow cancer, duodenum cancer, oesophageal cancer, thyroid cancer, or hematological cancer.

Other non-limiting examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Disease, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumours, Breast Cancer, Cancer of the Renal Pelvis and Urethra, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Glioblastoma, Childhood Cerebellar Astrocytoma, Childhood Cerebral Astrocytoma, Childhood Extracranial Germ Cell Tumours, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumours, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumours, Exocrine Pancreatic Cancer, Extracranial Germ Cell Tumour, Extragonadal Germ Cell Tumour, Extrahepatic Bile Duct Cancer, Eye Cancer, Female Breast Cancer, Gaucher's Disease, Gallbladder Cancer, Gastric Cancer, Gastrointestinal Carcinoid Tumour, Gastrointestinal Tumours, Germ Cell Tumours, Gestational Trophoblastic Tumour, Hairy Cell Leukemia, Head and Neck Cancer, Hepatocellular Cancer, Hodgkin's Disease, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma During Pregnancy, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumour, Ovarian Low Malignant Potential Tumour, Pancreatic Cancer, Paraproteinemias, Purpura, Parathyroid Cancer, Penile Cancer, Pheochromocytoma, Pituitary Tumour, Plasma Cell Neoplasm/Multiple Myeloma, Primary Central Nervous System Lymphoma, Primary Liver Cancer, Prostate Cancer, Rectal Cancer, Renal Cell Cancer, Renal Pelvis and Urethra Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumours, T-Cell Lymphoma, Testicular Cancer, Thymoma, Thyroid Cancer, Transitional Cell Cancer of the Renal Pelvis and Urethra, Transitional Renal Pelvis and Urethra Cancer, Trophoblastic Tumours, Urethra and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, or Wilms' Tumour.

As used throughout the present specification, the terms "autoimmune disease" or "autoimmune disorder" used interchangeably refer to a diseases or disorders caused by an immune response against a self-tissue or tissue component (self-antigen) and include a self-antibody response and/or cell-mediated response. The terms encompass organ-specific autoimmune diseases, in which an autoimmune response is directed against a single tissue, as well as non-organ specific autoimmune diseases, in which an autoimmune response is directed against a component present in two or more, several or many organs throughout the body.

Non-limiting examples of autoimmune diseases include but are not limited to acute disseminated encephalomyelitis (ADEM); Addison's disease; ankylosing spondylitis; antiphospholipid antibody syndrome (APS); aplastic anemia; autoimmune gastritis; autoimmune hepatitis; autoimmune thrombocytopenia; Behçet's disease; coeliac disease; dermatomyositis; diabetes mellitus type I; Goodpasture's syndrome; Graves' disease; Guillain-Barre syndrome (GBS); Hashimoto's disease; idiopathic thrombocytopenic purpura; inflammatory bowel disease (IBD) including Crohn's disease and ulcerative colitis; mixed connective tissue disease; multiple sclerosis (MS); myasthenia gravis; opsoclonus myoclonus syndrome (OMS); optic neuritis; Ord's thyroiditis; pemphigus; pernicious anaemia; polyarteritis nodosa; polymyositis; primary biliary cirrhosis; primary myoxedema; psoriasis; rheumatic fever; rheumatoid arthritis; Reiter's syndrome; scleroderma; Sjögren's syndrome; systemic lupus erythematosus; Takayasu's arteritis; temporal arteritis; vitiligo; warm autoimmune hemolytic anemia; or Wegener's granulomatosis.

In certain embodiments, the pathological condition is selected from the group consisting of diseases set forth in Tables E10B and E10C.

In certain embodiments, the immune cell or immune cell population may be autologous, syngeneic, allogeneic or xenogeneic to said subject, preferably autologous to said subject.

In certain embodiments, the method may comprise: a) isolating from a biological sample of the subject an immune cell or immune cell population as disclosed herein; b) in vitro expanding the immune cell or immune cell population of a); and c) administering the in vitro expanded immune cell or immune cell population of b) to the subject.

In certain embodiments, the method may further comprise formulating the in vitro expanded immune cell or immune cell population of b) into a pharmaceutical composition or vaccine, said pharmaceutical composition or vaccine optionally further comprising an antigen.

A further aspect of the invention relates to an in vitro method for differentiating an immune cell as disclosed herein into a comparatively more mature immune cell, comprising exposing the immune cell to one or more conditions and/or substances conducive to the differentiation. Such conditions and/or substances may be of physical, chemical, biochemical and/or biological nature. By means of an example, exposing the immune cell to such one or more substances, i.e., contacting the immune cell with such one or more substances, may be suitably achieved by including the one or more substances an aqueous composition comprising the immune cells, e.g., in the culture medium of the in vitro cultured immune cells, in a sufficient amount and for a sufficient duration of time to produce the desired effect on differentiation. Example substances that may be conducive to the differentiation of the immune cells include without limitation hormones, cytokines, lymphokines, growth factors, chemokines, cell surface receptor ligands such as cell surface receptor agonists or antagonists, mitogens, etc.

In certain embodiments, the one or more conditions and/or substances conducive to the differentiation comprise one or more or all (e.g., any one, any two, or all three) of FMS-like tyrosine kinase 3 ligand (FLT3L), stem cell factor (SCF), or granulocyte-macrophage colony-stimulating factor (GM-CSF).

In certain embodiments:
the immune cell as defined in e1), e2) or e3) differentiates into a CD1C positive dendritic cell, preferably into a dendritic cell as defined in any one of b1), b2) or b3), or part c1), c2) or c3);
the immune cell as defined in any one of g1), g2), g3), g4), g5) or g6) differentiates into a CD1C positive dendritic cell, preferably into a dendritic cell as defined in any one of b1), b2) or b3), or part c1), c2) or c3); or
the immune cell as defined in any one of g1), g2), g3), g4), g5) or g6) differentiates into a CD141 positive dendritic cell, preferably into a dendritic cell as defined in any one of a1), a2) or a3).

A further aspect of the invention relates to a method for treating or preventing a pathological condition in a subject in need thereof, the method comprising: a) isolating from a biological sample of the subject an immune cell or immune cell population as disclosed herein; b) in vitro differentiating the immune cell of a) into a comparatively more mature immune cell or immune cell population; and c) administering the in vitro differentiated immune cell or immune cell population of b) to the subject.

Suitably, the method may further comprise formulating the in vitro differentiated immune cell or immune cell population of b) into a pharmaceutical composition or vaccine, said pharmaceutical composition or vaccine optionally further comprising an antigen.

A further aspect of the invention relates to a method for preparing a composition comprising activated T cells, the method comprising isolating T cells from a biological sample of a subject and contacting said T cells in vitro with an immune cell or immune cell population as disclosed herein, wherein the immune cell or immune cell population has been loaded with an antigen.

"Activation" generally refers to the state of a cell, such as preferably T cell, following sufficient cell surface moiety ligation (e.g., interaction between the T cell receptor on the surface of a T cell (such as naturally-occurring TCR or genetically engineered TCR, e.g., chimeric antigen receptor, CAR) and MHC-bound antigen peptide presented on the surface of the immune cell as taught herein) to induce a noticeable biochemical or morphological change of the cell, such as preferably T cell. In particular, "activation" may refer to the state of a T cell that has been sufficiently stimulated to induce detectable cellular proliferation of the T cell. Activation can also encompass induced cytokine production, and detectable T cell effector functions, e.g., regulatory or cytolytic effector functions. The T cells and immune cells may be may be suitably contacted by admixing the T cells and immune cells in an aqueous composition, e.g., in a culture medium, in sufficient numbers and for a sufficient duration of time to produce the desired T cell activation.

In certain embodiments, the immune cell or immune cell population may be autologous, syngeneic, allogeneic or xenogeneic to said subject from whom the T cells are isolated, preferably autologous to said subject.

In certain embodiments, the method may comprise: a) isolating from a biological sample of said subject an immune cell or immune cell population as disclosed herein; b) loading said immune cell or immune cell population with an antigen; c) isolating T cells from a biological sample of said subject; d) in vitro contacting said T cells with an immune cell or immune cell population as disclosed herein loaded with antigen.

A further aspect of the invention relates to a method for adoptive immunotherapy in a subject in need thereof comprising administering to said subject a composition comprising activated T cells prepared with the method as taught above.

In certain embodiments, said T cells are CD8+ T cells, i.e., T cells expressing the CD8+ cell surface marker. More preferably, said T cells may be CD8+ T cells and said subject is suffering from proliferative disease.

In certain embodiments, the T cell, preferably a CD8+ T cell, may display specificity to a desired antigen, such as specificity to a tumor antigen (tumor antigen specificity). By means of an example, the T cell, preferably a CD8+ T cell, may have been isolated from a tumor of a subject. More preferably, the immune cell may be a tumor infiltrating lymphocyte (TIL). Generally, "tumor infiltrating lymphocytes" or "TILs" refer to white blood cells that have left the bloodstream and migrated into a tumor. Such T cells typically endogenously express a T cell receptor having specificity to an antigen expressed by the tumor cells (tumor antigen specificity).

In alternative embodiments, a T cell, preferably a CD8+ T cell, may be engineered to express a T cell receptor having specificity to a desired antigen, such as specificity to a tumor antigen (tumor antigen specificity). For example, the T cell, preferably a CD8+ T cell, may comprise a chimeric antigen receptor (CAR) having specificity to a desired antigen, such as a tumor-specific chimeric antigen receptor (CAR).

Accordingly, aspects of the invention involve the adoptive transfer of immune system cells, such as T cells, specific for selected antigens, such as tumor associated antigens.

Adoptive cell therapy (ACT) can refer to the transfer of cells, most commonly immune-derived cells, back into the same patient or into a new recipient host with the goal of transferring the immunologic functionality and characteristics into the new host. If possible, use of autologous cells helps the recipient by minimizing GVHD issues. The adoptive transfer of autologous tumor infiltrating lymphocytes (TIL) (Besser et al., (2010) Clin. Cancer Res 16 (9) 2646-55; Dudley et al., (2002) Science 298 (5594): 850-4; and Dudley et al., (2005) Journal of Clinical Oncology 23 (10): 2346-57.) or genetically re-directed peripheral blood mononuclear cells (Johnson et al., (2009) Blood 114 (3): 535-46; and Morgan et al., (2006) Science 314(5796)126-9) has been used to successfully treat patients with advanced solid tumors, including melanoma and colorectal carcinoma, as well as patients with CD19-expressing hematologic malignancies (Kalos et al., (2011) Science Translational Medicine 3 (95): 95ra73).

Aspects of the invention involve the adoptive transfer of immune system cells, such as T cells, specific for selected antigens, such as tumor associated antigens (see Maus et al., 2014, Adoptive Immunotherapy for Cancer or Viruses, Annual Review of Immunology, Vol. 32: 189-225; Rosenberg and Restifo, 2015, Adoptive cell transfer as personalized immunotherapy for human cancer, Science Vol. 348 no. 6230 pp. 62-68; Restifo et al., 2015, Adoptive immunotherapy for cancer: harnessing the T cell response. Nat. Rev. Immunol. 12(4): 269-281; and Jenson and Riddell, 2014, Design and implementation of adoptive therapy with chimeric antigen receptor-modified T cells. Immunol Rev. 257(1): 127-144). Various strategies may for example be employed to genetically modify T cells by altering the specificity of the T cell receptor (TCR) for example by introducing new TCR α and β chains with selected peptide specificity (see U.S. Pat. No. 8,697,854; PCT Patent Publications: WO2003020763, WO2004033685, WO2004044004, WO2005114215, WO2006000830, WO2008038002, WO2008039818, WO2004074322, WO2005113595, WO2006125962, WO2013166321, WO2013039889, WO2014018863, WO2014083173; U.S. Pat. No. 8,088,379).

As an alternative to, or addition to, TCR modifications, chimeric antigen receptors (CARs) may be used in order to generate immunoresponsive cells, such as T cells, specific for selected targets, such as malignant cells, with a wide variety of receptor chimera constructs having been described (see U.S. Pat. Nos. 5,843,728; 5,851,828; 5,912,170; 6,004,811; 6,284,240; 6,392,013; 6,410,014; 6,753,162; 8,211,422; and, PCT Publication WO9215322). Alternative CAR constructs may be characterized as belonging to successive generations. First-generation CARs typically consist of a single-chain variable fragment of an antibody specific for an antigen, for example comprising a $V_L$ linked to a $V_H$ of a specific antibody, linked by a flexible linker, for example by a CD8α hinge domain and a CD8α transmembrane domain, to the transmembrane and intracellular signaling domains of either CD3ζ or FcRγ (scFv-CD3ζ or scFv-FcRγ; see U.S. Pat. Nos. 7,741,465; 5,912,172; 5,906,936). Second-generation CARs incorporate the intracellular domains of one or more costimulatory molecules, such as CD28, OX40 (CD134), or 4-1BB (CD137) within the endodomain (for example scFv-CD28/OX40/4-1BB-CD3ζ; see U.S. Pat. Nos. 8,911,993; 8,916,381; 8,975,071; 9,101,584; 9,102,760; 9,102,761). Third-generation CARs include a combination of costimulatory endodomains, such as a CD3ζ-chain, CD97, GDI 1a-CD18, CD2, ICOS, CD27, CD154, CDS, OX40, 4-1BB, or CD28 signaling domains (for example scFv-CD28-4-1BB-CD3ζ or scFv-CD28-OX40-CD3ζ; see U.S. Pat. Nos. 8,906,682; 8,399,645; 5,686,281; PCT Publication No. WO2014134165; PCT Publication No. WO2012079000). Alternatively, costimulation may be orchestrated by expressing CARs in antigen-specific T cells, chosen so as to be activated and expanded following engagement of their native αβTCR, for example by antigen on professional antigen-presenting cells, with attendant costimulation. In addition, additional engineered receptors may be provided on the immunoresponsive cells, for example to improve targeting of a T-cell attack and/or minimize side effects.

Alternative techniques may be used to transform target immunoresponsive cells, such as protoplast fusion, lipofection, transfection or electroporation. A wide variety of vectors may be used, such as retroviral vectors, lentiviral vectors, adenoviral vectors, adeno-associated viral vectors, plasmids or transposons, such as a Sleeping Beauty transposon (see U.S. Pat. Nos. 6,489,458; 7,148,203; 7,160,682; 7,985,739; 8,227,432), may be used to introduce CARs, for example using 2nd generation antigen-specific CARs signaling through CD3ζ and either CD28 or CD137. Viral vectors may for example include vectors based on HIV, SV40, EBV, HSV or BPV.

Cells that are targeted for transformation may for example include T cells, Natural Killer (NK) cells, cytotoxic T lymphocytes (CTL), regulatory T cells, human embryonic stem cells, tumor-infiltrating lymphocytes (TIL) or a pluripotent stem cell from which lymphoid cells may be differentiated. T cells expressing a desired CAR may for example be selected through co-culture with γ-irradiated activating and propagating cells (AaPC), which co-express the cancer antigen and co-stimulatory molecules. The engineered CAR T-cells may be expanded, for example by co-culture on AaPC in presence of soluble factors, such as IL-2 and IL-21. This expansion may for example be carried out so as to provide memory CAR+ T cells (which may for example be assayed by non-enzymatic digital array and/or multi-panel flow cytometry). In this way, CAR T cells may be provided that have specific cytotoxic activity against antigen-bearing tumors (optionally in conjunction with production of desired chemokines such as interferon-γ). CAR T cells of this kind may for example be used in animal models, for example to treat tumor xenografts.

Approaches such as the foregoing may be adapted to provide methods of treating and/or increasing survival of a subject having a disease, such as a neoplasia, for example by administering an effective amount of an immunoresponsive cell comprising an antigen recognizing receptor that binds a selected antigen, wherein the binding activates the immunoresponsive cell, thereby treating or preventing the disease (such as a neoplasia, a pathogen infection, an autoimmune disorder, or an allogeneic transplant reaction).

In one embodiment, the treatment can be administrated into patients undergoing an immunosuppressive treatment. The cells or population of cells, may be made resistant to at least one immunosuppressive agent due to the inactivation of a gene encoding a receptor for such immunosuppressive agent. Not being bound by a theory, the immunosuppressive treatment should help the selection and expansion of the immunoresponsive or T cells according to the invention within the patient.

The administration of the cells or population of cells according to the present invention may be carried out in any convenient manner, including by aerosol inhalation, injection, ingestion, transfusion, implantation or transplantation. The cells or population of cells may be administered to a patient subcutaneously, intradermally, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. Dosing in CAR T cell therapies may for example involve administration of from $10^6$ to $10^9$ cells/kg, with or without a course of lymphodepletion, for example with cyclophosphamide. The cells or population of cells can be administrated in one or more doses. In another embodiment, the effective amount of cells are administrated as a single dose. In another embodiment, the effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions are within the skill of one in the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, the effective amount of cells or composition comprising those cells are administrated parenterally. The administration can be an intravenous administration. The administration can be directly done by injection within a tumor.

To guard against possible adverse reactions, engineered immunoresponsive cells may be equipped with a transgenic safety switch, in the form of a transgene that renders the cells vulnerable to exposure to a specific signal. For example, the herpes simplex viral thymidine kinase (TK) gene may be used in this way, for example by introduction into allogeneic T lymphocytes used as donor lymphocyte infusions following stem cell transplantation (Greco, et al., Improving the safety of cell therapy with the TK-suicide gene. Front. Pharmacol. 2015; 6: 95). In such cells, administration of a nucleoside prodrug such as ganciclovir or acyclovir causes cell death. Alternative safety switch constructs include inducible caspase 9, for example triggered by administration of a small-molecule dimerizer that brings together two nonfunctional icasp9 molecules to form the active enzyme. A wide variety of alternative approaches to implementing cellular proliferation controls have been described (see U.S. Patent Publication No. 20130071414; PCT Patent Publication WO2011146862; PCT Patent Publication WO2014011987; PCT Patent Publication WO2013040371; Zhou et al. BLOOD, 2014, 123/25:3895-3905; Di Stasi et al., The New England Journal of Medicine 2011; 365:1673-1683; Sadelain M, The New England Journal of Medicine 2011; 365:1735-173; Ramos et al., Stem Cells 28(6):1107-15 (2010)).

In a further refinement of adoptive therapies, genome editing may be used to tailor immunoresponsive cells to alternative implementations, for example providing edited CAR T cells (see Poirot et al., 2015, Multiplex genome edited T-cell manufacturing platform for "off-the-shelf" adoptive T-cell immunotherapies, Cancer Res 75 (18): 3853). Cells may be edited using any CRISPR system and method of use thereof as described herein. CRISPR systems may be delivered to an immune cell by any method described herein. In preferred embodiments, cells are edited ex vivo and transferred to a subject in need thereof. Immunoresponsive cells, CAR T cells or any cells used for adoptive cell transfer may be edited. Editing may be performed to eliminate potential alloreactive T-cell receptors (TCR), disrupt the target of a chemotherapeutic agent, block an immune checkpoint, activate a T cell, and/or increase the differentiation and/or proliferation of functionally exhausted or dysfunctional CD8+ T-cells (see PCT Patent Publications: WO2013176915, WO2014059173, WO2014172606, WO2014184744, and WO2014191128). Editing may result in inactivation of a gene.

By inactivating a gene it is intended that the gene of interest is not expressed in a functional protein form. In a particular embodiment, the CRISPR system specifically catalyzes cleavage in one targeted gene thereby inactivating said targeted gene. The nucleic acid strand breaks caused are commonly repaired through the distinct mechanisms of homologous recombination or non-homologous end joining (NHEJ). However, NHEJ is an imperfect repair process that often results in changes to the DNA sequence at the site of the cleavage. Repair via non-homologous end joining (NHEJ) often results in small insertions or deletions (Indel) and can be used for the creation of specific gene knockouts. Cells in which a cleavage induced mutagenesis event has occurred can be identified and/or selected by well-known methods in the art.

T cell receptors (TCR) are cell surface receptors that participate in the activation of T cells in response to the presentation of antigen. The TCR is generally made from two chains, α and β, which assemble to form a heterodimer and associates with the CD3-transducing subunits to form the T cell receptor complex present on the cell surface. Each α and β chain of the TCR consists of an immunoglobulin-like N-terminal variable (V) and constant (C) region, a hydrophobic transmembrane domain, and a short cytoplasmic region. As for immunoglobulin molecules, the variable region of the α and β chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of graft versus host disease (GVHD). The inactivation of TCRα or TCRβ can result in the elimination of the TCR from the surface of T cells preventing recognition of alloantigen and thus GVHD. However, TCR disruption generally results in the elimination of the CD3 signaling component and alters the means of further T cell expansion.

Allogeneic cells are rapidly rejected by the host immune system. It has been demonstrated that, allogeneic leukocytes present in non-irradiated blood products will persist for no more than 5 to 6 days (Boni, Muranski et al. 2008 Blood 1; 112(12):4746-54). Thus, to prevent rejection of allogeneic cells, the host's immune system usually has to be suppressed to some extent. However, in the case of adoptive cell transfer the use of immunosuppressive drugs also have a detrimental effect on the introduced therapeutic T cells. Therefore, to effectively use an adoptive immunotherapy approach in these conditions, the introduced cells would need to be resistant to the immunosuppressive treatment. Thus, in a particular embodiment, the present invention further comprises a step of modifying T cells to make them resistant to an immunosuppressive agent, preferably by inactivating at least one gene encoding a target for an immunosuppressive agent. An immunosuppressive agent is an agent that suppresses immune function by one of several mechanisms of action. An immunosuppressive agent can be, but is not limited to a calcineurin inhibitor, a target of rapamycin, an interleukin-2 receptor α-chain blocker, an inhibitor of inosine monophosphate dehydrogenase, an inhibitor of dihydrofolic acid reductase, a corticosteroid or an immunosuppressive antimetabolite. The present invention allows conferring immunosuppressive resistance to T cells for immunotherapy by inactivating the target of the immunosuppressive agent in T cells. As non-limiting examples, targets for an immunosuppressive agent can be a receptor for an immunosuppressive agent such as: CD52, glucocorticoid receptor (GR), a FKBP family gene member and a cyclophilin family gene member.

Immune checkpoints are inhibitory pathways that slow down or stop immune reactions and prevent excessive tissue damage from uncontrolled activity of immune cells. In certain embodiments, the immune checkpoint targeted is the programmed death-1 (PD-1 or CD279) gene (PDCD1). In other embodiments, the immune checkpoint targeted is cytotoxic T-lymphocyte-associated antigen (CTLA-4). In additional embodiments, the immune checkpoint targeted is another member of the CD28 and CTLA4 Ig superfamily such as BTLA, LAG3, ICOS, PDL1 or KIR. In further additional embodiments, the immune checkpoint targeted is a member of the TNFR superfamily such as CD40, OX40, CD137, GITR, CD27 or TIM-3.

Additional immune checkpoints include Src homology 2 domain-containing protein tyrosine phosphatase 1 (SHP-1) (Watson H A, et al., SHP-1: the next checkpoint target for cancer immunotherapy? Biochem Soc Trans. 2016 Apr. 15; 44(2):356-62). SHP-1 is a widely expressed inhibitory protein tyrosine phosphatase (PTP). In T-cells, it is a negative regulator of antigen-dependent activation and proliferation. It is a cytosolic protein, and therefore not amenable to antibody-mediated therapies, but its role in activation and proliferation makes it an attractive target for genetic manipulation in adoptive transfer strategies, such as chimeric antigen receptor (CAR) T cells. Immune checkpoints may also include T cell immunoreceptor with Ig and ITIM domains (TIGIT/Vstm3/WUCAM/VSIG9) and VISTA (Le Mercier I, et al., (2015) Beyond CTLA-4 and PD-1, the generation Z of negative checkpoint regulators. Front. Immunol. 6:418).

WO2014172606 relates to the use of MT1 and/or MT1 inhibitors to increase proliferation and/or activity of exhausted CD8+ T-cells and to decrease CD8+ T-cell exhaustion (e.g., decrease functionally exhausted or unresponsive CD8+ immune cells). In certain embodiments, metallothioneins are targeted by gene editing in adoptively transferred T cells.

In certain embodiments, targets of gene editing may be at least one targeted locus involved in the expression of an immune checkpoint protein. Such targets may include, but are not limited to CTLA4, PPP2CA, PPP2CB, PTPN6, PTPN22, PDCD1, ICOS (CD278), PDL1, KIR, LAG3, HAVCR2, BTLA, CD160, TIGIT, CD96, CRTAM, LAIR1, SIGLEC7, SIGLEC9, CD244 (2B4), TNFRSF10B, TNFRSF10A, CASP8, CASP10, CASP3, CASP6, CASP7, FADD, FAS, TGFBRII, TGFBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, VISTA, GUCY1A2, GUCY1A3, GUCY1B2, GUCY1B3, MT1, MT2, CD40, OX40, CD137, GITR, CD27, SHP-1 or TIM-3. In preferred embodiments, the gene locus involved in the expression of PD-1 or CTLA-4 genes is targeted. In other preferred embodiments, combinations of genes are targeted, such as but not limited to PD-1 and TIGIT.

In other embodiments, at least two genes are edited. Pairs of genes may include, but are not limited to PD1 and TCRα, PD1 and TCRβ, CTLA-4 and TCRα, CTLA-4 and TCRβ, LAG3 and TCRα, LAG3 and TCRβ, Tim3 and TCRα, Tim3 and TCRβ, BTLA and TCRα, BTLA and TCRβ, BY55 and TCRα, BY55 and TCRβ, TIGIT and TCRα, TIGIT and TCRβ, B7H5 and TCRα, B7H5 and TCRβ, LAIR1 and TCRα, LAIR1 and TCRβ, SIGLEC10 and TCRα, SIGLEC10 and TCRβ, 2B4 and TCRα, 2B4 and TCRβ.

Whether prior to or after genetic modification of the T cells, the T cells can be activated and expanded generally using methods as described, for example, in U.S. Pat. Nos. 6,352,694; 6,534,055; 6,905,680; 5,858,358; 6,887,466; 6,905,681; 7,144,575; 7,232,566; 7,175,843; 5,883,223; 6,905,874; 6,797,514; 6,867,041; and 7,572,631. T cells can be expanded in vitro or in vivo.

A further aspect of the invention relates to a method for identifying an immunomodulant capable of modulating one or more phenotypic aspects of an immune cell or immune cell population as disclosed herein, comprising: a) applying a candidate immunomodulant to the immune cell or immune cell population; b) detecting modulation of one or more phenotypic aspects of the immune cell or immune cell population by the candidate immunomodulant, thereby identifying the immunomodulant.

The term "modulate" broadly denotes a qualitative and/or quantitative alteration, change or variation in that which is being modulated. Where modulation can be assessed quantitatively—for example, where modulation comprises or consists of a change in a quantifiable variable such as a quantifiable property of a cell or where a quantifiable variable provides a suitable surrogate for the modulation—modulation specifically encompasses both increase (e.g., activation) or decrease (e.g., inhibition) in the measured variable. The term encompasses any extent of such modulation, e.g., any extent of such increase or decrease, and may more particularly refer to statistically significant increase or decrease in the measured variable. By means of example, modulation may encompass an increase in the value of the measured variable by at least about 10%, e.g., by at least about 20%, preferably by at least about 30%, e.g., by at least about 40%, more preferably by at least about 50%, e.g., by at least about 75%, even more preferably by at least about 100%, e.g., by at least about 150%, 200%, 250%, 300%, 400% or by at least about 500%, compared to a reference situation without said modulation; or modulation may encompass a decrease or reduction in the value of the measured variable by at least about 10%, e.g., by at least about 20%, by at least about 30%, e.g., by at least about 40%, by at least about 50%, e.g., by at least about 60%, by at least about 70%, e.g., by at least about 80%, by at least about 90%, e.g., by at least about 95%, such as by at least about 96%, 97%, 98%, 99% or even by 100%, compared to a reference situation without said modulation. Preferably, modulation may be specific or selective, hence, one or more desired phenotypic aspects of an immune cell or immune cell population may be modulated without substantially altering other (unintended, undesired) phenotypic aspect(s).

The term "immunomodulant" broadly encompasses any condition, substance or agent capable of modulating one or more phenotypic aspects of an immune cell or immune cell population as disclosed herein. Such conditions, substances or agents may be of physical, chemical, biochemical and/or biological nature. The term "candidate immunomodulant" refers to any condition, substance or agent that is being examined for the ability to modulate one or more phenotypic aspects of an immune cell or immune cell population as disclosed herein in a method comprising applying the candidate immunomodulant to the immune cell or immune cell population (e.g., exposing the immune cell or immune cell population to the candidate immunomodulant or contacting the immune cell or immune cell population with the candidate immunomodulant) and observing whether the desired modulation takes place.

Immunomodulants may include any potential class of biologically active conditions, substances or agents, such as for instance antibodies, proteins, peptides, nucleic acids, oligonucleotides, small molecules, or combinations thereof.

By means of example but without limitation, immunomodulants can include low molecular weight compounds, but may also be larger compounds, or any organic or inorganic molecule effective in the given situation, including modified and unmodified nucleic acids such as antisense nucleic acids, RNAi, such as siRNA or shRNA, CRISPR/Cas systems, peptides, peptidomimetics, receptors, ligands, and antibodies, aptamers, polypeptides, nucleic acid analogues or variants thereof. Examples include an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof. Agents can be selected from a group comprising: chemicals; small molecules; nucleic acid sequences; nucleic acid analogues; proteins; peptides; aptamers; antibodies; or fragments thereof. A nucleic acid sequence can be RNA or DNA, and can be single or double stranded, and can be selected from a group comprising; nucleic acid encoding a protein of interest, oligonucleotides, nucleic acid analogues, for example peptide-nucleic acid (PNA), pseudo-complementary PNA (pc-PNA), locked nucleic acid (LNA), modified RNA (mod-RNA), single guide RNA etc. Such nucleic acid sequences include, for example, but are not limited to, nucleic acid sequence encoding proteins, for example that act as transcriptional repressors, antisense molecules, ribozymes, small inhibitory nucleic acid sequences, for example but are not limited to RNAi, shRNAi, siRNA, micro RNAi (mRNAi), antisense oligonucleotides, CRISPR guide RNA, for example that target a CRISPR enzyme to a specific DNA target sequence etc. A protein and/or peptide or fragment thereof can be any protein of interest, for example, but are not limited to: mutated proteins; therapeutic proteins and truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, minibodies, triabodies, humanized proteins, humanized antibodies, chimeric antibodies, modified proteins and fragments thereof. Alternatively, the agent can be intracellular within the cell as a result of introduction of a nucleic acid sequence into the cell and its transcription resulting in the production of the nucleic acid and/or protein modulator of a gene within the cell. In some embodiments, the agent is any chemical, entity or moiety, including without limitation synthetic and naturally-occurring non-proteinaceous entities. In certain embodiments the agent is a small molecule having a chemical moiety. Agents can be known to have a desired activity and/or property, or can be selected from a library of diverse compounds.

In certain embodiments, an immunomodulant may be a hormone, a cytokine, a lymphokine, a growth factor, a chemokine, a cell surface receptor ligand such as a cell surface receptor agonist or antagonist, or a mitogen.

Non-limiting examples of hormones include growth hormone (GH), adrenocorticotropic hormone (ACTH), dehydroepiandrosterone (DHEA), cortisol, epinephrine, thyroid hormone, estrogen, progesterone, testosterone, or combinations thereof.

Non-limiting examples of cytokines include lymphokines (e.g., interferon-γ, IL-2, IL-3, IL-4, IL-6, granulocyte-macrophage colony-stimulating factor (GM-CSF), interferon-γ, leukocyte migration inhibitory factors (T-LIF, B-LIF), lymphotoxin-alpha, macrophage-activating factor (MAF), macrophage migration-inhibitory factor (MIF), neuroleukin, immunologic suppressor factors, transfer factors, or combinations thereof), monokines (e.g., IL-1, TNF-alpha, interferon-α, interferon-β, colony stimulating factors, e.g., CSF2, CSF3, macrophage CSF or GM-CSF, or combinations thereof), chemokines (e.g., beta-thromboglobulin, C chemokines, CC chemokines, CXC chemokines, CX3C chemokines, macrophage inflammatory protein (MIP), or combinations thereof), interleukins (e.g., IL-1, IL-2, IL-3, IL-4, IL-5, IL-6, IL-7, IL-8, IL-9, IL-10, IL-11, IL-12, IL-13, IL-14, IL-15, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, IL-36, or combinations thereof), and several related signalling molecules, such as tumour necrosis factor (TNF) and interferons (e.g., interferon-α, interferon-β, interferon-γ, interferon-λ, or combinations thereof).

Non-limiting examples of growth factors include those of fibroblast growth factor (FGF) family, bone morphogenic protein (BMP) family, platelet derived growth factor (PDGF) family, transforming growth factor beta (TGFbeta) family, nerve growth factor (NGF) family, epidermal growth factor (EGF) family, insulin related growth factor (IGF) family, hepatocyte growth factor (HGF) family, hematopoietic growth factors (HeGFs), platelet-derived endothelial cell growth factor (PD-ECGF), angiopoietin, vascular endothelial growth factor (VEGF) family, glucocorticoids, or combinations thereof.

Non-limiting examples of mitogens include phytohaemagglutinin (PHA), concanavalin A (conA), lipopolysaccharide (LPS), pokeweed mitogen (PWM), phorbol ester such as phorbol myristate acetate (PMA) with or without ionomycin, or combinations thereof.

Non-limiting examples of cell surface receptors the ligands of which may act as immunomodulants include Toll-like receptors (TLRs) (e.g., TLR1, TLR2, TLR3, TLR4, TLR5, TLR6, TLR7, TLR8, TLR9, TLR10, TLR11, TLR12 or TLR13), CD80, CD86, CD40, CCR7, or C-type lectin receptors.

In certain embodiments, an immunomodulant may comprise altering expression and/or activity of one or more endogenous genes of the immune cell. The term "altered expression" denotes that the modification of the immune cell alters, i.e., changes or modulates, the expression of the recited gene(s) or polypeptides(s). The term "altered expression" encompasses any direction and any extent of said alteration. Hence, "altered expression" may reflect qualitative and/or quantitative change(s) of expression, and specifically encompasses both increase (e.g., activation or stimulation) or decrease (e.g., inhibition) of expression.

The terms "increased" or "increase" or "upregulated" or "upregulate" as used herein generally mean an increase by a statically significant amount. For avoidance of doubt, "increased" means a statistically significant increase of at least 10% as compared to a reference level, including an increase of at least 20%, at least 30%, at least 40%, at least 50%, at least 60%, at least 70%, at least 80%, at least 90%, at least 100% or more, including, for example at least 2-fold, at least 3-fold, at least 4-fold, at least 5-fold, at least 10-fold increase or greater as compared to a reference level, as that term is defined herein.

The term "reduced" or "reduce" or "decrease" or "decreased" or "downregulate" or "downregulated" as used herein generally means a decrease by a statistically significant amount relative to a reference. For avoidance of doubt, "reduced" means statistically significant decrease of at least 10% as compared to a reference level, for example a decrease by at least 20%, at least 30%, at least 40%, at least t 50%, or least 60%, or least 70%, or least 80%, at least 90% or more, up to and including a 100% decrease (i.e., absent level as compared to a reference sample), or any decrease between 10-100% as compared to a reference level, as that term is defined herein. The term "abolish" or "abolished" may in particular refer to a decrease by 100%, i.e., absent level as compared to a reference sample.

Any one or more of the several successive molecular mechanisms involved in the expression of a given gene or polypeptide may be targeted by the immune cell modification as intended herein. Without limitation, these may include targeting the gene sequence (e.g., targeting the polypeptide-encoding, non-coding and/or regulatory portions of the gene sequence), the transcription of the gene into RNA, the polyadenylation and where applicable splicing and/or other post-transcriptional modifications of the RNA into mRNA, the localisation of the mRNA into cell cytoplasm, where applicable other post-transcriptional modifications of the mRNA, the translation of the mRNA into a polypeptide chain, where applicable post-translational modifications of the polypeptide, and/or folding of the polypeptide chain into the mature conformation of the polypeptide. For compartmentalised polypeptides, such as secreted polypeptides and transmembrane polypeptides, this may further include targeting trafficking of the polypeptides, i.e., the cellular mechanism by which polypeptides are transported to the appropriate sub-cellular compartment or organelle, membrane, e.g. the plasma membrane, or outside the cell.

Hence, "altered expression" may particularly denote altered production of the recited gene products by the modified immune cell. As used herein, the term "gene product(s)" includes RNA transcribed from a gene (e.g., mRNA), or a polypeptide encoded by a gene or translated from RNA.

Also, "altered expression" as intended herein may encompass modulating the activity of one or more endogenous gene products. Accordingly, "altered expression", "altering expression", "modulating expression", or "detecting expression" or similar may be used interchangeably with respectively "altered expression or activity", "altering expression or activity", "modulating expression or activity", or "detecting expression or activity" or similar. As used herein, "modulating" or "to modulate" generally means either reducing or inhibiting the activity of a target or antigen, or alternatively increasing the activity of the target or antigen, as measured using a suitable in vitro, cellular or in vivo assay. In particular, "modulating" or "to modulate" can mean either reducing or inhibiting the (relevant or intended) activity of, or alternatively increasing the (relevant or intended) biological activity of the target or antigen, as measured using a suitable in vitro, cellular or in vivo assay (which will usually depend on the target or antigen involved), by at least 5%, at least 10%, at least 25%, at least 50%, at least 60%, at least 70%, at least 80%, or 90% or more, compared to activity of the target or antigen in the same assay under the same conditions but without the presence of the inhibitor/antagonist agents or activator/agonist agents described herein.

As will be clear to the skilled person, "modulating" can also involve effecting a change (which can either be an increase or a decrease) in affinity, avidity, specificity and/or selectivity of a target or antigen, for one or more of its targets compared to the same conditions but without the presence of a modulating agent. Again, this can be determined in any suitable manner and/or using any suitable assay known per se, depending on the target. In particular, an action as an inhibitor/antagonist or activator/agonist can be such that an intended biological or physiological activity is increased or decreased, respectively, by at least 5%, at least 10%, at least 25%, at least 50%, at least 60%, at least 70%, at least 80%, or 90% or more, compared to the biological or physiological activity in the same assay under the same conditions but without the presence of the inhibitor/antagonist agent or activator/agonist agent. Modulating can also involve activating the target or antigen or the mechanism or pathway in which it is involved.

In certain embodiments, an immunomodulant may be or may result in a genetic modification (e.g., mutation, editing, transgenesis, or combinations thereof) of an immune cell, for example, a genetic perturbation, such as a knock-out (i.e., resulting in a complete absence of expression and/or activity) of one or more endogenous genes/gene products, or a knock-down (i.e., resulting in a partial absence of expression and/or activity) of one or more endogenous genes/gene products, or another type of genetic modification modulating the expression and/or activity of one or more endogenous genes/gene products, or for example, introduction of one or more transgenes, such as one or more transgenes encoding one or more gene products. Such transgene may be suitably operably linked to suitable regulatory sequences, e.g., may be comprised in an expression cassette or an expression vector comprising suitable regulatory sequences, or may be configured to become operably linked to suitable regulatory sequences once inserted into the genetic material (e.g., genome) of the immune cell.

Any types of mutations achieving the intended effects are contemplated herein. For example, suitable mutations may include deletions, insertions, and/or substitutions, The term "deletion" refers to a mutation wherein one or more nucleotides, typically consecutive nucleotides, of a nucleic acid are removed, i.e., deleted, from the nucleic acid. The term "insertion" refers to a mutation wherein one or more nucleotides, typically consecutive nucleotides, are added, i.e., inserted, into a nucleic acid. The term "substitution" refers to a mutation wherein one or more nucleotides of a nucleic acid are each independently replaced, i.e., substituted, by another nucleotide.

In certain embodiments, a mutation may introduce a premature in-frame stop codon into the open reading frame (ORF) encoding a gene product. Such premature stop codon may lead to production of a C-terminally truncated form of said polypeptide (this may preferably affect, such as diminish or abolish, some or all biological function(s) of the polypeptide) or, especially when the stop codon is introduced close to (e.g., about 20 or less, or about 10 or less amino acids downstream of) the translation initiation codon of the ORF, the stop codon may effectively abolish the production of the polypeptide. Various ways of introducing a premature in-frame stop codon are apparent to a skilled person. For example but without limitation, a suitable insertion, deletion or substitution of one or more nucleotides in the ORF may introduce the premature in-frame stop codon.

In other embodiments, a mutation may introduce a frame shift (e.g., +1 or +2 frame shift) in the ORF encoding a gene product. Typically, such frame shift may lead to a previously out-of-frame stop codon downstream of the mutation becoming an in-frame stop codon. Hence, such frame shift may lead to production of a form of the polypeptide having an alternative C-terminal portion and/or a C-terminally truncated form of said polypeptide (this may preferably affect, such as diminish or abolish, some or all biological function(s) of the polypeptide) or, especially when the mutation is introduced close to (e.g., about 20 or less, or about 10 or less amino acids downstream of) the translation initiation codon of the ORF, the frame shift may effectively abolish the production of the polypeptide. Various ways of introducing a frame shift are apparent to a skilled person. For example but without limitation, a suitable insertion or deletion of one or more (not multiple of 3) nucleotides in the ORF may lead to a frame shift.

In further embodiments, a mutation may delete at least a portion of the ORF encoding a gene product. Such deletion may lead to production of an N-terminally truncated form, a C-terminally truncated form and/or an internally deleted form of said polypeptide (this may preferably affect, such as diminish or abolish, some or all biological function(s) of the polypeptide). Preferably, the deletion may remove about 20% or more, or about 50% or more of the ORF's nucleotides. Especially when the deletion removes a sizeable portion of the ORF (e.g., about 50% or more, preferably about 60% or more, more preferably about 70% or more, even more preferably about 80% or more, still more preferably about 90% or more of the ORF's nucleotides) or when the deletion removes the entire ORF, the deletion may effectively abolish the production of the polypeptide. The skilled person can readily introduce such deletions.

In further embodiments, a mutation may delete at least a portion of a gene promoter, leading to impaired transcription of the gene product.

In certain other embodiments, a mutation may be a substitution of one or more nucleotides in the ORF encoding a gene product resulting in substitution of one or more amino acids of the polypeptide. Such mutation may typically preserve the production of the polypeptide, and may preferably affect, such as diminish or abolish, some or all biological function(s) of the polypeptide. The skilled person can readily introduce such substitutions.

In certain preferred embodiments, a mutation may abolish native splicing of a pre-mRNA encoding a gene product. In the absence of native splicing, the pre-mRNA may be degraded, or the pre-mRNA may be alternatively spliced, or the pre-mRNA may be spliced improperly employing latent splice site(s) if available. Hence, such mutation may typically effectively abolish the production of the polypeptide's mRNA and thus the production of the polypeptide. Various ways of interfering with proper splicing are available to a skilled person, such as for example but without limitation, mutations which alter the sequence of one or more sequence elements required for splicing to render them inoperable, or mutations which comprise or consist of a deletion of one or more sequence elements required for splicing. The terms "splicing", "splicing of a gene", "splicing of a pre-mRNA" and similar as used herein are synonymous and have their art-established meaning. By means of additional explanation, splicing denotes the process and means of removing intervening sequences (introns) from pre-mRNA in the process of producing mature mRNA. The reference to splicing particularly aims at native splicing such as occurs under normal physiological conditions. The terms "pre-mRNA" and "transcript" are used herein to denote RNA species that precede mature mRNA, such as in particular a primary RNA transcript and any partially processed forms thereof. Sequence elements required for splicing refer particularly to cis elements in the sequence of pre-mRNA which direct the cellular splicing machinery (spliceosome) towards correct and precise removal of introns from the pre-mRNA. Sequence elements involved in splicing are generally known per se and can be further determined by known techniques including inter alia mutation or deletion analysis. By means of further explanation, "splice donor site" or "5' splice site" generally refer to a conserved sequence immediately adjacent to an exon-intron boundary at the 5' end of an intron. Commonly, a splice donor site may contain a dinucleotide GU, and may involve a consensus sequence of about 8 bases at about positions +2 to −6. "Splice acceptor site" or "3' splice site" generally refers to a conserved sequence immediately adjacent to an intron-exon boundary at the 3' end of an intron. Commonly, a splice acceptor site may contain a dinucleotide AG, and may involve a consensus sequence of about 16 bases at about positions −14 to +2.

In certain embodiments, one or more endogenous genes may be modified using a nuclease.

The term "nuclease" as used herein broadly refers to an agent, for example a protein or a small molecule, capable of cleaving a phosphodiester bond connecting nucleotide residues in a nucleic acid molecule. In some embodiments, a nuclease may be a protein, e.g., an enzyme that can bind a nucleic acid molecule and cleave a phosphodiester bond connecting nucleotide residues within the nucleic acid molecule. A nuclease may be an endonuclease, cleaving a phosphodiester bonds within a polynucleotide chain, or an exonuclease, cleaving a phosphodiester bond at the end of the polynucleotide chain. Preferably, the nuclease is an endonuclease. Preferably, the nuclease is a site-specific nuclease, binding and/or cleaving a specific phosphodiester bond within a specific nucleotide sequence, which may be referred to as "recognition sequence", "nuclease target site", or "target site". In some embodiments, a nuclease may recognize a single stranded target site, in other embodiments a nuclease may recognize a double-stranded target site, for example a double-stranded DNA target site. Some endonucleases cut a double-stranded nucleic acid target site symmetrically, i.e., cutting both strands at the same position so that the ends comprise base-paired nucleotides, also known as blunt ends. Other endonucleases cut a double-stranded nucleic acid target sites asymmetrically, i.e., cutting each strand at a different position so that the ends comprise unpaired nucleotides. Unpaired nucleotides at the end of a double-stranded DNA molecule are also referred to as "overhangs", e.g., "5'-overhang" or "3'-overhang", depending on whether the unpaired nucleotide(s) form(s) the 5' or the 5' end of the respective DNA strand.

The nuclease may introduce one or more single-strand nicks and/or double-strand breaks in the endogenous gene, whereupon the sequence of the endogenous gene may be modified or mutated via non-homologous end joining (NHEJ) or homology-directed repair (HDR).

In certain embodiments, the nuclease may comprise (i) a DNA-binding portion configured to specifically bind to the endogenous gene and (ii) a DNA cleavage portion. Generally, the DNA cleavage portion will cleave the nucleic acid within or in the vicinity of the sequence to which the DNA-binding portion is configured to bind.

In certain embodiments, the DNA-binding portion may comprises a zinc finger protein or DNA-binding domain thereof, a transcription activator-like effector (TALE) protein or DNA-binding domain thereof, or an RNA-guided protein or DNA-binding domain thereof.

In certain embodiments, the DNA-binding portion may comprise (i) Cas9 or Cpf1 or any Cas protein described herein modified to eliminate its nuclease activity, or (ii) DNA-binding domain of Cas9 or Cpf1 or any Cas protein described herein.

In certain embodiments, the DNA cleavage portion comprises FokI or variant thereof or DNA cleavage domain of FokI or variant thereof.

In certain embodiments, the nuclease may be an RNA-guided nuclease, such as Cas9 or Cpf1 or any Cas protein described herein.

With respect to general information on CRISPR-Cas Systems, components thereof, and delivery of such components, including methods, materials, delivery vehicles, vectors, particles, AAV, and making and using thereof, including as to amounts and formulations, all useful in the practice of the instant invention, reference is made to: U.S. Pat. Nos. 8,999,641, 8,993,233, 8,945,839, 8,932,814, 8,906,616, 8,895,308, 8,889,418, 8,889,356, 8,871,445, 8,865,406, 8,795,965, 8,771,945 and 8,697,359; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US2014-0179006 A1 (U.S. application Ser. No. 14/183,486), US 2014-0170753 (U.S. application Ser. No. 14/183,429); European Patents EP 2 784 162 B1 and EP 2 771 468 B1; European Patent Applications EP 2 771 468 (EP13818570.7), EP 2 764 103 (EP13824232.6), and EP 2 784 162 (EP14170383.5); and PCT Patent Publications PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO2014/093701 (PCT/US2013/074800), WO2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809). Reference is also made to U.S. provisional patent applications 61/758,468; 61/802,174; 61/806,375; 61/814,263; 61/819,803 and 61/828,130, filed on Jan. 30, 2013; Mar. 15, 2013; Mar. 28, 2013; Apr. 20, 2013; May 6, 2013 and May 28, 2013 respectively. Reference is also made to U.S. provisional patent application 61/836,123, filed on Jun. 17, 2013. Reference is additionally made to U.S. provisional patent applications 61/835,931, 61/835,936, 61/836,127, 61/836,101, 61/836,080 and 61/835,973, each filed Jun. 17, 2013. Further reference is made to US provisional patent applications 61/862,468 and 61/862,355 filed on Aug. 5, 2013; 61/871,301 filed on Aug. 28, 2013; 61/960,777 filed on Sep. 25, 2013 and 61/961,980 filed on Oct. 28, 2013. Reference is yet further made to: PCT Patent applications Nos: PCT/US2014/041803, PCT/US2014/041800, PCT/US2014/041809, PCT/US2014/041804 and PCT/US2014/041806, each filed Jun. 10, 2014 6/10/14; PCT/US2014/041808 filed Jun. 11, 2014; and PCT/US2014/62558 filed Oct. 28, 2014, and U.S. Provisional Patent Applications Ser. Nos. 61/915,150, 61/915,301, 61/915,267 and 61/915,260, each filed Dec. 12, 2013; 61/757,972 and 61/768,959, filed on Jan. 29, 2013 and Feb. 25, 2013; 61/835,936, 61/836,127, 61/836,101, 61/836,080, 61/835,973, and 61/835,931, filed Jun. 17, 2013; 62/010,888 and 62/010,879, both filed Jun. 11, 2014; 62/010,329 and 62/010,441, each filed Jun. 10, 2014; 61/939,228 and 61/939,242, each filed Feb. 12, 2014; 61/980,012, filed Apr. 15, 2014; 62/038,358, filed Aug. 17, 2014; 62/054,490, 62/055,484, 62/055,460 and 62/055,487, each filed Sep. 25, 2014; and 62/069,243, filed Oct. 27, 2014. Reference is also made to U.S. provisional patent applications Nos. 62/055,484, 62/055,460, and 62/055,487, filed Sep. 25, 2014; U.S. provisional patent application 61/980,012, filed Apr. 15, 2014; and U.S. provisional patent application 61/939,242 filed Feb. 12, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013. Reference is made to US provisional patent application U.S. Ser. No. 61/980,012 filed Apr. 15, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013.

Mention is also made of U.S. application 62/091,455, filed, 12 Dec. 2014, PROTECTED GUIDE RNAS (PGRNAS); U.S. application 62/096,708, 24 Dec. 2014, PROTECTED GUIDE RNAS (PGRNAS); U.S. application 62/091,462, 12 Dec. 2014, DEAD GUIDES FOR CRISPR TRANSCRIPTION FACTORS; U.S. application 62/096,324, 23 Dec. 2014, DEAD GUIDES FOR CRISPR TRANSCRIPTION FACTORS; U.S. application 62/091,456, 12 Dec. 2014, ESCORTED AND FUNCTIONALIZED GUIDES FOR CRISPR-CAS SYSTEMS; U.S. application 62/091,461, 12 Dec. 2014, DELIVERY, USE AND THERAPEUTIC APPLICATIONS OF THE CRISPR-CAS SYSTEMS AND COMPOSITIONS FOR GENOME EDITING AS TO HEMATOPOETIC STEM CELLS (HSCs); U.S. application 62/094,903, 19 Dec. 2014, UNBIASED IDEN- TIFICATION OF DOUBLE-STRAND BREAKS AND GENOMIC REARRANGEMENT BY GENOME-WISE INSERT CAPTURE SEQUENCING; U.S. application 62/096,761, 24 Dec. 2014, ENGINEERING OF SYSTEMS, METHODS AND OPTIMIZED ENZYME AND GUIDE SCAFFOLDS FOR SEQUENCE MANIPULATION; U.S. application 62/098,059, 30 Dec. 2014, RNA-TARGETING SYSTEM; U.S. application 62/096,656, 24 Dec. 2014, CRISPR HAVING OR ASSOCIATED WITH DESTABILIZATION DOMAINS; U.S. application 62/096,697, 24 Dec. 2014, CRISPR HAVING OR ASSOCIATED WITH AAV; U.S. application 62/098,158, 30 Dec. 2014, ENGINEERED CRISPR COMPLEX INSERTIONAL TARGETING SYSTEMS; US application 62/151,052, 22 Apr. 2015, CELLULAR TARGETING FOR EXTRACELLULAR EXOSOMAL REPORTING; U.S. application 62/054,490, 24 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 62/055,484, 25 Sep. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/054,675, 24 Sep. 2014, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 2014, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 2014, MULTIFUNCTIONAL-CRISPR COMPLEXES AND/OR OPTIMIZED ENZYME LINKED FUNCTIONAL-CRISPR COMPLEXES; U.S. application 62/087,475, 4 Dec. 2014, FUNCTIONAL SCREENING WITH OPTIMIZED FUNCTIONAL CRISPR-CAS SYSTEMS; U.S. application 62/055,487, 25 Sep. 2014, FUNCTIONAL SCREENING WITH OPTIMIZED FUNCTIONAL CRISPR-CAS SYSTEMS; U.S. application 62/087,546, 4 Dec. 2014, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 2014, CRISPR MEDIATED IN VIVO MODELING AND GENETIC SCREENING OF TUMOR GROWTH AND METASTASIS.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

Also with respect to general information on CRISPR-Cas Systems, mention is made of the following (also hereby incorporated herein by reference): |Normal|ZZMPTAG|

Multiplex genome engineering using CRISPR/Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR/Cas-Mediated Genome Engineering. Wang H., Yang H., Shivalila C S., Dawlaty M M., Cheng A W., Zhang F., Jaenisch R. Cell May 9; 153(4): 910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463): 472-6. doi: 10.1038/Nature 12466. Epub 2013 Aug. 23 (2013);

Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5 (2013-A);

DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013);

Genome engineering using the CRISPR-Cas9 system. Ran, F A., Hsu, P D., Wright, J., Agarwala, V., Scott, D A., Zhang, F. Nature Protocols November; 8(11):2281-308 (2013-B);

Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, BL., Root, D E., Doench, J G., Zhang, F. Science December 12. (2013). [Epub ahead of print];

Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014 (2014);

Development and Applications of CRISPR-Cas9 for Genome Engineering, Hsu P D, Lander E S, Zhang F., Cell. June 5,157(6):1262-78 (2014).

Genetic screens in human cells using the CRISPR/Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh O O, Barcena C, Hsu P D, Habib N, Gootenberg J S, Nishimasu H, Nureki O, Zhang F., Nature. January 29; 517(7536):583-8 (2015).

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9:520(7546):186-91 (2015).

Shalem et al., "High-throughput functional genomics using CRISPR-Cas9," Nature Reviews Genetics 16, 299-311 (May 2015).

Xu et al., "Sequence determinants of improved CRISPR sgRNA design," Genome Research 25, 1147-1157 (August 2015).

Parnas et al., "A Genome-wide CRISPR Screen in Primary Immune Cells to Dissect Regulatory Networks," Cell 162, 675-686 (Jul. 30, 2015).

Ramanan et al., CRISPR/Cas9 cleavage of viral DNA efficiently suppresses hepatitis B virus," Scientific Reports 5:10833. doi: 10.1038/srep10833 (Jun. 2, 2015)

Nishimasu et al., Crystal Structure of *Staphylococcus aureus* Cas9," Cell 162, 1113-1126 (Aug. 27, 2015)

Zetsche et al., "Cpf1 Is a Single RNA-Guided Endonuclease of a Class 2 CRISPR-Cas System," Cell 163, 1-13 (Oct. 22, 2015)

Shmakov et al., "Discovery and Functional Characterization of Diverse Class 2 CRISPR-Cas Systems," Molecular Cell 60, 1-13 (Available online Oct. 22, 2015)

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli,* 65% that were recovered contained the mutation.

Wang et al. (2013) used the CRISPR/Cas system for the one-step generation of mice carrying mutations in multiple genes which were traditionally generated in multiple steps by sequential recombination in embryonic stem cells and/or time-consuming intercrossing of mice with a single mutation. The CRISPR/Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays.

Shalem et al. (2015) described ways in which catalytically inactive Cas9 (dCas9) fusions are used to synthetically repress (CRISPRi) or activate (CRISPRa) expression, showing advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR/Cas9 knockout and nucleotide preference at the cleavage site. The authors also found that the sequence preference for CRISPRi/a is substantially different from that for CRISPR/Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3'PAM and the 5'-TTGGGT-3' PAM. A structural comparison of SaCas9 with SpCas9 highlighted both structural conservation and divergence, explaining their distinct PAM specificities and orthologous sgRNA recognition.

Zetsche et al. (2015) reported the characterization of Cpf1, a putative class 2 CRISPR effector. It was demonstrated that Cpf1 mediates robust DNA interference with features distinct from Cas9. Identifying this mechanism of interference broadens our understanding of CRISPR-Cas systems and advances their genome editing applications.

Shmakov et al. (2015) reported the characterization of three distinct Class 2 CRISPR-Cas systems. The effectors of two of the identified systems, C2c1 and C2c3, contain RuvC like endonuclease domains distantly related to Cpf1. The third system, C2c2, contains an effector with two predicted HEPN RNase domains.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6); 569-77 (2014), relates to dimeric RNA-guided FokI Nucleases that recognize extended sequences and can edit endogenous genes with high efficiencies in human cells.

In addition, mention is made of PCT application PCT/US14/70057, entitled "DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS (claiming priority from one or more or all of US provisional patent applications: 62/054, 490, filed Sep. 24, 2014; 62/010,441, filed Jun. 10, 2014; and 61/915,118, 61/915,215 and 61/915,148, each filed on Dec. 12, 2013) ("the Particle Delivery PCT"), incorporated herein by reference, with respect to a method of preparing an sgRNA-and-Cas9 protein containing particle comprising admixing a mixture comprising an sgRNA and Cas9 protein (and optionally HDR template) with a mixture comprising or consisting essentially of or consisting of surfactant, phospholipid, biodegradable polymer, lipoprotein and alcohol; and particles from such a process. For example, wherein Cas9 protein and sgRNA were mixed together at a suitable, e.g., 3:1 to 1:3 or 2:1 to 1:2 or 1:1 molar ratio, at a suitable temperature, e.g., 15-30C, e.g., 20-25C, e.g., room temperature, for a suitable time, e.g., 15-45, such as 30 minutes, advantageously in sterile, nuclease free buffer, e.g., 1×PBS. Separately, particle components such as or comprising: a surfactant, e.g., cationic lipid, e.g., 1,2-dioleoyl-3-trimethylammonium-propane (DOTAP); phospholipid, e.g., dimyristoylphosphatidylcholine (DMPC); biodegradable polymer, such as an ethylene-glycol polymer or PEG, and a lipoprotein, such as a low-density lipoprotein, e.g., cholesterol were dissolved in an alcohol, advantageously a C1-6 alkyl alcohol, such as methanol, ethanol, isopropanol, e.g., 100% ethanol. The two solutions were mixed together to form particles containing the Cas9-sgRNA complexes. Accordingly, sgRNA may be pre-complexed with the Cas9 protein, before formulating the entire complex in a particle. Formulations may be made with a different molar ratio of different components known to promote delivery of nucleic acids into cells (e.g. 1,2-dioleoyl-3-trimethylammonium-propane (DOTAP), 1,2-ditetradecanoyl-sn-glycero-3-phosphocholine (DMPC), polyethylene glycol (PEG), and cholesterol) For example DOTAP:DMPC:PEG:Cholesterol Molar Ratios may be DOTAP 100, DMPC 0, PEG 0, Cholesterol 0; or DOTAP 90, DMPC 0, PEG 10, Cholesterol 0; or DOTAP 90, DMPC 0, PEG 5, Cholesterol 5. DOTAP 100, DMPC 0, PEG 0, Cholesterol 0. That application accordingly comprehends admixing sgRNA, Cas9 protein and components that form a particle; as well as particles from such admixing. Aspects of the instant invention can involve particles; for example, particles using a process analogous to that of the Particle Delivery PCT, e.g., by admixing a mixture comprising sgRNA and/or Cas9 as in the instant invention and components that form a particle, e.g., as in the Particle Delivery PCT, to form a particle and particles from such admixing (or, of course, other particles involving sgRNA and/or Cas9 as in the instant invention).

In general, the CRISPR-Cas or CRISPR system is as used in the foregoing documents, such as WO 2014/093622 (PCT/US2013/074667) and refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise any polynucleotide, such as DNA or RNA polynucleotides. In some embodiments, a target sequence is located in the nucleus or cytoplasm of a cell. In some embodiments, direct repeats may be identified in silico by searching for repetitive motifs that fulfill any or all of the following criteria: 1. found in a 2 Kb window of genomic sequence flanking the type II CRISPR locus; 2. span from 20 to 50 bp; and 3. interspaced by 20 to 50 bp. In some embodiments, 2 of these criteria may be used, for instance 1 and 2, 2 and 3, or 1 and 3. In some embodiments, all 3 criteria may be used.

In embodiments of the invention the terms guide sequence and guide RNA, i.e. RNA capable of guiding Cas to a target genomic locus, are used interchangeably as in foregoing cited documents such as WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies; available at www.novocraft.com), ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. Preferably the guide sequence is 10 30 nucleotides long. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

In a classic CRISPR-Cas systems, the degree of complementarity between a guide sequence and its corresponding target sequence can be about or more than about 50%, 60%, 75%, 80%, 85%, 90%, 95%, 97.5%, 99%, or 100%; a guide or RNA or sgRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length; or guide or RNA or sgRNA can be less than about 75, 50, 45, 40, 35, 30, 25, 20, 15, 12, or fewer nucleotides in length; and advantageously tracr RNA is 30 or 50 nucleotides in length. However, an aspect of the invention is to reduce off-target interactions, e.g., reduce the guide interacting with a target sequence having low complementarity. Indeed, in the examples, it is shown that the invention involves mutations that result in the CRISPR-Cas system being able to distinguish between target and off-target sequences that have greater than 80% to about 95% complementarity, e.g., 83%-84% or 88-89% or 94-95% complementarity (for instance, distinguishing between a target having 18 nucleotides from an off-target of 18 nucleotides having 1, 2 or 3 mismatches). Accordingly, in the context of the present invention the degree of complementarity between a guide sequence and its corresponding target sequence is greater than 94.5% or 95% or 95.5% or 96% or 96.5% or 97% or 97.5% or 98% or 98.5% or 99% or 99.5% or 99.9%, or 100%. Off target is less than 100% or 99.9% or 99.5% or 99% or 99% or 98.5% or 98% or 97.5% or 97% or 96.5% or 96% or 95.5% or 95% or 94.5% or 94% or 93% or 92% or 91% or 90% or 89% or 88% or 87% or 86% or 85% or 84% or 83% or 82% or 81% or 80% complementarity between the sequence and the guide, with it advantageous that off target is 100% or 99.9% or 99.5% or 99% or 99% or 98.5% or 98% or 97.5% or 97% or 96.5% or 96% or 95.5% or 95% or 94.5% complementarity between the sequence and the guide.

In particularly preferred embodiments according to the invention, the guide RNA (capable of guiding Cas to a target locus) may comprise (1) a guide sequence capable of hybridizing to a genomic target locus in the eukaryotic cell; (2) a tracr sequence; and (3) a tracr mate sequence. All (1) to (3) may reside in a single RNA, i.e. an sgRNA (arranged in a 5' to 3' orientation), or the tracr RNA may be a different RNA than the RNA containing the guide and tracr sequence. The tracr hybridizes to the tracr mate sequence and directs the CRISPR/Cas complex to the target sequence. In certain embodiments, the guide RNA does not comprise tracr sequence. For example, certain CRISPR-Cas systems and RNA-guided proteins, such as Cpf1, may not require tracr sequence.

The methods according to the invention as described herein comprehend inducing one or more mutations in a eukaryotic cell (in vitro, i.e. in an isolated eukaryotic cell) as herein discussed comprising delivering to cell a vector as herein discussed. The mutation(s) can include the introduction, deletion, or substitution of one or more nucleotides at each target sequence of cell(s) via the guide(s) RNA(s) or sgRNA(s). The mutations can include the introduction, deletion, or substitution of 1-75 nucleotides at each target sequence of said cell(s) via the guide(s) RNA(s) or sgRNA(s). The mutations can include the introduction, deletion, or substitution of 1, 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations include the introduction, deletion, or substitution of 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 40, 45, 50, 75, 100, 200, 300, 400 or 500 nucleotides at each target sequence of said cell(s) via the guide(s) RNA(s) or sgRNA(s).

For minimization of toxicity and off-target effect, it will be important to control the concentration of Cas mRNA and guide RNA delivered. Optimal concentrations of Cas mRNA and guide RNA can be determined by testing different concentrations in a cellular or non-human eukaryote animal model and using deep sequencing the analyze the extent of modification at potential off-target genomic loci. Alternatively, to minimize the level of toxicity and off-target effect, Cas nickase mRNA (for example S. pyogenes Cas9 with the D10A mutation) can be delivered with a pair of guide RNAs targeting a site of interest. Guide sequences and strategies to minimize toxicity and off-target effects can be as in WO 2014/093622 (PCT/US2013/074667); or, via mutation as herein.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence.

The nucleic acid molecule encoding a Cas is advantageously codon optimized Cas. An example of a codon optimized sequence, is in this instance a sequence optimized for expression in a eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a Cas is codon optimized for expression in particular cells, such as eukaryotic cells. The eukaryotic cells may be those of or derived from a particular organism, such as a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/ and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid.

In certain embodiments, the methods as described herein may comprise providing a Cas transgenic cell in which one or more nucleic acids encoding one or more guide RNAs are provided or introduced operably connected in the cell with a regulatory element comprising a promoter of one or more gene of interest. As used herein, the term "Cas transgenic cell" refers to a cell, such as a eukaryotic cell, in which a Cas gene has been genomically integrated. The nature, type, or origin of the cell are not particularly limiting according to the present invention. Also the way how the Cas transgene is introduced in the cell is may vary and can be any method as is known in the art. In certain embodiments, the Cas transgenic cell is obtained by introducing the Cas transgene in an isolated cell. In certain other embodiments, the Cas transgenic cell is obtained by isolating cells from a Cas transgenic organism. By means of example, and without limitation, the Cas transgenic cell as referred to herein may be derived from a Cas transgenic eukaryote, such as a Cas knock-in eukaryote. Reference is made to WO 2014/093622 (PCT/US13/74667), incorporated herein by reference. Methods of US Patent Publication Nos. 20120017290 and 20110265198 assigned to Sangamo BioSciences, Inc. directed to targeting the Rosa locus may be modified to utilize the CRISPR Cas system of the present invention. Methods of US Patent Publication No. 20130236946 assigned to Cellectis directed to targeting the Rosa locus may also be modified to utilize the CRISPR Cas system of the present invention. By means of further example reference is made to Platt et. al. (Cell; 159(2):440-455 (2014)), describing a Cas9 knock-in mouse, which is incorporated herein by reference. The Cas transgene can further comprise a Lox-Stop-polyA-Lox (LSL) cassette thereby rendering Cas expression inducible by Cre recombinase. Alternatively, the Cas transgenic cell may be obtained by introducing the Cas transgene in an isolated cell. Delivery systems for transgenes are well known in the art. By means of example, the Cas transgene may be delivered in for instance eukaryotic cell by means of vector (e.g., AAV, adenovirus, lentivirus) and/or particle and/or nanoparticle delivery, as also described herein elsewhere.

It will be understood by the skilled person that the cell, such as the Cas transgenic cell, as referred to herein may comprise further genomic alterations besides having an integrated Cas gene or the mutations arising from the sequence specific action of Cas when complexed with RNA capable of guiding Cas to a target locus, such as for instance one or more oncogenic mutations, as for instance and without limitation described in Platt et al. (2014), Chen et al., (2014) or Kumar et al. (2009).

In some embodiments, the Cas sequence is fused to one or more nuclear localization sequences (NLSs), such as about or more than about 1, 2, 3, 4, 5, 6, 7, 8, 9, 10, or more NLSs. In some embodiments, the Cas comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In a preferred embodiment of the invention, the Cas comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV (SEQ ID NO: 1); the NLS from nucleoplasmin (e.g. the nucleoplasmin bipartite NLS with the sequence KRPAATKKAGQAKKKK) (SEQ ID NO: 2); the c-myc NLS having the amino acid sequence PAAKRVKLD (SEQ ID NO: 3) or RQRRNELKRSP (SEQ ID NO: 4); the hRNPA1 M9 NLS having the sequence NQSSNFGPMKGGNFGGRSSGPYGGGGQYFAK-PRNQGGY (SEQ ID NO: 5); the sequence RMRIZFKNKGKDTAELRRRRVEVSVELRKAKKD-EQILKRRNV (SEQ ID NO: 6) of the IBB domain from importin-alpha, the sequences VSRKRPRP (SEQ ID NO: 7) and PPKKARED (SEQ ID NO: 8) of the myoma T protein; the sequence POPKKKPL (SEQ ID NO: 9) of human p53; the sequence SALIKKKKKMAP (SEQ ID NO: 10) of mouse c-abl IV; the sequences DRLRR (SEQ ID NO: 11) and PKQKKRK (SEQ ID NO: 12) of the influenza virus NS1; the sequence RKLKKKIKKL (SEQ ID NO: 13) of the Hepatitis virus delta antigen; the sequence REKKKFLKRR (SEQ ID NO: 14) of the mouse Mx1 protein; the sequence KRKGDEVDGVDEVAKKKSKK (SEQ ID NO: 15) of the human poly (ADP-ribose) polymerase; and the sequence RKCLQAGMNLEARKTKK (SEQ ID NO: 16) of the steroid hormone receptors (human) glucocorticoid. In general, the one or more NLSs are of sufficient strength to drive accumulation of the Cas in a detectable amount in the nucleus of a eukaryotic cell. In general, strength of nuclear localization activity may derive from the number of NLSs in the Cas, the particular NLS(s) used, or a combination of these factors. Detection of accumulation in the nucleus may be performed by any suitable technique. For example, a detectable marker may be fused to the Cas, such that location within a cell may be visualized, such as in combination with a means for detecting the location of the nucleus (e.g. a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g. assay for DNA cleavage or mutation at the target sequence, or assay for altered gene expression activity affected by CRISPR complex formation and/or Cas enzyme activity), as compared to a control no exposed to the Cas or complex, or exposed to a Cas lacking the one or more NLSs.

In certain embodiments, the DNA-binding portion may comprise a transcription activator-like effector (TALE) protein or DNA-binding domain thereof. Hence, certain embodiments may make use of isolated, non-naturally occurring, recombinant or engineered DNA binding proteins that comprise TALE monomers or TALE monomers or half monomers as a part of their organizational structure that enable the targeting of nucleic acid sequences with improved efficiency and expanded specificity.

Naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", "TALE monomers" or "monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is $X1\text{-}11\text{-}(X12X13)\text{-}X14\text{-}33$ or 34 or 35, where the subscript indicates the amino acid position and X represents any amino acid. X12X13 indicate the RVDs. In some polypeptide monomers, the variable amino acid at position 13 is missing or absent and in such monomers, the RVD consists of a single amino acid. In such cases the RVD may be alternatively represented as $X^*$, where X represents X12 and (*) indicates that X13 is absent. The DNA binding domain comprises several repeats of TALE monomers and this may be represented as $(X1\text{-}11\text{-}(X12X13)\text{-}X14\text{-}33$ or 34 or $35)z$, where in an advantageous embodiment, z is at least 5 to 40. In a further advantageous embodiment, z is at least 10 to 26.

The TALE monomers have a nucleotide binding affinity that is determined by the identity of the amino acids in its RVD. For example, polypeptide monomers with an RVD of NI preferentially bind to adenine (A), monomers with an RVD of NG preferentially bind to thymine (T), monomers with an RVD of HD preferentially bind to cytosine (C) and monomers with an RVD of NN preferentially bind to both adenine (A) and guanine (G). In yet another embodiment of the invention, monomers with an RVD of IG preferentially bind to T. Thus, the number and order of the polypeptide monomer repeats in the nucleic acid binding domain of a TALE determines its nucleic acid target specificity. In still further embodiments of the invention, monomers with an RVD of NS recognize all four base pairs and may bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011), each of which is incorporated by reference in its entirety.

The polypeptides used in methods of certain embodiments of the invention are isolated, non-naturally occurring, recombinant or engineered nucleic acid-binding proteins that have nucleic acid or DNA binding regions containing polypeptide monomer repeats that are designed to target specific nucleic acid sequences.

As described herein, polypeptide monomers having an RVD of HN or NH preferentially bind to guanine and thereby allow the generation of TALE polypeptides with high binding specificity for guanine containing target nucleic acid sequences. In a preferred embodiment of the invention, polypeptide monomers having RVDs RN, NN, NK, SN, NH, KN, HN, NQ, HH, RG, KH, RH and SS preferentially bind to guanine. In a much more advantageous embodiment of the invention, polypeptide monomers having RVDs RN, NK, NQ, HH, KH, RH, SS and SN preferentially bind to guanine and thereby allow the generation of TALE polypeptides with high binding specificity for guanine containing target nucleic acid sequences. In an even more advantageous embodiment of the invention, polypeptide monomers having RVDs HH, KH, NH, NK, NQ, RH, RN and SS preferentially bind to guanine and thereby allow the generation of TALE polypeptides with high binding specificity for guanine containing target nucleic acid sequences. In a further advantageous embodiment, the RVDs that have high binding specificity for guanine are RN, NH RH and KH. Furthermore, polypeptide monomers having an RVD of NV preferentially bind to adenine and guanine. In more preferred embodiments of the invention, monomers having RVDs of H*, HA, $K_A$, N*, NA, NC, NS, RA, and S* bind to adenine, guanine, cytosine and thymine with comparable affinity.

The predetermined N-terminal to C-terminal order of the one or more polypeptide monomers of the nucleic acid or DNA binding domain determines the corresponding predetermined target nucleic acid sequence to which the polypeptides of the invention will bind. As used herein the monomers and at least one or more half monomers are "specifically ordered to target" the genomic locus or gene of interest. In plant genomes, the natural TALE-binding sites always begin with a thymine (T), which may be specified by a cryptic signal within the non-repetitive N-terminus of the TALE polypeptide; in some cases this region may be referred to as repeat 0. In animal genomes, TALE binding sites do not necessarily have to begin with a thymine (T) and polypeptides of the invention may target DNA sequences that begin with T, A, G or C. The tandem repeat of TALE monomers always ends with a half-length repeat or a stretch of sequence that may share identity with only the first 20 amino acids of a repetitive full length TALE monomer and this half repeat may be referred to as a half-monomer. Therefore, it follows that the length of the nucleic acid or DNA being targeted is equal to the number of full monomers plus two.

As described in Zhang et al., Nature Biotechnology 29:149-153 (2011), TALE polypeptide binding efficiency may be increased by including amino acid sequences from the "capping regions" that are directly N-terminal or C-terminal of the DNA binding region of naturally occurring TALEs into the engineered TALEs at positions N-terminal or C-terminal of the engineered TALE DNA binding region. Thus, in certain embodiments, the TALE polypeptides described herein further comprise an N-terminal capping region and/or a C-terminal capping region.

An exemplary amino acid sequence of a N-terminal capping region is:
M D P I R S R T P S P A R E L L S G P Q P D G V Q
P T A D R G V S P P A G G P L D G L P A R R T M
S R T R L P S P P A P S P A F S A D S F S D L L R
Q F D P S L F N T S L F D S L P P F G A H H T E
A A T G E W D E V Q S G L R A A D A P P P T M
R V A V T A A R P P R A K P A P R R R A A Q P S
D A S P A A Q V D L P T L G Y S Q Q Q Q E K I K
P K V R S T V A Q H H E A L V G H G F T H A H
I V A L S Q H P A A L G T V A V K Y Q D M I A A
L P E A T H E A I V G V G K Q W S G A R A L E
A L L T V A G E L R G P P L Q L D T G Q L L K I
A K R G G V T A V E A V H A W R N A L T G A P
L N (SEQ ID NO:17)

An exemplary amino acid sequence of a C-terminal capping region is:
R P A L E S I V A Q L S R P D P A L A A L T N D H
L V A L A C L G G P P A L D A V K K G L P H A P
A L I K R T N R R I P E R T S H P V A D H A Q V
V R V L G F F Q C H S H P A Q A F D D A M T Q
F G M S R H G L L Q L F R P V G V T E L E A P S
G T L P P A S Q R W D R I L Q A S G M K R A K
P S P T S T Q T P D Q A S L H A F A D S L E R D
L D A P S P M H E G D Q T A S (SEQ ID NO:18)

As used herein the predetermined "N-terminus" to "C terminus" orientation of the N-terminal capping region, the DNA binding domain comprising the repeat TALE monomers and the C-terminal capping region provide structural basis for the organization of different domains in the d-TALEs or polypeptides of the invention.

The entire N-terminal and/or C-terminal capping regions are not necessary to enhance the binding activity of the DNA binding region. Therefore, in certain embodiments, fragments of the N-terminal and/or C-terminal capping regions are included in the TALE polypeptides described herein.

In certain embodiments, the TALE polypeptides described herein contain a N-terminal capping region fragment that included at least 10, 20, 30, 40, 50, 54, 60, 70, 80, 87, 90, 94, 100, 102, 110, 117, 120, 130, 140, 147, 150, 160, 170, 180, 190, 200, 210, 220, 230, 240, 250, 260 or 270 amino acids of an N-terminal capping region. In certain embodiments, the N-terminal capping region fragment amino acids are of the C-terminus (the DNA-binding region proximal end) of an N-terminal capping region. As described in Zhang et al., Nature Biotechnology 29:149-153 (2011), N-terminal capping region fragments that include the C-terminal 240 amino acids enhance binding activity equal to the full length capping region, while fragments that include the C-terminal 147 amino acids retain greater than 80% of the efficacy of the full length capping region, and fragments that include the C-terminal 117 amino acids retain greater than 50% of the activity of the full-length capping region.

In some embodiments, the TALE polypeptides described herein contain a C-terminal capping region fragment that included at least 6, 10, 20, 30, 37, 40, 50, 60, 68, 70, 80, 90, 100, 110, 120, 127, 130, 140, 150, 155, 160, 170, 180 amino acids of a C-terminal capping region. In certain embodiments, the C-terminal capping region fragment amino acids are of the N-terminus (the DNA-binding region proximal end) of a C-terminal capping region. As described in Zhang et al., Nature Biotechnology 29:149-153 (2011), C-terminal capping region fragments that include the C-terminal 68 amino acids enhance binding activity equal to the full length capping region, while fragments that include the C-terminal 20 amino acids retain greater than 50% of the efficacy of the full length capping region.

In certain embodiments, the capping regions of the TALE polypeptides described herein do not need to have identical sequences to the capping region sequences provided herein. Thus, in some embodiments, the capping region of the TALE polypeptides described herein have sequences that are at least 50%, 60%, 70%, 80%, 85%, 90%, 91%, 92%, 93%, 94%, 95%, 96%, 97%, 98% or 99% identical or share identity to the capping region amino acid sequences provided herein. Sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the TALE polypeptides described herein have sequences that are at least 95% identical or share identity to the capping region amino acid sequences provided herein.

Sequence homologies may be generated by any of a number of computer programs known in the art, which include but are not limited to BLAST or FASTA. Suitable computer program for carrying out alignments like the GCG Wisconsin Bestfit package may also be used. Once the software has produced an optimal alignment, it is possible to calculate % homology, preferably % sequence identity. The software typically does this as part of the sequence comparison and generates a numerical result.

In certain embodiments, the DNA-binding portion may comprise a zinc finger protein or DNA-binding domain thereof.

Artificial zinc-finger (ZF) technology allows to provide programmable DNA-binding domains, and involves arrays of ZF modules to target new DNA-binding sites in the genome. Each finger module in a ZF array targets three DNA bases. A customized array of individual zinc finger domains is assembled into a ZF protein (ZFP). ZFPs can comprise a functional domain. The first synthetic zinc finger nucleases (ZFNs) were developed by fusing a ZF protein to the catalytic domain of the Type IIS restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to Fok I cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79).

In certain embodiments, immunomodulant may comprise silencing one or more endogenous genes.

As used herein, "gene silencing" or "gene silenced" in reference to an activity of an RNAi molecule, for example a siRNA or miRNA refers to a decrease in the mRNA level in a cell for a target gene by at least about 5%, about 10%, about 20%, about 30%, about 40%, about 50%, about 60%, about 70%, about 80%, about 90%, about 95%, about 99%, about 100% of the mRNA level found in the cell without the presence of the miRNA or RNA interference molecule. In one preferred embodiment, the mRNA levels are decreased by at least about 70%, about 80%, about 90%, about 95%, about 99%, about 100%.

As used herein, the term "RNAi" refers to any type of interfering RNA, including but not limited to, siRNAi, shRNAi, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein). The term "RNAi" can include both gene silencing RNAi molecules, and also RNAi effector molecules which activate the expression of a gene.

As used herein, a "siRNA" refers to a nucleic acid that forms a double stranded RNA, which double stranded RNA has the ability to reduce or inhibit expression of a gene or target gene when the siRNA is present or expressed in the same cell as the target gene. The double stranded RNA siRNA can be formed by the complementary strands. In one embodiment, a siRNA refers to a nucleic acid that can form a double stranded siRNA. The sequence of the siRNA can correspond to the full-length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The terms "microRNA" or "miRNA" are used interchangeably herein are endogenous RNAs, some of which are known to regulate the expression of protein-coding genes at the posttranscriptional level. Endogenous microRNAs are small RNAs naturally present in the genome that are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and or RNAi pathways.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 1 16:281-297), comprises a dsRNA molecule.

In certain embodiments, an immunomodulant may comprise (i) a DNA-binding portion configured to specifically bind to the endogenous gene and (ii) an effector domain mediating a biological activity.

In certain embodiments, the DNA-binding portion may comprises a zinc finger protein or DNA-binding domain thereof, a transcription activator-like effector (TALE) protein or DNA-binding domain thereof, or an RNA-guided protein or DNA-binding domain thereof.

In certain embodiments, the DNA-binding portion may comprise (i) Cas9 or Cpf1 or any Cas protein described herein modified to eliminate its nuclease activity, or (ii) DNA-binding domain of Cas9 or Cpf1 or any Cas protein described herein.

In some embodiments the effector domain may be a transcriptional inhibitor (i.e., a repressor domain), such as an m Sin interaction domain (SID). SID4× domain or a Krüppel-associated box (KRAB) or fragments of the KRAB domain. In some embodiments the effector domain may be an enhancer of transcription (i.e. an activation domain), such as the VP16, VP64 or p65 activation domain. In some embodiments, the nucleic acid binding portion may be linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal. In some embodiments, the effector domain may be a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination the activities described herein.

In certain embodiments, an immunomodulant may comprise introducing one or more endogenous genes and/or one or more exogenous genes in expressible format into the immune cell, in accordance with the practice of transgenesis as taught elsewhere in this specification.

A further aspect provides an immunomodulant capable of modulating one or more phenotypic aspects of the immune cell or the immune cell population as taught herein, such as an immunomodulant identified using the above-described method.

In certain embodiments, the immunomodulant according may be capable of modulating the proliferation, differentiation, maturation, migration, cytokine expression, antigen presentation, and/or viability of the immune cell or immune cell population.

In certain embodiments, the immunomodulant may be capable of inducing or repressing the proliferation, differentiation, maturation, migration, cytokine expression, antigen presentation, and/or viability of the immune cell or immune cell population.

A further aspect provides a composition, pharmaceutical composition or vaccine comprising the immunomodulant as taught herein.

In certain embodiments, the immunomodulant may comprise an antigen, or the pharmaceutical composition or vaccine further comprise an antigen.

In certain embodiments, the antigen is an allergen, autoimmune antigen, tumor antigen, or pathogen antigen.

In certain embodiments, the pathogen is a bacterial, fungal, protozoal, parasitic, or viral pathogen.

In certain embodiments, the antigen is directly or indirectly, covalently or non-covalently linked with an agent capable of specifically binding to a gene product expressed on the cell surface of the immune cell. Hereby, antigens of interest can be selectively targeted to desired immune cell population(s) as taught herein in vivo, such as to elicit an immune response or immune tolerance to the antigen mediated by said immune cell population(s) in the subject.

In certain embodiments, the agent may be an antibody.

By means of an example but without limitation, the antigen may be indirectly and covalently linked to the agent, such as an antibody, by a connecting arm, structure, group or moiety, i.e., a cross-linking reagent. Cross-linking reagents and methods to provide for cross-linking of substances of interest, e.g., cross-linking of a substance of interest to a peptide, polypeptide or protein, e.g., cross-linking of two or more peptide, polypeptide or protein molecules (e.g., an antigen and an antibody), are known in the art and are commercially available. Cross-linking reagents may be typically homobifunctional, i.e., having two functional groups that undergo the same reaction, or heterobifunctional, i.e., having two different functional groups. A cross-linking reagent may react with one of the terminal ends of a peptide, polypeptide or protein, or may react with a side chain of one of the amino acids of the peptide, polypeptide or protein.

If both the antigen and the agent are each independently a peptide, polypeptide or protein, the linked antigen and agent (e.g., an antibody) can be produced by genetic engineering as a fusion polypeptide. The term "fusion protein" as used herein refers to a polypeptide formed by the joining of two or more polypeptides through a peptide bond formed between the amino terminus of one polypeptide and the carboxyl terminus of another polypeptide. The fusion protein may be expressed as a single polypeptide from a polynucleotide sequence encoding the single contiguous fusion protein. A single chain fusion protein is a fusion protein having a single contiguous polypeptide backbone. Such fusion polypeptides can conveniently be expressed in known suitable host cells. The antigen and the agent may be linked in the fusion polypeptide directly or via a peptide spacer or linker. The terms "spacer" or "linker" as used in reference to a fusion protein refers to a peptide that joins the proteins comprising a fusion protein. Generally, a spacer has no specific biological activity other than to join or to preserve some minimum distance or other spatial relationship between the proteins (e.g., the linker may be comparatively flexible, such that the molecules linked thereby have rotational and translational freedom). However, in certain embodiments, the constituent amino acids of a spacer may be selected to influence some property of the fusion molecule such as the folding, net charge, or hydrophobicity of the fusion molecule.

Preferred peptide linker sequences adopt a flexible extended conformation and do not exhibit a propensity for developing an ordered secondary structure that could interact with the molecules linked thereby. Typical amino acids in flexible protein regions include Gly, Asn and Ser. Virtually any permutation of amino acid sequences containing Gly, Asn and Ser would be expected to satisfy the above criteria for a linker sequence. Other near neutral amino acids, such as Thr and Ala, also may be used in the linker sequence. Still other amino acid sequences that may be used as linkers are disclosed in Maratea et al. (1985), Gene 40: 39-46; Murphy et al. (1986) Proc. Nat'l. Acad. Sci. USA 83: 8258-62; U.S. Pat. Nos. 4,935,233; and 4,751,180. The length of the peptide linker sequence may vary such that the linker does not significantly affect the biological activity of the fusion protein. By means of an example, a peptide linker sequence length of about 2 amino acids may be used, although longer linker sequences may be more common. For example, a linker sequence may be at least 3, 4, 5, 6, 7, 8, 9, 10, 15, or more, preferably 10 to 20 amino acids in length to allow for increased flexibility.

In certain embodiments, the immunomodulant comprises a portion capable of modulating the proliferation, differentiation, maturation, migration, cytokine expression, antigen presentation, or viability of the immune cell, directly or indirectly, covalently or non-covalently linked with an agent capable of specifically binding to a gene product expressed on the cell surface of the immune cell. Hereby, the desired immune cell population(s) can be selectively targeted to modulate their in vivo activity and impacts, when desired.

In certain embodiments, the immunomodulant comprises a portion capable of repressing the proliferation, differentiation, maturation, migration, cytokine expression, antigen presentation, or viability of the immune cell, directly or indirectly, covalently or non-covalently linked with an agent capable of specifically binding to a gene product expressed on the cell surface of the immune cell. Hereby, the desired immune cell population(s) can be selectively targeted to reduce their in vivo activity and impacts, when desired.

In certain embodiments, the immunomodulant comprises a portion capable of stimulating the proliferation, differentiation, maturation, migration, cytokine expression, antigen presentation, or viability of the immune cell, directly or indirectly, covalently or non-covalently linked with an agent capable of specifically binding to a gene product expressed on the cell surface of the immune cell. Hereby, the desired immune cell population(s) can be selectively targeted to increase their in vivo activity and impacts, when desired.

In certain embodiments, the agent capable of specifically binding to a gene product expressed on the cell surface of the immune cell is an antibody.

By means of an example, an agent, such as an antibody, capable of specifically binding to a gene product expressed on the cell surface of the immune cells may be conjugated with a therapeutic or effector agent for targeted delivery of the therapeutic or effector agent to the immune cells.

Examples of such therapeutic or effector agents include immunomodulatory classes as discussed herein, such as without limitation a toxin, drug, radionuclide, cytokine, lymphokine, chemokine, growth factor, tumor necrosis factor, hormone, hormone antagonist, enzyme, oligonucleotide, siRNA, RNAi, photoactive therapeutic agent, anti-angiogenic agent and pro-apoptotic agent.

Example toxins include ricin, abrin, alpha toxin, saporin, ribonuclease (RNase), DNase I, Staphylococcal enterotoxin-A, pokeweed antiviral protein, gelonin, diphtheria toxin, *Pseudomonas* exotoxin, or *Pseudomonas* endotoxin.

Example radionuclides include $^{103m}$Rh, $^{103}$Ru, $^{105}$Rh, $^{105}$Ru, $^{107}$Hg, $^{109}$Pd, $^{109}$Pt, $^{111}$Ag, $^{111}$In, $^{113m}$In $^{119}$Sb, $^{11}$C, $^{121m}$Te, $^{122m}$Te, $^{125}$I, $^{125m}$Te, $^{126}$I, $^{131}$I, $^{133}$I, $^{13}$N, $^{142}$Pr, $^{143}$Pr, $^{149}$Pm, $^{152}$Dy, $^{153}$Sm, $^{15}$O, $^{161}$Ho, $^{161}$Tb, $^{165}$Tm, $^{166}$Dy, $^{166}$Ho, $^{167}$Tm, $^{168}$Tm, $^{169}$Er, $^{169}$Yb, $^{177}$Lu, $^{186}$Re, $^{198}$Re, $^{189m}$Os, $^{189}$Re, $^{192}$Ir, $^{194}$Ir, $^{197}$Pt, $^{198}$Au, $^{199}$Au, $^{201}$Tl, $^{203}$Hg, $^{211}$At, $^{211}$Bi, $^{211}$Pb, $^{212}$Bi, $^{212}$Pb, $^{213}$Bi, $^{215}$Po, $^{217}$At, $^{219}$Rn, $^{221}$Fr, $^{223}$Ra, $^{224}$Ac, $^{225}$Ac, $^{225}$Fm, $^{32}$P, $^{33}$P, $^{47}$Sc, $^{51}$Cr, $^{57}$Co, $^{58}$Co, $^{59}$Fe, $^{62}$Cu, $^{67}$Cu, $^{67}$Ga, $^{75}$Br, $^{75}$Se, $^{76}$Br, $^{77}$As, $^{77}$Br, $^{80m}$Br, $^{89}$Sr, $^{90}$Y, $^{95}$Ru, $^{97}$Ru, $^{99}$Mo or $^{99m}$Tc. Preferably, the radionuclide may be an alpha-particle-emitting radionuclide.

Example enzymes include malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase or acetylcholinesterase. Such enzymes may be used, for example, in combination with prodrugs that are administered in relatively non-toxic form and converted at the target site by the enzyme into a cytotoxic agent. In other alternatives, a drug may be converted into less toxic form by endogenous enzymes in the subject but may be reconverted into a cytotoxic form by the therapeutic enzyme.

A further aspect provides a method for treating or preventing a pathological condition comprising administering to a subject in need thereof the immunomodulant, pharmaceutical composition or vaccine comprising such as taught herein.

In certain embodiments, the pathological condition may be an infection, inflammation, proliferative disease, autoimmune disease, or allergy.

In certain embodiments, the pathological condition is selected from the group consisting of diseases set forth in Tables E10B and E10C.

A further aspect provides a method for treating or preventing a pathological condition in a subject in need thereof comprising: a) applying to the immune cell or the immune cell population as taught herein the immunomodulant, pharmaceutical composition or vaccine comprising such as taught herein; and b) administering the immune cell or immune cell population of a) to the subject.

In certain embodiments, the immunomodulant is capable of repressing the proliferation, differentiation, maturation, migration, cytokine expression, antigen presentation, or viability of the immune cell as defined in any one of c1), c2) or c3) or e1), e2), or e3), wherein the subject is in need of reducing inflammation, such as local or systemic inflammation.

In a further aspect, the invention provides a method for determining the immune status of a subject, or for diagnosing, prognosing or monitoring a disease comprising an immune component in a subject, the method comprising detecting or quantifying in a biological sample of the subject immune cells as taught herein.

Also provided is a method for detecting or quantifying immune cells as taught herein in a biological sample of a subject, wherein the subject is suspected of having or being at risk of developing a disease comprising an immune component.

Also provided is a method for diagnosing and treating a disease comprising an immune component in a subject, the method comprising: obtaining a biological sample from the subject; detecting or quantifying immune cells as taught herein in the biological sample of the subject; diagnosing the subject as in need of treatment for the disease when said immune cells are detected in the sample and/or when the quantity of said immune cells differs from a reference value; and administering an effective amount of a treatment to the diagnosed subject.

The terms "diagnosis" and "monitoring" are commonplace and well-understood in medical practice. By means of further explanation and without limitation the term "diagnosis" generally refers to the process or act of recognising, deciding on or concluding on a disease or condition in a subject on the basis of symptoms and signs and/or from results of various diagnostic procedures (such as, for example, from knowing the presence, absence and/or quantity of one or more biomarkers characteristic of the diagnosed disease or condition).

The term "monitoring" generally refers to the follow-up of a disease or a condition in a subject for any changes which may occur over time.

The terms "prognosing" or "prognosis" generally refer to an anticipation on the progression of a disease or condition and the prospect (e.g., the probability, duration, and/or extent) of recovery. A good prognosis of the diseases or conditions taught herein may generally encompass anticipation of a satisfactory partial or complete recovery from the diseases or conditions, preferably within an acceptable time period. A good prognosis of such may more commonly encompass anticipation of not further worsening or aggravating of such, preferably within a given time period. A poor prognosis of the diseases or conditions as taught herein may generally encompass anticipation of a substandard recovery and/or unsatisfactorily slow recovery, or to substantially no recovery or even further worsening of such.

The terms also encompass prediction of a disease. The terms "predicting" or "prediction" generally refer to an advance declaration, indication or foretelling of a disease or condition in a subject not (yet) having said disease or condition. For example, a prediction of a disease or condition in a subject may indicate a probability, chance or risk that the subject will develop said disease or condition, for example within a certain time period or by a certain age. Said probability, chance or risk may be indicated inter alia as an absolute value, range or statistics, or may be indicated relative to a suitable control subject or subject population (such as, e.g., relative to a general, normal or healthy subject or subject population). Hence, the probability, chance or risk that a subject will develop a disease or condition may be advantageously indicated as increased or decreased, or as fold-increased or fold-decreased relative to a suitable control subject or subject population. As used herein, the term "prediction" of the conditions or diseases as taught herein in a subject may also particularly mean that the subject has a 'positive' prediction of such, i.e., that the subject is at risk of having such (e.g., the risk is significantly increased vis-à-vis a control subject or subject population). The term "prediction of no" diseases or conditions as taught herein as described herein in a subject may particularly mean that the subject has a 'negative' prediction of such, i.e., that the subject's risk of having such is not significantly increased vis-à-vis a control subject or subject population.

Suitably, an altered quantity or phenotype of the immune cells in the subject compared to a control subject having normal immune status or not having a disease comprising an immune component indicates that the subject has an impaired immune status or has a disease comprising an immune component or would benefit from an immune therapy.

Hence, the methods may rely on comparing the quantity of immune cell populations, biomarkers, or gene or gene product signatures measured in samples from patients with reference values, wherein said reference values represent known predictions, diagnoses and/or prognoses of diseases or conditions as taught herein.

For example, distinct reference values may represent the prediction of a risk (e.g., an abnormally elevated risk) of having a given disease or condition as taught herein vs. the prediction of no or normal risk of having said disease or condition. In another example, distinct reference values may represent predictions of differing degrees of risk of having such disease or condition.

In a further example, distinct reference values can represent the diagnosis of a given disease or condition as taught herein vs. the diagnosis of no such disease or condition (such as, e.g., the diagnosis of healthy, or recovered from said disease or condition, etc.). In another example, distinct reference values may represent the diagnosis of such disease or condition of varying severity.

In yet another example, distinct reference values may represent a good prognosis for a given disease or condition as taught herein vs. a poor prognosis for said disease or condition. In a further example, distinct reference values may represent varyingly favourable or unfavourable prognoses for such disease or condition.

Such comparison may generally include any means to determine the presence or absence of at least one difference and optionally of the size of such difference between values being compared. A comparison may include a visual inspection, an arithmetical or statistical comparison of measurements. Such statistical comparisons include, but are not limited to, applying a rule.

Reference values may be established according to known procedures previously employed for other cell populations, biomarkers and gene or gene product signatures. For example, a reference value may be established in an individual or a population of individuals characterised by a particular diagnosis, prediction and/or prognosis of said disease or condition (i.e., for whom said diagnosis, prediction and/or prognosis of the disease or condition holds true). Such population may comprise without limitation 2 or more, 10 or more, 100 or more, or even several hundred or more individuals.

A "deviation" of a first value from a second value may generally encompass any direction (e.g., increase: first value>second value; or decrease: first value<second value) and any extent of alteration.

For example, a deviation may encompass a decrease in a first value by, without limitation, at least about 10% (about 0.9-fold or less), or by at least about 20% (about 0.8-fold or less), or by at least about 30% (about 0.7-fold or less), or by at least about 40% (about 0.6-fold or less), or by at least about 50% (about 0.5-fold or less), or by at least about 60% (about 0.4-fold or less), or by at least about 70% (about 0.3-fold or less), or by at least about 80% (about 0.2-fold or less), or by at least about 90% (about 0.1-fold or less), relative to a second value with which a comparison is being made.

For example, a deviation may encompass an increase of a first value by, without limitation, at least about 10% (about 1.1-fold or more), or by at least about 20% (about 1.2-fold or more), or by at least about 30% (about 1.3-fold or more), or by at least about 40% (about 1.4-fold or more), or by at least about 50% (about 1.5-fold or more), or by at least about 60% (about 1.6-fold or more), or by at least about 70% (about 1.7-fold or more), or by at least about 80% (about 1.8-fold or more), or by at least about 90% (about 1.9-fold or more), or by at least about 100% (about 2-fold or more), or by at least about 150% (about 2.5-fold or more), or by at least about 200% (about 3-fold or more), or by at least about 500% (about 6-fold or more), or by at least about 700% (about 8-fold or more), or like, relative to a second value with which a comparison is being made.

Preferably, a deviation may refer to a statistically significant observed alteration. For example, a deviation may refer to an observed alteration which falls outside of error margins of reference values in a given population (as expressed, for example, by standard deviation or standard error, or by a predetermined multiple thereof, e.g., ±1×SD or ±2×SD or ±3×SD, or ±1×SE or ±2×SE or ±3×SE). Deviation may also refer to a value falling outside of a reference range defined by values in a given population (for example, outside of a range which comprises ≥40%, ≥50%, ≥60%, ≥70%, ≥75% or ≥80% or ≥85% or ≥90% or ≥95% or even ≥100% values in said population).

In a further embodiment, a deviation may be concluded if an observed alteration is beyond a given threshold or cut-off. Such threshold or cut-off may be selected as generally known in the art to provide for a chosen sensitivity and/or specificity of the prediction methods, e.g., sensitivity and/or specificity of at least 50%, or at least 60%, or at least 70%, or at least 80%, or at least 85%, or at least 90%, or at least 95%.

For example, receiver-operating characteristic (ROC) curve analysis can be used to select an optimal cut-off value of the quantity of a given immune cell population, biomarker or gene or gene product signatures, for clinical use of the present diagnostic tests, based on acceptable sensitivity and specificity, or related performance measures which are well-known per se, such as positive predictive value (PPV), negative predictive value (NPV), positive likelihood ratio (LR+), negative likelihood ratio (LR−), Youden index, or similar.

In certain embodiments, the disease may be an infection, inflammation, proliferative disease, autoimmune disease, or allergy.

In certain embodiments, the disease is selected from the group consisting of diseases set forth in Tables E10B and E10C.

In certain embodiments, the immune status of the subject may be determined before and after immune therapy, whereby the efficacy of the therapy is determined or monitored.

A further aspect provides a method for determining whether immune cells as taught herein contribute to pathology of a disease, such as a disease comprising an immune component, the method comprising detecting or quantifying immune cells as taught herein in a biological sample of a subject having the disease and a subject not having the disease, whereby altered quantity or phenotype of the immune cells between the subjects indicates that the immune cells contribute to pathology of the disease.

In certain embodiments, the disease may be an infection, inflammation, proliferative disease, autoimmune disease, or allergy.

In certain embodiments, the disease is selected from the group consisting of diseases set forth in Tables E10B and E10C.

In certain embodiments, the disease may be blastic plasmacytoid dendritic cell neoplasm (BPDCN) and the immune cells may be as defined in hi.

Hence, an aspect provides a method for diagnosing, prognosing or monitoring blastic plasmacytoid dendritic cell neoplasm (BPDCN) in a subject, the method comprising detecting or quantifying immune cells as defined in h1 in a biological sample of the subject.

A further aspect provides a method for detecting or quantifying immune cells as defined in h1 in a biological sample of a subject, wherein the subject is suspected of having or is at risk of developing BPDCN.

Another aspect provides a method for diagnosing and treating BPDCN in a subject, the method comprising: obtaining a biological sample from the subject; detecting or quantifying immune cells as defined in h1 in the biological sample of the subject; diagnosing the subject as in need of treatment for BPDCN when said immune cells are detected in the sample and/or when the quantity of said immune cells differs from a reference value; and administering an effective amount of a treatment to the diagnosed subject.

Aspects and embodiments of the present invention hence encompass, and the present specification describes, subject-matter as set forth in any one and all of the following Statements (1) to (94).

Statement (1). An isolated immune cell selected from the group consisting of:

a1) an immune cell characterised in that the immune cell comprises expression of HLA-DR, does not express CD3, CD56, CD19 and CD14, and comprises expression of CLEC9A;

a2) an immune cell which is HLA-DR positive, CD3 negative, CD56 negative, CD19 negative, CD14 negative, and CLEC9A positive;

a3) an immune cell characterised in that the immune cell comprises expression of HLA-DR, does not express CD3, CD56, CD19 and CD14, and comprises a gene or gene product signature, the signature comprising or consisting of one or more genes or gene products as set forth in Table E1 part a or in Table E2 part a or in FIG. 2C cluster 'DC1' or in FIG. 2D cluster 'DCV' or in FIG. 2G cluster 'DC1';

b1) an immune cell characterised in that the immune cell comprises expression of HLA-DR, does not express CD3, CD56, CD19 and CD14, and comprises expression of FCGR2B;

b2) an immune cell which is HLA-DR positive, CD3 negative, CD56 negative, CD19 negative and CD14 negative, and FCGR2B positive;

b3) an immune cell characterised in that the immune cell comprises expression of HLA-DR, does not express CD3, CD56, CD19 and CD14, and comprises a gene or gene product signature, the signature comprising or consisting of one or more genes or gene products as set forth in Table E1 part b or in Table E2 part b or in Table E3 part a or in FIG. 2C cluster 'DC2' or in FIG. 2D cluster 'DC2' or in FIG. 2G cluster 'DC2';

c1) an immune cell characterised in that the immune cell comprises expression of HLA-DR, does not express CD3, CD56 and CD19, and comprises expression of one or more genes or gene products selected from the group consisting of CD163, CD36, CD14, LYZ, S100A8, S100A9, and S100A12;

c2) an immune cell which is HLA-DR positive, CD3 negative, CD56 negative and CD19 negative, and positive for one or more genes or gene products selected from the group consisting of CD163, CD36, CD14, LYZ, S100A8, S100A9, and S100A12;

c3) an immune cell characterised in that the immune cell comprises expression of HLA-DR, does not express CD3, CD56 and CD19, and comprises a gene or gene product signature, the signature comprising or consisting of one or more genes or gene products as set forth in Table E1 part c or in Table E2 part c or in Table E3 part b or in FIG. 2C cluster 'DC3' or in FIG. 2D cluster 'DC3' or in FIG. 2G cluster 'DC3';

d1) an immune cell characterised in that the immune cell comprises expression of HLA-DR, does not express CD3, CD56, CD19 and CD14, and comprises expression of FCGR3A;

d2) an immune cell which is HLA-DR positive, CD3 negative, CD56 negative, CD19 negative and CD14 negative, and FCGR3A positive;

d3) an immune cell characterised in that the immune cell comprises expression of HLA-DR, does not express CD3, CD56, CD19 and CD14, and comprises a gene or gene product signature, the signature comprising or consisting of one or more genes or gene products as set forth in Table E1 part d or in Table E2 part d or in FIG. 2C cluster 'DC4' or in FIG. 2D cluster 'DC4' or in FIG. 2G cluster 'DC4';

e1) an immune cell characterised in that the immune cell comprises expression of HLA-DR, does not express CD3, CD56, CD19 and CD14, and comprises expression of one or more genes or gene products selected from the group consisting of AXL, SIGLEC6, SIGLEC1, PPP1R14A, CD22, CD5, and GPR146;

e2) an immune cell which is HLA-DR positive, CD3 negative, CD56 negative, CD19 negative and CD14 negative, and positive for one or more genes or gene products selected from the group consisting of AXL, SIGLEC6, SIGLEC1, PPP1R14A, CD22, CD5, and GPR146;

e3) an immune cell characterised in that the immune cell comprises expression of HLA-DR, does not express CD3, CD56, CD19 and CD14, and comprises a gene or gene product signature, the signature comprising or consisting of one or more genes or gene products as set forth in Table E1 part e or in Table E2 part e or in FIG. 2C cluster 'DC5' or in FIG. 2D cluster 'DC5' or in FIG. 2G cluster 'DC5';

f1) an immune cell characterised in that the immune cell comprises expression of HLA-DR, does not express CD3, CD56, CD19 and CD14, and comprises expression of one or more genes or gene products selected from the group consisting of GZMB, SELPLG, DERL3, PTPRCAP, BCL11A, LAMP5, SLA2, SELS, NRP1, SIDT1, TCF4, SLC15A4, PTCRA, IRF7, and TRAF4;

f2) an immune cell which is HLA-DR positive, CD3 negative, CD56 negative, CD19 negative and CD14 negative, and positive for one or more genes or gene products selected from the group consisting of GZMB, SELPLG, DERL3, PTPRCAP, BCL11A, LAMP5, SLA2, SELS, NRP1, SIDT1, TCF4, SLC15A4, PTCRA, IRF7, and TRAF4;

f3) an immune cell characterised in that the immune cell comprises expression of HLA-DR, does not express CD3, CD56, CD19 and CD14, and comprises a gene or gene product signature, the signature comprising or consisting of one or more genes or gene products as set forth in Table E1 part f or in Table E2 part f or in FIG. 2C cluster 'DC6' or in FIG. 2D cluster 'DC6' or in FIG. 2G cluster 'DC6' or in FIG. 6A cluster 'DC6';

g1) an immune cell characterised in that the immune cell comprises expression of HLA-DR, does not express CD3, CD56, CD19 and CD14, does not express CD11C, CD123 and CD39, and comprises expression of CD45RA, high expression of CD100, and intermediate expression of CD34;

g2) an immune cell which is HLA-DR positive, CD3 negative, CD56 negative, CD19 negative, CD14 negative, CD11C negative, CD123 negative, CD39 negative, CD45RA positive, CD100 high, CD34 intermediate;

g3) an immune cell characterised in that the immune cell comprises expression of HLA-DR, does not express CD3, CD56, CD19 and CD14, does not express CD11C, CD123 and CD39, and comprises expression of one or more genes or gene products selected from the group consisting of RUNX2, TNFRSF18, ID2, ACY3, RORC, SEMA4D, SATB1, KIT, AHR, HLX, and CCR7;

g4) an immune cell which is HLA-DR positive, CD3 negative, CD56 negative, CD19 negative, CD14 negative, CD11C negative, CD123 negative, CD39 negative, and positive for one or more genes or gene products selected from the group consisting of RUNX2, TNFRSF18, ID2, ACY3, RORC, SEMA4D, SATB1, KIT, AHR, HLX, and CCR7;

g5) an immune cell characterised in that the immune cell comprises expression of HLA-DR, does not express CD3, CD56, CD19 and CD14, does not express CD11C, CD123 an CD39, and is capable of differentiation to: the immune cell as defined in any one of a1), a2), or a3), the immune cell as defined in any one of b1), b2), or b3), and the immune cell as defined in any one of c1), c2), or c3);

g6) an immune cell which is HLA-DR positive, CD3 negative, CD56 negative, CD19 negative, CD14 negative, CD11C negative, CD123 negative, CD39 negative, and is capable of differentiation to: the immune cell as defined in any one of a1), a2), or a3), the immune cell as defined in any one of b1), b2), or b3), and the immune cell as defined in any one of c1), c2), or c3); or h1) an immune cell characterised in that the immune cell comprises expression of HLA-DR, CD45 and CD123, and comprises a gene or gene product signature, the signature comprising or consisting of one or more genes or gene products as set forth in Table E8 or in FIG. 8B clusters BPDCN_1 to 4.

Statement (2). The isolated immune cell according to Statement 1, wherein:

the immune cell as defined in any one of b1), b2), or b3) comprises expression of CD1C, or CD11C, or CD1C and CD11C;

the immune cell as defined in any one of b1), b2), or b3) is CD1C positive, or CD11C positive, or CD1C positive and CD11C positive;

the immune cell as defined in any one of c1), c2), or c3) comprises expression of CD1C, or CD11C, or CD1C and CD11C;

the immune cell as defined in any one of c1), c2), or c3) is CD1C positive, or CD11C positive, or CD1C positive and CD11C positive;

the immune cell as defined in c1) comprises expression of two or more, three or more, four or more, five or more, six or more, or all genes or gene products selected from the group consisting of CD163, CD36, CD14, LYZ, S100A8, S100A9, and S100A12;

the immune cell as defined in c1) comprises expression of CD163 and CD36;

the immune cell as defined in c2) is positive for two or more, three or more, four or more, five or more, six or more, or all genes or gene products selected from the group consisting of CD163, CD36, CD14, LYZ, S100A8, S100A9, and S100A12;

the immune cell as defined in c2) is CD163 positive and CD36 positive;

the immune cell as defined in any one of d1), d2), or d3) does not express CD1C, or CD141, or CD1C and CD141;

the immune cell as defined in any one of d1), d2), or d3) is CD1C negative, or CD141 negative, or CD1C negative and CD141 negative;

the immune cell as defined in e1) comprises expression of two or more, three or more, four or more, five or more, six or more, or all genes or gene products selected from the group consisting of AXL, SIGLEC6, SIGLEC1, PPP1R14A, CD22, CD5, and GPR146;

the immune cell as defined in e1) comprises expression of AXL and SIGLEC6;

the immune cell as defined in e2) is positive for two or more, three or more, four or more, five or more, six or more, or all genes or gene products selected from the group consisting of AXL, SIGLEC6, SIGLEC1, PPP1R14A, CD22, CD5, and GPR146;

the immune cell as defined in e2) is AXL positive and SIGLEC6 positive;

the immune cell as defined in any one of e1), e2), or e3) does not express CD141, or CD16, or CD141 and CD16;

the immune cell as defined in any one of e1), e2), or e3) is CD141 negative, or CD16 negative, or CD141 negative and CD16 negative;

the immune cell as defined in any one of e1), e2), or e3) comprises expression of CD123 and does not express or expresses low CD11C;

the immune cell as defined in any one of e1), e2), or e3) is CD123 positive and CD11C low or negative (CD123$^+$CD11C$^{lo/-}$);

the immune cell as defined in any one of e1), e2), or e3) comprises a gene or gene product signature, the signature comprising or consisting of one or more genes or gene products selected from the group consisting of PROC, IRF8, FMNL3, APP, SERPINF1, C1ORF186, CYBASC3, PLAC8, NRP1, CCDC50, TSPAN13, UGCG, LILRA4, MZB1, PTPRS, AK128525, IGJ, and IL3RA;

the immune cell as defined in any one of e1), e2), or e3) does not express ITGAX;

the immune cell as defined in any one of e1), e2), or e3) expresses low CD123 and comprises expression of CD11C;

the immune cell as defined in any one of e1), e2), or e3) is CD123 low and CD11C positive (CD123$^{lo}$CD11C$^+$);

the immune cell as defined in any one of e1), e2), or e3) comprises a gene or gene product signature, the signature comprising or consisting of one or more genes or gene products selected from the group consisting of ITGAX, IFI30, LGALS2, FGR, LY86, GLIPR2, TIMP1, LST1, AGPAT9, IFITM3, DUSP23, ENTPD1, LOC645638, and IL1RN;

the immune cell as defined in any one of e1), e2), or e3) comprises expression of ITGAX;

the immune cell as defined in f1) comprises expression of two or more, three or more, four or more, five or more, six or more, seven or more, eight or more, nine or more, ten or more, eleven or more, twelve or more, thirteen or more, fourteen or more, or all genes or gene products selected from the group consisting of GZMB, SELPLG, DERL3, PTPRCAP, BCL11A, LAMP5, SLA2, SELS, NRP1, SIDT1, TCF4, SLC15A4, PTCRA, IRF7, and TRAF4;

the immune cell as defined in f2) is positive for two or more, three or more, four or more, five or more, six or more, seven or more, eight or more, nine or more, ten or more, eleven or more, twelve or more, thirteen or more, fourteen or more, or all genes or gene products selected from the group consisting of GZMB, SELPLG, DERL3, PTPRCAP, BCL11A, LAMP5, SLA2, SELS, NRP1, SIDT1, TCF4, SLC15A4, PTCRA, IRF7, and TRAF4;

the immune cell as defined in any one of f1), f2), or f3) comprises expression of CD123, or does not express CD11C, or comprises expression of CD123 and does not express CD11C;

the immune cell as defined in any one of f1), f2), or f3) is CD123 positive, or CD11C negative, or CD123 positive and CD11C negative;

the immune cell as defined in any one of f1), f2), or f3) comprises expression of CD123, and does not express CD11C, CD141, AXL and SIGLE6;

the immune cell as defined in any one of f1), f2), or f3) is CD123 positive, CD11C negative, CD141 negative, AXL negative and SIGLE6 negative;

the immune cell as defined in g3) comprises expression of two or more, three or more, four or more, five or more, six or more, seven or more, eight or more, nine or more, ten or more, or all genes or gene products selected from the group consisting of RUNX2, TNFRSF18, ID2, ACY3, RORC, SEMA4D, SATB1, KIT, AHR, HLX, and CCR7; or the immune cell as defined in g4) is positive for two or more, three or more, four or more, five or more, six or more, seven or more, eight or more, nine or more, ten or more, or all genes or gene products selected from the group consisting of RUNX2, TNFRSF18, ID2, ACY3, RORC, SEMA4D, SATB1, KIT, AHR, HLX, and CCR7.

Statement (3). The isolated immune cell according to Statements (1) or (2), wherein:

the one or more genes or gene products comprised by or constituting the signature as defined in a3) are selected from the group consisting of genes or gene products as set forth in Table E2 part a which display AUC value of 0.70 or more, preferably 0.80 or more, more preferably 0.85 or more, even more preferably 0.90 or more, and still more preferably 0.95 or more, the one or more genes or gene products comprised by or constituting the signature as defined in b3) are selected from the group consisting of genes or gene products as set forth in Table E2 part b which display AUC value of 0.70 or more, preferably 0.80 or more, more preferably 0.85 or more, even more preferably 0.90 or more, and still more preferably 0.95 or more;

the one or more genes or gene products comprised by or constituting the signature as defined in b3) are selected from the group consisting of genes or gene products as set forth in Table E3 part a which display AUC value of 0.70 or more, preferably 0.80 or more, more preferably 0.85 or more, even more preferably 0.90 or more, and still more preferably 0.95 or more;

the one or more genes or gene products comprised by or constituting the signature as defined in c3) are selected from the group consisting of genes or gene products as set forth in Table E2 part c which display AUC value of 0.70 or more, preferably 0.80 or more, more preferably 0.85 or more, even more preferably 0.90 or more, and still more preferably 0.95 or more;

the one or more genes or gene products comprised by or constituting the signature as defined in c3) are selected from the group consisting of genes or gene products as set forth in Table E3 part b which display AUC value of 0.30 or less, preferably 0.20 or less, more preferably 0.15 or less, even more preferably 0.10 or less, and still more preferably 0.05 or less;

the one or more genes or gene products comprised by or constituting the signature as defined in d3) are selected from the group consisting of genes or gene products as set forth in Table E2 part d which display AUC value of 0.70 or more, preferably 0.80 or more, more preferably 0.85 or more, even more preferably 0.90 or more, and still more preferably 0.95 or more;

the one or more genes or gene products comprised by or constituting the signature as defined in e3) are selected from the group consisting of genes or gene products as set forth in Table E2 part e which display AUC value of 0.70 or more, preferably 0.80 or more, more preferably 0.85 or more, even more preferably 0.90 or more, and still more preferably 0.95 or more;

the one or more genes or gene products comprised by or constituting the signature as defined in f3) are selected from the group consisting of genes or gene products as set forth in Table E2 part f which display AUC value of 0.70 or more, preferably 0.80 or more, more preferably 0.85 or more, even more preferably 0.90 or more, and still more preferably 0.95 or more; or the one or more genes or gene products comprised by or constituting the signature as defined in h1) are selected from the group consisting of genes or gene products as set forth in Table E8 which display AUC value of 0.80 or more, preferably 0.85 or more, more preferably 0.90 or more, and even more preferably 0.95 or more.

Statement (4). The isolated immune cell according to any one of Statements (1) to (3), wherein:

the signature as defined in a3) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E2 part a; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E2 part a, which display AUC value of 0.70 or more, preferably 0.80 or more, more preferably 0.85 or more, even more preferably 0.90 or more, and still more preferably 0.95 or more;

the signature as defined in b3) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E2 part b; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E2 part b, which display AUC value of 0.70 or more, preferably 0.80 or more, more preferably 0.85 or more, even more preferably 0.90 or more, and still more preferably 0.95 or more;

the signature as defined in b3) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E3 part a; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E3 part a, which display AUC value of 0.70 or more, preferably 0.80 or more, more preferably 0.85 or more, even more preferably 0.90 or more, and still more preferably 0.95 or more;

the signature as defined in c3) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 400%, at least 50%, at least 60%, at least 70%, at least 80%, or at least 90%, or up to 100% (by number) of the genes or gene products as set forth in Table E2 part c; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E2 part c, which display AUC value of 0.70 or more, preferably 0.80 or more, more preferably 0.85 or more, even more preferably 0.90 or more, and still more preferably 0.95 or more;

the signature as defined in c3) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E3 part b; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E3 part b, which display AUC value of 0.30 or less, preferably 0.20 or less, more preferably 0.15 or less, even more preferably 0.10 or less, and still more preferably 0.05 or less;

the signature as defined in d3) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 400%, at least 50%, at least 60%, at least 70%, at least 80%, or at least 90%, or up to 100% (by number) of the genes or gene products as set forth in Table E2 part d; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E2 part d, which display AUC value of 0.70 or more, preferably 0.80 or more, more preferably 0.85 or more, even more preferably 0.90 or more, and still more preferably 0.95 or more;

the signature as defined in e3) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E2 part e; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E2 part e, which display AUC value of 0.70 or more, preferably 0.80 or more, more preferably 0.85 or more, even more preferably 0.90 or more, and still more preferably 0.95 or more;

the signature as defined in f3) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E2 part f; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E2 part f, which display AUC value of 0.70 or more, preferably 0.80 or more, more preferably 0.85 or more, even more preferably 0.90 or more, and still more preferably 0.95 or more; or the signature as defined in h1) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E8; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as forth in Table E8, which display AUC value of 0.70 or more, preferably 0.80 or more, more preferably 0.85 or more, even more preferably 0.90 or more, and still more preferably 0.95 or more.

Statement (5). The isolated immune cell according to any one of Statements (1) to (4), wherein the immune cell is a dendritic cell or a progenitor or precursor of a dendritic cell, preferably wherein:

the immune cell as defined in any one of a1) to a3), b1) to b3), c1) to c3), d1) to d3), f1) to f3), or h1) is a dendritic cell; or the immune cell as defined in any one of e1)-e3), or g1)-g6) is a progenitor or precursor of a dendritic cell.

Statement (6). The isolated immune cell according to any one of Statements (1) to (5), wherein the immune cell is a human cell.

Statement (7). An immune cell gene or gene product signature selected from the group consisting of:

a) a signature comprising or consisting of one or more genes or gene products as set forth in Table E1 part a or in Table E2 part a or in FIG. 2C cluster 'DC1' or in FIG. 2D cluster 'DC1' or in FIG. 2G cluster 'DC1';

b) a signature comprising or consisting of one or more genes or gene products as set forth in Table E1 part b or in Table E2 part b or in Table E3 part a or in FIG. 2C cluster 'DC2' or in FIG. 2D cluster 'DC2' or in FIG. 2G cluster 'DC2';

c) a signature comprising or consisting of one or more genes or gene products as set forth in Table E1 part c or in Table E2 part c or in Table E3 part b or in FIG. 2C cluster 'DC3' or in FIG. 2D cluster 'DC3' or in FIG. 2G cluster 'DC3';

d) a signature comprising or consisting of one or more genes or gene products as set forth in Table E1 part d or in Table E2 part d or in FIG. 2C cluster 'DC4' or in FIG. 2D cluster 'DC4' or in FIG. 2G cluster 'DC4';

e) a signature comprising or consisting of one or more genes or gene products as set forth in Table E1 part e or in Table E2 part e or in FIG. 2C cluster 'DC5' or in FIG. 2D cluster 'DC5' or in FIG. 2G cluster 'DC5';

f) a signature comprising or consisting of one or more genes or gene products as set forth in Table E1 part f or in Table E2 part f or in FIG. 2C cluster 'DC6' or in FIG. 2D cluster 'DC6' or in FIG. 2G cluster 'DC6' or in FIG. 6A cluster 'DC6';

g) a signature comprising or consisting of one or more genes or gene products selected from the group consisting of PROC, IRF8, FMNL3, APP, SERPINF1, C1ORF186, CYBASC3, PLAC8, NRP1, CCDC50, TSPAN13, UGCG, LILRA4, MZB1, PTPRS, AK128525, IGJ, and IL3RA;

h) a signature comprising or consisting of one or more genes or gene products selected from the group consisting of ITGAX, IFI30, LGALS2, FGR, LY86, GLIPR2, TIMP1, LST1, AGPAT9, IFITM3, DUSP23, ENTPD1, LOC645638, and IL1RN; or i) a signature comprising or consisting of one or more genes or gene products as set forth in Table E8 or in FIG. 8B clusters BPDCN_1 to 4.

Statement (8). The signature according to Statement (7), wherein:

the one or more genes or gene products comprised by or constituting the signature as defined in a) are selected from the group consisting of genes or gene products as set forth in Table E2 part a which display AUC value of 0.70 or more, preferably 0.80 or more, more preferably 0.85 or more, even more preferably 0.90 or more, and still more preferably 0.95 or more;

the one or more genes or gene products comprised by or constituting the signature as defined in b) are selected from the group consisting of genes or gene products as set forth in Table E2 part b which display AUC value of 0.70 or more, preferably 0.80 or more, more preferably 0.85 or more, even more preferably 0.90 or more, and still more preferably 0.95 or more;

the one or more genes or gene products comprised by or constituting the signature as defined in b) are selected from the group consisting of genes or gene products as set forth in Table E3 part a which display AUC value of 0.70 or more, preferably 0.80 or more, more preferably 0.85 or more, even more preferably 0.90 or more, and still more preferably 0.95 or more;

the one or more genes or gene products comprised by or constituting the signature as defined in c) are selected from the group consisting of genes or gene products as set forth in Table E2 part c which display AUC value of 0.70 or more, preferably 0.80 or more, more preferably 0.85 or more, even more preferably 0.90 or more, and still more preferably 0.95 or more;

the one or more genes or gene products comprised by or constituting the signature as defined in c) are selected from the group consisting of genes or gene products as set forth in Table E3 part b which display AUC value of 0.30 or less, preferably 0.20 or less, more preferably 0.15 or less, even more preferably 0.10 or less, and still more preferably 0.05 or less;

the one or more genes or gene products comprised by or constituting the signature as defined in d) are selected from the group consisting of genes or gene products as set forth in Table E2 part d which display AUC value of 0.70 or more, preferably 0.80 or more, more preferably 0.85 or more, even more preferably 0.90 or more, and still more preferably 0.95 or more;

the one or more genes or gene products comprised by or constituting the signature as defined in e) are selected from the group consisting of genes or gene products as set forth in Table E2 part e which display AUC value of 0.70 or more, preferably 0.80 or more, more preferably 0.85 or more, even more preferably 0.90 or more, and still more preferably 0.95 or more;

the one or more genes or gene products comprised by or constituting the signature as defined in f) are selected from the group consisting of genes or gene products as set forth in Table E2 part f which display AUC value of 0.70 or more, preferably 0.80 or more, more preferably 0.85 or more, even more preferably 0.90 or more, and still more preferably 0.95 or more; or the one or more genes or gene products comprised by or constituting the signature as defined in i) are selected from the group consisting of genes or gene products as set forth in Table E8 which display AUC value of 0.80 or more, preferably 0.85 or more, more preferably 0.90 or more, and even more preferably 0.95 or more.

Statement (9). The signature according to Statement (7), wherein:

the signature as defined in a) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E2 part a; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E2 part a, which display AUC value of 0.70 or more, preferably 0.80 or more, more preferably 0.85 or more, even more preferably 0.90 or more, and still more preferably 0.95 or more;

the signature as defined in b) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E2 part b; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E2 part b, which display AUC value of 0.70 or more, preferably 0.80 or more, more preferably 0.85 or more, even more preferably 0.90 or more, and still more preferably 0.95 or more;

the signature as defined in b) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 400/a, at least 50%, at least 60%, at least 70%, at least 80%, or at least 90%, or up to 100% (by number) of the genes or gene products as set forth in Table E3 part a; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E3 part a, which display AUC value of 0.70 or more, preferably 0.80 or more, more preferably 0.85 or more, even more preferably 0.90 or more, and still more preferably 0.95 or more;

the signature as defined in c) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E2 part c; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E2 part c, which display AUC value of 0.70 or more, preferably 0.80 or more, more preferably 0.85 or more, even more preferably 0.90 or more, and still more preferably 0.95 or more;

the signature as defined in c) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E3 part b; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E3 part b, which display AUC value of 0.30 or less, preferably 0.20 or less, more preferably 0.15 or less, even more preferably 0.10 or less, and still more preferably 0.05 or less;

the signature as defined in d) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E2 part d; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E2 part d, which display AUC value of 0.70 or more, preferably 0.80 or more, more preferably 0.85 or more, even more preferably 0.90 or more, and still more preferably 0.95 or more;

the signature as defined in e) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E2 part e; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E2 part e, which display AUC value of 0.70 or more, preferably 0.80 or more, more preferably 0.85 or more, even more preferably 0.90 or more, and still more preferably 0.95 or more;

the signature as defined in f) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E2 part f; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E2 part f, which display AUC value of 0.70 or more, preferably 0.80 or more, more preferably 0.85 or more, even more preferably 0.90 or more, and still more preferably 0.95 or more; or the signature as defined in i) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E8; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E8, which display AUC value of 0.70 or more, preferably 0.80 or more, more preferably 0.85 or more, even more preferably 0.90 or more, and still more preferably 0.95 or more.

Statement (10). A method for detecting or quantifying immune cells in a biological sample of a subject, or for isolating immune cells from a biological sample of a subject, the method comprising:
 a) providing a biological sample of a subject; and
 b) detecting or quantifying in the biological sample immune cells as defined in any one of Statements (1) to (6), or isolating from the biological sample immune cells as defined in any one of Statements (1) to (6).

Statement (11). The method according to Statement (10), wherein the immune cells are detected, quantified or isolated using a technique selected from the group consisting of flow cytometry, mass cytometry, fluorescence activated cell sorting, fluorescence microscopy, affinity separation, magnetic cell separation, microfluidic separation, and combinations thereof.

Statement (12). The method according to Statement (11), wherein the technique employs one or more agents capable of specifically binding to one or more gene products expressed or not expressed by the immune cells, preferably on the cell surface of the immune cells.

Statement (13). The method according to Statement (12), wherein the one or more agents are one or more antibodies.

Statement (14). A kit of parts or an article of manufacture for detecting, quantifying or isolating immune cells, the kit of parts or article of manufacture comprising:
 a') one or more agents capable of specifically binding to CLEC9A, optionally further comprising one or more agents capable of specifically binding to one or more gene products selected from the group consisting of HLA-DR, CD3, CD56, CD19 and CD14;
 a") one or more agents capable of specifically binding to one or more gene products comprised by or constituting the signature as defined in any one of Statements (7) to (9) part a), optionally further comprising one or more agents capable of specifically binding to one or more gene products selected from the group consisting of HLA-DR, CD3, CD56, CD19 and CD14;
 b') one or more agents capable of specifically binding to FCGR2B, optionally further comprising one or more agents capable of specifically binding to one or more gene products selected from the group consisting of HLA-DR, CD3, CD56, CD19 and CD14;
 b") one or more agents capable of specifically binding to one or more gene products comprised by or constituting the signature as defined in any one of Statements (7) to (9) part b), optionally further comprising one or more agents capable of specifically binding to one or more gene products selected from the group consisting of HLA-DR, CD3, CD56, CD19 and CD14;
 c') one or more agents capable of specifically binding to one or more gene products selected from the group consisting of CD163, CD36, CD14, LYZ, S100A8, S100A9, and S100A12, optionally further comprising one or more agents capable of specifically binding to one or more gene products selected from the group consisting of HLA-DR, CD3, CD56 and CD19;
 c") one or more agents capable of specifically binding to one or more gene products comprised by or constituting the signature as defined in any one of Statements (7) to (9) part c), optionally further comprising one or more agents capable of specifically binding to one or more gene products selected from the group consisting of HLA-DR, CD3, CD56 and CD19;
 d') one or more agents capable of specifically binding to FCGR3A, optionally further comprising one or more agents capable of specifically binding to one or more gene products selected from the group consisting of HLA-DR, CD3, CD56, CD19 and CD14;
 d") one or more agents capable of specifically binding to one or more gene products comprised by or constituting the signature as defined in any one of Statements (7) to (9) part d), optionally further comprising one or more agents capable of specifically binding to one or more gene products selected from the group consisting of HLA-DR, CD3, CD56, CD19 and CD14;
 e') one or more agents capable of specifically binding to one or more gene products selected from the group consisting of AXL, SIGLEC6, SIGLEC1, PPP1R14A, CD22, CD5, and GPR146, optionally further comprising one or more agents capable of specifically binding to one or more gene products selected from the group consisting of HLA-DR, CD3, CD56, CD19 and CD14;
 e") one or more agents capable of specifically binding to one or more gene products comprised by or constituting the signature as defined in any one of Statements (7) to (9) part e), optionally further comprising one or more agents capable of specifically binding to one or more gene products selected from the group consisting of HLA-DR, CD3, CD56, CD19 and CD14;

f') one or more agents capable of specifically binding to one or more gene products selected from the group consisting of GZMB, SELPLG, DERL3, PTPRCAP, BCL11A, LAMP5, SLA2, SELS, NRP1, SIDT1, TCF4, SLC15A4, PTCRA, IRF7, and TRAF4, optionally further comprising one or more agents capable of specifically binding to one or more gene products selected from the group consisting of HLA-DR, CD3, CD56, CD19 and CD14;

f") one or more agents capable of specifically binding to one or more gene products comprised by or constituting the signature as defined in any one of Statements (7) to (9) part f), optionally further comprising one or more agents capable of specifically binding to one or more gene products selected from the group consisting of HLA-DR, CD3, CD56, CD19 and CD14;

g') one or more agents capable of specifically binding to CD45RA, CD100, and CD34, optionally further comprising one or more agents capable of specifically binding to one or more gene products selected from the group consisting of HLA-DR, CD3, CD56, CD19, CD14, CD11C, CD123 and CD39;

g") one or more agents capable of specifically binding to one or more gene products selected from the group consisting of RUNX2, TNFRSF18, ID2, ACY3, RORC, SEMA4D, SATB1, KIT, AHR, HLX, and CCR7, optionally further comprising one or more agents capable of specifically binding to one or more gene products selected from the group consisting of HLA-DR, CD3, CD56, CD19, CD14, CD11C, CD123 and CD39; and/or h') one or more agents capable of specifically binding to one or more gene products comprised by or constituting the signature as defined in any one of Statements (7) to (9) part i), optionally further comprising one or more agents capable of specifically binding to one or more gene products selected from the group consisting of HLA-DR, CD45 and CD123.

Statement (15). The kit of parts or article of manufacture according to Statement (14), wherein:

the kit of parts or article of manufacture as defined in any one of b') or b") further comprises one or more agents capable of specifically binding to one or more gene products selected from the group consisting of CD1C and CD11C;

the kit of parts or article of manufacture as defined in any one of c') or c") further comprises one or more agents capable of specifically binding to one or more gene products selected from the group consisting of CD1C and CD11C;

the kit of parts or article of manufacture as defined in any one of c') or c") comprises agents capable of specifically binding to two or more, three or more, four or more, five or more, six or more, or all gene products selected from the group consisting of CD163, CD36, CD14, LYZ, S100A8, S100A9, and S100A12;

the kit of parts or article of manufacture as defined in any one of c') or c") comprises agents capable of specifically binding to CD163 and CD36;

the kit of parts or article of manufacture as defined in any one of d') or d") further comprises one or more agents capable of specifically binding to one or more gene products selected from the group consisting of CD1C and CD141;

the kit of parts or article of manufacture as defined in any one of e') or e") comprises agents capable of specifically binding to two or more, three or more, four or more, five or more, six or more, or all gene products selected from the group consisting of AXL, SIGLEC6, SIGLEC1, PPP1R14A, CD22, CD5, and GPR146;

the kit of parts or article of manufacture as defined in any one of e') or e") comprises agents capable of specifically binding to AXL and SIGLEC6;

the kit of parts or article of manufacture as defined in any one of e') or e") further comprises one or more agents capable of specifically binding to one or more gene products selected from the group consisting of CD141 and CD16;

the kit of parts or article of manufacture as defined in any one of e') or e") further comprises one or more agents capable of specifically binding to one or more gene products selected from the group consisting of CD123 and CD11C;

the kit of parts or article of manufacture as defined in any one of e') or e") comprises agents capable of specifically binding to one or more gene products selected from the group consisting of PROC, IRF8, FMNL3, APP, SERPINF1, C1ORF186, CYBASC3, PLAC8, NRP1, CCDC50, TSPAN13, UGCG, LILRA4, MZB1, PTPRS, AK128525, IGJ, and IL3RA;

the kit of parts or article of manufacture as defined in any one of e') or e") comprises agents capable of specifically binding to one or more gene products selected from the group consisting of ITGAX, IFI30, LGALS2, FGR, LY86, GLIPR2, TIMP1, LST1, AGPAT9, IFITM3, DUSP23, ENTPD1, LOC645638, and IL1RN;

the kit of parts or article of manufacture as defined in any one of e') or e") comprises agents capable of specifically binding to ITGAX;

the kit of parts or article of manufacture as defined in any one of f') or f") comprises agents capable of specifically binding to two or more, three or more, four or more, five or more, six or more, seven or more, eight or more, nine or more, ten or more, eleven or more, twelve or more, thirteen or more, fourteen or more, or all genes or gene products selected from the group consisting of GZMB, SELPLG, DERL3, PTPRCAP, BCL11A, LAMP5, SLA2, SELS, NRP1, SIDT1, TCF4, SLC15A4, PTCRA, IRF7, and TRAF4;

the kit of parts or article of manufacture as defined in any one of f') or f") further comprises one or more agents capable of specifically binding to one or more gene products selected from the group consisting of CD123 and CD11C;

the kit of parts or article of manufacture as defined in any one of f') or f") comprises agents capable of specifically binding to CD123, CD11C, CD141, AXL and SIGLE6; and/or the kit of parts or article of manufacture as defined in any one of g') or g") comprises agents capable of specifically binding to two or more, three or more, four or more, five or more, six or more, seven or more, eight or more, nine or more, ten or more, or all genes or gene products selected from the group consisting of RUNX2, TNFRSF18, ID2, ACY3, RORC, SEMA4D, SATB1, KIT, AHR, HLX, and CCR7.

Statement (16). The kit of parts or article of manufacture according to Statement (14) or (15), wherein the one or more agents are configured for use in a technique selected from the group consisting of flow cytometry, mass cytometry, fluorescence activated cell sorting, fluorescence microscopy, affinity separation, magnetic cell separation, microfluidic separation, and combinations thereof.

Statement (17). The kit of parts or article of manufacture according to any one of Statements (14) to (16), wherein the one or more agents are one or more antibodies.

Statement (18). The kit of parts or article of manufacture according to any one of Statements (14) to (17), which comprises a microfluidic system.

Statement (19). An isolated immune cell selected from the group consisting of:
- x) an immune cell characterised in that the immune cell does not express CD3, CD56, CD19, comprises expression of CD14, and comprises a gene or gene product signature, the signature comprising or consisting of one or more genes or gene products as set forth in Table E4 part a or in FIG. 4B cluster 'Mono1' or in FIG. 4D cluster 'Mono1' or in FIG. 4E cluster 'Mono1';
- y) an immune cell characterised in that the immune cell does not express CD3, CD56, CD19, comprises expression of CD14, and comprises a gene or gene product signature, the signature comprising or consisting of one or more genes or gene products as set forth in Table E4 part b or in FIG. 4B cluster 'Mono2' or in FIG. 4D cluster 'Mono2' or in FIG. 4E cluster 'Mono2';
- w) an immune cell characterised in that the immune cell does not express CD3, CD56, CD19, comprises expression of CD14, and comprises a gene or gene product signature, the signature comprising or consisting of one or more genes or gene products as set forth in Table E4 part c or in FIG. 4B cluster 'Mono3' or in FIG. 4D cluster 'Mono3' or in FIG. 4E cluster 'Mono3';
- z) an immune cell characterised in that the immune cell does not express CD3, CD56, CD19, comprises expression of CD14, and comprises a gene or gene product signature, the signature comprising or consisting of one or more genes or gene products as set forth in Table E4 part d or in FIG. 4B cluster 'Mono4' or in FIG. 4D cluster 'Mono4' or in FIG. 4E cluster 'Mono4'.

Statement (20). The isolated immune cell according to Statement (19), wherein:
- the one or more genes or gene products comprised by or constituting the signature as defined in x) are selected from the group consisting of genes or gene products as set forth in Table E4 part a which display AUC value of 0.70 or more, preferably 0.80 or more, more preferably 0.85 or more, even more preferably 0.90 or more, and still more preferably 0.95 or more;
- the one or more genes or gene products comprised by or constituting the signature as defined in y) are selected from the group consisting of genes or gene products as set forth in Table E4 part b which display AUC value of 0.70 or more, preferably 0.80 or more, more preferably 0.85 or more, even more preferably 0.90 or more, and still more preferably 0.95 or more;
- the one or more genes or gene products comprised by or constituting the signature as defined in w) are selected from the group consisting of genes or gene products as set forth in Table E4 part c which display AUC value of 0.70 or more, preferably 0.80 or more, more preferably 0.85 or more, even more preferably 0.90 or more, and still more preferably 0.95 or more; or
- the one or more genes or gene products comprised by or constituting the signature as defined in z) are selected from the group consisting of genes or gene products as set forth in Table E4 part d which display AUC value of 0.70 or more, preferably 0.80 or more, more preferably 0.85 or more, even more preferably 0.90 or more, and still more preferably 0.95 or more.

Statement (21). The isolated immune cell according to Statements (19) or (20), wherein:
- the signature as defined in x) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E4 part a; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E4 part a, which display AUC value of 0.70 or more, preferably 0.80 or more, more preferably 0.85 or more, even more preferably 0.90 or more, and still more preferably 0.95 or more;
- the signature as defined in y) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E4 part b; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E4 part b, which display AUC value of 0.70 or more, preferably 0.80 or more, more preferably 0.85 or more, even more preferably 0.90 or more, and still more preferably 0.95 or more;
- the signature as defined in w) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E4 part c; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E4 part c, which display AUC value of 0.70 or more, preferably 0.80 or more, more preferably 0.85 or more, even more preferably 0.90 or more, and still more preferably 0.95 or more; or
- the signature as defined in z) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E4 part d; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E4 part d, which display AUC value of 0.70 or more, preferably 0.80 or more, more preferably 0.85 or more, even more preferably 0.90 or more, and still more preferably 0.95 or more.

Statement (22). The isolated immune cell according to any one of Statements (19) to (21), wherein the immune cell is a monocyte or a progenitor or precursor of a monocyte.

Statement (23). The isolated immune cell according to any one of Statements (19) to (22), wherein the immune cell is a human cell.

Statement (24). An immune cell gene or gene product signature selected from the group consisting of:
  x) a signature comprising or consisting of one or more genes or gene products as set forth in as set forth in Table E4 part a or in FIG. 4B cluster 'Mono1' or in FIG. 4D cluster 'Mono1' or in FIG. 4E cluster 'Mono1';
  y) a signature comprising or consisting of one or more genes or gene products as set forth in as set forth in Table E4 part b or in FIG. 4B cluster 'Mono2' or in FIG. 4D cluster 'Mono2' or in FIG. 4E cluster 'Mono2';
  w) a signature comprising or consisting of one or more genes or gene products as set forth in as set forth in Table E4 part c or in FIG. 4B cluster 'Mono3' or in FIG. 4D cluster 'Mono3' or in FIG. 4E cluster 'Mono3'; or
  z) a signature comprising or consisting of one or more genes or gene products as set forth in as set forth in Table E4 part d or in FIG. 4B cluster 'Mono4' or in FIG. 4D cluster 'Mono4' or in FIG. 4E cluster 'Mono4'.

Statement (25). The signature according to Statement (24), wherein:
  the one or more genes or gene products comprised by or constituting the signature as defined in x) are selected from the group consisting of genes or gene products as set forth in Table E4 part a which display AUC value of 0.70 or more, preferably 0.80 or more, more preferably 0.85 or more, even more preferably 0.90 or more, and still more preferably 0.95 or more;
  the one or more genes or gene products comprised by or constituting the signature as defined in y) are selected from the group consisting of genes or gene products as set forth in Table E4 part b which display AUC value of 0.70 or more, preferably 0.80 or more, more preferably 0.85 or more, even more preferably 0.90 or more, and still more preferably 0.95 or more;
  the one or more genes or gene products comprised by or constituting the signature as defined in w) are selected from the group consisting of genes or gene products as set forth in Table E4 part c which display AUC value of 0.70 or more, preferably 0.80 or more, more preferably 0.85 or more, even more preferably 0.90 or more, and still more preferably 0.95 or more; or
  the one or more genes or gene products comprised by or constituting the signature as defined in z) are selected from the group consisting of genes or gene products as set forth in Table E4 part d which display AUC value of 0.70 or more, preferably 0.80 or more, more preferably 0.85 or more, even more preferably 0.90 or more, and still more preferably 0.95 or more.

Statement (26). The signature according to Statement (24), wherein:
  the signature as defined in x) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E4 part a; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E4 part a, which display AUC value of 0.70 or more, preferably 0.80 or more, more preferably 0.85 or more, even more preferably 0.90 or more, and still more preferably 0.95 or more;
  the signature as defined in y) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E4 part b; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E4 part b, which display AUC value of 0.70 or more, preferably 0.80 or more, more preferably 0.85 or more, even more preferably 0.90 or more, and still more preferably 0.95 or more;
  the signature as defined in w) comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or up to 100% (by number) of the genes or gene products as set forth in Table E4 part c; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 500%, at least 60%, at least 70%, at least 80%, or at least 90%, and up to 100% (by number) of the genes or gene products as set forth in Table E4 part c, which display AUC value of 0.70 or more, preferably 0.80 or more, more preferably 0.85 or more, even more preferably 0.90 or more, and still more preferably 0.95 or more; or
  the signature as defined in z) comprises or consists of at least 1%, at least 2%, at least 3%, at least 4%, at least 5%, at least 6%, at least 7%, at least 8%, at least 9%, at least 10%, at least 15%, at least 200%, at least 25%, at least 30%, at least 40%, at least 50%, at least 60%, at least 70%, at least 80%, or at least 90%, or up to 100% (by number) of the genes or gene products as set forth in Table E4 part d; preferably comprises or consists of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, and up to 100% (by number) of the genes or gene products as set forth in Table E4 part d, which display AUC value of 0.70 or more, preferably 0.80 or more, more preferably 0.85 or more, even more preferably 0.90 or more, and still more preferably 0.95 or more.

Statement (27). A method for detecting or quantifying immune cells in a biological sample of a subject, or for isolating immune cells from a biological sample of a subject, the method comprising:
   a) providing a biological sample of a subject; and
   b) detecting or quantifying in the biological sample immune cells as defined in any one of Statements (19) to (23), or isolating from the biological sample immune cells as defined in any one of Statements (19) to (23).

Statement (28). The method according to Statement (27), wherein the immune cells are detected, quantified or isolated using a technique selected from the group consisting of flow cytometry, mass cytometry, fluorescence activated cell sorting, fluorescence microscopy, affinity separation, magnetic cell separation, microfluidic separation, and combinations thereof.

Statement (29). The method according to Statement (28), wherein the technique employs one or more agents capable of specifically binding to one or more gene products expressed or not expressed by the immune cells, preferably on the cell surface of the immune cells.

Statement (30). The method according to Statement (29), wherein the one or more agents are one or more antibodies.

Statement (31). A kit of parts or an article of manufacture for detecting, quantifying or isolating immune cells, the kit of parts or article of manufacture comprising:
   x) one or more agents capable of specifically binding to one or more gene products comprised by or constituting the signature as defined in any one of Statements (24) to (26) part x), optionally further comprising one or more agents capable of specifically binding to one or more gene products selected from the group consisting of CD3, CD56, CD19, and CD14;
   y) one or more agents capable of specifically binding to one or more gene products comprised by or constituting the signature as defined in any one of Statements (24) to (26) part y), optionally further comprising one or more agents capable of specifically binding to one or more gene products selected from the group consisting of CD3, CD56, CD19, and CD14;
   w) one or more agents capable of specifically binding to one or more gene products comprised by or constituting the signature as defined in any one of Statements (24) to (26) part w), optionally further comprising one or more agents capable of specifically binding to one or more gene products selected from the group consisting of CD3, CD56, CD19, and CD14; and/or
   z) one or more agents capable of specifically binding to one or more gene products comprised by or constituting the signature as defined in any one of Statements (24) to (26) part z), optionally further comprising one or more agents capable of specifically binding to one or more gene products selected from the group consisting of CD3, CD56, CD19, and CD14.

Statement (32). The kit of parts or article of manufacture according to Statement (31), wherein the one or more agents are configured for use in a technique selected from the group consisting of flow cytometry, mass cytometry, fluorescence activated cell sorting, fluorescence microscopy, affinity separation, magnetic cell separation, microfluidic separation, and combinations thereof.

Statement (33). The kit of parts or article of manufacture according to Statement (31) or (32), wherein the one or more agents are one or more antibodies.

Statement (34). The kit of parts or article of manufacture according to any one of Statements (31) to (33), which comprises a microfluidic system.

Statement (35). A population of immune cells as defined in any one of Statements (1) to (6) or (19) to (23).

Statement (36). A composition, pharmaceutical composition or vaccine comprising the immune cell as defined in any one of Statements (1) to (6) or (19) to (23) or the immune cell population as defined in Statement (35).

Statement (37). The composition, pharmaceutical composition or vaccine according to Statement (36), further comprising an antigen.

Statement (38). The composition, pharmaceutical composition or vaccine according to Statement (37), wherein the immune cell or immune cell population has been loaded with the antigen.

Statement (39). The composition, pharmaceutical composition or vaccine according to Statement (37) or (38), wherein the antigen is an allergen, autoimmune antigen, tumor antigen, or pathogen antigen.

Statement (40). The composition, pharmaceutical composition or vaccine according to Statement (39), wherein the pathogen is a bacterial, fungal, protozoal, parasitic, or viral pathogen.

Statement (41). A method for preparing an immune cell vaccine comprising:
   a) isolating from a biological sample of a subject an immune cell as defined in any one of Statements (1) to (6) or (19) to (23) or an immune cell population as defined in Statement (35);
   b) optionally in vitro expanding the immune cell or immune cell population of a);
   c) loading said immune cell or immune cell population with an antigen; and
   d) isolating the antigen-loaded immune cell or immune cell population.

Statement (42). The method according to Statement (41), wherein the antigen is an allergen, autoimmune antigen, tumor antigen, or pathogen antigen.

Statement (43). The method according to Statement (42), wherein the pathogen is a bacterial, fungal, protozoal, parasitic, or viral pathogen.

Statement (44). A method for eliciting an immune response or immune tolerance to an antigen in a subject comprising administering to the subject the immune cell as defined in any one of Statements (1) to (6) or (19) to (23) or the immune cell population as defined in Statement (35) or the pharmaceutical composition or vaccine as defined in any one of Statements (36) to (40), wherein the immune cell or immune cell population has been loaded with said antigen.

Statement (45). The method according to Statement (44), wherein the immune cell or immune cell population is autologous to said subject.

Statement (46). The method according to Statement (45), comprising:
   a) isolating from a biological sample of the subject an immune cell as defined in any one of Statements (1) to (6) or (19) to (23) or an immune cell population as defined in Statement (35);
   b) optionally in vitro expanding the immune cell or immune cell population of a);
   c) loading said in vitro expanded immune cell or immune cell population of b) with said antigen;
   d) administering the in vitro expanded antigen loaded immune cell or immune cell population of c) to the subject.

Statement (47). A method for eliciting an immune response or immune tolerance to an antigen in a subject comprising:

a) isolating from a biological sample of the subject an immune cell as defined in any one of Statements (1) to (6) or (19) to (23) or a population of immune cells as defined in Statement (35);

b) in vitro differentiating the immune cell or immune cell population of a) into a comparatively more mature immune cell or immune cell population;

c) loading said in vitro differentiated immune cell or immune cell population of b) with said antigen;

d) administering the in vitro differentiated antigen loaded immune cell or immune cell population of c) to the subject.

Statement (48). The method according to Statement (46) or (47), further comprising formulating the in vitro expanded and/or differentiated immune cell or immune cell population of c) into a pharmaceutical composition or vaccine, said pharmaceutical composition or vaccine optionally further comprising an antigen.

Statement (49). The method according to any one of Statement (44) to (48) wherein said immune response comprises an antigen-specific T cell response and/or antigen-specific antibody response.

Statement (50). A method for treating or preventing a pathological condition comprising administering to a subject in need thereof the immune cell as defined in any one of Statements (1) to (6) or (19) to (23) or the immune cell population as defined in Statement (35) or the pharmaceutical composition or vaccine as defined in any one of Statements (36) to (40).

Statement (51). The method according to Statement (50), wherein said pathological condition is an infection, inflammation, proliferative disease, autoimmune disease, or allergy.

Statement (52). The method according to Statement (50) or (51), wherein said pathological condition is selected from the group consisting of diseases set forth in Tables E10B and E10C.

Statement (53). The method according to any one of Statements (50) to (52), wherein the immune cell or immune cell population is autologous to said subject.

Statement (54). The method according to Statement (53), comprising:

a) isolating from a biological sample of the subject an immune cell as defined in any one of Statements (1) to (6) or (19) to (23) or an immune cell population as defined in Statement (35);

b) in vitro expanding the immune cell or immune cell population of a);

c) administering the in vitro expanded immune cell or immune cell population of b) to the subject.

Statement (55). The method according to Statement (54), further comprising formulating the in vitro expanded immune cell or immune cell population of b) into a pharmaceutical composition or vaccine, said pharmaceutical composition or vaccine optionally further comprising an antigen.

Statement (56). An in vitro method for differentiating the immune cell as defined in any one of Statements (1) to (6) or (19) to (23) into a comparatively more mature immune cell, comprising exposing the immune cell to one or more conditions and/or substances conducive to the differentiation.

Statement (57). The method according to Statement (56), wherein the one or more conditions and/or substances conducive to the differentiation comprise one or more or all of FLT3L, SCF, or GM-CSF.

Statement (58). The method according to Statement (56) or (57), wherein:

the immune cell as defined in any one of Statements (1) to (6) part e1), e2) or e3) differentiates into a CD1C positive dendritic cell, preferably into a dendritic cell as defined in any one of Statements (1) to (6) part b1), b2) or b3), or part c1), c2) or c3);

the immune cell as defined in any one of Statements (1) to (6) part g1), g2), g3), g4), g5) or g6) differentiates into a CD1C positive dendritic cell, preferably into a dendritic cell as defined in any one of Statements (1) to (6) part b1), b2) or b3), or part c1), c2) or c3); or the immune cell as defined in any one of Statements (1) to (6) part g1), g2), g3), g4), g5) or g6) differentiates into a CD141 positive dendritic cell, preferably into a dendritic cell as defined in any one of Statements (1) to (6) part a1), a2) or a3).

Statement (59). A method for treating or preventing a pathological condition in a subject in need thereof, the method comprising:

a) isolating from a biological sample of the subject an immune cell as defined in any one of Statements (1) to (6) or (19) to (23) or a population of immune cells as defined in Statement (35);

b) in vitro differentiating the immune cell of a) into a comparatively more mature immune cell or immune cell population;

c) administering the in vitro differentiated immune cell or immune cell population of b) to the subject.

Statement (60). The method according to Statement (59), further comprising formulating the in vitro differentiated immune cell or immune cell population of b) into a pharmaceutical composition or vaccine, said pharmaceutical composition or vaccine optionally further comprising an antigen.

Statement (61). A method for preparing a composition comprising activated T cells, the method comprising isolating T cells from a biological sample of a subject and contacting said T cells in vitro with an immune cell according to any one of Statements (1) to (6) or (19) to (23) or a population of immune cells as defined in Statement (35), wherein the immune cell or immune cell population has been loaded with an antigen.

Statement (62). The method according to Statement (61) wherein the immune cell or immune cell population is autologous to said subject.

(63). The method according to Statement (62) comprising:

a) isolating from a biological sample of said subject an immune cell as defined in any one of Statements (1) to (6) or (19) to (23) or an immune cell population as defined in Statement (35);

b) loading said immune cell or immune cell population with an antigen;

c) isolating T cells from a biological sample of said subject;

d) in vitro contacting said T cells with an immune cells according to any one of Statements (1) to (6) or (19) to (23) or a population of immune cells as defined in Statement (35) loaded with antigen.

Statement (64). A method for adoptive immunotherapy in a subject in need thereof comprising administering to said subject a composition comprising activated T cells prepared with a method according to any one of Statements (61) to (63).

Statement (65). The method according to any one of Statements (61) to (64) wherein said T cells are CD8+ T cells and said subject is suffering from proliferative disease.

Statement (66). A method for identifying an immunomodulant capable of modulating one or more phenotypic aspects of the immune cell as defined in any one of Statements (1) to (6) or (19) to (23) or the immune cell population as defined in Statement (35), comprising:

a) applying a candidate immunomodulant to the immune cell or immune cell population;

b) detecting modulation of one or more phenotypic aspects of the immune cell or immune cell population by the candidate immunomodulant, thereby identifying the immunomodulant.

Statement (67). An immunomodulant capable of modulating one or more phenotypic aspects of the immune cell as defined in any one of Statements (1) to (6) or (19) to (23) or the immune cell population as defined in Statement (35), such as an immunomodulant identified using the method as defined in Statement (66).

Statement (68). The immunomodulant according to Statement (67), wherein the immunomodulant is capable of modulating the proliferation, differentiation, maturation, migration, cytokine expression, antigen presentation, and/or viability of the immune cell or immune cell population.

Statement (69). The immunomodulant according to Statement (67), wherein the immunomodulant is capable of inducing or repressing the proliferation, differentiation, maturation, migration, cytokine expression, antigen presentation, and/or viability of the immune cell or immune cell population.

Statement (70). A composition, pharmaceutical composition or vaccine comprising the immunomodulant as defined in any one of Statements (67) to (69).

Statement (71). The immunomodulant according to any one of Statements (67) to (69), or the composition, pharmaceutical composition or vaccine according to Statement (70), wherein the immunomodulant comprises an antigen, or wherein the pharmaceutical composition or vaccine further comprises an antigen.

Statement (72). The immunomodulant, composition, pharmaceutical composition or vaccine according to Statement (71), wherein the antigen is an allergen, autoimmune antigen, tumor antigen, or pathogen antigen.

Statement (73). The immunomodulant, composition, pharmaceutical composition or vaccine according to Statement (72), wherein the pathogen is a bacterial, fungal, protozoal, parasitic, or viral pathogen.

Statement (74). The immunomodulant, composition, pharmaceutical composition or vaccine according to any one of Statements (71) to (73), wherein the antigen is directly or indirectly, covalently or non-covalently linked with an agent capable of specifically binding to a gene product expressed on the cell surface of the immune cell.

Statement (75). The immunomodulant, composition, pharmaceutical composition or vaccine according to Statement (74), wherein the agent is an antibody.

Statement (76). The immunomodulant according to any one of Statements (67) to (69), or the composition, pharmaceutical composition or vaccine according to Statement (70), wherein the immunomodulant comprises a portion capable of repressing the proliferation, differentiation, maturation, migration, cytokine expression, antigen presentation, or viability of the immune cell, directly or indirectly, covalently or non-covalently linked with an agent capable of specifically binding to a gene product expressed on the cell surface of the immune cell.

Statement (77). The immunomodulant, composition, pharmaceutical composition or vaccine according to Statement (76), wherein the agent capable of specifically binding to a gene product expressed on the cell surface of the immune cell is an antibody.

Statement (78). A method for treating or preventing a pathological condition comprising administering to a subject in need thereof the immunomodulant, pharmaceutical composition or vaccine as defined in any one of Statements (67) to (77).

Statement (79). The method according to Statement (78), wherein said pathological condition is an infection, inflammation, proliferative disease, autoimmune disease, or allergy.

Statement (80). The method according to Statement (78) or (79), wherein said pathological condition is selected from the group consisting of diseases set forth in Tables E10B and E10C.

Statement (81). A method for treating or preventing a pathological condition in a subject in need thereof comprising:

a) applying to the immune cell as defined in any one of Statements (1) to (6) or (19) to (23) or the immune cell population as defined in Statement (35) the immunomodulant, pharmaceutical composition or vaccine as defined in any one of Statements (67) to (77): and b) administering the immune cell or immune cell population of a) to the subject.

Statement (82). The method according to any one of Statements (78) to (81), wherein the immunomodulant is capable of repressing the proliferation, differentiation, maturation, migration, cytokine expression, antigen presentation, or viability of the immune cell as defined in any one of Statements (1) to (6) part c1), c2) or c3) or part e1), e2), or e3), and wherein the subject is in need of reducing inflammation, such as local or systemic inflammation.

Statement (83). A method for determining the immune status of a subject, or for diagnosing, prognosing or monitoring a disease comprising an immune component in a subject, the method comprising detecting or quantifying in a biological sample of the subject immune cells as defined in any one of Statements (1) to (6) or (19) to (23).

Statement (84). The method according to Statement (83), wherein an altered quantity or phenotype of the immune cells in the subject compared to a control subject having normal immune status or not having a disease comprising an immune component indicates that the subject has an impaired immune status or has a disease comprising an immune component or would benefit from an immune therapy.

Statement (85). The method according to Statements (83) or (84), wherein the disease is an infection, inflammation, proliferative disease, autoimmune disease, or allergy.

Statement (86). The method according to any one of Statements (83) to (85), wherein said disease is selected from the group consisting of diseases set forth in Tables E10B and E10C.

Statement (87). The method according to any one of Statements (83) to (86), wherein the immune status of the subject is determined before and after immune therapy, whereby the efficacy of the therapy is determined or monitored.

Statement (88). A method for determining whether immune cells as defined in anyone of Statements (1) to (6)

or (19) to (23) contribute to pathology of a disease, such as a disease comprising an immune component, the method comprising detecting or quantifying immune cells as defined in any one of Statements (1) to (6) or (19) to (23) in a biological sample of a subject having the disease and a subject not having the disease, whereby altered quantity or phenotype of the immune cells between the subjects indicates that the immune cells contribute to pathology of the disease.

Statement (89). The method according to Statement (88), wherein the disease is an infection, inflammation, proliferative disease, autoimmune disease, or allergy.

Statement (90). The method according to any one of Statements (88) to (89), wherein said disease is selected from the group consisting of diseases set forth in Tables E10B and E10C.

Statement (91). A method for diagnosing, prognosing or monitoring blastic plasmacytoid dendritic cell neoplasm (BPDCN) in a subject, the method comprising detecting or quantifying immune cells as defined in any one of Statements (1) to (6) part h1) in a biological sample of the subject.

Statement (92). A method for detecting or quantifying immune cells as defined in any one of Statements (1) to (6) part h i) in a biological sample of a subject, wherein the subject is suspected of having or is at risk of developing BPDCN.

Statement (93). A method for diagnosing and treating BPDCN in a subject, the method comprising:
    obtaining a biological sample from the subject;
        detecting or quantifying immune cells as defined in any one of Statements (1) to (6) part h1) in the biological sample of the subject;
        diagnosing the subject as in need of treatment for BPDCN when said immune cells are detected in the sample and/or when the quantity of said immune cells differs from a reference value; and
    administering an effective amount of a treatment to the diagnosed subject.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

The mammalian, such as human, immune system comprises a variety of immune cells, the main types of which are schematically illustrated in FIG. 1.

Historically, immune cell types have been defined by the expression of restricted sets of surface markers. However, while the adoption of such cell detection and classification scheme has proved useful, many questions remain, for example, whether the conventional sets of surface markers define truly distinct immune cell types, whether more accurate markers and marker signatures may exist, whether heterogeneity may exist within immune cell populations considered homogeneous based on conventional marker sets, whether immune cell types that escaped characterisation by the conventional marker sets may exist, or whether the subsets can be used to map cells in disease.

Dendritic cells (DCs) are mononuclear phagocytes found in blood, lymphoid organs and all tissues (Haniffa et al. 2015, Mildner and Jung; Schraml and Reis e Sousa). One of their central functions is to ingest materials such as pathogens, present processed epitopes to T cells and regulate innate and adaptive immune responses. DCs are heterogeneous and consist of multiple subtypes with unique functions that have been defined over the past decade in mice and humans. However, it is not clear how many DC subtypes exist, how they are related to each other and how they differ from other mononuclear phagocytes.

The results of numerous studies have shown that human dendritic cells express high levels of major histocompatibility complex class II (HLA-DR), a molecule essential for antigen presentation, and lack key markers of T, B, NK, granulocytes and monocytes. In the blood, DC subtypes include $CD11C^+$ conventional DCs (cDCs), including either $CD141^+$ or $CD1C^+$ cells, and plasmacytoid DCs (pDC), including CD123-cells. cDCs are effective at antigen-specific stimulation of $CD4^+$ and $CD8^+$ T cells, while pDCs specialize in producing type I interferons in response to viruses. pDCs and cDC subtypes differ in their expression of numerous sensors, pathways and effectors and play distinct roles in the immune response (Haniffa et al. 2015; Mildner and Jung; Schraml and Reis e Sousa). The different DC subtypes have historically been defined by a combination of morphology, physical properties, localization, molecular markers, functions and developmental origins, converging to the current model described above (Haniffa et. al. 2015; Mildner and Jung; Schraml and Reis e Sousa). However, the definition of DCs is still likely to be biased by the limited markers available to identify, isolate and manipulate the cells. Such biases, in turn, would alter the assignment of function and ontogeny to each DC subtype. To overcome these limitations, the present inventors devised an unbiased strategy using a single-cell RNA sequencing (scRNA-seq) (Trapnell; Grun and van Oudenaarden) to better assess the diversity of blood DCs and monocytes, leading us to identify new subtypes of DCs and monocytes, refine their existing classification, and pinpoint a precursor of cDCs in the blood. Using discriminative markers associated with the newly defined DC subtypes, the inventors also assessed the functions of some of the DC subtypes. Overall, the inventors' analysis provided a comparatively unbiased and comprehensive map of human blood DCs and monocytes Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

Example 1

Strategy for discovery and validation of DC and monocyte subtypes. To determine the subtypes of DCs and monocytes in the human blood, Applicants developed an experimental and computational strategy to: (i) perform single-cell RNA-sequencing on DCs and monocytes derived from a single healthy individual; (ii) identify clusters of cells that are similar to each other; (iii) find discriminative markers per cluster; (iv) prospectively isolate cells corresponding to key clusters using newly identified surface markers; (v) validate the identity of the sorted cells using scRNA-seq; (vi) confirm the existence of these cell types in up to 10 independent healthy individuals; (v) perform functional analyses for selected cell types.

Single cell profiling of hood DCs and monocytes. Applicants analyzed blood DC and monocyte populations from ficoll-purified blood cells that were FACS-sorted and excluded for the major lineages (LIN), including B (CD19), T (CD3) and NK (CD56) markers. For DCs, Applicants sampled LIN$^-$HLA-DR$^+$CD14$^-$ cells across the CD11C$^+$ (to enrich for CD141$^+$ and CD1C$^+$ cDCs) and CD11C$^-$ (to enrich for CD123$^+$ pDCs) fractions. For monocytes, Applicants sampled LIN$^-$CD141$^{lo/+}$ cells (including classical CD14$^{++}$CD16$^-$, intermediate CD14$^{++}$CD16$^+$, and non-classical CD14$^+$CD16$^{++}$). Applicants used additional markers (DCs: CD123, CD141, CD1C; monocytes: CD14, CD16) to create overlapping gates that comprehensively and evenly sample DCs and monocytes, without excluding cells (FIG. 2A-B for DCs; monocytes described in FIG. 4; Methods).

To define subpopulations and identify useful markers for further isolation, Applicants performed deep scRNA-seq using a modified version of the Smart-Seq2 protocol (Methods), followed by sequencing of ~1-2 million paired end reads per cells (Picelli et al.; Trombetta et al.). Of 768 DCs and 384 monocytes initially profiled in the select individual for discovering subsets, Applicants focused on 742 DCs and 339 monocytes that passed quality control (QC) filters (Methods) with an average of 5,326 unique genes detected per cell. In subsequent validation and characterization phases, Applicants analyzed an additional 838 cells that passed QC.

Unbiased classification of LIN$^-$ HLA-DR$^+$ CD14$^-$ subsets. Applicants defined six cell clusters within the LIN$^-$HLA-DR$^+$CD14$^-$ population using unsupervised analysis that did not rely on any marker gene expression. Briefly, Applicants identified 595 genes exhibiting high variability across single cells, reduced the dimensionality of this data with principal components analysis (PCA), and identified five significant PCs using a previously described permutation test (Macosko et al.) (Methods). Applicants used these PC loadings as input to t-distributed stochastic neighbor embedding (tSNE) (van der Maaten) for visualization, and clustered cells using a graph-based approach similar to one recently developed for CyTOF data (Levine et al.) (Methods). Applicants observed 6 clusters: (a) 2 clusters mapping closely (but not perfectly) to the well-established DC subsets (cluster DC1 to CD141$^+$ DCs, and cluster DC6 to pDCs), based on the post-hoc overlap of transcript and surface marker expression; (b) 2 clusters containing the CD1C$^+$ cDCs, thus splitting them into 2 subsets: CD1C_A (cluster DC2) and CD1C_B (cluster DC3); (c) a cluster corresponding to the poorly characterized CD141$^-$CD1C$^-$ population (cluster DC4); (d) and one cluster corresponding to a putative novel population (cluster DC5) (FIG. 2C, E, F).

Applicants identified 242 genes (AUC≥0.85; see Methods for scoring of discriminative markers) that best classified cells into these 6 putative cell populations (FIG. 2D, G). See Tables E1 parts a-f and E2 parts a-f for lists of markers, including surface markers.

TABLE E1

(including parts a-f). Top 5 discriminative genes per subset identified through unbiased clustering in FIG. 2

| Gene.ID | AUC value | Avg. Diff.[1] | Power[2] | Pct.1[3] | Pct.2[4] | Cluster.ID | Associated.Cell.Population | Surface Marker[5] |
|---|---|---|---|---|---|---|---|---|
| part a ||||||||||
| CLEC9A | 0.99 | 5.494 | 0.972 | 0.976 | 0.056 | DC1 | CD141/CLEC9A | 1 |
| C1ORF54 | 0.98 | 4.264 | 0.966 | 0.976 | 0.076 | DC1 | CD141/CLEC9A | 0 |
| HLA-DPA1 | 0.98 | 1.243 | 0.954 | 1 | 0.998 | DC1 | CD141/CLEC9A | 1 |
| CADM1 | 0.97 | 5.288 | 0.946 | 0.952 | 0.042 | DC1 | CD141/CLEC9A | 1 |
| CAMK2D | 0.96 | 2.734 | 0.926 | 0.982 | 0.255 | DC1 | CD141/CLEC9A | 1 |
| part b ||||||||||
| CD1C | 0.94 | 2.905 | 0.874 | 0.943 | 0.228 | DC2 | CD1C_A | 1 |
| FCER1A | 0.89 | 1.720 | 0.776 | 0.952 | 0.487 | DC2 | CD1C_A | 1 |
| CLEC10A | 0.88 | 2.033 | 0.754 | 0.895 | 0.242 | DC2 | CD1C_A | 1 |
| ADAM8 | 0.82 | 1.522 | 0.634 | 0.867 | 0.334 | DC2 | CD1C_A | 1 |
| CD1D | 0.78 | 1.346 | 0.564 | 0.8 | 0.341 | DC2 | CD1C_A | 1 |
| part c ||||||||||
| S100A9 | 0.99 | 2.896 | 0.974 | 1 | 0.561 | DC3 | CD1C_B | 0 |
| S100A8 | 0.97 | 3.549 | 0.948 | 0.979 | 0.176 | DC3 | CD1C_B | 0 |
| VCAN | 0.97 | 2.802 | 0.946 | 1 | 0.24 | DC3 | CD1C_B | 1 |
| LYZ | 0.92 | 1.271 | 0.848 | 1 | 1 | DC3 | CD1C_B | 0 |
| ANXA1 | 0.92 | 1.383 | 0.84 | 1 | 0.733 | DC3 | CD1C_B | 0 |
| part d ||||||||||
| FCGR3A | 1.00 | 6.963 | 1 | 1 | 0.326 | DC4 | CD1C$^-$CD141$^-$ | 1 |
| FTL | 1.00 | 1.911 | 0.998 | 1 | 0.998 | DC4 | CD1C$^-$CD141$^-$ | 0 |
| SERPINA1 | 1.00 | 3.305 | 0.996 | 1 | 0.536 | DC4 | CD1C$^-$CD141$^-$ | 0 |
| LST1 | 0.99 | 2.333 | 0.988 | 1 | 0.728 | DC4 | CD1C$^-$CD141$^-$ | 1 |
| AIF1 | 0.99 | 2.083 | 0.98 | 1 | 0.774 | DC4 | CD1C$^-$CD141$^-$ | 0 |
| part e ||||||||||
| AXL | 1.00 | 3.782 | 0.994 | 1 | 0.824 | DC5 | AXL+SIGLEC6+ | 1 |
| PPP1R14A | 0.99 | 3.351 | 0.976 | 1 | 0.101 | DC5 | AXL+SIGLEC6+ | 0 |
| SIGLEC6 | 0.97 | 3.668 | 0.936 | 0.967 | 0.129 | DC5 | AXL+SIGLEC6+ | 1 |
| CD22 | 0.95 | 3.131 | 0.89 | 0.933 | 0.128 | DC5 | AXL+SIGLEC6+ | 1 |
| DAB2 | 0.92 | 1.984 | 0.83 | 0.967 | 0.292 | DC5 | AXL+SIGLEC6+ | 0 |

TABLE E1-continued (including parts a-f). Top 5 discriminative genes per subset identified through unbiased clustering in FIG. 2

| Gene.ID | AUC value | Avg. Diff.[1] | Power[2] | Pct.1[3] | Pct.2[4] | Cluster.ID | Associated.Cell.Population | Surface Marker[5] |
|---|---|---|---|---|---|---|---|---|
| part f | | | | | | | | |
| GZMB | 1.00 | 6.373 | 0.992 | 0.994 | 0.215 | DC6 | pDC | 0 |
| IGJ | 1.00 | 5.215 | 0.992 | 0.994 | 0.24 | DC6 | pDC | 0 |
| AK128525 | 1.00 | 4.852 | 0.99 | 0.994 | 0.117 | DC6 | pDC | 0 |
| SERPINF1 | 1.00 | 2.981 | 0.99 | 1 | 0.452 | DC6 | pDC | 0 |
| ITM2C | 0.99 | 3.502 | 0.98 | 0.994 | 0.345 | DC6 | pDC | 1 |

TABLE E2

(including parts a-f). All discriminative genes per subset identified through unbiased clustering in FIG. 2

| Rank | Gene.ID | AUC value | Avg. Diff.[1] | Power[2] | Pct.1[3] | Pct.2[4] | Cluster.ID | Associated.Cell.Population | Surface Marker[5] |
|---|---|---|---|---|---|---|---|---|---|
| | | | | part a | | | | | |
| 1 | CLEC9A | 0.99 | 5.49 | 0.97 | 0.976 | 0.056 | DC1 | CD141/CLEC9A | 1 |
| 2 | C1ORF54 | 0.98 | 4.26 | 0.97 | 0.976 | 0.076 | DC1 | CD141/CLEC9A | 0 |
| 3 | HLA-DPA1 | 0.98 | 1.24 | 0.95 | 1 | 0.998 | DC1 | CD141/CLEC9A | 1 |
| 4 | CADM1 | 0.97 | 5.29 | 0.95 | 0.952 | 0.042 | DC1 | CD141/CLEC9A | 1 |
| 5 | CAMK2D | 0.96 | 2.73 | 0.93 | 0.982 | 0.255 | DC1 | CD141/CLEC9A | 1 |
| 6 | CPVL | 0.96 | 2 | 0.92 | 0.994 | 0.778 | DC1 | CD141/CLEC9A | 1 |
| 7 | HLA-DPB2 | 0.96 | 1.26 | 0.91 | 1 | 0.997 | DC1 | CD141/CLEC9A | 1 |
| 8 | WDFY4 | 0.96 | 1.92 | 0.91 | 1 | 0.7 | DC1 | CD141/CLEC9A | 1 |
| 9 | CPNE3 | 0.95 | 1.9 | 0.91 | 1 | 0.556 | DC1 | CD141/CLEC9A | 0 |
| 10 | IDO1 | 0.95 | 4.78 | 0.91 | 0.958 | 0.462 | DC1 | CD141/CLEC9A | 0 |
| 11 | HLA-DPB1 | 0.94 | 1.29 | 0.88 | 1 | 0.932 | DC1 | CD141/CLEC9A | 1 |
| 12 | LOC645638 | 0.94 | 3.08 | 0.88 | 0.922 | 0.106 | DC1 | CD141/CLEC9A | 0 |
| 13 | HLA-DOB | 0.94 | 2.46 | 0.88 | 0.976 | 0.49 | DC1 | CD141/CLEC9A | 1 |
| 14 | HLA-DQB1 | 0.93 | 1.4 | 0.86 | 1 | 0.906 | DC1 | CD141/CLEC9A | 1 |
| 15 | HLA-DQB | 0.93 | 1.24 | 0.86 | 1 | 0.908 | DC1 | CD141/CLEC9A | 1 |
| 16 | CLNK | 0.92 | 3.46 | 0.84 | 0.952 | 0.46 | DC1 | CD141/CLEC9A | 0 |
| 17 | CSRP1 | 0.91 | 1.81 | 0.81 | 0.976 | 0.425 | DC1 | CD141/CLEC9A | 0 |
| 18 | SNX3 | 0.91 | 1.54 | 0.81 | 0.994 | 0.587 | DC1 | CD141/CLEC9A | 0 |
| 19 | ZNF366 | 0.9 | 2.7 | 0.8 | 0.867 | 0.108 | DC1 | CD141/CLEC9A | 0 |
| 20 | KIAA1598 | 0.89 | 1.5 | 0.78 | 0.994 | 0.644 | DC1 | CD141/CLEC9A | 0 |
| 21 | NDRG2 | 0.89 | 1.48 | 0.78 | 0.988 | 0.434 | DC1 | CD141/CLEC9A | 1 |
| 22 | ENPP1 | 0.89 | 2.9 | 0.77 | 0.94 | 0.741 | DC1 | CD141/CLEC9A | 1 |
| 23 | RGS10 | 0.88 | 1.41 | 0.76 | 0.982 | 0.568 | DC1 | CD141/CLEC9A | 0 |
| 24 | AX747832 | 0.88 | 4.25 | 0.76 | 0.765 | 0.03 | DC1 | CD141/CLEC9A | 0 |
| 25 | CYB5R3 | 0.88 | 1.33 | 0.75 | 1 | 0.774 | DC1 | CD141/CLEC9A | 1 |
| 26 | ID2 | 0.87 | 1.25 | 0.75 | 1 | 0.773 | DC1 | CD141/CLEC9A | 0 |
| 27 | XCR1 | 0.87 | 4.84 | 0.74 | 0.753 | 0.028 | DC1 | CD141/CLEC9A | 1 |
| 28 | FAM190A | 0.87 | 2.44 | 0.73 | 0.843 | 0.21 | DC1 | CD141/CLEC9A | 0 |
| 29 | ASAP1 | 0.87 | 1.37 | 0.73 | 0.976 | 0.429 | DC1 | CD141/CLEC9A | 0 |
| 30 | SLAMF8 | 0.87 | 2.93 | 0.73 | 0.789 | 0.099 | DC1 | CD141/CLEC9A | 1 |
| 31 | CD59 | 0.86 | 2.14 | 0.72 | 0.843 | 0.241 | DC1 | CD141/CLEC9A | 1 |
| 32 | DHRS3 | 0.86 | 2.53 | 0.72 | 0.789 | 0.115 | DC1 | CD141/CLEC9A | 1 |
| 33 | GCET2 | 0.86 | 3.35 | 0.72 | 0.759 | 0.076 | DC1 | CD141/CLEC9A | 0 |
| 34 | FNBP1 | 0.85 | 1.24 | 0.71 | 0.988 | 0.865 | DC1 | CD141/CLEC9A | 0 |
| 35 | TMEM14A | 0.85 | 2.16 | 0.7 | 0.795 | 0.106 | DC1 | CD141/CLEC9A | 1 |
| 36 | NET1 | 0.85 | 2.61 | 0.7 | 0.777 | 0.123 | DC1 | CD141/CLEC9A | 0 |
| 37 | BTLA | 0.85 | 1.5 | 0.7 | 0.855 | 0.17 | DC1 | CD141/CLEC9A | 1 |
| 38 | BCL6 | 0.84 | 1.19 | 0.68 | 0.958 | 0.509 | DC1 | CD141/CLEC9A | 0 |
| 39 | FLT3 | 0.84 | 1.17 | 0.67 | 0.97 | 0.429 | DC1 | CD141/CLEC9A | 1 |
| 40 | ADAM28 | 0.84 | 1.62 | 0.67 | 0.88 | 0.306 | DC1 | CD141/CLEC9A | 1 |
| 41 | SLAMF7 | 0.83 | 1.06 | 0.67 | 1 | 0.753 | DC1 | CD141/CLEC9A | 1 |
| 42 | BATF3 | 0.83 | 1.52 | 0.67 | 0.849 | 0.214 | DC1 | CD141/CLEC9A | 0 |
| 43 | LGALS2 | 0.83 | 1.25 | 0.66 | 0.964 | 0.351 | DC1 | CD141/CLEC9A | 0 |
| 44 | VAC14 | 0.83 | 2.21 | 0.66 | 0.771 | 0.16 | DC1 | CD141/CLEC9A | 0 |
| 45 | PPA1 | 0.83 | 1.12 | 0.66 | 0.976 | 0.545 | DC1 | CD141/CLEC9A | 0 |
| 46 | APOL3 | 0.82 | 1.68 | 0.64 | 0.825 | 0.286 | DC1 | CD141/CLEC9A | 0 |
| 47 | C1ORF21 | 0.82 | 2.01 | 0.64 | 0.663 | 0.028 | DC1 | CD141/CLEC9A | 0 |
| 48 | CCND1 | 0.82 | 3.86 | 0.64 | 0.645 | 0.021 | DC1 | CD141/CLEC9A | 0 |
| 49 | ANPEP | 0.81 | 1.01 | 0.61 | 0.934 | 0.401 | DC1 | CD141/CLEC9A | 1 |
| 50 | ELOVL5 | 0.81 | 1.04 | 0.61 | 0.988 | 0.651 | DC1 | CD141/CLEC9A | 1 |
| 51 | NCALD | 0.8 | 3.43 | 0.6 | 0.633 | 0.047 | DC1 | CD141/CLEC9A | 0 |
| 52 | ACTN1 | 0.8 | 1.57 | 0.6 | 0.91 | 0.76 | DC1 | CD141/CLEC9A | 1 |
| 53 | PIK3CB | 0.8 | 1.81 | 0.6 | 0.735 | 0.177 | DC1 | CD141/CLEC9A | 0 |

TABLE E2-continued (including parts a-f). All discriminative genes per subset identified through unbiased clustering in FIG. 2

| Rank | Gene.ID | AUC value | Avg. Diff.[1] | Power[2] | Pct.1[3] | Pct.2[4] | Cluster.ID | Associated.Cell.Population | Surface Marker[5] |
|---|---|---|---|---|---|---|---|---|---|
| 54 | HAVCR2 | 0.8 | 1.18 | 0.59 | 0.964 | 0.75 | DC1 | CD141/CLEC9A | 1 |
| 55 | GYPC | 0.79 | 1.16 | 0.59 | 0.837 | 0.28 | DC1 | CD141/CLEC9A | 1 |
| 56 | TLR10 | 0.79 | 1.7 | 0.58 | 0.843 | 0.474 | DC1 | CD141/CLEC9A | 1 |
| 57 | ASB2 | 0.79 | 2.33 | 0.58 | 0.663 | 0.101 | DC1 | CD141/CLEC9A | 0 |
| 58 | KIF16B | 0.79 | 1.65 | 0.58 | 0.711 | 0.163 | DC1 | CD141/CLEC9A | 0 |
| 59 | LRRC18 | 0.78 | 1.83 | 0.57 | 0.663 | 0.106 | DC1 | CD141/CLEC9A | 0 |
| 60 | DST | 0.78 | 1.1 | 0.57 | 0.849 | 0.345 | DC1 | CD141/CLEC9A | 0 |
| 61 | DENND1B | 0.78 | 1.36 | 0.56 | 0.741 | 0.191 | DC1 | CD141/CLEC9A | 1 |
| 62 | DNASE1L3 | 0.78 | 2.13 | 0.56 | 0.783 | 0.401 | DC1 | CD141/CLEC9A | 0 |
| 63 | SLC24A4 | 0.78 | 1.01 | 0.56 | 0.964 | 0.832 | DC1 | CD141/CLEC9A | 1 |
| 64 | VAV3 | 0.78 | 1.37 | 0.56 | 0.759 | 0.252 | DC1 | CD141/CLEC9A | 0 |
| 65 | THBD | 0.77 | 1.11 | 0.54 | 0.783 | 0.267 | DC1 | CD141/CLEC9A | 1 |
| 66 | NAV1 | 0.77 | 1.18 | 0.54 | 0.946 | 0.786 | DC1 | CD141/CLEC9A | 0 |
| 67 | GSTM4 | 0.77 | 1.06 | 0.54 | 0.819 | 0.34 | DC1 | CD141/CLEC9A | 0 |
| 68 | TRERF1 | 0.77 | 1.14 | 0.53 | 0.789 | 0.3 | DC1 | CD141/CLEC9A | 0 |
| 69 | B3GNT7 | 0.77 | 2.22 | 0.53 | 0.62 | 0.127 | DC1 | CD141/CLEC9A | 0 |
| 70 | LACC1 | 0.76 | 1.59 | 0.52 | 0.657 | 0.153 | DC1 | CD141/CLEC9A | 0 |
| 71 | LMNA | 0.76 | 1.29 | 0.52 | 0.693 | 0.196 | DC1 | CD141/CLEC9A | 1 |
| 72 | PTK2 | 0.76 | 1.78 | 0.51 | 0.627 | 0.135 | DC1 | CD141/CLEC9A | 0 |
| 73 | IDO2 | 0.76 | 2.8 | 0.51 | 0.88 | 0.726 | DC1 | CD141/CLEC9A | 0 |
| 74 | MTERFD3 | 0.75 | 2.36 | 0.5 | 0.554 | 0.062 | DC1 | CD141/CLEC9A | 0 |
| 75 | CD93 | 0.75 | 1.08 | 0.5 | 0.723 | 0.243 | DC1 | CD141/CLEC9A | 1 |
| 76 | DPP4 | 0.75 | 2.01 | 0.5 | 0.572 | 0.085 | DC1 | CD141/CLEC9A | 1 |
| 77 | SLC9A9 | 0.75 | 1.15 | 0.49 | 0.729 | 0.269 | DC1 | CD141/CLEC9A | 1 |
| 78 | FCRL6 | 0.74 | 3.52 | 0.48 | 0.518 | 0.054 | DC1 | CD141/CLEC9A | 1 |
| 79 | PDLIM7 | 0.74 | 1.31 | 0.48 | 0.645 | 0.175 | DC1 | CD141/CLEC9A | 0 |
| 80 | CYP2E1 | 0.74 | 3.05 | 0.48 | 0.56 | 0.146 | DC1 | CD141/CLEC9A | 0 |
| 81 | PDE4DIP | 0.74 | 1.37 | 0.47 | 0.663 | 0.215 | DC1 | CD141/CLEC9A | 0 |
| 82 | LIMA1 | 0.74 | 1.96 | 0.47 | 0.56 | 0.106 | DC1 | CD141/CLEC9A | 0 |
| 83 | CTTNBP2NL | 0.73 | 1.34 | 0.47 | 0.651 | 0.22 | DC1 | CD141/CLEC9A | 0 |
| 84 | PPM1M | 0.73 | 1.18 | 0.47 | 0.651 | 0.191 | DC1 | CD141/CLEC9A | 0 |
| 85 | OSBPL3 | 0.73 | 1.11 | 0.45 | 0.608 | 0.177 | DC1 | CD141/CLEC9A | 0 |
| 86 | PLCD1 | 0.73 | 1.94 | 0.45 | 0.53 | 0.095 | DC1 | CD141/CLEC9A | 0 |
| 87 | CD38 | 0.72 | 1.25 | 0.44 | 0.584 | 0.163 | DC1 | CD141/CLEC9A | 1 |
| 88 | EHD4 | 0.72 | 1.16 | 0.43 | 0.741 | 0.418 | DC1 | CD141/CLEC9A | 0 |
| 89 | ACSS2 | 0.72 | 1.46 | 0.43 | 0.584 | 0.182 | DC1 | CD141/CLEC9A | 1 |
| 90 | LOC541471 | 0.72 | 1.1 | 0.43 | 0.651 | 0.243 | DC1 | CD141/CLEC9A | 0 |
| 91 | FUCA1 | 0.7 | 1.11 | 0.41 | 0.633 | 0.241 | DC1 | CD141/CLEC9A | 0 |
| 92 | SNX22 | 0.7 | 1.97 | 0.39 | 0.837 | 0.648 | DC1 | CD141/CLEC9A | 0 |
| 93 | APOL1 | 0.7 | 1.62 | 0.39 | 0.867 | 0.785 | DC1 | CD141/CLEC9A | 1 |
| 94 | DUSP10 | 0.69 | 1.37 | 0.39 | 0.524 | 0.153 | DC1 | CD141/CLEC9A | 0 |
| 95 | FAM160A2 | 0.69 | 1.1 | 0.39 | 0.548 | 0.17 | DC1 | CD141/CLEC9A | 1 |
| 96 | INF2 | 0.69 | 1.04 | 0.39 | 0.542 | 0.163 | DC1 | CD141/CLEC9A | 0 |
| 97 | DUSP2 | 0.69 | 1.07 | 0.38 | 0.602 | 0.245 | DC1 | CD141/CLEC9A | 0 |
| 98 | PALM2 | 0.69 | 1.14 | 0.38 | 0.681 | 0.429 | DC1 | CD141/CLEC9A | 0 |
| 99 | RAB11FIP4 | 0.69 | 1.06 | 0.38 | 0.729 | 0.483 | DC1 | CD141/CLEC9A | 0 |
| 100 | DSE | 0.69 | 1.14 | 0.37 | 0.566 | 0.227 | DC1 | CD141/CLEC9A | 1 |
| 101 | FAM135A | 0.69 | 1.11 | 0.37 | 0.759 | 0.514 | DC1 | CD141/CLEC9A | 0 |
| 102 | KCNK6 | 0.68 | 1.1 | 0.37 | 0.602 | 0.29 | DC1 | CD141/CLEC9A | 1 |
| 103 | PPM1H | 0.68 | 1.35 | 0.36 | 0.608 | 0.347 | DC1 | CD141/CLEC9A | 0 |
| 104 | PAFAH1B3 | 0.68 | 1.07 | 0.35 | 0.512 | 0.16 | DC1 | CD141/CLEC9A | 0 |
| 105 | PDLIM1 | 0.68 | 1.02 | 0.35 | 0.518 | 0.168 | DC1 | CD141/CLEC9A | 0 |
| 106 | TGM2 | 0.67 | 2.18 | 0.34 | 0.584 | 0.359 | DC1 | CD141/CLEC9A | 0 |
| 107 | SCARF1 | 0.65 | 1.61 | 0.31 | 0.602 | 0.389 | DC1 | CD141/CLEC9A | 0 |
| 108 | CD40 | 0.65 | 1.32 | 0.3 | 0.572 | 0.354 | DC1 | CD141/CLEC9A | 1 |
| 109 | STX3 | 0.64 | 1.11 | 0.28 | 0.518 | 0.323 | DC1 | CD141/CLEC9A | 1 |
| 110 | WHAMMP3 | 0.63 | 1.11 | 0.27 | 0.584 | 0.385 | DC1 | CD141/CLEC9A | 0 |
| 111 | PRELID2 | 0.63 | 1.65 | 0.26 | 0.548 | 0.363 | DC1 | CD141/CLEC9A | 0 |
| 112 | PQLC2 | 0.62 | 1.17 | 0.24 | 0.687 | 0.559 | DC1 | CD141/CLEC9A | 1 |
| part b | | | | | | | | | |
| 113 | CD1C | 0.94 | 2.9 | 0.87 | 0.943 | 0.228 | DC2 | CD1C_A | 1 |
| 114 | FCER1A | 0.89 | 1.72 | 0.78 | 0.952 | 0.487 | DC2 | CD1C_A | 1 |
| 115 | CLEC10A | 0.88 | 2.03 | 0.75 | 0.895 | 0.242 | DC2 | CD1C_A | 1 |
| 116 | ADAM8 | 0.82 | 1 | 0.63 | 0.867 | 0.334 | DC2 | CD1C_A | 1 |
| 117 | CD1D | 0.78 | 1.35 | 0.56 | 0.8 | 0.341 | DC2 | CD1C_A | 1 |
| 118 | FCGR2B | 0.78 | 2.63 | 0.56 | 0.676 | 0.215 | DC2 | CD1C_A | 1 |
| 119 | CLEC4A | 0.77 | 1.04 | 0.55 | 0.914 | 0.463 | DC2 | CD1C_A | 1 |
| 120 | SLC2A3 | 0.77 | 1.03 | 0.54 | 0.8 | 0.32 | DC2 | CD1C_A | 1 |
| 121 | CD33 | 0.76 | 1.02 | 0.52 | 0.905 | 0.633 | DC2 | CD1C_A | 1 |
| 122 | ETS2 | 0.75 | 1.09 | 0.51 | 0.79 | 0.38 | DC2 | CD1C_A | 0 |
| 123 | CLIC2 | 0.75 | 1.11 | 0.49 | 0.81 | 0.396 | DC2 | CD1C_A | 0 |
| 124 | PEA15 | 0.75 | 1.06 | 0.49 | 0.867 | 0.477 | DC2 | CD1C_A | 0 |
| 125 | CACNA2D3 | 0.74 | 1.4 | 0.48 | 0.924 | 0.724 | DC2 | CD1C_A | 1 |

TABLE E2-continued (including parts a-f). All discriminative genes per subset identified through unbiased clustering in FIG. 2

| Rank | Gene.ID | AUC value | Avg. Diff.[1] | Power[2] | Pct.1[3] | Pct.2[4] | Cluster.ID | Associated.Cell.Population | Surface Marker[5] |
|---|---|---|---|---|---|---|---|---|---|
| 126 | CD1E | 0.73 | 2.81 | 0.46 | 0.514 | 0.066 | DC2 | CD1C_A | 1 |
| 127 | MBOAT7 | 0.73 | 1.32 | 0.45 | 0.686 | 0.295 | DC2 | CD1C_A | 1 |
| 128 | C10ORF128 | 0.72 | 2.15 | 0.44 | 0.533 | 0.11 | DC2 | CD1C_A | 1 |
| 129 | NR4A2 | 0.72 | 1.04 | 0.44 | 0.81 | 0.473 | DC2 | CD1C_A | 0 |
| 130 | AGPAT9 | 0.72 | 1.24 | 0.44 | 0.686 | 0.283 | DC2 | CD1C_A | 1 |
| 131 | ENTPD1 | 0.71 | 1.19 | 0.42 | 0.981 | 0.98 | DC2 | CD1C_A | 1 |
| 132 | CD2 | 0.7 | 1.31 | 0.4 | 0.524 | 0.135 | DC2 | CD1C_A | 1 |
| 133 | PER1 | 0.7 | 1.01 | 0.4 | 0.705 | 0.364 | DC2 | CD1C_A | 0 |
| 134 | PID1 | 0.69 | 1.35 | 0.39 | 0.524 | 0.146 | DC2 | CD1C_A | 0 |
| 135 | AREG | 0.69 | 1.44 | 0.38 | 0.543 | 0.193 | DC2 | CD1C_A | 1 |
| 136 | PTGS1 | 0.69 | 1.05 | 0.38 | 0.61 | 0.251 | DC2 | CD1C_A | 0 |
| 137 | SMA | 0.69 | 1.27 | 0.38 | 0.619 | 0.292 | DC2 | CD1C_A | 0 |
| 138 | CLEC17A | 0.69 | 2.36 | 0.37 | 0.514 | 0.204 | DC2 | CD1C_A | 1 |
| 139 | ITGA5 | 0.67 | 1 | 0.34 | 0.61 | 0.283 | DC2 | CD1C_A | 1 |
| 140 | CREB5 | 0.67 | 1.17 | 0.34 | 0.514 | 0.203 | DC2 | CD1C_A | 0 |
| 141 | PTAFR | 0.67 | 1.04 | 0.33 | 0.876 | 0.79 | DC2 | CD1C_A | 1 |
| 142 | NOD2 | 0.66 | 1.13 | 0.31 | 0.533 | 0.237 | DC2 | CD1C_A | 0 |
| 143 | CCR6 | 0.65 | 1.35 | 0.3 | 0.724 | 0.576 | DC2 | CD1C_A | 1 |
| part c | | | | | | | | | |
| 144 | S100A9 | 0.99 | 2.9 | 0.97 | 1 | 0.561 | DC3 | CD1C_B | 0 |
| 145 | S100A8 | 0.97 | 3.55 | 0.95 | 0.979 | 0.176 | DC3 | CD1C_B | 0 |
| 146 | VCAN | 0.97 | 2.8 | 0.95 | 1 | 0.24 | DC3 | CD1C_B | 1 |
| 147 | LYZ | 0.92 | 1.27 | 0.85 | 1 | 1 | DC3 | CD1C_B | 0 |
| 148 | ANXA1 | 0.92 | 1.38 | 0.84 | 1 | 0.733 | DC3 | CD1C_B | 0 |
| 149 | PLBD1 | 0.9 | 1.89 | 0.8 | 0.958 | 0.437 | DC3 | CD1C_B | 1 |
| 150 | RNASE2 | 0.9 | 4.11 | 0.79 | 0.811 | 0.051 | DC3 | CD1C_B | 0 |
| 151 | FCER1A | 0.88 | 1.39 | 0.75 | 0.989 | 0.488 | DC3 | CD1C_B | 1 |
| 152 | SLC2A3 | 0.86 | 1.92 | 0.72 | 0.905 | 0.312 | DC3 | CD1C_B | 1 |
| 153 | CD163 | 0.86 | 2.58 | 0.71 | 0.779 | 0.099 | DC3 | CD1C_B | 1 |
| 154 | CSF3R | 0.85 | 1.78 | 0.7 | 0.895 | 0.338 | DC3 | CD1C_B | 1 |
| 155 | MNDA | 0.85 | 1.08 | 0.69 | 1 | 0.711 | DC3 | CD1C_B | 0 |
| 156 | CD14 | 0.84 | 3.53 | 0.69 | 0.737 | 0.096 | DC3 | CD1C_B | 1 |
| 157 | NAIP | 0.84 | 1.52 | 0.69 | 0.968 | 0.706 | DC3 | CD1C_B | 0 |
| 158 | CSTA | 0.83 | 1.31 | 0.66 | 0.916 | 0.32 | DC3 | CD1C_B | 0 |
| 159 | FCN1 | 0.83 | 1 | 0.66 | 0.989 | 0.501 | DC3 | CD1C_B | 1 |
| 160 | CD1D | 0.83 | 1.87 | 0.66 | 0.832 | 0.343 | DC3 | CD1C_B | 1 |
| 161 | FPR1 | 0.82 | 1.21 | 0.63 | 0.916 | 0.371 | DC3 | CD1C_B | 1 |
| 162 | F13A1 | 0.81 | 3.15 | 0.63 | 0.674 | 0.076 | DC3 | CD1C_B | 1 |
| 163 | CLEC10A | 0.81 | 1.33 | 0.62 | 0.842 | 0.26 | DC3 | CD1C_B | 1 |
| 164 | CES1 | 0.8 | 2.46 | 0.61 | 0.684 | 0.122 | DC3 | CD1C_B | 1 |
| 165 | PID1 | 0.8 | 1.88 | 0.61 | 0.716 | 0.124 | DC3 | CD1C_B | 0 |
| 166 | S100A12 | 0.79 | 3.07 | 0.59 | 0.621 | 0.043 | DC3 | CD1C_B | 0 |
| 167 | MTMR11 | 0.79 | 1.41 | 0.59 | 0.768 | 0.207 | DC3 | CD1C_B | 0 |
| 168 | SMA | 0.79 | 1.26 | 0.59 | 0.8 | 0.27 | DC3 | CD1C_B | 0 |
| 169 | LAT2 | 0.79 | 1.19 | 0.58 | 0.884 | 0.49 | DC3 | CD1C_B | 0 |
| 170 | RETN | 0.78 | 1.68 | 0.56 | 0.695 | 0.164 | DC3 | CD1C_B | 0 |
| 171 | TMEM173 | 0.78 | 1.17 | 0.56 | 0.811 | 0.303 | DC3 | CD1C_B | 1 |
| 172 | AOAH | 0.78 | 1.02 | 0.56 | 0.958 | 0.621 | DC3 | CD1C_B | 0 |
| 173 | RAB3D | 0.78 | 1.26 | 0.55 | 0.863 | 0.544 | DC3 | CD1C_B | 0 |
| 174 | CD36 | 0.77 | 1.03 | 0.53 | 0.926 | 0.68 | DC3 | CD1C_B | 1 |
| 175 | MGST1 | 0.76 | 1.33 | 0.53 | 0.726 | 0.255 | DC3 | CD1C_B | 1 |
| 176 | TREM1 | 0.76 | 1.97 | 0.51 | 0.611 | 0.127 | DC3 | CD1C_B | 1 |
| 177 | HNMT | 0.74 | 1.37 | 0.48 | 0.642 | 0.176 | DC3 | CD1C_B | 0 |
| 178 | CES1P1 | 0.74 | 1.71 | 0.48 | 0.526 | 0.059 | DC3 | CD1C_B | 0 |
| 179 | ADAM15 | 0.74 | 1.3 | 0.47 | 0.705 | 0.281 | DC3 | CD1C_B | 1 |
| 180 | IL13RA1 | 0.73 | 1.34 | 0.47 | 0.747 | 0.391 | DC3 | CD1C_B | 1 |
| 181 | MICAL2 | 0.73 | 1.53 | 0.47 | 0.611 | 0.168 | DC3 | CD1C_B | 1 |
| 182 | ITGA5 | 0.73 | 1.32 | 0.46 | 0.674 | 0.278 | DC3 | CD1C_B | 1 |
| 183 | CREB5 | 0.73 | 1.42 | 0.45 | 0.6 | 0.195 | DC3 | CD1C_B | 0 |
| 184 | IL1B | 0.73 | 2.26 | 0.45 | 0.516 | 0.068 | DC3 | CD1C_B | 0 |
| 185 | NR4A2 | 0.73 | 1.04 | 0.45 | 0.832 | 0.474 | DC3 | CD1C_B | 0 |
| 186 | MPP7 | 0.72 | 1.86 | 0.45 | 0.568 | 0.172 | DC3 | CD1C_B | 0 |
| 187 | PTAFR | 0.72 | 1.37 | 0.44 | 0.874 | 0.791 | DC3 | CD1C_B | 1 |
| 188 | HBEGF | 0.72 | 2.35 | 0.44 | 0.505 | 0.076 | DC3 | CD1C_B | 1 |
| 189 | NFE2 | 0.72 | 2.02 | 0.44 | 0.516 | 0.08 | DC3 | CD1C_B | 0 |
| 190 | ASGR1 | 0.72 | 1.65 | 0.43 | 0.526 | 0.091 | DC3 | CD1C_B | 0 |
| 191 | BST1 | 0.72 | 1.26 | 0.43 | 0.579 | 0.147 | DC3 | CD1C_B | 1 |
| 192 | IL1RN | 0.71 | 1.73 | 0.43 | 0.547 | 0.134 | DC3 | CD1C_B | 0 |
| 193 | NOD2 | 0.71 | 1.11 | 0.41 | 0.611 | 0.23 | DC3 | CD1C_B | 0 |
| 194 | NLRP3 | 0.7 | 1.45 | 0.41 | 0.705 | 0.467 | DC3 | CD1C_B | 0 |
| 195 | DQ575504 | 0.69 | 1 | 0.39 | 0.832 | 0.56 | DC3 | CD1C_B | 0 |
| 196 | LMNA | 0.69 | 1.21 | 0.37 | 0.611 | 0.263 | DC3 | CD1C_B | 1 |
| 197 | C9ORF89 | 0.68 | 1.15 | 0.36 | 0.558 | 0.201 | DC3 | CD1C_B | 1 |

TABLE E2-continued (including parts a-f). All discriminative genes per subset identified through unbiased clustering in FIG. 2

| Rank | Gene.ID | AUC value | Avg. Diff.[1] | Power[2] | Pct.1[3] | Pct.2[4] | Cluster.ID | Associated.Cell.Population | Surface Marker[5] |
|---|---|---|---|---|---|---|---|---|---|
| 198 | IL27RA | 0.68 | 1.11 | 0.35 | 0.568 | 0.269 | DC3 | CD1C_B | 1 |
| 199 | NLRP12 | 0.62 | 1.02 | 0.24 | 0.884 | 0.866 | DC3 | CD1C_B | 0 |
| 200 | RAB27A | 0.62 | 1.24 | 0.23 | 0.695 | 0.589 | DC3 | CD1C_B | 0 |
| 201 | EREG | 0.6 | 1.74 | 0.21 | 0.653 | 0.546 | DC3 | CD1C_B | 1 |
| 202 | LOC284454 | 0.6 | 1.3 | 0.21 | 0.895 | 0.864 | DC3 | CD1C_B | 0 |
| | | | | part d | | | | | |
| 203 | FCGR3A | 1 | 6.96 | 1 | 1 | 0.326 | DC4 | CD1C⁻CD141⁻ | 1 |
| 204 | FTL | 1 | 1.91 | 1 | 1 | 0.998 | DC4 | CD1C⁻CD141⁻ | 0 |
| 205 | SERPINA1 | 1 | 3.31 | 1 | 1 | 0.536 | DC4 | CD1C⁻CD141⁻ | 0 |
| 206 | LST1 | 0.99 | 2.33 | 0.99 | 1 | 0.728 | DC4 | CD1C⁻CD141⁻ | 1 |
| 207 | AIF1 | 0.99 | 2.08 | 0.98 | 1 | 0.774 | DC4 | CD1C⁻CD141⁻ | 0 |
| 208 | SAT1 | 0.99 | 2.17 | 0.98 | 1 | 0.958 | DC4 | CD1C⁻CD141⁻ | 0 |
| 209 | CTSS | 0.99 | 1.99 | 0.98 | 1 | 0.995 | DC4 | CD1C⁻CD141⁻ | 0 |
| 210 | MTSS1 | 0.99 | 3.95 | 0.97 | 0.989 | 0.106 | DC4 | CD1C⁻CD141⁻ | 0 |
| 211 | TCF7L2 | 0.98 | 4.59 | 0.96 | 0.971 | 0.076 | DC4 | CD1C⁻CD141⁻ | 0 |
| 212 | AK307192 | 0.98 | 4.96 | 0.96 | 0.971 | 0.141 | DC4 | CD1C⁻CD141⁻ | 0 |
| 213 | PSAP | 0.98 | 1.23 | 0.96 | 1 | 1 | DC4 | CD1C⁻CD141⁻ | 1 |
| 214 | FTH1 | 0.98 | 1 | 0.96 | 1 | 1 | DC4 | CD1C⁻CD141⁻ | 0 |
| 215 | IFITM3 | 0.98 | 2.6 | 0.96 | 1 | 0.774 | DC4 | CD1C⁻CD141⁻ | 1 |
| 216 | MS4A7 | 0.98 | 3.4 | 0.96 | 0.989 | 0.489 | DC4 | CD1C⁻CD141⁻ | 1 |
| 217 | LILRB2 | 0.98 | 2.65 | 0.96 | 1 | 0.57 | DC4 | CD1C⁻CD141⁻ | 1 |
| 218 | PILRA | 0.96 | 2.6 | 0.93 | 1 | 0.342 | DC4 | CD1C⁻CD141⁻ | 1 |
| 219 | CSF1R | 0.96 | 2.38 | 0.91 | 1 | 0.504 | DC4 | CD1C⁻CD141⁻ | 1 |
| 220 | ASAH1 | 0.95 | 2.38 | 0.91 | 0.983 | 0.631 | DC4 | CD1C⁻CD141⁻ | 1 |
| 221 | LRRC25 | 0.95 | 1.91 | 0.91 | 1 | 0.758 | DC4 | CD1C⁻CD141⁻ | 1 |
| 222 | HLA-E | 0.95 | 1.18 | 0.9 | 1 | 0.998 | DC4 | CD1C⁻CD141⁻ | 1 |
| 223 | IFITM2 | 0.94 | 1.65 | 0.89 | 1 | 0.862 | DC4 | CD1C⁻CD141⁻ | 1 |
| 224 | LYST | 0.94 | 2.18 | 0.88 | 1 | 0.481 | DC4 | CD1C⁻CD141⁻ | 0 |
| 225 | HCK | 0.94 | 1.6 | 0.88 | 1 | 0.755 | DC4 | CD1C⁻CD141⁻ | 0 |
| 226 | C5AR1 | 0.94 | 3.82 | 0.88 | 0.909 | 0.203 | DC4 | CD1C⁻CD141⁻ | 1 |
| 227 | WARS | 0.94 | 2.01 | 0.88 | 1 | 0.85 | DC4 | CD1C⁻CD141⁻ | 0 |
| 228 | PECAM1 | 0.94 | 2.02 | 0.87 | 1 | 0.871 | DC4 | CD1C⁻CD141⁻ | 1 |
| 229 | CTSL1 | 0.94 | 4.58 | 0.87 | 0.903 | 0.155 | DC4 | CD1C⁻CD141⁻ | 1 |
| 230 | S100A11 | 0.93 | 1.25 | 0.86 | 1 | 0.942 | DC4 | CD1C⁻CD141⁻ | 0 |
| 231 | CFD | 0.93 | 2.98 | 0.85 | 0.931 | 0.312 | DC4 | CD1C⁻CD141⁻ | 0 |
| 232 | HK3 | 0.93 | 3.34 | 0.85 | 0.897 | 0.141 | DC4 | CD1C⁻CD141⁻ | 0 |
| 233 | MAFB | 0.92 | 3.64 | 0.85 | 0.874 | 0.076 | DC4 | CD1C⁻CD141⁻ | 0 |
| 234 | TNFRSF1B | 0.92 | 2.06 | 0.85 | 0.983 | 0.644 | DC4 | CD1C⁻CD141⁻ | 1 |
| 235 | DUSP6 | 0.92 | 3.03 | 0.83 | 0.914 | 0.229 | DC4 | CD1C⁻CD141⁻ | 0 |
| 236 | CASP1 | 0.92 | 1.55 | 0.83 | 1 | 0.614 | DC4 | CD1C⁻CD141⁻ | 0 |
| 237 | SIGLEC10 | 0.92 | 2.38 | 0.83 | 0.977 | 0.822 | DC4 | CD1C⁻CD141⁻ | 1 |
| 238 | FGR | 0.91 | 1.53 | 0.83 | 0.994 | 0.675 | DC4 | CD1C⁻CD141⁻ | 0 |
| 239 | SLC7A7 | 0.91 | 2.89 | 0.82 | 0.92 | 0.444 | DC4 | CD1C⁻CD141⁻ | 1 |
| 240 | BIN2 | 0.91 | 1.89 | 0.82 | 0.977 | 0.621 | DC4 | CD1C⁻CD141⁻ | 0 |
| 241 | LILRA2 | 0.91 | 1.87 | 0.82 | 0.994 | 0.575 | DC4 | CD1C⁻CD141⁻ | 1 |
| 242 | SIDT2 | 0.91 | 2.54 | 0.82 | 0.931 | 0.305 | DC4 | CD1C⁻CD141⁻ | 1 |
| 243 | NEAT1 | 0.91 | 1.95 | 0.82 | 1 | 0.903 | DC4 | CD1C⁻CD141⁻ | 0 |
| 244 | PTPN6 | 0.91 | 1.33 | 0.82 | 0.994 | 0.859 | DC4 | CD1C⁻CD141⁻ | 0 |
| 245 | RHOC | 0.91 | 1.94 | 0.81 | 0.96 | 0.681 | DC4 | CD1C⁻CD141⁻ | 0 |
| 246 | SLC11A1 | 0.91 | 3.43 | 0.81 | 0.92 | 0.547 | DC4 | CD1C⁻CD141⁻ | 1 |
| 247 | LOC200772 | 0.91 | 4.61 | 0.81 | 0.817 | 0.025 | DC4 | CD1C⁻CD141⁻ | 0 |
| 248 | TYROBP | 0.9 | 1.01 | 0.81 | 1 | 0.838 | DC4 | CD1C⁻CD141⁻ | 1 |
| 249 | IFI30 | 0.9 | 1.4 | 0.8 | 1 | 0.81 | DC4 | CD1C⁻CD141⁻ | 1 |
| 250 | EMR2 | 0.9 | 2.4 | 0.8 | 0.937 | 0.48 | DC4 | CD1C⁻CD141⁻ | 1 |
| 251 | GIMAP4 | 0.9 | 2.81 | 0.8 | 0.886 | 0.219 | DC4 | CD1C⁻CD141⁻ | 1 |
| 252 | DUSP1 | 0.9 | 1.29 | 0.79 | 1 | 0.88 | DC4 | CD1C⁻CD141⁻ | 0 |
| 253 | TNFSF10 | 0.9 | 2.56 | 0.79 | 0.943 | 0.423 | DC4 | CD1C⁻CD141⁻ | 1 |
| 254 | GBP2 | 0.9 | 3.19 | 0.79 | 0.857 | 0.164 | DC4 | CD1C⁻CD141⁻ | 0 |
| 255 | FAM110A | 0.89 | 2.48 | 0.78 | 0.874 | 0.201 | DC4 | CD1C⁻CD141⁻ | 0 |
| 256 | LY6E | 0.89 | 1.73 | 0.78 | 0.977 | 0.612 | DC4 | CD1C⁻CD141⁻ | 1 |
| 257 | TXNIP | 0.89 | 1.28 | 0.78 | 1 | 0.952 | DC4 | CD1C⁻CD141⁻ | 0 |
| 258 | TSC22D3 | 0.89 | 1.64 | 0.77 | 0.989 | 0.723 | DC4 | CD1C⁻CD141⁻ | 0 |
| 259 | HMOX1 | 0.89 | 2.68 | 0.77 | 0.891 | 0.295 | DC4 | CD1C⁻CD141⁻ | 1 |
| 260 | CD68 | 0.88 | 1.2 | 0.76 | 1 | 0.905 | DC4 | CD1C⁻CD141⁻ | 1 |
| 261 | CD52 | 0.88 | 1.41 | 0.76 | 0.966 | 0.707 | DC4 | CD1C⁻CD141⁻ | 1 |
| 262 | TBXAS1 | 0.88 | 1.94 | 0.76 | 0.949 | 0.448 | DC4 | CD1C⁻CD141⁻ | 1 |
| 263 | TMEM176B | 0.88 | 2.77 | 0.75 | 0.829 | 0.159 | DC4 | CD1C⁻CD141⁻ | 1 |
| 264 | C10ORF54 | 0.87 | 1.14 | 0.75 | 0.989 | 0.873 | DC4 | CD1C⁻CD141⁻ | 1 |
| 265 | S100A4 | 0.87 | 1.12 | 0.74 | 1 | 0.843 | DC4 | CD1C⁻CD141⁻ | 0 |
| 266 | BCL2A1 | 0.87 | 2.43 | 0.74 | 0.857 | 0.266 | DC4 | CD1C⁻CD141⁻ | 0 |
| 267 | CD97 | 0.87 | 1.77 | 0.74 | 0.983 | 0.647 | DC4 | CD1C⁻CD141⁻ | 1 |
| 268 | PTPRC | 0.87 | 1.32 | 0.74 | 1 | 0.982 | DC4 | CD1C⁻CD141⁻ | 1 |
| 269 | FAM26F | 0.87 | 2.18 | 0.73 | 0.874 | 0.291 | DC4 | CD1C⁻CD141⁻ | 1 |

TABLE E2-continued (including parts a-f). All discriminative genes per subset
identified through unbiased clustering in FIG. 2

| Rank | Gene.ID | AUC value | Avg. Diff.[1] | Power[2] | Pct.1[3] | Pct.2[4] | Cluster.ID | Associated.Cell.Population | Surface Marker[5] |
|---|---|---|---|---|---|---|---|---|---|
| 270 | FCN1 | 0.87 | 1.65 | 0.73 | 0.96 | 0.441 | DC4 | CD1C−CD141− | 1 |
| 271 | ITGAL | 0.86 | 1.55 | 0.73 | 0.989 | 0.813 | DC4 | CD1C−CD141− | 1 |
| 272 | OAS1 | 0.86 | 1.41 | 0.72 | 0.977 | 0.557 | DC4 | CD1C−CD141− | 0 |
| 273 | FYB | 0.86 | 1.49 | 0.72 | 1 | 0.691 | DC4 | CD1C−CD141− | 0 |
| 274 | ABI3 | 0.86 | 1.65 | 0.72 | 0.949 | 0.478 | DC4 | CD1C−CD141− | 0 |
| 275 | ITM2B | 0.86 | 1.21 | 0.72 | 0.983 | 0.866 | DC4 | CD1C−CD141− | 1 |
| 276 | LILRA6 | 0.86 | 1.68 | 0.72 | 0.989 | 0.81 | DC4 | CD1C−CD141− | 1 |
| 277 | TSPAN14 | 0.86 | 2.06 | 0.72 | 0.926 | 0.61 | DC4 | CD1C−CD141− | 1 |
| 278 | CD79B | 0.86 | 2.97 | 0.71 | 0.783 | 0.141 | DC4 | CD1C−CD141− | 1 |
| 279 | LILRA5 | 0.86 | 2.19 | 0.71 | 0.88 | 0.325 | DC4 | CD1C−CD141− | 1 |
| 280 | SLC31A2 | 0.86 | 2.2 | 0.71 | 0.869 | 0.337 | DC4 | CD1C−CD141− | 1 |
| 281 | NFKBIZ | 0.85 | 1.59 | 0.7 | 0.977 | 0.697 | DC4 | CD1C−CD141− | 0 |
| 282 | LILRB1 | 0.85 | 1.56 | 0.7 | 0.96 | 0.587 | DC4 | CD1C−CD141− | 1 |
| 283 | FCGR3B | 0.85 | 3.06 | 0.7 | 0.731 | 0.058 | DC4 | CD1C−CD141− | 1 |
| 284 | CD300LF | 0.85 | 1.93 | 0.7 | 0.874 | 0.316 | DC4 | CD1C−CD141− | 1 |
| 285 | SOD2 | 0.85 | 1.84 | 0.7 | 0.909 | 0.52 | DC4 | CD1C−CD141− | 0 |
| 286 | CLEC7A | 0.85 | 1.49 | 0.7 | 0.983 | 0.894 | DC4 | CD1C−CD141− | 1 |
| 287 | MYO1G | 0.85 | 1.61 | 0.69 | 0.943 | 0.623 | DC4 | CD1C−CD141− | 0 |
| 288 | NAMPT | 0.85 | 1.48 | 0.69 | 0.989 | 0.802 | DC4 | CD1C−CD141− | 0 |
| 289 | CX3CR1 | 0.84 | 1.92 | 0.69 | 0.886 | 0.363 | DC4 | CD1C−CD141− | 1 |
| 290 | RAP1B | 0.84 | 1.17 | 0.69 | 1 | 0.947 | DC4 | CD1C−CD141− | 0 |
| 291 | MSN | 0.84 | 1.13 | 0.68 | 0.994 | 0.857 | DC4 | CD1C−CD141− | 0 |
| 292 | FCGR2C | 0.84 | 1.74 | 0.68 | 0.874 | 0.295 | DC4 | CD1C−CD141− | 0 |
| 293 | RAB24 | 0.84 | 1.58 | 0.68 | 0.903 | 0.476 | DC4 | CD1C−CD141− | 0 |
| 294 | GLUL | 0.84 | 1.45 | 0.67 | 0.954 | 0.571 | DC4 | CD1C−CD141− | 0 |
| 295 | GPBAR1 | 0.83 | 2.65 | 0.67 | 0.76 | 0.176 | DC4 | CD1C−CD141− | 1 |
| 296 | CHST15 | 0.83 | 2.3 | 0.66 | 0.766 | 0.148 | DC4 | CD1C−CD141− | 1 |
| 297 | CPPED1 | 0.83 | 1.23 | 0.66 | 0.983 | 0.898 | DC4 | CD1C−CD141− | 0 |
| 298 | CDKN1C | 0.83 | 3.74 | 0.66 | 0.669 | 0.028 | DC4 | CD1C−CD141− | 0 |
| 299 | TAGLN | 0.83 | 2.94 | 0.66 | 0.72 | 0.106 | DC4 | CD1C−CD141− | 0 |
| 300 | TKT | 0.83 | 1.17 | 0.66 | 0.983 | 0.804 | DC4 | CD1C−CD141− | 0 |
| 301 | BID | 0.83 | 1.11 | 0.65 | 0.983 | 0.829 | DC4 | CD1C−CD141− | 0 |
| 302 | NCF2 | 0.83 | 1.34 | 0.65 | 0.96 | 0.575 | DC4 | CD1C−CD141− | 0 |
| 303 | SMAP2 | 0.83 | 1.76 | 0.65 | 0.886 | 0.395 | DC4 | CD1C−CD141− | 0 |
| 304 | CD300E | 0.83 | 2.69 | 0.65 | 0.766 | 0.233 | DC4 | CD1C−CD141− | 1 |
| 305 | EMR1 | 0.83 | 3.21 | 0.65 | 0.703 | 0.085 | DC4 | CD1C−CD141− | 1 |
| 306 | TIMP1 | 0.82 | 1.26 | 0.63 | 0.943 | 0.554 | DC4 | CD1C−CD141− | 1 |
| 307 | PTP4A3 | 0.82 | 2.83 | 0.63 | 0.68 | 0.062 | DC4 | CD1C−CD141− | 0 |
| 308 | VMP1 | 0.81 | 1.69 | 0.63 | 0.897 | 0.547 | DC4 | CD1C−CD141− | 1 |
| 309 | NINJ1 | 0.81 | 2.32 | 0.62 | 0.726 | 0.198 | DC4 | CD1C−CD141− | 1 |
| 310 | POU2F2 | 0.81 | 1.81 | 0.62 | 0.851 | 0.392 | DC4 | CD1C−CD141− | 0 |
| 311 | GNS | 0.81 | 1.42 | 0.62 | 0.96 | 0.79 | DC4 | CD1C−CD141− | 1 |
| 312 | RNF144B | 0.81 | 1.68 | 0.62 | 0.92 | 0.616 | DC4 | CD1C−CD141− | 1 |
| 313 | ICAM2 | 0.81 | 1.79 | 0.61 | 0.811 | 0.354 | DC4 | CD1C−CD141− | 1 |
| 314 | STX11 | 0.8 | 1.81 | 0.61 | 0.891 | 0.642 | DC4 | CD1C−CD141− | 0 |
| 315 | STXBP2 | 0.8 | 1.09 | 0.61 | 0.983 | 0.714 | DC4 | CD1C−CD141− | 0 |
| 316 | FLNA | 0.8 | 1.11 | 0.6 | 0.949 | 0.734 | DC4 | CD1C−CD141− | 1 |
| 317 | NEURL | 0.8 | 2.84 | 0.6 | 0.669 | 0.102 | DC4 | CD1C−CD141− | 0 |
| 318 | PIK3AP1 | 0.8 | 1.65 | 0.6 | 0.886 | 0.503 | DC4 | CD1C−CD141− | 0 |
| 319 | SH2D1B | 0.8 | 5.13 | 0.59 | 0.617 | 0.046 | DC4 | CD1C−CD141− | 0 |
| 320 | MARCKS | 0.8 | 2.21 | 0.59 | 0.731 | 0.226 | DC4 | CD1C−CD141− | 1 |
| 321 | SLC44A2 | 0.8 | 1.09 | 0.59 | 0.977 | 0.7 | DC4 | CD1C−CD141− | 1 |
| 322 | TUBA1A | 0.8 | 1.03 | 0.59 | 0.977 | 0.845 | DC4 | CD1C−CD141− | 0 |
| 323 | DPEP2 | 0.79 | 2.36 | 0.59 | 0.714 | 0.199 | DC4 | CD1C−CD141− | 1 |
| 324 | CXCL16 | 0.79 | 1.36 | 0.58 | 0.909 | 0.621 | DC4 | CD1C−CD141− | 1 |
| 325 | HSPA7 | 0.79 | 1.95 | 0.58 | 0.743 | 0.247 | DC4 | CD1C−CD141− | 0 |
| 326 | SSH2 | 0.79 | 1.52 | 0.58 | 0.949 | 0.806 | DC4 | CD1C−CD141− | 0 |
| 327 | FCGR2A | 0.79 | 1.62 | 0.58 | 0.834 | 0.399 | DC4 | CD1C−CD141− | 1 |
| 328 | C3AR1 | 0.79 | 4.06 | 0.58 | 0.617 | 0.072 | DC4 | CD1C−CD141− | 1 |
| 329 | DRAP1 | 0.79 | 1.18 | 0.58 | 0.869 | 0.49 | DC4 | CD1C−CD141− | 0 |
| 330 | CYTIP | 0.79 | 1.4 | 0.57 | 0.914 | 0.665 | DC4 | CD1C−CD141− | 0 |
| 331 | RXRA | 0.79 | 1.87 | 0.57 | 0.771 | 0.342 | DC4 | CD1C−CD141− | 0 |
| 332 | LYN | 0.79 | 1.2 | 0.57 | 0.949 | 0.667 | DC4 | CD1C−CD141− | 0 |
| 333 | NAP1L1 | 0.79 | 1.05 | 0.57 | 0.994 | 0.975 | DC4 | CD1C−CD141− | 0 |
| 334 | IFIT3 | 0.78 | 2.55 | 0.57 | 0.834 | 0.61 | DC4 | CD1C−CD141− | 0 |
| 335 | IFITM1 | 0.78 | 1.7 | 0.57 | 0.743 | 0.235 | DC4 | CD1C−CD141− | 1 |
| 336 | NAAA | 0.78 | 1.11 | 0.57 | 0.977 | 0.862 | DC4 | CD1C−CD141− | 1 |
| 337 | CD300A | 0.78 | 1.14 | 0.57 | 0.903 | 0.584 | DC4 | CD1C−CD141− | 1 |
| 338 | DOK3 | 0.78 | 3.27 | 0.57 | 0.6 | 0.051 | DC4 | CD1C−CD141− | 0 |
| 339 | CALML4 | 0.78 | 1.86 | 0.56 | 0.731 | 0.229 | DC4 | CD1C−CD141− | 0 |
| 340 | NADK | 0.78 | 1.24 | 0.56 | 0.88 | 0.587 | DC4 | CD1C−CD141− | 0 |
| 341 | PHTF2 | 0.78 | 1.85 | 0.56 | 0.749 | 0.3 | DC4 | CD1C−CD141− | 1 |
| 342 | TESC | 0.78 | 3.73 | 0.56 | 0.594 | 0.056 | DC4 | CD1C−CD141− | 0 |
| 343 | MS4A4A | 0.78 | 2.16 | 0.56 | 0.72 | 0.266 | DC4 | CD1C−CD141− | 1 |

TABLE E2-continued (including parts a-f). All discriminative genes per subset
identified through unbiased clustering in FIG. 2

| Rank | Gene.ID | AUC value | Avg. Diff.[1] | Power[2] | Pct.1[3] | Pct.2[4] | Cluster.ID | Associated.Cell.Population | Surface Marker[5] |
|---|---|---|---|---|---|---|---|---|---|
| 344 | ALOX5 | 0.78 | 1.36 | 0.56 | 0.846 | 0.383 | DC4 | CD1C−CD141− | 0 |
| 345 | PAG1 | 0.78 | 1.19 | 0.56 | 0.926 | 0.675 | DC4 | CD1C−CD141− | 0 |
| 346 | SDCBP | 0.78 | 1.06 | 0.56 | 0.937 | 0.767 | DC4 | CD1C−CD141− | 0 |
| 347 | MT2A | 0.78 | 1.97 | 0.55 | 0.714 | 0.247 | DC4 | CD1C−CD141− | 0 |
| 348 | P2RX1 | 0.78 | 1.83 | 0.55 | 0.754 | 0.335 | DC4 | CD1C−CD141− | 1 |
| 349 | ZEB2 | 0.78 | 1.14 | 0.55 | 0.949 | 0.718 | DC4 | CD1C−CD141− | 0 |
| 350 | ARAP1 | 0.78 | 1.46 | 0.55 | 0.857 | 0.474 | DC4 | CD1C−CD141− | 0 |
| 351 | DOK2 | 0.77 | 1.16 | 0.55 | 0.834 | 0.372 | DC4 | CD1C−CD141− | 0 |
| 352 | HSBP1 | 0.77 | 1.35 | 0.55 | 0.931 | 0.656 | DC4 | CD1C−CD141− | 0 |
| 353 | LGALS3 | 0.77 | 1.02 | 0.55 | 0.92 | 0.549 | DC4 | CD1C−CD141− | 0 |
| 354 | TTYH3 | 0.77 | 1.83 | 0.54 | 0.68 | 0.187 | DC4 | CD1C−CD141− | 1 |
| 355 | C19ORF38 | 0.77 | 1.52 | 0.54 | 0.783 | 0.4 | DC4 | CD1C−CD141− | 1 |
| 356 | WSB1 | 0.77 | 1.06 | 0.54 | 0.96 | 0.868 | DC4 | CD1C−CD141− | 0 |
| 357 | CLEC4F | 0.77 | 3.69 | 0.53 | 0.56 | 0.046 | DC4 | CD1C−CD141− | 1 |
| 358 | GBP4 | 0.77 | 2.46 | 0.53 | 0.931 | 0.832 | DC4 | CD1C−CD141− | 0 |
| 359 | HK1 | 0.77 | 1.24 | 0.53 | 0.846 | 0.49 | DC4 | CD1C−CD141− | 0 |
| 360 | IRAK3 | 0.77 | 1.92 | 0.53 | 0.789 | 0.418 | DC4 | CD1C−CD141− | 0 |
| 361 | BLVRA | 0.76 | 1.68 | 0.53 | 0.72 | 0.325 | DC4 | CD1C−CD141− | 0 |
| 362 | ATP1B3 | 0.76 | 1.08 | 0.53 | 0.931 | 0.735 | DC4 | CD1C−CD141− | 1 |
| 363 | RNF149 | 0.76 | 1.16 | 0.52 | 0.931 | 0.734 | DC4 | CD1C−CD141− | 1 |
| 364 | TCIRG1 | 0.76 | 1.17 | 0.52 | 0.869 | 0.582 | DC4 | CD1C−CD141− | 1 |
| 365 | PRAM1 | 0.76 | 1.43 | 0.52 | 0.76 | 0.344 | DC4 | CD1C−CD141− | 0 |
| 366 | SPN | 0.76 | 1.31 | 0.51 | 0.983 | 0.993 | DC4 | CD1C−CD141− | 1 |
| 367 | ZCCHC6 | 0.76 | 1.49 | 0.51 | 0.949 | 0.82 | DC4 | CD1C−CD141− | 0 |
| 368 | CLEC12A | 0.75 | 1.61 | 0.51 | 0.766 | 0.393 | DC4 | CD1C−CD141− | 1 |
| 369 | CNIH4 | 0.75 | 1.46 | 0.51 | 0.874 | 0.697 | DC4 | CD1C−CD141− | 1 |
| 370 | IFI6 | 0.75 | 1.21 | 0.51 | 0.731 | 0.25 | DC4 | CD1C−CD141− | 1 |
| 371 | MAP3K1 | 0.75 | 1.31 | 0.51 | 0.817 | 0.469 | DC4 | CD1C−CD141− | 1 |
| 372 | INSIG1 | 0.75 | 1.63 | 0.51 | 0.749 | 0.37 | DC4 | CD1C−CD141− | 1 |
| 373 | SLC2A6 | 0.75 | 1.64 | 0.51 | 0.811 | 0.517 | DC4 | CD1C−CD141− | 1 |
| 374 | DMXL2 | 0.75 | 1 | 0.5 | 0.834 | 0.497 | DC4 | CD1C−CD141− | 1 |
| 375 | AK124399 | 0.75 | 2.83 | 0.5 | 0.503 | 0.011 | DC4 | CD1C−CD141− | 0 |
| 376 | ALDH3B1 | 0.75 | 1.72 | 0.5 | 0.863 | 0.69 | DC4 | CD1C−CD141− | 0 |
| 377 | TLR4 | 0.75 | 2.22 | 0.5 | 0.6 | 0.141 | DC4 | CD1C−CD141− | 1 |
| 378 | C11ORF21 | 0.75 | 1.68 | 0.49 | 0.703 | 0.309 | DC4 | CD1C−CD141− | 0 |
| 379 | C20ORF112 | 0.75 | 1.67 | 0.49 | 0.731 | 0.333 | DC4 | CD1C−CD141− | 0 |
| 380 | CKB | 0.75 | 4.07 | 0.49 | 0.509 | 0.028 | DC4 | CD1C−CD141− | 0 |
| 381 | NPL | 0.75 | 3.62 | 0.49 | 0.52 | 0.046 | DC4 | CD1C−CD141− | 0 |
| 382 | NDUFB3 | 0.74 | 1.07 | 0.48 | 0.897 | 0.705 | DC4 | CD1C−CD141− | 1 |
| 383 | RAB10 | 0.74 | 1.02 | 0.48 | 0.891 | 0.697 | DC4 | CD1C−CD141− | 0 |
| 384 | TMC6 | 0.74 | 1.46 | 0.48 | 0.829 | 0.524 | DC4 | CD1C−CD141− | 1 |
| 385 | ICAM4 | 0.74 | 2.4 | 0.48 | 0.68 | 0.295 | DC4 | CD1C−CD141− | 1 |
| 386 | DNASE2 | 0.74 | 1.9 | 0.48 | 0.697 | 0.349 | DC4 | CD1C−CD141− | 0 |
| 387 | C9ORF72 | 0.74 | 1.26 | 0.48 | 0.84 | 0.552 | DC4 | CD1C−CD141− | 0 |
| 388 | GIMAP7 | 0.74 | 2.05 | 0.48 | 0.589 | 0.146 | DC4 | CD1C−CD141− | 0 |
| 389 | KLF3 | 0.74 | 1.94 | 0.47 | 0.651 | 0.224 | DC4 | CD1C−CD141− | 0 |
| 390 | DKFZP451J181 | 0.74 | 1.25 | 0.47 | 0.834 | 0.51 | DC4 | CD1C−CD141− | 0 |
| 391 | TIAM1 | 0.74 | 1.56 | 0.47 | 0.743 | 0.388 | DC4 | CD1C−CD141− | 0 |
| 392 | CDC42EP3 | 0.74 | 2.05 | 0.47 | 0.646 | 0.247 | DC4 | CD1C−CD141− | 0 |
| 393 | STK10 | 0.74 | 1.02 | 0.47 | 0.909 | 0.792 | DC4 | CD1C−CD141− | 0 |
| 394 | TLR2 | 0.74 | 1.46 | 0.47 | 0.709 | 0.279 | DC4 | CD1C−CD141− | 1 |
| 395 | AGTRAP | 0.73 | 1.39 | 0.47 | 0.703 | 0.332 | DC4 | CD1C−CD141− | 1 |
| 396 | APOL6 | 0.73 | 1.68 | 0.47 | 0.903 | 0.797 | DC4 | CD1C−CD141− | 0 |
| 397 | CDH23 | 0.73 | 1.25 | 0.47 | 0.863 | 0.582 | DC4 | CD1C−CD141− | 1 |
| 398 | FPR1 | 0.73 | 1.11 | 0.47 | 0.737 | 0.349 | DC4 | CD1C−CD141− | 1 |
| 399 | AL137655 | 0.73 | 1.62 | 0.46 | 0.754 | 0.471 | DC4 | CD1C−CD141− | 0 |
| 400 | VAMP5 | 0.73 | 1.94 | 0.46 | 0.611 | 0.222 | DC4 | CD1C−CD141− | 1 |
| 401 | IRF1 | 0.73 | 1.24 | 0.46 | 0.989 | 0.97 | DC4 | CD1C−CD141− | 0 |
| 402 | SH3BP2 | 0.73 | 1.13 | 0.46 | 0.926 | 0.818 | DC4 | CD1C−CD141− | 0 |
| 403 | YPEL2 | 0.73 | 1.92 | 0.46 | 0.623 | 0.194 | DC4 | CD1C−CD141− | 0 |
| 404 | GRAMD1A | 0.73 | 1.7 | 0.46 | 0.691 | 0.282 | DC4 | CD1C−CD141− | 1 |
| 405 | ISG15 | 0.73 | 1.06 | 0.46 | 0.794 | 0.503 | DC4 | CD1C−CD141− | 0 |
| 406 | LRP1 | 0.73 | 1.01 | 0.45 | 0.731 | 0.298 | DC4 | CD1C−CD141− | 1 |
| 407 | MXD3 | 0.73 | 1.82 | 0.45 | 0.589 | 0.159 | DC4 | CD1C−CD141− | 0 |
| 408 | AMPD2 | 0.73 | 1.35 | 0.45 | 0.766 | 0.451 | DC4 | CD1C−CD141− | 0 |
| 409 | CD244 | 0.73 | 1.66 | 0.45 | 0.629 | 0.219 | DC4 | CD1C−CD141− | 1 |
| 410 | GBP1 | 0.73 | 1.82 | 0.45 | 0.646 | 0.252 | DC4 | CD1C−CD141− | 0 |
| 411 | LCP2 | 0.73 | 1.23 | 0.45 | 0.817 | 0.499 | DC4 | CD1C−CD141− | 0 |
| 412 | ZFAND5 | 0.73 | 1.01 | 0.45 | 0.937 | 0.734 | DC4 | CD1C−CD141− | 0 |
| 413 | HEG1 | 0.73 | 2.62 | 0.45 | 0.503 | 0.069 | DC4 | CD1C−CD141− | 1 |
| 414 | LOC388312 | 0.73 | 1.87 | 0.45 | 0.623 | 0.252 | DC4 | CD1C−CD141− | 0 |
| 415 | ARRB1 | 0.72 | 1.26 | 0.45 | 0.754 | 0.434 | DC4 | CD1C−CD141− | 0 |
| 416 | FAM46A | 0.72 | 1.21 | 0.45 | 0.783 | 0.436 | DC4 | CD1C−CD141− | 0 |
| 417 | ABCC3 | 0.72 | 2.72 | 0.45 | 0.771 | 0.506 | DC4 | CD1C−CD141− | 1 |

TABLE E2-continued (including parts a-f). All discriminative genes per subset identified through unbiased clustering in FIG. 2

| Rank | Gene.ID | AUC value | Avg. Diff.[1] | Power[2] | Pct.1[3] | Pct.2[4] | Cluster.ID | Associated.Cell.Population | Surface Marker[5] |
|---|---|---|---|---|---|---|---|---|---|
| 418 | GBP5 | 0.72 | 2.82 | 0.45 | 0.554 | 0.162 | DC4 | CD1C⁻CD141⁻ | 0 |
| 419 | SVIL | 0.72 | 1.73 | 0.45 | 0.617 | 0.22 | DC4 | CD1C⁻CD141⁻ | 0 |
| 420 | ARRB2 | 0.72 | 1.18 | 0.44 | 0.737 | 0.376 | DC4 | CD1C⁻CD141⁻ | 0 |
| 421 | FAM45B | 0.72 | 1.68 | 0.44 | 0.646 | 0.266 | DC4 | CD1C⁻CD141⁻ | 0 |
| 422 | LTA4H | 0.72 | 1.04 | 0.44 | 0.903 | 0.774 | DC4 | CD1C⁻CD141⁻ | 0 |
| 423 | NFAM1 | 0.72 | 1.4 | 0.44 | 0.72 | 0.43 | DC4 | CD1C⁻CD141⁻ | 1 |
| 424 | CSK | 0.72 | 1.01 | 0.44 | 0.891 | 0.695 | DC4 | CD1C⁻CD141⁻ | 0 |
| 425 | TBC1D8 | 0.72 | 1.72 | 0.44 | 0.651 | 0.282 | DC4 | CD1C⁻CD141⁻ | 1 |
| 426 | GNG2 | 0.72 | 1.33 | 0.43 | 0.766 | 0.501 | DC4 | CD1C⁻CD141⁻ | 0 |
| 427 | MYOF | 0.72 | 1.42 | 0.43 | 0.697 | 0.326 | DC4 | CD1C⁻CD141⁻ | 1 |
| 428 | RAB37 | 0.72 | 3.58 | 0.43 | 0.514 | 0.123 | DC4 | CD1C⁻CD141⁻ | 0 |
| 429 | VPS53 | 0.72 | 1.15 | 0.43 | 0.983 | 0.945 | DC4 | CD1C⁻CD141⁻ | 0 |
| 430 | APOBEC3A | 0.72 | 3.8 | 0.43 | 0.68 | 0.474 | DC4 | CD1C⁻CD141⁻ | 0 |
| 431 | ITGB1 | 0.71 | 1.08 | 0.43 | 0.817 | 0.594 | DC4 | CD1C⁻CD141⁻ | 1 |
| 432 | P2RY13 | 0.71 | 1.96 | 0.43 | 0.566 | 0.183 | DC4 | CD1C⁻CD141⁻ | 1 |
| 433 | C15ORF39 | 0.71 | 1.05 | 0.43 | 0.84 | 0.584 | DC4 | CD1C⁻CD141⁻ | 0 |
| 434 | DENND5A | 0.71 | 1.29 | 0.42 | 0.749 | 0.474 | DC4 | CD1C⁻CD141⁻ | 1 |
| 435 | NBEAL2 | 0.71 | 1.33 | 0.42 | 0.703 | 0.33 | DC4 | CD1C⁻CD141⁻ | 0 |
| 436 | PLIN2 | 0.71 | 1.72 | 0.42 | 0.634 | 0.272 | DC4 | CD1C⁻CD141⁻ | 0 |
| 437 | PIK3IP1 | 0.71 | 2.51 | 0.42 | 0.617 | 0.309 | DC4 | CD1C⁻CD141⁻ | 1 |
| 438 | SCIMP | 0.71 | 1.04 | 0.42 | 0.994 | 0.961 | DC4 | CD1C⁻CD141⁻ | 1 |
| 439 | TMPO | 0.71 | 1.4 | 0.42 | 0.851 | 0.667 | DC4 | CD1C⁻CD141⁻ | 1 |
| 440 | KIAA0513 | 0.71 | 1.5 | 0.41 | 0.726 | 0.48 | DC4 | CD1C⁻CD141⁻ | 0 |
| 441 | C10ORF46 | 0.71 | 1.08 | 0.41 | 0.914 | 0.852 | DC4 | CD1C⁻CD141⁻ | 0 |
| 442 | CASP4 | 0.71 | 1.03 | 0.41 | 0.766 | 0.474 | DC4 | CD1C⁻CD141⁻ | 0 |
| 443 | FGD4 | 0.71 | 1.56 | 0.41 | 0.829 | 0.605 | DC4 | CD1C⁻CD141⁻ | 0 |
| 444 | IFNGR2 | 0.71 | 1.07 | 0.41 | 0.789 | 0.511 | DC4 | CD1C⁻CD141⁻ | 1 |
| 445 | PTGER2 | 0.7 | 2.16 | 0.41 | 0.503 | 0.115 | DC4 | CD1C⁻CD141⁻ | 1 |
| 446 | SAMSN1 | 0.7 | 1.77 | 0.41 | 0.554 | 0.176 | DC4 | CD1C⁻CD141⁻ | 0 |
| 447 | UBXN11 | 0.7 | 1.15 | 0.41 | 0.709 | 0.358 | DC4 | CD1C⁻CD141⁻ | 0 |
| 448 | TBCD | 0.7 | 1.8 | 0.41 | 0.554 | 0.19 | DC4 | CD1C⁻CD141⁻ | 1 |
| 449 | VASP | 0.7 | 1.58 | 0.41 | 0.6 | 0.256 | DC4 | CD1C⁻CD141⁻ | 0 |
| 450 | CCM2 | 0.7 | 1.58 | 0.4 | 0.663 | 0.362 | DC4 | CD1C⁻CD141⁻ | 0 |
| 451 | NLRP1 | 0.7 | 1.29 | 0.4 | 0.674 | 0.347 | DC4 | CD1C⁻CD141⁻ | 0 |
| 452 | GIMAP1 | 0.7 | 2.33 | 0.4 | 0.617 | 0.344 | DC4 | CD1C⁻CD141⁻ | 1 |
| 453 | NR4A1 | 0.7 | 1.69 | 0.4 | 0.6 | 0.263 | DC4 | CD1C⁻CD141⁻ | 0 |
| 454 | TNFRSF14 | 0.7 | 1.12 | 0.4 | 0.754 | 0.527 | DC4 | CD1C⁻CD141⁻ | 1 |
| 455 | MBD2 | 0.7 | 1.71 | 0.39 | 0.549 | 0.189 | DC4 | CD1C⁻CD141⁻ | 0 |
| 456 | SCPEP1 | 0.69 | 1.18 | 0.39 | 0.68 | 0.376 | DC4 | CD1C⁻CD141⁻ | 0 |
| 457 | DENND3 | 0.69 | 1.43 | 0.39 | 0.754 | 0.575 | DC4 | CD1C⁻CD141⁻ | 1 |
| 458 | IFIT2 | 0.69 | 1.44 | 0.38 | 0.543 | 0.189 | DC4 | CD1C⁻CD141⁻ | 0 |
| 459 | NECAP2 | 0.69 | 1.08 | 0.38 | 0.743 | 0.547 | DC4 | CD1C⁻CD141⁻ | 0 |
| 460 | PTGER4 | 0.69 | 1.18 | 0.38 | 0.709 | 0.455 | DC4 | CD1C⁻CD141⁻ | 1 |
| 461 | RASGRP4 | 0.69 | 1.13 | 0.38 | 0.783 | 0.545 | DC4 | CD1C⁻CD141⁻ | 0 |
| 462 | TMBIM1 | 0.69 | 1.28 | 0.38 | 0.651 | 0.349 | DC4 | CD1C⁻CD141⁻ | 1 |
| 463 | SIRPB1 | 0.69 | 1.12 | 0.38 | 0.703 | 0.409 | DC4 | CD1C⁻CD141⁻ | 1 |
| 464 | STK38 | 0.69 | 1.19 | 0.38 | 0.737 | 0.496 | DC4 | CD1C⁻CD141⁻ | 0 |
| 465 | EVL | 0.69 | 1.07 | 0.38 | 0.691 | 0.353 | DC4 | CD1C⁻CD141⁻ | 0 |
| 466 | GIMAP2 | 0.69 | 1.86 | 0.38 | 0.503 | 0.152 | DC4 | CD1C⁻CD141⁻ | 1 |
| 467 | LIMS1 | 0.69 | 1.01 | 0.37 | 0.937 | 0.875 | DC4 | CD1C⁻CD141⁻ | 0 |
| 468 | FGD3 | 0.68 | 1.21 | 0.37 | 0.703 | 0.45 | DC4 | CD1C⁻CD141⁻ | 0 |
| 469 | SLA | 0.68 | 1.19 | 0.37 | 0.674 | 0.397 | DC4 | CD1C⁻CD141⁻ | 0 |
| 470 | SULT1A1 | 0.68 | 1.62 | 0.36 | 0.583 | 0.309 | DC4 | CD1C⁻CD141⁻ | 0 |
| 471 | WDR11 | 0.68 | 1.25 | 0.36 | 0.691 | 0.439 | DC4 | CD1C⁻CD141⁻ | 1 |
| 472 | PSTPIP2 | 0.68 | 1.66 | 0.36 | 0.8 | 0.7 | DC4 | CD1C⁻CD141⁻ | 0 |
| 473 | PDLIM5 | 0.68 | 1.09 | 0.36 | 0.914 | 0.829 | DC4 | CD1C⁻CD141⁻ | 1 |
| 474 | RALB | 0.68 | 1.12 | 0.36 | 0.686 | 0.407 | DC4 | CD1C⁻CD141⁻ | 0 |
| 475 | ABHD3 | 0.68 | 1.18 | 0.36 | 0.651 | 0.36 | DC4 | CD1C⁻CD141⁻ | 1 |
| 476 | ARRDC3 | 0.68 | 1.23 | 0.36 | 0.703 | 0.48 | DC4 | CD1C⁻CD141⁻ | 0 |
| 477 | KLF11 | 0.68 | 1.44 | 0.36 | 0.543 | 0.212 | DC4 | CD1C⁻CD141⁻ | 0 |
| 478 | TMTC1 | 0.68 | 2.1 | 0.36 | 0.571 | 0.312 | DC4 | CD1C⁻CD141⁻ | 1 |
| 479 | RAP1GAP2 | 0.68 | 1.15 | 0.35 | 0.6 | 0.291 | DC4 | CD1C⁻CD141⁻ | 0 |
| 480 | SNX18 | 0.68 | 1.18 | 0.35 | 0.617 | 0.302 | DC4 | CD1C⁻CD141⁻ | 0 |
| 481 | RAB3D | 0.68 | 1.13 | 0.35 | 0.754 | 0.533 | DC4 | CD1C⁻CD141⁻ | 0 |
| 482 | ADRBK1 | 0.68 | 1.04 | 0.35 | 0.743 | 0.529 | DC4 | CD1C⁻CD141⁻ | 0 |
| 483 | ARHGEF3 | 0.68 | 1.24 | 0.35 | 0.617 | 0.312 | DC4 | CD1C⁻CD141⁻ | 0 |
| 484 | BACH1 | 0.68 | 1.36 | 0.35 | 0.674 | 0.427 | DC4 | CD1C⁻CD141⁻ | 0 |
| 485 | DDX60 | 0.68 | 1.31 | 0.35 | 0.686 | 0.432 | DC4 | CD1C⁻CD141⁻ | 0 |
| 486 | PIEZO1 | 0.68 | 1.15 | 0.35 | 0.674 | 0.399 | DC4 | CD1C⁻CD141⁻ | 1 |
| 487 | CMTM7 | 0.67 | 1.13 | 0.35 | 0.606 | 0.333 | DC4 | CD1C⁻CD141⁻ | 1 |
| 488 | IMPDH1 | 0.67 | 1.23 | 0.35 | 0.589 | 0.298 | DC4 | CD1C⁻CD141⁻ | 0 |
| 489 | TSPAN32 | 0.67 | 1.08 | 0.35 | 0.634 | 0.33 | DC4 | CD1C⁻CD141⁻ | 1 |
| 490 | DDX58 | 0.67 | 1.93 | 0.34 | 0.56 | 0.303 | DC4 | CD1C⁻CD141⁻ | 0 |
| 491 | CCPG1 | 0.67 | 1.33 | 0.34 | 0.789 | 0.624 | DC4 | CD1C⁻CD141⁻ | 1 |

TABLE E2-continued (including parts a-f). All discriminative genes per subset
identified through unbiased clustering in FIG. 2

| Rank | Gene.ID | AUC value | Avg. Diff.[1] | Power[2] | Pct.1[3] | Pct.2[4] | Cluster.ID | Associated.Cell.Population | Surface Marker[5] |
|---|---|---|---|---|---|---|---|---|---|
| 492 | DDX60L | 0.67 | 1.3 | 0.34 | 0.709 | 0.52 | DC4 | CD1C−CD141− | 0 |
| 493 | PNPLA6 | 0.67 | 1.02 | 0.34 | 0.64 | 0.369 | DC4 | CD1C−CD141− | 1 |
| 494 | UNC13D | 0.67 | 1.36 | 0.34 | 0.829 | 0.727 | DC4 | CD1C−CD141− | 0 |
| 495 | SYTL1 | 0.67 | 1.18 | 0.34 | 0.606 | 0.325 | DC4 | CD1C−CD141− | 0 |
| 496 | CSGALNACT2 | 0.67 | 1.13 | 0.33 | 0.64 | 0.384 | DC4 | CD1C−CD141− | 0 |
| 497 | TLE4 | 0.67 | 1.43 | 0.33 | 0.543 | 0.242 | DC4 | CD1C−CD141− | 0 |
| 498 | SIRPB2 | 0.67 | 1.43 | 0.33 | 0.703 | 0.476 | DC4 | CD1C−CD141− | 1 |
| 499 | UPP1 | 0.66 | 1.44 | 0.32 | 0.514 | 0.224 | DC4 | CD1C−CD141− | 0 |
| 500 | ARAP2 | 0.66 | 1.37 | 0.32 | 0.554 | 0.259 | DC4 | CD1C−CD141− | 0 |
| 501 | ERICH1 | 0.66 | 1.12 | 0.32 | 0.697 | 0.459 | DC4 | CD1C−CD141− | 0 |
| 502 | PPM1F | 0.66 | 1.08 | 0.32 | 0.76 | 0.564 | DC4 | CD1C−CD141− | 0 |
| 503 | GPR155 | 0.66 | 1.22 | 0.32 | 0.897 | 0.84 | DC4 | CD1C−CD141− | 1 |
| 504 | MPP1 | 0.66 | 1.02 | 0.32 | 0.606 | 0.36 | DC4 | CD1C−CD141− | 0 |
| 505 | PELI1 | 0.66 | 1.61 | 0.31 | 0.891 | 0.875 | DC4 | CD1C−CD141− | 0 |
| 506 | TMEM154 | 0.66 | 1.2 | 0.31 | 0.629 | 0.409 | DC4 | CD1C−CD141− | 1 |
| 507 | L1TD1 | 0.66 | 2.57 | 0.31 | 0.646 | 0.457 | DC4 | CD1C−CD141− | 0 |
| 508 | WDFY1 | 0.66 | 1.21 | 0.31 | 0.537 | 0.252 | DC4 | CD1C−CD141− | 0 |
| 509 | FOXO1 | 0.65 | 1.65 | 0.3 | 0.709 | 0.513 | DC4 | CD1C−CD141− | 0 |
| 510 | PLXNC1 | 0.65 | 1.23 | 0.3 | 0.594 | 0.362 | DC4 | CD1C−CD141− | 1 |
| 511 | MCTP1 | 0.65 | 1.03 | 0.3 | 0.64 | 0.392 | DC4 | CD1C−CD141− | 1 |
| 512 | AP2A1 | 0.65 | 1.08 | 0.29 | 0.754 | 0.628 | DC4 | CD1C−CD141− | 0 |
| 513 | DNAJB1 | 0.65 | 1.17 | 0.29 | 0.617 | 0.395 | DC4 | CD1C−CD141− | 0 |
| 514 | SWAP70 | 0.65 | 1.35 | 0.29 | 0.726 | 0.587 | DC4 | CD1C−CD141− | 0 |
| 515 | TMEM11 | 0.65 | 1.08 | 0.29 | 0.531 | 0.289 | DC4 | CD1C−CD141− | 1 |
| 516 | TMEM134 | 0.64 | 1.25 | 0.29 | 0.52 | 0.289 | DC4 | CD1C−CD141− | 1 |
| 517 | CABP4 | 0.64 | 1.71 | 0.29 | 0.937 | 0.958 | DC4 | CD1C−CD141− | 0 |
| 518 | LOC100133161 | 0.64 | 1.14 | 0.29 | 0.566 | 0.356 | DC4 | CD1C−CD141− | 0 |
| 519 | ARL4A | 0.64 | 1.23 | 0.28 | 0.526 | 0.275 | DC4 | CD1C−CD141− | 0 |
| 520 | EHD1 | 0.64 | 1.2 | 0.28 | 0.509 | 0.3 | DC4 | CD1C−CD141− | 0 |
| 521 | ACOT9 | 0.64 | 1.01 | 0.28 | 0.566 | 0.342 | DC4 | CD1C−CD141− | 0 |
| 522 | KSR1 | 0.64 | 1.22 | 0.28 | 0.674 | 0.508 | DC4 | CD1C−CD141− | 0 |
| 523 | KDM1B | 0.64 | 1.13 | 0.27 | 0.817 | 0.718 | DC4 | CD1C−CD141− | 0 |
| 524 | PDP1 | 0.64 | 1.11 | 0.27 | 0.531 | 0.302 | DC4 | CD1C−CD141− | 0 |
| 525 | AK123771 | 0.64 | 1.59 | 0.27 | 0.777 | 0.656 | DC4 | CD1C−CD141− | 0 |
| 526 | PITPNM1 | 0.63 | 1.06 | 0.27 | 0.651 | 0.462 | DC4 | CD1C−CD141− | 0 |
| 527 | FAM126A | 0.63 | 1.06 | 0.26 | 0.503 | 0.261 | DC4 | CD1C−CD141− | 0 |
| 528 | MAGED2 | 0.63 | 1.13 | 0.26 | 0.52 | 0.298 | DC4 | CD1C−CD141− | 0 |
| 529 | CAMK1 | 0.63 | 1.11 | 0.26 | 0.823 | 0.713 | DC4 | CD1C−CD141− | 1 |
| 530 | IL12RB1 | 0.63 | 1.04 | 0.26 | 0.903 | 0.877 | DC4 | CD1C−CD141− | 1 |
| 531 | PYGL | 0.63 | 1.31 | 0.26 | 0.743 | 0.649 | DC4 | CD1C−CD141− | 0 |
| 532 | CORO2A | 0.63 | 1.33 | 0.26 | 0.914 | 0.84 | DC4 | CD1C−CD141− | 0 |
| 533 | ZNFX1 | 0.63 | 1.1 | 0.26 | 0.691 | 0.54 | DC4 | CD1C−CD141− | 0 |
| 534 | TYMP | 0.63 | 1.02 | 0.25 | 0.623 | 0.46 | DC4 | CD1C−CD141− | 0 |
| 535 | NUDT16 | 0.62 | 1.17 | 0.24 | 0.571 | 0.379 | DC4 | CD1C−CD141− | 0 |
| 536 | SGPL1 | 0.62 | 1.02 | 0.24 | 0.743 | 0.637 | DC4 | CD1C−CD141− | 1 |
| 537 | MEFV | 0.62 | 1.08 | 0.24 | 0.92 | 0.903 | DC4 | CD1C−CD141− | 0 |
| 538 | RELT | 0.62 | 1.01 | 0.24 | 0.583 | 0.444 | DC4 | CD1C−CD141− | 1 |
| 539 | PTPN13 | 0.61 | 1.04 | 0.23 | 0.594 | 0.429 | DC4 | CD1C−CD141− | 0 |
| 540 | FCAR | 0.61 | 1.89 | 0.23 | 0.794 | 0.748 | DC4 | CD1C−CD141− | 1 |
| 541 | SASH1 | 0.61 | 1.51 | 0.22 | 0.583 | 0.459 | DC4 | CD1C−CD141− | 0 |
| 542 | PLEKHO2 | 0.61 | 1 | 0.22 | 0.531 | 0.37 | DC4 | CD1C−CD141− | 0 |
| 543 | BLOC1S3 | 0.61 | 1.56 | 0.22 | 0.583 | 0.46 | DC4 | CD1C−CD141− | 0 |
| 544 | CAMKK2 | 0.61 | 1.04 | 0.22 | 0.589 | 0.437 | DC4 | CD1C−CD141− | 1 |
| | | | | | | part e | | | |
| 545 | AXL | 1 | 3.78 | 0.99 | 1 | 0.824 | DC5 | AXL+SIGLEC6+ | 1 |
| 546 | PPP1R14A | 0.99 | 3.35 | 0.98 | 1 | 0.101 | DC5 | AXL+SIGLEC6+ | 0 |
| 547 | SIGLEC6 | 0.97 | 3.67 | 0.94 | 0.967 | 0.129 | DC5 | AXL+SIGLEC6+ | 1 |
| 548 | CD22 | 0.95 | 3.13 | 0.89 | 0.933 | 0.128 | DC5 | AXL+SIGLEC6+ | 1 |
| 549 | DAB2 | 0.92 | 1.98 | 0.83 | 0.967 | 0.292 | DC5 | AXL+SIGLEC6+ | 0 |
| 550 | S100A10 | 0.91 | 1.01 | 0.82 | 1 | 0.897 | DC5 | AXL+SIGLEC6+ | 1 |
| 551 | FAM105A | 0.88 | 1.5 | 0.75 | 1 | 0.645 | DC5 | AXL+SIGLEC6+ | 1 |
| 552 | MED12L | 0.86 | 2.01 | 0.72 | 0.8 | 0.097 | DC5 | AXL+SIGLEC6+ | 0 |
| 553 | ALDH2 | 0.86 | 1.07 | 0.71 | 0.967 | 0.715 | DC5 | AXL+SIGLEC6+ | 0 |
| 554 | LTK | 0.85 | 2.18 | 0.7 | 0.767 | 0.087 | DC5 | AXL+SIGLEC6+ | 1 |
| 555 | DPYSL2 | 0.85 | 1 | 0.7 | 1 | 0.927 | DC5 | AXL+SIGLEC6+ | 0 |
| 556 | LGMN | 0.85 | 1.19 | 0.7 | 1 | 0.631 | DC5 | AXL+SIGLEC6+ | 1 |
| 557 | IRF4 | 0.83 | 1.09 | 0.67 | 0.967 | 0.43 | DC5 | AXL+SIGLEC6+ | 0 |
| 558 | SEPT6' | 0.83 | 1.33 | 0.67 | 0.967 | 0.688 | DC5 | AXL+SIGLEC6+ | 0 |
| 559 | PLAC8 | 0.83 | 1 | 0.66 | 1 | 0.919 | DC5 | AXL+SIGLEC6+ | 0 |
| 560 | CCND3 | 0.82 | 1.01 | 0.65 | 0.967 | 0.806 | DC5 | AXL+SIGLEC6+ | 0 |
| 561 | MYO1E | 0.82 | 1.6 | 0.65 | 0.867 | 0.379 | DC5 | AXL+SIGLEC6+ | 0 |
| 562 | SLC41A2 | 0.82 | 1.21 | 0.65 | 0.933 | 0.48 | DC5 | AXL+SIGLEC6+ | 1 |
| 563 | SCN9A | 0.82 | 1.35 | 0.64 | 0.867 | 0.393 | DC5 | AXL+SIGLEC6+ | 1 |

TABLE E2-continued (including parts a-f). All discriminative genes per subset
identified through unbiased clustering in FIG. 2

| Rank | Gene.ID | AUC value | Avg. Diff.[1] | Power[2] | Pct.1[3] | Pct.2[4] | Cluster.ID | Associated.Cell.Population | Surface Marker[5] |
|---|---|---|---|---|---|---|---|---|---|
| 564 | SIGLEC1 | 0.82 | 2.11 | 0.64 | 0.733 | 0.135 | DC5 | AXL+SIGLEC6+ | 1 |
| 565 | CX3CR1 | 0.82 | 1.17 | 0.63 | 0.933 | 0.468 | DC5 | AXL+SIGLEC6+ | 1 |
| 566 | NDRG1 | 0.81 | 1.23 | 0.61 | 0.867 | 0.416 | DC5 | AXL+SIGLEC6+ | 0 |
| 567 | VASH1 | 0.8 | 1.48 | 0.6 | 0.833 | 0.397 | DC5 | AXL+SIGLEC6+ | 0 |
| 568 | CD5 | 0.8 | 3.34 | 0.6 | 0.633 | 0.046 | DC5 | AXL+SIGLEC6+ | 1 |
| 569 | BHLHE40 | 0.8 | 1.2 | 0.6 | 0.967 | 0.635 | DC5 | AXL+SIGLEC6+ | 0 |
| 570 | SNRNP25 | 0.8 | 1.35 | 0.59 | 0.867 | 0.412 | DC5 | AXL+SIGLEC6+ | 0 |
| 571 | USF2 | 0.8 | 1.33 | 0.59 | 0.833 | 0.305 | DC5 | AXL+SIGLEC6+ | 0 |
| 572 | SLC20A1 | 0.79 | 1.25 | 0.58 | 0.9 | 0.558 | DC5 | AXL+SIGLEC6+ | 1 |
| 573 | ATF5 | 0.79 | 1.16 | 0.57 | 0.767 | 0.195 | DC5 | AXL+SIGLEC6+ | 0 |
| 574 | FAM129A | 0.79 | 1.33 | 0.57 | 0.9 | 0.565 | DC5 | AXL+SIGLEC6+ | 0 |
| 575 | KLF4 | 0.78 | 1.16 | 0.57 | 0.933 | 0.56 | DC5 | AXL+SIGLEC6+ | 0 |
| 576 | RUNX2 | 0.78 | 1.07 | 0.56 | 0.9 | 0.434 | DC5 | AXL+SIGLEC6+ | 0 |
| 577 | ARHGAP18 | 0.77 | 1.44 | 0.54 | 0.733 | 0.279 | DC5 | AXL+SIGLEC6+ | 0 |
| 578 | APEX1 | 0.77 | 1.02 | 0.53 | 0.933 | 0.697 | DC5 | AXL+SIGLEC6+ | 0 |
| 579 | ENTPD7 | 0.76 | 1.62 | 0.53 | 0.767 | 0.329 | DC5 | AXL+SIGLEC6+ | 1 |
| 580 | SLC35C2 | 0.76 | 1.15 | 0.52 | 0.867 | 0.458 | DC5 | AXL+SIGLEC6+ | 1 |
| 581 | CDH1 | 0.76 | 2.4 | 0.52 | 0.733 | 0.442 | DC5 | AXL+SIGLEC6+ | 1 |
| 582 | GPR146 | 0.76 | 3.71 | 0.52 | 0.533 | 0.022 | DC5 | AXL+SIGLEC6+ | 1 |
| 583 | BAIAP2 | 0.75 | 1.53 | 0.51 | 0.667 | 0.199 | DC5 | AXL+SIGLEC6+ | 0 |
| 584 | CDKN1A | 0.75 | 1.03 | 0.5 | 0.833 | 0.435 | DC5 | AXL+SIGLEC6+ | 0 |
| 585 | UPK3A | 0.75 | 1.7 | 0.5 | 0.667 | 0.264 | DC5 | AXL+SIGLEC6+ | 1 |
| 586 | GNAQ | 0.75 | 1.12 | 0.49 | 0.833 | 0.493 | DC5 | AXL+SIGLEC6+ | 0 |
| 587 | THBD | 0.74 | 1.16 | 0.49 | 0.767 | 0.367 | DC5 | AXL+SIGLEC6+ | 1 |
| 588 | TNFSF12 | 0.74 | 1.08 | 0.49 | 0.867 | 0.541 | DC5 | AXL+SIGLEC6+ | 0 |
| 589 | SOX4 | 0.74 | 1.5 | 0.48 | 0.8 | 0.521 | DC5 | AXL+SIGLEC6+ | 0 |
| 590 | CXCR2 | 0.74 | 3.22 | 0.48 | 0.6 | 0.223 | DC5 | AXL+SIGLEC6+ | 1 |
| 591 | HIP1 | 0.73 | 1.06 | 0.45 | 0.967 | 0.831 | DC5 | AXL+SIGLEC6+ | 0 |
| 592 | STX18 | 0.73 | 1.06 | 0.45 | 0.767 | 0.413 | DC5 | AXL+SIGLEC6+ | 1 |
| 593 | CTSW | 0.72 | 1.42 | 0.44 | 0.6 | 0.157 | DC5 | AXL+SIGLEC6+ | 0 |
| 594 | ATP2B4 | 0.72 | 1.29 | 0.44 | 0.8 | 0.478 | DC5 | AXL+SIGLEC6+ | 1 |
| 595 | CD72 | 0.72 | 1.83 | 0.43 | 0.567 | 0.176 | DC5 | AXL+SIGLEC6+ | 1 |
| 596 | MGLL | 0.72 | 1.29 | 0.43 | 0.667 | 0.308 | DC5 | AXL+SIGLEC6+ | 0 |
| 597 | SUSD1 | 0.71 | 1.29 | 0.43 | 0.6 | 0.216 | DC5 | AXL+SIGLEC6+ | 1 |
| 598 | RNF141 | 0.71 | 1.04 | 0.43 | 0.9 | 0.754 | DC5 | AXL+SIGLEC6+ | 0 |
| 599 | TNNI2 | 0.71 | 1.19 | 0.42 | 0.9 | 0.213 | DC5 | AXL+SIGLEC6+ | 0 |
| 600 | GGTA1P | 0.71 | 1.82 | 0.41 | 0.533 | 0.145 | DC5 | AXL+SIGLEC6+ | 0 |
| 601 | C5ORF25 | 0.71 | 1.24 | 0.41 | 0.7 | 0.36 | DC5 | AXL+SIGLEC6+ | 0 |
| 602 | PTGDS | 0.7 | 1.84 | 0.41 | 0.533 | 0.139 | DC5 | AXL+SIGLEC6+ | 0 |
| 603 | TSEN54 | 0.7 | 1.22 | 0.41 | 0.6 | 0.208 | DC5 | AXL+SIGLEC6+ | 0 |
| 604 | KLF12 | 0.7 | 1.09 | 0.41 | 0.6 | 0.209 | DC5 | AXL+SIGLEC6+ | 0 |
| 605 | MYH11 | 0.7 | 1.63 | 0.4 | 0.667 | 0.319 | DC5 | AXL+SIGLEC6+ | 0 |
| 606 | TXN | 0.7 | 1.16 | 0.39 | 0.9 | 0.754 | DC5 | AXL+SIGLEC6+ | 0 |
| 607 | AK125727 | 0.7 | 1.3 | 0.39 | 0.8 | 0.718 | DC5 | AXL+SIGLEC6+ | 0 |
| 608 | CD300LB | 0.69 | 1.16 | 0.37 | 0.533 | 0.184 | DC5 | AXL+SIGLEC6+ | 1 |
| 609 | SUCLA2 | 0.69 | 1.16 | 0.37 | 0.633 | 0.324 | DC5 | AXL+SIGLEC6+ | 0 |
| 610 | BIN1 | 0.69 | 1.27 | 0.37 | 0.567 | 0.24 | DC5 | AXL+SIGLEC6+ | 0 |
| 611 | MRPS6 | 0.68 | 1.03 | 0.37 | 0.733 | 0.465 | DC5 | AXL+SIGLEC6+ | 0 |
| 612 | ZNF789 | 0.68 | 1.1 | 0.37 | 0.567 | 0.233 | DC5 | AXL+SIGLEC6+ | 0 |
| 613 | RAD1 | 0.68 | 1.54 | 0.36 | 0.833 | 0.631 | DC5 | AXL+SIGLEC6+ | 0 |
| 614 | PIM2 | 0.68 | 1.06 | 0.36 | 0.7 | 0.416 | DC5 | AXL+SIGLEC6+ | 1 |
| 615 | PLA2G16 | 0.68 | 1.07 | 0.35 | 0.533 | 0.195 | DC5 | AXL+SIGLEC6+ | 1 |
| 616 | TBC1D9 | 0.68 | 1.25 | 0.35 | 0.6 | 0.344 | DC5 | AXL+SIGLEC6+ | 0 |
| 617 | ADAM33 | 0.67 | 2.28 | 0.34 | 0.633 | 0.382 | DC5 | AXL+SIGLEC6+ | 1 |
| 618 | ZEB1 | 0.67 | 1.34 | 0.34 | 0.533 | 0.225 | DC5 | AXL+SIGLEC6+ | 0 |
| 619 | CD300LG | 0.66 | 2.48 | 0.33 | 0.6 | 0.326 | DC5 | AXL+SIGLEC6+ | 1 |
| 620 | SEC4A3 | 0.66 | 1.02 | 0.31 | 0.533 | 0.24 | DC5 | AXL+SIGLEC6+ | 1 |
| 621 | STAG3L4 | 0.64 | 1 | 0.29 | 0.533 | 0.285 | DC5 | AXL+SIGLEC6+ | 0 |
| 622 | MECR | 0.63 | 1.21 | 0.26 | 0.733 | 0.566 | DC5 | AXL+SIGLEC6+ | 0 |
| 623 | COQ7 | 0.62 | 1.09 | 0.25 | 0.667 | 0.42 | DC5 | AXL+SIGLEC6+ | 1 |
| 624 | RBL1 | 0.62 | 1.45 | 0.24 | 0.6 | 0.468 | DC5 | AXL+SIGLEC6+ | 1 |
| 625 | CEP95 | 0.62 | 1.31 | 0.24 | 0.6 | 0.367 | DC5 | AXL+SIGLEC6+ | 1 |
| 626 | RNASEL | 0.62 | 1.57 | 0.23 | 0.567 | 0.403 | DC5 | AXL+SIGLEC6+ | 0 |
| 627 | ACPP | 0.61 | 1.15 | 0.22 | 0.567 | 0.407 | DC5 | AXL+SIGLEC6+ | 1 |
| 628 | SP4 | 0.61 | 1.2 | 0.22 | 0.533 | 0.42 | DC5 | AXL+SIGLEC6+ | 0 |
| 629 | LAX1 | 0.61 | 1.34 | 0.22 | 0.567 | 0.388 | DC5 | AXL+SIGLEC6+ | 1 |
| | | | | | part f | | | | |
| 630 | GZMB | 1 | 6.37 | 0.99 | 0.994 | 0.215 | DC6 | pDC | 0 |
| 631 | IGJ | 1 | 5.22 | 0.99 | 0.994 | 0.24 | DC6 | pDC | 0 |
| 632 | AK128525 | 1 | 4.85 | 0.99 | 0.994 | 0.117 | DC6 | pDC | 0 |
| 633 | SERPINF1 | 1 | 2.98 | 0.99 | 1 | 0.452 | DC6 | pDC | 0 |
| 634 | ITM2C | 0.99 | 3.5 | 0.98 | 0.994 | 0.345 | DC6 | pDC | 1 |
| 635 | PLD4 | 0.99 | 2.46 | 0.98 | 1 | 0.785 | DC6 | pDC | 1 |

TABLE E2-continued (including parts a-f). All discriminative genes per subset identified through unbiased clustering in FIG. 2

| Rank | Gene.ID | AUC value | Avg. Diff.[1] | Power[2] | Pct.1[3] | Pct.2[4] | Cluster.ID | Associated.Cell.Population | Surface Marker[5] |
|---|---|---|---|---|---|---|---|---|---|
| 636 | CCDC50 | 0.99 | 3.24 | 0.98 | 0.994 | 0.464 | DC6 | pDC | 0 |
| 637 | IRF7 | 0.99 | 2.92 | 0.97 | 0.994 | 0.601 | DC6 | pDC | 0 |
| 638 | PTPRS | 0.99 | 3.41 | 0.97 | 0.994 | 0.436 | DC6 | pDC | 1 |
| 639 | ALOX5AP | 0.99 | 3.13 | 0.97 | 0.994 | 0.271 | DC6 | pDC | 1 |
| 640 | TCF4 | 0.99 | 3.03 | 0.97 | 1 | 0.448 | DC6 | pDC | 0 |
| 641 | BCL11A | 0.98 | 2.23 | 0.95 | 1 | 0.73 | DC6 | pDC | 0 |
| 642 | LILRA4 | 0.98 | 3.3 | 0.95 | 0.988 | 0.41 | DC6 | pDC | 1 |
| 643 | PLAC8 | 0.97 | 2.18 | 0.95 | 0.994 | 0.9 | DC6 | pDC | 0 |
| 644 | C12ORF75 | 0.97 | 3.3 | 0.95 | 0.977 | 0.17 | DC6 | pDC | 0 |
| 645 | FAM129C | 0.97 | 3.85 | 0.94 | 0.988 | 0.702 | DC6 | pDC | 0 |
| 646 | CYBASC3 | 0.97 | 2.63 | 0.94 | 0.994 | 0.559 | DC6 | pDC | 0 |
| 647 | MZB1 | 0.97 | 4.43 | 0.94 | 0.953 | 0.06 | DC6 | pDC | 0 |
| 648 | UGCG | 0.97 | 3.53 | 0.94 | 0.971 | 0.142 | DC6 | pDC | 1 |
| 649 | DERL3 | 0.96 | 5.1 | 0.92 | 0.924 | 0.033 | DC6 | pDC | 1 |
| 650 | IL3RA | 0.96 | 3.07 | 0.92 | 0.965 | 0.268 | DC6 | pDC | 1 |
| 651 | SPIB | 0.96 | 2.99 | 0.91 | 0.982 | 0.879 | DC6 | pDC | 0 |
| 652 | ZFAT | 0.95 | 3.63 | 0.91 | 0.947 | 0.217 | DC6 | pDC | 0 |
| 653 | SMPD3 | 0.95 | 3.99 | 0.91 | 0.93 | 0.182 | DC6 | pDC | 1 |
| 654 | NRP1 | 0.95 | 3.89 | 0.9 | 0.936 | 0.219 | DC6 | pDC | 1 |
| 655 | TSPAN13 | 0.95 | 3.59 | 0.9 | 0.93 | 0.102 | DC6 | pDC | 1 |
| 656 | LIME1 | 0.95 | 3.77 | 0.9 | 0.924 | 0.093 | DC6 | pDC | 0 |
| 657 | CLEC4C | 0.95 | 3.32 | 0.9 | 0.942 | 0.186 | DC6 | pDC | 1 |
| 658 | CLIC3 | 0.95 | 3.6 | 0.89 | 0.924 | 0.128 | DC6 | pDC | 0 |
| 659 | SPCS1 | 0.95 | 1.75 | 0.89 | 0.977 | 0.785 | DC6 | pDC | 1 |
| 660 | NPC1 | 0.94 | 2.89 | 0.88 | 0.965 | 0.285 | DC6 | pDC | 1 |
| 661 | HIGD1A | 0.94 | 2.06 | 0.88 | 1 | 0.753 | DC6 | pDC | 1 |
| 662 | CTSB | 0.94 | 1.42 | 0.88 | 1 | 0.963 | DC6 | pDC | 0 |
| 663 | NPC2 | 0.94 | 1.29 | 0.87 | 0.994 | 0.958 | DC6 | pDC | 0 |
| 664 | SEC61B | 0.94 | 1.52 | 0.87 | 0.994 | 0.762 | DC6 | pDC | 1 |
| 665 | C1ORF186 | 0.93 | 1.9 | 0.86 | 0.982 | 0.347 | DC6 | pDC | 1 |
| 666 | TNFRSF21 | 0.93 | 3.12 | 0.86 | 0.918 | 0.166 | DC6 | pDC | 1 |
| 667 | IRF8 | 0.93 | 1.41 | 0.86 | 1 | 0.923 | DC6 | pDC | 0 |
| 668 | HERPUD1 | 0.93 | 1.64 | 0.85 | 0.994 | 0.888 | DC6 | pDC | 1 |
| 669 | PLP2 | 0.93 | 1.51 | 0.85 | 1 | 0.748 | DC6 | pDC | 1 |
| 670 | SLC15A4 | 0.93 | 2.94 | 0.85 | 0.924 | 0.219 | DC6 | pDC | 1 |
| 671 | CD164 | 0.92 | 1.51 | 0.84 | 0.977 | 0.918 | DC6 | pDC | 1 |
| 672 | BLNK | 0.92 | 2.78 | 0.84 | 0.924 | 0.203 | DC6 | pDC | 0 |
| 673 | NCF1C | 0.92 | 2.6 | 0.84 | 0.936 | 0.35 | DC6 | pDC | 0 |
| 674 | HSP90B1 | 0.92 | 1.27 | 0.83 | 1 | 0.912 | DC6 | pDC | 1 |
| 675 | OGT | 0.92 | 1.83 | 0.83 | 1 | 0.8 | DC6 | pDC | 0 |
| 676 | SELS | 0.92 | 2.49 | 0.83 | 0.947 | 0.406 | DC6 | pDC | 0 |
| 677 | IRF4 | 0.91 | 2.48 | 0.83 | 0.947 | 0.303 | DC6 | pDC | 0 |
| 678 | APP | 0.91 | 2.47 | 0.82 | 0.959 | 0.513 | DC6 | pDC | 1 |
| 679 | TXN | 0.91 | 1.65 | 0.82 | 0.971 | 0.697 | DC6 | pDC | 0 |
| 680 | RUNX2 | 0.91 | 2.24 | 0.81 | 0.953 | 0.303 | DC6 | pDC | 0 |
| 681 | PTPRCAP | 0.91 | 3.42 | 0.81 | 0.854 | 0.175 | DC6 | pDC | 0 |
| 682 | GPR114 | 0.91 | 4 | 0.81 | 0.836 | 0.075 | DC6 | pDC | 1 |
| 683 | STMN1 | 0.91 | 2.55 | 0.81 | 0.936 | 0.553 | DC6 | pDC | 0 |
| 684 | RNASE6 | 0.9 | 1.71 | 0.81 | 0.965 | 0.492 | DC6 | pDC | 0 |
| 685 | PFKFB2 | 0.9 | 3.1 | 0.8 | 0.871 | 0.156 | DC6 | pDC | 0 |
| 686 | MAP1A | 0.9 | 4.04 | 0.8 | 0.807 | 0.032 | DC6 | pDC | 0 |
| 687 | NUCB2 | 0.9 | 2.57 | 0.8 | 0.988 | 0.891 | DC6 | pDC | 0 |
| 688 | SSR4 | 0.9 | 1.28 | 0.8 | 0.994 | 0.842 | DC6 | pDC | 1 |
| 689 | LAMP5 | 0.89 | 3.46 | 0.79 | 0.825 | 0.063 | DC6 | pDC | 1 |
| 690 | NCF1 | 0.89 | 2.08 | 0.79 | 0.936 | 0.532 | DC6 | pDC | 0 |
| 691 | B4GALT1 | 0.89 | 1.91 | 0.78 | 0.971 | 0.776 | DC6 | pDC | 1 |
| 692 | IGFLR1 | 0.89 | 1.29 | 0.78 | 0.982 | 0.748 | DC6 | pDC | 1 |
| 693 | NOTCH4 | 0.89 | 2.46 | 0.77 | 0.965 | 0.739 | DC6 | pDC | 1 |
| 694 | GPR183 | 0.88 | 1.67 | 0.77 | 0.977 | 0.676 | DC6 | pDC | 1 |
| 695 | EPHB1 | 0.88 | 3.69 | 0.77 | 0.807 | 0.1 | DC6 | pDC | 1 |
| 696 | LOC285972 | 0.88 | 4.42 | 0.76 | 0.86 | 0.398 | DC6 | pDC | 0 |
| 697 | MYBL2 | 0.88 | 4.48 | 0.76 | 0.772 | 0.023 | DC6 | pDC | 0 |
| 698 | PTCRA | 0.88 | 4.84 | 0.76 | 0.784 | 0.079 | DC6 | pDC | 1 |
| 699 | SLA2 | 0.88 | 4.08 | 0.75 | 0.848 | 0.356 | DC6 | pDC | 0 |
| 700 | AK093551 | 0.87 | 1.71 | 0.75 | 0.93 | 0.391 | DC6 | pDC | 0 |
| 701 | PLXNA4 | 0.87 | 3.22 | 0.75 | 0.778 | 0.047 | DC6 | pDC | 1 |
| 702 | SEPT1' | 0.87 | 2.81 | 0.74 | 0.836 | 0.228 | DC6 | pDC | 0 |
| 703 | C10ORF118 | 0.87 | 2.26 | 0.74 | 0.883 | 0.436 | DC6 | pDC | 0 |
| 704 | LILRB4 | 0.87 | 1.81 | 0.74 | 0.936 | 0.59 | DC6 | pDC | 1 |
| 705 | GAPT | 0.87 | 2.07 | 0.74 | 0.906 | 0.429 | DC6 | pDC | 0 |
| 706 | IDH3A | 0.87 | 1.57 | 0.73 | 0.953 | 0.673 | DC6 | pDC | 0 |
| 707 | MS4A6A | 0.87 | 1.83 | 0.73 | 0.912 | 0.331 | DC6 | pDC | 1 |
| 708 | FMNL3 | 0.87 | 2.4 | 0.73 | 0.836 | 0.201 | DC6 | pDC | 0 |
| 709 | SNRPN | 0.87 | 2.15 | 0.73 | 0.889 | 0.443 | DC6 | pDC | 0 |

TABLE E2-continued (including parts a-f). All discriminative genes per subset
identified through unbiased clustering in FIG. 2

| Rank | Gene.ID | AUC value | Avg. Diff.[1] | Power[2] | Pct.1[3] | Pct.2[4] | Cluster.ID | Associated.Cell.Population | Surface Marker[5] |
|---|---|---|---|---|---|---|---|---|---|
| 710 | KIAA0226L | 0.86 | 1.91 | 0.73 | 0.906 | 0.312 | DC6 | pDC | 0 |
| 711 | BC051760 | 0.86 | 2.37 | 0.72 | 0.854 | 0.303 | DC6 | pDC | 0 |
| 712 | ST6GALNAC4 | 0.86 | 2.7 | 0.72 | 0.807 | 0.156 | DC6 | pDC | 1 |
| 713 | OFD1 | 0.86 | 1.98 | 0.72 | 0.924 | 0.406 | DC6 | pDC | 0 |
| 714 | C9ORF142 | 0.86 | 1.66 | 0.71 | 0.924 | 0.524 | DC6 | pDC | 0 |
| 715 | TGFBI | 0.86 | 1.02 | 0.71 | 0.994 | 0.942 | DC6 | pDC | 0 |
| 716 | SELL | 0.85 | 1.02 | 0.71 | 0.994 | 0.898 | DC6 | pDC | 1 |
| 717 | SIDT1 | 0.85 | 3.69 | 0.71 | 0.772 | 0.184 | DC6 | pDC | 1 |
| 718 | TRAF4 | 0.85 | 2.91 | 0.7 | 0.749 | 0.1 | DC6 | pDC | 0 |
| 719 | DCK | 0.85 | 1.93 | 0.7 | 0.895 | 0.44 | DC6 | pDC | 0 |
| 720 | ERN1 | 0.85 | 2.61 | 0.7 | 0.743 | 0.082 | DC6 | pDC | 1 |
| 721 | TPM2 | 0.85 | 4.3 | 0.7 | 0.719 | 0.049 | DC6 | pDC | 0 |
| 722 | PARK7 | 0.84 | 1.01 | 0.68 | 0.971 | 0.9 | DC6 | pDC | 0 |
| 723 | TLR7 | 0.84 | 2.89 | 0.68 | 0.83 | 0.399 | DC6 | pDC | 1 |
| 724 | CARD11 | 0.84 | 2.84 | 0.68 | 0.749 | 0.126 | DC6 | pDC | 0 |
| 725 | DAB2 | 0.84 | 1.92 | 0.68 | 0.807 | 0.173 | DC6 | pDC | 0 |
| 726 | ERP29 | 0.84 | 1.24 | 0.68 | 0.953 | 0.792 | DC6 | pDC | 0 |
| 727 | PACSIN1 | 0.84 | 3.32 | 0.68 | 0.69 | 0.019 | DC6 | pDC | 0 |
| 728 | LOC644961 | 0.84 | 1.36 | 0.68 | 0.924 | 0.664 | DC6 | pDC | 0 |
| 729 | RABGAP1L | 0.84 | 1.31 | 0.68 | 0.994 | 0.942 | DC6 | pDC | 1 |
| 730 | ADAM19 | 0.83 | 1.69 | 0.67 | 0.912 | 0.399 | DC6 | pDC | 1 |
| 731 | SORL1 | 0.83 | 2 | 0.67 | 0.865 | 0.343 | DC6 | pDC | 1 |
| 732 | PPP1R14B | 0.83 | 2.86 | 0.67 | 0.725 | 0.096 | DC6 | pDC | 0 |
| 733 | SCAMP5 | 0.83 | 3.88 | 0.66 | 0.673 | 0.021 | DC6 | pDC | 1 |
| 734 | USP24 | 0.83 | 1.76 | 0.66 | 0.918 | 0.415 | DC6 | pDC | 0 |
| 735 | ZDHHC17 | 0.83 | 1.98 | 0.66 | 0.848 | 0.354 | DC6 | pDC | 1 |
| 736 | CXCR3 | 0.83 | 2.25 | 0.65 | 0.784 | 0.264 | DC6 | pDC | 1 |
| 737 | MAN2B1 | 0.83 | 1.11 | 0.65 | 0.982 | 0.832 | DC6 | pDC | 1 |
| 738 | RNASET2 | 0.83 | 1.01 | 0.65 | 0.971 | 0.886 | DC6 | pDC | 0 |
| 739 | FCHSD2 | 0.82 | 1.83 | 0.65 | 0.895 | 0.403 | DC6 | pDC | 0 |
| 740 | LAIR1 | 0.82 | 1.46 | 0.64 | 0.942 | 0.608 | DC6 | pDC | 1 |
| 741 | OVOS2 | 0.82 | 3.71 | 0.64 | 0.69 | 0.126 | DC6 | pDC | 0 |
| 742 | P2RY14 | 0.82 | 1.77 | 0.64 | 0.86 | 0.385 | DC6 | pDC | 1 |
| 743 | CYTH4 | 0.82 | 1.25 | 0.64 | 0.965 | 0.792 | DC6 | pDC | 0 |
| 744 | PPM1K | 0.82 | 2.28 | 0.64 | 0.854 | 0.485 | DC6 | pDC | 0 |
| 745 | ABHD15 | 0.82 | 3.03 | 0.63 | 0.795 | 0.419 | DC6 | pDC | 0 |
| 746 | EIF4A3 | 0.82 | 1.48 | 0.63 | 0.906 | 0.657 | DC6 | pDC | 0 |
| 747 | P4HB | 0.82 | 1.26 | 0.63 | 0.918 | 0.743 | DC6 | pDC | 0 |
| 748 | NCF1B | 0.82 | 2.52 | 0.63 | 0.731 | 0.193 | DC6 | pDC | 0 |
| 749 | TSPAN3 | 0.82 | 1.63 | 0.63 | 0.871 | 0.532 | DC6 | pDC | 1 |
| 750 | TRAM1 | 0.81 | 1.12 | 0.63 | 0.947 | 0.846 | DC6 | pDC | 1 |
| 751 | ABPARTS | 0.81 | 1.15 | 0.63 | 0.982 | 0.827 | DC6 | pDC | 0 |
| 752 | COBLL1 | 0.81 | 3.58 | 0.62 | 0.795 | 0.448 | DC6 | pDC | 0 |
| 753 | CREB3L2 | 0.81 | 1.63 | 0.62 | 0.865 | 0.45 | DC6 | pDC | 1 |
| 754 | TMEM109 | 0.81 | 1.25 | 0.62 | 0.936 | 0.629 | DC6 | pDC | 1 |
| 755 | SCN9A | 0.81 | 2.11 | 0.61 | 0.789 | 0.299 | DC6 | pDC | 1 |
| 756 | CYP46A1 | 0.81 | 2.23 | 0.61 | 0.895 | 0.718 | DC6 | pDC | 0 |
| 757 | LGMN | 0.8 | 1.43 | 0.61 | 0.901 | 0.569 | DC6 | pDC | 1 |
| 758 | NGLY1 | 0.8 | 1.61 | 0.6 | 0.883 | 0.478 | DC6 | pDC | 1 |
| 759 | C17ORF109 | 0.8 | 4.79 | 0.6 | 0.608 | 0.016 | DC6 | pDC | 0 |
| 760 | PLA2G16 | 0.8 | 3.01 | 0.6 | 0.649 | 0.077 | DC6 | pDC | 1 |
| 761 | SLC38A1 | 0.8 | 1.28 | 0.6 | 0.959 | 0.734 | DC6 | pDC | 1 |
| 762 | PHEX | 0.8 | 4.41 | 0.6 | 0.608 | 0.019 | DC6 | pDC | 0 |
| 763 | CD99 | 0.8 | 1.21 | 0.6 | 0.889 | 0.585 | DC6 | pDC | 1 |
| 764 | PPM1J | 0.8 | 1.96 | 0.6 | 0.76 | 0.24 | DC6 | pDC | 0 |
| 765 | C10ORF58 | 0.8 | 3.28 | 0.6 | 0.813 | 0.562 | DC6 | pDC | 0 |
| 766 | KIAA0226 | 0.8 | 1.37 | 0.6 | 0.965 | 0.758 | DC6 | pDC | 0 |
| 767 | DHRS7 | 0.8 | 1.05 | 0.59 | 0.924 | 0.736 | DC6 | pDC | 0 |
| 768 | CNP | 0.8 | 1.52 | 0.59 | 0.877 | 0.569 | DC6 | pDC | 0 |
| 769 | CDCA7L | 0.8 | 2.53 | 0.59 | 0.69 | 0.191 | DC6 | pDC | 0 |
| 770 | SIT1 | 0.8 | 3.7 | 0.59 | 0.614 | 0.042 | DC6 | pDC | 1 |
| 771 | TACC1 | 0.8 | 1.32 | 0.59 | 0.942 | 0.702 | DC6 | pDC | 0 |
| 772 | RASD1 | 0.79 | 3.9 | 0.59 | 0.602 | 0.026 | DC6 | pDC | 0 |
| 773 | TMIGD2 | 0.79 | 3.49 | 0.58 | 0.667 | 0.198 | DC6 | pDC | 1 |
| 774 | KRT5 | 0.79 | 4.93 | 0.58 | 0.585 | 0.007 | DC6 | pDC | 0 |
| 775 | ASPH | 0.79 | 2.19 | 0.58 | 0.778 | 0.391 | DC6 | pDC | 1 |
| 776 | LOC652276 | 0.79 | 1.81 | 0.58 | 0.854 | 0.564 | DC6 | pDC | 0 |
| 777 | PDIA4 | 0.79 | 1.44 | 0.58 | 0.865 | 0.585 | DC6 | pDC | 0 |
| 778 | AHI1 | 0.79 | 2.19 | 0.58 | 0.766 | 0.405 | DC6 | pDC | 0 |
| 779 | GPM6B | 0.79 | 4.02 | 0.58 | 0.608 | 0.054 | DC6 | pDC | 1 |
| 780 | HPS4 | 0.79 | 1.04 | 0.58 | 0.953 | 0.793 | DC6 | pDC | 0 |
| 781 | SIVA1 | 0.79 | 1.29 | 0.58 | 0.924 | 0.699 | DC6 | pDC | 0 |
| 782 | LOG100507600 | 0.79 | 3.65 | 0.57 | 0.591 | 0.033 | DC6 | pDC | 0 |
| 783 | UBE2J1 | 0.79 | 1.57 | 0.57 | 0.86 | 0.574 | DC6 | pDC | 1 |

TABLE E2-continued (including parts a-f). All discriminative genes per subset
identified through unbiased clustering in FIG. 2

| Rank | Gene.ID | AUC value | Avg. Diff.[1] | Power[2] | Pct.1[3] | Pct.2[4] | Cluster.ID | Associated.Cell.Population | Surface Marker[5] |
|---|---|---|---|---|---|---|---|---|---|
| 784 | FAM160A1 | 0.78 | 2.23 | 0.57 | 0.632 | 0.081 | DC6 | pDC | 0 |
| 785 | IFI44L | 0.78 | 1.71 | 0.57 | 0.789 | 0.405 | DC6 | pDC | 0 |
| 786 | MAPKAPK2 | 0.78 | 1.92 | 0.57 | 0.661 | 0.126 | DC6 | pDC | 1 |
| 787 | CMKLR1 | 0.78 | 3.04 | 0.57 | 0.62 | 0.075 | DC6 | pDC | 1 |
| 788 | AX747844 | 0.78 | 1.65 | 0.56 | 0.743 | 0.319 | DC6 | pDC | 0 |
| 789 | GGA2 | 0.78 | 1.73 | 0.55 | 0.836 | 0.543 | DC6 | pDC | 0 |
| 790 | TP53I13 | 0.78 | 2.15 | 0.55 | 0.684 | 0.187 | DC6 | pDC | 1 |
| 791 | CSF2RB | 0.78 | 1.61 | 0.55 | 0.789 | 0.359 | DC6 | pDC | 1 |
| 792 | LOC100233209 | 0.78 | 1.2 | 0.55 | 0.848 | 0.623 | DC6 | pDC | 0 |
| 793 | TCL1A | 0.78 | 6.54 | 0.55 | 0.585 | 0.063 | DC6 | pDC | 0 |
| 794 | ATP2A3 | 0.78 | 2.19 | 0.55 | 0.684 | 0.187 | DC6 | pDC | 1 |
| 795 | FLNB | 0.77 | 1.6 | 0.55 | 0.778 | 0.324 | DC6 | pDC | 0 |
| 796 | NEK8 | 0.77 | 3.6 | 0.55 | 0.678 | 0.324 | DC6 | pDC | 0 |
| 797 | TBC1D4 | 0.77 | 2.89 | 0.55 | 0.608 | 0.091 | DC6 | pDC | 0 |
| 798 | CUX2 | 0.77 | 3.01 | 0.54 | 0.55 | 0.011 | DC6 | pDC | 1 |
| 799 | PDCD4 | 0.77 | 1.23 | 0.54 | 0.947 | 0.736 | DC6 | pDC | 0 |
| 800 | SND1 | 0.77 | 1.1 | 0.54 | 0.924 | 0.681 | DC6 | pDC | 0 |
| 801 | SLC2A1 | 0.77 | 1.82 | 0.54 | 0.766 | 0.378 | DC6 | pDC | 1 |
| 802 | SMC6 | 0.77 | 1.98 | 0.53 | 0.702 | 0.24 | DC6 | pDC | 0 |
| 803 | LY9 | 0.77 | 2.82 | 0.53 | 0.643 | 0.194 | DC6 | pDC | 1 |
| 804 | STAMBPL1 | 0.77 | 2.58 | 0.53 | 0.86 | 0.643 | DC6 | pDC | 0 |
| 805 | KIRREL3 | 0.76 | 2.75 | 0.53 | 0.719 | 0.38 | DC6 | pDC | 1 |
| 806 | SCARB2 | 0.76 | 1.61 | 0.52 | 0.825 | 0.613 | DC6 | pDC | 1 |
| 807 | EMB | 0.76 | 1.29 | 0.52 | 0.848 | 0.483 | DC6 | pDC | 1 |
| 808 | PAFAH2 | 0.76 | 2.74 | 0.52 | 0.784 | 0.517 | DC6 | pDC | 0 |
| 809 | VEGFB | 0.76 | 2.76 | 0.52 | 0.573 | 0.081 | DC6 | pDC | 0 |
| 810 | AL833181 | 0.76 | 2.4 | 0.52 | 0.608 | 0.121 | DC6 | pDC | 0 |
| 811 | DQ572107 | 0.76 | 2.82 | 0.52 | 0.766 | 0.545 | DC6 | pDC | 0 |
| 812 | ZCCHC11 | 0.76 | 1.93 | 0.52 | 0.807 | 0.574 | DC6 | pDC | 0 |
| 813 | DUSP5 | 0.76 | 2.59 | 0.51 | 0.567 | 0.063 | DC6 | pDC | 0 |
| 814 | SLC38A2 | 0.76 | 1.21 | 0.51 | 0.918 | 0.669 | DC6 | pDC | 1 |
| 815 | SLC7A5 | 0.76 | 2.88 | 0.51 | 0.567 | 0.082 | DC6 | pDC | 1 |
| 816 | TTC24 | 0.76 | 3.03 | 0.51 | 0.538 | 0.037 | DC6 | pDC | 0 |
| 817 | ANKRD36 | 0.76 | 1.53 | 0.51 | 0.889 | 0.772 | DC6 | pDC | 0 |
| 818 | TMEM19 | 0.76 | 1.5 | 0.51 | 0.895 | 0.771 | DC6 | pDC | 1 |
| 819 | LOC100131564 | 0.75 | 1.15 | 0.51 | 0.942 | 0.876 | DC6 | pDC | 0 |
| 820 | CD2AP | 0.75 | 1.7 | 0.51 | 0.684 | 0.229 | DC6 | pDC | 0 |
| 821 | GAS6 | 0.75 | 2.11 | 0.51 | 0.661 | 0.222 | DC6 | pDC | 0 |
| 822 | IGFBP3 | 0.75 | 5.2 | 0.51 | 0.52 | 0.028 | DC6 | pDC | 1 |
| 823 | MIF4GD | 0.75 | 1.29 | 0.5 | 0.83 | 0.487 | DC6 | pDC | 0 |
| 824 | IRF2BP2 | 0.75 | 1.46 | 0.5 | 0.789 | 0.417 | DC6 | pDC | 0 |
| 825 | CRYM | 0.75 | 5.17 | 0.49 | 0.503 | 0.023 | DC6 | pDC | 0 |
| 826 | DKFZP586I1420 | 0.75 | 2.39 | 0.49 | 0.614 | 0.177 | DC6 | pDC | 0 |
| 827 | DKFZP667P0924 | 0.74 | 1.66 | 0.49 | 0.766 | 0.392 | DC6 | pDC | 0 |
| 828 | TEX2 | 0.74 | 2.19 | 0.49 | 0.608 | 0.17 | DC6 | pDC | 1 |
| 829 | FLJ43663 | 0.74 | 1.48 | 0.48 | 0.667 | 0.259 | DC6 | pDC | 0 |
| 830 | FKBP2 | 0.74 | 1.21 | 0.48 | 0.772 | 0.504 | DC6 | pDC | 0 |
| 831 | SPICE1 | 0.74 | 1.06 | 0.48 | 0.959 | 0.9 | DC6 | pDC | 0 |
| 832 | AHNAK2 | 0.74 | 2.31 | 0.48 | 0.532 | 0.079 | DC6 | pDC | 0 |
| 833 | ANKRD36BP1 | 0.74 | 1.16 | 0.48 | 0.93 | 0.715 | DC6 | pDC | 0 |
| 834 | RNF5 | 0.74 | 1.5 | 0.48 | 0.702 | 0.438 | DC6 | pDC | 1 |
| 835 | RRBP1 | 0.74 | 1.83 | 0.47 | 0.725 | 0.429 | DC6 | pDC | 1 |
| 836 | SLC12A3 | 0.74 | 3 | 0.47 | 0.579 | 0.189 | DC6 | pDC | 1 |
| 837 | SLC3A2 | 0.74 | 1.13 | 0.47 | 0.842 | 0.618 | DC6 | pDC | 1 |
| 838 | SEC61G | 0.73 | 1.17 | 0.47 | 0.795 | 0.608 | DC6 | pDC | 1 |
| 839 | ATP13A2 | 0.73 | 2.03 | 0.47 | 0.678 | 0.403 | DC6 | pDC | 1 |
| 840 | LRRC36 | 0.73 | 2.68 | 0.47 | 0.684 | 0.422 | DC6 | pDC | 0 |
| 841 | AK095700 | 0.73 | 1.21 | 0.46 | 0.813 | 0.559 | DC6 | pDC | 0 |
| 842 | C12ORF44 | 0.73 | 1.47 | 0.46 | 0.678 | 0.324 | DC6 | pDC | 0 |
| 843 | POLB | 0.73 | 1.79 | 0.46 | 0.637 | 0.233 | DC6 | pDC | 0 |
| 844 | LMAN1 | 0.73 | 1.83 | 0.46 | 0.614 | 0.229 | DC6 | pDC | 1 |
| 845 | AK057596 | 0.73 | 1.27 | 0.45 | 0.877 | 0.764 | DC6 | pDC | 0 |
| 846 | PHC3 | 0.73 | 1.1 | 0.45 | 0.965 | 0.93 | DC6 | pDC | 0 |
| 847 | SUSD1 | 0.73 | 2.21 | 0.45 | 0.556 | 0.135 | DC6 | pDC | 1 |
| 848 | ANKRD36B | 0.73 | 1.82 | 0.45 | 0.754 | 0.436 | DC6 | pDC | 0 |
| 849 | CRIM1 | 0.73 | 1.92 | 0.45 | 0.515 | 0.077 | DC6 | pDC | 1 |
| 850 | MGAT4A | 0.73 | 2.06 | 0.45 | 0.719 | 0.504 | DC6 | pDC | 0 |
| 851 | SEL1L3 | 0.73 | 2.03 | 0.45 | 0.602 | 0.189 | DC6 | pDC | 1 |
| 852 | SLC7A11 | 0.73 | 1.96 | 0.45 | 0.76 | 0.588 | DC6 | pDC | 1 |
| 853 | MILR1 | 0.72 | 1.26 | 0.45 | 0.895 | 0.737 | DC6 | pDC | 1 |
| 854 | PAPLN | 0.72 | 1.95 | 0.45 | 0.871 | 0.762 | DC6 | pDC | 0 |
| 855 | CLN8 | 0.72 | 1.52 | 0.45 | 0.889 | 0.814 | DC6 | pDC | 1 |
| 856 | VAMP1 | 0.72 | 2.24 | 0.44 | 0.55 | 0.142 | DC6 | pDC | 1 |
| 857 | CCDC69 | 0.72 | 1.25 | 0.44 | 0.825 | 0.602 | DC6 | pDC | 0 |

TABLE E2-continued (including parts a-f). All discriminative genes per subset
identified through unbiased clustering in FIG. 2

| Rank | Gene.ID | AUC value | Avg. Diff.[1] | Power[2] | Pct.1[3] | Pct.2[4] | Cluster.ID | Associated.Cell.Population | Surface Marker[5] |
|---|---|---|---|---|---|---|---|---|---|
| 858 | KANK1 | 0.72 | 1.83 | 0.44 | 0.918 | 0.897 | DC6 | pDC | 0 |
| 859 | LTB | 0.72 | 2.58 | 0.44 | 0.532 | 0.138 | DC6 | pDC | 1 |
| 860 | STRBP | 0.72 | 2.16 | 0.44 | 0.538 | 0.13 | DC6 | pDC | 0 |
| 861 | SLC20A1 | 0.72 | 1.15 | 0.44 | 0.807 | 0.501 | DC6 | pDC | 1 |
| 862 | SNURF-SNRPN | 0.72 | 2.42 | 0.44 | 0.813 | 0.665 | DC6 | pDC | 0 |
| 863 | SOLH | 0.72 | 1.68 | 0.44 | 0.561 | 0.173 | DC6 | pDC | 0 |
| 864 | PARP10 | 0.72 | 2.5 | 0.43 | 0.532 | 0.145 | DC6 | pDC | 0 |
| 865 | BX647938 | 0.72 | 2.04 | 0.43 | 0.632 | 0.345 | DC6 | pDC | 0 |
| 866 | PAIP1 | 0.71 | 1.94 | 0.43 | 0.643 | 0.335 | DC6 | pDC | 0 |
| 867 | MAGED1 | 0.71 | 2.08 | 0.42 | 0.55 | 0.18 | DC6 | pDC | 0 |
| 868 | DHTKD1 | 0.71 | 1.26 | 0.42 | 0.889 | 0.793 | DC6 | pDC | 0 |
| 869 | IL28RA | 0.71 | 2.45 | 0.42 | 0.725 | 0.517 | DC6 | pDC | 0 |
| 870 | C5ORF62 | 0.71 | 2.12 | 0.41 | 0.538 | 0.154 | DC6 | pDC | 0 |
| 871 | SLC35E2 | 0.71 | 1.09 | 0.41 | 0.953 | 0.893 | DC6 | pDC | 1 |
| 872 | FZD3 | 0.71 | 1.09 | 0.41 | 0.906 | 0.781 | DC6 | pDC | 1 |
| 873 | EGLN3 | 0.71 | 1.23 | 0.41 | 0.62 | 0.224 | DC6 | pDC | 0 |
| 874 | MEF2D | 0.71 | 1.18 | 0.41 | 0.655 | 0.313 | DC6 | pDC | 0 |
| 875 | TNFAIP3 | 0.71 | 1.04 | 0.41 | 0.749 | 0.447 | DC6 | pDC | 0 |
| 876 | COL24A1 | 0.7 | 2.42 | 0.41 | 0.556 | 0.238 | DC6 | pDC | 0 |
| 877 | MCOLN2 | 0.7 | 1.32 | 0.41 | 0.749 | 0.478 | DC6 | pDC | 1 |
| 878 | TUBB6 | 0.7 | 1.49 | 0.41 | 0.678 | 0.357 | DC6 | pDC | 1 |
| 879 | CLCN5 | 0.7 | 1.97 | 0.41 | 0.655 | 0.394 | DC6 | pDC | 1 |
| 880 | FUT7 | 0.7 | 2.12 | 0.4 | 0.509 | 0.144 | DC6 | pDC | 0 |
| 881 | SFT2D2 | 0.7 | 1.16 | 0.4 | 0.836 | 0.627 | DC6 | pDC | 1 |
| 882 | CSNK1E | 0.7 | 1.26 | 0.4 | 0.819 | 0.62 | DC6 | pDC | 0 |
| 883 | NOP56 | 0.7 | 1.01 | 0.4 | 0.83 | 0.506 | DC6 | pDC | 1 |
| 884 | ST3GAL4 | 0.7 | 2.14 | 0.4 | 0.52 | 0.177 | DC6 | pDC | 1 |
| 885 | DPPA4 | 0.7 | 3.1 | 0.4 | 0.602 | 0.347 | DC6 | pDC | 0 |
| 886 | GNG7 | 0.7 | 1.36 | 0.39 | 0.661 | 0.406 | DC6 | pDC | 0 |
| 887 | SEC61A1 | 0.7 | 1.11 | 0.39 | 0.871 | 0.695 | DC6 | pDC | 1 |
| 888 | DSN1 | 0.69 | 2.05 | 0.39 | 0.538 | 0.201 | DC6 | pDC | 0 |
| 889 | FLJ42627 | 0.69 | 1.55 | 0.39 | 0.807 | 0.699 | DC6 | pDC | 0 |
| 890 | ZDHHC4 | 0.69 | 1.71 | 0.39 | 0.55 | 0.226 | DC6 | pDC | 1 |
| 891 | CCR2 | 0.69 | 1.5 | 0.39 | 0.573 | 0.224 | DC6 | pDC | 1 |
| 892 | C6ORF25 | 0.69 | 2.49 | 0.38 | 0.719 | 0.56 | DC6 | pDC | 1 |
| 893 | ITPR2 | 0.69 | 1.16 | 0.38 | 0.719 | 0.419 | DC6 | pDC | 1 |
| 894 | TMEM63A | 0.69 | 1.67 | 0.38 | 0.579 | 0.242 | DC6 | pDC | 1 |
| 895 | ABCA2 | 0.69 | 2.15 | 0.38 | 0.503 | 0.17 | DC6 | pDC | 1 |
| 896 | ADA | 0.69 | 1.19 | 0.38 | 0.661 | 0.361 | DC6 | pDC | 0 |
| 897 | FOXRED2 | 0.69 | 1.36 | 0.38 | 0.801 | 0.713 | DC6 | pDC | 0 |
| 898 | ST3GAL2 | 0.69 | 1.53 | 0.38 | 0.684 | 0.433 | DC6 | pDC | 1 |
| 899 | PMS2P5 | 0.69 | 1.09 | 0.38 | 0.719 | 0.487 | DC6 | pDC | 0 |
| 900 | SGSM3 | 0.69 | 1.29 | 0.37 | 0.649 | 0.35 | DC6 | pDC | 1 |
| 901 | USP11 | 0.69 | 1.44 | 0.37 | 0.561 | 0.238 | DC6 | pDC | 0 |
| 902 | GAB1 | 0.69 | 1.2 | 0.37 | 0.544 | 0.196 | DC6 | pDC | 0 |
| 903 | STT3A | 0.69 | 1.14 | 0.37 | 0.754 | 0.489 | DC6 | pDC | 1 |
| 904 | SULF2 | 0.69 | 1.02 | 0.37 | 0.807 | 0.599 | DC6 | pDC | 1 |
| 905 | C18ORF8 | 0.68 | 1.31 | 0.37 | 0.62 | 0.303 | DC6 | pDC | 0 |
| 906 | DENND5B | 0.68 | 1.45 | 0.36 | 0.673 | 0.431 | DC6 | pDC | 1 |
| 907 | NFX1 | 0.68 | 1.09 | 0.36 | 0.877 | 0.772 | DC6 | pDC | 0 |
| 908 | SUZ12P | 0.68 | 1.62 | 0.36 | 0.62 | 0.378 | DC6 | pDC | 0 |
| 909 | CTNS | 0.68 | 1.79 | 0.36 | 0.596 | 0.342 | DC6 | pDC | 1 |
| 910 | TXNDC5 | 0.68 | 1.34 | 0.36 | 0.725 | 0.536 | DC6 | pDC | 0 |
| 911 | SETBP1 | 0.68 | 1.13 | 0.36 | 0.561 | 0.24 | DC6 | pDC | 0 |
| 912 | TATDN3 | 0.68 | 1.21 | 0.36 | 0.86 | 0.783 | DC6 | pDC | 0 |
| 913 | LOC642776 | 0.68 | 1.03 | 0.36 | 0.515 | 0.196 | DC6 | pDC | 0 |
| 914 | MDFIC | 0.68 | 1.31 | 0.36 | 0.719 | 0.524 | DC6 | pDC | 1 |
| 915 | SEC11C | 0.68 | 1.35 | 0.36 | 0.655 | 0.419 | DC6 | pDC | 1 |
| 916 | UBA5 | 0.68 | 1.11 | 0.35 | 0.942 | 0.881 | DC6 | pDC | 1 |
| 917 | MYO1E | 0.68 | 1.05 | 0.35 | 0.632 | 0.329 | DC6 | pDC | 0 |
| 918 | TASP1 | 0.68 | 1.38 | 0.35 | 0.538 | 0.215 | DC6 | pDC | 0 |
| 919 | PIK3CD | 0.67 | 1.01 | 0.35 | 0.877 | 0.795 | DC6 | pDC | 0 |
| 920 | MDN1 | 0.67 | 1.26 | 0.35 | 0.608 | 0.31 | DC6 | pDC | 0 |
| 921 | PPARA | 0.67 | 1.06 | 0.34 | 0.848 | 0.715 | DC6 | pDC | 0 |
| 922 | DQ576756 | 0.67 | 1.01 | 0.34 | 0.86 | 0.753 | DC6 | pDC | 0 |
| 923 | TCL6 | 0.67 | 1.9 | 0.34 | 0.655 | 0.478 | DC6 | pDC | 0 |
| 924 | TGFBR2 | 0.67 | 1.22 | 0.34 | 0.567 | 0.256 | DC6 | pDC | 1 |
| 925 | TP53I11 | 0.67 | 1.36 | 0.34 | 0.503 | 0.187 | DC6 | pDC | 1 |
| 926 | 11/sep | 0.67 | 1.69 | 0.34 | 0.678 | 0.48 | DC6 | pDC | 0 |
| 927 | SBDS | 0.67 | 1.14 | 0.34 | 0.673 | 0.462 | DC6 | pDC | 0 |
| 928 | ZFYVE26 | 0.67 | 1.55 | 0.34 | 0.772 | 0.639 | DC6 | pDC | 0 |
| 929 | BTAF1 | 0.67 | 1.29 | 0.33 | 0.784 | 0.622 | DC6 | pDC | 0 |
| 930 | C5ORF45 | 0.67 | 1.05 | 0.33 | 0.947 | 0.93 | DC6 | pDC | 0 |
| 931 | PTK7 | 0.67 | 1.92 | 0.33 | 0.661 | 0.515 | DC6 | pDC | 1 |

TABLE E2-continued (including parts a-f). All discriminative genes per subset
identified through unbiased clustering in FIG. 2

| Rank | Gene.ID | AUC value | Avg. Diff.[1] | Power[2] | Pct.1[3] | Pct.2[4] | Cluster.ID | Associated.Cell.Population | Surface Marker[5] |
|---|---|---|---|---|---|---|---|---|---|
| 932 | SRPR | 0.67 | 1.01 | 0.33 | 0.749 | 0.573 | DC6 | pDC | 0 |
| 933 | ERO1LB | 0.66 | 1.12 | 0.33 | 0.661 | 0.434 | DC6 | pDC | 1 |
| 934 | NAPSA | 0.66 | 1.67 | 0.33 | 0.813 | 0.651 | DC6 | pDC | 0 |
| 935 | C9ORF91 | 0.66 | 1.61 | 0.33 | 0.632 | 0.412 | DC6 | pDC | 1 |
| 936 | STAG3L3 | 0.66 | 1.22 | 0.32 | 0.772 | 0.641 | DC6 | pDC | 0 |
| 937 | TULP4 | 0.66 | 1.5 | 0.32 | 0.579 | 0.333 | DC6 | pDC | 0 |
| 938 | CYSLTR1 | 0.66 | 1.02 | 0.32 | 0.55 | 0.259 | DC6 | pDC | 1 |
| 939 | LOC284551 | 0.66 | 1.76 | 0.32 | 0.772 | 0.644 | DC6 | pDC | 0 |
| 940 | SNRNP25 | 0.66 | 1.05 | 0.32 | 0.608 | 0.377 | DC6 | pDC | 0 |
| 941 | ALG2 | 0.66 | 1.28 | 0.32 | 0.567 | 0.296 | DC6 | pDC | 1 |
| 942 | ITGAE | 0.66 | 1.22 | 0.32 | 0.538 | 0.273 | DC6 | pDC | 1 |
| 943 | MAP2K6 | 0.66 | 1.45 | 0.32 | 0.509 | 0.231 | DC6 | pDC | 0 |
| 944 | TBCC | 0.66 | 1.25 | 0.32 | 0.585 | 0.336 | DC6 | pDC | 0 |
| 945 | OCLN | 0.66 | 1.02 | 0.31 | 0.86 | 0.816 | DC6 | pDC | 1 |
| 946 | DCPS | 0.66 | 1.28 | 0.31 | 0.567 | 0.361 | DC6 | pDC | 0 |
| 947 | LRP8 | 0.65 | 1.65 | 0.31 | 0.696 | 0.567 | DC6 | pDC | 1 |
| 948 | STAG3L1 | 0.65 | 1.04 | 0.31 | 0.667 | 0.51 | DC6 | pDC | 0 |
| 949 | KRR1 | 0.65 | 1.11 | 0.31 | 0.661 | 0.431 | DC6 | pDC | 0 |
| 950 | C12ORF45 | 0.65 | 1.12 | 0.3 | 0.573 | 0.382 | DC6 | pDC | 0 |
| 951 | PCYOX1 | 0.65 | 1.16 | 0.3 | 0.865 | 0.844 | DC6 | pDC | 1 |
| 952 | SPNS3 | 0.65 | 1.25 | 0.3 | 0.579 | 0.357 | DC6 | pDC | 1 |
| 953 | TPST2 | 0.65 | 1.1 | 0.3 | 0.573 | 0.356 | DC6 | pDC | 0 |
| 954 | MYB | 0.65 | 1.63 | 0.29 | 0.596 | 0.415 | DC6 | pDC | 0 |
| 955 | SLC12A2 | 0.65 | 1.15 | 0.29 | 0.696 | 0.553 | DC6 | pDC | 1 |
| 956 | ZBTB33 | 0.65 | 1.03 | 0.29 | 0.596 | 0.387 | DC6 | pDC | 0 |
| 957 | ABI2 | 0.65 | 1.26 | 0.29 | 0.713 | 0.59 | DC6 | pDC | 0 |
| 958 | PMS2L2 | 0.65 | 1.32 | 0.29 | 0.509 | 0.277 | DC6 | pDC | 0 |
| 959 | GLCE | 0.64 | 1.31 | 0.29 | 0.526 | 0.278 | DC6 | pDC | 1 |
| 960 | ITPR1 | 0.64 | 1.35 | 0.29 | 0.532 | 0.289 | DC6 | pDC | 1 |
| 961 | MRPL36 | 0.64 | 1.27 | 0.29 | 0.503 | 0.278 | DC6 | pDC | 0 |
| 962 | C5ORF64 | 0.64 | 2.43 | 0.28 | 0.573 | 0.433 | DC6 | pDC | 0 |
| 963 | PFKP | 0.64 | 1.68 | 0.28 | 0.585 | 0.422 | DC6 | pDC | 0 |
| 964 | S100PBP | 0.64 | 1.73 | 0.28 | 0.667 | 0.541 | DC6 | pDC | 0 |
| 965 | SPON2 | 0.64 | 2.57 | 0.28 | 0.538 | 0.347 | DC6 | pDC | 0 |
| 966 | SPG20 | 0.64 | 1.27 | 0.28 | 0.556 | 0.329 | DC6 | pDC | 0 |
| 967 | TRDMT1 | 0.64 | 1.29 | 0.28 | 0.585 | 0.38 | DC6 | pDC | 0 |
| 968 | N4BP2L1 | 0.64 | 1.02 | 0.28 | 0.673 | 0.527 | DC6 | pDC | 0 |
| 969 | PPP6R1 | 0.64 | 1.06 | 0.28 | 0.655 | 0.489 | DC6 | pDC | 0 |
| 970 | RCL1 | 0.64 | 1.49 | 0.27 | 0.649 | 0.503 | DC6 | pDC | 0 |
| 971 | ZNF506 | 0.64 | 1.12 | 0.27 | 0.854 | 0.841 | DC6 | pDC | 0 |
| 972 | AHCY | 0.64 | 1.04 | 0.27 | 0.596 | 0.44 | DC6 | pDC | 0 |
| 973 | CXORF21 | 0.64 | 1.14 | 0.27 | 0.626 | 0.452 | DC6 | pDC | 0 |
| 974 | CCS | 0.63 | 1.02 | 0.27 | 0.556 | 0.361 | DC6 | pDC | 0 |
| 975 | RNASEH2B | 0.63 | 1.12 | 0.27 | 0.573 | 0.396 | DC6 | pDC | 0 |
| 976 | SYS1 | 0.63 | 1.31 | 0.27 | 0.538 | 0.345 | DC6 | pDC | 1 |
| 977 | P2RY6 | 0.63 | 1.05 | 0.27 | 0.561 | 0.349 | DC6 | pDC | 1 |
| 978 | PPFIBP1 | 0.63 | 1.36 | 0.27 | 0.731 | 0.615 | DC6 | pDC | 0 |
| 979 | NFATC2IP | 0.63 | 1.1 | 0.26 | 0.76 | 0.694 | DC6 | pDC | 0 |
| 980 | ZNF527 | 0.63 | 1.02 | 0.26 | 0.766 | 0.699 | DC6 | pDC | 0 |
| 981 | MINA | 0.63 | 1.18 | 0.26 | 0.526 | 0.291 | DC6 | pDC | 0 |
| 982 | TAX1BP3 | 0.63 | 1.11 | 0.26 | 0.538 | 0.34 | DC6 | pDC | 0 |
| 983 | DAAM1 | 0.63 | 1.66 | 0.26 | 0.515 | 0.338 | DC6 | pDC | 0 |
| 984 | GALNT2 | 0.63 | 1.05 | 0.26 | 0.544 | 0.352 | DC6 | pDC | 0 |
| 985 | LOC400657 | 0.63 | 1.47 | 0.26 | 0.544 | 0.37 | DC6 | pDC | 0 |
| 986 | C1ORF55 | 0.63 | 1.11 | 0.26 | 0.836 | 0.809 | DC6 | pDC | 0 |
| 987 | RREB1 | 0.63 | 1.04 | 0.26 | 0.766 | 0.646 | DC6 | pDC | 0 |
| 988 | VIPR2 | 0.63 | 2.58 | 0.26 | 0.52 | 0.377 | DC6 | pDC | 1 |
| 989 | ARL6IP6 | 0.63 | 1.01 | 0.25 | 0.526 | 0.336 | DC6 | pDC | 1 |
| 990 | QDPR | 0.63 | 1.15 | 0.25 | 0.503 | 0.326 | DC6 | pDC | 0 |
| 991 | ABCA7 | 0.63 | 1.06 | 0.25 | 0.515 | 0.291 | DC6 | pDC | 1 |
| 992 | SLC23A2 | 0.63 | 1.16 | 0.25 | 0.515 | 0.319 | DC6 | pDC | 1 |
| 993 | BEX4 | 0.62 | 1.11 | 0.25 | 0.509 | 0.354 | DC6 | pDC | 0 |
| 994 | SLC33A1 | 0.62 | 1.02 | 0.25 | 0.901 | 0.883 | DC6 | pDC | 1 |
| 995 | THSD1P1 | 0.62 | 1.11 | 0.25 | 0.807 | 0.729 | DC6 | pDC | 0 |
| 996 | ARHGEF4 | 0.62 | 1.29 | 0.24 | 0.632 | 0.532 | DC6 | pDC | 0 |
| 997 | C6ORF170 | 0.62 | 1.22 | 0.24 | 0.585 | 0.468 | DC6 | pDC | 0 |
| 998 | N4BP2 | 0.62 | 1.21 | 0.24 | 0.667 | 0.564 | DC6 | pDC | 0 |
| 999 | SPATA5 | 0.62 | 1.11 | 0.24 | 0.871 | 0.844 | DC6 | pDC | 0 |
| 1000 | CRYM-AS1 | 0.62 | 1.97 | 0.24 | 0.55 | 0.427 | DC6 | pDC | 0 |
| 1001 | IQGAP2 | 0.62 | 1.02 | 0.24 | 0.561 | 0.38 | DC6 | pDC | 0 |
| 1002 | DAPK2 | 0.62 | 2.09 | 0.23 | 0.585 | 0.492 | DC6 | pDC | 1 |
| 1003 | MFSD2A | 0.62 | 1.19 | 0.23 | 0.526 | 0.357 | DC6 | pDC | 1 |
| 1004 | PCMTD1 | 0.61 | 1.02 | 0.23 | 0.673 | 0.55 | DC6 | pDC | 0 |
| 1005 | ANKS3 | 0.61 | 1.06 | 0.23 | 0.643 | 0.496 | DC6 | pDC | 0 |

TABLE E2-continued (including parts a-f). All discriminative genes per subset
identified through unbiased clustering in FIG. 2

| Rank | Gene.ID | AUC value | Avg. Diff.[1] | Power[2] | Pct.1[3] | Pct.2[4] | Cluster.ID | Associated.Cell.Population | Surface Marker[5] |
|---|---|---|---|---|---|---|---|---|---|
| 1006 | CEP135 | 0.61 | 1.06 | 0.23 | 0.836 | 0.75 | DC6 | pDC | 0 |
| 1007 | LOC100131089 | 0.61 | 1.79 | 0.23 | 0.614 | 0.506 | DC6 | pDC | 0 |
| 1008 | ALDH5A1 | 0.61 | 2.22 | 0.22 | 0.509 | 0.368 | DC6 | pDC | 0 |
| 1009 | BC034268 | 0.61 | 1.06 | 0.22 | 0.649 | 0.522 | DC6 | pDC | 0 |
| 1010 | MAP4K4 | 0.61 | 1.17 | 0.22 | 0.573 | 0.427 | DC6 | pDC | 0 |
| 1011 | SERTAD2 | 0.61 | 1.07 | 0.22 | 0.608 | 0.455 | DC6 | pDC | 0 |
| 1012 | PCNX | 0.61 | 1.29 | 0.22 | 0.509 | 0.347 | DC6 | pDC | 1 |
| 1013 | PHLPP2 | 0.61 | 1.51 | 0.22 | 0.567 | 0.419 | DC6 | pDC | 0 |
| 1014 | EFHC1 | 0.61 | 1.35 | 0.22 | 0.614 | 0.499 | DC6 | pDC | 0 |
| 1015 | SP4 | 0.61 | 1.18 | 0.21 | 0.515 | 0.398 | DC6 | pDC | 0 |
| 1016 | TRRAP | 0.61 | 1.01 | 0.21 | 0.661 | 0.529 | DC6 | pDC | 1 |
| 1017 | NICN1 | 0.6 | 1.04 | 0.21 | 0.725 | 0.669 | DC6 | pDC | 0 |
| 1018 | TRIM74 | 0.6 | 1.16 | 0.2 | 0.509 | 0.375 | DC6 | pDC | 0 |
| 1019 | HNRNPA1L2 | 0.6 | 1.14 | 0.2 | 0.509 | 0.354 | DC6 | pDC | 0 |

Footnotes in Tables E1 and E2: 1—Value refers to average differential expression within one subset (log fold change); 2—Value refers to discriminatory power of each marker; 3—Percentage of cells, within the cluster ID for which the gene is a marker, that detect the gene; 4—Percentage of all the other cells, excluding the cluster ID for which the gene is a marker, that detect the gene; 5—"1" refers to predicted surface marker, "0" refers to predicted not a surface marker, according to the Protein Atlas: Protein Atlas: http://www.proteinatlas.org/search/protein_class:Predicted+membrane+proteins Cluster DC1, which mapped most closely to CD141$^+$ DCs, showed significantly increased expression of 36 genes. However, the commonly used CD141 (THBD/BDCA-3) was a poor discriminator of this cluster, being expressed in the clusters containing the novel (DC5) and pDC (DC6) populations (FIG. 2H; see FIG. 5H-N). As CLEC9A appeared to be a perfect discriminative surface marker for the DC1 cluster, Applicants refer to these cells henceforth as CLEC9A$^+$ DCs. CD1C was the best and sole marker uniquely shared by both DC2 and DC3 clusters mapping to CD1C$^+$ DCs, relative to the remaining 4 clusters (see below for markers splitting the 2 CD1C$^+$ subsets). The cluster mapping to the CD141$^-$CD1C$^-$ population (DC4) was almost perfectly marked by FCGR3A/CD16. The DC5 cluster, corresponding to the novel population, was best defined by the surface markers AXL and SIGLEC6. Finally, for the DC6 cluster mapping to pDCs, 92 of the 242 genes were good classifiers; however, markers commonly used to identify these cells (IL3RA/CD123, CLEC4C/CD303) were also expressed in the novel population cluster (DC5), and a new combination of markers was needed to distinguish pDCs from the novel population (FIG. 5). Altogether, Applicants identified discriminative markers that can be used in combination to isolate cell populations that correspond to the known DC subsets, but with higher purity, and discovered previously uncharacterized and novel populations.

Figure 3A:
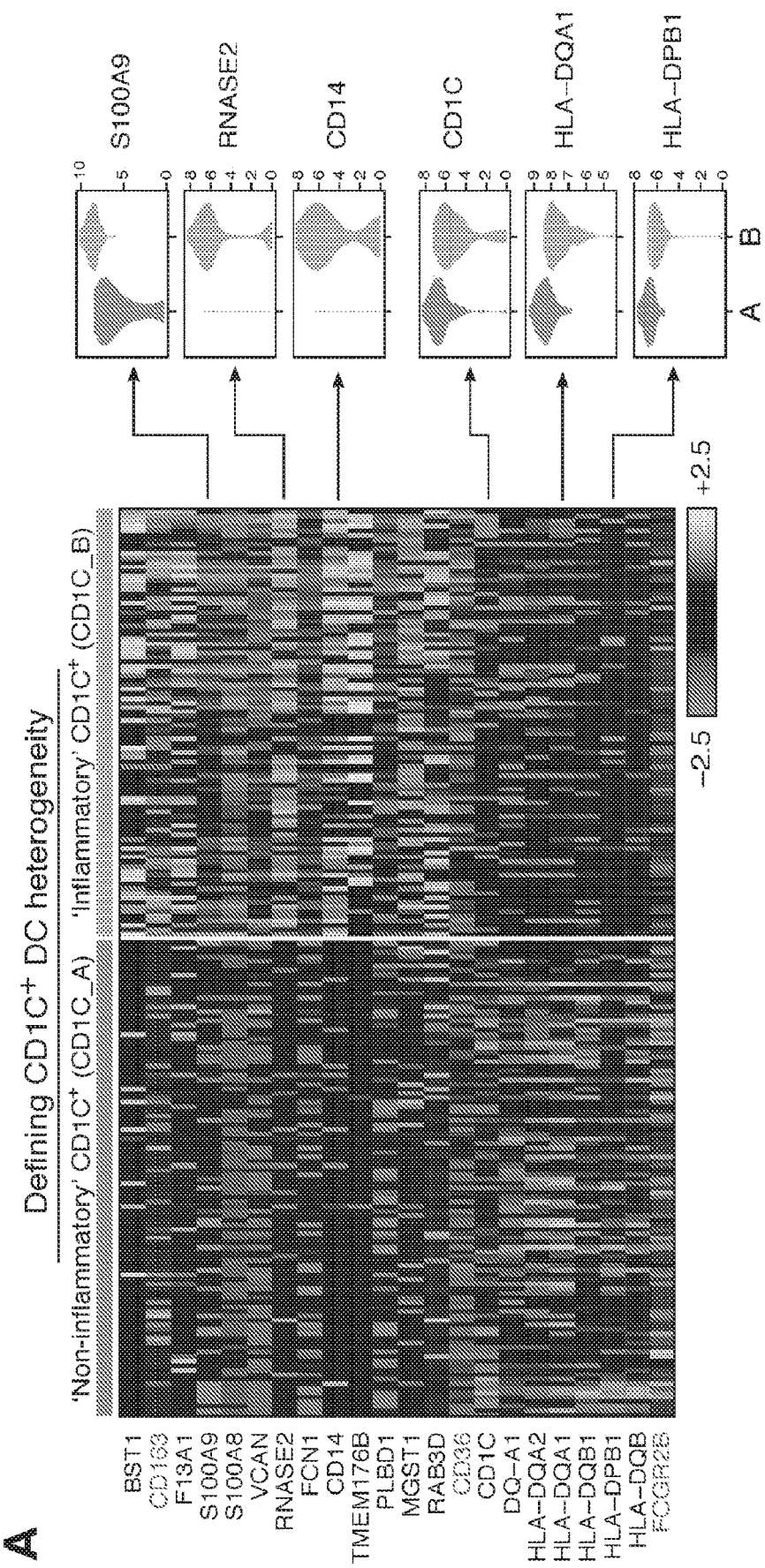

Deciphering heterogeneity within the CD1C$^+$ DC population identifies two subpopulation. The CD1C$^+$ DCs were distributed across two clusters with similar numbers of cells, which Applicants termed CD1C_A (cluster DC2) and CD1C_B (cluster DC3). Comparing the two clusters, the CD1C_B cells can be distinguished through their expression of a strong unique signature that is consistent with acute and chronic inflammatory response (Liu et al.; Pascual et al.; Mesko et al), including CD14, S100A9 and S100A8, while CD1C_A cells are marked only by slightly higher levels of MHC class II genes (FIG. 3A and Table E3 parts a-b).

TABLE E3

(including parts a-b). Discriminative markers between CD1C subsets: CD1C_A
('non-inflammatory'; DC2 cluster) versus CD1C_B ('inflammatory'; DC3 cluster)

| Gene.ID | AUC value | Avg. Diff.[1] | Power[2] | Pct.1[3] | Pct.2[4] | CD1C marker tests: p_val | Comments | Surface Marker[5] |
|---|---|---|---|---|---|---|---|---|
| part a | | | | | | | | |
| HLA-DQB | 0.85 | 0.77 | 0.70 | 0.99 | 1.00 | 0 | Higher in CD1C_A (cluster DC2)/ Lower in CD1C_B (cluster DC3) | 1 |
| HLA-DPB1 | 0.85 | 0.73 | 0.69 | 1.00 | 0.97 | 0 | Higher in CD1C_A (cluster DC2)/ Lower in CD1C_B (cluster DC3) | 1 |
| HLA-DQB1 | 0.84 | 0.91 | 0.69 | 0.99 | 0.99 | 0 | Higher in CD1C_A (cluster DC2)/ Lower in CD1C_B (cluster DC3) | 1 |
| HLA-DQA1 | 0.84 | 0.73 | 0.68 | 1.00 | 1.00 | 0 | Higher in CD1C_A (cluster DC2)/ Lower in CD1C_B (cluster DC3) | 1 |
| HLA-DQA2 | 0.79 | 0.75 | 0.58 | 1.00 | 0.98 | 2.27E−13 | Higher in CD1C_A (cluster DC2)/ Lower in CD1C_B (cluster DC3) | 1 |
| DQ-A1 | 0.79 | 0.86 | 0.57 | 0.93 | 0.77 | 9.14E−14 | Higher in CD1C_A (cluster DC2)/ Lower in CD1C_B (cluster DC3) | 1 |
| CD1C | 0.78 | 1.13 | 0.55 | 0.94 | 0.87 | 2.94E−13 | Higher in CD1C_A (cluster DC2)/ Lower in CD1C_B (cluster DC3) | 1 |
| HLA-DOB | 0.72 | 1.75 | 0.44 | 0.70 | 0.37 | 9.36E−08 | Higher in CD1C_A (cluster DC2)/ Lower in CD1C_B (cluster DC3) | 1 |

TABLE E3-continued (including parts a-b). Discriminative markers between CD1C subsets: CD1C_A
('non-inflammatory'; DC2 cluster) versus CD1C_B ('inflammatory'; DC3 cluster)

| Gene.ID | AUC value | Avg. Diff.[1] | Power[2] | Pct.1[3] | Pct.2[4] | CD1C marker tests: p_val | Comments | Surface Marker[5] |
|---|---|---|---|---|---|---|---|---|
| P2RY14 | 0.71 | 2.44 | 0.42 | 0.55 | 0.18 | 3.33E−09 | Higher in CD1C_A (cluster DC2)/ Lower in CD1C_B (cluster DC3) | 1 |
| ARL4C | 0.70 | 0.75 | 0.39 | 0.87 | 0.64 | 4.78E−05 | Higher in CD1C_A (cluster DC2)/ Lower in CD1C_B (cluster DC3) | 0 |
| CLIC2 | 0.69 | 0.82 | 0.38 | 0.81 | 0.56 | 1.62E−04 | Higher in CD1C_A (cluster DC2)/ Lower in CD1C_B (cluster DC3) | 0 |
| CLEC17A | 0.69 | 2.62 | 0.37 | 0.51 | 0.21 | 4.95E−11 | Higher in CD1C_A (cluster DC2)/ Lower in CD1C_B (cluster DC3) | 1 |
| C10ORF128 | 0.68 | 1.34 | 0.36 | 0.53 | 0.19 | 4.38E−06 | Higher in CD1C_A (cluster DC2)/ Lower in CD1C_B (cluster DC3) | 1 |
| FAM26F | 0.67 | 1.42 | 0.34 | 0.58 | 0.33 | 6.98E−05 | Higher in CD1C_A (cluster DC2)/ Lower in CD1C_B (cluster DC3) | 1 |
| ASAP1 | 0.66 | 0.88 | 0.32 | 0.69 | 0.44 | 6.99E−04 | Higher in CD1C_A (cluster DC2)/ Lower in CD1C_B (cluster DC3) | 0 |
| SLC41A2 | 0.66 | 0.88 | 0.32 | 0.62 | 0.33 | 2.59E−04 | Higher in CD1C_A (cluster DC2)/ Lower in CD1C_B (cluster DC3) | 1 |
| SLAMF7 | 0.66 | 0.92 | 0.32 | 0.71 | 0.50 | 3.34E−04 | Higher in CD1C_A (cluster DC2)/ Lower in CD1C_B (cluster DC3) | 1 |
| CST7 | 0.65 | 1.45 | 0.31 | 0.44 | 0.15 | 1.61E−05 | Higher in CD1C_A (cluster DC2)/ Lower in CD1C_B (cluster DC3) | 0 |
| PKIB | 0.65 | 1.33 | 0.30 | 0.48 | 0.21 | 4.19E−04 | Higher in CD1C_A (cluster DC2)/ Lower in CD1C_B (cluster DC3) | 0 |
| HSPA7 | 0.64 | 0.78 | 0.29 | 0.70 | 0.48 | 5.35E−03 | Higher in CD1C_A (cluster DC2)/ Lower in CD1C_B (cluster DC3) | 0 |
| CXCL16 | 0.64 | 0.96 | 0.29 | 0.71 | 0.54 | 2.42E−03 | Higher in CD1C_A (cluster DC2)/ Lower in CD1C_B (cluster DC3) | 1 |
| RUNX3 | 0.64 | 0.71 | 0.28 | 0.47 | 0.20 | 8.26E−04 | Higher in CD1C_A (cluster DC2)/ Lower in CD1C_B (cluster DC3) | 0 |
| WDFY4 | 0.64 | 0.94 | 0.27 | 0.81 | 0.67 | 5.39E−03 | Higher in CD1C_A (cluster DC2)/ Lower in CD1C_B (cluster DC3) | 1 |
| IL18R1 | 0.63 | 1.57 | 0.26 | 0.39 | 0.14 | 3.60E−04 | Higher in CD1C_A (cluster DC2)/ Lower in CD1C_B (cluster DC3) | 1 |
| FCGR2B | 0.63 | 0.96 | 0.26 | 0.68 | 0.59 | 2.56E−03 | Higher in CD1C_A (cluster DC2)/ Lower in CD1C_B (cluster DC3) | 1 |
| MYO1E | 0.63 | 0.82 | 0.25 | 0.54 | 0.32 | 5.82E−03 | Higher in CD1C_A (cluster DC2)/ Lower in CD1C_B (cluster DC3) | 0 |
| AXL | 0.63 | 1.10 | 0.25 | 0.86 | 0.83 | 1.61E−05 | Higher in CD1C_A (cluster DC2)/ Lower in CD1C_B (cluster DC3) | 1 |
| PEA15 | 0.63 | 0.73 | 0.25 | 0.87 | 0.77 | 8.77E−03 | Higher in CD1C_A (cluster DC2)/ Lower in CD1C_B (cluster DC3) | 0 |
| SIGLEC10 | 0.62 | 1.25 | 0.24 | 0.80 | 0.75 | 3.11E−05 | Higher in CD1C_A (cluster DC2)/ Lower in CD1C_B (cluster DC3) | 1 |
| CD1E | 0.62 | 1.04 | 0.24 | 0.51 | 0.34 | 1.01E−03 | Higher in CD1C_A (cluster DC2)/ Lower in CD1C_B (cluster DC3) | 1 |
| GOLGA8B | 0.62 | 1.02 | 0.23 | 0.53 | 0.36 | 7.77E−03 | Higher in CD1C_A (cluster DC2)/ Lower in CD1C_B (cluster DC3) | 0 |
| IFITM1 | 0.61 | 0.91 | 0.23 | 0.54 | 0.37 | 2.59E−02 | Higher in CD1C_A (cluster DC2)/ Lower in CD1C_B (cluster DC3) | 1 |
| LOC100505746 | 0.61 | 0.85 | 0.23 | 0.59 | 0.44 | 6.82E−03 | Higher in CD1C_A (cluster DC2)/ Lower in CD1C_B (cluster DC3) | 0 |
| FEZ1 | 0.61 | 0.94 | 0.22 | 0.48 | 0.26 | 2.48E−03 | Higher in CD1C_A (cluster DC2)/ Lower in CD1C_B (cluster DC3) | 0 |
| INSIG1 | 0.61 | 0.92 | 0.22 | 0.44 | 0.24 | 8.33E−03 | Higher in CD1C_A (cluster DC2)/ Lower in CD1C_B (cluster DC3) | 1 |
| SPATS2L | 0.61 | 0.93 | 0.22 | 0.71 | 0.62 | 2.94E−03 | Higher in CD1C_A (cluster DC2)/ Lower in CD1C_B (cluster DC3) | 0 |
| GRIP1 | 0.61 | 1.86 | 0.22 | 0.30 | 0.08 | 2.62E−04 | Higher in CD1C_A (cluster DC2)/ Lower in CD1C_B (cluster DC3) | 0 |
| MCOLN2 | 0.61 | 1.09 | 0.22 | 0.53 | 0.38 | 4.39E−03 | Higher in CD1C_A (cluster DC2)/ Lower in CD1C_B (cluster DC3) | 1 |
| SERTAD3 | 0.61 | 0.90 | 0.22 | 0.48 | 0.30 | 1.89E−02 | Higher in CD1C_A (cluster DC2)/ Lower in CD1C_B (cluster DC3) | 0 |
| PPP1R14A | 0.61 | 1.84 | 0.21 | 0.28 | 0.07 | 2.52E−05 | Higher in CD1C_A (cluster DC2)/ Lower in CD1C_B (cluster DC3) | 0 |
| UVRAG | 0.61 | 0.79 | 0.21 | 0.78 | 0.71 | 2.57E−02 | Higher in CD1C_A (cluster DC2)/ Lower in CD1C_B (cluster DC3) | 0 |
| SIGLEC6 | 0.61 | 2.09 | 0.21 | 0.31 | 0.12 | 1.39E−05 | Higher in CD1C_A (cluster DC2)/ Lower in CD1C_B (cluster DC3) | 1 |
| KPNA6 | 0.60 | 0.81 | 0.21 | 0.84 | 0.81 | 2.19E−02 | Higher in CD1C_A (cluster DC2)/ Lower in CD1C_B (cluster DC3) | 0 |
| LGMN | 0.60 | 1.52 | 0.21 | 0.57 | 0.46 | 5.99E−04 | Higher in CD1C_A (cluster DC2)/ Lower in CD1C_B (cluster DC3) | 1 |
| SPIB | 0.60 | 1.07 | 0.21 | 0.93 | 0.90 | 8.34E−07 | Higher in CD1C_A (cluster DC2)/ Lower in CD1C_B (cluster DC3) | 0 |

TABLE E3-continued (including parts a-b). Discriminative markers between CD1C subsets: CD1C_A
('non-inflammatory'; DC2 cluster) versus CD1C_B ('inflammatory'; DC3 cluster)

| Gene.ID | AUC value | Avg. Diff.[1] | Power[2] | Pct.1[3] | Pct.2[4] | CD1C marker tests: p_val | Comments | Surface Marker[5] |
|---|---|---|---|---|---|---|---|---|
| SNURF-SNRPN | 0.60 | 1.02 | 0.21 | 0.67 | 0.53 | 9.16E−04 | Higher in CD1C_A (cluster DC2)/ Lower in CD1C_B (cluster DC3) | 0 |
| LOC645638 | 0.60 | 1.91 | 0.20 | 0.27 | 0.07 | 6.50E−05 | Higher in CD1C_A (cluster DC2)/ Lower in CD1C_B (cluster DC3) | 0 |
| TOP1MT | 0.60 | 0.73 | 0.20 | 0.45 | 0.24 | 1.59E−02 | Higher in CD1C_A (cluster DC2)/ Lower in CD1C_B (cluster DC3) | 0 |
| part b | | | | | | | | |
| AK307192 | 0.40 | −0.91 | 0.20 | 0.16 | 0.36 | 1.30E−02 | Lower in CD1C_A (cluster DC2)/ Higher in CD1C_B (cluster DC3) | 0 |
| BACH1 | 0.40 | −0.70 | 0.20 | 0.37 | 0.56 | 5.51E−02 | Lower in CD1C_A (cluster DC2)/ Higher in CD1C_B (cluster DC3) | 0 |
| CA5BP1 | 0.40 | −1.33 | 0.20 | 0.67 | 0.73 | 1.35E−05 | Lower in CD1C_A (cluster DC2)/ Higher in CD1C_B (cluster DC3) | 0 |
| TSC2 | 0.40 | −0.86 | 0.20 | 0.21 | 0.40 | 2.43E−02 | Lower in CD1C_A (cluster DC2)/ Higher in CD1C_B (cluster DC3) | 1 |
| SHOC2 | 0.40 | −0.82 | 0.21 | 0.50 | 0.61 | 1.91E−02 | Lower in CD1C_A (cluster DC2)/ Higher in CD1C_B (cluster DC3) | 0 |
| HPCAL1 | 0.40 | −1.02 | 0.21 | 0.69 | 0.73 | 5.80E−04 | Lower in CD1C_A (cluster DC2)/ Higher in CD1C_B (cluster DC3) | 0 |
| PVR | 0.40 | −0.73 | 0.21 | 0.36 | 0.54 | 2.69E−02 | Lower in CD1C_A (cluster DC2)/ Higher in CD1C_B (cluster DC3) | 1 |
| RIPK2 | 0.40 | −0.88 | 0.21 | 0.57 | 0.67 | 2.41E−02 | Lower in CD1C_A (cluster DC2)/ Higher in CD1C_B (cluster DC3) | 0 |
| STIM1 | 0.40 | −0.78 | 0.21 | 0.27 | 0.46 | 2.79E−02 | Lower in CD1C_A (cluster DC2)/ Higher in CD1C_B (cluster DC3) | 1 |
| ID1 | 0.39 | −1.97 | 0.22 | 0.04 | 0.25 | 1.21E−04 | Lower in CD1C_A (cluster DC2)/ Higher in CD1C_B (cluster DC3) | 0 |
| IKBKE | 0.39 | −2.20 | 0.22 | 0.09 | 0.28 | 4.31E−06 | Lower in CD1C_A (cluster DC2)/ Higher in CD1C_B (cluster DC3) | 0 |
| KCNN4 | 0.39 | −0.96 | 0.22 | 0.20 | 0.40 | 1.20E−03 | Lower in CD1C_A (cluster DC2)/ Higher in CD1C_B (cluster DC3) | 1 |
| EMP1 | 0.39 | −1.11 | 0.22 | 0.14 | 0.36 | 4.14E−03 | Lower in CD1C_A (cluster DC2)/ Higher in CD1C_B (cluster DC3) | 1 |
| LPPR2 | 0.39 | −1.49 | 0.22 | 0.05 | 0.26 | 5.20E−05 | Lower in CD1C_A (cluster DC2)/ Higher in CD1C_B (cluster DC3) | 1 |
| GPBAR1 | 0.39 | −0.89 | 0.22 | 0.31 | 0.47 | 3.07E−07 | Lower in CD1C_A (cluster DC2)/ Higher in CD1C_B (cluster DC3) | 1 |
| LOC284454 | 0.39 | −1.23 | 0.23 | 0.87 | 0.90 | 5.36E−07 | Lower in CD1C_A (cluster DC2)/ Higher in CD1C_B (cluster DC3) | 0 |
| MKNK1 | 0.39 | −1.43 | 0.23 | 0.16 | 0.37 | 1.86E−03 | Lower in CD1C_A (cluster DC2)/ Higher in CD1C_B (cluster DC3) | 1 |
| KIAA0513 | 0.39 | −0.88 | 0.23 | 0.48 | 0.58 | 4.18E−05 | Lower in CD1C_A (cluster DC2)/ Higher in CD1C_B (cluster DC3) | 0 |
| FOXO3 | 0.39 | −1.16 | 0.23 | 0.20 | 0.41 | 7.71E−04 | Lower in CD1C_A (cluster DC2)/ Higher in CD1C_B (cluster DC3) | 0 |
| TMEM111 | 0.39 | −0.71 | 0.23 | 0.77 | 0.83 | 1.29E−02 | Lower in CD1C_A (cluster DC2)/ Higher in CD1C_B (cluster DC3) | 0 |
| YWHAG | 0.39 | −0.88 | 0.23 | 0.28 | 0.47 | 3.96E−03 | Lower in CD1C_A (cluster DC2)/ Higher in CD1C_B (cluster DC3) | 0 |
| ECRP | 0.38 | −3.07 | 0.24 | 0.01 | 0.25 | 3.67E−07 | Lower in CD1C_A (cluster DC2)/ Higher in CD1C_B (cluster DC3) | 0 |
| TAB1 | 0.38 | −0.89 | 0.24 | 0.65 | 0.75 | 3.35E−03 | Lower in CD1C_A (cluster DC2)/ Higher in CD1C_B (cluster DC3) | 0 |
| OSM | 0.38 | −1.90 | 0.25 | 0.21 | 0.41 | 7.13E−05 | Lower in CD1C_A (cluster DC2)/ Higher in CD1C_B (cluster DC3) | 0 |
| GABARAPL1 | 0.37 | −0.93 | 0.25 | 0.20 | 0.45 | 1.88E−03 | Lower in CD1C_A (cluster DC2)/ Higher in CD1C_B (cluster DC3) | 0 |
| ASPH | 0.37 | −0.95 | 0.26 | 0.33 | 0.52 | 4.83E−05 | Lower in CD1C_A (cluster DC2)/ Higher in CD1C_B (cluster DC3) | 1 |
| PDLIM7 | 0.37 | −1.45 | 0.26 | 0.12 | 0.38 | 1.71E−04 | Lower in CD1C_A (cluster DC2)/ Higher in CD1C_B (cluster DC3) | 0 |
| QPCT | 0.37 | −1.10 | 0.26 | 0.24 | 0.47 | 2.41E−04 | Lower in CD1C_A (cluster DC2)/ Higher in CD1C_B (cluster DC3) | 0 |
| RIN2 | 0.37 | −0.72 | 0.26 | 0.16 | 0.43 | 3.46E−04 | Lower in CD1C_A (cluster DC2)/ Higher in CD1C_B (cluster DC3) | 0 |
| MRPS23 | 0.37 | −0.88 | 0.26 | 0.21 | 0.46 | 1.09E−03 | Lower in CD1C_A (cluster DC2)/ Higher in CD1C_B (cluster DC3) | 0 |
| PLXND1 | 0.37 | −1.10 | 0.26 | 0.17 | 0.42 | 6.94E−04 | Lower in CD1C_A (cluster DC2)/ Higher in CD1C_B (cluster DC3) | 1 |
| CLEC12A | 0.37 | −0.82 | 0.27 | 0.51 | 0.65 | 6.30E−05 | Lower in CD1C_A (cluster DC2)/ Higher in CD1C_B (cluster DC3) | 1 |
| TMEM176A | 0.37 | −3.36 | 0.27 | 0.03 | 0.30 | 1.23E−07 | Lower in CD1C_A (cluster DC2)/ Higher in CD1C_B (cluster DC3) | 1 |

TABLE E3-continued (including parts a-b). Discriminative markers between CD1C subsets: CD1C_A ('non-inflammatory'; DC2 cluster) versus CD1C_B ('inflammatory'; DC3 cluster)

| Gene.ID | AUC value | Avg. Diff.[1] | Power[2] | Pct.1[3] | Pct.2[4] | CD1C marker tests: p_val | Comments | Surface Marker[5] |
|---|---|---|---|---|---|---|---|---|
| PISD | 0.36 | −1.01 | 0.27 | 0.32 | 0.55 | 1.80E−03 | Lower in CD1C_A (cluster DC2)/ Higher in CD1C_B (cluster DC3) | 1 |
| PLA2G1 | 0.36 | −2.22 | 0.27 | 0.05 | 0.32 | 3.69E−06 | Lower in CD1C_A (cluster DC2)/ Higher in CD1C_B (cluster DC3) | 0 |
| TMEM141 | 0.36 | −0.85 | 0.27 | 0.13 | 0.42 | 4.27E−05 | Lower in CD1C_A (cluster DC2)/ Higher in CD1C_B (cluster DC3) | 1 |
| NINJ1 | 0.36 | −1.33 | 0.28 | 0.23 | 0.48 | 5.06E−04 | Lower in CD1C_A (cluster DC2)/ Higher in CD1C_B (cluster DC3) | 1 |
| AGTRAP | 0.36 | −0.70 | 0.28 | 0.61 | 0.75 | 1.46E−03 | Lower in CD1C_A (cluster DC2)/ Higher in CD1C_B (cluster DC3) | 1 |
| BLVRA | 0.36 | −1.04 | 0.28 | 0.32 | 0.54 | 2.24E−05 | Lower in CD1C_A (cluster DC2)/ Higher in CD1C_B (cluster DC3) | 0 |
| HBEGF | 0.36 | −1.03 | 0.29 | 0.23 | 0.51 | 4.84E−04 | Lower in CD1C_A (cluster DC2)/ Higher in CD1C_B (cluster DC3) | 1 |
| DMXL2 | 0.36 | −1.86 | 0.29 | 0.39 | 0.61 | 2.91E−06 | Lower in CD1C_A (cluster DC2)/ Higher in CD1C_B (cluster DC3) | 1 |
| C9ORF89 | 0.35 | −0.87 | 0.29 | 0.28 | 0.56 | 7.60E−04 | Lower in CD1C_A (cluster DC2)/ Higher in CD1C_B (cluster DC3) | 1 |
| IL1B | 0.35 | −1.01 | 0.29 | 0.23 | 0.52 | 3.97E−04 | Lower in CD1C_A (cluster DC2)/ Higher in CD1C_B (cluster DC3) | 0 |
| NLRP12 | 0.35 | −1.09 | 0.29 | 0.82 | 0.88 | 2.81E−08 | Lower in CD1C_A (cluster DC2)/ Higher in CD1C_B (cluster DC3) | 0 |
| SORL1 | 0.35 | −0.73 | 0.29 | 0.32 | 0.60 | 7.77E−04 | Lower in CD1C_A (cluster DC2)/ Higher in CD1C_B (cluster DC3) | 1 |
| NFE2 | 0.35 | −0.96 | 0.30 | 0.23 | 0.52 | 3.80E−04 | Lower in CD1C_A (cluster DC2)/ Higher in CD1C_B (cluster DC3) | 0 |
| ADAM15 | 0.35 | −0.71 | 0.30 | 0.47 | 0.71 | 1.04E−03 | Lower in CD1C_A (cluster DC2)/ Higher in CD1C_B (cluster DC3) | 1 |
| CCDC69 | 0.35 | −0.89 | 0.30 | 0.52 | 0.75 | 1.81E−03 | Lower in CD1C_A (cluster DC2)/ Higher in CD1C_B (cluster DC3) | 0 |
| SULT1A1 | 0.35 | −1.07 | 0.30 | 0.33 | 0.58 | 3.78E−04 | Lower in CD1C_A (cluster DC2)/ Higher in CD1C_B (cluster DC3) | 0 |
| TOM1 | 0.35 | −0.92 | 0.30 | 0.31 | 0.57 | 2.36E−05 | Lower in CD1C_A (cluster DC2)/ Higher in CD1C_B (cluster DC3) | 0 |
| KCNE3 | 0.35 | −0.75 | 0.31 | 0.49 | 0.70 | 1.23E−03 | Lower in CD1C_A (cluster DC2)/ Higher in CD1C_B (cluster DC3) | 1 |
| PYGL | 0.35 | −0.99 | 0.31 | 0.60 | 0.71 | 3.37E−06 | Lower in CD1C_A (cluster DC2)/ Higher in CD1C_B (cluster DC3) | 0 |
| SLC11A1 | 0.34 | −2.12 | 0.31 | 0.52 | 0.67 | 0 | Lower in CD1C_A (cluster DC2)/ Higher in CD1C_B (cluster DC3) | 1 |
| HK3 | 0.34 | −1.67 | 0.31 | 0.13 | 0.43 | 1.43E−05 | Lower in CD1C_A (cluster DC2)/ Higher in CD1C_B (cluster DC3) | 0 |
| ACSL1 | 0.34 | −1.85 | 0.32 | 0.13 | 0.43 | 9.18E−06 | Lower in CD1C_A (cluster DC2)/ Higher in CD1C_B (cluster DC3) | 1 |
| IER3 | 0.34 | −1.51 | 0.32 | 0.14 | 0.45 | 1.44E−05 | Lower in CD1C_A (cluster DC2)/ Higher in CD1C_B (cluster DC3) | 1 |
| CFD | 0.34 | −1.16 | 0.33 | 0.36 | 0.58 | 5.83E−06 | Lower in CD1C_A (cluster DC2)/ Higher in CD1C_B (cluster DC3) | 0 |
| LMNA | 0.34 | −0.91 | 0.33 | 0.32 | 0.61 | 6.19E−05 | Lower in CD1C_A (cluster DC2)/ Higher in CD1C_B (cluster DC3) | 1 |
| SEPX1 | 0.33 | −0.72 | 0.34 | 0.42 | 0.70 | 7.48E−04 | Lower in CD1C_A (cluster DC2)/ Higher in CD1C_B (cluster DC3) | 0 |
| TREM1 | 0.33 | −0.97 | 0.34 | 0.31 | 0.61 | 5.90E−06 | Lower in CD1C_A (cluster DC2)/ Higher in CD1C_B (cluster DC3) | 1 |
| PILRA | 0.33 | −0.80 | 0.34 | 0.70 | 0.86 | 8.98E−04 | Lower in CD1C_A (cluster DC2)/ Higher in CD1C_B (cluster DC3) | 1 |
| ASGR1 | 0.33 | −1.09 | 0.35 | 0.18 | 0.53 | 5.91E−06 | Lower in CD1C_A (cluster DC2)/ Higher in CD1C_B (cluster DC3) | 0 |
| TXNRD1 | 0.33 | −0.88 | 0.35 | 0.58 | 0.80 | 2.79E−04 | Lower in CD1C_A (cluster DC2)/ Higher in CD1C_B (cluster DC3) | 0 |
| GLUL | 0.32 | −0.72 | 0.36 | 0.74 | 0.91 | 2.99E−05 | Lower in CD1C_A (cluster DC2)/ Higher in CD1C_B (cluster DC3) | 0 |
| PSTPIP1 | 0.32 | −0.87 | 0.37 | 0.46 | 0.71 | 2.04E−06 | Lower in CD1C_A (cluster DC2)/ Higher in CD1C_B (cluster DC3) | 0 |
| CSF3R | 0.31 | −0.74 | 0.37 | 0.74 | 0.90 | 1.19E−06 | Lower in CD1C_A (cluster DC2)/ Higher in CD1C_B (cluster DC3) | 1 |
| STAB1 | 0.31 | −2.68 | 0.38 | 0.07 | 0.43 | 1.85E−10 | Lower in CD1C_A (cluster DC2)/ Higher in CD1C_B (cluster DC3) | 1 |
| RETN | 0.31 | −0.92 | 0.39 | 0.36 | 0.70 | 1.34E−06 | Lower in CD1C_A (cluster DC2)/ Higher in CD1C_B (cluster DC3) | 0 |
| SERPINA1 | 0.30 | −0.74 | 0.40 | 0.81 | 0.93 | 1.20E−06 | Lower in CD1C_A (cluster DC2)/ Higher in CD1C_B (cluster DC3) | 0 |
| SLC7A7 | 0.30 | −1.61 | 0.40 | 0.49 | 0.71 | 1.20E−07 | Lower in CD1C_A (cluster DC2)/ Higher in CD1C_B (cluster DC3) | 1 |

TABLE E3-continued (including parts a-b). Discriminative markers between CD1C subsets: CD1C_A
('non-inflammatory'; DC2 cluster) versus CD1C_B ('inflammatory'; DC3 cluster)

| Gene.ID | AUC value | Avg. Diff.[1] | Power[2] | Pct.1[3] | Pct.2[4] | CD1C marker tests: p_val | Comments | Surface Marker[5] |
|---|---|---|---|---|---|---|---|---|
| CTSD | 0.30 | −0.92 | 0.40 | 0.55 | 0.83 | 1.27E−05 | Lower in CD1C_A (cluster DC2)/ Higher in CD1C_B (cluster DC3) | 1 |
| NEAT1 | 0.30 | −0.70 | 0.40 | 0.96 | 0.98 | 1.46E−05 | Lower in CD1C_A (cluster DC2)/ Higher in CD1C_B (cluster DC3) | 0 |
| CES1P1 | 0.29 | −1.40 | 0.42 | 0.13 | 0.53 | 1.95E−09 | Lower in CD1C_A (cluster DC2)/ Higher in CD1C_B (cluster DC3) | 0 |
| FPR1 | 0.28 | −0.72 | 0.44 | 0.67 | 0.92 | 3.58E−10 | Lower in CD1C_A (cluster DC2)/ Higher in CD1C_B (cluster DC3) | 1 |
| CD163 | 0.27 | −1.03 | 0.46 | 0.39 | 0.78 | 7.53E−08 | Lower in CD1C_A (cluster DC2)/ Higher in CD1C_B (cluster DC3) | 1 |
| S100A12 | 0.27 | −1.55 | 0.46 | 0.20 | 0.62 | 2.08E−12 | Lower in CD1C_A (cluster DC2)/ Higher in CD1C_B (cluster DC3) | 0 |
| CYBB | 0.26 | −0.89 | 0.47 | 0.63 | 0.90 | 4.46E−08 | Lower in CD1C_A (cluster DC2)/ Higher in CD1C_B (cluster DC3) | 1 |
| F13A1 | 0.26 | −1.73 | 0.47 | 0.29 | 0.67 | 1.26E−11 | Lower in CD1C_A (cluster DC2)/ Higher in CD1C_B (cluster DC3) | 1 |
| CES1 | 0.26 | −1.62 | 0.48 | 0.34 | 0.68 | 7.26E−14 | Lower in CD1C_A (cluster DC2)/ Higher in CD1C_B (cluster DC3) | 1 |
| BST1 | 0.26 | −1.96 | 0.48 | 0.11 | 0.58 | 4.20E−13 | Lower in CD1C_A (cluster DC2)/ Higher in CD1C_B (cluster DC3) | 1 |
| MTMR11 | 0.26 | −1.08 | 0.48 | 0.33 | 0.77 | 5.14E−09 | Lower in CD1C_A (cluster DC2)/ Higher in CD1C_B (cluster DC3) | 0 |
| CD36 | 0.25 | −1.04 | 0.51 | 0.73 | 0.93 | 1.99E−11 | Lower in CD1C_A (cluster DC2)/ Higher in CD1C_B (cluster DC3) | 1 |
| MGST1 | 0.25 | −1.21 | 0.51 | 0.30 | 0.73 | 3.22E−15 | Lower in CD1C_A (cluster DC2)/ Higher in CD1C_B (cluster DC3) | 1 |
| RAB3D | 0.25 | −1.14 | 0.51 | 0.52 | 0.86 | 1.77E−09 | Lower in CD1C_A (cluster DC2)/ Higher in CD1C_B (cluster DC3) | 0 |
| PLBD1 | 0.24 | −0.86 | 0.53 | 0.76 | 0.96 | 8.90E−11 | Lower in CD1C_A (cluster DC2)/ Higher in CD1C_B (cluster DC3) | 1 |
| TMEM176B | 0.23 | −4.72 | 0.54 | 0.08 | 0.58 | 0 | Lower in CD1C_A (cluster DC2)/ Higher in CD1C_B (cluster DC3) | 1 |
| CD14 | 0.18 | −2.99 | 0.64 | 0.20 | 0.74 | 0 | Lower in CD1C_A (cluster DC2)/ Higher in CD1C_B (cluster DC3) | 1 |
| FCN1 | 0.15 | −1.20 | 0.70 | 0.80 | 0.99 | 0 | Lower in CD1C_A (cluster DC2)/ Higher in CD1C_B (cluster DC3) | 1 |
| RNASE2 | 0.13 | −2.73 | 0.73 | 0.16 | 0.81 | 0 | Lower in CD1C_A (cluster DC2)/ Higher in CD1C_B (cluster DC3) | 0 |
| VCAN | 0.13 | −1.31 | 0.74 | 0.64 | 1.00 | 0 | Lower in CD1C_A (cluster DC2)/ Higher in CD1C_B (cluster DC3) | 1 |
| S100A8 | 0.06 | −2.51 | 0.89 | 0.41 | 0.98 | 0 | Lower in CD1C_A (cluster DC2)/ Higher in CD1C_B (cluster DC3) | 0 |
| S100A9 | 0.04 | −2.08 | 0.93 | 0.84 | 1.00 | 0 | Lower in CD1C_A (cluster DC2)/ Higher in CD1C_B (cluster DC3) | 0 |

Footnotes in Table E3: 1—Value refers to average differential expression within one subset (log fold change); 2—Value refers to discriminatory power of each marker; 3—Percentage of cells, within the cluster ID for which the gene is a marker, that detect the gene; 4—Percentage of all the other cells, excluding the cluster ID for which the gene is a marker, that detect the gene; 5—"1" refers to predicted surface marker; "0" refers to predicted not a surface marker according to the Protein Atlas: Protein Atlas: http://www.proteinatlas.org/search/protein_class:Predicted+membrane+proteins.

Figure 3B:
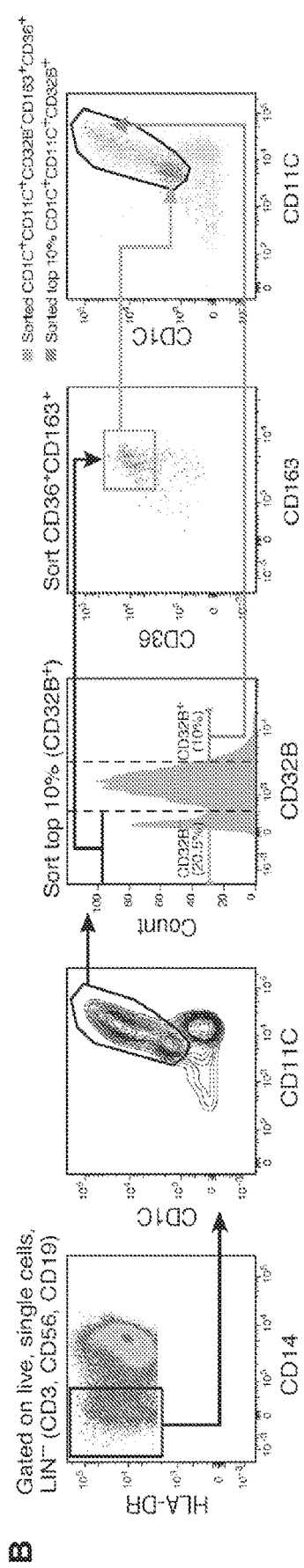
Figure 3C:
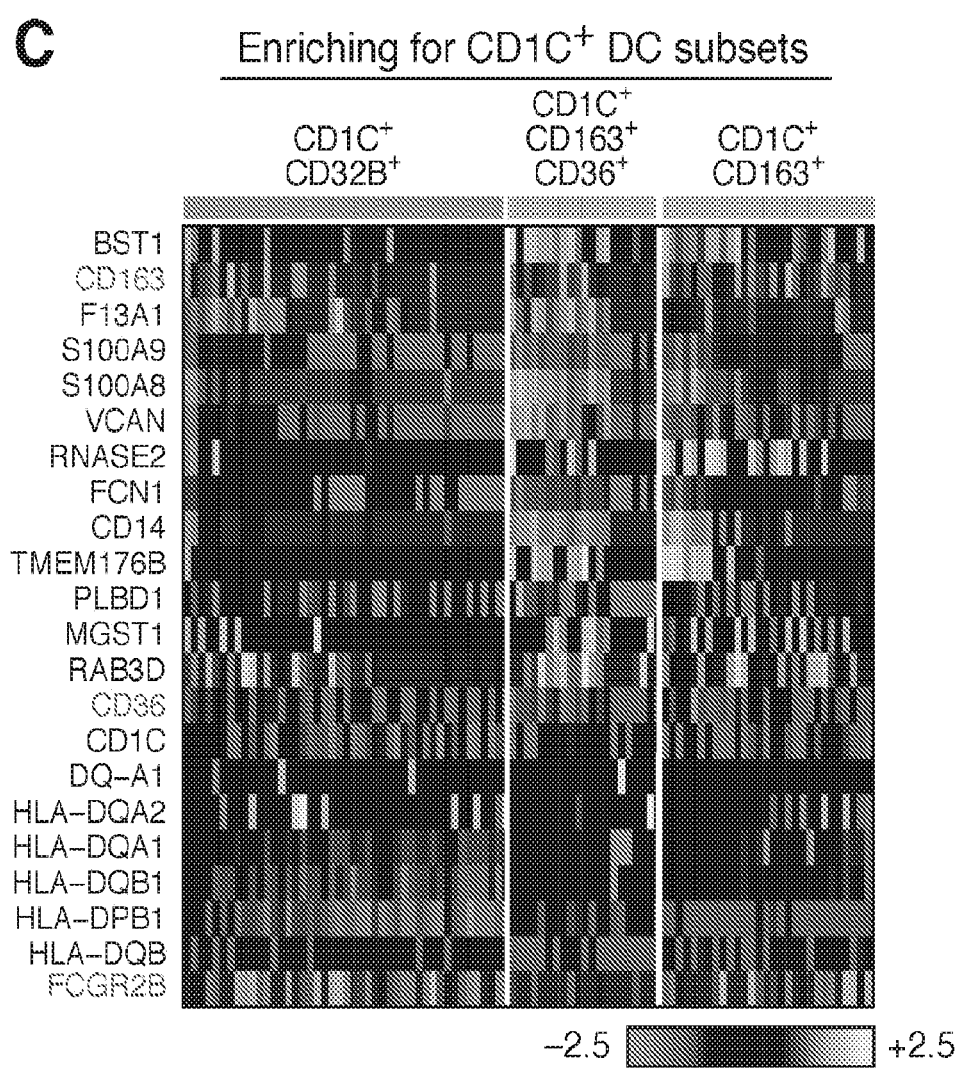

Applicants then validated the presence of the two populations by combining prospective isolation with a new sorting panel followed by scRNA-seq. To isolate these cells by flow sorting, Applicants developed a panel incorporating surface markers derived from the set of uniquely expressed genes: FCGR2B (CD32B) for 'non-inflammatory' CD1C_A, and CD163 and CD36 for 'inflammatory' CD1C_B subsets (FIG. 3B). scRNA-seq of prospectively isolated cells from each subset recapitulated the original split observed in CD1C+ DCs (FIG. 3C). Unlike monocytes and pDCs, both CD1C_A and CD1C_B subsets (isolated with the newly identified markers) were potent stimulators of naïve T cell proliferation (p<0.05), consistent with the functional characteristics of conventional DCs (FIG. 3D). Thus, scRNA-seq was able to reveal unappreciated heterogeneity in this particular subset, leading to new hypotheses about the functions of CD1C' DCs.

Discovering Monocyte Subset and their Relationships to DC Subsets.

Some key genes that were known to be associated with monocytes were also expressed by 'inflammatory' CD1C_B (cluster DC3) and CD141⁻CD1C⁻ (cluster DC4) cells (e.g., CD14 and FCGR3A/CD16, respectively). To analyze the relationships between monocytes and CD1C_B cells, Applicants first profiled 384 single blood monocytes (FIG. 2A, FIG. 4A). Based on 339 monocytes that passed QC, Applicants identified four clusters (FIG. 4B, FIG. 4D) distinguished by 102 classifier genes (AUC≥0.85; FIG. 4C, FIG. 4E, and Table E4 parts a-e).

TABLE E4

(including parts a-e). Discriminative genes for monocyte subsets reported in FIG. 4

| Gene.ID | AUC value | Avg. Diff.[1] | Power[2] | Pct.1[3] | Pct.2[4] | Cluster ID | Associated.Cell.Population | Surface Marker[5] |
|---|---|---|---|---|---|---|---|---|
| | | | | | part a | | | |
| CD14 | 0.97 | 2.52 | 0.94 | 1.00 | 0.31 | Mono1 | mostly CD14++CD16− classical monocyte | 1 |
| VCAN | 0.96 | 2.32 | 0.92 | 1.00 | 0.44 | Mono1 | mostly CD14++CD16− classical monocyte | 1 |
| S100A8 | 0.93 | 1.98 | 0.86 | 0.99 | 0.40 | Mono1 | mostly CD14++CD16− classical monocyte | 0 |
| S100A9 | 0.93 | 1.76 | 0.85 | 1.00 | 0.69 | Mono1 | mostly CD14++CD16− classical monocyte | 0 |
| FCN1 | 0.92 | 1.35 | 0.84 | 1.00 | 0.65 | Mono1 | mostly CD14++CD16− classical monocyte | 1 |
| ITGB2 | 0.91 | 1.00 | 0.82 | 1.00 | 0.96 | Mono1 | mostly CD14++CD16− classical monocyte | 1 |
| LRP1 | 0.91 | 1.68 | 0.81 | 0.99 | 0.51 | Mono1 | mostly CD14++CD16− classical monocyte | 1 |
| CSF3R | 0.91 | 1.66 | 0.81 | 0.99 | 0.50 | Mono1 | mostly CD14++CD16− classical monocyte | 1 |
| TKT | 0.91 | 1.30 | 0.81 | 0.99 | 0.87 | Mono1 | mostly CD14++CD16− classical monocyte | 0 |
| LYZ | 0.90 | 1.10 | 0.81 | 1.00 | 1.00 | Mono1 | mostly CD14++CD16− classical monocyte | 0 |
| APLP2 | 0.90 | 1.31 | 0.79 | 1.00 | 0.78 | Mono1 | mostly CD14++CD16− classical monocyte | 1 |
| FPR1 | 0.89 | 1.37 | 0.77 | 1.00 | 0.54 | Mono1 | mostly CD14++CD16− classical monocyte | 1 |
| CD36 | 0.89 | 1.50 | 0.77 | 0.99 | 0.75 | Mono1 | mostly CD14++CD16− classical monocyte | 1 |
| S100A12 | 0.88 | 2.32 | 0.77 | 0.87 | 0.18 | Mono1 | mostly CD14++CD16− classical monocyte | 0 |
| CLEC4E | 0.87 | 2.39 | 0.75 | 0.89 | 0.46 | Mono1 | mostly CD14++CD16− classical monocyte | 1 |
| ITGAM | 0.87 | 1.84 | 0.74 | 0.91 | 0.25 | Mono1 | mostly CD14++CD16− classical monocyte | 1 |
| SLC2A3 | 0.87 | 1.80 | 0.74 | 0.96 | 0.43 | Mono1 | mostly CD14++CD16− classical monocyte | 1 |
| CTSD | 0.87 | 1.25 | 0.74 | 0.98 | 0.74 | Mono1 | mostly CD14++CD16− classical monocyte | 1 |
| NEAT1 | 0.86 | 1.10 | 0.72 | 1.00 | 0.94 | Mono1 | mostly CD14++CD16− classical monocyte | 0 |
| PTAFR | 0.86 | 1.57 | 0.71 | 0.98 | 0.82 | Mono1 | mostly CD14++CD16− classical monocyte | 1 |
| TREM1 | 0.85 | 1.71 | 0.70 | 0.89 | 0.29 | Mono1 | mostly CD14++CD16− classical monocyte | 1 |
| NAIP | 0.85 | 1.46 | 0.69 | 0.98 | 0.76 | Mono1 | mostly CD14++CD16− classical monocyte | 0 |
| NCF1 | 0.85 | 1.41 | 0.69 | 0.97 | 0.67 | Mono1 | mostly CD14++CD16− classical monocyte | 0 |
| FCGR2A | 0.84 | 1.27 | 0.68 | 0.98 | 0.58 | Mono1 | mostly CD14++CD16− classical monocyte | 1 |
| SCPEP1 | 0.84 | 1.26 | 0.68 | 0.96 | 0.54 | Mono1 | mostly CD14++CD16− classical monocyte | 0 |
| CTSA | 0.84 | 1.25 | 0.68 | 0.95 | 0.60 | Mono1 | mostly CD14++CD16− classical monocyte | 1 |
| NLRP3 | 0.84 | 1.80 | 0.67 | 0.94 | 0.55 | Mono1 | mostly CD14++CD16− classical monocyte | 0 |
| ACSL1 | 0.84 | 1.59 | 0.67 | 0.93 | 0.38 | Mono1 | mostly CD14++CD16− classical monocyte | 1 |
| SDCBP | 0.83 | 1.01 | 0.66 | 0.99 | 0.84 | Mono1 | mostly CD14++CD16− classical monocyte | 0 |
| SLC11A1 | 0.83 | 1.15 | 0.66 | 0.99 | 0.70 | Mono1 | mostly CD14++CD16− classical monocyte | 1 |
| IRS2 | 0.83 | 1.66 | 0.66 | 0.82 | 0.19 | Mono1 | mostly CD14++CD16− classical monocyte | 0 |
| VNN2 | 0.83 | 1.84 | 0.66 | 0.82 | 0.23 | Mono1 | mostly CD14++CD16− classical monocyte | 1 |
| DPYD | 0.82 | 1.29 | 0.65 | 0.96 | 0.54 | Mono1 | mostly CD14++CD16− classical monocyte | 0 |
| CLEC7A | 0.82 | 1.08 | 0.65 | 0.98 | 0.93 | Mono1 | mostly CD14++CD16− classical monocyte | 1 |
| BST1 | 0.82 | 1.73 | 0.64 | 0.82 | 0.28 | Mono1 | mostly CD14++CD16− classical monocyte | 1 |
| PLBD1 | 0.82 | 1.37 | 0.64 | 0.94 | 0.57 | Mono1 | mostly CD14++CD16− classical monocyte | 1 |
| PYGL | 0.82 | 1.44 | 0.64 | 0.93 | 0.70 | Mono1 | mostly CD14++CD16− classical monocyte | 0 |
| QPCT | 0.82 | 2.30 | 0.63 | 0.75 | 0.18 | Mono1 | mostly CD14++CD16− classical monocyte | 0 |
| BC013828 | 0.81 | 1.47 | 0.63 | 0.82 | 0.26 | Mono1 | mostly CD14++CD16− classical monocyte | 0 |
| CD163 | 0.81 | 1.84 | 0.63 | 0.79 | 0.22 | Mono1 | mostly CD14++CD16− classical monocyte | 1 |
| AQP9 | 0.81 | 1.97 | 0.62 | 0.75 | 0.14 | Mono1 | mostly CD14++CD16− classical monocyte | 1 |
| PELI1 | 0.81 | 1.26 | 0.62 | 0.96 | 0.89 | Mono1 | mostly CD14++CD16− classical monocyte | 0 |
| FAM198B | 0.81 | 1.70 | 0.61 | 0.81 | 0.27 | Mono1 | mostly CD14++CD16− classical monocyte | 1 |
| GAS7 | 0.80 | 1.31 | 0.61 | 0.92 | 0.56 | Mono1 | mostly CD14++CD16− classical monocyte | 0 |
| STAB1 | 0.80 | 2.03 | 0.61 | 0.74 | 0.15 | Mono1 | mostly CD14++CD16− classical monocyte | 1 |
| CDA | 0.80 | 1.74 | 0.61 | 0.75 | 0.19 | Mono1 | mostly CD14++CD16− classical monocyte | 0 |
| DOK3 | 0.80 | 1.40 | 0.61 | 0.84 | 0.29 | Mono1 | mostly CD14++CD16− classical monocyte | 0 |
| IRAK3 | 0.80 | 1.28 | 0.60 | 0.94 | 0.59 | Mono1 | mostly CD14++CD16− classical monocyte | 0 |
| PLAUR | 0.80 | 1.39 | 0.60 | 0.92 | 0.59 | Mono1 | mostly CD14++CD16− classical monocyte | 1 |
| AL137655 | 0.80 | 1.47 | 0.60 | 0.89 | 0.61 | Mono1 | mostly CD14++CD16− classical monocyte | 0 |
| LILRA6 | 0.80 | 1.01 | 0.60 | 1.00 | 0.88 | Mono1 | mostly CD14++CD16− classical monocyte | 1 |
| TLR4 | 0.80 | 1.32 | 0.59 | 0.87 | 0.37 | Mono1 | mostly CD14++CD16− classical monocyte | 1 |
| AX747598 | 0.80 | 1.63 | 0.59 | 0.81 | 0.30 | Mono1 | mostly CD14++CD16− classical monocyte | 0 |
| TLR2 | 0.79 | 1.03 | 0.58 | 0.93 | 0.49 | Mono1 | mostly CD14++CD16− classical monocyte | 1 |
| AGTRAP | 0.79 | 1.05 | 0.58 | 0.92 | 0.51 | Mono1 | mostly CD14++CD16− classical monocyte | 1 |
| CRISPLD2 | 0.79 | 2.35 | 0.58 | 0.81 | 0.50 | Mono1 | mostly CD14++CD16− classical monocyte | 0 |
| CCR1 | 0.78 | 1.51 | 0.57 | 0.78 | 0.27 | Mono1 | mostly CD14++CD16− classical monocyte | 1 |
| NFAM1 | 0.78 | 1.18 | 0.57 | 0.90 | 0.57 | Mono1 | mostly CD14++CD16− classical monocyte | 1 |
| ETS2 | 0.78 | 1.24 | 0.56 | 0.90 | 0.52 | Mono1 | mostly CD14++CD16− classical monocyte | 0 |
| RAB27A | 0.78 | 1.46 | 0.56 | 0.87 | 0.62 | Mono1 | mostly CD14++CD16− classical monocyte | 0 |
| BNIP3L | 0.78 | 1.11 | 0.56 | 0.93 | 0.64 | Mono1 | mostly CD14++CD16− classical monocyte | 1 |
| HPSE | 0.78 | 1.68 | 0.56 | 0.92 | 0.79 | Mono1 | mostly CD14++CD16− classical monocyte | 0 |
| PER1 | 0.78 | 1.26 | 0.56 | 0.91 | 0.51 | Mono1 | mostly CD14++CD16− classical monocyte | 0 |
| MEGF9 | 0.78 | 1.35 | 0.55 | 0.90 | 0.72 | Mono1 | mostly CD14++CD16− classical monocyte | 1 |
| CD300E | 0.77 | 1.06 | 0.55 | 0.87 | 0.45 | Mono1 | mostly CD14++CD16− classical monocyte | 1 |
| CYP1B1 | 0.77 | 2.26 | 0.55 | 0.62 | 0.09 | Mono1 | mostly CD14++CD16− classical monocyte | 1 |
| FCAR | 0.77 | 1.84 | 0.55 | 0.87 | 0.77 | Mono1 | mostly CD14++CD16− classical monocyte | 1 |
| SOD2 | 0.77 | 1.16 | 0.54 | 0.93 | 0.68 | Mono1 | mostly CD14++CD16− classical monocyte | 0 |
| UPP1 | 0.77 | 1.40 | 0.54 | 0.81 | 0.39 | Mono1 | mostly CD14++CD16− classical monocyte | 0 |
| IER3 | 0.77 | 1.75 | 0.53 | 0.67 | 0.16 | Mono1 | mostly CD14++CD16− classical monocyte | 1 |
| C5AR1 | 0.77 | 1.07 | 0.53 | 0.89 | 0.48 | Mono1 | mostly CD14++CD16− classical monocyte | 1 |
| NLRP12 | 0.76 | 1.38 | 0.52 | 0.94 | 0.87 | Mono1 | mostly CD14++CD16− classical monocyte | 0 |
| SMA | 0.76 | 1.51 | 0.52 | 0.76 | 0.37 | Mono1 | mostly CD14++CD16− classical monocyte | 0 |

TABLE E4-continued (including parts a-e). Discriminative genes for monocyte subsets reported in FIG. 4

| Gene.ID | AUC value | Avg. Diff.[1] | Power[2] | Pct.1[3] | Pct.2[4] | Cluster ID | Associated.Cell.Population | Surface Marker[5] |
|---|---|---|---|---|---|---|---|---|
| DMXL2 | 0.76 | 1.07 | 0.51 | 0.96 | 0.65 | Mono1 | mostly CD14++CD16− classical monocyte | 1 |
| NCF1B | 0.75 | 1.08 | 0.50 | 0.82 | 0.37 | Mono1 | mostly CD14++CD16− classical monocyte | 0 |
| CREB5 | 0.75 | 1.37 | 0.50 | 0.72 | 0.29 | Mono1 | mostly CD14++CD16− classical monocyte | 0 |
| CR1 | 0.75 | 1.39 | 0.50 | 0.71 | 0.34 | Mono1 | mostly CD14++CD16− classical monocyte | 1 |
| ALDH1A1 | 0.75 | 2.62 | 0.49 | 0.55 | 0.07 | Mono1 | mostly CD14++CD16− classical monocyte | 0 |
| ASGR1 | 0.74 | 1.56 | 0.49 | 0.67 | 0.23 | Mono1 | mostly CD14++CD16− classical monocyte | 0 |
| FNDC3B | 0.74 | 1.33 | 0.48 | 0.84 | 0.63 | Mono1 | mostly CD14++CD16− classical monocyte | 1 |
| DUSP6 | 0.74 | 1.05 | 0.47 | 0.84 | 0.48 | Mono1 | mostly CD14++CD16− classical monocyte | 0 |
| TOM1 | 0.74 | 1.08 | 0.47 | 0.82 | 0.40 | Mono1 | mostly CD14++CD16− classical monocyte | 0 |
| CDC42EP3 | 0.73 | 1.24 | 0.46 | 0.78 | 0.43 | Mono1 | mostly CD14++CD16− classical monocyte | 0 |
| ZBTB16 | 0.73 | 1.69 | 0.46 | 0.70 | 0.45 | Mono1 | mostly CD14++CD16− classical monocyte | 0 |
| DYSF | 0.72 | 1.92 | 0.44 | 0.55 | 0.12 | Mono1 | mostly CD14++CD16− classical monocyte | 1 |
| KCNE3 | 0.72 | 1.19 | 0.44 | 0.77 | 0.54 | Mono1 | mostly CD14++CD16− classical monocyte | 1 |
| CD93 | 0.72 | 1.14 | 0.44 | 0.78 | 0.41 | Mono1 | mostly CD14++CD16− classical monocyte | 1 |
| CEBPD | 0.72 | 1.14 | 0.44 | 0.65 | 0.23 | Mono1 | mostly CD14++CD16− classical monocyte | 0 |
| FCGR1A | 0.72 | 1.69 | 0.44 | 0.57 | 0.15 | Mono1 | mostly CD14++CD16− classical monocyte | 1 |
| PLEKHM1 | 0.72 | 1.11 | 0.44 | 0.83 | 0.51 | Mono1 | mostly CD14++CD16− classical monocyte | 0 |
| CPM | 0.72 | 1.05 | 0.44 | 0.91 | 0.81 | Mono1 | mostly CD14++CD16− classical monocyte | 1 |
| MPP7 | 0.72 | 1.29 | 0.43 | 0.63 | 0.25 | Mono1 | mostly CD14++CD16− classical monocyte | 0 |
| AK302511 | 0.72 | 1.69 | 0.43 | 0.56 | 0.15 | Mono1 | mostly CD14++CD16− classical monocyte | 0 |
| IL1B | 0.72 | 1.76 | 0.43 | 0.60 | 0.20 | Mono1 | mostly CD14++CD16− classical monocyte | 0 |
| PFKFB3 | 0.71 | 1.09 | 0.43 | 0.75 | 0.41 | Mono1 | mostly CD14++CD16− classical monocyte | 0 |
| PLD3 | 0.71 | 1.22 | 0.42 | 0.78 | 0.61 | Mono1 | mostly CD14++CD16− classical monocyte | 1 |
| SMA3 | 0.71 | 1.08 | 0.41 | 0.84 | 0.68 | Mono1 | mostly CD14++CD16− classical monocyte | 0 |
| F13A1 | 0.71 | 1.54 | 0.41 | 0.55 | 0.17 | Mono1 | mostly CD14++CD16− classical monocyte | 1 |
| G0S2 | 0.71 | 1.57 | 0.41 | 0.58 | 0.20 | Mono1 | mostly CD14++CD16− classical monocyte | 0 |
| LOG100133161 | 0.71 | 1.26 | 0.41 | 0.72 | 0.46 | Mono1 | mostly CD14++CD16− classical monocyte | 0 |
| PHF21A | 0.70 | 1.05 | 0.41 | 0.71 | 0.37 | Mono1 | mostly CD14++CD16− classical monocyte | 0 |
| TLR8 | 0.70 | 1.07 | 0.41 | 0.66 | 0.29 | Mono1 | mostly CD14++CD16− classical monocyte | 1 |
| CLMN | 0.70 | 1.25 | 0.40 | 0.64 | 0.35 | Mono1 | mostly CD14++CD16− classical monocyte | 1 |
| TNFAIP3 | 0.70 | 1.16 | 0.40 | 0.82 | 0.56 | Mono1 part b | mostly CD14++CD16− classical monocyte | 0 |
| LAIR2 | 0.91 | 2.20 | 0.83 | 0.93 | 0.19 | Mono2 | mostly CD14+CD16++ non-classical monocyte | 0 |
| ASAH1 | 0.84 | 1.08 | 0.68 | 1.00 | 0.78 | Mono2 | mostly CD14+CD16++ non-classical monocyte | 1 |
| APOBEC3A | 0.84 | 1.67 | 0.67 | 0.92 | 0.62 | Mono2 | mostly CD14+CD16++ non-classical monocyte | 0 |
| TSPAN14 | 0.83 | 1.19 | 0.65 | 0.97 | 0.75 | Mono2 | mostly CD14+CD16++ non-classical monocyte | 1 |
| LIPA | 0.82 | 1.27 | 0.63 | 0.96 | 0.72 | Mono2 | mostly CD14+CD16++ non-classical monocyte | 1 |
| CYTIP | 0.80 | 1.05 | 0.61 | 0.99 | 0.77 | Mono2 | mostly CD14+CD16++ non-classical monocyte | 0 |
| SIGLEC10 | 0.79 | 1.07 | 0.57 | 0.98 | 0.87 | Mono2 | mostly CD14+CD16++ non-classical monocyte | 1 |
| LILRB1 | 0.78 | 1.06 | 0.57 | 0.97 | 0.73 | Mono2 | mostly CD14+CD16++ non-classical monocyte | 1 |
| EMR1 | 0.78 | 1.42 | 0.55 | 0.77 | 0.28 | Mono2 | mostly CD14+CD16++ non-classical monocyte | 1 |
| TTYH3 | 0.77 | 1.14 | 0.53 | 0.81 | 0.38 | Mono2 | mostly CD14+CD16++ non-classical monocyte | 1 |
| CAMKK2 | 0.76 | 1.08 | 0.53 | 0.88 | 0.55 | Mono2 | mostly CD14+CD16++ non-classical monocyte | 1 |
| CX3CR1 | 0.76 | 1.08 | 0.52 | 0.88 | 0.53 | Mono2 | mostly CD14+CD16++ non-classical monocyte | 1 |
| C3AR1 | 0.76 | 1.29 | 0.52 | 0.75 | 0.29 | Mono2 | mostly CD14+CD16++ non-classical monocyte | 1 |
| BC013828 | 0.76 | 1.02 | 0.51 | 0.78 | 0.29 | Mono2 | mostly CD14+CD16++ non-classical monocyte | 0 |
| RASGEF1B | 0.76 | 1.24 | 0.51 | 0.86 | 0.58 | Mono2 | mostly CD14+CD16++ non-classical monocyte | 0 |
| BIRC3 | 0.75 | 1.34 | 0.50 | 0.72 | 0.33 | Mono2 | mostly CD14+CD16++ non-classical monocyte | 0 |
| PLIN2 | 0.74 | 1.03 | 0.48 | 0.79 | 0.40 | Mono2 | mostly CD14+CD16++ non-classical monocyte | 0 |
| CD300C | 0.74 | 1.43 | 0.47 | 0.75 | 0.45 | Mono2 | mostly CD14+CD16++ non-classical monocyte | 1 |
| CD83 | 0.72 | 1.16 | 0.43 | 0.82 | 0.63 | Mono2 | mostly CD14+CD16++ non-classical monocyte | 1 |
| XYLT1 | 0.71 | 1.24 | 0.43 | 0.63 | 0.24 | Mono2 | mostly CD14+CD16++ non-classical monocyte | 0 |
| KLF2 | 0.71 | 1.34 | 0.41 | 0.58 | 0.28 | Mono2 | mostly CD14+CD16++ non-classical monocyte | 0 |
| FBP1 | 0.70 | 1.04 | 0.40 | 0.74 | 0.44 | Mono2 part c | mostly CD14+CD16++ non-classical monocyte | 0 |
| G0S2 | 0.95 | 2.47 | 0.90 | 1.00 | 0.24 | Mono3 | New population | 0 |
| NAMPT | 0.95 | 1.91 | 0.90 | 1.00 | 0.89 | Mono3 | New population | 0 |
| NEAT1 | 0.95 | 1.60 | 0.89 | 1.00 | 0.95 | Mono3 | New population | 0 |
| AL137655 | 0.94 | 1.73 | 0.88 | 1.00 | 0.64 | Mono3 | New population | 0 |
| CSF3R | 0.94 | 1.86 | 0.88 | 1.00 | 0.56 | Mono3 | New population | 1 |
| FCGR3B | 0.94 | 4.19 | 0.87 | 0.90 | 0.24 | Mono3 | New population | 1 |
| SRGN | 0.93 | 1.14 | 0.87 | 1.00 | 1.00 | Mono3 | New population | 0 |
| TREM1 | 0.93 | 1.99 | 0.86 | 1.00 | 0.36 | Mono3 | New population | 1 |
| TNFRSF10C | 0.93 | 3.53 | 0.86 | 0.90 | 0.08 | Mono3 | New population | 1 |
| MXD1 | 0.93 | 2.03 | 0.85 | 1.00 | 0.61 | Mono3 | New population | 0 |
| SOD2 | 0.93 | 1.56 | 0.85 | 1.00 | 0.71 | Mono3 | New population | 0 |
| CXCR2 | 0.92 | 3.55 | 0.84 | 0.90 | 0.25 | Mono3 | New population | 1 |
| SLC25A37 | 0.92 | 2.44 | 0.83 | 0.97 | 0.38 | Mono3 | New population | 0 |
| S100A8 | 0.91 | 1.71 | 0.83 | 1.00 | 0.47 | Mono3 | New population | 0 |
| FPR1 | 0.91 | 1.46 | 0.82 | 1.00 | 0.60 | Mono3 | New population | 1 |
| ITM2B | 0.91 | 1.21 | 0.82 | 1.00 | 0.92 | Mono3 | New population | 1 |
| MNDA | 0.91 | 1.41 | 0.81 | 1.00 | 0.81 | Mono3 | New population | 0 |
| VNN2 | 0.90 | 2.14 | 0.81 | 0.94 | 0.31 | Mono3 | New population | 1 |

TABLE E4-continued (including parts a-e). Discriminative genes for monocyte subsets reported in FIG. 4

| Gene.ID | AUC value | Avg. Diff.[1] | Power[2] | Pct.1[3] | Pct.2[4] | Cluster ID | Associated.Cell.Population | Surface Marker[5] |
|---|---|---|---|---|---|---|---|---|
| SDCBP | 0.90 | 1.25 | 0.80 | 1.00 | 0.86 | Mono3 | New population | 0 |
| CXCR1 | 0.90 | 4.16 | 0.80 | 0.81 | 0.02 | Mono3 | New population | 1 |
| S100A9 | 0.89 | 1.36 | 0.79 | 1.00 | 0.73 | Mono3 | New population | 0 |
| AQP9 | 0.89 | 2.04 | 0.78 | 0.90 | 0.22 | Mono3 | New population | 1 |
| SORL1 | 0.89 | 1.47 | 0.78 | 1.00 | 0.59 | Mono3 | New population | 1 |
| ACSL1 | 0.89 | 1.81 | 0.78 | 0.97 | 0.45 | Mono3 | New population | 1 |
| AX747598 | 0.89 | 1.72 | 0.78 | 0.94 | 0.36 | Mono3 | New population | 0 |
| R3HDM4 | 0.89 | 2.42 | 0.78 | 0.94 | 0.21 | Mono3 | New population | 0 |
| NCF1 | 0.89 | 1.54 | 0.77 | 1.00 | 0.70 | Mono3 | New population | 0 |
| IFITM2 | 0.89 | 1.31 | 0.77 | 1.00 | 0.91 | Mono3 | New population | 1 |
| FCGR2A | 0.88 | 1.58 | 0.76 | 1.00 | 0.63 | Mono3 | New population | 1 |
| XPO6 | 0.88 | 2.30 | 0.76 | 0.97 | 0.37 | Mono3 | New population | 0 |
| GCA | 0.87 | 1.59 | 0.75 | 0.97 | 0.66 | Mono3 | New population | 0 |
| C5AR1 | 0.87 | 1.29 | 0.74 | 1.00 | 0.53 | Mono3 | New population | 1 |
| TKT | 0.87 | 1.00 | 0.74 | 1.00 | 0.89 | Mono3 | New population | 0 |
| PELI1 | 0.87 | 1.66 | 0.74 | 0.97 | 0.90 | Mono3 | New population | 0 |
| SLC2A3 | 0.86 | 1.80 | 0.73 | 0.94 | 0.50 | Mono3 | New population | 1 |
| CLEC4E | 0.86 | 1.78 | 0.73 | 0.90 | 0.52 | Mono3 | New population | 1 |
| MMP25 | 0.86 | 2.76 | 0.71 | 0.74 | 0.05 | Mono3 | New population | 0 |
| GLUL | 0.86 | 1.19 | 0.71 | 1.00 | 0.75 | Mono3 | New population | 0 |
| CD14 | 0.86 | 1.35 | 0.71 | 0.94 | 0.40 | Mono3 | New population | 1 |
| LOC388312 | 0.86 | 1.68 | 0.71 | 0.94 | 0.43 | Mono3 | New population | 0 |
| NCF1C | 0.85 | 1.26 | 0.71 | 1.00 | 0.59 | Mono3 | New population | 0 |
| VMP1 | 0.85 | 1.34 | 0.71 | 1.00 | 0.72 | Mono3 | New population | 1 |
| RTN3 | 0.85 | 1.03 | 0.70 | 1.00 | 0.80 | Mono3 | New population | 1 |
| ACTN1 | 0.85 | 1.23 | 0.69 | 1.00 | 0.79 | Mono3 | New population | 1 |
| PTAFR | 0.85 | 1.47 | 0.69 | 1.00 | 0.84 | Mono3 | New population | 1 |
| S100A12 | 0.84 | 1.56 | 0.69 | 0.87 | 0.26 | Mono3 | New population | 0 |
| SEC14L1 | 0.84 | 1.71 | 0.69 | 1.00 | 0.92 | Mono3 | New population | 0 |
| DQ574721 | 0.84 | 1.90 | 0.68 | 0.87 | 0.33 | Mono3 | New population | 0 |
| LITAF | 0.84 | 1.41 | 0.68 | 1.00 | 0.82 | Mono3 | New population | 1 |
| TLR2 | 0.84 | 1.28 | 0.68 | 1.00 | 0.54 | Mono3 | New population | 1 |
| SHKBP1 | 0.84 | 1.14 | 0.67 | 1.00 | 0.74 | Mono3 | New population | 0 |
| LIMK2 | 0.84 | 2.10 | 0.67 | 0.81 | 0.21 | Mono3 | New population | 0 |
| LOC100505702 | 0.84 | 1.44 | 0.67 | 0.90 | 0.62 | Mono3 | New population | 0 |
| PYGL | 0.84 | 1.62 | 0.67 | 0.97 | 0.73 | Mono3 | New population | 0 |
| RNF24 | 0.83 | 1.30 | 0.67 | 0.90 | 0.26 | Mono3 | New population | 1 |
| DNAJC25-GNG10 | 0.83 | 1.42 | 0.66 | 0.90 | 0.65 | Mono3 | New population | 0 |
| IL8 | 0.83 | 2.19 | 0.66 | 0.77 | 0.20 | Mono3 | New population | 0 |
| FPR2 | 0.83 | 1.95 | 0.66 | 0.81 | 0.21 | Mono3 | New population | 1 |
| LOC731275 | 0.83 | 1.03 | 0.66 | 0.94 | 0.57 | Mono3 | New population | 0 |
| SLC12A6 | 0.83 | 1.80 | 0.65 | 0.97 | 0.88 | Mono3 | New population | 1 |
| IL1R2 | 0.83 | 3.28 | 0.65 | 0.71 | 0.07 | Mono3 | New population | 1 |
| VNN3 | 0.83 | 2.30 | 0.65 | 0.71 | 0.07 | Mono3 | New population | 0 |
| CFD | 0.82 | 1.02 | 0.65 | 1.00 | 0.61 | Mono3 | New population | 0 |
| VCAN | 0.82 | 1.15 | 0.65 | 0.94 | 0.51 | Mono3 | New population | 1 |
| BC013828 | 0.82 | 1.46 | 0.64 | 0.84 | 0.33 | Mono3 | New population | 0 |
| NAIP | 0.82 | 1.31 | 0.64 | 0.97 | 0.79 | Mono3 | New population | 0 |
| ZBTB16 | 0.82 | 1.41 | 0.64 | 0.90 | 0.47 | Mono3 | New population | 0 |
| BCL2A1 | 0.82 | 1.26 | 0.63 | 0.94 | 0.53 | Mono3 | New population | 0 |
| FAM129A | 0.82 | 1.77 | 0.63 | 0.94 | 0.59 | Mono3 | New population | 0 |
| PLAUR | 0.82 | 1.14 | 0.63 | 1.00 | 0.63 | Mono3 | New population | 1 |
| FNDC3B | 0.81 | 1.13 | 0.62 | 0.94 | 0.66 | Mono3 | New population | 1 |
| FP15737 | 0.81 | 2.01 | 0.62 | 0.87 | 0.62 | Mono3 | New population | 0 |
| SEPX1 | 0.81 | 1.14 | 0.62 | 0.90 | 0.53 | Mono3 | New population | 0 |
| LOC100133161 | 0.81 | 1.69 | 0.62 | 0.84 | 0.49 | Mono3 | New population | 0 |
| PER1 | 0.81 | 1.17 | 0.61 | 0.90 | 0.56 | Mono3 | New population | 0 |
| FBXL5 | 0.81 | 1.04 | 0.61 | 0.94 | 0.75 | Mono3 | New population | 0 |
| IL17RA | 0.81 | 1.13 | 0.61 | 0.97 | 0.78 | Mono3 | New population | 1 |
| TLR4 | 0.81 | 1.21 | 0.61 | 0.90 | 0.43 | Mono3 | New population | 1 |
| IGF2R | 0.80 | 1.58 | 0.61 | 0.81 | 0.28 | Mono3 | New population | 1 |
| ITGAM | 0.80 | 1.45 | 0.61 | 0.84 | 0.34 | Mono3 | New population | 1 |
| HIST1H2AC | 0.80 | 2.18 | 0.61 | 0.74 | 0.18 | Mono3 | New population | 0 |
| LRP1 | 0.80 | 1.11 | 0.60 | 0.90 | 0.57 | Mono3 | New population | 1 |
| KREMEN1 | 0.80 | 1.21 | 0.60 | 1.00 | 0.89 | Mono3 | New population | 1 |
| C12ORF35 | 0.80 | 1.41 | 0.60 | 1.00 | 0.55 | Mono3 | New population | 0 |
| PRRG4 | 0.80 | 1.00 | 0.59 | 0.97 | 0.85 | Mono3 | New population | 1 |
| CR1 | 0.80 | 1.84 | 0.59 | 0.81 | 0.39 | Mono3 | New population | 1 |
| RAB27A | 0.80 | 1.66 | 0.59 | 0.90 | 0.65 | Mono3 | New population | 0 |
| LOC100505815 | 0.79 | 1.29 | 0.59 | 0.94 | 0.70 | Mono3 | New population | 0 |
| BST1 | 0.79 | 1.40 | 0.58 | 0.84 | 0.35 | Mono3 | New population | 1 |
| NUMB | 0.79 | 1.01 | 0.58 | 0.97 | 0.76 | Mono3 | New population | 0 |
| USP15 | 0.79 | 1.30 | 0.58 | 1.00 | 0.82 | Mono3 | New population | 0 |
| CDA | 0.79 | 1.20 | 0.58 | 0.84 | 0.26 | Mono3 | New population | 0 |

TABLE E4-continued (including parts a-e). Discriminative genes for monocyte subsets reported in FIG. 4

| Gene.ID | AUC value | Avg. Diff.[1] | Power[2] | Pct.1[3] | Pct.2[4] | Cluster ID | Associated.Cell.Population | Surface Marker[5] |
|---|---|---|---|---|---|---|---|---|
| IER3 | 0.79 | 1.63 | 0.58 | 0.74 | 0.22 | Mono3 | New population | 1 |
| ACADSB | 0.79 | 1.09 | 0.57 | 0.97 | 0.85 | Mono3 | New population | 0 |
| DYSF | 0.79 | 1.14 | 0.57 | 0.74 | 0.17 | Mono3 | New population | 1 |
| PXN | 0.79 | 1.68 | 0.57 | 0.97 | 0.84 | Mono3 | New population | 0 |
| PDP2 | 0.79 | 1.17 | 0.57 | 0.97 | 0.81 | Mono3 | New population | 0 |
| TNFRSF1A | 0.78 | 1.28 | 0.57 | 0.90 | 0.72 | Mono3 | New population | 1 |
| LRG1 | 0.78 | 1.99 | 0.57 | 0.81 | 0.51 | Mono3 | New population | 0 |
| LOC91948 | 0.78 | 1.18 | 0.56 | 0.90 | 0.63 | Mono3 | New population | 0 |
| FLJ45445 | 0.78 | 1.60 | 0.56 | 0.65 | 0.12 | Mono3 | New population | 0 |
| SMAP2 | 0.78 | 1.09 | 0.56 | 0.97 | 0.63 | Mono3 | New population | 0 |
| LOC643802 | 0.78 | 2.00 | 0.55 | 0.65 | 0.12 | Mono3 | New population | 0 |
| NINJ1 | 0.78 | 1.08 | 0.55 | 0.94 | 0.48 | Mono3 | New population | 1 |
| ABTBI | 0.78 | 1.34 | 0.55 | 0.90 | 0.39 | Mono3 | New population | 0 |
| CCNY | 0.78 | 1.27 | 0.55 | 0.81 | 0.32 | Mono3 | New population | 0 |
| TMEM154 | 0.78 | 1.25 | 0.55 | 0.87 | 0.53 | Mono3 | New population | 1 |
| CCR1 | 0.77 | 1.31 | 0.55 | 0.84 | 0.34 | Mono3 | New population | 1 |
| CARD8 | 0.77 | 1.19 | 0.54 | 1.00 | 0.98 | Mono3 | New population | 0 |
| TACC3 | 0.77 | 1.59 | 0.54 | 0.74 | 0.32 | Mono3 | New population | 0 |
| TMEM71 | 0.77 | 1.69 | 0.54 | 0.74 | 0.25 | Mono3 | New population | 1 |
| PTGS2 | 0.77 | 2.06 | 0.54 | 0.71 | 0.20 | Mono3 | New population | 1 |
| HPSE | 0.77 | 1.04 | 0.54 | 0.94 | 0.81 | Mono3 | New population | 0 |
| C3ORF72 | 0.77 | 1.14 | 0.53 | 0.97 | 0.86 | Mono3 | New population | 0 |
| FAM157A | 0.77 | 1.64 | 0.53 | 0.71 | 0.30 | Mono3 | New population | 0 |
| AK130076 | 0.76 | 1.20 | 0.52 | 0.90 | 0.69 | Mono3 | New population | 0 |
| CD163 | 0.76 | 1.23 | 0.52 | 0.77 | 0.29 | Mono3 | New population | 1 |
| NBEAL2 | 0.76 | 1.14 | 0.52 | 0.87 | 0.53 | Mono3 | New population | 0 |
| IL1RAP | 0.76 | 1.58 | 0.52 | 0.61 | 0.11 | Mono3 | New population | 1 |
| GK | 0.76 | 1.86 | 0.52 | 0.71 | 0.31 | Mono3 | New population | 1 |
| AZGP1P1 | 0.76 | 1.38 | 0.51 | 0.90 | 0.72 | Mono3 | New population | 0 |
| DOK3 | 0.76 | 1.02 | 0.51 | 0.84 | 0.36 | Mono3 | New population | 0 |
| PROK2 | 0.76 | 3.80 | 0.51 | 0.55 | 0.05 | Mono3 | New population | 0 |
| FAM115C | 0.76 | 1.38 | 0.51 | 0.87 | 0.60 | Mono3 | New population | 0 |
| QPCT | 0.76 | 1.42 | 0.51 | 0.71 | 0.26 | Mono3 | New population | 0 |
| ALPL | 0.76 | 4.32 | 0.51 | 0.52 | 0.01 | Mono3 | New population | 1 |
| BEST1 | 0.75 | 1.59 | 0.51 | 0.71 | 0.38 | Mono3 | New population | 1 |
| CES3 | 0.75 | 1.09 | 0.50 | 0.84 | 0.55 | Mono3 | New population | 0 |
| CREB5 | 0.75 | 1.35 | 0.50 | 0.74 | 0.35 | Mono3 | New population | 0 |
| SPAG9 | 0.75 | 1.21 | 0.50 | 0.94 | 0.79 | Mono3 | New population | 1 |
| GPR97 | 0.75 | 3.66 | 0.50 | 0.52 | 0.02 | Mono3 | New population | 1 |
| TBL1X | 0.75 | 1.73 | 0.50 | 0.68 | 0.24 | Mono3 | New population | 0 |
| FAM198B | 0.75 | 1.19 | 0.49 | 0.77 | 0.34 | Mono3 | New population | 1 |
| FCAR | 0.75 | 1.07 | 0.49 | 0.90 | 0.78 | Mono3 | New population | 1 |
| PHF21A | 0.75 | 1.00 | 0.49 | 0.74 | 0.41 | Mono3 | New population | 0 |
| IRS2 | 0.75 | 1.50 | 0.49 | 0.68 | 0.28 | Mono3 | New population | 0 |
| CYP1B1 | 0.74 | 1.80 | 0.49 | 0.61 | 0.16 | Mono3 | New population | 1 |
| NCF1B | 0.74 | 1.13 | 0.49 | 0.84 | 0.42 | Mono3 | New population | 0 |
| BC048113 | 0.74 | 1.40 | 0.48 | 0.87 | 0.82 | Mono3 | New population | 0 |
| BACH1 | 0.74 | 1.01 | 0.48 | 0.90 | 0.60 | Mono3 | New population | 0 |
| AX747405 | 0.74 | 1.09 | 0.47 | 0.77 | 0.39 | Mono3 | New population | 0 |
| RCBTB2 | 0.74 | 1.07 | 0.47 | 0.74 | 0.32 | Mono3 | New population | 0 |
| CEBPD | 0.74 | 1.16 | 0.47 | 0.71 | 0.28 | Mono3 | New population | 0 |
| ALPK1 | 0.74 | 1.33 | 0.47 | 0.90 | 0.64 | Mono3 | New population | 1 |
| LAT2 | 0.74 | 1.02 | 0.47 | 0.84 | 0.60 | Mono3 | New population | 0 |
| OSBPL8 | 0.74 | 1.41 | 0.47 | 0.94 | 0.75 | Mono3 | New population | 1 |
| PCNX | 0.74 | 1.05 | 0.47 | 0.77 | 0.46 | Mono3 | New population | 1 |
| LPPR2 | 0.73 | 1.75 | 0.47 | 0.61 | 0.19 | Mono3 | New population | 1 |
| CCPG1 | 0.73 | 1.05 | 0.46 | 0.90 | 0.71 | Mono3 | New population | 1 |
| DOCK5 | 0.73 | 1.16 | 0.46 | 0.97 | 0.75 | Mono3 | New population | 0 |
| TUBA4A | 0.73 | 1.18 | 0.46 | 0.71 | 0.32 | Mono3 | New population | 1 |
| F2RL3 | 0.73 | 1.10 | 0.46 | 0.84 | 0.69 | Mono3 | New population | 1 |
| NCF4 | 0.73 | 1.47 | 0.46 | 0.87 | 0.51 | Mono3 | New population | 0 |
| FAM157B | 0.73 | 1.73 | 0.46 | 0.55 | 0.13 | Mono3 | New population | 0 |
| TECPR2 | 0.73 | 1.78 | 0.46 | 0.58 | 0.17 | Mono3 | New population | 0 |
| SLA | 0.73 | 1.11 | 0.45 | 0.87 | 0.54 | Mono3 | New population | 0 |
| TM6SF1 | 0.73 | 1.65 | 0.45 | 0.61 | 0.18 | Mono3 | New population | 1 |
| CRISPLD2 | 0.72 | 1.54 | 0.45 | 0.74 | 0.54 | Mono3 | New population | 0 |
| FAS | 0.72 | 1.12 | 0.44 | 0.94 | 0.74 | Mono3 | New population | 1 |
| PADI4 | 0.72 | 1.51 | 0.44 | 0.58 | 0.15 | Mono3 | New population | 0 |
| RUFY1 | 0.72 | 1.07 | 0.44 | 1.00 | 0.92 | Mono3 | New population | 0 |
| AK302511 | 0.72 | 1.58 | 0.44 | 0.58 | 0.20 | Mono3 | New population | 0 |
| PDE4B | 0.72 | 1.13 | 0.44 | 0.77 | 0.46 | Mono3 | New population | 1 |
| AK091866 | 0.72 | 2.55 | 0.43 | 0.55 | 0.19 | Mono3 | New population | 0 |
| DQ580909 | 0.72 | 1.44 | 0.43 | 0.55 | 0.12 | Mono3 | New population | 0 |
| FAM126B | 0.72 | 1.18 | 0.43 | 0.87 | 0.80 | Mono3 | New population | 0 |
| LRP10 | 0.72 | 1.19 | 0.43 | 0.77 | 0.53 | Mono3 | New population | 1 |

TABLE E4-continued (including parts a-e). Discriminative genes for monocyte subsets reported in FIG. 4

| Gene.ID | AUC value | Avg. Diff.[1] | Power[2] | Pct.1[3] | Pct.2[4] | Cluster ID | Associated.Cell.Population | Surface Marker[5] |
|---|---|---|---|---|---|---|---|---|
| PADI2 | 0.72 | 2.59 | 0.43 | 0.58 | 0.21 | Mono3 | New population | 0 |
| TRIB1 | 0.72 | 1.31 | 0.43 | 0.65 | 0.24 | Mono3 | New population | 0 |
| ZDHHC18 | 0.72 | 1.22 | 0.43 | 0.61 | 0.21 | Mono3 | New population | 1 |
| F5 | 0.71 | 1.41 | 0.43 | 0.61 | 0.26 | Mono3 | New population | 1 |
| PDLIM7 | 0.71 | 1.44 | 0.43 | 0.68 | 0.32 | Mono3 | New population | 0 |
| RBM47 | 0.71 | 1.08 | 0.43 | 0.81 | 0.48 | Mono3 | New population | 0 |
| SIRPA | 0.71 | 1.41 | 0.43 | 0.58 | 0.21 | Mono3 | New population | 1 |
| ARHGAP26 | 0.71 | 1.09 | 0.43 | 0.84 | 0.72 | Mono3 | New population | 1 |
| DSTYK | 0.71 | 1.57 | 0.43 | 0.90 | 0.81 | Mono3 | New population | 0 |
| TLR6 | 0.71 | 1.26 | 0.43 | 0.68 | 0.41 | Mono3 | New population | 1 |
| FBXL13 | 0.71 | 1.28 | 0.42 | 0.65 | 0.36 | Mono3 | New population | 0 |
| LOC649305 | 0.71 | 1.11 | 0.42 | 0.84 | 0.65 | Mono3 | New population | 0 |
| P2RY8 | 0.71 | 1.76 | 0.42 | 0.61 | 0.26 | Mono3 | New population | 1 |
| HBP1 | 0.71 | 1.01 | 0.42 | 0.90 | 0.68 | Mono3 | New population | 0 |
| SGSM1 | 0.71 | 1.06 | 0.42 | 0.71 | 0.49 | Mono3 | New population | 0 |
| ABCA1 | 0.70 | 1.80 | 0.41 | 0.55 | 0.17 | Mono3 | New population | 1 |
| SEMA4D | 0.70 | 1.24 | 0.41 | 0.68 | 0.36 | Mono3 | New population | 1 |
| ABHD5 | 0.70 | 1.50 | 0.40 | 0.61 | 0.27 | Mono3 | New population | 0 |
| MRS2P2 | 0.70 | 1.32 | 0.40 | 0.71 | 0.43 | Mono3 | New population | 0 |
| part d | | | | | | | | |
| PRF1 | 1.00 | 6.15 | 1.00 | 1.00 | 0.04 | Mono4 | New population | 1 |
| GNLY | 0.98 | 6.50 | 0.95 | 0.96 | 0.03 | Mono4 | New population | 0 |
| KLRC4-KLRK1 | 0.98 | 5.18 | 0.95 | 0.96 | 0.01 | Mono4 | New population | 1 |
| TCRBV3S1 | 0.97 | 4.33 | 0.95 | 0.96 | 0.02 | Mono4 | New population | 0 |
| CTSW | 0.97 | 3.24 | 0.95 | 1.00 | 0.13 | Mono4 | New population | 0 |
| CCL5 | 0.97 | 2.87 | 0.94 | 1.00 | 0.97 | Mono4 | New population | 1 |
| KLRD1 | 0.97 | 3.29 | 0.94 | 1.00 | 0.88 | Mono4 | New population | 1 |
| FGFBP2 | 0.96 | 5.24 | 0.91 | 0.91 | 0.01 | Mono4 | New population | 0 |
| NKG7 | 0.96 | 3.94 | 0.91 | 0.96 | 0.17 | Mono4 | New population | 1 |
| IL2RB | 0.95 | 3.84 | 0.91 | 0.91 | 0.01 | Mono4 | New population | 1 |
| SPON2 | 0.95 | 3.46 | 0.90 | 0.96 | 0.38 | Mono4 | New population | 0 |
| HOPX | 0.94 | 3.71 | 0.89 | 0.91 | 0.04 | Mono4 | New population | 0 |
| GZMA | 0.93 | 5.02 | 0.87 | 0.87 | 0.01 | Mono4 | New population | 0 |
| CST7 | 0.93 | 3.40 | 0.86 | 0.91 | 0.09 | Mono4 | New population | 0 |
| ZAP70 | 0.93 | 4.46 | 0.86 | 0.87 | 0.02 | Mono4 | New population | 0 |
| GPR56 | 0.92 | 3.61 | 0.85 | 0.87 | 0.06 | Mono4 | New population | 1 |
| SYNE2 | 0.91 | 2.58 | 0.83 | 1.00 | 0.48 | Mono4 | New population | 1 |
| KLRF1 | 0.91 | 4.59 | 0.81 | 0.83 | 0.02 | Mono4 | New population | 1 |
| GZMH | 0.91 | 4.44 | 0.81 | 0.83 | 0.02 | Mono4 | New population | 1 |
| IL32 | 0.90 | 4.19 | 0.80 | 0.87 | 0.31 | Mono4 | New population | 0 |
| TXK | 0.90 | 4.16 | 0.80 | 0.83 | 0.07 | Mono4 | New population | 0 |
| IFITM1 | 0.89 | 1.81 | 0.78 | 0.96 | 0.33 | Mono4 | New population | 1 |
| IKZF3 | 0.89 | 4.50 | 0.78 | 0.78 | 0.01 | Mono4 | New population | 0 |
| LCK | 0.89 | 3.59 | 0.77 | 0.78 | 0.01 | Mono4 | New population | 0 |
| TC2N | 0.89 | 2.71 | 0.77 | 0.78 | 0.01 | Mono4 | New population | 0 |
| S1PR5 | 0.88 | 4.22 | 0.76 | 0.78 | 0.06 | Mono4 | New population | 1 |
| S100A8 | 0.88 | 1.45 | 0.76 | 1.00 | 0.48 | Mono4 | New population | 0 |
| MCTP2 | 0.87 | 1.48 | 0.74 | 0.91 | 0.47 | Mono4 | New population | 1 |
| S100A12 | 0.87 | 1.46 | 0.74 | 0.96 | 0.27 | Mono4 | New population | 0 |
| CD96 | 0.87 | 2.72 | 0.73 | 0.83 | 0.30 | Mono4 | New population | 1 |
| SAMD3 | 0.86 | 3.89 | 0.73 | 0.74 | 0.03 | Mono4 | New population | 0 |
| TRGC2 | 0.85 | 4.32 | 0.70 | 0.78 | 0.20 | Mono4 | New population | 0 |
| TTC38 | 0.85 | 2.07 | 0.70 | 0.83 | 0.15 | Mono4 | New population | 0 |
| PXN | 0.84 | 1.38 | 0.68 | 1.00 | 0.84 | Mono4 | New population | 0 |
| S100A9 | 0.84 | 1.16 | 0.68 | 1.00 | 0.73 | Mono4 | New population | 0 |
| SH2D1B | 0.84 | 1.27 | 0.68 | 0.83 | 0.17 | Mono4 | New population | 0 |
| LAIR2 | 0.84 | 1.24 | 0.68 | 0.91 | 0.26 | Mono4 | New population | 0 |
| SYNE1 | 0.84 | 1.58 | 0.67 | 0.96 | 0.68 | Mono4 | New population | 1 |
| PRKCH | 0.83 | 2.25 | 0.67 | 0.74 | 0.07 | Mono4 | New population | 0 |
| RARRES3 | 0.83 | 1.44 | 0.66 | 0.87 | 0.25 | Mono4 | New population | 1 |
| PIK3R1 | 0.83 | 1.96 | 0.66 | 0.87 | 0.28 | Mono4 | New population | 0 |
| CCL4 | 0.83 | 2.45 | 0.65 | 0.70 | 0.04 | Mono4 | New population | 0 |
| PARP8 | 0.83 | 1.37 | 0.65 | 0.91 | 0.33 | Mono4 | New population | 0 |
| TGFBR3 | 0.83 | 2.18 | 0.65 | 0.70 | 0.10 | Mono4 | New population | 1 |
| GSTM1 | 0.82 | 1.48 | 0.65 | 0.78 | 0.16 | Mono4 | New population | 0 |
| CD2 | 0.82 | 1.85 | 0.65 | 0.78 | 0.15 | Mono4 | New population | 1 |
| CD247 | 0.82 | 4.33 | 0.65 | 0.65 | 0.01 | Mono4 | New population | 1 |
| PDE4D | 0.82 | 1.44 | 0.64 | 0.74 | 0.10 | Mono4 | New population | 0 |
| PRDM1 | 0.82 | 1.82 | 0.64 | 0.74 | 0.11 | Mono4 | New population | 0 |
| CBLB | 0.82 | 1.19 | 0.63 | 0.87 | 0.26 | Mono4 | New population | 0 |
| GIMAP1 | 0.81 | 1.33 | 0.63 | 0.87 | 0.46 | Mono4 | New population | 1 |
| BC013828 | 0.81 | 1.25 | 0.61 | 0.87 | 0.33 | Mono4 | New population | 0 |
| DENND2D | 0.80 | 1.87 | 0.60 | 0.74 | 0.13 | Mono4 | New population | 0 |
| GZMM | 0.80 | 4.04 | 0.60 | 0.61 | 0.00 | Mono4 | New population | 0 |

TABLE E4-continued (including parts a-e). Discriminative genes for monocyte subsets reported in FIG. 4

| Gene.ID | AUC value | Avg. Diff.[1] | Power[2] | Pct.1[3] | Pct.2[4] | Cluster ID | Associated.Cell.Population | Surface Marker[5] |
|---|---|---|---|---|---|---|---|---|
| SKAP1 | 0.80 | 3.55 | 0.60 | 0.61 | 0.01 | Mono4 | New population | 0 |
| TMEM41A | 0.80 | 1.16 | 0.60 | 0.96 | 0.79 | Mono4 | New population | 1 |
| KLRB1 | 0.80 | 4.42 | 0.60 | 0.61 | 0.01 | Mono4 | New population | 1 |
| PLEKHG3 | 0.80 | 1.75 | 0.60 | 0.65 | 0.05 | Mono4 | New population | 0 |
| FCRL6 | 0.80 | 2.10 | 0.60 | 0.70 | 0.12 | Mono4 | New population | 1 |
| PYHIN1 | 0.80 | 3.83 | 0.60 | 0.61 | 0.02 | Mono4 | New population | 0 |
| AAK1 | 0.80 | 1.21 | 0.60 | 1.00 | 0.89 | Mono4 | New population | 0 |
| CCR1 | 0.80 | 1.00 | 0.60 | 0.96 | 0.34 | Mono4 | New population | 1 |
| IRS2 | 0.80 | 1.36 | 0.60 | 0.83 | 0.28 | Mono4 | New population | 0 |
| STAT4 | 0.80 | 2.18 | 0.59 | 0.74 | 0.19 | Mono4 | New population | 0 |
| IL18RAP | 0.79 | 3.20 | 0.59 | 0.61 | 0.03 | Mono4 | New population | 1 |
| INADL | 0.79 | 1.53 | 0.58 | 0.91 | 0.70 | Mono4 | New population | 0 |
| DIP2A | 0.79 | 1.41 | 0.58 | 0.91 | 0.70 | Mono4 | New population | 1 |
| LOC388692 | 0.79 | 1.39 | 0.58 | 0.87 | 0.59 | Mono4 | New population | 0 |
| FAIM3 | 0.79 | 2.20 | 0.58 | 0.61 | 0.03 | Mono4 | New population | 1 |
| CD160 | 0.79 | 3.75 | 0.57 | 0.70 | 0.27 | Mono4 | New population | 1 |
| PAPD5 | 0.79 | 1.52 | 0.57 | 0.87 | 0.31 | Mono4 | New population | 0 |
| PAM | 0.78 | 1.09 | 0.57 | 0.70 | 0.12 | Mono4 | New population | 1 |
| PIK3IP1 | 0.78 | 1.24 | 0.56 | 0.87 | 0.44 | Mono4 | New population | 1 |
| PRSS23 | 0.78 | 3.99 | 0.56 | 0.57 | 0.01 | Mono4 | New population | 1 |
| PVRIG | 0.78 | 3.41 | 0.56 | 0.61 | 0.08 | Mono4 | New population | 1 |
| VNN2 | 0.78 | 1.07 | 0.56 | 0.83 | 0.31 | Mono4 | New population | 1 |
| CREB5 | 0.78 | 1.15 | 0.55 | 0.83 | 0.35 | Mono4 | New population | 0 |
| CCND2 | 0.77 | 1.38 | 0.54 | 0.65 | 0.12 | Mono4 | New population | 0 |
| RORA | 0.77 | 1.48 | 0.54 | 0.57 | 0.03 | Mono4 | New population | 0 |
| ATXN7 | 0.77 | 1.06 | 0.53 | 0.83 | 0.33 | Mono4 | New population | 0 |
| PTPN4 | 0.76 | 2.13 | 0.52 | 0.70 | 0.28 | Mono4 | New population | 0 |
| LIMK2 | 0.76 | 1.57 | 0.52 | 0.70 | 0.22 | Mono4 | New population | 0 |
| SEPX1 | 0.76 | 1.11 | 0.52 | 0.96 | 0.53 | Mono4 | New population | 0 |
| KLF12 | 0.76 | 1.32 | 0.52 | 0.70 | 0.19 | Mono4 | New population | 0 |
| TRDC | 0.76 | 4.31 | 0.52 | 0.52 | 0.01 | Mono4 | New population | 0 |
| AK094156 | 0.76 | 1.16 | 0.51 | 0.78 | 0.31 | Mono4 | New population | 0 |
| NCR3 | 0.76 | 4.03 | 0.51 | 0.52 | 0.01 | Mono4 | New population | 1 |
| KIF21B | 0.76 | 1.36 | 0.51 | 0.70 | 0.21 | Mono4 | New population | 0 |
| PTGDR | 0.76 | 3.52 | 0.51 | 0.52 | 0.01 | Mono4 | New population | 1 |
| IER3 | 0.76 | 1.10 | 0.51 | 0.74 | 0.23 | Mono4 | New population | 1 |
| ITK | 0.76 | 2.61 | 0.51 | 0.52 | 0.01 | Mono4 | New population | 0 |
| BTN3A2 | 0.75 | 1.13 | 0.51 | 0.91 | 0.72 | Mono4 | New population | 1 |
| CPD | 0.75 | 1.37 | 0.51 | 0.70 | 0.18 | Mono4 | New population | 1 |
| NCAM1 | 0.75 | 2.32 | 0.50 | 0.52 | 0.02 | Mono4 | New population | 1 |
| ZBTB16 | 0.75 | 1.11 | 0.50 | 0.78 | 0.48 | Mono4 | New population | 0 |
| RAB27A | 0.75 | 1.08 | 0.50 | 0.87 | 0.66 | Mono4 | New population | 0 |
| RUNX3 | 0.75 | 1.19 | 0.50 | 0.83 | 0.35 | Mono4 | New population | 0 |
| SLC25A37 | 0.75 | 1.47 | 0.50 | 0.78 | 0.39 | Mono4 | New population | 0 |
| SLFN13 | 0.75 | 1.26 | 0.50 | 0.74 | 0.44 | Mono4 | New population | 0 |
| GCA | 0.75 | 1.03 | 0.50 | 0.96 | 0.66 | Mono4 | New population | 0 |
| RASA3 | 0.75 | 1.06 | 0.50 | 0.74 | 0.26 | Mono4 | New population | 0 |
| IPCEF1 | 0.75 | 1.26 | 0.49 | 0.74 | 0.39 | Mono4 | New population | 0 |
| SCML4 | 0.75 | 1.51 | 0.49 | 0.87 | 0.54 | Mono4 | New population | 0 |
| NID1 | 0.75 | 1.20 | 0.49 | 0.65 | 0.16 | Mono4 | New population | 0 |
| PADI4 | 0.75 | 1.12 | 0.49 | 0.65 | 0.16 | Mono4 | New population | 0 |
| S1PR1 | 0.75 | 1.83 | 0.49 | 0.52 | 0.03 | Mono4 | New population | 1 |
| ZBTB38 | 0.74 | 1.02 | 0.49 | 0.70 | 0.22 | Mono4 | New population | 0 |
| FCGR1A | 0.74 | 1.14 | 0.48 | 0.70 | 0.20 | Mono4 | New population | 1 |
| PAR15 | 0.74 | 1.81 | 0.48 | 0.61 | 0.13 | Mono4 | New population | 0 |
| ETS1 | 0.74 | 1.16 | 0.48 | 0.57 | 0.08 | Mono4 | New population | 0 |
| LAT | 0.74 | 2.63 | 0.48 | 0.52 | 0.05 | Mono4 | New population | 1 |
| TRPM2 | 0.74 | 1.07 | 0.48 | 0.61 | 0.12 | Mono4 | New population | 1 |
| FNDC3B | 0.74 | 1.14 | 0.47 | 0.87 | 0.66 | Mono4 | New population | 1 |
| CCL3 | 0.74 | 1.66 | 0.47 | 0.61 | 0.12 | Mono4 | New population | 0 |
| CLEC4D | 0.74 | 1.62 | 0.47 | 0.57 | 0.09 | Mono4 | New population | 1 |
| OPTN | 0.73 | 1.22 | 0.47 | 0.65 | 0.30 | Mono4 | New population | 0 |
| RASSF3 | 0.73 | 1.13 | 0.47 | 0.70 | 0.27 | Mono4 | New population | 0 |
| LOC100216546 | 0.73 | 1.16 | 0.47 | 0.74 | 0.39 | Mono4 | New population | 0 |
| IL1B | 0.73 | 1.86 | 0.46 | 0.70 | 0.25 | Mono4 | New population | 0 |
| GBP5 | 0.73 | 1.47 | 0.46 | 0.70 | 0.30 | Mono4 | New population | 0 |
| ENC1 | 0.73 | 2.13 | 0.46 | 0.52 | 0.06 | Mono4 | New population | 0 |
| KLRG1 | 0.73 | 3.56 | 0.46 | 0.52 | 0.09 | Mono4 | New population | 1 |
| SYTL3 | 0.73 | 1.05 | 0.46 | 0.57 | 0.11 | Mono4 | New population | 0 |
| BC051736 | 0.73 | 1.15 | 0.45 | 0.87 | 0.69 | Mono4 | New population | 0 |
| TRAPPC10 | 0.73 | 1.12 | 0.45 | 0.74 | 0.30 | Mono4 | New population | 0 |
| LIN54 | 0.73 | 1.20 | 0.45 | 0.78 | 0.45 | Mono4 | New population | 0 |
| LOC374443 | 0.73 | 1.11 | 0.45 | 0.74 | 0.30 | Mono4 | New population | 0 |
| ZNF44 | 0.73 | 1.23 | 0.45 | 0.74 | 0.40 | Mono4 | New population | 0 |
| F2R | 0.72 | 2.81 | 0.45 | 0.70 | 0.44 | Mono4 | New population | 1 |

TABLE E4-continued (including parts a-e). Discriminative genes for monocyte subsets reported in FIG. 4

| Gene.ID | AUC value | Avg. Diff.[1] | Power[2] | Pct.1[3] | Pct.2[4] | Cluster ID | Associated.Cell.Population | Surface Marker[5] |
|---|---|---|---|---|---|---|---|---|
| TFDP2 | 0.72 | 1.01 | 0.45 | 1.00 | 0.92 | Mono4 | New population | 0 |
| CEP78 | 0.72 | 1.51 | 0.45 | 0.57 | 0.12 | Mono4 | New population | 0 |
| CXCR2 | 0.72 | 1.41 | 0.43 | 0.61 | 0.26 | Mono4 | New population | 1 |
| G0S2 | 0.72 | 1.10 | 0.43 | 0.65 | 0.25 | Mono4 | New population | 0 |
| GABARAPL1 | 0.72 | 1.05 | 0.43 | 0.70 | 0.27 | Mono4 | New population | 0 |
| TUBD1 | 0.72 | 1.89 | 0.43 | 0.61 | 0.22 | Mono4 | New population | 0 |
| PDPR | 0.72 | 1.31 | 0.43 | 0.70 | 0.32 | Mono4 | New population | 0 |
| DQ573668 | 0.71 | 1.22 | 0.42 | 0.83 | 0.62 | Mono4 | New population | 0 |
| FXYD6-FXYD2 | 0.71 | 1.41 | 0.42 | 0.52 | 0.09 | Mono4 | New population | 1 |
| BRF2 | 0.71 | 1.30 | 0.42 | 0.52 | 0.09 | Mono4 | New population | 0 |
| SLAMF6 | 0.71 | 2.82 | 0.42 | 0.57 | 0.26 | Mono4 | New population | 1 |
| CREM | 0.71 | 1.12 | 0.42 | 0.57 | 0.14 | Mono4 | New population | 0 |
| TGIF1 | 0.71 | 1.13 | 0.42 | 0.57 | 0.15 | Mono4 | New population | 0 |
| SLFN5 | 0.71 | 1.35 | 0.41 | 0.61 | 0.22 | Mono4 | New population | 0 |
| ARHGAP24 | 0.71 | 1.06 | 0.41 | 0.57 | 0.16 | Mono4 | New population | 0 |
| ZMYM5 | 0.71 | 1.01 | 0.41 | 0.78 | 0.45 | Mono4 | New population | 1 |
| ZNF276 | 0.71 | 1.08 | 0.41 | 0.78 | 0.50 | Mono4 | New population | 0 |
| SUPV3L1 | 0.71 | 1.14 | 0.41 | 0.61 | 0.19 | Mono4 | New population | 0 |
| FAM190B | 0.70 | 1.05 | 0.41 | 0.70 | 0.43 | Mono4 | New population | 0 |
| LPIN1 | 0.70 | 1.10 | 0.40 | 0.70 | 0.41 | Mono4 | New population | 0 |
| | | | | | | part e | | |
| CLEC9A | 0.99 | 5.13 | 0.97 | 0.98 | 0.04 | DC1 | CD141/CLEC9A | 1 |
| C1ORF54 | 0.98 | 4.40 | 0.97 | 0.98 | 0.07 | DC1 | CD141/CLEC9A | 0 |
| HLA-DPA1 | 0.98 | 1.42 | 0.97 | 1.00 | 0.97 | DC1 | CD141/CLEC9A | 1 |
| CADM1 | 0.97 | 4.82 | 0.94 | 0.95 | 0.04 | DC1 | CD141/CLEC9A | 1 |
| HLA-DPB2 | 0.97 | 1.49 | 0.94 | 1.00 | 0.96 | DC1 | CD141/CLEC9A | 1 |
| WDFY4 | 0.97 | 2.18 | 0.93 | 1.00 | 0.63 | DC1 | CD141/CLEC9A | 1 |
| CPVL | 0.96 | 1.90 | 0.93 | 0.99 | 0.84 | DC1 | CD141/CLEC9A | 1 |
| CD74 | 0.96 | 1.08 | 0.92 | 1.00 | 1.00 | DC1 | CD141/CLEC9A | 1 |
| HLA-DPB1 | 0.96 | 1.66 | 0.92 | 1.00 | 0.75 | DC1 | CD141/CLEC9A | 1 |
| CPNE3 | 0.96 | 1.91 | 0.91 | 1.00 | 0.57 | DC1 | CD141/CLEC9A | 0 |
| HLA-DQB1 | 0.96 | 1.63 | 0.91 | 1.00 | 0.92 | DC1 | CD141/CLEC9A | 1 |
| HLA-DQB | 0.96 | 1.60 | 0.91 | 1.00 | 0.86 | DC1 | CD141/CLEC9A | 1 |
| CAMK2D | 0.95 | 2.43 | 0.91 | 0.98 | 0.30 | DC1 | CD141/CLEC9A | 1 |
| IDO1 | 0.95 | 4.90 | 0.91 | 0.96 | 0.44 | DC1 | CD141/CLEC9A | 0 |
| HLA-DOB | 0.95 | 2.77 | 0.90 | 0.98 | 0.46 | DC1 | CD141/CLEC9A | 1 |
| LOC645638 | 0.95 | 3.45 | 0.90 | 0.92 | 0.07 | DC1 | CD141/CLEC9A | 0 |
| HLA-DRB1 | 0.94 | 1.17 | 0.89 | 1.00 | 1.00 | DC1 | CD141/CLEC9A | 1 |
| HLA-DRA | 0.94 | 1.03 | 0.87 | 1.00 | 1.00 | DC1 | CD141/CLEC9A | 1 |
| SNX3 | 0.93 | 1.75 | 0.86 | 0.99 | 0.52 | DC1 | CD141/CLEC9A | 0 |
| NDRG2 | 0.93 | 1.92 | 0.86 | 0.99 | 0.29 | DC1 | CD141/CLEC9A | 1 |
| HLA-DRB5 | 0.92 | 1.12 | 0.84 | 1.00 | 0.98 | DC1 | CD141/CLEC9A | 1 |
| HLA-DQA1 | 0.92 | 1.25 | 0.84 | 1.00 | 0.83 | DC1 | CD141/CLEC9A | 1 |
| HLA-DQA2 | 0.91 | 1.40 | 0.82 | 1.00 | 0.59 | DC1 | CD141/CLEC9A | 1 |
| ZNF366 | 0.91 | 3.08 | 0.82 | 0.87 | 0.08 | DC1 | CD141/CLEC9A | 0 |
| KIAA1598 | 0.91 | 1.64 | 0.82 | 0.99 | 0.61 | DC1 | CD141/CLEC9A | 0 |
| CLNK | 0.91 | 3.18 | 0.82 | 0.95 | 0.47 | DC1 | CD141/CLEC9A | 0 |
| HLA-DRB4 | 0.91 | 1.20 | 0.81 | 1.00 | 0.78 | DC1 | CD141/CLEC9A | 1 |
| CSRP1 | 0.90 | 1.78 | 0.81 | 0.98 | 0.45 | DC1 | CD141/CLEC9A | 0 |
| CYB5R3 | 0.89 | 1.42 | 0.78 | 1.00 | 0.78 | DC1 | CD141/CLEC9A | 1 |
| FLT3 | 0.89 | 1.60 | 0.78 | 0.97 | 0.30 | DC1 | CD141/CLEC9A | 1 |
| RGS10 | 0.89 | 1.47 | 0.77 | 0.98 | 0.56 | DC1 | CD141/CLEC9A | 0 |
| DQ-A1 | 0.88 | 1.39 | 0.77 | 0.98 | 0.43 | DC1 | CD141/CLEC9A | 0 |
| SLAMF7 | 0.88 | 1.38 | 0.76 | 1.00 | 0.70 | DC1 | CD141/CLEC9A | 1 |
| FAM190A | 0.88 | 2.76 | 0.76 | 0.84 | 0.17 | DC1 | CD141/CLEC9A | 0 |
| CST3 | 0.88 | 1.10 | 0.76 | 1.00 | 0.99 | DC1 | CD141/CLEC9A | 0 |
| ENPP1 | 0.88 | 2.71 | 0.76 | 0.94 | 0.73 | DC1 | CD141/CLEC9A | 1 |
| AX747832 | 0.88 | 4.04 | 0.75 | 0.77 | 0.02 | DC1 | CD141/CLEC9A | 0 |
| BTLA | 0.88 | 1.92 | 0.75 | 0.86 | 0.11 | DC1 | CD141/CLEC9A | 1 |
| XCR1 | 0.87 | 4.81 | 0.74 | 0.75 | 0.03 | DC1 | CD141/CLEC9A | 1 |
| SLAMF8 | 0.87 | 3.15 | 0.74 | 0.79 | 0.09 | DC1 | CD141/CLEC9A | 1 |
| DHRS3 | 0.87 | 2.80 | 0.74 | 0.79 | 0.09 | DC1 | CD141/CLEC9A | 1 |
| TMEM14A | 0.87 | 2.57 | 0.73 | 0.80 | 0.07 | DC1 | CD141/CLEC9A | 1 |
| GCET2 | 0.87 | 3.64 | 0.73 | 0.76 | 0.05 | DC1 | CD141/CLEC9A | 0 |
| CD59 | 0.87 | 2.24 | 0.73 | 0.84 | 0.24 | DC1 | CD141/CLEC9A | 1 |
| PPA1 | 0.86 | 1.35 | 0.73 | 0.98 | 0.49 | DC1 | CD141/CLEC9A | 0 |
| ADAM28 | 0.86 | 1.94 | 0.72 | 0.88 | 0.24 | DC1 | CD141/CLEC9A | 1 |
| FNBP1 | 0.85 | 1.22 | 0.70 | 0.99 | 0.89 | DC1 | CD141/CLEC9A | 0 |
| NET1 | 0.85 | 2.49 | 0.70 | 0.78 | 0.11 | DC1 | CD141/CLEC9A | 0 |
| BATF3 | 0.84 | 1.65 | 0.69 | 0.85 | 0.20 | DC1 | CD141/CLEC9A | 0 |
| HLA-DRB6 | 0.84 | 1.23 | 0.68 | 0.95 | 0.49 | DC1 | CD141/CLEC9A | 1 |
| ASAP1 | 0.84 | 1.10 | 0.68 | 0.98 | 0.48 | DC1 | CD141/CLEC9A | 0 |
| IRF8 | 0.84 | 1.00 | 0.67 | 1.00 | 0.89 | DC1 | CD141/CLEC9A | 0 |
| VAC14 | 0.83 | 2.11 | 0.65 | 0.77 | 0.17 | DC1 | CD141/CLEC9A | 0 |

TABLE E4-continued (including parts a-e). Discriminative genes for monocyte subsets reported in FIG. 4

| Gene.ID | AUC value | Avg. Diff.[1] | Power[2] | Pct.1[3] | Pct.2[4] | Cluster ID | Associated.Cell.Population | Surface Marker[5] |
|---|---|---|---|---|---|---|---|---|
| CCND1 | 0.82 | 3.88 | 0.64 | 0.65 | 0.02 | DC1 | CD141/CLEC9A | 0 |
| C1ORF21 | 0.82 | 1.89 | 0.63 | 0.66 | 0.04 | DC1 | CD141/CLEC9A | 0 |
| GYPC | 0.82 | 1.37 | 0.63 | 0.84 | 0.25 | DC1 | CD141/CLEC9A | 1 |
| DNASE1L3 | 0.81 | 2.53 | 0.62 | 0.78 | 0.31 | DC1 | CD141/CLEC9A | 0 |
| TLR10 | 0.81 | 2.04 | 0.62 | 0.84 | 0.45 | DC1 | CD141/CLEC9A | 1 |
| APOL3 | 0.81 | 1.47 | 0.61 | 0.83 | 0.32 | DC1 | CD141/CLEC9A | 0 |
| DST | 0.80 | 1.33 | 0.61 | 0.85 | 0.31 | DC1 | CD141/CLEC9A | 0 |
| NCALD | 0.80 | 3.22 | 0.60 | 0.63 | 0.04 | DC1 | CD141/CLEC9A | 0 |
| ASB2 | 0.80 | 2.51 | 0.60 | 0.66 | 0.09 | DC1 | CD141/CLEC9A | 0 |
| THBD | 0.80 | 1.34 | 0.59 | 0.78 | 0.22 | DC1 | CD141/CLEC9A | 1 |
| LRRC18 | 0.80 | 2.02 | 0.59 | 0.66 | 0.08 | DC1 | CD141/CLEC9A | 0 |
| PON2 | 0.80 | 1.02 | 0.59 | 0.86 | 0.28 | DC1 | CD141/CLEC9A | 1 |
| RAB7L1 | 0.80 | 1.02 | 0.59 | 0.98 | 0.67 | DC1 | CD141/CLEC9A | 0 |
| HAVCR2 | 0.79 | 1.18 | 0.59 | 0.96 | 0.77 | DC1 | CD141/CLEC9A | 1 |
| VAV3 | 0.79 | 1.58 | 0.59 | 0.76 | 0.23 | DC1 | CD141/CLEC9A | 0 |
| KIF16B | 0.79 | 1.73 | 0.58 | 0.71 | 0.16 | DC1 | CD141/CLEC9A | 0 |
| CLIC2 | 0.79 | 1.16 | 0.58 | 0.82 | 0.26 | DC1 | CD141/CLEC9A | 0 |
| DENND1B | 0.79 | 1.45 | 0.57 | 0.74 | 0.20 | DC1 | CD141/CLEC9A | 1 |
| PIK3CB | 0.77 | 1.40 | 0.54 | 0.74 | 0.24 | DC1 | CD141/CLEC9A | 0 |
| B3GNT7 | 0.76 | 2.26 | 0.53 | 0.62 | 0.13 | DC1 | CD141/CLEC9A | 0 |
| PTK2 | 0.76 | 1.87 | 0.52 | 0.63 | 0.12 | DC1 | CD141/CLEC9A | 0 |
| DPP4 | 0.76 | 2.21 | 0.52 | 0.57 | 0.06 | DC1 | CD141/CLEC9A | 1 |
| GSTM4 | 0.76 | 1.10 | 0.52 | 0.82 | 0.38 | DC1 | CD141/CLEC9A | 0 |
| LACC1 | 0.76 | 1.58 | 0.52 | 0.66 | 0.16 | DC1 | CD141/CLEC9A | 0 |
| TRERF1 | 0.76 | 1.03 | 0.52 | 0.79 | 0.31 | DC1 | CD141/CLEC9A | 0 |
| MTERFD3 | 0.76 | 2.63 | 0.51 | 0.55 | 0.05 | DC1 | CD141/CLEC9A | 0 |
| NAV1 | 0.76 | 1.23 | 0.51 | 0.95 | 0.79 | DC1 | CD141/CLEC9A | 0 |
| CTTNBP2NL | 0.75 | 1.61 | 0.51 | 0.65 | 0.18 | DC1 | CD141/CLEC9A | 0 |
| CYP2S1 | 0.75 | 1.28 | 0.50 | 0.68 | 0.18 | DC1 | CD141/CLEC9A | 1 |
| PLEKHM3 | 0.75 | 1.02 | 0.50 | 0.86 | 0.55 | DC1 | CD141/CLEC9A | 0 |
| CCDC6 | 0.75 | 1.05 | 0.50 | 0.77 | 0.29 | DC1 | CD141/CLEC9A | 0 |
| LIMA1 | 0.75 | 2.27 | 0.50 | 0.56 | 0.08 | DC1 | CD141/CLEC9A | 0 |
| OSBPL9 | 0.75 | 1.00 | 0.50 | 0.86 | 0.44 | DC1 | CD141/CLEC9A | 0 |
| SERPINF2 | 0.75 | 1.23 | 0.49 | 0.65 | 0.16 | DC1 | CD141/CLEC9A | 0 |
| LMNA | 0.75 | 1.22 | 0.49 | 0.69 | 0.22 | DC1 | CD141/CLEC9A | 1 |
| P2RY6 | 0.74 | 1.01 | 0.49 | 0.70 | 0.21 | DC1 | CD141/CLEC9A | 1 |
| CYP2E1 | 0.74 | 3.37 | 0.49 | 0.56 | 0.13 | DC1 | CD141/CLEC9A | 0 |
| EGLN3 | 0.74 | 1.26 | 0.49 | 0.63 | 0.15 | DC1 | CD141/CLEC9A | 0 |
| ITGB7 | 0.74 | 1.07 | 0.48 | 0.69 | 0.22 | DC1 | CD141/CLEC9A | 1 |
| IDO2 | 0.74 | 2.82 | 0.48 | 0.88 | 0.73 | DC1 | CD141/CLEC9A | 0 |
| VOPP1 | 0.74 | 1.11 | 0.47 | 0.73 | 0.30 | DC1 | CD141/CLEC9A | 1 |
| FCRL6 | 0.74 | 2.85 | 0.47 | 0.52 | 0.06 | DC1 | CD141/CLEC9A | 1 |
| LYRM4 | 0.74 | 1.03 | 0.47 | 0.88 | 0.61 | DC1 | CD141/CLEC9A | 0 |
| AGPAT1 | 0.73 | 1.10 | 0.46 | 0.71 | 0.31 | DC1 | CD141/CLEC9A | 1 |
| BC015662 | 0.73 | 1.05 | 0.46 | 0.68 | 0.25 | DC1 | CD141/CLEC9A | 0 |
| SLC9A9 | 0.73 | 1.03 | 0.46 | 0.73 | 0.29 | DC1 | CD141/CLEC9A | 1 |
| PDE4DIP | 0.73 | 1.26 | 0.45 | 0.66 | 0.24 | DC1 | CD141/CLEC9A | 0 |
| CD38 | 0.73 | 1.40 | 0.45 | 0.58 | 0.15 | DC1 | CD141/CLEC9A | 1 |
| NSMAF | 0.72 | 1.08 | 0.44 | 0.72 | 0.33 | DC1 | CD141/CLEC9A | 0 |
| OSBPL3 | 0.72 | 1.11 | 0.44 | 0.61 | 0.18 | DC1 | CD141/CLEC9A | 0 |
| PLCD1 | 0.72 | 1.77 | 0.43 | 0.53 | 0.11 | DC1 | CD141/CLEC9A | 0 |
| PPM1M | 0.71 | 1.13 | 0.43 | 0.65 | 0.25 | DC1 | CD141/CLEC9A | 0 |
| LOC541471 | 0.71 | 1.04 | 0.43 | 0.65 | 0.24 | DC1 | CD141/CLEC9A | 0 |
| DUSP2 | 0.71 | 1.23 | 0.42 | 0.60 | 0.21 | DC1 | CD141/CLEC9A | 0 |
| INF2 | 0.70 | 1.05 | 0.40 | 0.54 | 0.15 | DC1 | CD141/CLEC9A | 0 |
| ACSS2 | 0.70 | 1.23 | 0.40 | 0.58 | 0.21 | DC1 | CD141/CLEC9A | 1 |
| CD1C | 0.95 | 3.20 | 0.89 | 0.94 | 0.20 | DC2 | CD1C_A | 1 |
| FCER1A | 0.92 | 2.10 | 0.83 | 0.95 | 0.35 | DC2 | CD1C_A | 1 |
| CLEC10A | 0.89 | 2.35 | 0.79 | 0.90 | 0.21 | DC2 | CD1C_A | 1 |
| HLA-DQA1 | 0.89 | 1.18 | 0.77 | 1.00 | 0.85 | DC2 | CD1C_A | 1 |
| HLA-DQA2 | 0.88 | 1.29 | 0.75 | 1.00 | 0.62 | DC2 | CD1C_A | 1 |
| HLA-DQB | 0.86 | 1.13 | 0.72 | 0.99 | 0.87 | DC2 | CD1C_A | 1 |
| HLA-DRB4 | 0.85 | 1.01 | 0.71 | 1.00 | 0.80 | DC2 | CD1C_A | 1 |
| DQ-A1 | 0.85 | 1.30 | 0.69 | 0.93 | 0.47 | DC2 | CD1C_A | 0 |
| HLA-DQB1 | 0.85 | 1.02 | 0.69 | 0.99 | 0.93 | DC2 | CD1C_A | 1 |
| NDRG2 | 0.82 | 1.18 | 0.63 | 0.92 | 0.34 | DC2 | CD1C_A | 1 |
| ADAM8 | 0.80 | 1.38 | 0.61 | 0.87 | 0.36 | DC2 | CD1C_A | 1 |
| CLIC2 | 0.79 | 1.43 | 0.57 | 0.81 | 0.30 | DC2 | CD1C_A | 0 |
| FCGR2B | 0.79 | 2.71 | 0.57 | 0.68 | 0.20 | DC2 | CD1C_A | 1 |
| HLA-DOA | 0.78 | 1.14 | 0.56 | 0.92 | 0.64 | DC2 | CD1C_A | 1 |
| PEA15 | 0.75 | 1.10 | 0.50 | 0.87 | 0.47 | DC2 | CD1C_A | 0 |
| NR4A2 | 0.74 | 1.14 | 0.49 | 0.81 | 0.43 | DC2 | CD1C_A | 0 |
| CD1E | 0.74 | 3.20 | 0.48 | 0.51 | 0.05 | DC2 | CD1C_A | 1 |
| AGPAT9 | 0.73 | 1.37 | 0.46 | 0.69 | 0.26 | DC2 | CD1C_A | 1 |
| C10ORF128 | 0.73 | 2.33 | 0.46 | 0.53 | 0.09 | DC2 | CD1C_A | 1 |

TABLE E4-continued (including parts a-e). Discriminative genes for monocyte subsets reported in FIG. 4

| Gene.ID | AUC value | Avg. Diff.[1] | Power[2] | Pct.1[3] | Pct.2[4] | Cluster ID | Associated.Cell.Population | Surface Marker[5] |
|---|---|---|---|---|---|---|---|---|
| ALCAM | 0.73 | 1.01 | 0.45 | 0.76 | 0.35 | DC2 | CD1C_A | 1 |
| CACNA2D3 | 0.71 | 1.22 | 0.42 | 0.92 | 0.73 | DC2 | CD1C_A | 1 |
| CD2 | 0.70 | 1.42 | 0.41 | 0.52 | 0.12 | DC2 | CD1C_A | 1 |
| PON2 | 0.70 | 1.22 | 0.41 | 0.69 | 0.33 | DC2 | CD1C_A | 1 |
| FCER1A | 0.91 | 1.77 | 0.83 | 0.99 | 0.36 | DC3 | CD1C_B | 1 |
| RNASE2 | 0.86 | 2.46 | 0.72 | 0.81 | 0.14 | DC3 | CD1C_B | 0 |
| CLEC10A | 0.84 | 1.68 | 0.68 | 0.84 | 0.22 | DC3 | CD1C_B | 1 |
| CD1C | 0.84 | 1.04 | 0.68 | 0.87 | 0.21 | DC3 | CD1C_B | 1 |
| RETN | 0.78 | 1.67 | 0.55 | 0.70 | 0.18 | DC3 | CD1C_B | 0 |
| CD1D | 0.78 | 1.34 | 0.55 | 0.83 | 0.45 | DC3 | CD1C_B | 1 |
| CES1 | 0.78 | 1.77 | 0.55 | 0.68 | 0.18 | DC3 | CD1C_B | 1 |
| F13A1 | 0.76 | 1.68 | 0.52 | 0.67 | 0.19 | DC3 | CD1C_B | 1 |
| PID1 | 0.75 | 1.29 | 0.50 | 0.72 | 0.24 | DC3 | CD1C_B | 0 |
| NR4A2 | 0.75 | 1.15 | 0.50 | 0.83 | 0.43 | DC3 | CD1C_B | 0 |
| MGST1 | 0.75 | 1.17 | 0.49 | 0.73 | 0.29 | DC3 | CD1C_B | 1 |
| ADAM15 | 0.72 | 1.16 | 0.43 | 0.71 | 0.33 | DC3 | CD1C_B | 1 |
| IL13RA1 | 0.71 | 1.23 | 0.43 | 0.75 | 0.43 | DC3 | CD1C_B | 1 |
| CES1P1 | 0.71 | 1.02 | 0.41 | 0.53 | 0.12 | DC3 | CD1C_B | 0 |
| FCGR2B | 0.70 | 1.05 | 0.41 | 0.59 | 0.21 | DC3 | CD1C_B | 1 |
| HBEGF | 0.70 | 1.73 | 0.40 | 0.51 | 0.11 | DC3 | CD1C_B | 1 |
| FCGR3A | 0.99 | 2.56 | 0.97 | 1.00 | 0.48 | DC4 | CD1C⁻CD141⁻ | 1 |
| LST1 | 0.97 | 1.67 | 0.94 | 1.00 | 0.82 | DC4 | CD1C⁻CD141⁻ | 1 |
| AK307192 | 0.95 | 2.62 | 0.89 | 0.96 | 0.35 | DC4 | CD1C⁻CD141⁻ | 0 |
| AIF1 | 0.94 | 1.39 | 0.89 | 1.00 | 0.85 | DC4 | CD1C⁻CD141⁻ | 0 |
| IFITM3 | 0.94 | 1.83 | 0.88 | 1.00 | 0.84 | DC4 | CD1C⁻CD141⁻ | 1 |
| MTSS1 | 0.93 | 2.23 | 0.86 | 0.99 | 0.28 | DC4 | CD1C⁻CD141⁻ | 0 |
| TCF7L2 | 0.93 | 2.47 | 0.85 | 0.97 | 0.26 | DC4 | CD1C⁻CD141⁻ | 0 |
| MS4A7 | 0.92 | 1.83 | 0.83 | 0.99 | 0.63 | DC4 | CD1C⁻CD141⁻ | 1 |
| SERPINA1 | 0.91 | 1.35 | 0.82 | 1.00 | 0.71 | DC4 | CD1C⁻CD141⁻ | 1 |
| FTL | 0.90 | 1.01 | 0.80 | 1.00 | 1.00 | DC4 | CD1C⁻CD141⁻ | 0 |
| CSF1R | 0.90 | 1.54 | 0.80 | 1.00 | 0.66 | DC4 | CD1C⁻CD141⁻ | 1 |
| SAT1 | 0.90 | 1.16 | 0.80 | 1.00 | 0.97 | DC4 | CD1C⁻CD141⁻ | 0 |
| CTSL1 | 0.90 | 2.54 | 0.79 | 0.90 | 0.26 | DC4 | CD1C⁻CD141⁻ | 1 |
| LOC200772 | 0.89 | 3.84 | 0.78 | 0.81 | 0.06 | DC4 | CD1C⁻CD141⁻ | 0 |
| LILRB2 | 0.89 | 1.34 | 0.78 | 1.00 | 0.72 | DC4 | CD1C⁻CD141⁻ | 1 |
| RHOC | 0.89 | 1.74 | 0.78 | 0.96 | 0.63 | DC4 | CD1C⁻CD141⁻ | 0 |
| LRRC25 | 0.89 | 1.27 | 0.77 | 1.00 | 0.84 | DC4 | CD1C⁻CD141⁻ | 1 |
| PECAM1 | 0.88 | 1.38 | 0.75 | 1.00 | 0.91 | DC4 | CD1C⁻CD141⁻ | 1 |
| IFITM2 | 0.88 | 1.09 | 0.75 | 1.00 | 0.90 | DC4 | CD1C⁻CD141⁻ | 1 |
| LY6E | 0.87 | 1.59 | 0.75 | 0.98 | 0.60 | DC4 | CD1C⁻CD141⁻ | 1 |
| SIDT2 | 0.87 | 1.92 | 0.74 | 0.93 | 0.40 | DC4 | CD1C⁻CD141⁻ | 1 |
| FAM110A | 0.87 | 2.18 | 0.74 | 0.87 | 0.26 | DC4 | CD1C⁻CD141⁻ | 0 |
| PTPN6 | 0.86 | 1.04 | 0.73 | 1.00 | 0.90 | DC4 | CD1C⁻CD141⁻ | 0 |
| WARS | 0.86 | 1.28 | 0.73 | 1.00 | 0.89 | DC4 | CD1C⁻CD141⁻ | 0 |
| TMEM176B | 0.86 | 2.80 | 0.72 | 0.80 | 0.16 | DC4 | CD1C⁻CD141⁻ | 1 |
| SIGLEC10 | 0.86 | 1.50 | 0.71 | 0.98 | 0.86 | DC4 | CD1C⁻CD141⁻ | 1 |
| PIERA | 0.85 | 1.25 | 0.70 | 1.00 | 0.58 | DC4 | CD1C⁻CD141⁻ | 1 |
| LILRA2 | 0.85 | 1.31 | 0.70 | 1.00 | 0.71 | DC4 | CD1C⁻CD141⁻ | 1 |
| OAS1 | 0.84 | 1.33 | 0.68 | 0.97 | 0.58 | DC4 | CD1C⁻CD141⁻ | 0 |
| CD52 | 0.84 | 1.09 | 0.67 | 0.97 | 0.76 | DC4 | CD1C⁻CD141⁻ | 1 |
| ABI3 | 0.83 | 1.38 | 0.66 | 0.95 | 0.52 | DC4 | CD1C⁻CD141⁻ | 0 |
| EMR2 | 0.83 | 1.55 | 0.66 | 0.93 | 0.61 | DC4 | CD1C⁻CD141⁻ | 1 |
| MAFB | 0.83 | 1.64 | 0.66 | 0.87 | 0.31 | DC4 | CD1C⁻CD141⁻ | 0 |
| TNFRSF1B | 0.83 | 1.12 | 0.66 | 0.98 | 0.77 | DC4 | CD1C⁻CD141⁻ | 1 |
| LYST | 0.83 | 1.08 | 0.66 | 1.00 | 0.66 | DC4 | CD1C⁻CD141⁻ | 0 |
| CD79B | 0.83 | 2.06 | 0.65 | 0.79 | 0.22 | DC4 | CD1C⁻CD141⁻ | 1 |
| TNFSF10 | 0.83 | 1.68 | 0.65 | 0.93 | 0.54 | DC4 | CD1C⁻CD141⁻ | 1 |
| BIN2 | 0.82 | 1.10 | 0.65 | 0.98 | 0.73 | DC4 | CD1C⁻CD141⁻ | 0 |
| HMOX1 | 0.82 | 1.66 | 0.64 | 0.89 | 0.44 | DC4 | CD1C⁻CD141⁻ | 1 |
| FCGR2C | 0.81 | 1.59 | 0.63 | 0.86 | 0.36 | DC4 | CD1C⁻CD141⁻ | 0 |
| FAM26F | 0.80 | 1.40 | 0.61 | 0.87 | 0.43 | DC4 | CD1C⁻CD141⁻ | 1 |
| ITGAL | 0.80 | 1.07 | 0.61 | 0.99 | 0.87 | DC4 | CD1C⁻CD141⁻ | 1 |
| TSC22D3 | 0.80 | 1.01 | 0.60 | 0.99 | 0.82 | DC4 | CD1C⁻CD141⁻ | 0 |
| TAGLN | 0.80 | 2.23 | 0.59 | 0.72 | 0.20 | DC4 | CD1C⁻CD141⁻ | 0 |
| GBP2 | 0.79 | 1.32 | 0.59 | 0.86 | 0.38 | DC4 | CD1C⁻CD141⁻ | 0 |
| GIMAP4 | 0.79 | 1.26 | 0.59 | 0.89 | 0.44 | DC4 | CD1C⁻CD141⁻ | 1 |
| CDKN1C | 0.79 | 2.17 | 0.59 | 0.68 | 0.12 | DC4 | CD1C⁻CD141⁻ | 0 |
| PTP4A3 | 0.79 | 2.24 | 0.58 | 0.68 | 0.13 | DC4 | CD1C⁻CD141⁻ | 0 |
| HK3 | 0.79 | 1.04 | 0.58 | 0.90 | 0.43 | DC4 | CD1C⁻CD141⁻ | 0 |
| CD97 | 0.79 | 1.13 | 0.57 | 0.98 | 0.75 | DC4 | CD1C⁻CD141⁻ | 1 |
| CD300LF | 0.78 | 1.35 | 0.57 | 0.86 | 0.46 | DC4 | CD1C⁻CD141⁻ | 1 |
| HSPA7 | 0.78 | 1.91 | 0.57 | 0.73 | 0.24 | DC4 | CD1C⁻CD141⁻ | 0 |
| SH2D1B | 0.78 | 2.98 | 0.56 | 0.63 | 0.09 | DC4 | CD1C⁻CD141⁻ | 0 |
| NFKBIZ | 0.78 | 1.01 | 0.56 | 0.98 | 0.78 | DC4 | CD1C⁻CD141⁻ | 0 |
| NEURL | 0.78 | 2.25 | 0.56 | 0.67 | 0.15 | DC4 | CD1C⁻CD141⁻ | 0 |

TABLE E4-continued (including parts a-e). Discriminative genes for monocyte subsets reported in FIG. 4

| Gene.ID | AUC value | Avg. Diff.[1] | Power[2] | Pct.1[3] | Pct.2[4] | Cluster ID | Associated.Cell.Population | Surface Marker[5] |
|---|---|---|---|---|---|---|---|---|
| GPBAR1 | 0.78 | 1.63 | 0.56 | 0.76 | 0.32 | DC4 | CD1C−CD141− | 1 |
| SLC31A2 | 0.78 | 1.34 | 0.56 | 0.87 | 0.52 | DC4 | CD1C−CD141− | 1 |
| CX3CR1 | 0.77 | 1.20 | 0.55 | 0.89 | 0.50 | DC4 | CD1C−CD141− | 1 |
| DRAP1 | 0.77 | 1.05 | 0.54 | 0.87 | 0.50 | DC4 | CD1C−CD141− | 0 |
| MS4A4A | 0.77 | 1.99 | 0.53 | 0.71 | 0.28 | DC4 | CD1C−CD141− | 1 |
| IFITM1 | 0.76 | 1.45 | 0.53 | 0.74 | 0.26 | DC4 | CD1C−CD141− | 1 |
| LILRA5 | 0.76 | 1.18 | 0.53 | 0.88 | 0.50 | DC4 | CD1C−CD141− | 1 |
| ICAM2 | 0.76 | 1.39 | 0.53 | 0.81 | 0.44 | DC4 | CD1C−CD141− | 1 |
| IFIT3 | 0.76 | 2.03 | 0.52 | 0.84 | 0.62 | DC4 | CD1C−CD141− | 0 |
| WSB1 | 0.76 | 1.05 | 0.52 | 0.95 | 0.87 | DC4 | CD1C−CD141− | 0 |
| PIK3AP1 | 0.75 | 1.25 | 0.51 | 0.89 | 0.56 | DC4 | CD1C−CD141− | 0 |
| TESC | 0.75 | 2.47 | 0.51 | 0.60 | 0.13 | DC4 | CD1C−CD141− | 0 |
| POU2F2 | 0.75 | 1.27 | 0.50 | 0.86 | 0.53 | DC4 | CD1C−CD141− | 0 |
| SPN | 0.75 | 1.21 | 0.50 | 0.98 | 0.99 | DC4 | CD1C−CD141− | 1 |
| INSIG1 | 0.74 | 1.52 | 0.49 | 0.74 | 0.36 | DC4 | CD1C−CD141− | 1 |
| EMR1 | 0.74 | 1.24 | 0.48 | 0.71 | 0.25 | DC4 | CD1C−CD141− | 1 |
| MARCKS | 0.74 | 1.63 | 0.47 | 0.73 | 0.36 | DC4 | CD1C−CD141− | 1 |
| NDUFB3 | 0.74 | 1.02 | 0.47 | 0.90 | 0.72 | DC4 | CD1C−CD141− | 1 |
| CKB | 0.74 | 3.08 | 0.47 | 0.51 | 0.06 | DC4 | CD1C−CD141− | 0 |
| CLEC4F | 0.74 | 2.44 | 0.47 | 0.55 | 0.10 | DC4 | CD1C−CD141− | 1 |
| CALML4 | 0.73 | 1.28 | 0.47 | 0.73 | 0.32 | DC4 | CD1C−CD141− | 0 |
| PHTF2 | 0.73 | 1.28 | 0.46 | 0.75 | 0.41 | DC4 | CD1C−CD141− | 1 |
| IFR6 | 0.73 | 1.05 | 0.46 | 0.73 | 0.32 | DC4 | CD1C−CD141− | 1 |
| ISG15 | 0.73 | 1.10 | 0.46 | 0.80 | 0.50 | DC4 | CD1C−CD141− | 0 |
| DKFZP451J181 | 0.73 | 1.24 | 0.46 | 0.83 | 0.52 | DC4 | CD1C−CD141− | 0 |
| CHST15 | 0.73 | 1.20 | 0.45 | 0.76 | 0.36 | DC4 | CD1C−CD141− | 1 |
| ICAM4 | 0.73 | 2.04 | 0.45 | 0.68 | 0.31 | DC4 | CD1C−CD141− | 1 |
| C11ORF21 | 0.73 | 1.54 | 0.45 | 0.69 | 0.36 | DC4 | CD1C−CD141− | 0 |
| AK124399 | 0.72 | 2.04 | 0.44 | 0.50 | 0.07 | DC4 | CD1C−CD141− | 0 |
| PRAM1 | 0.72 | 1.13 | 0.44 | 0.76 | 0.44 | DC4 | CD1C−CD141− | 0 |
| P2RX1 | 0.72 | 1.22 | 0.44 | 0.76 | 0.46 | DC4 | CD1C−CD141− | 1 |
| CDH23 | 0.72 | 1.30 | 0.43 | 0.86 | 0.61 | DC4 | CD1C−CD141− | 1 |
| DPEP2 | 0.71 | 1.25 | 0.42 | 0.72 | 0.37 | DC4 | CD1C−CD141− | 1 |
| MT2A | 0.71 | 1.22 | 0.42 | 0.72 | 0.37 | DC4 | CD1C−CD141− | 0 |
| C20ORF112 | 0.71 | 1.29 | 0.42 | 0.74 | 0.41 | DC4 | CD1C−CD141− | 0 |
| GBP4 | 0.71 | 1.67 | 0.42 | 0.93 | 0.84 | DC4 | CD1C−CD141− | 0 |
| VAMP5 | 0.71 | 1.54 | 0.41 | 0.61 | 0.29 | DC4 | CD1C−CD141− | 1 |
| GRAMD1A | 0.70 | 1.42 | 0.41 | 0.68 | 0.32 | DC4 | CD1C−CD141− | 1 |
| AXL | 1.00 | 3.87 | 1.00 | 1.00 | 0.84 | DC5 | New population: AXL+SIGLEC6+ | 1 |
| PPP1R14A | 0.99 | 3.67 | 0.98 | 1.00 | 0.07 | DC5 | New population: AXL+SIGLEC6+ | 0 |
| SIGLEC6 | 0.97 | 3.96 | 0.94 | 0.97 | 0.10 | DC5 | New population: AXL+SIGLEC6+ | 1 |
| CD22 | 0.95 | 3.30 | 0.90 | 0.93 | 0.10 | DC5 | New population: AXL+SIGLEC6+ | 1 |
| DAB2 | 0.93 | 2.26 | 0.86 | 0.97 | 0.24 | DC5 | New population: AXL+SIGLEC6+ | 0 |
| S100A10 | 0.93 | 1.10 | 0.85 | 1.00 | 0.92 | DC5 | New population: AXL+SIGLEC6+ | 1 |
| FAM105A | 0.90 | 1.67 | 0.80 | 1.00 | 0.59 | DC5 | New population: AXL+SIGLEC6+ | 1 |
| LGMN | 0.90 | 1.57 | 0.79 | 1.00 | 0.49 | DC5 | New population: AXL+SIGLEC6+ | 1 |
| PLAC8 | 0.88 | 1.29 | 0.76 | 1.00 | 0.91 | DC5 | New population: AXL+SIGLEC6+ | 0 |
| IRF4 | 0.88 | 1.45 | 0.75 | 0.97 | 0.34 | DC5 | New population: AXL+SIGLEC6+ | 0 |
| DPYSL2 | 0.87 | 1.12 | 0.74 | 1.00 | 0.92 | DC5 | New population: AXL+SIGLEC6+ | 0 |
| MED12L | 0.87 | 2.24 | 0.74 | 0.80 | 0.08 | DC5 | New population: AXL+SIGLEC6+ | 0 |
| LILRA4 | 0.87 | 1.32 | 0.74 | 0.97 | 0.41 | DC5 | New population: AXL+SIGLEC6+ | 1 |
| SLC41A2 | 0.86 | 1.51 | 0.73 | 0.93 | 0.37 | DC5 | New population: AXL+SIGLEC6+ | 1 |
| LTK | 0.86 | 2.55 | 0.72 | 0.77 | 0.06 | DC5 | New population: AXL+SIGLEC6+ | 1 |
| SEPT5 | 0.86 | 1.55 | 0.72 | 0.97 | 0.60 | DC5 | New population: AXL+SIGLEC6+ | 0 |
| CYBASC3 | 0.85 | 1.16 | 0.71 | 1.00 | 0.58 | DC5 | New population: AXL+SIGLEC6+ | 0 |
| SCN9A | 0.85 | 1.72 | 0.70 | 0.87 | 0.31 | DC5 | New population: AXL+SIGLEC6+ | 1 |
| MYO1E | 0.84 | 1.81 | 0.69 | 0.87 | 0.32 | DC5 | New population: AXL+SIGLEC6+ | 0 |
| ARL4C | 0.84 | 1.13 | 0.67 | 1.00 | 0.55 | DC5 | New population: AXL+SIGLEC6+ | 0 |
| GPR183 | 0.83 | 1.02 | 0.66 | 1.00 | 0.65 | DC5 | New population: AXL+SIGLEC6+ | 1 |
| RUNX2 | 0.83 | 1.40 | 0.65 | 0.90 | 0.34 | DC5 | New population: AXL+SIGLEC6+ | 0 |
| C12ORF75 | 0.83 | 1.12 | 0.65 | 0.90 | 0.24 | DC5 | New population: AXL+SIGLEC6+ | 0 |
| VASH1 | 0.83 | 1.71 | 0.65 | 0.83 | 0.33 | DC5 | New population: AXL+SIGLEC6+ | 0 |
| NDRG1 | 0.82 | 1.39 | 0.65 | 0.87 | 0.39 | DC5 | New population: AXL+SIGLEC6+ | 0 |
| SIGLEC1 | 0.82 | 2.21 | 0.65 | 0.73 | 0.12 | DC5 | New population: AXL+SIGLEC6+ | 1 |
| SNRNP25 | 0.82 | 1.57 | 0.64 | 0.87 | 0.35 | DC5 | New population: AXL+SIGLEC6+ | 0 |
| PPA1 | 0.81 | 1.07 | 0.63 | 0.97 | 0.55 | DC5 | New population: AXL+SIGLEC6+ | 0 |
| BHLHE40 | 0.81 | 1.28 | 0.62 | 0.97 | 0.60 | DC5 | New population: AXL+SIGLEC6+ | 0 |
| SLAMF7 | 0.81 | 1.06 | 0.62 | 0.97 | 0.74 | DC5 | New population: AXL+SIGLEC6+ | 1 |
| CD5 | 0.80 | 3.47 | 0.60 | 0.63 | 0.05 | DC5 | New population: AXL+SIGLEC6+ | 1 |
| USF2 | 0.80 | 1.37 | 0.59 | 0.83 | 0.31 | DC5 | New population: AXL+SIGLEC6+ | 0 |
| APEX1 | 0.79 | 1.15 | 0.58 | 0.93 | 0.66 | DC5 | New population: AXL+SIGLEC6+ | 0 |
| ATF5 | 0.79 | 1.28 | 0.58 | 0.77 | 0.19 | DC5 | New population: AXL+SIGLEC6+ | 0 |
| KLF4 | 0.79 | 1.19 | 0.58 | 0.93 | 0.56 | DC5 | New population: AXL+SIGLEC6+ | 0 |
| CLEC4C | 0.79 | 1.04 | 0.57 | 0.80 | 0.26 | DC5 | New population: AXL+SIGLEC6+ | 1 |
| SLC35C2 | 0.78 | 1.32 | 0.57 | 0.87 | 0.42 | DC5 | New population: AXL+SIGLEC6+ | 1 |

TABLE E4-continued (including parts a-e). Discriminative genes for monocyte subsets reported in FIG. 4

| Gene.ID | AUC value | Avg. Diff.[1] | Power[2] | Pct.1[3] | Pct.2[4] | Cluster ID | Associated.Cell.Population | Surface Marker[5] |
|---|---|---|---|---|---|---|---|---|
| ARHGAP18 | 0.78 | 1.54 | 0.55 | 0.73 | 0.26 | DC5 | New population: AXL+SIGLEC6+ | 0 |
| THBD | 0.77 | 1.40 | 0.55 | 0.77 | 0.30 | DC5 | New population: AXL+SIGLEC6+ | 1 |
| ANTXR2 | 0.77 | 1.19 | 0.55 | 0.90 | 0.56 | DC5 | New population: AXL+SIGLEC6+ | 1 |
| FAM129A | 0.77 | 1.13 | 0.54 | 0.90 | 0.59 | DC5 | New population: AXL+SIGLEC6+ | 0 |
| SLC20A1 | 0.77 | 1.15 | 0.53 | 0.90 | 0.61 | DC5 | New population: AXL+SIGLEC6+ | 1 |
| UPK3A | 0.77 | 1.96 | 0.53 | 0.67 | 0.21 | DC5 | New population: AXL+SIGLEC6+ | 1 |
| CXCR3 | 0.76 | 1.07 | 0.53 | 0.77 | 0.26 | DC5 | New population: AXL+SIGLEC6+ | 1 |
| ENTPD7 | 0.76 | 1.68 | 0.52 | 0.77 | 0.32 | DC5 | New population: AXL+SIGLEC6+ | 1 |
| CDH1 | 0.76 | 2.53 | 0.52 | 0.73 | 0.44 | DC5 | New population: AXL+SIGLEC6+ | 1 |
| GPR146 | 0.76 | 3.79 | 0.52 | 0.53 | 0.02 | DC5 | New population: AXL+SIGLEC6+ | 1 |
| BAIAP2 | 0.75 | 1.55 | 0.50 | 0.67 | 0.22 | DC5 | New population: AXL+SIGLEC6+ | 0 |
| TXN | 0.75 | 1.44 | 0.50 | 0.90 | 0.67 | DC5 | New population: AXL+SIGLEC6+ | 0 |
| STX18 | 0.74 | 1.21 | 0.49 | 0.77 | 0.37 | DC5 | New population: AXL+SIGLEC6+ | 1 |
| LPXN | 0.74 | 1.08 | 0.48 | 0.90 | 0.59 | DC5 | New population: AXL+SIGLEC6+ | 0 |
| CLIC2 | 0.74 | 1.09 | 0.48 | 0.73 | 0.34 | DC5 | New population: AXL+SIGLEC6+ | 0 |
| CD72 | 0.74 | 2.16 | 0.47 | 0.57 | 0.13 | DC5 | New population: AXL+SIGLEC6+ | 1 |
| SOX4 | 0.74 | 1.44 | 0.47 | 0.80 | 0.54 | DC5 | New population: AXL+SIGLEC6+ | 0 |
| HIP1 | 0.73 | 1.19 | 0.47 | 0.97 | 0.81 | DC5 | New population: AXL+SIGLEC6+ | 0 |
| PON2 | 0.73 | 1.10 | 0.46 | 0.73 | 0.36 | DC5 | New population: AXL+SIGLEC6+ | 1 |
| PRDX2 | 0.73 | 1.17 | 0.46 | 0.73 | 0.33 | DC5 | New population: AXL+SIGLEC6+ | 0 |
| CTSW | 0.73 | 1.24 | 0.46 | 0.60 | 0.14 | DC5 | New population: AXL+SIGLEC6+ | 0 |
| ATP2B4 | 0.73 | 1.36 | 0.46 | 0.80 | 0.46 | DC5 | New population: AXL+SIGLEC6+ | 1 |
| TNNI2 | 0.73 | 1.43 | 0.45 | 0.60 | 0.18 | DC5 | New population: AXL+SIGLEC6+ | 0 |
| GNAQ | 0.72 | 1.01 | 0.45 | 0.83 | 0.54 | DC5 | New population: AXL+SIGLEC6+ | 0 |
| SLC2A1 | 0.72 | 1.09 | 0.45 | 0.73 | 0.34 | DC5 | New population: AXL+SIGLEC6+ | 1 |
| PTGDS | 0.72 | 2.23 | 0.44 | 0.53 | 0.11 | DC5 | New population: AXL+SIGLEC6+ | 0 |
| TSEN54 | 0.72 | 1.46 | 0.44 | 0.60 | 0.18 | DC5 | New population: AXL+SIGLEC6+ | 0 |
| MGLL | 0.72 | 1.31 | 0.44 | 0.67 | 0.30 | DC5 | New population: AXL+SIGLEC6+ | 0 |
| CXCR2 | 0.72 | 2.02 | 0.44 | 0.60 | 0.26 | DC5 | New population: AXL+SIGLEC6+ | 1 |
| SUSD1 | 0.72 | 1.41 | 0.43 | 0.60 | 0.23 | DC5 | New population: AXL+SIGLEC6+ | 1 |
| GGTA1P | 0.71 | 2.01 | 0.43 | 0.53 | 0.13 | DC5 | New population: AXL+SIGLEC6+ | 0 |
| KLF12 | 0.71 | 1.15 | 0.42 | 0.60 | 0.19 | DC5 | New population: AXL+SIGLEC6+ | 0 |
| ST14 | 0.71 | 1.15 | 0.42 | 0.63 | 0.24 | DC5 | New population: AXL+SIGLEC6+ | 1 |
| BIN1 | 0.71 | 1.52 | 0.41 | 0.57 | 0.20 | DC5 | New population: AXL+SIGLEC6+ | 0 |
| AK125727 | 0.70 | 1.41 | 0.41 | 0.80 | 0.71 | DC5 | New population: AXL+SIGLEC6+ | 0 |
| ZNF789 | 0.70 | 1.36 | 0.40 | 0.57 | 0.20 | DC5 | New population: AXL+SIGLEC6+ | 0 |
| GZMB | 1.00 | 5.69 | 0.99 | 0.99 | 0.18 | DC6 | pDC | 0 |
| IGJ | 1.00 | 5.47 | 0.99 | 0.99 | 0.17 | DC6 | pDC | 0 |
| SERPINF1 | 1.00 | 3.33 | 0.99 | 1.00 | 0.32 | DC6 | pDC | 1 |
| AK128525 | 0.99 | 4.64 | 0.99 | 0.99 | 0.12 | DC6 | pDC | 0 |
| PLD4 | 0.99 | 2.86 | 0.99 | 1.00 | 0.57 | DC6 | pDC | 1 |
| ITM2C | 0.99 | 3.88 | 0.98 | 0.99 | 0.24 | DC6 | pDC | 1 |
| CCDC50 | 0.99 | 3.43 | 0.98 | 0.99 | 0.44 | DC6 | pDC | 0 |
| IRF7 | 0.99 | 3.18 | 0.98 | 0.99 | 0.52 | DC6 | pDC | 0 |
| TCF4 | 0.99 | 3.33 | 0.98 | 1.00 | 0.37 | DC6 | pDC | 0 |
| PTPRS | 0.98 | 3.27 | 0.97 | 0.99 | 0.46 | DC6 | pDC | 1 |
| ALOX5AP | 0.98 | 2.81 | 0.97 | 0.99 | 0.35 | DC6 | pDC | 1 |
| BCL11A | 0.98 | 2.49 | 0.97 | 1.00 | 0.59 | DC6 | pDC | 0 |
| PLAC8 | 0.98 | 2.35 | 0.96 | 0.99 | 0.90 | DC6 | pDC | 0 |
| LILRA4 | 0.98 | 3.70 | 0.96 | 0.99 | 0.32 | DC6 | pDC | 1 |
| C12ORF75 | 0.98 | 3.62 | 0.96 | 0.98 | 0.13 | DC6 | pDC | 0 |
| CYBASC3 | 0.98 | 2.86 | 0.95 | 0.99 | 0.51 | DC6 | pDC | 0 |
| UGCG | 0.97 | 3.80 | 0.94 | 0.97 | 0.13 | DC6 | pDC | 1 |
| MZB1 | 0.97 | 4.66 | 0.94 | 0.95 | 0.05 | DC6 | pDC | 0 |
| FAM129C | 0.96 | 3.55 | 0.93 | 0.99 | 0.72 | DC6 | pDC | 0 |
| DERL3 | 0.96 | 4.96 | 0.92 | 0.93 | 0.03 | DC6 | pDC | 1 |
| SPIB | 0.96 | 3.15 | 0.92 | 0.98 | 0.86 | DC6 | pDC | 0 |
| SMPD3 | 0.96 | 4.13 | 0.91 | 0.93 | 0.14 | DC6 | pDC | 1 |
| TSPAN13 | 0.96 | 3.97 | 0.91 | 0.93 | 0.07 | DC6 | pDC | 1 |
| ZFAT | 0.96 | 3.70 | 0.91 | 0.95 | 0.22 | DC6 | pDC | 0 |
| CLEC4C | 0.96 | 3.72 | 0.91 | 0.94 | 0.15 | DC6 | pDC | 1 |
| IRF8 | 0.95 | 1.77 | 0.91 | 1.00 | 0.89 | DC6 | pDC | 0 |
| IL3RA | 0.95 | 2.73 | 0.91 | 0.97 | 0.29 | DC6 | pDC | 1 |
| NRP1 | 0.95 | 4.02 | 0.90 | 0.94 | 0.22 | DC6 | pDC | 1 |
| CLIC3 | 0.95 | 3.78 | 0.90 | 0.93 | 0.11 | DC6 | pDC | 0 |
| LIME1 | 0.95 | 3.88 | 0.90 | 0.92 | 0.08 | DC6 | pDC | 0 |
| SPCS1 | 0.95 | 1.78 | 0.89 | 0.98 | 0.76 | DC6 | pDC | 1 |
| C1ORF186 | 0.95 | 2.20 | 0.89 | 0.98 | 0.27 | DC6 | pDC | 1 |
| HIGD1A | 0.94 | 2.09 | 0.89 | 1.00 | 0.75 | DC6 | pDC | 1 |
| SEC61B | 0.94 | 1.61 | 0.88 | 0.99 | 0.73 | DC6 | pDC | 1 |
| BLNK | 0.94 | 3.20 | 0.87 | 0.93 | 0.14 | DC6 | pDC | 0 |
| NPC1 | 0.93 | 2.66 | 0.86 | 0.97 | 0.33 | DC6 | pDC | 1 |
| TNFRSF21 | 0.93 | 3.20 | 0.86 | 0.92 | 0.17 | DC6 | pDC | 1 |
| IRF4 | 0.93 | 2.78 | 0.86 | 0.95 | 0.25 | DC6 | pDC | 0 |
| HERPUD1 | 0.93 | 1.60 | 0.85 | 0.99 | 0.89 | DC6 | pDC | 1 |

TABLE E4-continued (including parts a-e). Discriminative genes for monocyte subsets reported in FIG. 4

| Gene.ID | AUC value | Avg. Diff.[1] | Power[2] | Pct.1[3] | Pct.2[4] | Cluster ID | Associated.Cell.Population | Surface Marker[5] |
|---|---|---|---|---|---|---|---|---|
| RUNX2 | 0.93 | 2.55 | 0.85 | 0.95 | 0.25 | DC6 | pDC | 0 |
| HSP90B1 | 0.92 | 1.37 | 0.85 | 1.00 | 0.88 | DC6 | pDC | 1 |
| CD164 | 0.92 | 1.50 | 0.85 | 0.98 | 0.90 | DC6 | pDC | 1 |
| TXN | 0.92 | 1.89 | 0.85 | 0.97 | 0.62 | DC6 | pDC | 0 |
| SLC15A4 | 0.92 | 2.90 | 0.84 | 0.92 | 0.24 | DC6 | pDC | 1 |
| RNASE6 | 0.92 | 1.87 | 0.83 | 0.97 | 0.49 | DC6 | pDC | 0 |
| SSR4 | 0.91 | 1.38 | 0.83 | 0.99 | 0.81 | DC6 | pDC | 1 |
| STMN1 | 0.91 | 2.85 | 0.83 | 0.94 | 0.52 | DC6 | pDC | 0 |
| PLP2 | 0.91 | 1.38 | 0.82 | 1.00 | 0.77 | DC6 | pDC | 1 |
| NPC2 | 0.91 | 1.08 | 0.82 | 0.99 | 0.96 | DC6 | pDC | 0 |
| OGT | 0.91 | 1.75 | 0.82 | 1.00 | 0.77 | DC6 | pDC | 0 |
| PTPRCAP | 0.91 | 3.37 | 0.81 | 0.86 | 0.16 | DC6 | pDC | 0 |
| GPR114 | 0.91 | 4.14 | 0.81 | 0.83 | 0.07 | DC6 | pDC | 1 |
| IGFLR1 | 0.91 | 1.44 | 0.81 | 0.98 | 0.68 | DC6 | pDC | 1 |
| SELS | 0.91 | 2.36 | 0.81 | 0.94 | 0.42 | DC6 | pDC | 0 |
| GPR183 | 0.90 | 1.92 | 0.81 | 0.98 | 0.60 | DC6 | pDC | 1 |
| APP | 0.90 | 2.42 | 0.80 | 0.95 | 0.53 | DC6 | pDC | 1 |
| LAMP5 | 0.90 | 3.75 | 0.80 | 0.83 | 0.05 | DC6 | pDC | 1 |
| MAP1A | 0.89 | 3.82 | 0.78 | 0.80 | 0.04 | DC6 | pDC | 0 |
| PPIB | 0.89 | 1.10 | 0.78 | 0.99 | 0.95 | DC6 | pDC | 1 |
| IDH3A | 0.89 | 1.78 | 0.78 | 0.95 | 0.59 | DC6 | pDC | 0 |
| PFKFB2 | 0.89 | 2.75 | 0.77 | 0.87 | 0.19 | DC6 | pDC | 0 |
| EPHB1 | 0.88 | 3.70 | 0.77 | 0.81 | 0.10 | DC6 | pDC | 1 |
| KIAA0226L | 0.88 | 2.17 | 0.77 | 0.91 | 0.26 | DC6 | pDC | 0 |
| OFD1 | 0.88 | 2.24 | 0.77 | 0.93 | 0.34 | DC6 | pDC | 0 |
| MYBL2 | 0.88 | 3.73 | 0.76 | 0.78 | 0.02 | DC6 | pDC | 0 |
| PTCRA | 0.88 | 4.57 | 0.76 | 0.79 | 0.08 | DC6 | pDC | 1 |
| AUG30 | 0.88 | 2.97 | 0.76 | 0.84 | 0.20 | DC6 | pDC | 0 |
| PLXNA4 | 0.88 | 3.37 | 0.76 | 0.78 | 0.04 | DC6 | pDC | 1 |
| NUCB2 | 0.88 | 2.28 | 0.75 | 0.99 | 0.90 | DC6 | pDC | 0 |
| FMNL3 | 0.87 | 2.51 | 0.74 | 0.84 | 0.19 | DC6 | pDC | 0 |
| SNRPN | 0.87 | 2.19 | 0.74 | 0.89 | 0.41 | DC6 | pDC | 0 |
| LOC285972 | 0.87 | 4.12 | 0.74 | 0.86 | 0.41 | DC6 | pDC | 0 |
| C10ORF118 | 0.87 | 2.18 | 0.73 | 0.88 | 0.42 | DC6 | pDC | 0 |
| SLA2 | 0.86 | 3.84 | 0.73 | 0.85 | 0.38 | DC6 | pDC | 0 |
| AK093551 | 0.86 | 1.64 | 0.73 | 0.93 | 0.39 | DC6 | pDC | 0 |
| BC051760 | 0.86 | 2.45 | 0.73 | 0.86 | 0.30 | DC6 | pDC | 0 |
| C9ORF142 | 0.86 | 1.72 | 0.73 | 0.93 | 0.51 | DC6 | pDC | 0 |
| ST6GALNAC4 | 0.86 | 2.73 | 0.72 | 0.81 | 0.16 | DC6 | pDC | 1 |
| VAMP8 | 0.86 | 1.05 | 0.72 | 0.97 | 0.86 | DC6 | pDC | 1 |
| NOTCH4 | 0.86 | 2.32 | 0.72 | 0.97 | 0.76 | DC6 | pDC | 1 |
| GAPT | 0.86 | 1.95 | 0.71 | 0.91 | 0.47 | DC6 | pDC | 0 |
| P2RY14 | 0.86 | 2.20 | 0.71 | 0.86 | 0.25 | DC6 | pDC | 1 |
| DCK | 0.86 | 2.02 | 0.71 | 0.90 | 0.40 | DC6 | pDC | 0 |
| SIDT1 | 0.86 | 3.81 | 0.71 | 0.78 | 0.17 | DC6 | pDC | 1 |
| ADAM19 | 0.85 | 1.79 | 0.71 | 0.91 | 0.35 | DC6 | pDC | 1 |
| LGMN | 0.85 | 1.89 | 0.71 | 0.90 | 0.42 | DC6 | pDC | 1 |
| RABGAP1L | 0.85 | 1.42 | 0.71 | 0.99 | 0.95 | DC6 | pDC | 1 |
| TRAF4 | 0.85 | 2.89 | 0.71 | 0.75 | 0.08 | DC6 | pDC | 0 |
| LILRB4 | 0.85 | 1.63 | 0.70 | 0.94 | 0.65 | DC6 | pDC | 1 |
| SLC38A1 | 0.85 | 1.62 | 0.70 | 0.96 | 0.64 | DC6 | pDC | 1 |
| DAB2 | 0.85 | 2.17 | 0.70 | 0.81 | 0.16 | DC6 | pDC | 0 |
| PARK7 | 0.85 | 1.05 | 0.70 | 0.97 | 0.88 | DC6 | pDC | 0 |
| TPM2 | 0.85 | 4.31 | 0.70 | 0.72 | 0.05 | DC6 | pDC | 0 |
| CXCR3 | 0.85 | 2.67 | 0.70 | 0.79 | 0.18 | DC6 | pDC | 1 |
| B4GALT1 | 0.85 | 1.51 | 0.70 | 0.97 | 0.80 | DC6 | pDC | 1 |
| CARD11 | 0.85 | 3.12 | 0.70 | 0.75 | 0.10 | DC6 | pDC | 0 |
| RNASET2 | 0.85 | 1.16 | 0.70 | 0.97 | 0.86 | DC6 | pDC | 0 |
| PACSIN1 | 0.84 | 3.35 | 0.69 | 0.69 | 0.02 | DC6 | pDC | 0 |
| TMEM109 | 0.84 | 1.48 | 0.69 | 0.94 | 0.58 | DC6 | pDC | 1 |
| ZDHHC17 | 0.84 | 2.08 | 0.68 | 0.85 | 0.30 | DC6 | pDC | 1 |
| EIF4A3 | 0.84 | 1.68 | 0.67 | 0.90 | 0.55 | DC6 | pDC | 0 |
| PPP1R14B | 0.83 | 2.99 | 0.67 | 0.72 | 0.09 | DC6 | pDC | 0 |
| SCAMP5 | 0.83 | 3.93 | 0.67 | 0.68 | 0.02 | DC6 | pDC | 1 |
| TRAM1 | 0.83 | 1.25 | 0.66 | 0.95 | 0.80 | DC6 | pDC | 1 |
| TSPAN3 | 0.83 | 1.82 | 0.66 | 0.87 | 0.48 | DC6 | pDC | 1 |
| SCN9A | 0.83 | 2.49 | 0.66 | 0.79 | 0.23 | DC6 | pDC | 1 |
| PPM1K | 0.83 | 2.54 | 0.66 | 0.86 | 0.46 | DC6 | pDC | 0 |
| PPM1J | 0.83 | 2.40 | 0.66 | 0.76 | 0.16 | DC6 | pDC | 0 |
| USP24 | 0.83 | 1.80 | 0.66 | 0.92 | 0.42 | DC6 | pDC | 0 |
| ERN1 | 0.82 | 2.00 | 0.65 | 0.74 | 0.14 | DC6 | pDC | 1 |
| TLR7 | 0.82 | 2.55 | 0.65 | 0.83 | 0.43 | DC6 | pDC | 1 |
| ERP29 | 0.82 | 1.13 | 0.65 | 0.95 | 0.80 | DC6 | pDC | 0 |
| FCHSD2 | 0.82 | 1.84 | 0.65 | 0.89 | 0.40 | DC6 | pDC | 0 |
| TMED10 | 0.82 | 1.10 | 0.63 | 0.98 | 0.85 | DC6 | pDC | 1 |

TABLE E4-continued (including parts a-e). Discriminative genes for monocyte subsets reported in FIG. 4

| Gene.ID | AUC value | Avg. Diff.[1] | Power[2] | Pct.1[3] | Pct.2[4] | Cluster ID | Associated.Cell.Population | Surface Marker[5] |
|---|---|---|---|---|---|---|---|---|
| LOC644961 | 0.81 | 1.25 | 0.63 | 0.93 | 0.65 | DC6 | pDC | 0 |
| ABHD15 | 0.81 | 3.19 | 0.63 | 0.80 | 0.42 | DC6 | pDC | 0 |
| NGLY1 | 0.81 | 1.75 | 0.62 | 0.88 | 0.46 | DC6 | pDC | 1 |
| OVOS2 | 0.81 | 3.46 | 0.62 | 0.68 | 0.13 | DC6 | pDC | 0 |
| KIAA0226 | 0.81 | 1.53 | 0.62 | 0.97 | 0.76 | DC6 | pDC | 0 |
| ARL4C | 0.81 | 1.35 | 0.61 | 0.90 | 0.50 | DC6 | pDC | 0 |
| CDCA7L | 0.81 | 2.76 | 0.61 | 0.69 | 0.16 | DC6 | pDC | 0 |
| NCF1C | 0.81 | 1.13 | 0.61 | 0.94 | 0.54 | DC6 | pDC | 0 |
| ABPARTS | 0.81 | 1.13 | 0.61 | 0.98 | 0.83 | DC6 | pDC | 0 |
| IFI44L | 0.80 | 1.98 | 0.61 | 0.78 | 0.32 | DC6 | pDC | 0 |
| LDHB | 0.80 | 1.08 | 0.60 | 0.95 | 0.71 | DC6 | pDC | 0 |
| SLC2A1 | 0.80 | 2.21 | 0.60 | 0.76 | 0.27 | DC6 | pDC | 1 |
| CNP | 0.80 | 1.54 | 0.60 | 0.88 | 0.56 | DC6 | pDC | 0 |
| PDIA4 | 0.80 | 1.53 | 0.60 | 0.86 | 0.55 | DC6 | pDC | 0 |
| SIT1 | 0.80 | 3.91 | 0.59 | 0.61 | 0.03 | DC6 | pDC | 1 |
| FAM160A1 | 0.80 | 2.43 | 0.59 | 0.64 | 0.06 | DC6 | pDC | 0 |
| C17ORF109 | 0.80 | 4.41 | 0.59 | 0.60 | 0.02 | DC6 | pDC | 0 |
| FLNB | 0.80 | 1.80 | 0.59 | 0.78 | 0.28 | DC6 | pDC | 0 |
| COBLL1 | 0.79 | 3.37 | 0.59 | 0.79 | 0.46 | DC6 | pDC | 0 |
| GPM6B | 0.79 | 4.14 | 0.59 | 0.61 | 0.04 | DC6 | pDC | 1 |
| PHEX | 0.79 | 4.18 | 0.59 | 0.61 | 0.03 | DC6 | pDC | 0 |
| DHRS7 | 0.79 | 1.05 | 0.59 | 0.92 | 0.73 | DC6 | pDC | 0 |
| TP53I13 | 0.79 | 2.39 | 0.59 | 0.69 | 0.15 | DC6 | pDC | 1 |
| PDCD4 | 0.79 | 1.36 | 0.58 | 0.95 | 0.70 | DC6 | pDC | 0 |
| RASD1 | 0.79 | 3.71 | 0.58 | 0.61 | 0.04 | DC6 | pDC | 0 |
| UBE2J1 | 0.79 | 1.65 | 0.58 | 0.86 | 0.56 | DC6 | pDC | 1 |
| TMIGD2 | 0.79 | 3.12 | 0.58 | 0.67 | 0.20 | DC6 | pDC | 1 |
| CREB3L2 | 0.79 | 1.47 | 0.58 | 0.87 | 0.47 | DC6 | pDC | 1 |
| KRT5 | 0.79 | 4.95 | 0.58 | 0.58 | 0.00 | DC6 | pDC | 0 |
| PLA2G16 | 0.79 | 2.69 | 0.58 | 0.65 | 0.12 | DC6 | pDC | 1 |
| C10ORF58 | 0.79 | 3.05 | 0.57 | 0.82 | 0.55 | DC6 | pDC | 0 |
| SIVA1 | 0.79 | 1.30 | 0.57 | 0.93 | 0.70 | DC6 | pDC | 0 |
| CYTH4 | 0.79 | 1.05 | 0.57 | 0.97 | 0.84 | DC6 | pDC | 0 |
| LOC100507600 | 0.79 | 3.80 | 0.57 | 0.59 | 0.03 | DC6 | pDC | 0 |
| MS4A6A | 0.78 | 1.16 | 0.57 | 0.91 | 0.52 | DC6 | pDC | 1 |
| AHI1 | 0.78 | 2.19 | 0.57 | 0.77 | 0.40 | DC6 | pDC | 0 |
| P4HB | 0.78 | 1.01 | 0.56 | 0.92 | 0.78 | DC6 | pDC | 0 |
| TACC1 | 0.78 | 1.26 | 0.56 | 0.94 | 0.74 | DC6 | pDC | 0 |
| AX747844 | 0.78 | 1.53 | 0.56 | 0.74 | 0.30 | DC6 | pDC | 0 |
| MAPKAPK2 | 0.78 | 1.78 | 0.56 | 0.67 | 0.13 | DC6 | pDC | 1 |
| TBC1D4 | 0.78 | 3.04 | 0.56 | 0.61 | 0.08 | DC6 | pDC | 0 |
| ATP2A3 | 0.78 | 2.21 | 0.56 | 0.69 | 0.19 | DC6 | pDC | 1 |
| TCL1A | 0.78 | 6.56 | 0.55 | 0.58 | 0.05 | DC6 | pDC | 0 |
| CD2AP | 0.77 | 1.92 | 0.55 | 0.68 | 0.17 | DC6 | pDC | 0 |
| GAS6 | 0.77 | 2.49 | 0.55 | 0.66 | 0.17 | DC6 | pDC | 0 |
| LY9 | 0.77 | 3.05 | 0.54 | 0.64 | 0.16 | DC6 | pDC | 1 |
| MIF4GD | 0.77 | 1.43 | 0.54 | 0.83 | 0.43 | DC6 | pDC | 0 |
| ASPH | 0.77 | 1.90 | 0.54 | 0.78 | 0.43 | DC6 | pDC | 1 |
| CMKLR1 | 0.77 | 2.83 | 0.54 | 0.61 | 0.10 | DC6 | pDC | 1 |
| DKFZP667P0924 | 0.77 | 1.93 | 0.54 | 0.76 | 0.33 | DC6 | pDC | 0 |
| GGA2 | 0.77 | 1.67 | 0.54 | 0.84 | 0.54 | DC6 | pDC | 0 |
| LOC100233209 | 0.77 | 1.11 | 0.54 | 0.85 | 0.59 | DC6 | pDC | 0 |
| VEGFB | 0.77 | 2.84 | 0.54 | 0.58 | 0.06 | DC6 | pDC | 0 |
| AL833181 | 0.77 | 2.60 | 0.53 | 0.61 | 0.10 | DC6 | pDC | 0 |
| LOC652276 | 0.77 | 1.52 | 0.53 | 0.86 | 0.59 | DC6 | pDC | 0 |
| NEK8 | 0.77 | 3.37 | 0.53 | 0.68 | 0.31 | DC6 | pDC | 0 |
| SMC6 | 0.77 | 2.00 | 0.53 | 0.69 | 0.22 | DC6 | pDC | 0 |
| CUX2 | 0.77 | 2.93 | 0.53 | 0.54 | 0.02 | DC6 | pDC | 1 |
| SLC7A5 | 0.76 | 3.01 | 0.53 | 0.57 | 0.07 | DC6 | pDC | 1 |
| TTC24 | 0.76 | 3.15 | 0.52 | 0.54 | 0.02 | DC6 | pDC | 0 |
| DUSP5 | 0.76 | 2.47 | 0.52 | 0.57 | 0.06 | DC6 | pDC | 0 |
| SLC38A2 | 0.76 | 1.17 | 0.52 | 0.91 | 0.64 | DC6 | pDC | 1 |
| SND1 | 0.76 | 1.00 | 0.51 | 0.93 | 0.69 | DC6 | pDC | 0 |
| ANKRD36 | 0.76 | 1.58 | 0.51 | 0.89 | 0.76 | DC6 | pDC | 0 |
| CYP46A1 | 0.75 | 1.98 | 0.51 | 0.90 | 0.74 | DC6 | pDC | 0 |
| FKBP2 | 0.75 | 1.30 | 0.51 | 0.78 | 0.49 | DC6 | pDC | 0 |
| RGS1 | 0.75 | 1.44 | 0.51 | 0.78 | 0.37 | DC6 | pDC | 0 |
| IGFBP3 | 0.75 | 5.21 | 0.50 | 0.51 | 0.02 | DC6 | pDC | 1 |
| MCOLN2 | 0.75 | 1.72 | 0.50 | 0.75 | 0.38 | DC6 | pDC | 1 |
| KIRREL3 | 0.75 | 2.56 | 0.50 | 0.72 | 0.37 | DC6 | pDC | 1 |
| SEC61G | 0.75 | 1.26 | 0.50 | 0.80 | 0.57 | DC6 | pDC | 1 |
| TEX2 | 0.75 | 2.29 | 0.49 | 0.61 | 0.16 | DC6 | pDC | 1 |
| AHNAK2 | 0.75 | 2.37 | 0.49 | 0.54 | 0.06 | DC6 | pDC | 0 |
| ZCCHC11 | 0.75 | 1.82 | 0.49 | 0.81 | 0.58 | DC6 | pDC | 0 |
| EGLN3 | 0.74 | 1.70 | 0.49 | 0.62 | 0.15 | DC6 | pDC | 0 |

TABLE E4-continued (including parts a-e). Discriminative genes for monocyte subsets reported in FIG. 4

| Gene.ID | AUC value | Avg. Diff.[1] | Power[2] | Pct.1[3] | Pct.2[4] | Cluster ID | Associated.Cell.Population | Surface Marker[5] |
|---|---|---|---|---|---|---|---|---|
| IRF2BP2 | 0.74 | 1.50 | 0.49 | 0.79 | 0.44 | DC6 | pDC | 0 |
| RNF5 | 0.74 | 1.60 | 0.49 | 0.69 | 0.40 | DC6 | pDC | 1 |
| SEL1L3 | 0.74 | 2.32 | 0.49 | 0.60 | 0.15 | DC6 | pDC | 1 |
| TMEM19 | 0.74 | 1.60 | 0.49 | 0.90 | 0.77 | DC6 | pDC | 1 |
| CDK2AP2 | 0.74 | 1.01 | 0.48 | 0.88 | 0.61 | DC6 | pDC | 0 |
| DKFZP586I1420 | 0.74 | 2.26 | 0.48 | 0.61 | 0.18 | DC6 | pDC | 0 |
| DQ572107 | 0.74 | 2.40 | 0.48 | 0.77 | 0.53 | DC6 | pDC | 0 |
| LAIR1 | 0.74 | 1.05 | 0.48 | 0.94 | 0.74 | DC6 | pDC | 1 |
| ANKRD36B | 0.74 | 1.95 | 0.48 | 0.76 | 0.43 | DC6 | pDC | 0 |
| POLB | 0.74 | 1.99 | 0.48 | 0.64 | 0.20 | DC6 | pDC | 0 |
| SEC12A3 | 0.74 | 3.12 | 0.48 | 0.58 | 0.18 | DC6 | pDC | 1 |
| MX1 | 0.74 | 1.08 | 0.48 | 0.86 | 0.56 | DC6 | pDC | 0 |
| C12ORF44 | 0.74 | 1.59 | 0.48 | 0.67 | 0.29 | DC6 | pDC | 0 |
| EMB | 0.74 | 1.06 | 0.48 | 0.85 | 0.51 | DC6 | pDC | 1 |
| PAFAH2 | 0.74 | 2.57 | 0.48 | 0.78 | 0.53 | DC6 | pDC | 0 |
| LOC100131564 | 0.74 | 1.12 | 0.47 | 0.94 | 0.88 | DC6 | pDC | 0 |
| RRBP1 | 0.74 | 1.72 | 0.47 | 0.73 | 0.44 | DC6 | pDC | 1 |
| FLJ43663 | 0.73 | 1.45 | 0.47 | 0.67 | 0.27 | DC6 | pDC | 0 |
| CSF2RB | 0.73 | 1.16 | 0.46 | 0.79 | 0.46 | DC6 | pDC | 1 |
| STAMBPL1 | 0.73 | 2.44 | 0.46 | 0.86 | 0.68 | DC6 | pDC | 0 |
| LMAN1 | 0.73 | 1.82 | 0.46 | 0.62 | 0.23 | DC6 | pDC | 1 |
| NAPSA | 0.73 | 1.93 | 0.46 | 0.82 | 0.50 | DC6 | pDC | 0 |
| STRBP | 0.73 | 2.28 | 0.45 | 0.54 | 0.11 | DC6 | pDC | 0 |
| GNG7 | 0.73 | 1.67 | 0.45 | 0.67 | 0.34 | DC6 | pDC | 0 |
| PAIP1 | 0.73 | 1.97 | 0.45 | 0.64 | 0.29 | DC6 | pDC | 0 |
| NCF1B | 0.73 | 1.09 | 0.45 | 0.73 | 0.38 | DC6 | pDC | 0 |
| SCARB2 | 0.72 | 1.34 | 0.45 | 0.83 | 0.66 | DC6 | pDC | 1 |
| VAMP1 | 0.72 | 2.33 | 0.44 | 0.54 | 0.13 | DC6 | pDC | 1 |
| ATP13A2 | 0.72 | 1.84 | 0.44 | 0.68 | 0.42 | DC6 | pDC | 1 |
| LTB | 0.72 | 2.63 | 0.44 | 0.53 | 0.14 | DC6 | pDC | 1 |
| CRIM1 | 0.72 | 1.80 | 0.44 | 0.52 | 0.10 | DC6 | pDC | 1 |
| SOLH | 0.72 | 1.67 | 0.44 | 0.56 | 0.17 | DC6 | pDC | 0 |
| FUT7 | 0.72 | 2.47 | 0.43 | 0.51 | 0.10 | DC6 | pDC | 0 |
| MAGED1 | 0.72 | 2.30 | 0.43 | 0.54 | 0.16 | DC6 | pDC | 0 |
| S1K1 | 0.72 | 1.11 | 0.43 | 0.79 | 0.46 | DC6 | pDC | 1 |
| PARP10 | 0.72 | 2.40 | 0.43 | 0.53 | 0.13 | DC6 | pDC | 0 |
| LRRC36 | 0.71 | 2.34 | 0.42 | 0.69 | 0.44 | DC6 | pDC | 0 |
| ST3GAL4 | 0.71 | 2.40 | 0.42 | 0.52 | 0.14 | DC6 | pDC | 1 |
| SFT2D2 | 0.71 | 1.27 | 0.42 | 0.84 | 0.61 | DC6 | pDC | 1 |
| TUBB6 | 0.71 | 1.54 | 0.42 | 0.68 | 0.34 | DC6 | pDC | 1 |
| NOP56 | 0.71 | 1.07 | 0.42 | 0.83 | 0.48 | DC6 | pDC | 1 |
| STT3A | 0.71 | 1.32 | 0.42 | 0.76 | 0.43 | DC6 | pDC | 1 |
| RAP1GDS1 | 0.71 | 1.09 | 0.41 | 0.80 | 0.51 | DC6 | pDC | 0 |
| CSNK1E | 0.71 | 1.38 | 0.41 | 0.82 | 0.62 | DC6 | pDC | 0 |
| DHTKD1 | 0.70 | 1.38 | 0.41 | 0.89 | 0.78 | DC6 | pDC | 0 |
| SUSD1 | 0.70 | 1.95 | 0.41 | 0.55 | 0.18 | DC6 | pDC | 1 |
| AK095700 | 0.70 | 1.10 | 0.40 | 0.81 | 0.56 | DC6 | pDC | 0 |
| SLC7A11 | 0.70 | 1.86 | 0.40 | 0.76 | 0.58 | DC6 | pDC | 1 |

Footnotes in Table E4: 1—Value refers to average differential expression within one subset (log fold change); 2—Value refers to discriminatory power of each marker; 3—Percentage of cells, within the cluster ID for which the gene is a marker, that detect the gene; 4—Percentage of all the other cells, excluding the cluster ID for which the gene is a marker, that detect the gene; 5—"1" refers to predicted surface marker; "0" refers to predicted not a surface marker according to the Protein Atlas: Protein Atlas: http://www.proteinatlas.org/search/protein_class:Predicted+membrane+proteins.

The two largest clusters, Mono1 and Mono2, contained the CD14++CD16− ('classical') and CD14+CD16++ ('non-classical'), respectively. However, Mono1 and Mono2 also included 88 of the 128 cells derived from the 'intermediate' monocyte gate (CD14++CD16+) (FIG. 4D), demonstrating that the 'intermediate' monocytes do not form a homogenous population. The two smaller clusters, Mono3 and Mono4, contained 40 of the 128 'intermediate' cells and expressed many of the Mono1 ('classical' monocyte) signature genes. One of these clusters, Mono3, also uniquely expressed genes involved in cell cycle arrest and cell differentiation inhibition (e.g., G0S2, MXD1), as well as trafficking (e.g., CXCR1, CXCR2, VNN2), while the other cluster, Mono4, distinctively expressed a cytotoxic gene signature (FIG. 4C) resembling previously reported 'natural killer dendritic cells' (Welner et al.; Taieb et al.; Chan et al.). Applicants conclude that the previously defined 'classical' and 'non-classical' subtypes are contained in 2 distinct clusters (Mono1 and Mono2), but that the 'intermediate' monocytes are far more heterogeneous than previously appreciated, being distributed across 2 known and 2 new clusters (FIG. 4D).

All monocyte subtypes shared a signature that distinguished monocytes collectively from CD1C+ DC (cluster DC2 and DC3), CLEC9A+ DC (cluster DC1), and pDC (cluster DC6) populations (e.g., ITGAM/CD11B, ITGB2, TLR2, and CLEC7A) (FIG. 4B, FIG. 4C, FIG. 4E). Importantly, despite co-expressing genes such as CD14 and S100A8, Mono1 cells (mostly corresponding to the 'classical' monocyte gate) and 'inflammatory' CD1C_B DCs (cluster DC3) did not form a single cluster (FIGS. 4B and C), with CD1C+ DCs (DC2 and DC3) expressing unique markers (e.g., CD1C, CLEC10A, FCER1A, FCGR2B, and CD1D) enriched for antigen processing ($p<2.66^{-10}$), MHC II ($p<1.79^{-8}$) and leukocyte activation ($p<1.14^{-6}$) gene ontology (GO) terms (FIG. 4C, Table E5, Methods). In contrast, Mono1 cells were enriched for defense response ($p<2.15^{-14}$), inflammatory response ($p<9.59^{-14}$), and chemotaxis ($p<6.77^{-10}$) genes.

TABLE E5

Discriminative markers between CD1C_B (inflammatory CD1C; DC3 cluster) and Mono1 (CD14++ DC16− classical monocyte subsets)

| Gene.ID | AUC value | Avg. Diff.[1] | Power[2] | Pct.1[3] | Pct.2[4] | Comments | Surface Marker[5] |
|---|---|---|---|---|---|---|---|
| HLA-DRB4 | 1.00 | 5.42 | 1.00 | 1.00 | 0.40 | Higher in CD1C_B (DC3)/Lower in Mono1 (classical CD14++CD16− mono) | 1 |
| CD74 | 0.99 | 1.30 | 0.98 | 1.00 | 1.00 | Higher in CD1C_B (DC3)/Lower in Mono1 (classical CD14++CD16− mono) | 1 |
| HLA-DQA2 | 0.98 | 3.94 | 0.97 | 0.98 | 0.09 | Higher in CD1C_B (DC3)/Lower in Mono1 (classical CD14++CD16− mono) | 1 |
| FCER1A | 0.98 | 3.57 | 0.96 | 0.99 | 0.13 | Higher in CD1C_B (DC3)/Lower in Mono1 (classical CD14++CD16− mono) | 1 |
| HLA-DQB | 0.97 | 2.06 | 0.94 | 1.00 | 0.78 | Higher in CD1C_B (DC3)/Lower in Mono1 (classical CD14++CD16− mono) | 1 |
| HLA-DRB1 | 0.97 | 1.34 | 0.94 | 1.00 | 1.00 | Higher in CD1C_B (DC3)/Lower in Mono1 (classical CD14++CD16− mono) | 1 |
| HLA-DQA1 | 0.97 | 2.38 | 0.94 | 1.00 | 0.55 | Higher in CD1C_B (DC3)/Lower in Mono1 (classical CD14++CD16− mono) | 1 |
| HLA-DRA | 0.96 | 1.18 | 0.93 | 1.00 | 1.00 | Higher in CD1C_B (DC3)/Lower in Mono1 (classical CD14++CD16− mono) | 1 |
| HLA-DPB1 | 0.95 | 2.22 | 0.89 | 0.97 | 0.37 | Higher in CD1C_B (DC3)/Lower in Mono1 (classical CD14++CD16− mono) | 1 |
| CST3 | 0.94 | 1.17 | 0.89 | 1.00 | 0.98 | Higher in CD1C_B (DC3)/Lower in Mono1 (classical CD14++CD16− mono) | 0 |
| HLA-DPB2 | 0.93 | 1.32 | 0.87 | 1.00 | 0.87 | Higher in CD1C_B (DC3)/Lower in Mono1 (classical CD14++CD16− mono) | 1 |
| HLA-DPA1 | 0.92 | 1.13 | 0.84 | 1.00 | 0.91 | Higher in CD1C_B (DC3)/Lower in Mono1 (classical CD14++CD16− mono) | 1 |
| PLD4 | 0.92 | 1.89 | 0.83 | 0.95 | 0.18 | Higher in CD1C_B (DC3)/Lower in Mono1 (classical CD14++CD16− mono) | 1 |
| HLA-DMA | 0.91 | 1.10 | 0.81 | 1.00 | 0.86 | Higher in CD1C_B (DC3)/Lower in Mono1 (classical CD14++CD16− mono) | 1 |
| NDRG2 | 0.90 | 3.69 | 0.81 | 0.84 | 0.08 | Higher in CD1C_B (DC3)/Lower in Mono1 (classical CD14++CD16− mono) | 1 |
| CD1C | 0.90 | 3.30 | 0.81 | 0.87 | 0.14 | Higher in CD1C_B (DC3)/Lower in Mono1 (classical CD14++CD16− mono) | 1 |
| CLEC10A | 0.90 | 3.50 | 0.79 | 0.84 | 0.13 | Higher in CD1C_B (DC3)/Lower in Mono1 (classical CD14++CD16− mono) | 1 |
| HLA-DRB6 | 0.88 | 2.14 | 0.75 | 0.86 | 0.17 | Higher in CD1C_B (DC3)/Lower in Mono1 (classical CD14++CD16− mono) | 1 |
| DQ-A1 | 0.87 | 3.18 | 0.73 | 0.77 | 0.09 | Higher in CD1C_B (DC3)/Lower in Mono1 (classical CD14++CD16− mono) | 0 |
| CYTOCHROME B | 0.86 | 1.11 | 0.72 | 1.00 | 1.00 | Higher in CD1C_B (DC3)/Lower in Mono1 (classical CD14++CD16− mono) | 0 |
| HLA-DQB1 | 0.83 | 1.05 | 0.66 | 0.99 | 0.95 | Higher in CD1C_B (DC3)/Lower in Mono1 (classical CD14++CD16− mono) | 1 |
| PEBP1 | 0.82 | 1.51 | 0.65 | 0.88 | 0.45 | Higher in CD1C_B (DC3)/Lower in Mono1 (classical CD14++CD16− mono) | 0 |
| PPA1 | 0.82 | 1.36 | 0.64 | 0.88 | 0.43 | Higher in CD1C_B (DC3)/Lower in Mono1 (classical CD14++CD16− mono) | 0 |
| FABP5 | 0.81 | 1.31 | 0.61 | 0.77 | 0.22 | Higher in CD1C_B (DC3)/Lower in Mono1 (classical CD14++CD16− mono) | 0 |
| GPR183 | 0.79 | 1.06 | 0.57 | 0.94 | 0.57 | Higher in CD1C_B (DC3)/Lower in Mono1 (classical CD14++CD16− mono) | 1 |
| SLC38A1 | 0.78 | 1.32 | 0.57 | 0.91 | 0.53 | Higher in CD1C_B (DC3)/Lower in Mono1 (classical CD14++CD16− mono) | 1 |
| RGS1 | 0.78 | 3.08 | 0.56 | 0.59 | 0.04 | Higher in CD1C_B (DC3)/Lower in Mono1 (classical CD14++CD16− mono) | 0 |
| HMGN1 | 0.77 | 1.11 | 0.55 | 0.91 | 0.59 | Higher in CD1C_B (DC3)/Lower in Mono1 (classical CD14++CD16− mono) | 0 |
| C20ORF27 | 0.77 | 1.02 | 0.54 | 0.88 | 0.48 | Higher in CD1C_B (DC3)/Lower in Mono1 (classical CD14++CD16− mono) | 0 |
| C1QBP | 0.76 | 1.01 | 0.53 | 0.85 | 0.57 | Higher in CD1C_B (DC3)/Lower in Mono1 (classical CD14++CD16− mono) | 0 |
| NR4A2 | 0.76 | 1.24 | 0.53 | 0.83 | 0.42 | Higher in CD1C_B (DC3)/Lower in Mono1 (classical CD14++CD16− mono) | 0 |
| SPINT2 | 0.76 | 1.07 | 0.53 | 0.81 | 0.50 | Higher in CD1C_B (DC3)/Lower in Mono1 (classical CD14++CD16− mono) | 1 |
| HLA-DOA | 0.76 | 2.06 | 0.52 | 0.79 | 0.49 | Higher in CD1C_B (DC3)/Lower in Mono1 (classical CD14++CD16− mono) | 1 |

TABLE E5-continued

Discriminative markers between CD1C_B (inflammatory CD1C; DC3 cluster) and
Mono1 (CD14++ DC16− classical monocyte subsets)

| Gene.ID | AUC value | Avg. Diff.[1] | Power[2] | Pct.1[3] | Pct.2[4] | Comments | Surface Marker[5] |
|---|---|---|---|---|---|---|---|
| RETN | 0.76 | 1.44 | 0.51 | 0.70 | 0.25 | Higher in CD1C_B (DC3)/Lower in Mono1 (classical CD14++CD16− mono) | 0 |
| ADAM28 | 0.75 | 1.78 | 0.50 | 0.64 | 0.15 | Higher in CD1C_B (DC3)/Lower in Mono1 (classical CD14++CD16− mono) | 1 |
| RNASE2 | 0.75 | 1.15 | 0.50 | 0.81 | 0.42 | Higher in CD1C_B (DC3)/Lower in Mono1 (classical CD14++CD16− mono) | 0 |
| MAP4K1 | 0.75 | 1.19 | 0.49 | 0.70 | 0.21 | Higher in CD1C_B (DC3)/Lower in Mono1 (classical CD14++CD16− mono) | 0 |
| MX1 | 0.74 | 1.33 | 0.47 | 0.72 | 0.30 | Higher in CD1C_B (DC3)/Lower in Mono1 (classical CD14++CD16− mono) | 0 |
| CLIC2 | 0.74 | 2.13 | 0.47 | 0.56 | 0.10 | Higher in CD1C_B (DC3)/Lower in Mono1 (classical CD14++CD16− mono) | 0 |
| PON2 | 0.73 | 1.79 | 0.46 | 0.59 | 0.15 | Higher in CD1C_B (DC3)/Lower in Mono1 (classical CD14++CD16− mono) | 1 |
| DYNLL1 | 0.73 | 1.05 | 0.45 | 0.75 | 0.42 | Higher in CD1C_B (DC3)/Lower in Mono1 (classical CD14++CD16− mono) | 0 |
| FCGR2B | 0.73 | 1.71 | 0.45 | 0.59 | 0.18 | Higher in CD1C_B (DC3)/Lower in Mono1 (classical CD14++CD16− mono) | 1 |
| HDAC9 | 0.73 | 1.43 | 0.45 | 0.68 | 0.34 | Higher in CD1C_B (DC3)/Lower in Mono1 (classical CD14++CD16− mono) | 0 |
| TMEM176B | 0.73 | 1.87 | 0.45 | 0.58 | 0.16 | Higher in CD1C_B (DC3)/Lower in Mono1 (classical CD14++CD16− mono) | 1 |
| DUSP23 | 0.72 | 1.13 | 0.44 | 0.70 | 0.33 | Higher in CD1C_B (DC3)/Lower in Mono1 (classical CD14++CD16− mono) | 0 |
| FLT3 | 0.77 | 2.40 | 0.43 | 0.52 | 0.11 | Higher in CD1C_B (DC3)/Lower in Mono1 (classical CD14++CD16− mono) | 1 |
| ITGB7 | 0.70 | 1.88 | 0.41 | 0.53 | 0.15 | Higher in CD1C_B (DC3)/Lower in Mono1 (classical CD14++CD16− mono) | 1 |
| ARL4C | 0.70 | 1.17 | 0.39 | 0.64 | 0.30 | Higher in CD1C_B (DC3)/Lower in Mono1 (classical CD14++CD16− mono) | 0 |
| ALCAM | 0.70 | 1.26 | 0.39 | 0.62 | 0.26 | Higher in CD1C_B (DC3)/Lower in Mono1 (classical CD14++CD16− mono) | 1 |
| KPNA2 | 0.68 | 1.49 | 0.36 | 0.54 | 0.21 | Higher in CD1C_B (DC3)/Lower in Mono1 (classical CD14++CD16− mono) | 0 |
| NREP | 0.67 | 1.64 | 0.35 | 0.68 | 0.50 | Higher in CD1C_B (DC3)/Lower in Mono1 (classical CD14++CD16− mono) | 0 |
| MRPL13 | 0.66 | 1.21 | 0.32 | 0.52 | 0.24 | Higher in CD1C_B (DC3)/Lower in Mono1 (classical CD14++CD16− mono) | 0 |
| HBEGF | 0.65 | 1.28 | 0.30 | 0.51 | 0.23 | Higher in CD1C_B (DC3)/Lower in Mono1 (classical CD14++CD16− mono) | 1 |
| TOR3A | 0.65 | 1.08 | 0.30 | 0.51 | 0.23 | Higher in CD1C_B (DC3)/Lower in Mono1 (classical CD14++CD16− mono) | 1 |
| DEF6 | 0.65 | 1.03 | 0.29 | 0.56 | 0.30 | Higher in CD1C_B (DC3)/Lower in Mono1 (classical CD14++CD16− mono) | 0 |
| HMOX2 | 0.64 | 1.19 | 0.27 | 0.63 | 0.42 | Higher in CD1C_B (DC3)/Lower in Mono1 (classical CD14++CD16− mono) | 1 |
| MAF1 | 0.64 | 1.00 | 0.27 | 0.51 | 0.27 | Higher in CD1C_B (DC3)/Lower in Mono1 (classical CD14++CD16− mono) | 0 |
| LOC283788 | 0.62 | 1.16 | 0.24 | 0.53 | 0.32 | Higher in CD1C_B (DC3)/Lower in Mono1 (classical CD14++CD16− mono) | 0 |
| CCR6 | 0.62 | 1.79 | 0.24 | 0.70 | 0.56 | Higher in CD1C_B (DC3)/Lower in Mono1 (classical CD14++CD16− mono) | 1 |
| MCCC2 | 0.61 | 1.16 | 0.23 | 0.78 | 0.62 | Higher in CD1C_B (DC3)/Lower in Mono1 (classical CD14++CD16− mono) | 0 |
| ZMYM2 | 0.40 | −1.01 | 0.20 | 0.46 | 0.57 | Lower in CD1C_B (DC3)/Higher in Mono1 (classical CD14++CD16− mono) | 0 |
| IL1B | 0.40 | −2.11 | 0.21 | 0.52 | 0.58 | Lower in CD1C_B (DC3)/Higher in Mono1 (classical CD14++CD16− mono) | 0 |
| LRG1 | 0.40 | −1.25 | 0.21 | 0.58 | 0.60 | Lower in CD1C_B (DC3)/Higher in Mono1 (classical CD14++CD16− mono) | 0 |
| SNX29 | 0.40 | −1.02 | 0.21 | 0.47 | 0.58 | Lower in CD1C_B (DC3)/Higher in Mono1 (classical CD14++CD16− mono) | 0 |
| AX747730 | 0.39 | −1.32 | 0.21 | 0.57 | 0.59 | Lower in CD1C_B (DC3)/Higher in Mono1 (classical CD14++CD16− mono) | 0 |
| NBPF1 | 0.39 | −1.06 | 0.22 | 0.44 | 0.58 | Lower in CD1C_B (DC3)/Higher in Mono1 (classical CD14++CD16− mono) | 0 |
| SYT17 | 0.39 | −1.18 | 0.22 | 0.48 | 0.53 | Lower in CD1C_B (DC3)/Higher in Mono1 (classical CD14++CD16− mono) | 0 |
| RAB5B | 0.39 | −1.19 | 0.22 | 0.47 | 0.56 | Lower in CD1C_B (DC3)/Higher in Mono1 (classical CD14++CD16− mono) | 0 |
| GPNMB | 0.39 | −1.08 | 0.23 | 0.44 | 0.52 | Lower in CD1C_B (DC3)/Higher in Mono1 (classical CD14++CD16− mono) | 1 |
| PRR5 | 0.39 | −1.50 | 0.23 | 0.43 | 0.52 | Lower in CD1C_B (DC3)/Higher in Mono1 (classical CD14++CD16− mono) | 0 |

TABLE E5-continued

Discriminative markers between CD1C_B (inflammatory CD1C; DC3 cluster) and Mono1 (CD14++ DC16− classical monocyte subsets)

| Gene.ID | AUC value | Avg. Diff.[1] | Power[2] | Pct.1[3] | Pct.2[4] | Comments | Surface Marker[5] |
|---|---|---|---|---|---|---|---|
| TJP2 | 0.38 | −1.11 | 0.23 | 0.43 | 0.52 | Lower in CD1C_B (DC3)/Higher in Mono1 (classical CD14++CD16− mono) | 0 |
| March6' | 0.38 | −1.05 | 0.23 | 0.45 | 0.58 | Lower in CD1C_B (DC3)/Higher in Mono1 (classical CD14++CD16− mono) | 1 |
| MGC16703 | 0.38 | −1.06 | 0.23 | 0.43 | 0.52 | Lower in CD1C_B (DC3)/Higher in Mono1 (classical CD14++CD16− mono) | 0 |
| AK094156 | 0.38 | −1.28 | 0.24 | 0.36 | 0.52 | Lower in CD1C_B (DC3)/Higher in Mono1 (classical CD14++CD16− mono) | 0 |
| RCL1 | 0.38 | −1.06 | 0.24 | 0.44 | 0.56 | Lower in CD1C_B (DC3)/Higher in Mono1 (classical CD14++CD16− mono) | 0 |
| AX747182 | 0.38 | −1.10 | 0.24 | 0.46 | 0.56 | Lower in CD1C_B (DC3)/Higher in Mono1 (classical CD14++CD16− mono) | 0 |
| AL832262 | 0.38 | −1.04 | 0.24 | 0.43 | 0.57 | Lower in CD1C_B (DC3)/Higher in Mono1 (classical CD14++CD16− mono) | 0 |
| BEST1 | 0.38 | −1.31 | 0.24 | 0.36 | 0.52 | Lower in CD1C_B (DC3)/Higher in Mono1 (classical CD14++CD16− mono) | 1 |
| ANKS3 | 0.38 | −1.51 | 0.25 | 0.46 | 0.56 | Lower in CD1C_B (DC3)/Higher in Mono1 (classical CD14++CD16− mono) | 0 |
| RABGEF1 | 0.38 | −1.37 | 0.25 | 0.37 | 0.53 | Lower in CD1C_B (DC3)/Higher in Mono1 (classical CD14++CD16− mono) | 0 |
| AF007147 | 0.38 | −1.33 | 0.25 | 0.43 | 0.56 | Lower in CD1C_B (DC3)/Higher in Mono1 (classical CD14++CD16− mono) | 0 |
| SEL1L | 0.37 | −1.03 | 0.25 | 0.47 | 0.67 | Lower in CD1C_B (DC3)/Higher in Mono1 (classical CD14++CD16− mono) | 1 |
| ABCG1 | 0.37 | −1.26 | 0.25 | 0.38 | 0.50 | Lower in CD1C_B (DC3)/Higher in Mono1 (classical CD14++CD16− mono) | 1 |
| LOC729603 | 0.37 | −1.71 | 0.25 | 0.57 | 0.60 | Lower in CD1C_B (DC3)/Higher in Mono1 (classical CD14++CD16− mono) | 0 |
| FRY | 0.37 | −1.27 | 0.26 | 0.35 | 0.53 | Lower in CD1C_B (DC3)/Higher in Mono1 (classical CD14++CD16− mono) | 0 |
| C20ORF112 | 0.37 | −1.20 | 0.26 | 0.32 | 0.50 | Lower in CD1C_B (DC3)/Higher in Mono1 (classical CD14++CD16− mono) | 0 |
| GTF2E1 | 0.37 | −1.35 | 0.26 | 0.37 | 0.55 | Lower in CD1C_B (DC3)/Higher in Mono1 (classical CD14++CD16− mono) | 0 |
| RRP12 | 0.37 | −1.09 | 0.26 | 0.37 | 0.57 | Lower in CD1C_B (DC3)/Higher in Mono1 (classical CD14++CD16− mono) | 1 |
| ZFP30 | 0.37 | −1.25 | 0.26 | 0.47 | 0.55 | Lower in CD1C_B (DC3)/Higher in Mono1 (classical CD14++CD16− mono) | 0 |
| C20ORF177 | 0.37 | −1.25 | 0.26 | 0.63 | 0.69 | Lower in CD1C_B (DC3)/Higher in Mono1 (classical CD14++CD16− mono) | 0 |
| C3ORF62 | 0.37 | −1.27 | 0.26 | 0.62 | 0.69 | Lower in CD1C_B (DC3)/Higher in Mono1 (classical CD14++CD16− mono) | 0 |
| CLNK | 0.37 | −1.01 | 0.26 | 0.40 | 0.53 | Lower in CD1C_B (DC3)/Higher in Mono1 (classical CD14++CD16− mono) | 0 |
| NME9 | 0.37 | −1.35 | 0.26 | 0.43 | 0.54 | Lower in CD1C_B (DC3)/Higher in Mono1 (classical CD14++CD16− mono) | 0 |
| FKBP9 | 0.37 | −1.15 | 0.26 | 0.40 | 0.55 | Lower in CD1C_B (DC3)/Higher in Mono1 (classical CD14++CD16− mono) | 1 |
| TK2 | 0.37 | −1.07 | 0.27 | 0.50 | 0.64 | Lower in CD1C_B (DC3)/Higher in Mono1 (classical CD14++CD16− mono) | 0 |
| EXOC7 | 0.37 | −1.08 | 0.27 | 0.60 | 0.70 | Lower in CD1C_B (DC3)/Higher in Mono1 (classical CD14++CD16− mono) | 0 |
| AK123872 | 0.36 | −1.21 | 0.27 | 0.43 | 0.54 | Lower in CD1C_B (DC3)/Higher in Mono1 (classical CD14++CD16− mono) | 0 |
| AX748261 | 0.36 | −1.03 | 0.27 | 0.42 | 0.55 | Lower in CD1C_B (DC3)/Higher in Mono1 (classical CD14++CD16− mono) | 0 |
| LLGL1 | 0.36 | −1.07 | 0.27 | 0.37 | 0.52 | Lower in CD1C_B (DC3)/Higher in Mono1 (classical CD14++CD16− mono) | 0 |
| EPG5 | 0.36 | −1.46 | 0.27 | 0.27 | 0.50 | Lower in CD1C_B (DC3)/Higher in Mono1 (classical CD14++CD16− mono) | 0 |
| GIMAP2 | 0.36 | −1.01 | 0.28 | 0.31 | 0.54 | Lower in CD1C_B (DC3)/Higher in Mono1 (classical CD14++CD16− mono) | 1 |
| BC014119 | 0.36 | −1.27 | 0.28 | 0.47 | 0.62 | Lower in CD1C_B (DC3)/Higher in Mono1 (classical CD14++CD16− mono) | 0 |
| AF079515 | 0.36 | −1.19 | 0.28 | 0.35 | 0.55 | Lower in CD1C_B (DC3)/Higher in Mono1 (classical CD14++CD16− mono) | 0 |
| MIIP | 0.36 | −1.05 | 0.28 | 0.41 | 0.61 | Lower in CD1C_B (DC3)/Higher in Mono1 (classical CD14++CD16− mono) | 0 |
| ZNF263 | 0.36 | −1.43 | 0.28 | 0.35 | 0.52 | Lower in CD1C_B (DC3)/Higher in Mono1 (classical CD14++CD16− mono) | 0 |
| AK311282 | 0.36 | −1.12 | 0.29 | 0.40 | 0.54 | Lower in CD1C_B (DC3)/Higher in Mono1 (classical CD14++CD16− mono) | 0 |
| CSF2RB | 0.36 | −1.03 | 0.29 | 0.41 | 0.63 | Lower in CD1C_B (DC3)/Higher in Mono1 (classical CD14++CD16− mono) | 1 |

TABLE E5-continued

Discriminative markers between CD1C_B (inflammatory CD1C; DC3 cluster) and Mono1 (CD14$^{++}$ DC16$^-$ classical monocyte subsets)

| Gene.ID | AUC value | Avg. Diff.[1] | Power[2] | Pct.1[3] | Pct.2[4] | Comments | Surface Marker[5] |
|---|---|---|---|---|---|---|---|
| FAM115C | 0.36 | −1.21 | 0.29 | 0.57 | 0.66 | Lower in CD1C_B (DC3)/Higher in Mono1 (classical CD14$^{++}$CD16$^-$ mono) | 0 |
| L1TD1 | 0.36 | −1.47 | 0.29 | 0.41 | 0.63 | Lower in CD1C_B (DC3)/Higher in Mono1 (classical CD14$^{++}$CD16$^-$ mono) | 0 |
| PDPK1 | 0.36 | −1.01 | 0.29 | 0.41 | 0.63 | Lower in CD1C_B (DC3)/Higher in Mono1 (classical CD14$^{++}$CD16$^-$ mono) | 0 |
| TMEM188 | 0.36 | −1.11 | 0.29 | 0.44 | 0.63 | Lower in CD1C_B (DC3)/Higher in Mono1 (classical CD14$^{++}$CD16$^-$ mono) | 0 |
| XPR1 | 0.36 | −1.21 | 0.29 | 0.45 | 0.64 | Lower in CD1C_B (DC3)/Higher in Mono1 (classical CD14$^{++}$CD16$^-$ mono) | 1 |
| LOC440944 | 0.36 | −1.69 | 0.29 | 0.35 | 0.53 | Lower in CD1C_B (DC3)/Higher in Mono1 (classical CD14$^{++}$CD16$^-$ mono) | 0 |
| LOC286186 | 0.35 | −1.05 | 0.29 | 0.54 | 0.60 | Lower in CD1C_B (DC3)/Higher in Mono1 (classical CD14$^{++}$CD16$^-$ mono) | 0 |
| EPB41L4A | 0.35 | −1.87 | 0.29 | 0.44 | 0.57 | Lower in CD1C_B (DC3)/Higher in Mono1 (classical CD14$^{++}$CD16$^-$ mono) | 0 |
| LOC100506757 | 0.35 | −1.05 | 0.29 | 0.38 | 0.53 | Lower in CD1C_B (DC3)/Higher in Mono1 (classical CD14$^{++}$CD16$^-$ mono) | 0 |
| ADRA1A | 0.35 | −1.06 | 0.30 | 0.56 | 0.65 | Lower in CD1C_B (DC3)/Higher in Mono1 (classical CD14$^{++}$CD16$^-$ mono) | 1 |
| AK021876 | 0.35 | −1.05 | 0.30 | 0.31 | 0.53 | Lower in CD1C_B (DC3)/Higher in Mono1 (classical CD14$^{++}$CD16$^-$ mono) | 0 |
| C2CD3 | 0.35 | −1.19 | 0.30 | 0.47 | 0.63 | Lower in CD1C_B (DC3)/Higher in Mono1 (classical CD14$^{++}$CD16$^-$ mono) | 0 |
| FFAR2 | 0.35 | −1.71 | 0.30 | 0.46 | 0.61 | Lower in CD1C_B (DC3)/Higher in Mono1 (classical CD14$^{++}$CD16$^-$ mono) | 1 |
| GRINA | 0.35 | −1.14 | 0.30 | 0.41 | 0.59 | Lower in CD1C_B (DC3)/Higher in Mono1 (classical CD14$^{++}$CD16$^-$ mono) | 1 |
| AX747408 | 0.35 | −1.08 | 0.31 | 0.34 | 0.52 | Lower in CD1C_B (DC3)/Higher in Mono1 (classical CD14$^{++}$CD16$^-$ mono) | 0 |
| C1ORF210 | 0.35 | −1.05 | 0.31 | 0.43 | 0.59 | Lower in CD1C_B (DC3)/Higher in Mono1 (classical CD14$^{++}$CD16$^-$ mono) | 1 |
| AX748265 | 0.35 | −1.03 | 0.31 | 0.54 | 0.65 | Lower in CD1C_B (DC3)/Higher in Mono1 (classical CD14$^{++}$CD16$^-$ mono) | 0 |
| ENDOGENOUS RETROVIRUS ERV9 | 0.35 | −1.32 | 0.31 | 0.26 | 0.52 | Lower in CD1C_B (DC3)/Higher in Mono1 (classical CD14$^{++}$CD16$^-$ mono) | 0 |
| SORT1 | 0.35 | −1.17 | 0.31 | 0.35 | 0.57 | Lower in CD1C_B (DC3)/Higher in Mono1 (classical CD14$^{++}$CD16$^-$ mono) | 1 |
| PMS2 | 0.34 | −1.07 | 0.31 | 0.71 | 0.76 | Lower in CD1C_B (DC3)/Higher in Mono1 (classical CD14$^{++}$CD16$^-$ mono) | 0 |
| SEC14L4 | 0.34 | −1.03 | 0.31 | 0.56 | 0.63 | Lower in CD1C_B (DC3)/Higher in Mono1 (classical CD14$^{++}$CD16$^-$ mono) | 0 |
| C17ORF103 | 0.34 | −1.44 | 0.31 | 0.31 | 0.51 | Lower in CD1C_B (DC3)/Higher in Mono1 (classical CD14$^{++}$CD16$^-$ mono) | 0 |
| DICER1 | 0.34 | −1.02 | 0.32 | 0.41 | 0.65 | Lower in CD1C_B (DC3)/Higher in Mono1 (classical CD14$^{++}$CD16$^-$ mono) | 0 |
| DQ592442 | 0.34 | −1.20 | 0.32 | 0.32 | 0.56 | Lower in CD1C_B (DC3)/Higher in Mono1 (classical CD14$^{++}$CD16$^-$ mono) | 0 |
| FAM26F | 0.34 | −1.2.3 | 0.32 | 0.33 | 0.57 | Lower in CD1C_B (DC3)/Higher in Mono1 (classical CD14$^{++}$CD16$^-$ mono) | 1 |
| LATS1 | 0.34 | −1.25 | 0.32 | 0.48 | 0.68 | Lower in CD1C_B (DC3)/Higher in Mono1 (classical CD14$^{++}$CD16$^-$ mono) | 0 |
| EHD1 | 0.34 | −1.31 | 0.32 | 0.27 | 0.55 | Lower in CD1C_B (DC3)/Higher in Mono1 (classical CD14$^{++}$CD16$^-$ mono) | 0 |
| A4GALT | 0.34 | −1.11 | 0.32 | 0.50 | 0.66 | Lower in CD1C_B (DC3)/Higher in Mono1 (classical CD14$^{++}$CD16$^-$ mono) | 1 |
| BIRC3 | 0.34 | −1.62 | 0.32 | 0.24 | 0.50 | Lower in CD1C_B (DC3)/Higher in Mono1 (classical CD14$^{++}$CD16$^-$ mono) | 0 |
| FLJ00310 | 0.34 | −1.38 | 0.32 | 0.36 | 0.58 | Lower in CD1C_B (DC3)/Higher in Mono1 (classical CD14$^{++}$CD16$^-$ mono) | 0 |
| GGA1 | 0.34 | −1.48 | 0.32 | 0.42 | 0.63 | Lower in CD1C_B (DC3)/Higher in Mono1 (classical CD14$^{++}$CD16$^-$ mono) | 0 |
| HIPK3 | 0.34 | −1.25 | 0.32 | 0.44 | 0.63 | Lower in CD1C_B (DC3)/Higher in Mono1 (classical CD14$^{++}$CD16$^-$ mono) | 1 |
| AK092619 | 0.34 | −1.05 | 0.33 | 0.40 | 0.57 | Lower in CD1C_B (DC3)/Higher in Mono1 (classical CD14$^{++}$CD16$^-$ mono) | 0 |
| FLVCR2 | 0.34 | −1.45 | 0.33 | 0.21 | 0.51 | Lower in CD1C_B (DC3)/Higher in Mono1 (classical CD14$^{++}$CD16$^-$ mono) | 1 |
| SNX10 | 0.34 | −1.01 | 0.33 | 0.47 | 0.69 | Lower in CD1C_B (DC3)/Higher in Mono1 (classical CD14$^{++}$CD16$^-$ mono) | 0 |
| ZNF277 | 0.34 | −1.00 | 0.33 | 0.56 | 0.72 | Lower in CD1C_B (DC3)/Higher in Mono1 (classical CD14$^{++}$CD16$^-$ mono) | 0 |

TABLE E5-continued

Discriminative markers between CD1C_B (inflammatory CD1C; DC3 cluster) and Mono1 (CD14$^{++}$ DC16$^-$ classical monocyte subsets)

| Gene.ID | AUC value | Avg. Diff.[1] | Power[2] | Pct.1[3] | Pct.2[4] | Comments | Surface Marker[5] |
|---|---|---|---|---|---|---|---|
| LOC100128288 | 0.34 | −1.16 | 0.33 | 0.47 | 0.62 | Lower in CD1C_B (DC3)/Higher in Mono1 (classical CD14$^{++}$CD16$^-$ mono) | 0 |
| LOC100506033 | 0.34 | −1.12 | 0.33 | 0.38 | 0.58 | Lower in CD1C_B (DC3)/Higher in Mono1 (classical CD14$^{++}$CD16$^-$ mono) | 0 |
| FAM129C | 0.33 | −1.13 | 0.33 | 0.73 | 0.78 | Lower in CD1C_B (DC3)/Higher in Mono1 (classical CD14$^{++}$CD16$^-$ mono) | 0 |
| GTPBP10 | 0.33 | −1.00 | 0.33 | 0.62 | 0.72 | Lower in CD1C_B (DC3)/Higher in Mono1 (classical CD14$^{++}$CD16$^-$ mono) | 0 |
| DKFZP761E198 | 0.33 | −1.33 | 0.33 | 0.34 | 0.57 | Lower in CD1C_B (DC3)/Higher in Mono1 (classical CD14$^{++}$CD16$^-$ mono) | 0 |
| TBC1D2 | 0.33 | −1.55 | 0.33 | 0.26 | 0.54 | Lower in CD1C_B (DC3)/Higher in Mono1 (classical CD14$^{++}$CD16$^-$ mono) | 0 |
| ABTB1 | 0.33 | −1.04 | 0.34 | 0.32 | 0.60 | Lower in CD1C_B (DC3)/Higher in Mono1 (classical CD14$^{++}$CD16$^-$ mono) | 0 |
| AK098727 | 0.33 | −1.22 | 0.34 | 0.41 | 0.60 | Lower in CD1C_B (DC3)/Higher in Mono1 (classical CD14$^{++}$CD16$^-$ mono) | 0 |
| MCTP2 | 0.33 | −2.50 | 0.34 | 0.39 | 0.57 | Lower in CD1C_B (DC3)/Higher in Mono1 (classical CD14$^{++}$CD16$^-$ mono) | 1 |
| PTPRS | 0.33 | −1.14 | 0.34 | 0.38 | 0.57 | Lower in CD1C_B (DC3)/Higher in Mono1 (classical CD14$^{++}$CD16$^-$ mono) | 1 |
| SNURF-SNRPN | 0.33 | −1.55 | 0.34 | 0.53 | 0.69 | Lower in CD1C_B (DC3)/Higher in Mono1 (classical CD14$^{++}$CD16$^-$ mono) | 0 |
| TLR8 | 0.33 | −1.06 | 0.34 | 0.38 | 0.67 | Lower in CD1C_B (DC3)/Higher in Mono1 (classical CD14$^{++}$CD16$^-$ mono) | 1 |
| TRAF6 | 0.33 | −1.03 | 0.34 | 0.46 | 0.66 | Lower in CD1C_B (DC3)/Higher in Mono1 (classical CD14$^{++}$CD16$^-$ mono) | 0 |
| ATXN1 | 0.33 | −1.03 | 0.34 | 0.28 | 0.58 | Lower in CD1C_B (DC3)/Higher in Mono1 (classical CD14$^{++}$CD16$^-$ mono) | 0 |
| CPAMD8 | 0.33 | −1.06 | 0.34 | 0.51 | 0.64 | Lower in CD1C_B (DC3)/Higher in Mono1 (classical CD14$^{++}$CD16$^-$ mono) | 0 |
| PLEKHO2 | 0.33 | −1.24 | 0.34 | 0.41 | 0.65 | Lower in CD1C_B (DC3)/Higher in Mono1 (classical CD14$^{++}$CD16$^-$ mono) | 0 |
| BC090058 | 0.33 | −1.36 | 0.34 | 0.64 | 0.71 | Lower in CD1C_B (DC3)/Higher in Mono1 (classical CD14$^{++}$CD16$^-$ mono) | 0 |
| SMCR8 | 0.33 | −1.22 | 0.35 | 0.40 | 0.63 | Lower in CD1C_B (DC3)/Higher in Mono1 (classical CD14$^{++}$CD16$^-$ mono) | 0 |
| TUBA4A | 0.33 | −1.32 | 0.35 | 0.18 | 0.52 | Lower in CD1C_B (DC3)/Higher in Mono1 (classical CD14$^{++}$CD16$^-$ mono) | 1 |
| AK096668 | 0.33 | −1.08 | 0.35 | 0.44 | 0.65 | Lower in CD1C_B (DC3)/Higher in Mono1 (classical CD14$^{++}$CD16$^-$ mono) | 0 |
| IL8 | 0.33 | −3.04 | 0.35 | 0.21 | 0.51 | Lower in CD1C_B (DC3)/Higher in Mono1 (classical CD14$^{++}$CD16$^-$ mono) | 0 |
| LOC100505746 | 0.33 | −1.13 | 0.35 | 0.44 | 0.68 | Lower in CD1C_B (DC3)/Higher in Mono1 (classical CD14$^{++}$CD16$^-$ mono) | 0 |
| AK055746 | 0.33 | −1.29 | 0.35 | 0.34 | 0.59 | Lower in CD1C_B (DC3)/Higher in Mono1 (classical CD14$^{++}$CD16$^-$ mono) | 0 |
| FAM116A | 0.33 | −1.05 | 0.35 | 0.73 | 0.76 | Lower in CD1C_B (DC3)/Higher in Mono1 (classical CD14$^{++}$CD16$^-$ mono) | 0 |
| FCGR1A | 0.33 | −1.24 | 0.35 | 0.25 | 0.56 | Lower in CD1C_B (DC3)/Higher in Mono1 (classical CD14$^{++}$CD16$^-$ mono) | 1 |
| RAP1GAP2 | 0.33 | −1.19 | 0.35 | 0.31 | 0.58 | Lower in CD1C_B (DC3)/Higher in Mono1 (classical CD14$^{++}$CD16$^-$ mono) | 0 |
| TMEM181 | 0.33 | −1.08 | 0.35 | 0.75 | 0.83 | Lower in CD1C_B (DC3)/Higher in Mono1 (classical CD14$^{++}$CD16$^-$ mono) | 1 |
| TOP1MT | 0.33 | −1.42 | 0.35 | 0.24 | 0.55 | Lower in CD1C_B (DC3)/Higher in Mono1 (classical CD14$^{++}$CD16$^-$ mono) | 0 |
| ADAP2 | 0.32 | −1.66 | 0.35 | 0.30 | 0.56 | Lower in CD1C_B (DC3)/Higher in Mono1 (classical CD14$^{++}$CD16$^-$ mono) | 0 |
| EIF4E3 | 0.32 | −1.34 | 0.35 | 0.16 | 0.50 | Lower in CD1C_B (DC3)/Higher in Mono1 (classical CD14$^{++}$CD16$^-$ mono) | 0 |
| SLC20A1 | 0.32 | −1.10 | 0.35 | 0.54 | 0.74 | Lower in CD1C_B (DC3)/Higher in Mono1 (classical CD14$^{++}$CD16$^-$ mono) | 1 |
| SPC25 | 0.32 | −1.03 | 0.35 | 0.54 | 0.69 | Lower in CD1C_B (DC3)/Higher in Mono1 (classical CD14$^{++}$CD16$^-$ mono) | 0 |
| AX747766 | 0.32 | −1.09 | 0.35 | 0.68 | 0.73 | Lower in CD1C_B (DC3)/Higher in Mono1 (classical CD14$^{++}$CD16$^-$ mono) | 0 |
| CERS5 | 0.32 | −1.05 | 0.35 | 0.59 | 0.72 | Lower in CD1C_B (DC3)/Higher in Mono1 (classical CD14$^{++}$CD16$^-$ mono) | 1 |
| AK307192 | 0.32 | −1.49 | 0.36 | 0.36 | 0.60 | Lower in CD1C_B (DC3)/Higher in Mono1 (classical CD14$^{++}$CD16$^-$ mono) | 0 |
| NOTCH4 | 0.32 | −1.33 | 0.36 | 0.73 | 0.78 | Lower in CD1C_B (DC3)/Higher in Mono1 (classical CD14$^{++}$CD16$^-$ mono) | 1 |
| TCL6 | 0.32 | −1.15 | 0.36 | 0.47 | 0.63 | Lower in CD1C_B (DC3)/Higher in Mono1 (classical CD14$^{++}$CD16$^-$ mono) | 0 |

TABLE E5-continued

Discriminative markers between CD1C_B (inflammatory CD1C; DC3 cluster) and
Mono1 (CD14++ DC16− classical monocyte subsets)

| Gene.ID | AUC value | Avg. Diff.[1] | Power[2] | Pct.1[3] | Pct.2[4] | Comments | Surface Marker[5] |
|---|---|---|---|---|---|---|---|
| AX746683 | 0.32 | −1.07 | 0.36 | 0.55 | 0.67 | Lower in CD1C_B (DC3)/Higher in Mono1 (classical CD14++CD16− mono) | 0 |
| DNASE2 | 0.32 | −1.72 | 0.36 | 0.32 | 0.57 | Lower in CD1C_B (DC3)/Higher in Mono1 (classical CD14++CD16− mono) | 0 |
| EXD1 | 0.32 | −1.05 | 0.36 | 0.53 | 0.67 | Lower in CD1C_B (DC3)/Higher in Mono1 (classical CD14++CD16− mono) | 0 |
| MTRNR2L4 | 0.32 | −1.02 | 0.36 | 0.60 | 0.68 | Lower in CD1C_B (DC3)/Higher in Mono1 (classical CD14++CD16− mono) | 0 |
| OLAH | 0.32 | −1.08 | 0.36 | 0.37 | 0.59 | Lower in CD1C_B (DC3)/Higher in Mono1 (classical CD14++CD16− mono) | 0 |
| SASH1 | 0.32 | −1.37 | 0.36 | 0.46 | 0.62 | Lower in CD1C_B (DC3)/Higher in Mono1 (classical CD14++CD16− mono) | 0 |
| UBXN2B | 0.32 | −1.01 | 0.36 | 0.59 | 0.75 | Lower in CD1C_B (DC3)/Higher in Mono1 (classical CD14++CD16− mono) | 0 |
| SHISA2 | 0.32 | −1.01 | 0.36 | 0.51 | 0.64 | Lower in CD1C_B (DC3)/Higher in Mono1 (classical CD14++CD16− mono) | 1 |
| PTGER2 | 0.32 | −1.67 | 0.37 | 0.22 | 0.54 | Lower in CD1C_B (DC3)/Higher in Mono1 (classical CD14++CD16− mono) | 1 |
| C4ORF26 | 0.32 | −1.15 | 0.37 | 0.38 | 0.61 | Lower in CD1C_B (DC3)/Higher in Mono1 (classical CD14++CD16− mono) | 0 |
| H6PD | 0.32 | −1.17 | 0.37 | 0.54 | 0.69 | Lower in CD1C_B (DC3)/Higher in Mono1 (classical CD14++CD16− mono) | 0 |
| TFRC | 0.32 | −1.15 | 0.37 | 0.42 | 0.69 | Lower in CD1C_B (DC3)/Higher in Mono1 (classical CD14++CD16− mono) | 1 |
| CHRM3 | 0.32 | −1.61 | 0.37 | 0.40 | 0.62 | Lower in CD1C_B (DC3)/Higher in Mono1 (classical CD14++CD16− mono) | 1 |
| DRAM1 | 0.32 | −1.40 | 0.37 | 0.22 | 0.54 | Lower in CD1C_B (DC3)/Higher in Mono1 (classical CD14++CD16− mono) | 1 |
| TNFAIP3 | 0.31 | −1.16 | 0.37 | 0.66 | 0.84 | Lower in CD1C_B (DC3)/Higher in Mono1 (classical CD14++CD16− mono) | 0 |
| STAB1 | 0.31 | −1.08 | 0.37 | 0.43 | 0.74 | Lower in CD1C_B (DC3)/Higher in Mono1 (classical CD14++CD16− mono) | 1 |
| NXN | 0.31 | −1.12 | 0.38 | 0.43 | 0.61 | Lower in CD1C_B (DC3)/Higher in Mono1 (classical CD14++CD16− mono) | 0 |
| NLRP3 | 0.31 | −1.02 | 0.38 | 0.71 | 0.91 | Lower in CD1C_B (DC3)/Higher in Mono1 (classical CD14++CD16− mono) | 0 |
| PNMA2 | 0.31 | −1.11 | 0.38 | 0.56 | 0.67 | Lower in CD1C_B (DC3)/Higher in Mono1 (classical CD14++CD16− mono) | 0 |
| AAK1 | 0.31 | −1.06 | 0.38 | 0.84 | 0.94 | Lower in CD1C_B (DC3)/Higher in Mono1 (classical CD14++CD16− mono) | 0 |
| P2RX1 | 0.31 | −1.45 | 0.38 | 0.32 | 0.62 | Lower in CD1C_B (DC3)/Higher in Mono1 (classical CD14++CD16− mono) | 1 |
| QPCT | 0.31 | −1.32 | 0.39 | 0.47 | 0.70 | Lower in CD1C_B (DC3)/Higher in Mono1 (classical CD14++CD16− mono) | 0 |
| LILRA5 | 0.31 | −1.03 | 0.39 | 0.56 | 0.76 | Lower in CD1C_B (DC3)/Higher in Mono1 (classical CD14++CD16− mono) | 1 |
| C1ORF220 | 0.31 | −1.01 | 0.39 | 0.45 | 0.64 | Lower in CD1C_B (DC3)/Higher in Mono1 (classical CD14++CD16− mono) | 0 |
| MICU1 | 0.31 | −1.09 | 0.39 | 0.36 | 0.68 | Lower in CD1C_B (DC3)/Higher in Mono1 (classical CD14++CD16− mono) | 0 |
| RASGEF1B | 0.30 | −1.72 | 0.39 | 0.54 | 0.72 | Lower in CD1C_B (DC3)/Higher in Mono1 (classical CD14++CD16− mono) | 0 |
| SLA | 0.30 | −1.09 | 0.39 | 0.58 | 0.78 | Lower in CD1C_B (DC3)/Higher in Mono1 (classical CD14++CD16− mono) | 0 |
| ZNF267 | 0.30 | −1.60 | 0.39 | 0.31 | 0.62 | Lower in CD1C_B (DC3)/Higher in Mono1 (classical CD14++CD16− mono) | 0 |
| FOXO3 | 0.30 | −1.40 | 0.39 | 0.41 | 0.67 | Lower in CD1C_B (DC3)/Higher in Mono1 (classical CD14++CD16− mono) | 0 |
| LOC100190986 | 0.30 | −1.22 | 0.39 | 0.55 | 0.75 | Lower in CD1C_B (DC3)/Higher in Mono1 (classical CD14++CD16− mono) | 0 |
| MXD1 | 0.30 | −1.05 | 0.39 | 0.72 | 0.89 | Lower in CD1C_B (DC3)/Higher in Mono1 (classical CD14++CD16− mono) | 0 |
| AL050141 | 0.30 | −1.60 | 0.40 | 0.38 | 0.62 | Lower in CD1C_B (DC3)/Higher in Mono1 (classical CD14++CD16− mono) | 0 |
| LRRN4CL | 0.30 | −1.07 | 0.40 | 0.58 | 0.70 | Lower in CD1C_B (DC3)/Higher in Mono1 (classical CD14++CD16− mono) | 1 |
| FBLN1 | 0.30 | −1.04 | 0.40 | 0.56 | 0.71 | Lower in CD1C_B (DC3)/Higher in Mono1 (classical CD14++CD16− mono) | 0 |
| KDM1B | 0.30 | −1.04 | 0.40 | 0.62 | 0.81 | Lower in CD1C_B (DC3)/Higher in Mono1 (classical CD14++CD16− mono) | 0 |
| PLEKHM1P | 0.30 | −1.03 | 0.40 | 0.58 | 0.83 | Lower in CD1C_B (DC3)/Higher in Mono1 (classical CD14++CD16− mono) | 0 |
| ABCC3 | 0.30 | −2.17 | 0.40 | 0.52 | 0.67 | Lower in CD1C_B (DC3)/Higher in Mono1 (classical CD14++CD16− mono) | 1 |

TABLE E5-continued

Discriminative markers between CD1C_B (inflammatory CD1C; DC3 cluster) and
Mono1 (CD14++ DC16− classical monocyte subsets)

| Gene.ID | AUC value | Avg. Diff.[1] | Power[2] | Pct.1[3] | Pct.2[4] | Comments | Surface Marker[5] |
|---|---|---|---|---|---|---|---|
| CLMN | 0.30 | −1.39 | 0.40 | 0.36 | 0.64 | Lower in CD1C_B (DC3)/Higher in Mono1 (classical CD14++CD16− mono) | 1 |
| BC041434 | 0.30 | −1.08 | 0.41 | 0.46 | 0.70 | Lower in CD1C_B (DC3)/Higher in Mono1 (classical CD14++CD16− mono) | 0 |
| RBP7 | 0.30 | −3.59 | 0.41 | 0.18 | 0.50 | Lower in CD1C_B (DC3)/Higher in Mono1 (classical CD14++CD16− mono) | 0 |
| MAP3K3 | 0.30 | −1.34 | 0.41 | 0.52 | 0.78 | Lower in CD1C_B (DC3)/Higher in Mono1 (classical CD14++CD16− mono) | 0 |
| GBP4 | 0.29 | −1.01 | 0.41 | 0.77 | 0.85 | Lower in CD1C_B (DC3)/Higher in Mono1 (classical CD14++CD16− mono) | 0 |
| PAG1 | 0.29 | −1.33 | 0.41 | 0.66 | 0.80 | Lower in CD1C_B (DC3)/Higher in Mono1 (classical CD14++CD16− mono) | 0 |
| TTYH3 | 0.29 | −1.40 | 0.41 | 0.33 | 0.64 | Lower in CD1C_B (DC3)/Higher in Mono1 (classical CD14++CD16− mono) | 1 |
| USP15 | 0.29 | −1.02 | 0.41 | 0.84 | 0.95 | Lower in CD1C_B (DC3)/Higher in Mono1 (classical CD14++CD16− mono) | 0 |
| LOC100132774 | 0.29 | −1.17 | 0.41 | 0.66 | 0.80 | Lower in CD1C_B (DC3)/Higher in Mono1 (classical CD14++CD16− mono) | 0 |
| NRIP3 | 0.29 | −1.41 | 0.41 | 0.50 | 0.68 | Lower in CD1C_B (DC3)/Higher in Mono1 (classical CD14++CD16− mono) | 0 |
| PIGX | 0.29 | −1.05 | 0.41 | 0.82 | 0.85 | Lower in CD1C_B (DC3)/Higher in Mono1 (classical CD14++CD16− mono) | 1 |
| PAPLN | 0.29 | −1.03 | 0.42 | 0.77 | 0.86 | Lower in CD1C_B (DC3)/Higher in Mono1 (classical CD14++CD16− mono) | 0 |
| PCNX | 0.29 | −1.59 | 0.42 | 0.47 | 0.69 | Lower in CD1C_B (DC3)/Higher in Mono1 (classical CD14++CD16− mono) | 1 |
| SAMD8 | 0.29 | −1.20 | 0.42 | 0.63 | 0.79 | Lower in CD1C_B (DC3)/Higher in Mono1 (classical CD14++CD16− mono) | 1 |
| UTP23 | 0.29 | −1.19 | 0.42 | 0.60 | 0.76 | Lower in CD1C_B (DC3)/Higher in Mono1 (classical CD14++CD16− mono) | 0 |
| ZNF619 | 0.29 | −1.16 | 0.42 | 0.63 | 0.77 | Lower in CD1C_B (DC3)/Higher in Mono1 (classical CD14++CD16− mono) | 0 |
| AF420437 | 0.29 | −1.28 | 0.42 | 0.59 | 0.77 | Lower in CD1C_B (DC3)/Higher in Mono1 (classical CD14++CD16− mono) | 0 |
| CES3 | 0.29 | −1.02 | 0.42 | 0.53 | 0.74 | Lower in CD1C_B (DC3)/Higher in Mono1 (classical CD14++CD16− mono) | 0 |
| DPEP2 | 0.29 | −1.24 | 0.42 | 0.33 | 0.67 | Lower in CD1C_B (DC3)/Higher in Mono1 (classical CD14++CD16− mono) | 1 |
| HRH2 | 0.29 | −1.11 | 0.42 | 0.48 | 0.74 | Lower in CD1C_B (DC3)/Higher in Mono1 (classical CD14++CD16− mono) | 1 |
| NFAT5 | 0.29 | −1.16 | 0.43 | 0.79 | 0.83 | Lower in CD1C_B (DC3)/Higher in Mono1 (classical CD14++CD16− mono) | 0 |
| TMEM127 | 0.29 | −1.04 | 0.43 | 0.56 | 0.81 | Lower in CD1C_B (DC3)/Higher in Mono1 (classical CD14++CD16− mono) | 1 |
| BC041449 | 0.29 | −1.16 | 0.43 | 0.53 | 0.74 | Lower in CD1C_B (DC3)/Higher in Mono1 (classical CD14++CD16− mono) | 0 |
| CALCOCO2 | 0.28 | −1.09 | 0.43 | 0.70 | 0.83 | Lower in CD1C_B (DC3)/Higher in Mono1 (classical CD14++CD16− mono) | 0 |
| F5 | 0.28 | −2.17 | 0.43 | 0.20 | 0.56 | Lower in CD1C_B (DC3)/Higher in Mono1 (classical CD14++CD16− mono) | 1 |
| SAMSN1 | 0.28 | −1.24 | 0.43 | 0.40 | 0.74 | Lower in CD1C_B (DC3)/Higher in Mono1 (classical CD14++CD16− mono) | 0 |
| ZNF527 | 0.28 | −1.03 | 0.43 | 0.61 | 0.78 | Lower in CD1C_B (DC3)/Higher in Mono1 (classical CD14++CD16− mono) | 0 |
| DSTYK | 0.28 | −1.01 | 0.43 | 0.75 | 0.90 | Lower in CD1C_B (DC3)/Higher in Mono1 (classical CD14++CD16− mono) | 0 |
| RHD | 0.28 | −1.06 | 0.43 | 0.70 | 0.76 | Lower in CD1C_B (DC3)/Higher in Mono1 (classical CD14++CD16− mono) | 1 |
| DQ573668 | 0.28 | −1.16 | 0.44 | 0.55 | 0.74 | Lower in CD1C_B (DC3)/Higher in Mono1 (classical CD14++CD16− mono) | 0 |
| FCGR3A | 0.28 | −4.55 | 0.44 | 0.36 | 0.61 | Lower in CD1C_B (DC3)/Higher in Mono1 (classical CD14++CD16− mono) | 1 |
| LPAR6 | 0.28 | −1.99 | 0.44 | 0.33 | 0.63 | Lower in CD1C_B (DC3)/Higher in Mono1 (classical CD14++CD16− mono) | 1 |
| MED18 | 0.28 | −1.09 | 0.44 | 0.70 | 0.79 | Lower in CD1C_B (DC3)/Higher in Mono1 (classical CD14++CD16− mono) | 0 |
| MAP4K4 | 0.28 | −1.06 | 0.44 | 0.34 | 0.68 | Lower in CD1C_B (DC3)/Higher in Mono1 (classical CD14++CD16− mono) | 0 |
| SYF2 | 0.28 | −1.03 | 0.44 | 0.81 | 0.91 | Lower in CD1C_B (DC3)/Higher in Mono1 (classical CD14++CD16− mono) | 0 |
| LOC91948 | 0.28 | −1.29 | 0.44 | 0.51 | 0.71 | Lower in CD1C_B (DC3)/Higher in Mono1 (classical CD14++CD16− mono) | 0 |
| LOC100507032 | 0.28 | −1.05 | 0.44 | 0.33 | 0.65 | Lower in CD1C_B (DC3)/Higher in Mono1 (classical CD14++CD16− mono) | 0 |

TABLE E5-continued

Discriminative markers between CD1C_B (inflammatory CD1C; DC3 cluster) and Mono1 (CD14$^{++}$ DC16$^-$ classical monocyte subsets)

| Gene.ID | AUC value | Avg. Diff.[1] | Power[2] | Pct.1[3] | Pct.2[4] | Comments | Surface Marker[5] |
|---|---|---|---|---|---|---|---|
| FNDC3B | 0.28 | −1.11 | 0.45 | 0.65 | 0.85 | Lower in CD1C_B (DC3)/Higher in Mono1 (classical CD14$^{++}$CD16$^-$ mono) | 1 |
| PTPRJ | 0.28 | −1.57 | 0.45 | 0.51 | 0.79 | Lower in CD1C_B (DC3)/Higher in Mono1 (classical CD14$^{++}$CD16$^-$ mono) | 1 |
| ZNF687 | 0.28 | −1.31 | 0.45 | 0.66 | 0.81 | Lower in CD1C_B (DC3)/Higher in Mono1 (classical CD14$^{++}$CD16$^-$ mono) | 0 |
| AX746871 | 0.28 | −1.02 | 0.45 | 0.76 | 0.82 | Lower in CD1C_B (DC3)/Higher in Mono1 (classical CD14$^{++}$CD16$^-$ mono) | 0 |
| ERVK13-1 | 0.28 | −1.69 | 0.45 | 0.56 | 0.77 | Lower in CD1C_B (DC3)/Higher in Mono1 (classical CD14$^{++}$CD16$^-$ mono) | 0 |
| MLXIPL | 0.28 | −1.03 | 0.45 | 0.61 | 0.78 | Lower in CD1C_B (DC3)/Higher in Mono1 (classical CD14$^{++}$CD16$^-$ mono) | 0 |
| CD93 | 0.27 | −1.19 | 0.45 | 0.42 | 0.78 | Lower in CD1C_B (DC3)/Higher in Mono1 (classical CD14$^{++}$CD16$^-$ mono) | 1 |
| LOC100506334 | 0.27 | −1.04 | 0.46 | 0.63 | 0.80 | Lower in CD1C_B (DC3)/Higher in Mono1 (classical CD14$^{++}$CD16$^-$ mono) | 0 |
| WNK4 | 0.27 | −1.11 | 0.46 | 0.64 | 0.79 | Lower in CD1C_B (DC3)/Higher in Mono1 (classical CD14$^{++}$CD16$^-$ mono) | 0 |
| DENND3 | 0.27 | −1.02 | 0.46 | 0.70 | 0.89 | Lower in CD1C_B (DC3)/Higher in Mono1 (classical CD14$^{++}$CD16$^-$ mono) | 1 |
| GIMAP4 | 0.27 | −1.14 | 0.46 | 0.54 | 0.82 | Lower in CD1C_B (DC3)/Higher in Mono1 (classical CD14$^{++}$CD16$^-$ mono) | 1 |
| IFNGR2 | 0.27 | −1.17 | 0.46 | 0.56 | 0.86 | Lower in CD1C_B (DC3)/Higher in Mono1 (classical CD14$^{++}$CD16$^-$ mono) | 1 |
| SYNE2 | 0.27 | −1.95 | 0.46 | 0.38 | 0.67 | Lower in CD1C_B (DC3)/Higher in Mono1 (classical CD14$^{++}$CD16$^-$ mono) | 1 |
| CR936688 | 0.27 | −1.54 | 0.46 | 0.70 | 0.82 | Lower in CD1C_B (DC3)/Higher in Mono1 (classical CD14$^{++}$CD16$^-$ mono) | 0 |
| LOC158696 | 0.27 | −1.13 | 0.46 | 0.41 | 0.67 | Lower in CD1C_B (DC3)/Higher in Mono1 (classical CD14$^{++}$CD16$^-$ mono) | 0 |
| ZFP106 | 0.27 | −1.02 | 0.46 | 0.91 | 0.98 | Lower in CD1C_B (DC3)/Higher in Mono1 (classical CD14$^{++}$CD16$^-$ mono) | 0 |
| AK298300 | 0.27 | −1.17 | 0.47 | 0.53 | 0.77 | Lower in CD1C_B (DC3)/Higher in Mono1 (classical CD14$^{++}$CD16$^-$ mono) | 0 |
| ZNF780A | 0.27 | −1.37 | 0.47 | 0.26 | 0.64 | Lower in CD1C_B (DC3)/Higher in Mono1 (classical CD14$^{++}$CD16$^-$ mono) | 0 |
| TMEM136 | 0.27 | −1.13 | 0.47 | 0.60 | 0.74 | Lower in CD1C_B (DC3)/Higher in Mono1 (classical CD14$^{++}$CD16$^-$ mono) | 1 |
| ZNF714 | 0.27 | −1.10 | 0.47 | 0.86 | 0.93 | Lower in CD1C_B (DC3)/Higher in Mono1 (classical CD14$^{++}$CD16$^-$ mono) | 0 |
| BST1 | 0.26 | −1.28 | 0.47 | 0.58 | 0.82 | Lower in CD1C_B (DC3)/Higher in Mono1 (classical CD14$^{++}$CD16$^-$ mono) | 1 |
| PLEKHM1 | 0.26 | −1.20 | 0.47 | 0.51 | 0.82 | Lower in CD1C_B (DC3)/Higher in Mono1 (classical CD14$^{++}$CD16$^-$ mono) | 0 |
| ITGAL | 0.26 | −1.03 | 0.47 | 0.81 | 0.95 | Lower in CD1C_B (DC3)/Higher in Mono1 (classical CD14$^{++}$CD16$^-$ mono) | 1 |
| C10ORF82 | 0.26 | −1.10 | 0.48 | 0.74 | 0.80 | Lower in CD1C_B (DC3)/Higher in Mono1 (classical CD14$^{++}$CD16$^-$ mono) | 0 |
| RTDR1 | 0.26 | −1.03 | 0.48 | 0.82 | 0.83 | Lower in CD1C_B (DC3)/Higher in Mono1 (classical CD14$^{++}$CD16$^-$ mono) | 0 |
| CYTH4 | 0.26 | −1.08 | 0.48 | 0.64 | 0.88 | Lower in CD1C_B (DC3)/Higher in Mono1 (classical CD14$^{++}$CD16$^-$ mono) | 0 |
| TREM1 | 0.26 | −1.11 | 0.48 | 0.61 | 0.88 | Lower in CD1C_B (DC3)/Higher in Mono1 (classical CD14$^{++}$CD16$^-$ mono) | 1 |
| SEC14L1 | 0.26 | −1.13 | 0.48 | 0.84 | 0.96 | Lower in CD1C_B (DC3)/Higher in Mono1 (classical CD14$^{++}$CD16$^-$ mono) | 0 |
| ECE1 | 0.26 | −2.95 | 0.48 | 0.38 | 0.65 | Lower in CD1C_B (DC3)/Higher in Mono1 (classical CD14$^{++}$CD16$^-$ mono) | 1 |
| GBP2 | 0.26 | −1.55 | 0.48 | 0.43 | 0.76 | Lower in CD1C_B (DC3)/Higher in Mono1 (classical CD14$^{++}$CD16$^-$ mono) | 0 |
| MPP4 | 0.26 | −1.01 | 0.49 | 0.82 | 0.87 | Lower in CD1C_B (DC3)/Higher in Mono1 (classical CD14$^{++}$CD16$^-$ mono) | 0 |
| NAAA | 0.26 | −1.19 | 0.49 | 0.85 | 0.94 | Lower in CD1C_B (DC3)/Higher in Mono1 (classical CD14$^{++}$CD16$^-$ mono) | 1 |
| GLOD5 | 0.26 | −1.02 | 0.49 | 0.73 | 0.83 | Lower in CD1C_B (DC3)/Higher in Mono1 (classical CD14$^{++}$CD16$^-$ mono) | 0 |
| SLC12A6 | 0.26 | −1.36 | 0.49 | 0.91 | 0.94 | Lower in CD1C_B (DC3)/Higher in Mono1 (classical CD14$^{++}$CD16$^-$ mono) | 1 |
| BC039319 | 0.25 | −1.07 | 0.49 | 0.68 | 0.81 | Lower in CD1C_B (DC3)/Higher in Mono1 (classical CD14$^{++}$CD16$^-$ mono) | 0 |
| G0S2 | 0.25 | −3.11 | 0.50 | 0.38 | 0.61 | Lower in CD1C_B (DC3)/Higher in Mono1 (classical CD14$^{++}$CD16$^-$ mono) | 0 |
| LOC100505702 | 0.25 | −1.34 | 0.50 | 0.57 | 0.75 | Lower in CD1C_B (DC3)/Higher in Mono1 (classical CD14$^{++}$CD16$^-$ mono) | 0 |

TABLE E5-continued

Discriminative markers between CD1C_B (inflammatory CD1C; DC3 cluster) and
Mono1 (CD14$^{++}$ DC16$^-$ classical monocyte subsets)

| Gene.ID | AUC value | Avg. Diff.[1] | Power[2] | Pct.1[3] | Pct.2[4] | Comments | Surface Marker[5] |
|---|---|---|---|---|---|---|---|
| PER1 | 0.25 | −1.38 | 0.50 | 0.68 | 0.90 | Lower in CD1C_B (DC3)/Higher in Mono1 (classical CD14$^{++}$CD16$^-$ mono) | 0 |
| UPP1 | 0.25 | −1.43 | 0.50 | 0.54 | 0.81 | Lower in CD1C_B (DC3)/Higher in Mono1 (classical CD14$^{++}$CD16$^-$ mono) | 0 |
| AK055694 | 0.25 | −1.14 | 0.50 | 0.59 | 0.83 | Lower in CD1C_B (DC3)/Higher in Mono1 (classical CD14$^{++}$CD16$^-$ mono) | 0 |
| CCR1 | 0.25 | −1.37 | 0.50 | 0.44 | 0.81 | Lower in CD1C_B (DC3)/Higher in Mono1 (classical CD14$^{++}$CD16$^-$ mono) | 1 |
| S100A12 | 0.25 | −1.33 | 0.50 | 0.62 | 0.85 | Lower in CD1C_B (DC3)/Higher in Mono1 (classical CD14$^{++}$CD16$^-$ mono) | 0 |
| CCPG1 | 0.25 | −1.77 | 0.50 | 0.64 | 0.84 | Lower in CD1C_B (DC3)/Higher in Mono1 (classical CD14$^{++}$CD16$^-$ mono) | 1 |
| MAFB | 0.25 | −1.55 | 0.50 | 0.20 | 0.67 | Lower in CD1C_B (DC3)/Higher in Mono1 (classical CD14$^{++}$CD16$^-$ mono) | 0 |
| MS4A7 | 0.25 | −1.67 | 0.50 | 0.65 | 0.82 | Lower in CD1C_B (DC3)/Higher in Mono1 (classical CD14$^{++}$CD16$^-$ mono) | 1 |
| PIK3IP1 | 0.25 | −3.12 | 0.50 | 0.23 | 0.62 | Lower in CD1C_B (DC3)/Higher in Mono1 (classical CD14$^{++}$CD16$^-$ mono) | 1 |
| DPY19L2P2 | 0.25 | −1.21 | 0.51 | 0.67 | 0.89 | Lower in CD1C_B (DC3)/Higher in Mono1 (classical CD14$^{++}$CD16$^-$ mono) | 0 |
| CD82 | 0.25 | −2.31 | 0.51 | 0.38 | 0.70 | Lower in CD1C_B (DC3)/Higher in Mono1 (classical CD14$^{++}$CD16$^-$ mono) | 1 |
| C3AR1 | 0.25 | −3.08 | 0.51 | 0.13 | 0.58 | Lower in CD1C_B (DC3)/Higher in Mono1 (classical CD14$^{++}$CD16$^-$ mono) | 1 |
| FAM198B | 0.25 | −1.49 | 0.51 | 0.39 | 0.79 | Lower in CD1C_B (DC3)/Higher in Mono1 (classical CD14$^{++}$CD16$^-$ mono) | 1 |
| LRRK2 | 0.24 | −1.24 | 0.51 | 0.42 | 0.83 | Lower in CD1C_B (DC3)/Higher in Mono1 (classical CD14$^{++}$CD16$^-$ mono) | 0 |
| C12ORF50 | 0.24 | −1.09 | 0.51 | 0.71 | 0.85 | Lower in CD1C_B (DC3)/Higher in Mono1 (classical CD14$^{++}$CD16$^-$ mono) | 0 |
| CCL5 | 0.24 | −1.10 | 0.51 | 0.95 | 0.98 | Lower in CD1C_B (DC3)/Higher in Mono1 (classical CD14$^{++}$CD16$^-$ mono) | 1 |
| ZYG11A | 0.24 | −1.05 | 0.51 | 0.70 | 0.81 | Lower in CD1C_B (DC3)/Higher in Mono1 (classical CD14$^{++}$CD16$^-$ mono) | 0 |
| CR1 | 0.24 | −1.39 | 0.52 | 0.33 | 0.71 | Lower in CD1C_B (DC3)/Higher in Mono1 (classical CD14$^{++}$CD16$^-$ mono) | 1 |
| PLAUR | 0.24 | −1.17 | 0.52 | 0.84 | 0.93 | Lower in CD1C_B (DC3)/Higher in Mono1 (classical CD14$^{++}$CD16$^-$ mono) | 1 |
| CYTIP | 0.24 | −1.10 | 0.52 | 0.70 | 0.92 | Lower in CD1C_B (DC3)/Higher in Mono1 (classical CD14$^{++}$CD16$^-$ mono) | 0 |
| ALDH1A1 | 0.24 | −5.39 | 0.52 | 0.00 | 0.52 | Lower in CD1C_B (DC3)/Higher in Mono1 (classical CD14$^{++}$CD16$^-$ mono) | 0 |
| BC042616 | 0.24 | −1.03 | 0.52 | 0.75 | 0.90 | Lower in CD1C_B (DC3)/Higher in Mono1 (classical CD14$^{++}$CD16$^-$ mono) | 0 |
| GLIPR1L2 | 0.24 | −1.00 | 0.52 | 0.76 | 0.89 | Lower in CD1C_B (DC3)/Higher in Mono1 (classical CD14$^{++}$CD16$^-$ mono) | 1 |
| FAM73A | 0.24 | −1.00 | 0.52 | 0.75 | 0.86 | Lower in CD1C_B (DC3)/Higher in Mono1 (classical CD14$^{++}$CD16$^-$ mono) | 1 |
| PFKFB3 | 0.24 | −1.45 | 0.52 | 0.25 | 0.73 | Lower in CD1C_B (DC3)/Higher in Mono1 (classical CD14$^{++}$CD16$^-$ mono) | 0 |
| ZDHHC20 | 0.24 | −1.19 | 0.52 | 0.58 | 0.89 | Lower in CD1C_B (DC3)/Higher in Mono1 (classical CD14$^{++}$CD16$^-$ mono) | 1 |
| ZSWIM1 | 0.24 | −1.03 | 0.52 | 0.72 | 0.84 | Lower in CD1C_B (DC3)/Higher in Mono1 (classical CD14$^{++}$CD16$^-$ mono) | 0 |
| SLC44A2 | 0.24 | −2.58 | 0.53 | 0.54 | 0.75 | Lower in CD1C_B (DC3)/Higher in Mono1 (classical CD14$^{++}$CD16$^-$ mono) | 1 |
| AL832007 | 0.24 | −1.01 | 0.53 | 0.74 | 0.85 | Lower in CD1C_B (DC3)/Higher in Mono1 (classical CD14$^{++}$CD16$^-$ mono) | 0 |
| NUMB | 0.24 | −1.05 | 0.53 | 0.75 | 0.95 | Lower in CD1C_B (DC3)/Higher in Mono1 (classical CD14$^{++}$CD16$^-$ mono) | 0 |
| PYGL | 0.24 | −1.36 | 0.53 | 0.71 | 0.92 | Lower in CD1C_B (DC3)/Higher in Mono1 (classical CD14$^{++}$CD16$^-$ mono) | 0 |
| ZCCHC6 | 0.24 | −1.22 | 0.53 | 0.80 | 0.97 | Lower in CD1C_B (DC3)/Higher in Mono1 (classical CD14$^{++}$CD16$^-$ mono) | 0 |
| ABCB9 | 0.24 | −1.00 | 0.53 | 0.72 | 0.84 | Lower in CD1C_B (DC3)/Higher in Mono1 (classical CD14$^{++}$CD16$^-$ mono) | 1 |
| NCKAP5 | 0.24 | −1.04 | 0.53 | 0.76 | 0.86 | Lower in CD1C_B (DC3)/Higher in Mono1 (classical CD14$^{++}$CD16$^-$ mono) | 0 |
| DENND5A | 0.23 | −1.21 | 0.53 | 0.59 | 0.90 | Lower in CD1C_B (DC3)/Higher in Mono1 (classical CD14$^{++}$CD16$^-$ mono) | 1 |
| RABL5 | 0.23 | −1.04 | 0.53 | 0.86 | 0.93 | Lower in CD1C_B (DC3)/Higher in Mono1 (classical CD14$^{++}$CD16$^-$ mono) | 0 |
| AK302511 | 0.23 | −3.35 | 0.54 | 0.02 | 0.55 | Lower in CD1C_B (DC3)/Higher in Mono1 (classical CD14$^{++}$CD16$^-$ mono) | 0 |

TABLE E5-continued

Discriminative markers between CD1C_B (inflammatory CD1C; DC3 cluster) and Mono1 (CD14$^{++}$ DC16$^{-}$ classical monocyte subsets)

| Gene.ID | AUC value | Avg. Diff.[1] | Power[2] | Pct.1[3] | Pct.2[4] | Comments | Surface Marker[5] |
|---|---|---|---|---|---|---|---|
| APOL4 | 0.23 | −1.27 | 0.54 | 0.62 | 0.84 | Lower in CD1C_B (DC3)/Higher in Mono1 (classical CD14$^{++}$CD16$^{-}$ mono) | 1 |
| GSG1 | 0.23 | −1.07 | 0.54 | 0.63 | 0.84 | Lower in CD1C_B (DC3)/Higher in Mono1 (classical CD14$^{++}$CD16$^{-}$ mono) | 1 |
| TEX9 | 0.23 | −1.09 | 0.54 | 0.67 | 0.81 | Lower in CD1C_B (DC3)/Higher in Mono1 (classical CD14$^{++}$CD16$^{-}$ mono) | 0 |
| DYSF | 0.23 | −3.20 | 0.54 | 0.01 | 0.55 | Lower in CD1C_B (DC3)/Higher in Mono1 (classical CD14$^{++}$CD16$^{-}$ mono) | 1 |
| FLCN | 0.23 | −1.34 | 0.54 | 0.77 | 0.86 | Lower in CD1C_B (DC3)/Higher in Mono1 (classical CD14$^{++}$CD16$^{-}$ mono) | 0 |
| LOC100130451 | 0.23 | −1.09 | 0.54 | 0.70 | 0.86 | Lower in CD1C_B (DC3)/Higher in Mono1 (classical CD14$^{++}$CD16$^{-}$ mono) | 0 |
| SIRPB1 | 0.23 | −1.44 | 0.54 | 0.55 | 0.85 | Lower in CD1C_B (DC3)/Higher in Mono1 (classical CD14$^{++}$CD16$^{-}$ mono) | 1 |
| WDR37 | 0.23 | −1.04 | 0.54 | 0.63 | 0.89 | Lower in CD1C_B (DC3)/Higher in Mono1 (classical CD14$^{++}$CD16$^{-}$ mono) | 0 |
| ZNF695 | 0.23 | −1.17 | 0.54 | 0.66 | 0.83 | Lower in CD1C_B (DC3)/Higher in Mono1 (classical CD14$^{++}$CD16$^{-}$ mono) | 0 |
| KREMEN1 | 0.23 | −1.05 | 0.54 | 0.83 | 0.93 | Lower in CD1C_B (DC3)/Higher in Mono1 (classical CD14$^{++}$CD16$^{-}$ mono) | 1 |
| NTNJ1 | 0.23 | −1.03 | 0.54 | 0.48 | 0.89 | Lower in CD1C_B (DC3)/Higher in Mono1 (classical CD14$^{++}$CD16$^{-}$ mono) | 1 |
| CORO2A | 0.23 | −1.10 | 0.55 | 0.75 | 0.91 | Lower in CD1C_B (DC3)/Higher in Mono1 (classical CD14$^{++}$CD16$^{-}$ mono) | 0 |
| BC038201 | 0.23 | −1.12 | 0.55 | 0.77 | 0.87 | Lower in CD1C_B (DC3)/Higher in Mono1 (classical CD14$^{++}$CD16$^{-}$ mono) | 0 |
| IQSEC1 | 0.23 | −1.52 | 0.55 | 0.52 | 0.85 | Lower in CD1C_B (DC3)/Higher in Mono1 (classical CD14$^{++}$CD16$^{-}$ mono) | 0 |
| AL832447 | 0.22 | −1.13 | 0.55 | 0.55 | 0.87 | Lower in CD1C_B (DC3)/Higher in Mono1 (classical CD14$^{++}$CD16$^{-}$ mono) | 0 |
| FLJ13197 | 0.22 | −1.01 | 0.55 | 0.83 | 0.93 | Lower in CD1C_B (DC3)/Higher in Mono1 (classical CD14$^{++}$CD16$^{-}$ mono) | 0 |
| MDM2 | 0.22 | −1.01 | 0.55 | 0.93 | 0.99 | Lower in CD1C_B (DC3)/Higher in Mono1 (classical CD14$^{++}$CD16$^{-}$ mono) | 0 |
| ANKRD16 | 0.22 | −1.01 | 0.56 | 0.79 | 0.91 | Lower in CD1C_B (DC3)/Higher in Mono1 (classical CD14$^{++}$CD16$^{-}$ mono) | 0 |
| AX746699 | 0.22 | −1.09 | 0.56 | 0.82 | 0.89 | Lower in CD1C_B (DC3)/Higher in Mono1 (classical CD14$^{++}$CD16$^{-}$ mono) | 0 |
| ROCK1P1 | 0.22 | −1.01 | 0.56 | 0.57 | 0.92 | Lower in CD1C_B (DC3)/Higher in Mono1 (classical CD14$^{++}$CD16$^{-}$ mono) | 0 |
| CRISPLD2 | 0.22 | −3.06 | 0.56 | 0.50 | 0.77 | Lower in CD1C_B (DC3)/Higher in Mono1 (classical CD14$^{++}$CD16$^{-}$ mono) | 0 |
| DZIP3 | 0.22 | −1.07 | 0.56 | 0.85 | 0.97 | Lower in CD1C_B (DC3)/Higher in Mono1 (classical CD14$^{++}$CD16$^{-}$ mono) | 1 |
| LOC728558 | 0.22 | −1.09 | 0.56 | 0.82 | 0.97 | Lower in CD1C_B (DC3)/Higher in Mono1 (classical CD14$^{++}$CD16$^{-}$ mono) | 0 |
| AX747172 | 0.22 | −1.08 | 0.56 | 0.80 | 0.90 | Lower in CD1C_B (DC3)/Higher in Mono1 (classical CD14$^{++}$CD16$^{-}$ mono) | 0 |
| IGF2R | 0.22 | −2.05 | 0.56 | 0.10 | 0.63 | Lower in CD1C_B (DC3)/Higher in Mono1 (classical CD14$^{++}$CD16$^{-}$ mono) | 1 |
| TBXAS1 | 0.22 | −1.09 | 0.56 | 0.70 | 0.95 | Lower in CD1C_B (DC3)/Higher in Mono1 (classical CD14$^{++}$CD16$^{-}$ mono) | 1 |
| DQ574721 | 0.22 | −3.11 | 0.56 | 0.15 | 0.63 | Lower in CD1C_B (DC3)/Higher in Mono1 (classical CD14$^{++}$CD16$^{-}$ mono) | 0 |
| CAMKK2 | 0.22 | −1.65 | 0.57 | 0.47 | 0.82 | Lower in CD1C_B (DC3)/Higher in Mono1 (classical CD14$^{++}$CD16$^{-}$ mono) | 1 |
| PHF12 | 0.22 | −1.26 | 0.57 | 0.80 | 0.93 | Lower in CD1C_B (DC3)/Higher in Mono1 (classical CD14$^{++}$CD16$^{-}$ mono) | 0 |
| RNF144B | 0.22 | −1.21 | 0.57 | 0.64 | 0.94 | Lower in CD1C_B (DC3)/Higher in Mono1 (classical CD14$^{++}$CD16$^{-}$ mono) | 1 |
| SRRM2 | 0.22 | −1.04 | 0.57 | 0.94 | 0.99 | Lower in CD1C_B (DC3)/Higher in Mono1 (classical CD14$^{++}$CD16$^{-}$ mono) | 0 |
| ZNF788 | 0.22 | −1.09 | 0.57 | 0.77 | 0.92 | Lower in CD1C_B (DC3)/Higher in Mono1 (classical CD14$^{++}$CD16$^{-}$ mono) | 0 |
| S100A8 | 0.21 | −1.04 | 0.57 | 0.98 | 0.99 | Lower in CD1C_B (DC3)/Higher in Mono1 (classical CD14$^{++}$CD16$^{-}$ mono) | 0 |
| GAS7 | 0.21 | −1.38 | 0.57 | 0.66 | 0.91 | Lower in CD1C_B (DC3)/Higher in Mono1 (classical CD14$^{++}$CD16$^{-}$ mono) | 0 |
| SIGLEC10 | 0.21 | −2.07 | 0.58 | 0.75 | 0.89 | Lower in CD1C_B (DC3)/Higher in Mono1 (classical CD14$^{++}$CD16$^{-}$ mono) | 1 |
| LILRB2 | 0.21 | −1.06 | 0.58 | 0.92 | 0.96 | Lower in CD1C_B (DC3)/Higher in Mono1 (classical CD14$^{++}$CD16$^{-}$ mono) | 1 |
| DMXL2 | 0.21 | −1.34 | 0.58 | 0.61 | 0.94 | Lower in CD1C_B (DC3)/Higher in Mono1 (classical CD14$^{++}$CD16$^{-}$ mono) | 1 |

TABLE E5-continued

Discriminative markers between CD1C_B (inflammatory CD1C; DC3 cluster) and
Mono1 (CD14++ DC16− classical monocyte subsets)

| Gene.ID | AUC value | Avg. Diff.[1] | Power[2] | Pct.1[3] | Pct.2[4] | Comments | Surface Marker[5] |
|---|---|---|---|---|---|---|---|
| GNS | 0.21 | −1.12 | 0.58 | 0.86 | 0.97 | Lower in CD1C_B (DC3)/Higher in Mono1 (classical CD14++CD16− mono) | 1 |
| AK124179 | 0.21 | −1.22 | 0.59 | 0.66 | 0.89 | Lower in CD1C_B (DC3)/Higher in Mono1 (classical CD14++CD16− mono) | 0 |
| CCDC144B | 0.21 | −1.03 | 0.59 | 0.96 | 0.98 | Lower in CD1C_B (DC3)/Higher in Mono1 (classical CD14++CD16− mono) | 0 |
| NBEAL2 | 0.21 | −2.01 | 0.59 | 0.39 | 0.78 | Lower in CD1C_B (DC3)/Higher in Mono1 (classical CD14++CD16− mono) | 0 |
| NFAM1 | 0.21 | −1.39 | 0.59 | 0.64 | 0.91 | Lower in CD1C_B (DC3)/Higher in Mono1 (classical CD14++CD16− mono) | 1 |
| TBC1D24 | 0.21 | −1.00 | 0.59 | 0.79 | 0.91 | Lower in CD1C_B (DC3)/Higher in Mono1 (classical CD14++CD16− mono) | 0 |
| LOC100129716 | 0.21 | −1.03 | 0.59 | 0.67 | 0.87 | Lower in CD1C_B (DC3)/Higher in Mono1 (classical CD14++CD16− mono) | 0 |
| CDC42EP3 | 0.20 | −1.97 | 0.59 | 0.30 | 0.80 | Lower in CD1C_B (DC3)/Higher in Mono1 (classical CD14++CD16− mono) | 0 |
| BTG2 | 0.20 | −1.57 | 0.60 | 0.55 | 0.86 | Lower in CD1C_B (DC3)/Higher in Mono1 (classical CD14++CD16− mono) | 0 |
| HPSE | 0.20 | −1.65 | 0.60 | 0.75 | 0.93 | Lower in CD1C_B (DC3)/Higher in Mono1 (classical CD14++CD16− mono) | 0 |
| LOC100133161 | 0.20 | −2.57 | 0.60 | 0.27 | 0.74 | Lower in CD1C_B (DC3)/Higher in Mono1 (classical CD14++CD16− mono) | 0 |
| NPL | 0.20 | −4.08 | 0.60 | 0.08 | 0.63 | Lower in CD1C_B (DC3)/Higher in Mono1 (classical CD14++CD16− mono) | 0 |
| LOC644215 | 0.20 | −1.32 | 0.61 | 0.87 | 0.91 | Lower in CD1C_B (DC3)/Higher in Mono1 (classical CD14++CD16− mono) | 0 |
| PGPEP1 | 0.20 | −1.02 | 0.61 | 0.91 | 0.95 | Lower in CD1C_B (DC3)/Higher in Mono1 (classical CD14++CD16− mono) | 0 |
| AK127270 | 0.19 | −1.27 | 0.61 | 0.62 | 0.89 | Lower in CD1C_B (DC3)/Higher in Mono1 (classical CD14++CD16− mono) | 0 |
| CXCL16 | 0.19 | −1.74 | 0.61 | 0.54 | 0.87 | Lower in CD1C_B (DC3)/Higher in Mono1 (classical CD14++CD16− mono) | 1 |
| FDPSL2A | 0.19 | −1.02 | 0.61 | 0.93 | 0.97 | Lower in CD1C_B (DC3)/Higher in Mono1 (classical CD14++CD16− mono) | 0 |
| GPR155 | 0.19 | −1.39 | 0.61 | 0.79 | 0.92 | Lower in CD1C_B (DC3)/Higher in Mono1 (classical CD14++CD16− mono) | 1 |
| PLEK | 0.19 | −1.15 | 0.62 | 0.91 | 0.98 | Lower in CD1C_B (DC3)/Higher in Mono1 (classical CD14++CD16− mono) | 0 |
| CYP1B1 | 0.19 | −3.93 | 0.62 | 0.02 | 0.63 | Lower in CD1C_B (DC3)/Higher in Mono1 (classical CD14++CD16− mono) | 1 |
| LOC388312 | 0.19 | −2.60 | 0.62 | 0.23 | 0.73 | Lower in CD1C_B (DC3)/Higher in Mono1 (classical CD14++CD16− mono) | 0 |
| FBXO15 | 0.19 | −1.07 | 0.62 | 0.71 | 0.90 | Lower in CD1C_B (DC3)/Higher in Mono1 (classical CD14++CD16− mono) | 0 |
| TGOLN2 | 0.19 | −1.06 | 0.62 | 0.93 | 0.98 | Lower in CD1C_B (DC3)/Higher in Mono1 (classical CD14++CD16− mono) | 1 |
| HERC2P4 | 0.19 | −1.20 | 0.62 | 0.76 | 0.93 | Lower in CD1C_B (DC3)/Higher in Mono1 (classical CD14++CD16− mono) | 0 |
| SORL1 | 0.19 | −1.31 | 0.62 | 0.60 | 0.96 | Lower in CD1C_B (DC3)/Higher in Mono1 (classical CD14++CD16− mono) | 1 |
| ZBTB16 | 0.19 | −3.29 | 0.62 | 0.37 | 0.74 | Lower in CD1C_B (DC3)/Higher in Mono1 (classical CD14++CD16− mono) | 0 |
| TSPAN14 | 0.19 | −1.58 | 0.63 | 0.71 | 0.94 | Lower in CD1C_B (DC3)/Higher in Mono1 (classical CD14++CD16− mono) | 1 |
| SLC24A4 | 0.19 | −1.33 | 0.63 | 0.77 | 0.93 | Lower in CD1C_B (DC3)/Higher in Mono1 (classical CD14++CD16− mono) | 1 |
| LOC100133331 | 0.18 | −2.16 | 0.63 | 0.20 | 0.74 | Lower in CD1C_B (DC3)/Higher in Mono1 (classical CD14++CD16− mono) | 0 |
| RTN3 | 0.18 | −1.21 | 0.63 | 0.79 | 0.97 | Lower in CD1C_B (DC3)/Higher in Mono1 (classical CD14++CD16− mono) | 1 |
| BC073807 | 0.18 | −1.01 | 0.64 | 0.95 | 0.97 | Lower in CD1C_B (DC3)/Higher in Mono1 (classical CD14++CD16− mono) | 0 |
| ZFP36L1 | 0.18 | −1.29 | 0.64 | 0.93 | 0.96 | Lower in CD1C_B (DC3)/Higher in Mono1 (classical CD14++CD16− mono) | 0 |
| ZNF665 | 0.18 | −1.06 | 0.64 | 0.76 | 0.92 | Lower in CD1C_B (DC3)/Higher in Mono1 (classical CD14++CD16− mono) | 0 |
| PGM5P2 | 0.18 | −1.36 | 0.64 | 0.72 | 0.89 | Lower in CD1C_B (DC3)/Higher in Mono1 (classical CD14++CD16− mono) | 0 |
| SCPEP1 | 0.18 | −1.17 | 0.64 | 0.66 | 0.97 | Lower in CD1C_B (DC3)/Higher in Mono1 (classical CD14++CD16− mono) | 0 |
| IRAK3 | 0.17 | −1.78 | 0.65 | 0.65 | 0.93 | Lower in CD1C_B (DC3)/Higher in Mono1 (classical CD14++CD16− mono) | 0 |
| CHST15 | 0.17 | −3.15 | 0.66 | 0.11 | 0.71 | Lower in CD1C_B (DC3)/Higher in Mono1 (classical CD14++CD16− mono) | 1 |

TABLE E5-continued

Discriminative markers between CD1C_B (inflammatory CD1C; DC3 cluster) and
Mono1 (CD14++ DC16− classical monocyte subsets)

| Gene.ID | AUC value | Avg. Diff.[1] | Power[2] | Pct.1[3] | Pct.2[4] | Comments | Surface Marker[5] |
|---|---|---|---|---|---|---|---|
| IRS2 | 0.17 | −1.93 | 0.66 | 0.38 | 0.79 | Lower in CD1C_B (DC3)/Higher in Mono1 (classical CD14++CD16− mono) | 0 |
| CTSA | 0.17 | −1.24 | 0.66 | 0.76 | 0.94 | Lower in CD1C_B (DC3)/Higher in Mono1 (classical CD14++CD16− mono) | 1 |
| KLRD1 | 0.17 | −1.70 | 0.66 | 0.83 | 0.93 | Lower in CD1C_B (DC3)/Higher in Mono1 (classical CD14++CD16− mono) | 1 |
| FCGR2A | 0.17 | −1.37 | 0.66 | 0.79 | 0.97 | Lower in CD1C_B (DC3)/Higher in Mono1 (classical CD14++CD16− mono) | 1 |
| SSH2 | 0.17 | −1.53 | 0.66 | 0.83 | 0.99 | Lower in CD1C_B (DC3)/Higher in Mono1 (classical CD14++CD16− mono) | 0 |
| TLR4 | 0.17 | −1.89 | 0.66 | 0.42 | 0.87 | Lower in CD1C_B (DC3)/Higher in Mono1 (classical CD14++CD16− mono) | 1 |
| PECAM1 | 0.17 | −1.32 | 0.66 | 0.90 | 0.97 | Lower in CD1C_B (DC3)/Higher in Mono1 (classical CD14++CD16− mono) | 1 |
| CD300E | 0.17 | −2.00 | 0.67 | 0.41 | 0.86 | Lower in CD1C_B (DC3)/Higher in Mono1 (classical CD14++CD16− mono) | 1 |
| AK123584 | 0.17 | −1.03 | 0.67 | 0.94 | 0.97 | Lower in CD1C_B (DC3)/Higher in Mono1 (classical CD14++CD16− mono) | 0 |
| CYBB | 0.17 | −1.14 | 0.67 | 0.90 | 0.99 | Lower in CD1C_B (DC3)/Higher in Mono1 (classical CD14++CD16− mono) | 1 |
| HTRA4 | 0.17 | −1.25 | 0.67 | 0.68 | 0.91 | Lower in CD1C_B (DC3)/Higher in Mono1 (classical CD14++CD16− mono) | 0 |
| ACSL1 | 0.16 | −1.85 | 0.67 | 0.43 | 0.93 | Lower in CD1C_B (DC3)/Higher in Mono1 (classical CD14++CD16− mono) | 1 |
| CLEC4E | 0.36 | −2.23 | 0.68 | 0.46 | 0.86 | Lower in CD1C_B (DC3)/Higher in Mono1 (classical CD14++CD16− mono) | 1 |
| VCAN | 0.16 | −1.06 | 0.68 | 1.00 | 0.99 | Lower in CD1C_B (DC3)/Higher in Mono1 (classical CD14++CD16− mono) | 1 |
| DUSP6 | 0.16 | −2.47 | 0.68 | 0.38 | 0.84 | Lower in CD1C_B (DC3)/Higher in Mono1 (classical CD14++CD16− mono) | 0 |
| NAMPT | 0.16 | −1.46 | 0.68 | 0.94 | 0.99 | Lower in CD1C_B (DC3)/Higher in Mono1 (classical CD14++CD16− mono) | 0 |
| LOC731275 | 0.15 | −1.92 | 0.69 | 0.40 | 0.83 | Lower in CD1C_B (DC3)/Higher in Mono1 (classical CD14++CD16− mono) | 0 |
| PELI1 | 0.15 | −1.79 | 0.69 | 0.90 | 0.97 | Lower in CD1C_B (DC3)/Higher in Mono1 (classical CD14++CD16− mono) | 0 |
| UNC80 | 0.15 | −1.24 | 0.69 | 0.87 | 0.97 | Lower in CD1C_B (DC3)/Higher in Mono1 (classical CD14++CD16− mono) | 0 |
| NCF1B | 0.15 | 2.42 | 0.69 | 0.18 | 0.81 | Lower in CD1C_B (DC3)/Higher in Mono1 (classical CD14++CD16− mono) | 0 |
| FPR1 | 0.15 | −1.09 | 0.70 | 0.92 | 0.99 | Lower in CD1C_B (DC3)/Higher in Mono1 (classical CD14++CD16− mono) | 1 |
| FCAR | 0.15 | −3.04 | 0.70 | 0.72 | 0.89 | Lower in CD1C_B (DC3)/Higher in Mono1 (classical CD14++CD16− mono) | 1 |
| FLJ44955 | 0.15 | −1.28 | 0.70 | 0.86 | 0.96 | Lower in CD1C_B (DC3)/Higher in Mono1 (classical CD14++CD16− mono) | 0 |
| HK3 | 0.15 | −1.76 | 0.70 | 0.43 | 0.92 | Lower in CD1C_B (DC3)/Higher in Mono1 (classical CD14++CD16− mono) | 0 |
| FLJ34690 | 0.15 | −1.05 | 0.70 | 0.92 | 0.97 | Lower in CD1C_B (DC3)/Higher in Mono1 (classical CD14++CD16− mono) | 0 |
| BCL2A1 | 0.15 | −3.10 | 0.70 | 0.25 | 0.80 | Lower in CD1C_B (DC3)/Higher in Mono1 (classical CD14++CD16− mono) | 0 |
| ITGAM | 0.15 | −1.91 | 0.70 | 0.38 | 0.90 | Lower in CD1C_B (DC3)/Higher in Mono1 (classical CD14++CD16− mono) | 1 |
| LAIR2 | 0.15 | −4.60 | 0.70 | 0.00 | 0.71 | Lower in CD1C_B (DC3)/Higher in Mono1 (classical CD14++CD16− mono) | 1 |
| SLC7A7 | 0.14 | −1.51 | 0.71 | 0.71 | 0.96 | Lower in CD1C_B (DC3)/Higher in Mono1 (classical CD14++CD16− mono) | 1 |
| FYB | 0.14 | −1.54 | 0.71 | 0.83 | 0.96 | Lower in CD1C_B (DC3)/Higher in Mono1 (classical CD14++CD16− mono) | 0 |
| DOK3 | 0.14 | −2.63 | 0.72 | 0.20 | 0.81 | Lower in CD1C_B (DC3)/Higher in Mono1 (classical CD14++CD16− mono) | 0 |
| VMP1 | 0.14 | −1.55 | 0.72 | 0.64 | 0.96 | Lower in CD1C_B (DC3)/Higher in Mono1 (classical CD14++CD16− mono) | 1 |
| ORAI2 | 0.14 | −1.03 | 0.72 | 1.00 | 1.00 | Lower in CD1C_B (DC3)/Higher in Mono1 (classical CD14++CD16− mono) | 1 |
| AQP9 | 0.14 | −4.33 | 0.72 | 0.01 | 0.73 | Lower in CD1C_B (DC3)/Higher in Mono1 (classical CD14++CD16− mono) | 1 |
| AX746880 | 0.14 | −1.05 | 0.73 | 0.93 | 0.99 | Lower in CD1C_B (DC3)/Higher in Mono1 (classical CD14++CD16− mono) | 0 |
| SHISA9 | 0.13 | −1.02 | 0.73 | 0.88 | 1.00 | Lower in CD1C_B (DC3)/Higher in Mono1 (classical CD14++CD16− mono) | 1 |
| VNN2 | 0.13 | −3.24 | 0.73 | 0.16 | 0.80 | Lower in CD1C_B (DC3)/Higher in Mono1 (classical CD14++CD16− mono) | 1 |

TABLE E5-continued

Discriminative markers between CD1C_B (inflammatory CD1C; DC3 cluster) and
Mono1 (CD14++ DC16− classical monocyte subsets)

| Gene.ID | AUC value | Avg. Diff.[1] | Power[2] | Pct.1[3] | Pct.2[4] | Comments | Surface Marker[5] |
|---|---|---|---|---|---|---|---|
| C2ORF77 | 0.13 | −1.17 | 0.74 | 0.88 | 0.98 | Lower in CD1C_B (DC3)/Higher in Mono1 (classical CD14++CD16− mono) | 0 |
| HLA-F | 0.13 | −1.44 | 0.74 | 0.80 | 0.98 | Lower in CD1C_B (DC3)/Higher in Mono1 (classical CD14++CD16− mono) | 1 |
| REXO1L1 | 0.13 | −1.33 | 0.75 | 0.93 | 0.97 | Lower in CD1C_B (DC3)/Higher in Mono1 (classical CD14++CD16− mono) | 0 |
| SDCBP | 0.13 | −1.22 | 0.75 | 0.90 | 0.99 | Lower in CD1C_B (DC3)/Higher in Mono1 (classical CD14++CD16− mono) | 0 |
| AK124194 | 0.12 | −1.01 | 0.75 | 0.99 | 0.99 | Lower in CD1C_B (DC3)/Higher in Mono1 (classical CD14++CD16− mono) | 0 |
| SERPTNB9 | 0.12 | −1.81 | 0.76 | 0.67 | 0.99 | Lower in CD1C_B (DC3)/Higher in Mono1 (classical CD14++CD16− mono) | 0 |
| BC040909 | 0.12 | −1.06 | 0.76 | 0.97 | 1.00 | Lower in CD1C_B (DC3)/Higher in Mono1 (classical CD14++CD16− mono) | 0 |
| LRP1 | 0.12 | −1.51 | 0.76 | 0.91 | 0.99 | Lower in CD1C_B (DC3)/Higher in Mono1 (classical CD14++CD16− mono) | 1 |
| AX747598 | 0.12 | −3.76 | 0.76 | 0.07 | 0.79 | Lower in CD1C_B (DC3)/Higher in Mono1 (classical CD14++CD16− mono) | 0 |
| BC013828 | 0.12 | −3.08 | 0.77 | 0.12 | 0.81 | Lower in CD1C_B (DC3)/Higher in Mono1 (classical CD14++CD16− mono) | 0 |
| CDA | 0.12 | −4.58 | 0.77 | 0.01 | 0.78 | Lower in CD1C_B (DC3)/Higher in Mono1 (classical CD14++CD16− mono) | 0 |
| CLEC7A | 0.12 | −1.45 | 0.77 | 0.92 | 0.99 | Lower in CD1C_B (DC3)/Higher in Mono1 (classical CD14++CD16− mono) | 1 |
| LOC400084 | 0.12 | −1.06 | 0.77 | 0.94 | 1.00 | Lower in CD1C_B (DC3)/Higher in Mono1 (classical CD14++CD16− mono) | 0 |
| ADAMTSL3 | 0.12 | −1.07 | 0.77 | 0.99 | 1.00 | Lower in CD1C_B (DC3)/Higher in Mono1 (classical CD14++CD16− mono) | 0 |
| CD68 | 0.12 | −1.10 | 0.77 | 0.91 | 3.00 | Lower in CD1C_B (DC3)/Higher in Mono1 (classical CD14++CD16− mono) | 1 |
| ASAH1 | 0.11 | −1.55 | 0.78 | 0.85 | 0.99 | Lower in CD1C_B (DC3)/Higher in Mono1 (classical CD14++CD16− mono) | 1 |
| SOD2 | 0.11 | −2.29 | 0.78 | 0.65 | 0.95 | Lower in CD1C_B (DC3)/Higher in Mono1 (classical CD14++CD16− mono) | 0 |
| AX747658 | 0.11 | −1.00 | 0.78 | 0.97 | 1.00 | Lower in CD1C_B (DC3)/Higher in Mono1 (classical CD14++CD16− mono) | 0 |
| EVI2B | 0.10 | −1.35 | 0.80 | 0.92 | 0.99 | Lower in CD1C_B (DC3)/Higher in Mono1 (classical CD14++CD16− mono) | 1 |
| SAT1 | 0.10 | −1.20 | 0.80 | 1.00 | 3.00 | Lower in CD1C_B (DC3)/Higher in Mono1 (classical CD14++CD16− mono) | 0 |
| ABCC9 | 0.10 | −1.17 | 0.80 | 0.93 | 3.00 | Lower in CD1C_B (DC3)/Higher in Mono1 (classical CD14++CD16− mono) | 1 |
| LAIR1 | 0.10 | −2.30 | 0.80 | 0.57 | 0.96 | Lower in CD1C_B (DC3)/Higher in Mono1 (classical CD14++CD16− mono) | 1 |
| AX747062 | 0.10 | −1.15 | 0.81 | 0.97 | 1.00 | Lower in CD1C_B (DC3)/Higher in Mono1 (classical CD14++CD16− mono) | 0 |
| CTSD | 0.10 | −1.54 | 0.81 | 0.83 | 0.98 | Lower in CD1C_B (DC3)/Higher in Mono1 (classical CD14++CD16− mono) | 1 |
| CR627206 | 0.10 | −1.01 | 0.81 | 1.00 | 1.00 | Lower in CD1C_B (DC3)/Higher in Mono1 (classical CD14++CD16− mono) | 0 |
| APOBEC3A | 0.09 | −3.55 | 0.81 | 0.50 | 0.92 | Lower in CD1C_B (DC3)/Higher in Mono1 (classical CD14++CD16− mono) | 0 |
| AX747187 | 0.09 | −1.17 | 0.81 | 1.00 | 1.00 | Lower in CD1C_B (DC3)/Higher in Mono1 (classical CD14++CD16− mono) | 0 |
| TBC1D8B | 0.09 | −1.16 | 0.81 | 1.00 | 1.00 | Lower in CD1C_B (DC3)/Higher in Mono1 (classical CD14++CD16− mono) | 0 |
| AK097143 | 0.09 | −1.18 | 0.82 | 1.00 | 1.00 | Lower in CD1C_B (DC3)/Higher in Mono1 (classical CD14++CD16− mono) | 0 |
| AL137655 | 0.09 | −3.10 | 0.82 | 0.38 | 0.90 | Lower in CD1C_B (DC3)/Higher in Mono1 (classical CD14++CD16− mono) | 0 |
| ASTN2 | 0.09 | −1.08 | 0.82 | 1.00 | 1.00 | Lower in CD1C_B (DC3)/Higher in Mono1 (classical CD14++CD16− mono) | 1 |
| AK056558 | 0.09 | −1.11 | 0.82 | 1.00 | 1.00 | Lower in CD1C_B (DC3)/Higher in Mono1 (classical CD14++CD16− mono) | 0 |
| CFD | 0.09 | −1.91 | 0.83 | 0.58 | 0.96 | Lower in CD1C_B (DC3)/Higher in Mono1 (classical CD14++CD16− mono) | 0 |
| BC037952 | 0.08 | −1.07 | 0.83 | 1.00 | 1.00 | Lower in CD1C_B (DC3)/Higher in Mono1 (classical CD14++CD16− mono) | 0 |
| FCN1 | 0.08 | −1.03 | 0.83 | 0.99 | 1.00 | Lower in CD1C_B (DC3)/Higher in Mono1 (classical CD14++CD16− mono) | 1 |
| AK311113 | 0.08 | −1.24 | 0.84 | 0.97 | 1.00 | Lower in CD1C_B (DC3)/Higher in Mono1 (classical CD14++CD16− mono) | 0 |
| TMEM45A | 0.08 | −1.03 | 0.85 | 1.00 | 1.00 | Lower in CD1C_B (DC3)/Higher in Mono1 (classical CD14++CD16− mono) | 0 |

TABLE E5-continued

Discriminative markers between CD1C_B (inflammatory CD1C; DC3 cluster) and Mono1 (CD14$^{++}$ DC16$^-$ classical monocyte subsets)

| Gene.ID | AUC value | Avg. Diff.[1] | Power[2] | Pct.1[3] | Pct.2[4] | Comments | Surface Marker[5] |
|---|---|---|---|---|---|---|---|
| LOC646214 | 0.08 | −1.03 | 0.85 | 0.99 | 1.00 | Lower in CD1C_B (DC3)/Higher in Mono1 (classical CD14$^{++}$CD16$^-$ mono) | 0 |
| SLC11A1 | 0.07 | −2.37 | 0.85 | 0.67 | 0.99 | Lower in CD1C_B (DC3)/Higher in Mono1 (classical CD14$^{++}$CD16$^-$ mono) | 1 |
| MORC4 | 0.07 | −1.07 | 0.86 | 1.00 | 1.00 | Lower in CD1C_B (DC3)/Higher in Mono1 (classical CD14$^{++}$CD16$^-$ mono) | 0 |
| NCF1C | 0.07 | −2.69 | 0.86 | 0.36 | 0.94 | Lower in CD1C_B (DC3)/Higher in Mono1 (classical CD14$^{++}$CD16$^-$ mono) | 0 |
| AK123889 | 0.07 | −1.18 | 0.86 | 1.00 | 1.00 | Lower in CD1C_B (DC3)/Higher in Mono1 (classical CD14$^{++}$CD16$^-$ mono) | 0 |
| AX747756 | 0.07 | −1.28 | 0.87 | 1.00 | 1.00 | Lower in CD1C_B (DC3)/Higher in Mono1 (classical CD14$^{++}$CD16$^-$ mono) | 0 |
| C5AR1 | 0.06 | −3.57 | 0.87 | 0.22 | 0.91 | Lower in CD1C_B (DC3)/Higher in Mono1 (classical CD14$^{++}$CD16$^-$ mono) | 1 |
| KIAA1328 | 0.06 | −1.30 | 0.87 | 1.00 | 3.00 | Lower in CD1C_B (DC3)/Higher in Mono1 (classical CD14$^{++}$CD16$^-$ mono) | 0 |
| SERPINA1 | 0.06 | −1.47 | 0.87 | 0.93 | 1.00 | Lower in CD1C_B (DC3)/Higher in Mono1 (classical CD14$^{++}$CD16$^-$ mono) | 0 |
| HLA-E | 0.06 | −1.18 | 0.88 | 1.00 | 1.00 | Lower in CD1C_B (DC3)/Higher in Mono1 (classical CD14$^{++}$CD16$^-$ mono) | 1 |
| NCF1 | 0.06 | −2.89 | 0.89 | 0.54 | 0.97 | Lower in CD1C_B (DC3)/Higher in Mono1 (classical CD14$^{++}$CD16$^-$ mono) | 0 |
| CD14 | 0.05 | −2.03 | 0.89 | 0.74 | 0.98 | Lower in CD1C_B (DC3)/Higher in Mono1 (classical CD14$^{++}$CD16$^-$ mono) | 1 |
| MGC4836 | 0.05 | −1.22 | 0.90 | 1.00 | 3.00 | Lower in CD1C_B (DC3)/Higher in Mono1 (classical CD14$^{++}$CD16$^-$ mono) | 0 |
| NEAT1 | 0.05 | −1.81 | 0.91 | 0.98 | 1.00 | Lower in CD1C_B (DC3)/Higher in Mono1 (classical CD14$^{++}$CD16$^-$ mono) | 0 |
| TKT | 0.05 | −1.46 | 0.91 | 0.96 | 1.00 | Lower in CD1C_B (DC3)/Higher in Mono1 (classical CD14$^{++}$CD16$^-$ mono) | 0 |
| HLA-B | 0.03 | −1.02 | 0.95 | 1.00 | 1.00 | Lower in CD1C_B (DC3)/Higher in Mono1 (classical CD14$^{++}$CD16$^-$ mono) | 1 |
| CTSS | 0.02 | −1.62 | 0.96 | 1.00 | 1.00 | Lower in CD1C_B (DC3)/Higher in Mono1 (classical CD14$^{++}$CD16$^-$ mono) | 0 |

Footnotes in Table E5: Footnotes:
[1]Value refers to average differential expression within one subset (log fold change);
[2]Value refers to discriminatory power of each marker;
[3]Percentage of cells, within the cluster ID for which the gene is a marker, that detect the gene;
[4]Percentage of all the other cells, excluding the cluster ID for which the gene is a marker, that detect the gene;
[5]"1" refers to predicted surface marker; "0" refers to predicted not a surface marker according to the Protein Atlas: Protein Atlas: http://www.proteinatlas.org/search/protein_class:Predicted+membrane+proteins.

Applicants further asked whether the CD16-expressing CD141$^-$CD1C$^-$ cells (cluster DC4) were the same as or similar to CD16$^+$ monocytes (cluster Mono2). Applicants found that they formed distinct clusters (FIG. 4B), and although the two populations shared many genes (e.g., FCGR3A), they each expressed a unique gene set that distinguished them (FIG. 4C, Tables E6 and E7). CD141$^-$CD1C$^-$ cells were enriched for type I interferon signaling pathway ($p<1.53^{-13}$) and response to virus ($p<4.77E^{-9}$), while CD16$^+$ monocytes were enriched for immune system process ($p<1.09^{-14}$) and leukocyte migration ($p<3.57^{-8}$) GO terms. Although Applicants conclude that monocytes and DCs are distinct from each other in the steady state, our data cannot distinguish interconversion between cell fates versus distinct ontogeny.

TABLE E6

Discriminative markers between CD1C$^-$CD141$^-$ (cluster DC4) and Mono2 (CD14$^+$CD16$^{++}$ non-classical monocyte subsets)

| Gene.ID | AUC value | Avg Diff.[1] | Power[2] | Pct.1[3] | Pct2[4] | Comments | Surface Marker[5] |
|---|---|---|---|---|---|---|---|
| HLA-DRB4 | 0.97 | 4.22 | 0.95 | 0.99 | 0.53 | Higher in CD1C$^-$CD141$^-$ (DC4)/Lower in Mono2 (CD16$^+$ non-classical mono) | 1 |
| TMEM176B | 0.88 | 3.05 | 0.76 | 0.83 | 0.15 | Higher in CD1C$^-$CD141$^-$ (DC4)/Lower in Mono2 (CD16$^+$ non-classical mono) | 1 |
| LOC200772 | 0.87 | 2.94 | 0.74 | 0.82 | 0.16 | Higher in CD1C$^-$CD141$^-$ (DC4)/Lower in Mono2 (CD16$^+$ non-classical mono) | 0 |
| AK307192 | 0.83 | 1.04 | 0.66 | 0.97 | 0.87 | Higher in CD1C$^-$CD141$^-$ (DC4)/Lower in Mono2 (CD16$^+$ non-classical mono) | 0 |
| FAM110A | 0.81 | 1.47 | 0.62 | 0.87 | 0.51 | Higher in CD1C$^-$CD141$^-$ (DC4)/Lower in Mono2 (CD16$^+$ non-classical mono) | 0 |
| PLD4 | 0.80 | 1.84 | 0.60 | 0.80 | 0.28 | Higher in CD1C$^-$CD141$^-$ (DC4)/Lower in Mono2 (CD16$^+$ non-classical mono) | 1 |

TABLE E6-continued

Discriminative markers between CD1C⁻CD141⁻ (cluster DC4) and Mono2
(CD14⁺CD16⁺⁺ non-classical monocyte subsets)

| Gene.ID | AUC value | Avg Diff.[1] | Power[2] | Pct.1[3] | Pct2[4] | Comments | Surface Marker[5] |
|---|---|---|---|---|---|---|---|
| HLA-H | 0.80 | 1.07 | 0.60 | 0.95 | 0.69 | Higher in CD1C⁻CD141⁻ (DC4)/Lower in Mono2 (CD16⁺ non-classical mono) | 1 |
| FCGR2C | 0.78 | 1.34 | 0.55 | 0.87 | 0.51 | Higher in CD1C⁻CD141⁻ (DC4)/Lower in Mono2 (CD16⁺ non-classical mono) | 0 |
| HSPA7 | 0.77 | 1.69 | 0.54 | 0.74 | 0.28 | Higher in CD1C⁻CD141⁻ (DC4)/Lower in Mono2 (CD16⁺ non-classical mono) | 0 |
| FOS | 0.74 | 1.08 | 0.48 | 0.99 | 0.94 | Higher in CD1C⁻CD141⁻ (DC4)/Lower in Mono2 (CD16⁺ non-classical mono) | 0 |
| HLA-DQA2 | 0.73 | 1.46 | 0.46 | 0.70 | 0.29 | Higher in CD1C⁻CD141⁻ (DC4)/Lower in Mono2 (CD16⁺ non-classical mono) | 1 |
| IFITM1 | 0.72 | 1.01 | 0.44 | 0.74 | 0.36 | Higher in CD1C⁻CD141⁻ (DC4)/Lower in Mono2 (CD16⁺ non-classical mono) | 1 |
| MX1 | 0.71 | 1.44 | 0.42 | 0.67 | 0.27 | Higher in CD1C⁻CD141⁻ (DC4)/Lower in Mono2 (CD16⁺ non-classical mono) | 0 |
| IFIT3 | 0.71 | 1.23 | 0.42 | 0.83 | 0.59 | Higher in CD1C⁻CD141⁻ (DC4)/Lower in Mono2 (CD16⁺ non-classical mono) | 0 |
| CKB | 0.71 | 2.21 | 0.41 | 0.51 | 0.12 | Higher in CD1C⁻CD141⁻ (DC4)/Lower in Mono2 (CD16⁺ non-classical mono) | 0 |
| GRAMD1A | 0.71 | 1.59 | 0.41 | 0.69 | 0.33 | Higher in CD1C⁻CD141⁻ (DC4)/Lower in Mono2 (CD16⁺ non-classical mono) | 1 |
| IFI44L | 0.70 | 1.79 | 0.41 | 0.53 | 0.13 | Higher in CD1C⁻CD141⁻ (DC4)/Lower in Mono2 (CD16⁺ non-classical mono) | 0 |
| IFI44 | 0.70 | 1.35 | 0.40 | 0.64 | 0.27 | Higher in CD1C⁻CD141⁻ (DC4)/Lower in Mono2 (CD16⁺ non-classical mono) | 0 |
| C11ORF21 | 0.70 | 1.32 | 0.40 | 0.70 | 0.45 | Higher in CD1C⁻CD141⁻ (DC4)/Lower in Mono2 (CD16⁺ non-classical mono) | 0 |
| C1ORF63 | 0.70 | 1.30 | 0.39 | 0.78 | 0.59 | Higher in CD1C⁻CD141⁻ (DC4)/Lower in Mono2 (CD16⁺ non-classical mono) | 0 |
| DKFZP451J181 | 0.70 | 1.15 | 0.39 | 0.83 | 0.67 | Higher in CD1C⁻CD141⁻ (DC4)/Lower in Mono2 (CD16⁺ non-classical mono) | 0 |
| SH2D1B | 0.69 | 1.29 | 0.39 | 0.62 | 0.23 | Higher in CD1C⁻CD141⁻ (DC4)/Lower in Mono2 (CD16⁺ non-classical mono) | 0 |
| ISG15 | 0.69 | 1.01 | 0.38 | 0.79 | 0.61 | Higher in CD1C⁻CD141⁻ (DC4)/Lower in Mono2 (CD16⁺ non-classical mono) | 0 |
| MS4A4A | 0.69 | 1.15 | 0.38 | 0.72 | 0.45 | Higher in CD1C⁻CD141⁻ (DC4)/Lower in Mono2 (CD16⁺ non-classical mono) | 1 |
| NEURL | 0.69 | 1.20 | 0.38 | 0.67 | 0.36 | Higher in CD1C⁻CD141⁻ (DC4)/Lower in Mono2 (CD16⁺ non-classical mono) | 0 |
| TMTC1 | 0.69 | 2.11 | 0.38 | 0.57 | 0.25 | Higher in CD1C⁻CD141⁻ (DC4)/Lower in Mono2 (CD16⁺ non-classical mono) | 1 |
| TESC | 0.68 | 1.27 | 0.36 | 0.59 | 0.30 | Higher in CD1C⁻CD141⁻ (DC4)/Lower in Mono2 (CD16⁺ non-classical mono) | 0 |
| TAGLN | 0.68 | 1.15 | 0.36 | 0.72 | 0.51 | Higher in CD1C⁻CD141⁻ (DC4)/Lower in Mono2 (CD16⁺ non-classical mono) | 0 |
| ICAM4 | 0.67 | 1.14 | 0.35 | 0.68 | 0.35 | Higher in CD1C⁻CD141⁻ (DC4)/Lower in Mono2 (CD16⁺ non-classical mono) | 1 |
| IRF7 | 0.66 | 1.18 | 0.33 | 0.57 | 0.30 | Higher in CD1C⁻CD141⁻ (DC4)/Lower in Mono2 (CD16⁺ non-classical mono) | 0 |
| CDH23 | 0.66 | 1.19 | 0.32 | 0.86 | 0.73 | Higher in CD1C⁻CD141⁻ (DC4)/Lower in Mono2 (CD16⁺ non-classical mono) | 1 |
| DDX58 | 0.66 | 1.65 | 0.32 | 0.56 | 0.29 | Higher in CD1C⁻CD141⁻ (DC4)/Lower in Mono2 (CD16⁺ non-classical mono) | 0 |
| UNC119 | 0.66 | 1.13 | 0.31 | 0.64 | 0.41 | Higher in CD1C⁻CD141⁻ (DC4)/Lower in Mono2 (CD16⁺ non-classical mono) | 0 |
| CCM2 | 0.65 | 1.07 | 0.30 | 0.66 | 0.44 | Higher in CD1C⁻CD141⁻ (DC4)/Lower in Mono2 (CD16⁺ non-classical mono) | 0 |
| SIK1 | 0.65 | 1.09 | 0.29 | 0.61 | 0.34 | Higher in CD1C⁻CD141⁻ (DC4)/Lower in Mono2 (CD16⁺ non-classical mono) | 1 |
| AK124399 | 0.64 | 1.09 | 0.29 | 0.50 | 0.25 | Higher in CD1C⁻CD141⁻ (DC4)/Lower in Mono2 (CD16⁺ non-classical mono) | 0 |
| BCAT1 | 0.63 | 1.04 | 0.26 | 0.51 | 0.26 | Higher in CD1C⁻CD141⁻ (DC4)/Lower in Mono2 (CD16⁺ non-classical mono) | 0 |
| MARCKS | 0.63 | 1.09 | 0.26 | 0.73 | 0.65 | Higher in CD1C⁻CD141⁻ (DC4)/Lower in Mono2 (CD16⁺ non-classical mono) | 1 |
| SAMD9L | 0.63 | 1.11 | 0.25 | 0.58 | 0.41 | Higher in CD1C⁻CD141⁻ (DC4)/Lower in Mono2 (CD16⁺ non-classical mono) | 0 |
| HERPUD2 | 0.62 | 1.33 | 0.24 | 0.55 | 0.33 | Higher in CD1C⁻CD141⁻ (DC4)/Lower in Mono2 (CD16⁺ non-classical mono) | 1 |
| CCDC53 | 0.62 | 1.02 | 0.24 | 0.53 | 0.34 | Higher in CD1C⁻CD141⁻ (DC4)/Lower in Mono2 (CD16⁺ non-classical mono) | 0 |
| RAB37 | 0.62 | 1.04 | 0.23 | 0.51 | 0.31 | Higher in CD1C⁻CD141⁻ (DC4)/Lower in Mono2 (CD16⁺ non-classical mono) | 0 |
| ACSL6 | 0.61 | 1.38 | 0.22 | 0.50 | 0.27 | Higher in CD1C⁻CD141⁻ (DC4)/Lower in Mono2 (CD16⁺ non-classical mono) | 1 |

TABLE E6-continued

Discriminative markers between CD1C⁻CD141⁻ (cluster DC4) and Mono2
(CD14⁺CD16⁺⁺ non-classical monocyte subsets)

| Gene.ID | AUC value | Avg Diff.[1] | Power[2] | Pct.1[3] | Pct2[4] | Comments | Surface Marker[5] |
|---|---|---|---|---|---|---|---|
| ADCK4 | 0.61 | 1.38 | 0.22 | 0.51 | 0.29 | Higher in CD1C⁻CD141⁻ (DC4)/Lower in Mono2 (CD16⁺ non-classical mono) | 0 |
| RMND5A | 0.61 | 1.12 | 0.21 | 0.63 | 0.60 | Higher in CD1C⁻CD141⁻ (DC4)/Lower in Mono2 (CD16⁺ non-classical mono) | 0 |
| FP15737 | 0.39 | −1.11 | 0.22 | 0.58 | 0.63 | Lower in CD1C⁻CD141⁻ (DC4)/Higher in Mono2 (CD16⁺ non-classical mono) | 0 |
| AK130076 | 0.38 | −1.01 | 0.24 | 0.59 | 0.67 | Lower in CD1C⁻CD141⁻ (DC4)/Higher in Mono2 (CD16⁺ non-classical mono) | 0 |
| AK289390 | 0.37 | −1.06 | 0.26 | 0.66 | 0.69 | Lower in CD1C⁻CD141⁻ (DC4)/Higher in Mono2 (CD16⁺ non-classical mono) | 0 |
| FAM115C | 0.37 | −1.89 | 0.26 | 0.53 | 0.61 | Lower in CD1C⁻CD141⁻ (DC4)/Higher in Mono2 (CD16⁺ non-classical mono) | 0 |
| ELK4 | 0.34 | −1.05 | 0.31 | 0.53 | 0.65 | Lower in CD1C⁻CD141⁻ (DC4)/Higher in Mono2 (CD16⁺ non-classical mono) | 0 |
| FLOT1 | 0.34 | −1.05 | 0.31 | 0.21 | 0.51 | Lower in CD1C⁻CD141⁻ (DC4)/Higher in Mono2 (CD16⁺ non-classical mono) | 0 |
| CD300C | 0.34 | −1.03 | 0.32 | 0.55 | 0.71 | Lower in CD1C⁻CD141⁻ (DC4)/Higher in Mono2 (CD16⁺ non-classical mono) | 1 |
| DQ573668 | 0.34 | −1.13 | 0.32 | 0.57 | 0.69 | Lower in CD1C⁻CD141⁻ (DC4)/Higher in Mono2 (CD16⁺ non-classical mono) | 0 |
| TLR8 | 0.34 | −1.01 | 0.32 | 0.33 | 0.62 | Lower in CD1C⁻CD141⁻ (DC4)/Higher in Mono2 (CD16⁺ non-classical mono) | 1 |
| SLCA3 | 0.34 | −2.25 | 0.32 | 0.25 | 0.50 | Lower in CD1C⁻CD141⁻ (DC4)/Higher in Mono2 (CD16⁺ non-classical mono) | 1 |
| S100A9 | 0.34 | −1.10 | 0.32 | 0.88 | 0.97 | Lower in CD1C⁻CD141⁻ (DC4)/Higher in Mono2 (CD16⁺ non-classical mono) | 0 |
| KLRD1 | 0.34 | −1.38 | 0.33 | 0.86 | 0.90 | Lower in CD1C⁻CD141⁻ (DC4)/Higher in Mono2 (CD16⁺ non-classical mono) | 1 |
| FAM198B | 0.33 | −1.25 | 0.34 | 0.29 | 0.60 | Lower in CD1C⁻CD141⁻ (DC4)/Higher in Mono2 (CD16⁺ non-classical mono) | 1 |
| SLC25A25 | 0.33 | −1.48 | 0.34 | 0.21 | 0.51 | Lower in CD1C⁻CD141⁻ (DC4)/Higher in Mono2 (CD16⁺ non-classical mono) | 0 |
| ZNF267 | 0.33 | −1.21 | 0.34 | 0.28 | 0.57 | Lower in CD1C⁻CD141⁻ (DC4)/Higher in Mono2 (CD16⁺ non-classical mono) | 0 |
| ASGR1 | 0.33 | −1.07 | 0.35 | 0.19 | 0.54 | Lower in CD1C⁻CD141⁻ (DC4)/Higher in Mono2 (CD16⁺ non-classical mono) | 0 |
| GM2A | 0.32 | −1.88 | 0.36 | 0.40 | 0.60 | Lower in CD1C⁻CD141⁻ (DC4)/Higher in Mono2 (CD16⁺ non-classical mono) | 0 |
| CLEC4E | 0.32 | −2.34 | 0.36 | 0.38 | 0.60 | Lower in CD1C⁻CD141⁻ (DC4)/Higher in Mono2 (CD16⁺ non-classical mono) | 1 |
| CPM | 0.32 | −1.44 | 0.36 | 0.79 | 0.84 | Lower in CD1C⁻CD141⁻ (DC4)/Higher in Mono2 (CD16⁺ non-classical mono) | 1 |
| PLBD2 | 0.31 | −1.01 | 0.38 | 0.49 | 0.74 | Lower in CD1C⁻CD141⁻ (DC4)/Higher in Mono2 (CD16⁺ non-classical mono) | 1 |
| PXN | 0.31 | −1.67 | 0.39 | 0.75 | 0.77 | Lower in CD1C⁻CD141⁻ (DC4)/Higher in Mono2 (CD16⁺ non-classical mono) | 0 |
| LITAF | 0.30 | −1.15 | 0.39 | 0.63 | 0.84 | Lower in CD1C⁻CD141⁻ (DC4)/Higher in Mono2 (CD16⁺ non-classical mono) | 1 |
| SELL | 0.30 | −1.14 | 0.40 | 0.69 | 0.82 | Lower in CD1C⁻CD141⁻ (DC4)/Higher in Mono2 (CD16⁺ non-classical mono) | 1 |
| PION | 0.30 | −1.28 | 0.40 | 0.27 | 0.64 | Lower in CD1C⁻CD141⁻ (DC4)/Higher in Mono2 (CD16⁺ non-classical mono) | 0 |
| TREM1 | 0.30 | −1.75 | 0.41 | 0.23 | 0.59 | Lower in CD1C⁻CD141⁻ (DC4)/Higher in Mono2 (CD16⁺ non-classical mono) | 1 |
| CD93 | 0.29 | −1.78 | 0.41 | 0.17 | 0.55 | Lower in CD1C⁻CD141⁻ (DC4)/Higher in Mono2 (CD16⁺ non-classical mono) | 1 |
| CMTM3 | 0.29 | −1.29 | 0.41 | 0.15 | 0.56 | Lower in CD1C⁻CD141⁻ (DC4)/Higher in Mono2 (CD16⁺ non-classical mono) | 1 |
| AQP9 | 0.29 | −1.81 | 0.42 | 0.13 | 0.53 | Lower in CD1C⁻CD141⁻ (DC4)/Higher in Mono2 (CD16⁺ non-classical mono) | 1 |
| HIPK2 | 0.29 | −1.21 | 0.42 | 0.33 | 0.68 | Lower in CD1C⁻CD141⁻ (DC4)/Higher in Mono2 (CD16⁺ non-classical mono) | 1 |
| SULF2 | 0.29 | −1.33 | 0.42 | 0.29 | 0.65 | Lower in CD1C⁻CD141⁻ (DC4)/Higher in Mono2 (CD16⁺ non-classical mono) | 1 |
| CDA | 0.29 | −1.21 | 0.43 | 0.23 | 0.65 | Lower in CD1C⁻CD141⁻ (DC4)/Higher in Mono2 (CD16⁺ non-classical mono) | 0 |
| GANAB | 0.29 | −1.19 | 0.43 | 0.43 | 0.74 | Lower in CD1C⁻CD141⁻ (DC4)/Higher in Mono2 (CD16⁺ non-classical mono) | 0 |
| ALDH2 | 0.27 | −1.57 | 0.46 | 0.37 | 0.70 | Lower in CD1C⁻CD141⁻ (DC4)/Higher in Mono2 (CD16⁺ non-classical mono) | 0 |
| NAIP | 0.27 | −1.54 | 0.46 | 0.66 | 0.79 | Lower in CD1C⁻CD141⁻ (DC4)/Higher in Mono2 (CD16⁺ non-classical mono) | 0 |
| LOC100506190 | 0.27 | −1.05 | 0.46 | 0.93 | 0.94 | Lower in CD1C⁻CD141⁻ (DC4)/Higher in Mono2 (CD16⁺ non-classical mono) | 0 |

TABLE E6-continued

Discriminative markers between CD1C⁻CD141⁻ (cluster DC4) and Mono2
(CD14⁺CD16⁺⁺ non-classical monocyte subsets)

| Gene.ID | AUC value | Avg Diff.[1] | Power[2] | Pct.1[3] | Pct2[4] | Comments | Surface Marker[5] |
|---|---|---|---|---|---|---|---|
| NLRP3 | 0.26 | −1.74 | 0.48 | 0.45 | 0.72 | Lower in CD1C⁻CD141⁻ (DC4)/Higher in Mono2 (CD16⁺ non-classical mono) | 0 |
| MS4A6A | 0.26 | −1.83 | 0.48 | 0.21 | 0.63 | Lower in CD1C⁻CD141⁻ (DC4)/Higher in Mono2 (CD16⁺ non-classical mono) | 1 |
| DDIT4 | 0.26 | −1.66 | 0.49 | 0.39 | 0.73 | Lower in CD1C⁻CD141⁻ (DC4)/Higher in Mono2 (CD16⁺ non-classical mono) | 0 |
| TNFAIP3 | 0.26 | −1.58 | 0.49 | 0.27 | 0.69 | Lower in CD1C⁻CD141⁻ (DC4)/Higher in Mono2 (CD16⁺ non-classical mono) | 0 |
| CSF3R | 0.24 | −1.48 | 0.51 | 0.37 | 0.78 | Lower in CD1C⁻CD141⁻ (DC4)/Higher in Mono2 (CD16⁺ non-classical mono) | 1 |
| ENTPD1 | 0.24 | −1.10 | 0.51 | 0.97 | 0.99 | Lower in CD1C⁻CD141⁻ (DC4)/Higher in Mono2 (CD16⁺ non-classical mono) | 1 |
| LRP1 | 0.24 | −1.03 | 0.52 | 0.73 | 0.92 | Lower in CD1C⁻CD141⁻ (DC4)/Higher in Mono2 (CD16⁺ non-classical mono) | 1 |
| CXCR4 | 0.24 | −1.29 | 0.52 | 0.66 | 0.88 | Lower in CD1C⁻CD141⁻ (DC4)/Higher in Mono2 (CD16⁺ non-classical mono) | 1 |
| NCF1C | 0.23 | −2.24 | 0.54 | 0.14 | 0.67 | Lower in CD1C⁻CD141⁻ (DC4)/Higher in Mono2 (CD16⁺ non-classical mono) | 0 |
| ITGAM | 0.23 | −2.43 | 0.54 | 0.11 | 0.62 | Lower in CD1C⁻CD141⁻ (DC4)/Higher in Mono2 (CD16⁺ non-classical mono) | 1 |
| FKBP5 | 0.23 | −1.06 | 0.54 | 0.71 | 0.93 | Lower in CD1C⁻CD141⁻ (DC4)/Higher in Mono2 (CD16⁺ non-classical mono) | 0 |
| NCF1 | 0.23 | −2.47 | 0.55 | 0.41 | 0.76 | Lower in CD1C⁻CD141⁻ (DC4)/Higher in Mono2 (CD16⁺ non-classical mono) | 0 |
| CD36 | 0.22 | −1.57 | 0.57 | 0.57 | 0.88 | Lower in CD1C⁻CD141⁻ (DC4)/Higher in Mono2 (CD16⁺ non-classical mono) | 1 |
| LGALS2 | 0.22 | −3.36 | 0.57 | 0.05 | 0.60 | Lower in CD1C⁻CD141⁻ (DC4)/Higher in Mono2 (CD16⁺ non-classical mono) | 0 |
| VCAN | 0.22 | −2.00 | 0.57 | 0.35 | 0.77 | Lower in CD1C⁻CD141⁻ (DC4)/Higher in Mono2 (CD16⁺ non-classical mono) | 1 |
| LYZ | 0.19 | −1.10 | 0.63 | 1.00 | 1.00 | Lower in CD1C⁻CD141⁻ (DC4)/Higher in Mono2 (CD16⁺ non-classical mono) | 0 |
| PER1 | 0.16 | −1.74 | 0.67 | 0.41 | 0.88 | Lower in CD1C⁻CD141⁻ (DC4)/Higher in Mono2 (CD16⁺ non-classical mono) | 0 |
| HLA-DQB1 | 0.16 | −1.04 | 0.67 | 0.78 | 0.94 | Lower in CD1C⁻CD141⁻ (DC4)/Higher in Mono2 (CD16⁺ non-classical mono) | 1 |
| S100A8 | 0.16 | −2.82 | 0.68 | 0.34 | 0.84 | Lower in CD1C⁻CD141⁻ (DC4)/Higher in Mono2 (CD16⁺ non-classical mono) | 0 |
| GRN | 0.16 | −1.01 | 0.68 | 0.90 | 0.98 | Lower in CD1C⁻CD141⁻ (DC4)/Higher in Mono2 (CD16⁺ non-classical mono) | 1 |
| CD14 | 0.14 | −3.06 | 0.72 | 0.18 | 0.80 | Lower in CD1C⁻CD141⁻ (DC4)/Higher in Mono2 (CD16⁺ non-classical mono) | 1 |
| BC013828 | 0.13 | −2.62 | 0.75 | 0.14 | 0.81 | Lower in CD1C⁻CD141⁻ (DC4)/Higher in Mono2 (CD16⁺ non-classical mono) | 0 |
| RPS26 | 0.08 | −1.37 | 0.84 | 0.79 | 0.99 | Lower in CD1C⁻CD141⁻ (DC4)/Higher in Mono2 (CD16⁺ non-classical mono) | 0 |
| LAIR2 | 0.06 | −4.69 | 0.88 | 0.03 | 0.88 | Lower in CD1C⁻CD141⁻ (DC4)/Higher in Mono2 (CD16⁺ non-classical mono) | 1 |

TABLE E7

Discriminative markers between CD1C⁻CD141⁻ (cluster DC4) and all monocyte subsets

| Gene.ID | AUC value | Avg. Diff.[1] | Power[2] | Pct.1[3] | Pct.2[4] | Comments | Surface Marker[5] |
|---|---|---|---|---|---|---|---|
| HLA-DRB4 | 0.98 | 4.40 | 0.96 | 0.99 | 0.44 | Higher in CD1C⁻CD141⁻ (DC4)/Lower in monocytes | 1 |
| FCGR3A | 0.96 | 1.53 | 0.92 | 1.00 | 0.74 | Higher in CD1C⁻CD141⁻ (DC4)/Lower in monocytes | 1 |
| LST1 | 0.91 | 1.05 | 0.83 | 1.00 | 0.97 | Higher in CD1C⁻CD141⁻ (DC4)/Lower in monocytes | 1 |
| AK307192 | 0.90 | 1.69 | 0.81 | 0.97 | 0.70 | Higher in CD1C⁻CD141⁻ (DC4)/Lower in monocytes | 0 |
| TMEM176B | 0.88 | 2.94 | 0.76 | 0.83 | 0.16 | Higher in CD1C⁻CD141⁻ (DC4)/Lower in monocytes | 1 |
| LOC200772 | 0.88 | 3.13 | 0.75 | 0.82 | 0.14 | Higher in CD1C⁻CD141⁻ (DC4)/Lower in monocytes | 0 |
| IFITM3 | 0.88 | 1.16 | 0.75 | 1.00 | 0.95 | Higher in CD1C⁻CD141⁻ (DC4)/Lower in monocytes | 1 |

TABLE E7-continued

Discriminative markers between CD1C⁻CD141⁻ (cluster DC4) and all monocyte subsets

| Gene.ID | AUC value | Avg. Diff.[1] | Power[2] | Pct.1[3] | Pct.2[4] | Comments | Surface Marker[5] |
|---|---|---|---|---|---|---|---|
| RHOC | 0.86 | 1.43 | 0.72 | 0.96 | 0.56 | Higher in CD1C⁻CD141⁻ (DC4)/ Lower in monocytes | 0 |
| LY6E | 0.85 | 1.42 | 0.71 | 0.98 | 0.59 | Higher in CD1C⁻CD141⁻ (DC4)/ Lower in monocytes | 1 |
| FAM110A | 0.85 | 1.86 | 0.70 | 0.87 | 0.36 | Higher in CD1C⁻CD141⁻ (DC4)/ Lower in monocytes | 0 |
| OAS1 | 0.84 | 1.29 | 0.68 | 0.98 | 0.62 | Higher in CD1C⁻CD141⁻ (DC4)/ Lower in monocytes | 0 |
| CTSL1 | 0.83 | 1.65 | 0.67 | 0.90 | 0.45 | Higher in CD1C⁻CD141⁻ (DC4)/ Lower in monocytes | 1 |
| MTSS1 | 0.83 | 1.33 | 0.67 | 0.99 | 0.59 | Higher in CD1C⁻CD141⁻ (DC4)/ Lower in monocytes | 0 |
| PLD4 | 0.82 | 1.65 | 0.64 | 0.80 | 0.21 | Higher in CD1C⁻CD141⁻ (DC4)/ Lower in monocytes | 1 |
| TCF7L2 | 0.82 | 1.53 | 0.64 | 0.97 | 0.57 | Higher in CD1C⁻CD141⁻ (DC4)/ Lower in monocytes | 0 |
| SIDT2 | 0.81 | 1.35 | 0.62 | 0.93 | 0.57 | Higher in CD1C⁻CD141⁻ (DC4)/ Lower in monocytes | 1 |
| FCGR2C | 0.80 | 1.45 | 0.61 | 0.87 | 0.46 | Higher in CD1C⁻CD141⁻ (DC4)/ Lower in monocytes | 0 |
| HSPA7 | 0.79 | 1.96 | 0.58 | 0.74 | 0.23 | Higher in CD1C⁻CD141⁻ (DC4)/ Lower in monocytes | 0 |
| HLA-DQA2 | 0.79 | 2.04 | 0.58 | 0.70 | 0.16 | Higher in CD1C⁻CD141⁻ (DC4)/ Lower in monocytes | 1 |
| ABI3 | 0.78 | 1.05 | 0.57 | 0.95 | 0.60 | Higher in CD1C⁻CD141⁻ (DC4)/ Lower in monocytes | 0 |
| SOD1 | 0.78 | 1.20 | 0.56 | 0.90 | 0.64 | Higher in CD1C⁻CD141⁻ (DC4)/ Lower in monocytes | 0 |
| HLA-H | 0.78 | 1.02 | 0.56 | 0.95 | 0.71 | Higher in CD1C⁻CD141⁻ (DC4)/ Lower in monocytes | 1 |
| WSB1 | 0.77 | 1.11 | 0.55 | 0.96 | 0.87 | Higher in CD1C⁻CD141⁻ (DC4)/ Lower in monocytes | 0 |
| CD79B | 0.76 | 1.34 | 0.52 | 0.78 | 0.37 | Higher in CD1C⁻CD141⁻ (DC4)/ Lower in monocytes | 1 |
| MS4A4A | 0.76 | 1.80 | 0.51 | 0.72 | 0.31 | Higher in CD1C⁻CD141⁻ (DC4)/ Lower in monocytes | 1 |
| NEURL | 0.74 | 1.69 | 0.49 | 0.67 | 0.24 | Higher in CD1C⁻CD141⁻ (DC4)/ Lower in monocytes | 0 |
| DKFZP451J181 | 0.74 | 1.35 | 0.49 | 0.83 | 0.54 | Higher in CD1C⁻CD141⁻ (DC4)/ Lower in monocytes | 0 |
| PTP4A3 | 0.74 | 1.57 | 0.48 | 0.68 | 0.25 | Higher in CD1C⁻CD141⁻ (DC4)/ Lower in monocytes | 0 |
| INSIG1 | 0.74 | 1.35 | 0.48 | 0.75 | 0.35 | Higher in CD1C⁻CD141⁻ (DC4)/ Lower in monocytes | 1 |
| TAGLN | 0.74 | 1.60 | 0.48 | 0.72 | 0.36 | Higher in CD1C⁻CD141⁻ (DC4)/ Lower in monocytes | 0 |
| ISG15 | 0.74 | 1.20 | 0.48 | 0.79 | 0.51 | Higher in CD1C⁻CD141⁻ (DC4)/ Lower in monocytes | 0 |
| IFITM1 | 0.74 | 1.16 | 0.47 | 0.74 | 0.31 | Higher in CD1C⁻CD141⁻ (DC4)/ Lower in monocytes | 1 |
| SH2D1B | 0.73 | 1.88 | 0.46 | 0.62 | 0.18 | Higher in CD1C⁻CD141⁻ (DC4)/ Lower in monocytes | 0 |
| SPN | 0.73 | 1.05 | 0.45 | 0.98 | 0.99 | Higher in CD1C⁻CD141⁻ (DC4)/ Lower in monocytes | 1 |
| IFIT3 | 0.71 | 1.52 | 0.42 | 0.83 | 0.65 | Higher in CD1C⁻CD141⁻ (DC4)/ Lower in monocytes | 0 |
| CKB | 0.71 | 2.25 | 0.42 | 0.51 | 0.12 | Higher in CD1C⁻CD141⁻ (DC4)/ Lower in monocytes | 0 |
| MX1 | 0.71 | 1.32 | 0.41 | 0.67 | 0.29 | Higher in CD1C⁻CD141⁻ (DC4)/ Lower in monocytes | 0 |
| C11ORF21 | 0.71 | 1.39 | 0.41 | 0.70 | 0.45 | Higher in CD1C⁻CD141⁻ (DC4)/ Lower in monocytes | 0 |
| CLEC4F | 0.71 | 1.71 | 0.41 | 0.56 | 0.18 | Higher in CD1C⁻CD141⁻ (DC4)/ Lower in monocytes | 1 |
| CDKN1C | 0.70 | 1.13 | 0.41 | 0.67 | 0.29 | Higher in CD1C⁻CD141⁻ (DC4)/ Lower in monocytes | 0 |
| CDH23 | 0.70 | 1.48 | 0.40 | 0.86 | 0.66 | Higher in CD1C⁻CD141⁻ (DC4)/ Lower in monocytes | 1 |
| TESC | 0.70 | 1.56 | 0.40 | 0.59 | 0.26 | Higher in CD1C⁻CD141⁻ (DC4)/ Lower in monocytes | 0 |
| HLA-DRB6 | 0.69 | 1.11 | 0.39 | 0.57 | 0.17 | Higher in CD1C⁻CD141⁻ (DC4)/ Lower in monocytes | 1 |
| ADA | 0.69 | 1.26 | 0.38 | 0.62 | 0.30 | Higher in CD1C⁻CD141⁻ (DC4)/ Lower in monocytes | 0 |

TABLE E7-continued

Discriminative markers between CD1C⁻CD141⁻ (cluster DC4) and all monocyte subsets

| Gene.ID | AUC value | Avg. Diff.[1] | Power[2] | Pct.1[3] | Pct.2[4] | Comments | Surface Marker[5] |
|---|---|---|---|---|---|---|---|
| ICAM4 | 0.69 | 1.60 | 0.38 | 0.68 | 0.35 | Higher in CD1C⁻CD141⁻ (DC4)/ Lower in monocytes | 1 |
| EVL | 0.69 | 1.06 | 0.38 | 0.69 | 0.35 | Higher in CD1C⁻CD141⁻ (DC4)/ Lower in monocytes | 0 |
| UNC119 | 0.68 | 1.28 | 0.37 | 0.64 | 0.34 | Higher in CD1C⁻CD141⁻ (DC4)/ Lower in monocytes | 0 |
| CALHM2 | 0.68 | 1.01 | 0.35 | 0.71 | 0.47 | Higher in CD1C⁻CD141⁻ (DC4)/ Lower in monocytes | 1 |
| IFI44L | 0.68 | 1.53 | 0.35 | 0.53 | 0.18 | Higher in CD1C⁻CD141⁻ (DC4)/ Lower in monocytes | 0 |
| AK124399 | 0.67 | 1.43 | 0.35 | 0.50 | 0.18 | Higher in CD1C⁻CD141⁻ (DC4)/ Lower in monocytes | 0 |
| GRAMD1A | 0.67 | 1.04 | 0.34 | 0.69 | 0.38 | Higher in CD1C⁻CD141⁻ (DC4)/ Lower in monocytes | 1 |
| SYTL1 | 0.67 | 1.07 | 0.34 | 0.61 | 0.31 | Higher in CD1C⁻CD141⁻ (DC4)/ Lower in monocytes | 0 |
| TMTC1 | 0.67 | 1.97 | 0.33 | 0.57 | 0.28 | Higher in CD1C⁻CD141⁻ (DC4)/ Lower in monocytes | 1 |
| IFI44 | 0.66 | 1.23 | 0.32 | 0.64 | 0.36 | Higher in CD1C⁻CD141⁻ (DC4)/ Lower in monocytes | 0 |
| SIK1 | 0.66 | 1.01 | 0.31 | 0.61 | 0.32 | Higher in CD1C⁻CD141⁻ (DC4)/ Lower in monocytes | 1 |
| VAMP5 | 0.66 | 1.11 | 0.31 | 0.61 | 0.41 | Higher in CD1C⁻CD141⁻ (DC4)/ Lower in monocytes | 1 |
| BCAT1 | 0.66 | 1.42 | 0.31 | 0.51 | 0.22 | Higher in CD1C⁻CD141⁻ (DC4)/ Lower in monocytes | 0 |
| FCGR3B | 0.66 | −1.11 | 0.31 | 0.73 | 0.35 | Higher in CD1C⁻CD141⁻ (DC4)/ Lower in monocytes | 1 |
| MARCKS | 0.65 | 1.15 | 0.31 | 0.73 | 0.58 | Higher in CD1C⁻CD141⁻ (DC4)/ Lower in monocytes | 1 |
| OAS2 | 0.65 | 1.03 | 0.30 | 0.71 | 0.50 | Higher in CD1C⁻CD141⁻ (DC4)/ Lower in monocytes | 0 |
| CCM2 | 0.65 | 1.10 | 0.30 | 0.66 | 0.44 | Higher in CD1C⁻CD141⁻ (DC4)/ Lower in monocytes | 0 |
| HEG1 | 0.65 | 1.47 | 0.29 | 0.50 | 0.24 | Higher in CD1C⁻CD141⁻ (DC4)/ Lower in monocytes | 1 |
| BC035647 | 0.65 | 1.09 | 0.29 | 0.55 | 0.26 | Higher in CD1C⁻CD141⁻ (DC4)/ Lower in monocytes | 0 |
| SAMD9L | 0.64 | 1.10 | 0.29 | 0.58 | 0.36 | Higher in CD1C⁻CD141⁻ (DC4)/ Lower in monocytes | 0 |
| CCDC53 | 0.64 | 1.22 | 0.27 | 0.53 | 0.31 | Higher in CD1C⁻CD141⁻ (DC4)/ Lower in monocytes | 0 |
| RAB7L1 | 0.64 | 1.07 | 0.27 | 0.81 | 0.62 | Higher in CD1C⁻CD141⁻ (DC4)/ Lower in monocytes | 0 |
| SCRN1 | 0.63 | 1.16 | 0.26 | 0.50 | 0.27 | Higher in CD1C⁻CD141⁻ (DC4)/ Lower in monocytes | 0 |
| TMEM134 | 0.63 | 1.19 | 0.26 | 0.52 | 0.35 | Higher in CD1C⁻CD141⁻ (DC4)/ Lower in monocytes | 1 |
| GBP4 | 0.62 | 1.05 | 0.24 | 0.93 | 0.85 | Higher in CD1C⁻CD141⁻ (DC4)/ Lower in monocytes | 0 |
| MRPS18B | 0.62 | 1.03 | 0.24 | 0.63 | 0.47 | Higher in CD1C⁻CD141⁻ (DC4)/ Lower in monocytes | 0 |
| DDX58 | 0.61 | 1.27 | 0.22 | 0.56 | 0.39 | Higher in CD1C⁻CD141⁻ (DC4)/ Lower in monocytes | 0 |
| HERPUD2 | 0.61 | 1.55 | 0.22 | 0.55 | 0.37 | Higher in CD1C⁻CD141⁻ (DC4)/ Lower in monocytes | 1 |
| SIAE | 0.40 | −1.02 | 0.20 | 0.52 | 0.56 | Lower in CD1C⁻CD141⁻ (DC4)/ Higher in monocytes | 0 |
| EREG | 0.40 | −1.63 | 0.20 | 0.54 | 0.61 | Lower in CD1C⁻CD141⁻ (DC4)/ Higher in monocytes | 1 |
| LOC729603 | 0.39 | −1.27 | 0.22 | 0.54 | 0.58 | Lower in CD1C⁻CD141⁻ (DC4)/ Higher in monocytes | 0 |
| MCTP2 | 0.39 | −1.03 | 0.22 | 0.50 | 0.56 | Lower in CD1C⁻CD141⁻ (DC4)/ Higher in monocytes | 1 |
| EPB41 | 0.39 | −1.12 | 0.23 | 0.52 | 0.61 | Lower in CD1C⁻CD141⁻ (DC4)/ Higher in monocytes | 0 |
| BC014119 | 0.38 | −1.35 | 0.25 | 0.43 | 0.56 | Lower in CD1C⁻CD141⁻ (DC4)/ Higher in monocytes | 0 |
| GSN | 0.38 | −1.30 | 0.25 | 0.36 | 0.52 | Lower in CD1C⁻CD141⁻ (DC4)/ Higher in monocytes | 0 |
| LRG1 | 0.38 | −1.98 | 0.25 | 0.49 | 0.56 | Lower in CD1C⁻CD141⁻ (DC4)/ Higher in monocytes | 0 |
| SMAD5 | 0.37 | −1.02 | 0.25 | 0.57 | 0.64 | Lower in CD1C⁻CD141⁻ (DC4)/ Higher in monocytes | 0 |

TABLE E7-continued

Discriminative markers between CD1C⁻CD141⁻ (cluster DC4) and all monocyte subsets

| Gene.ID | AUC value | Avg. Diff.[1] | Power[2] | Pct.1[3] | Pct.2[4] | Comments | Surface Marker[5] |
|---|---|---|---|---|---|---|---|
| APP | 0.37 | −1.22 | 0.26 | 0.43 | 0.56 | Lower in CD1C⁻CD141⁻ (DC4)/ Higher in monocytes | 1 |
| FW340055 | 0.37 | −1.05 | 0.26 | 0.45 | 0.60 | Lower in CD1C⁻CD141⁻ (DC4)/ Higher in monocytes | 0 |
| FLJ00310 | 0.37 | −1.30 | 0.26 | 0.37 | 0.53 | Lower in CD1C⁻CD141⁻ (DC4)/ Higher in monocytes | 0 |
| LOC388692 | 0.37 | −1.03 | 0.27 | 0.55 | 0.62 | Lower in CD1C⁻CD141⁻ (DC4)/ Higher in monocytes | 0 |
| DGKZ | 0.37 | −1.07 | 0.27 | 0.47 | 0.61 | Lower in CD1C⁻CD141⁻ (DC4)/ Higher in monocytes | 0 |
| MGAT4A | 0.36 | −1.39 | 0.27 | 0.47 | 0.57 | Lower in CD1C⁻CD141⁻ (DC4)/ Higher in monocytes | 0 |
| KDELR1 | 0.35 | −1.05 | 0.29 | 0.26 | 0.52 | Lower in CD1C⁻CD141⁻ (DC4)/ Higher in monocytes | 1 |
| SLC25A37 | 0.35 | −1.20 | 0.29 | 0.34 | 0.60 | Lower in CD1C⁻CD141⁻ (DC4)/ Higher in monocytes | 0 |
| SPTAN1 | 0.35 | −1.07 | 0.29 | 0.51 | 0.51 | Lower in CD1C⁻CD141⁻ (DC4)/ Higher in monocytes | 0 |
| IL13RA1 | 0.35 | −1.09 | 0.30 | 0.27 | 0.51 | Lower in CD1C⁻CD141⁻ (DC4)/ Higher in monocytes | 1 |
| DRAM1 | 0.35 | −1.15 | 0.30 | 0.28 | 0.51 | Lower in CD1C⁻CD141⁻ (DC4)/ Higher in monocytes | 1 |
| TAB1 | 0.35 | −1.31 | 0.30 | 0.50 | 0.62 | Lower in CD1C⁻CD141⁻ (DC4)/ Higher in monocytes | 0 |
| TMEM170B | 0.35 | −1.10 | 0.31 | 0.42 | 0.58 | Lower in CD1C⁻CD141⁻ (DC4)/ Higher in monocytes | 1 |
| CLMN | 0.34 | −1.30 | 0.32 | 0.34 | 0.55 | Lower in CD1C⁻CD141⁻ (DC4)/ Higher in monocytes | 1 |
| FAM115C | 0.34 | −2.01 | 0.32 | 0.53 | 0.64 | Lower in CD1C⁻CD141⁻ (DC4)/ Higher in monocytes | 0 |
| MBOAT7 | 0.34 | −1.16 | 0.32 | 0.25 | 0.55 | Lower in CD1C⁻CD141⁻ (DC4)/ Higher in monocytes | 1 |
| NRIP3 | 0.34 | −1.03 | 0.33 | 0.56 | 0.65 | Lower in CD1C⁻CD141⁻ (DC4)/ Higher in monocytes | 0 |
| CR1 | 0.34 | −1.02 | 0.33 | 0.38 | 0.62 | Lower in CD1C⁻CD141⁻ (DC4)/ Higher in monocytes | 1 |
| G0S2 | 0.34 | −1.54 | 0.33 | 0.29 | 0.57 | Lower in CD1C⁻CD141⁻ (DC4)/ Higher in monocytes | 0 |
| CCNY | 0.34 | −1.39 | 0.33 | 0.20 | 0.51 | Lower in CD1C⁻CD141⁻ (DC4)/ Higher in monocytes | 0 |
| CR936688 | 0.33 | −1.35 | 0.34 | 0.70 | 0.78 | Lower in CD1C⁻CD141⁻ (DC4)/ Higher in monocytes | 0 |
| TTC7A | 0.33 | −1.26 | 0.34 | 0.23 | 0.54 | Lower in CD1C⁻CD141⁻ (DC4)/ Higher in monocytes | 0 |
| ELK4 | 0.33 | −1.06 | 0.35 | 0.53 | 0.67 | Lower in CD1C⁻CD141⁻ (DC4)/ Higher in monocytes | 0 |
| FP15737 | 0.33 | −1.63 | 0.35 | 0.58 | 0.68 | Lower in CD1C⁻CD141⁻ (DC4)/ Higher in monocytes | 0 |
| CD82 | 0.32 | −1.90 | 0.35 | 0.48 | 0.63 | Lower in CD1C⁻CD141⁻ (DC4)/ Higher in monocytes | 1 |
| AK289390 | 0.32 | −1.15 | 0.36 | 0.66 | 0.73 | Lower in CD1C⁻CD141⁻ (DC4)/ Higher in monocytes | 0 |
| CRISPLD2 | 0.32 | −2.37 | 0.36 | 0.53 | 0.66 | Lower in CD1C⁻CD141⁻ (DC4)/ Higher in monocytes | 0 |
| NT5DC3 | 0.32 | −1.04 | 0.36 | 0.77 | 0.79 | Lower in CD1C⁻CD141⁻ (DC4)/ Higher in monocytes | 0 |
| PION | 0.32 | −1.07 | 0.36 | 0.77 | 0.60 | Lower in CD1C⁻CD141⁻ (DC4)/ Higher in monocytes | 0 |
| AK130076 | 0.32 | −1.06 | 0.37 | 0.59 | 0.74 | Lower in CD1C⁻CD141⁻ (DC4)/ Higher in monocytes | 0 |
| CYFIP1 | 0.31 | −1.34 | 0.37 | 0.27 | 0.58 | Lower in CD1C⁻CD141⁻ (DC4)/ Higher in monocytes | 0 |
| BHLHE40 | 0.31 | −1.64 | 0.38 | 0.20 | 0.53 | Lower in CD1C⁻CD141⁻ (DC4)/ Higher in monocytes | 0 |
| CEBPD | 0.31 | −1.01 | 0.38 | 0.21 | 0.59 | Lower in CD1C⁻CD141⁻ (DC4)/ Higher in monocytes | 0 |
| KCTD20 | 0.31 | −1.15 | 0.38 | 0.46 | 0.67 | Lower in CD1C⁻CD141⁻ (DC4)/ Higher in monocytes | 0 |
| ZNF267 | 0.31 | −1.14 | 0.38 | 0.28 | 0.60 | Lower in CD1C⁻CD141⁻ (DC4)/ Higher in monocytes | 0 |
| DQ573668 | 0.31 | −1.28 | 0.38 | 0.57 | 0.72 | Lower in CD1C⁻CD141⁻ (DC4)/ Higher in monocytes | 0 |
| LOC100507032 | 0.31 | −1.04 | 0.38 | 0.31 | 0.62 | Lower in CD1C⁻CD141⁻ (DC4)/ Higher in monocytes | 0 |

TABLE E7-continued

Discriminative markers between CD1C⁻CD141⁻ (cluster DC4) and all monocyte subsets

| Gene.ID | AUC value | Avg. Diff.[1] | Power[2] | Pct.1[3] | Pct.2[4] | Comments | Surface Marker[5] |
|---|---|---|---|---|---|---|---|
| ZBTB16 | 0.31 | −1.64 | 0.38 | 0.47 | 0.65 | Lower in CD1C⁻CD141⁻ (DC4)/ Higher in monocytes | 0 |
| AX747598 | 0.31 | −1.03 | 0.39 | 0.49 | 0.76 | Lower in CD1C⁻CD141⁻ (DC4)/ Higher in monocytes | 0 |
| GANAB | 0.31 | −1.08 | 0.39 | 0.43 | 0.72 | Lower in CD1C⁻CD141⁻ (DC4)/ Higher in monocytes | 0 |
| RUNX1 | 0.31 | −1.15 | 0.39 | 0.66 | 0.78 | Lower in CD1C⁻CD141⁻ (DC4)/ Higher in monocytes | 0 |
| RBM47 | 0.30 | −1.26 | 0.39 | 0.33 | 0.66 | Lower in CD1C⁻CD141⁻ (DC4)/ Higher in monocytes | 0 |
| SMA3 | 0.30 | −1.28 | 0.40 | 0.62 | 0.76 | Lower in CD1C⁻CD141⁻ (DC4)/ Higher in monocytes | 0 |
| NLRP12 | 0.30 | −1.04 | 0.40 | 0.87 | 0.90 | Lower in CD1C⁻CD141⁻ (DC4)/ Higher in monocytes | 0 |
| CMTM3 | 0.30 | −1.24 | 0.40 | 0.15 | 0.55 | Lower in CD1C⁻CD141⁻ (DC4)/ Higher in monocytes | 1 |
| FAM129A | 0.30 | −1.74 | 0.40 | 0.39 | 0.64 | Lower in CD1C⁻CD141⁻ (DC4)/ Higher in monocytes | 0 |
| HEXB | 0.30 | −1.09 | 0.41 | 0.45 | 0.75 | Lower in CD1C⁻CD141⁻ (DC4)/ Higher in monocytes | 1 |
| ICAM1 | 0.30 | −1.31 | 0.41 | 0.34 | 0.65 | Lower in CD1C⁻CD141⁻ (DC4)/ Higher in monocytes | 1 |
| PPIF | 0.30 | −1.52 | 0.41 | 0.22 | 0.58 | Lower in CD1C⁻CD141⁻ (DC4)/ Higher in monocytes | 0 |
| UBR4 | 0.30 | −1.05 | 0.41 | 0.66 | 0.84 | Lower in CD1C⁻CD141⁻ (DC4)/ Higher in monocytes | 1 |
| CACNA2D3 | 0.30 | −1.19 | 0.41 | 0.66 | 0.75 | Lower in CD1C⁻CD141⁻ (DC4)/ Higher in monocytes | 1 |
| HEXA | 0.29 | −1.47 | 0.41 | 0.20 | 0.58 | Lower in CD1C⁻CD141⁻ (DC4)/ Higher in monocytes | 1 |
| ACTN1 | 0.29 | −1.70 | 0.42 | 0.66 | 0.80 | Lower in CD1C⁻CD141⁻ (DC4)/ Higher in monocytes | 1 |
| FCGR1A | 0.29 | −1.98 | 0.42 | 0.10 | 0.51 | Lower in CD1C⁻CD141⁻ (DC4)/ Higher in monocytes | 1 |
| LITAF | 0.29 | −1.05 | 0.42 | 0.63 | 0.87 | Lower in CD1C⁻CD141⁻ (DC4)/ Higher in monocytes | 1 |
| PCNX | 0.29 | −1.27 | 0.42 | 0.31 | 0.64 | Lower in CD1C⁻CD141⁻ (DC4)/ Higher in monocytes | 1 |
| DD1T4 | 0.29 | −1.45 | 0.42 | 0.39 | 0.69 | Lower in CD1C⁻CD141⁻ (DC4)/ Higher in monocytes | 0 |
| DQ575504 | 0.29 | −1.35 | 0.42 | 0.42 | 0.74 | Lower in CD1C⁻CD141⁻ (DC4)/ Higher in monocytes | 0 |
| SGSH | 0.29 | −1.28 | 0.43 | 0.26 | 0.61 | Lower in CD1C⁻CD141⁻ (DC4)/ Higher in monocytes | 0 |
| AL137655 | 0.29 | −1.04 | 0.43 | 0.75 | 0.89 | Lower in CD1C⁻CD141⁻ (DC4)/ Higher in monocytes | 0 |
| MILR1 | 0.29 | −1.09 | 0.43 | 0.73 | 0.83 | Lower in CD1C⁻CD141⁻ (DC4)/ Higher in monocytes | 1 |
| MXD1 | 0.29 | −1.06 | 0.43 | 0.58 | 0.84 | Lower in CD1C⁻CD141⁻ (DC4)/ Higher in monocytes | 0 |
| CD1D | 0.28 | −1.62 | 0.43 | 0.29 | 0.64 | Lower in CD1C⁻CD141⁻ (DC4)/ Higher in monocytes | 1 |
| MPST | 0.28 | −1.12 | 0.43 | 0.86 | 0.89 | Lower in CD1C⁻CD141⁻ (DC4)/ Higher in monocytes | 0 |
| GCA | 0.28 | −1.10 | 0.44 | 0.57 | 0.83 | Lower in CD1C⁻CD141⁻ (DC4)/ Higher in monocytes | 0 |
| IRS2 | 0.28 | −1.05 | 0.44 | 0.26 | 0.69 | Lower in CD1C⁻CD141⁻ (DC4)/ Higher in monocytes | 0 |
| B4GALT1 | 0.28 | −1.13 | 0.44 | 0.69 | 0.85 | Lower in CD1C⁻CD141⁻ (DC4)/ Higher in monocytes | 1 |
| IGF2R | 0.28 | −1.28 | 0.44 | 0.10 | 0.54 | Lower in CD1C⁻CD141⁻ (DC4)/ Higher in monocytes | 1 |
| RAB27A | 0.28 | −1.57 | 0.44 | 0.66 | 0.78 | Lower in CD1C⁻CD141⁻ (DC4)/ Higher in monocytes | 0 |
| CCR1 | 0.27 | −1.36 | 0.45 | 0.28 | 0.69 | Lower in CD1C⁻CD141⁻ (DC4)/ Higher in monocytes | 1 |
| KLRD1 | 0.27 | −1.38 | 0.46 | 0.86 | 0.92 | Lower in CD1C⁻CD141⁻ (DC4)/ Higher in monocytes | 1 |
| ASGR1 | 0.27 | −1.50 | 0.46 | 0.19 | 0.63 | Lower in CD1C⁻CD141⁻ (DC4)/ Higher in monocytes | 0 |
| SERINC5 | 0.27 | −1.35 | 0.46 | 0.33 | 0.68 | Lower in CD1C⁻CD141⁻ (DC4)/ Higher in monocytes | 1 |
| FNDC3B | 0.27 | −1.37 | 0.46 | 0.63 | 0.80 | Lower in CD1C⁻CD141⁻ (DC4)/ Higher in monocytes | 1 |

TABLE E7-continued

Discriminative markers between CD1C⁻CD141⁻ (cluster DC4) and all monocyte subsets

| Gene.ID | AUC value | Avg. Diff.[1] | Power[2] | Pct.1[3] | Pct.2[4] | Comments | Surface Marker[5] |
|---|---|---|---|---|---|---|---|
| PLD3 | 0.27 | −1.76 | 0.46 | 0.40 | 0.70 | Lower in CD1C⁻CD141⁻ (DC4)/ Higher in monocytes | 1 |
| HIPK2 | 0.27 | −1.25 | 0.47 | 0.33 | 0.72 | Lower in CD1C⁻CD141⁻ (DC4)/ Higher in monocytes | 1 |
| JAR1D2 | 0.27 | −1.01 | 0.47 | 0.33 | 0.73 | Lower in CD1C⁻CD141⁻ (DC4)/ Higher in monocytes | 0 |
| SLC27A1 | 0.26 | −1.14 | 0.47 | 0.82 | 0.89 | Lower in CD1C⁻CD141⁻ (DC4)/ Higher in monocytes | 1 |
| PGPEP1 | 0.26 | −1.06 | 0.47 | 0.94 | 0.93 | Lower in CD1C⁻CD141⁻ (DC4)/ Higher in monocytes | 0 |
| SLC12A6 | 0.26 | −1.24 | 0.48 | 0.85 | 0.91 | Lower in CD1C⁻CD141⁻ (DC4)/ Higher in monocytes | 1 |
| MEGF9 | 0.26 | −1.11 | 0.48 | 0.69 | 0.87 | Lower in CD1C⁻CD141⁻ (DC4)/ Higher in monocytes | 1 |
| FLOT1 | 0.26 | −1.58 | 0.49 | 0.21 | 0.66 | Lower in CD1C⁻CD141⁻ (DC4)/ Higher in monocytes | 0 |
| HPSE | 0.26 | −1.47 | 0.49 | 0.81 | 0.88 | Lower in CD1C⁻CD141⁻ (DC4)/ Higher in monocytes | 0 |
| VNN2 | 0.26 | −1.71 | 0.49 | 0.22 | 0.66 | Lower in CD1C⁻CD141⁻ (DC4)/ Higher in monocytes | 1 |
| BAZ2B | 0.25 | −1.15 | 0.49 | 0.59 | 0.86 | Lower in CD1C⁻CD141⁻ (DC4)/ Higher in monocytes | 0 |
| BST1 | 0.25 | −1.63 | 0.50 | 0.24 | 0.69 | Lower in CD1C⁻CD141⁻ (DC4)/ Higher in monocytes | 1 |
| EMB | 0.25 | −3.07 | 0.50 | 0.09 | 0.55 | Lower in CD1C⁻CD141⁻ (DC4)/ Higher in monocytes | 1 |
| SULF2 | 0.25 | −1.52 | 0.50 | 0.29 | 0.71 | Lower in CD1C⁻CD141⁻ (DC4)/ Higher in monocytes | 1 |
| IL1B | 0.25 | −4.24 | 0.50 | 0.05 | 0.54 | Lower in CD1C⁻CD141⁻ (DC4)/ Higher in monocytes | 0 |
| FAM198B | 0.25 | −1.67 | 0.51 | 0.29 | 0.72 | Lower in CD1C⁻CD141⁻ (DC4)/ Higher in monocytes | 1 |
| TBC1D24 | 0.25 | −1.13 | 0.51 | 0.85 | 0.89 | Lower in CD1C⁻CD141⁻ (DC4)/ Higher in monocytes | 0 |
| IER3 | 0.24 | −4.10 | 0.51 | 0.03 | 0.53 | Lower in CD1C⁻CD141⁻ (DC4)/ Higher in monocytes | 1 |
| PLAUR | 0.24 | −1.14 | 0.51 | 0.72 | 0.94 | Lower in CD1C⁻CD141⁻ (DC4)/ Higher in monocytes | 1 |
| QPCT | 0.24 | −4.09 | 0.52 | 0.05 | 0.54 | Lower in CD1C⁻CD141⁻ (DC4)/ Higher in monocytes | 0 |
| GAS7 | 0.24 | −1.06 | 0.52 | 0.54 | 0.85 | Lower in CD1C⁻CD141⁻ (DC4)/ Higher in monocytes | 0 |
| PGD | 0.24 | −1.15 | 0.52 | 0.71 | 0.91 | Lower in CD1C⁻CD141⁻ (DC4)/ Higher in monocytes | 0 |
| ACSL1 | 0.24 | −1.20 | 0.52 | 0.43 | 0.85 | Lower in CD1C⁻CD141⁻ (DC4)/ Higher in monocytes | 1 |
| CREB5 | 0.24 | −3.33 | 0.52 | 0.15 | 0.60 | Lower in CD1C⁻CD141⁻ (DC4)/ Higher in monocytes | 0 |
| SMA | 0.24 | −2.63 | 0.52 | 0.19 | 0.63 | Lower in CD1C⁻CD141⁻ (DC4)/ Higher in monocytes | 0 |
| CDA | 0.24 | −1.46 | 0.53 | 0.23 | 0.73 | Lower in CD1C⁻CD141⁻ (DC4)/ Higher in monocytes | 0 |
| CPM | 0.24 | −1.70 | 0.53 | 0.79 | 0.89 | Lower in CD1C⁻CD141⁻ (DC4)/ Higher in monocytes | 1 |
| ETS2 | 0.23 | −1.19 | 0.53 | 0.56 | 0.88 | Lower in CD1C⁻CD141⁻ (DC4)/ Higher in monocytes | 0 |
| LOC649305 | 0.23 | −1.25 | 0.53 | 0.54 | 0.81 | Lower in CD1C⁻CD141⁻ (DC4)/ Higher in monocytes | 0 |
| PLP2 | 0.23 | −1.34 | 0.53 | 0.44 | 0.81 | Lower in CD1C⁻CD141⁻ (DC4)/ Higher in monocytes | 1 |
| CD163 | 0.23 | −4.21 | 0.54 | 0.05 | 0.57 | Lower in CD1C⁻CD141⁻ (DC4)/ Higher in monocytes | 1 |
| PTPRE | 0.23 | −1.10 | 0.54 | 0.59 | 0.91 | Lower in CD1C⁻CD141⁻ (DC4)/ Higher in monocytes | 1 |
| KCTD12 | 0.23 | −1.14 | 0.55 | 0.37 | 0.83 | Lower in CD1C⁻CD141⁻ (DC4)/ Higher in monocytes | 0 |
| ANXA1 | 0.22 | −1.18 | 0.55 | 0.76 | 0.93 | Lower in CD1C⁻CD141⁻ (DC4)/ Higher in monocytes | 0 |
| CAPG | 0.22 | −1.45 | 0.56 | 0.47 | 0.81 | Lower in CD1C⁻CD141⁻ (DC4)/ Higher in monocytes | 0 |
| CCL5 | 0.22 | 1.25 | 0.56 | 0.95 | 0.98 | Lower in CD1C⁻CD141⁻ (DC4)/ Higher in monocytes | 1 |
| LOC100506190 | 0.22 | −1.35 | 0.56 | 0.93 | 0.96 | Lower in CD1C⁻CD141⁻ (DC4)/ Higher in monocytes | 0 |

TABLE E7-continued

Discriminative markers between CD1C⁻CD141⁻ (cluster DC4) and all monocyte subsets

| Gene.ID | AUC value | Avg. Diff.[1] | Power[2] | Pct.1[3] | Pct.2[4] | Comments | Surface Marker[5] |
|---|---|---|---|---|---|---|---|
| AQP9 | 0.22 | −2.32 | 0.56 | 0.13 | 0.66 | Lower in CD1C⁻CD141⁻ (DC4)/ Higher in monocytes | 1 |
| STAB1 | 0.22 | −3.41 | 0.56 | 0.04 | 0.59 | Lower in CD1C⁻CD141⁻ (DC4)/ Higher in monocytes | 1 |
| PTAFR | 0.22 | −1.40 | 0.57 | 0.82 | 0.94 | Lower in CD1C⁻CD141⁻ (DC4)/ Higher in monocytes | 1 |
| CRTAP | 0.21 | −1.47 | 0.57 | 0.59 | 0.86 | Lower in CD1C⁻CD141⁻ (DC4)/ Higher in monocytes | 1 |
| CXCR4 | 0.21 | −1.30 | 0.58 | 0.66 | 0.92 | Lower in CD1C⁻CD141⁻ (DC4)/ Higher in monocytes | 1 |
| CD93 | 0.21 | −2.22 | 0.58 | 0.17 | 0.70 | Lower in CD1C⁻CD141⁻ (DC4)/ Higher in monocytes | 1 |
| SORL1 | 0.20 | −1.37 | 0.59 | 0.47 | 0.88 | Lower in CD1C⁻CD141⁻ (DC4)/ Higher in monocytes | 1 |
| GPX1 | 0.20 | −1.14 | 0.60 | 0.78 | 0.93 | Lower in CD1C⁻CD141⁻ (DC4)/ Higher in monocytes | 0 |
| TNFAIP3 | 0.20 | −1.96 | 0.60 | 0.27 | 0.79 | Lower in CD1C⁻CD141⁻ (DC4)/ Higher in monocytes | 0 |
| GM2A | 0.20 | −2.67 | 0.61 | 0.40 | 0.76 | Lower in CD1C⁻CD141⁻ (DC4)/ Higher in monocytes | 0 |
| NCF1B | 0.19 | −3.00 | 0.62 | 0.10 | 0.69 | Lower in CD1C⁻CD141⁻ (DC4)/ Higher in monocytes | 0 |
| S100A12 | 0.19 | −5.10 | 0.62 | 0.02 | 0.63 | Lower in CD1C⁻CD141⁻ (DC4)/ Higher in monocytes | 0 |
| FPR1 | 0.18 | −1.16 | 0.63 | 0.74 | 0.98 | Lower in CD1C⁻CD141⁻ (DC4)/ Higher in monocytes | 1 |
| PLBD1 | 0.18 | −1.78 | 0.63 | 0.49 | 0.88 | Lower in CD1C⁻CD141⁻ (DC4)/ Higher in monocytes | 1 |
| CLECAE | 0.18 | −3.75 | 0.64 | 0.38 | 0.77 | Lower in CD1C⁻CD141⁻ (DC4)/ Higher in monocytes | 1 |
| TREM1 | 0.18 | −2.27 | 0.65 | 0.23 | 0.78 | Lower in CD1C⁻CD141⁻ (DC4)/ Higher in monocytes | 1 |
| FKBP5 | 0.17 | −1.46 | 0.65 | 0.71 | 0.95 | Lower in CD1C⁻CD141⁻ (DC4)/ Higher in monocytes | 0 |
| CD99 | 0.17 | −3.04 | 0.66 | 0.14 | 0.73 | Lower in CD1C⁻CD141⁻ (DC4)/ Higher in monocytes | 1 |
| NLRP3 | 0.17 | −2.36 | 0.66 | 0.45 | 0.84 | Lower in CD1C⁻CD141⁻ (DC4)/ Higher in monocytes | 0 |
| PXN | 0.17 | −2.41 | 0.66 | 0.75 | 0.89 | Lower in CD1C⁻CD141⁻ (DC4)/ Higher in monocytes | 0 |
| SLC2A3 | 0.17 | −3.02 | 0.66 | 0.25 | 0.77 | Lower in CD1C⁻CD141⁻ (DC4)/ Higher in monocytes | 1 |
| ALDH2 | 0.16 | −2.09 | 0.67 | 0.37 | 0.84 | Lower in CD1C⁻CD141⁻ (DC4)/ Higher in monocytes | 0 |
| ENTPD1 | 0.16 | −1.43 | 0.68 | 0.97 | 1.00 | Lower in CD1C⁻CD141⁻ (DC4)/ Higher in monocytes | 1 |
| SELL | 0.16 | −1.88 | 0.68 | 0.69 | 0.92 | Lower in CD1C⁻CD141⁻ (DC4)/ Higher in monocytes | 1 |
| HLA-DQB1 | 0.16 | −1.01 | 0.69 | 0.78 | 0.95 | Lower in CD1C⁻CD141⁻ (DC4)/ Higher in monocytes | 1 |
| LRP1 | 0.15 | −1.47 | 0.69 | 0.73 | 0.96 | Lower in CD1C⁻CD141⁻ (DC4)/ Higher in monocytes | 1 |
| PER1 | 0.15 | −1.85 | 0.70 | 0.41 | 0.90 | Lower in CD1C⁻CD141⁻ (DC4)/ Higher in monocytes | 0 |
| S100A9 | 0.14 | −2.22 | 0.73 | 0.88 | 0.99 | Lower in CD1C⁻CD141⁻ (DC4)/ Higher in monocytes | 0 |
| NAIP | 0.13 | −2.59 | 0.73 | 0.66 | 0.91 | Lower in CD1C⁻CD141⁻ (DC4)/ Higher in monocytes | 0 |
| VIM | 0.13 | −1.13 | 0.73 | 0.99 | 1.00 | Lower in CD1C⁻CD141⁻ (DC4)/ Higher in monocytes | 1 |
| EEF2 | 0.13 | −1.07 | 0.74 | 0.96 | 0.99 | Lower in CD1C⁻CD141⁻ (DC4)/ Higher in monocytes | 0 |
| ITGAM | 0.13 | −2.95 | 0.74 | 0.11 | 0.81 | Lower in CD1C⁻CD141⁻ (DC4)/ Higher in monocytes | 1 |
| BC013828 | 0.12 | −2.70 | 0.75 | 0.14 | 0.81 | Lower in CD1C⁻CD141⁻ (DC4)/ Higher in monocytes | 0 |
| MS4A6A | 0.12 | −2.65 | 0.75 | 0.21 | 0.84 | Lower in CD1C⁻CD141⁻ (DC4)/ Higher in monocytes | 1 |
| LAIR2 | 0.12 | −4.31 | 0.76 | 0.03 | 0.77 | Lower in CD1C⁻CD141⁻ (DC4)/ Higher in monocytes | 1 |
| CSF3R | 0.12 | −2.28 | 0.76 | 0.37 | 0.91 | Lower in CD1C⁻CD141⁻ (DC4)/ Higher in monocytes | 1 |
| NCF1C | 0.12 | −2.90 | 0.77 | 0.14 | 0.85 | Lower in CD1C⁻CD141⁻ (DC4)/ Higher in monocytes | 0 |

TABLE E7-continued

Discriminative markers between CD1C⁻CD141⁻ (cluster DC4) and all monocyte subsets

| Gene.ID | AUC value | Avg. Diff.[1] | Power[2] | Pct.1[3] | Pct.2[4] | Comments | Surface Marker[5] |
|---|---|---|---|---|---|---|---|
| LGALS2 | 0.11 | −4.24 | 0.78 | 0.05 | 0.80 | Lower in CD1C⁻CD141⁻ (DC4)/ Higher in monocytes | 0 |
| CD36 | 0.11 | −2.32 | 0.79 | 0.57 | 0.95 | Lower in CD1C⁻CD141⁻ (DC4)/ Higher in monocytes | 1 |
| NCF1 | 0.11 | −3.20 | 0.79 | 0.41 | 0.89 | Lower in CD1C⁻CD141⁻ (DC4)/ Higher in monocytes | 0 |
| RPS26 | 0.09 | −1.31 | 0.82 | 0.79 | 0.98 | Lower in CD1C⁻CD141⁻ (DC4)/ Higher in monocytes | 0 |
| GRN | 0.08 | −1.43 | 0.83 | 0.90 | 0.99 | Lower in CD1C⁻CD141⁻ (DC4)/ Higher in monocytes | 1 |
| VCAN | 0.08 | −3.65 | 0.84 | 0.35 | 0.91 | Lower in CD1C⁻CD141⁻ (DC4)/ Higher in monocytes | 1 |
| LYZ | 0.08 | −2.06 | 0.84 | 1.00 | 1.00 | Lower in CD1C⁻CD141⁻ (DC4)/ Higher in monocytes | 0 |
| S100A8 | 0.07 | −3.71 | 0.87 | 0.34 | 0.94 | Lower in CD1C⁻CD141⁻ (DC4)/ Higher in monocytes | 0 |
| CD14 | 0.06 | −4.31 | 0.89 | 0.18 | 0.92 | Lower in CD1C⁻CD141⁻ (DC4)/ Higher in monocytes | 1 |

Footnotes in Tables E6 and E7: 1—Value refers to average differential expression within one subset (log fold change); 2—Value refers to discriminatory power of each marker; 3—Percentage of cells, within the cluster ID for which the gene is a marker, that detect the gene; 4—Percentage of all the other cells, excluding the cluster ID for which the gene is a marker, that detect the gene; 5—"1" refers to predicted surface marker; "0" refers to predicted not a surface marker according to the Protein Atlas: Protein Atlas: http://www.proteinatlas.org/search/protein_class:Predicted+membrane+proteins.

Figure 5A:
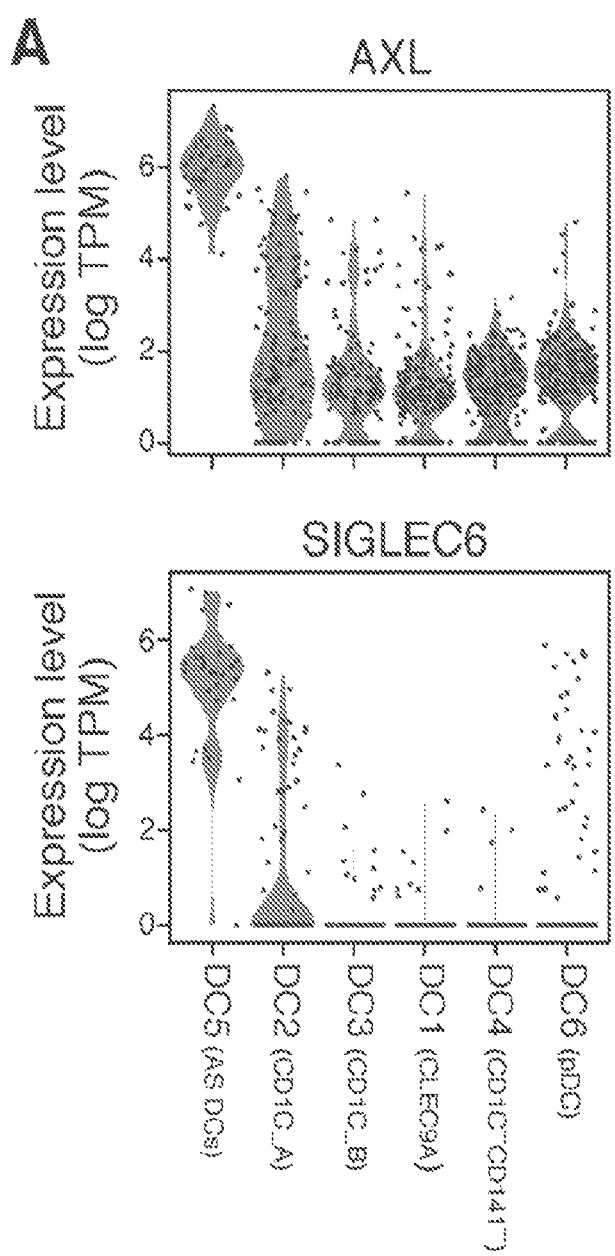
FIG. 5A-5N illustrates identification of novel DC population expressing AXL and SIGLEC6 (AS DCs). (A) Violin plots showing expression distribution of surface markers AXL and SIGLEC6 uniquely expressed in newly identified DC population captured by cluster DC5 (FIG. 2D). These markers were subsequently used to enrich for this new population. Other DC populations are depicted on the x-axis and each dot represents an individual cell. (B) Flow cytometry gating strategy to identify AXL$^+$SIGLEC6$^+$ cells within human blood LIN(CD3, CD19, CD20, CD161)$^-$ and HLA-DR$^+$ mononuclear fraction. AXL$^+$SIGLEC6$^+$ cells were subsequently further distinguished (refer to FIG. 5D) by the relative expression of CD123/IL3RA and CD11C/ITGAX, consistent with mRNA expression (1=CD123$^+$CD11c$^{-/lo}$ (pink) and 2=CD123$^{lo}$CD11c$^+$ (blue)). Data shown is a representative analysis of at least ten healthy individuals. (C) t-SNE analysis of all DCs (n=742), along with prospectively isolated and successfully profiled AXL$^+$SIGLEC6$^+$ single cells (n=105) using gating strategy in panel B (purple gate). Newly isolated AXL$^+$SIGLEC6$^+$ cells overlap with the originally identified DC5 cluster (n=30; see FIG. 2C) in the purple dashed circle, validating the use of AXL and SIGLEC6 as surface markers to enrich for this new population. (D) Heatmap reporting scaled expression (log TPM values) of discriminative gene sets (AUC cutoff≥0.75), highlighting the expression continuum of AXL$^+$SIGLEC6$^+$ cells (including prospectively isolated cells, and cells from DC5 cluster), with one end enriched for pDC gene sets and the other end for cDC gene sets. Top bar graph defines an AXL$^+$SIGLEC6$^+$ population purity score (Methods) based on the top 10 most discriminative genes for this population with AUC≥0.85 (i.e. AXL, PPP1R14A, SIGLEC6, CD22, DAB2, S100A10, FAM105A, MED12L, ALDH2, LTK). (E) Heatmap reporting scaled expression (log TPM values) of prospective enrichment of both AXL$^+$SIGLEC6$^+$ populations (n=90) by leveraging CD11C/ITGAX and CD123/IL3RA expression levels (labeled in red in panel D) using the gating strategy illustrated in panel B. 43 single AXL$^+$SIGLEC6$^+$CD11C$^-$ (pink gate, panel B) and 47 single AXL$^+$SIGLEC6$^+$CD11C$^+$ (blue gate, panel B) were sequenced. The average expression values of the original CD1C$^+$ (combining clusters DC2 and DC3), CD141$^+$/CLEC9A$^+$ (cluster DC1) and pDC (cluster DC6) single cells (from FIG. 2) were used as reference to highlight enrichment of cDC-like and pDC-like gene signatures. Top bar graph defines an AXL$^+$SIGLEC6$^+$ population purity score as described in panel D. (F) Frequency of AXL$^+$SIGLEC6$^+$CD123$^+$CD11C$^{-/lo}$ (population 1 (pink): % mean±SEM; 0.1±0.014) and AXL$^+$SIGLEC6$^+$CD123$^{lo}$CD11C$^+$ (population 2 (blue): % mean±SEM; 0.04 t 0.01) as a % of LIN(CD3, CD19, CD20, CD161)$^-$HLA-DR$^+$ PBMCs. Scatter plot of data from nine healthy individuals with mean±SEM shown. (G) t-SNE analysis of flow cytometry data for LIN(CD3, CD19, CD20, CD161)$^-$HLA-DR$^+$CD14$^-$CD16$^-$ PBMCs based on the protein expression levels of AXL, SIGLEC6, CD1C, CD11C, CD22, CD33, CD34, CD45RA, CD100, CD123, CD303 and HLA-DR (refer to FIG. 9 for characterization of CD100$^{hi}$CD34$^{int}$ population). Overlay of populations defined by conventional flow cytometry gating on clusters derived by t-SNE analysis shown in the following colors: 1=AXL$^+$SIGLEC6$^{++}$CD123$^+$CD11C$^-$ (pink); 2=AXL$^+$SIGLEC6$^+$CD123$^+$CD11C$^{lo}$ (blue); 3=AXL$^+$SIGLEC6$^+$CD123$^{lo}$CD11C$^+$ (green); 4=CD1C$^+$ DCs (purple) cells; 5=pDCs (dark blue); 6=CLEC9A$^+$ DCs (red); 7=CD34$^+$CD45RA$^-$ (yellow); 8=CD34$^+$CD45RA$^+$ (brown); 9=CD100$^{hi}$CD34$^{int}$ (beige); 10=CD34$^-$CD100$^{lo}$ (cyan). (H) Violin plots showing expression distribution of surface markers uniquely expressed in newly identified DC (DC5 cluster) population (FIG. 2C). Other DC populations are depicted on the X-axis and each dot represents an individual cell. (I) Violin plots showing expression level of AXL and SIGLEC6 genes in prospectively isolated single AXL$^+$SIGLEC6$^+$ cells (labeled in red on the x-axis), showing good enrichment with the originally identified cells in DC5 cluster (n=30; see FIG. 2C), validating the use of AXL and SIGLEC6 as markers to enrich for this new cell population. Other DC populations are depicted on the X-axis, with each dot representing an individual cell. (J) Heatmap reporting scaled expression (log TPM values) of prospective enrichment of both AXL$^+$SIGLEC6$^+$ populations (n=90) by CD11C/ITGAX and CD123/IL3RA expression levels (ID labeled in red) using the gating strategy illustrated in FIG. 5B. 43 single AXL$^+$SIGLEC6$^+$CD11C$^-$ (pink gate, FIG. 5B) and 47 single AXL$^+$SIGLEC6$^+$CD11C$^+$ (blue gate, FIG. 5B) were sequenced. Single cell expression values of the DC1 (CD141/CLEC9A), DC2 (CD1C_A), DC3 (CD1C_B) and DC6 (pDC) from FIG. 2 were used as reference to highlight enrichment of cDC- and pDC-like gene signatures. Top bar graph defines an AXL$^+$SIGLEC6$^+$ population purity score as described in panel FIG. 5D. (K) Flow cytometry dot plot overlay of AXL$^+$SIGLEC6$^+$CD123$^+$CD11C$^-$ (pink), AXL$^+$SIGLEC6$^+$CD123$^{lo}$CD11C$^+$ (blue) on the gating strategy from FIG. 2B used to perform single cell sorting of DC population. Overlay dot plots illustrate that the AXL$^+$SIGLEC6$^+$CD123$^+$CD11C$^-$ cells were located within the conventional CD123$^+$ 'pDC' and 'CD141$^+$' gates. The AXL$^+$SIGLEC6$^+$CD123$^{lo}$CD11C$^+$ cells are mostly located in the bottom right portion of the CD141 gate, close to CD1C$^+$ DCs. (L) Flow cytometry dot plot overlay of AXL$^+$SIGLEC6$^+$CD123$^+$CD11C$^-$ (pink), AXL$^+$SIGLEC6$^+$CD123$^{lo}$CD11C$^+$ (blue), AXL$^+$SIGLEC6$^-$CD123$^-$CD11C$^-$CD39$^-$CD45RA$^+$CD100$^+$CD34$^{int}$ (orange; see FIG. 9 for more details about this population) on LIN(CD3, CD19, CD20, CD161)$^-$HLA-DR$^+$CD14$^-$CD16$^-$ blood mononuclear cells. Overlay dot plots highlight the location of the novel DC populations and progenitors using commonly used DC gating strategies. Data shown is a representative analysis of at least ten healthy individuals. (M) Flow cytometry dot plot overlay of 1=AXL$^+$SIGLEC6$^+$CD123$^+$CD11C$^-$ (pink), 2=AXL$^+$SIGLEC6$^+$CD123CD11C$^{lo}$ (blue), 3=AXL$^+$SIGLEC6$^+$CD123$^{lo}$CD11C$^+$ (green) and 4=CD1C$^+$ DCs (purple) cells on LIN(CD3, CD19, CD20, CD161)$^-$HLA-DR$^+$CD14$^-$CD16$^-$ blood mononuclear cells. Data shown is a representative analysis of at least ten healthy individuals. (N) Flow cytometry dot plot overlay of AXL$^+$SIGLEC6$^+$ (pink), CD1C$^+$ DCs (blue), pDC (green) and CD141$^+$ DCs (purple) cells on LIN(CD3, CD19, CD20, CD161)$^-$HLA-DR$^+$CD14$^-$CD16$^-$ blood mononuclear cells. Upper panels illustrate the expression of CD123, CD304 and CD303 commonly used to isolate pDCs. Overlay dot plot highlights that only CD304/NRP1 is highly expressed by pDCs, unlike CD123/IL3RA and CD303/CLEC4C (BDCA-2), which are also expressed by AXL$^+$SIGLEC6$^+$ cells. This suggests that CD304/NRP1 (BDCA-4) is a superior pDC surface marker, supporting the scRNA-seq data identifying NRP1 as being uniquely expressed in pDC. Bottom panel shows expression of CD141 and CLEC9A, confirming that AXL$^+$SIGLEC6$^+$ cells express some levels of CD141 protein, but not CLEC9A. Data shown is a representative analysis of at least ten healthy individuals.

A novel AXL⁺SIGLEC6⁺ population and its relation to cDCs and DCs. As described above, a novel population emerged from the unbiased cluster analysis (cluster DC5; FIG. 2), defined by expression of unique markers (e.g., SIGLEC6, SIGLEC1 and CD22/SIGLEC2, AXL) (FIG. 5A, H, Tables E1-E2). Flow cytometry analysis of PBMCs from 10 independent donors confirmed the existence of AXL⁺SIGLEC6⁺ cells ('AS DCs') within the original DC gate (FIG. 5B), at a 2-3% frequency consistent with what was originally observed in the initial scRNA-seq analysis (30 of 768 DCs; FIG. 2C). scRNA-seq profiling of prospectively sorted AS DCs cells (isolated with the gating strategy in FIG. 5B) showed the newly sorted cells clustering together with the original cluster (FIG. 5C, FIG. 5I), further validating our successful enrichment strategy.

Figures 5B, 5C:
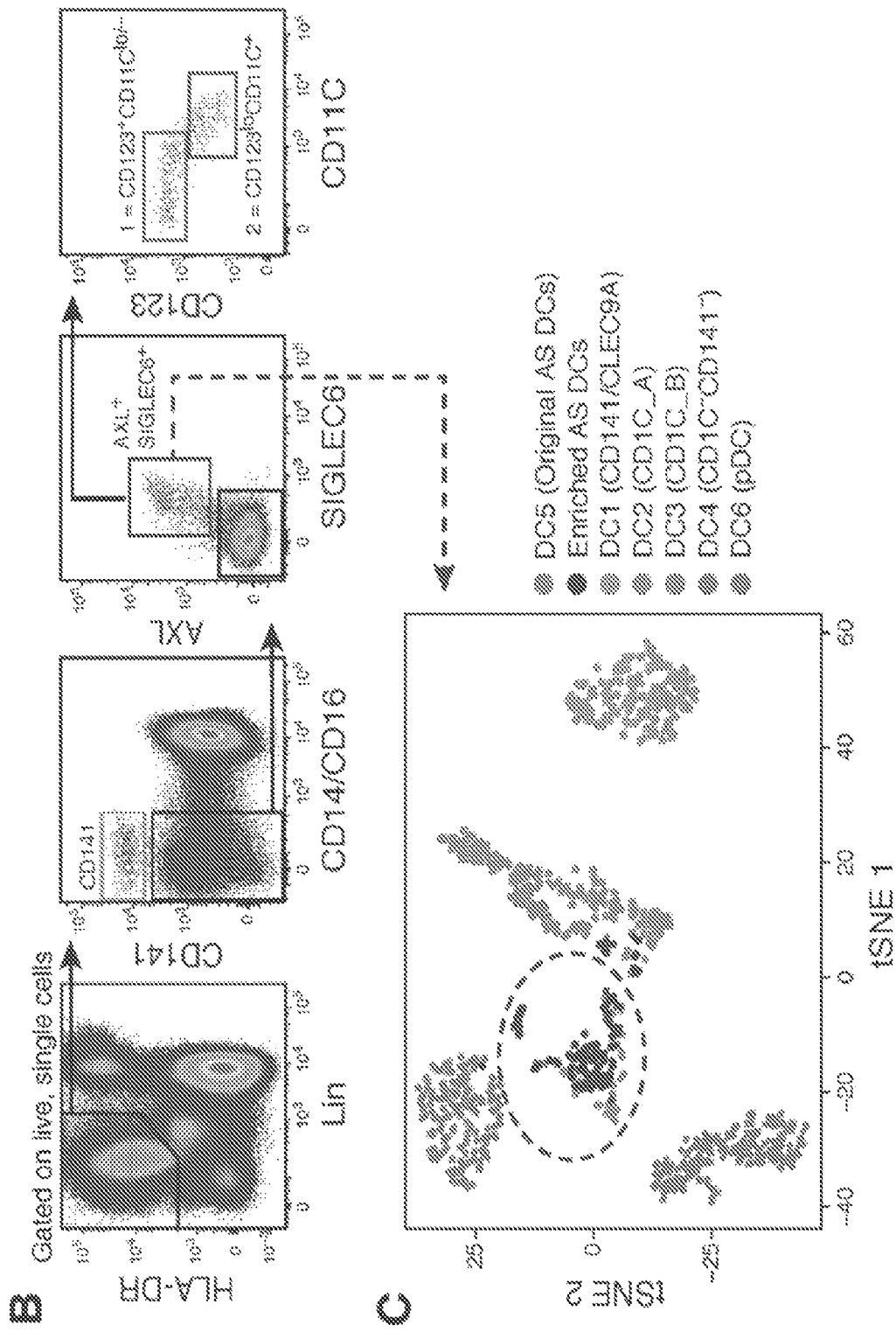
Figures 5D, 5E:
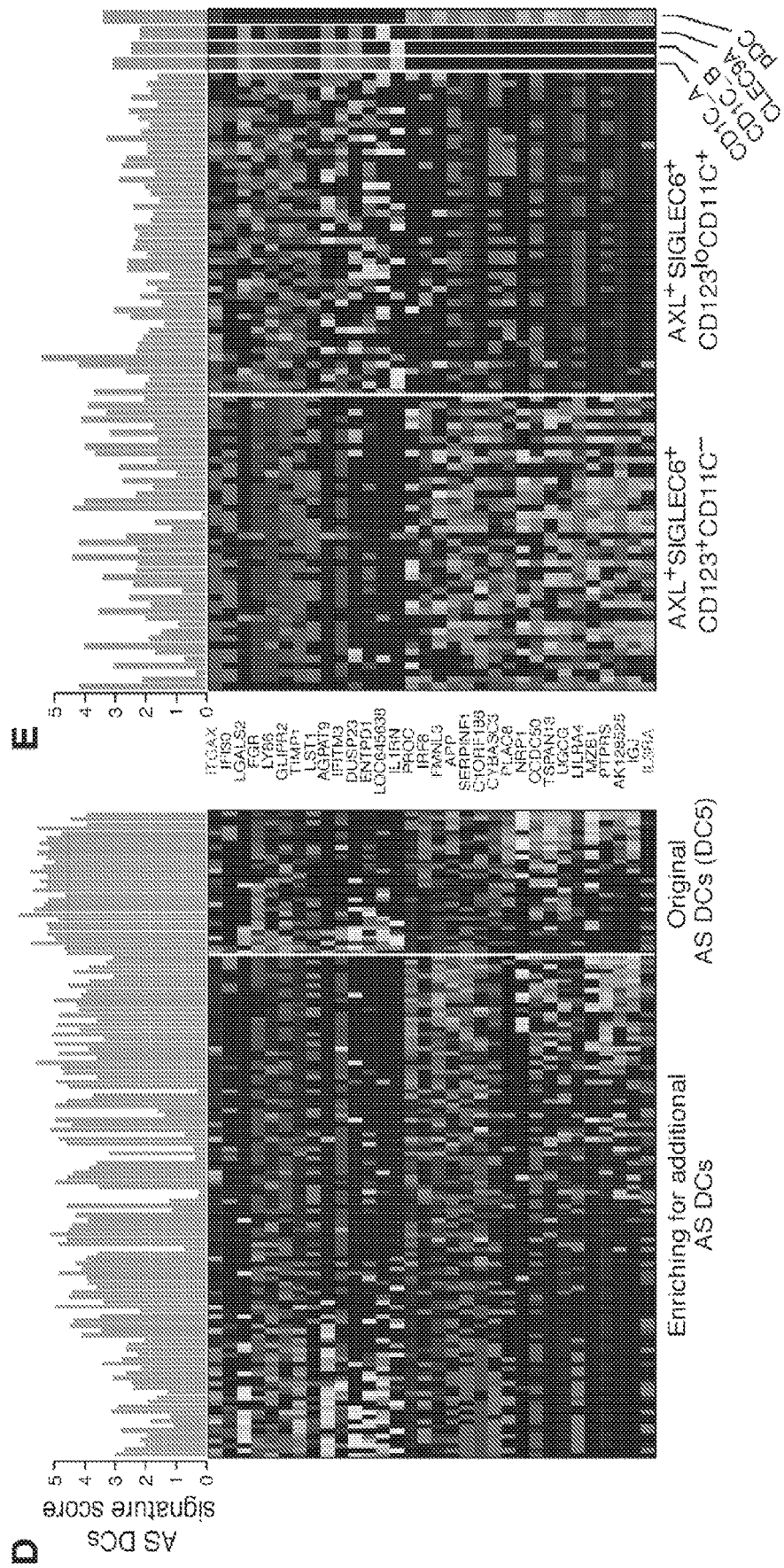
Figure 5F:
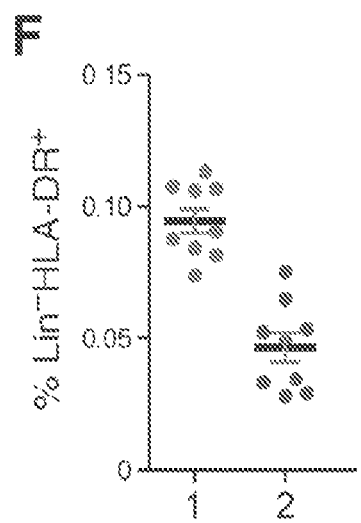
Figure 5G:
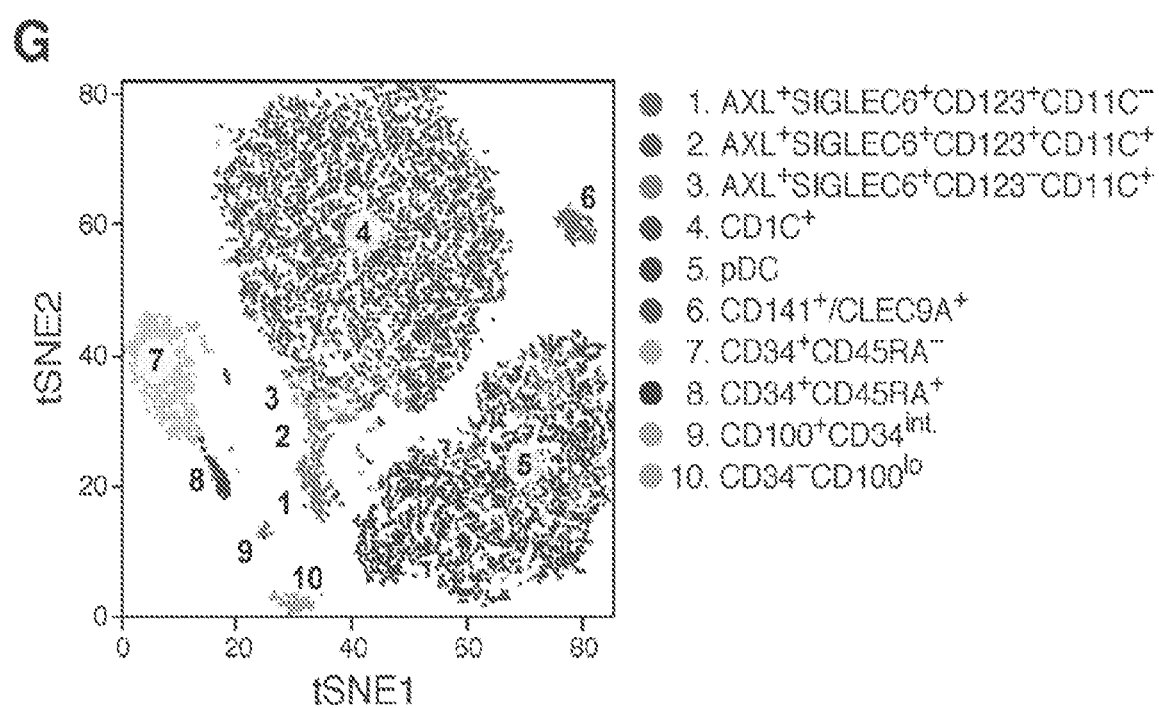
Figure 5J:
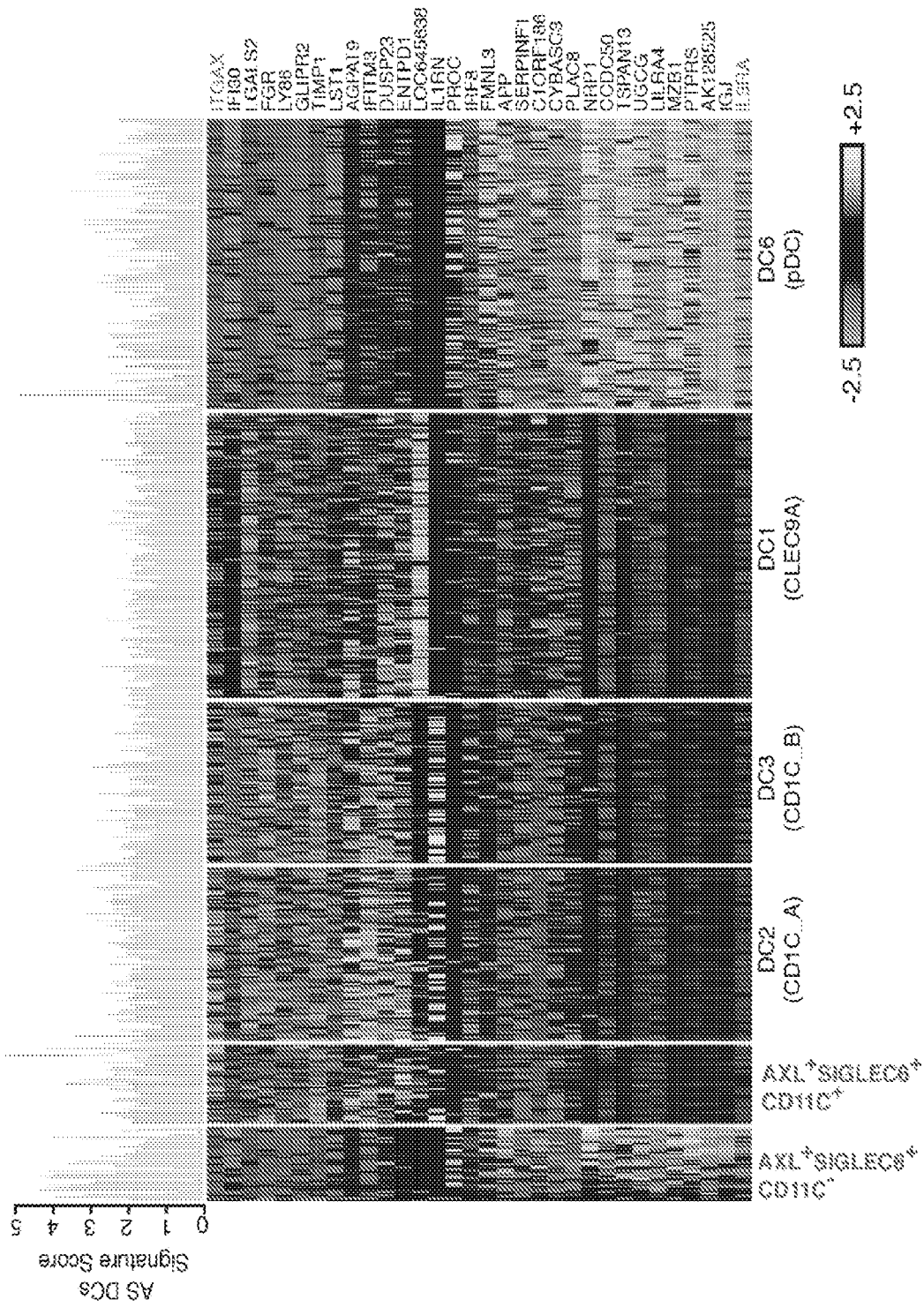
Figure 5L:
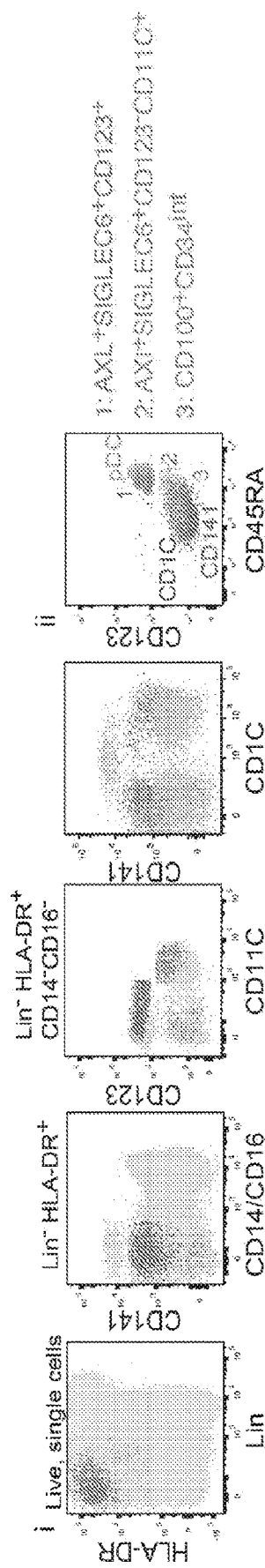
Figure 6B:
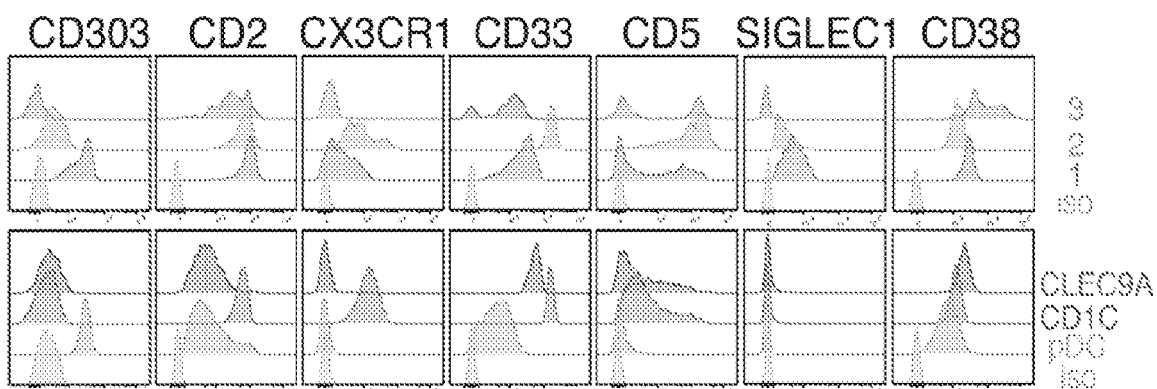
Figure 7A:
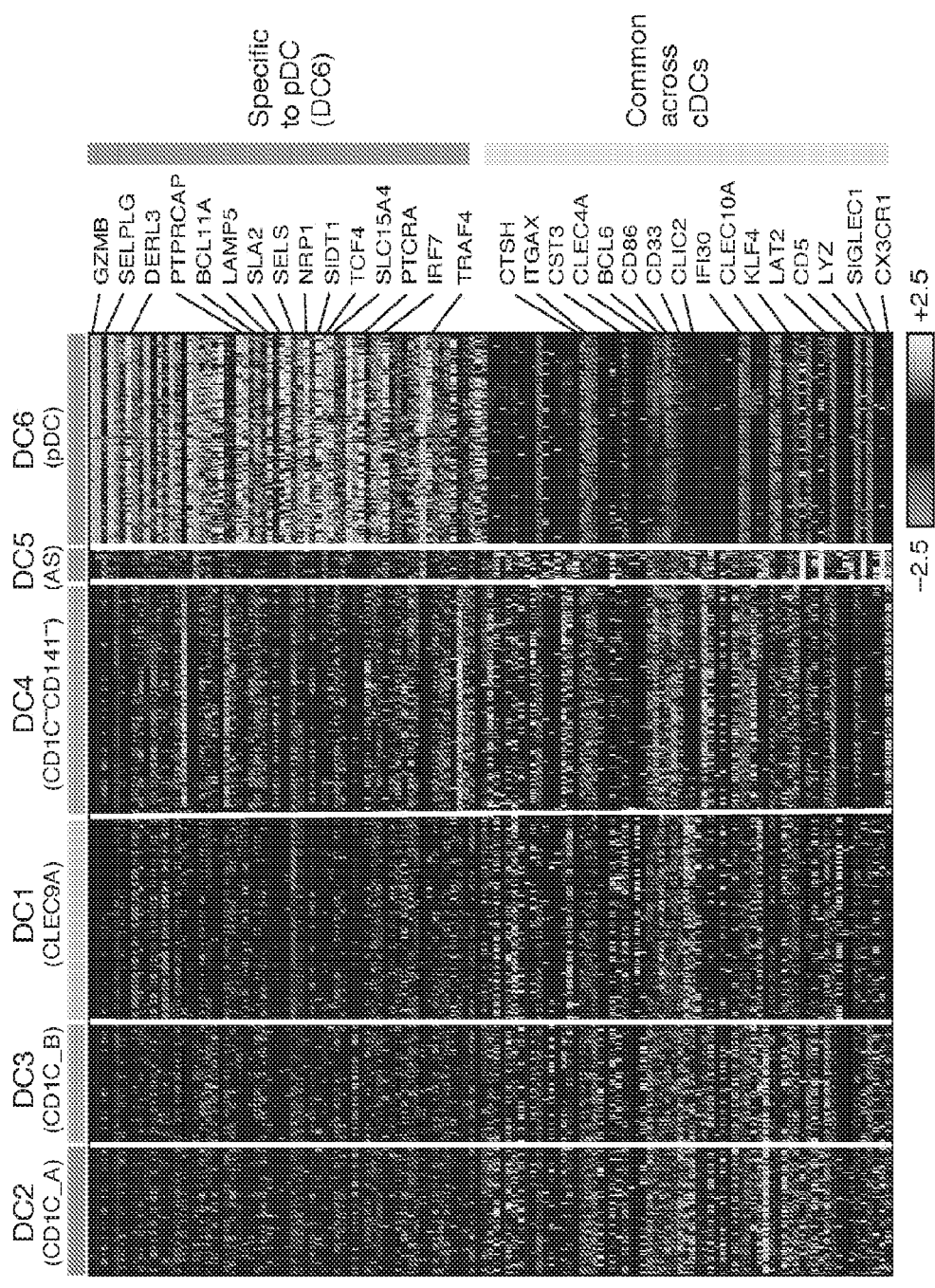
FIG. 7A-7F illustrates phenotypic and functional characterization of AXL$^+$SIGLEC6$^+$ DCs (AS DCs) and pure pDCs. (A) Heatmap reporting scaled expression (log TPM values) of gene signatures common between AXL$^+$SIGLEC6$^+$ DCs (DC5) and cDCs (clusters DC1-DC4), and genes uniquely expressed in pDCs (DC6). Gene sets were generated through K-means clustering using the doK means function in the Seurat package. See FIG. 6A for more a detailed heatmap. (B) Morphology of pDCs, CD1C$^+$ DCs, CLEC9A$^+$ DCs, AXL$^+$SIGLEC6$^+$CD123$^+$CD11C$^{-/lo}$ and AXL$^+$SIGLEC6$^+$CD123$^{lo}$CD11C$^+$ by Giemsa-Wright stain. Scale bar=10 μm. (C) IFNα (left panel) and IL-12p70 (right panel) concentration in supernatant 24 hours after CpG and LPS stimulation of CD14$^+$CD16$^-$ monocytes, pDCs, CLEC9A$^+$ DCs, CD1C$^+$ DCs, CD100$^{hi}$CD34$^{int}$ cells (3, beige), AXL$^+$SIGLEC6$^+$CD123$^{lo}$CD11C$^+$ (2, blue), and AXL$^+$SIGLEC6$^+$CD123$^+$CD11C$^{-/lo}$ (1, pink) cells. Composite data from four donors is shown. Mean±SEM, **p<0.01, Mann-Whitney U test. (D) Proliferation of allogeneic CD4$^+$ and CD8$^+$ T cells five days after co-culture with pDCs contaminated with AXL$^+$SIGLEC6$^+$ cells (i.e. the traditional isolation of pDC subset) compared with pDCs devoid of AXL$^+$SIGLEC6$^+$ cells, in the context of LPS or LPS combined with R848 (TLR7/TLR8 ligand) to activate DCs. Top panel depicts representative pseudocolor dot plot and bottom panel bar graphs of composite data (n=4, mean±SEM, *p<0.05, paired t-test). (E) Proliferation of allogeneic CD4$^+$ and CD8$^+$ T cells five days after co-culture with CD14$^+$CD16$^-$ monocytes, pDCs, CLEC9A$^+$ DCs, CD1C$^+$ DCs, AXL$^+$SIGLEC6$^+$CD123$^+$CD11C$^{-/lo}$ (1, beige), AXL$^+$SIGLEC6$^+$CD123$^{lo}$CD11C$^+$ (2, blue) cells and CD100$^{hi}$CD34$^{int}$ (3, beige) cells. Top panel depicts representative pseudocolor dot plot, and bottom panel bar graphs of composite data (n=7, mean±SEM, **p<0.01 paired t-test). (F) Top panel: immunohistochemical staining of human tonsil with AXL (brown), CD123 (purple) and CD3 (green). Brown arrows depict AXL$^+$CD123$^+$ cells adjacent to CD3$^+$ T cells. Data shown is representative of at least four donors. Scale bar=50 μm. Middle panel: frequency of AXL$^+$ SIGLEC6$^+$CD123$^+$ and CD123$^{lo/-}$ cells in human tonsil determined by flow cytometry analysis, as a percentage of CD45$^+$LIN(CD3, CD19, CD20, CD56, CD161)$^-$HLA-DR$^+$ cells (mean±SEM of three donors shown; AXL$^+$SIGLEC6$^+$ CD123$^+$: 0.7%±0.2%, and AXL$^+$SIGLEC6$^+$CD123$^{lo/-}$: 1.7%±0.2%). Bottom panel: representative pseudocolor dot plot of AXL$^+$SIGLEC6$^+$CD123$^+$ (pop. 1, pink) and AXL$^+$ SIGLEC6$^+$CD123$^{lo/-}$ (pop. 2, blue) cells in human tonsil by flow cytometry analysis (n=3).
Figures 7B, 7C:
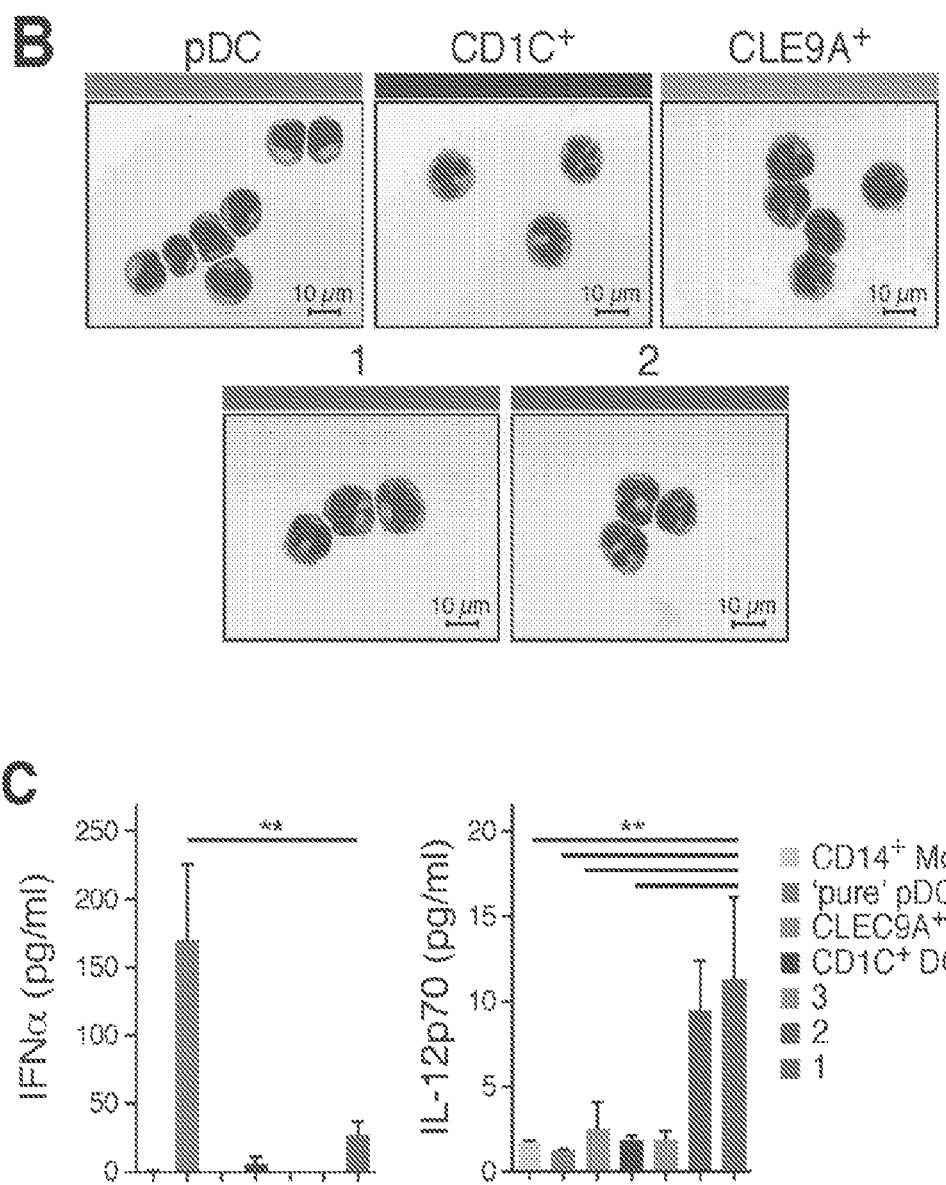

AS DCs exhibited a spectrum of states based on gene expression (FIG. 5D), with one end enriched for a pDC-like signature (e.g., IL3RA, IGJ, NRP1, MZB1) and the other enriched with a cDC-like signature (IFI30, ITGAX, LY86, GLIPR2, FGR, LYZ, ENIPD1). Applicants validated this observation by flow cytometry, using the surface markers CD123/IL3R4 and CD11C/ITGAX that respectively correlated with pDC and cDC gene signatures (FIG. 5B, FIG. 5D, FIG. 5K). Applicants exploited the combinatorial expression of AXL, SIGLEC6, CD123 and CD11C (at mRNA and protein level) to prospectively isolate the 2 putative AS DC subtypes (see gating strategy in FIG. 5B), and further validated their identities by scRNA-seq (FIG. 5E, FIG. 5J). Across all ten individuals tested, the two AS DC subpopulations represent a very small fraction of the Lin⁻HLA-DR⁺ populations: 0.1% for AXL⁺SIGLEC6 ⁺CD123⁺CD11C⁻/ˡᵒ cells and 0.04% for AXL⁺SIGLEC6⁺CD123ˡᵒCD11C⁺ cells (FIG. 5F). Notably, lower levels of AXL and SIGLEC6 protein were associated with increased HLA-DR, CD11C and CD1C, while higher levels of AXL and SIGLEC6 were associated with increased CD123, CD303, CD141 and lower HLA-DR (FIG. 5 K-N). This latter relationship was also observed by t-SNE analysis of flow cytometry data, where a peninsula with graded expression of AS DCs was located at the base of the CD1C⁺ DC cluster and adjacent to the pDC cluster (FIG. 5G). Taken together, our data suggest that AXL⁺SIGLEC6⁺ DCs are related but not identical to cDCs or pDCs.

pDCs are phenotypically and functionally distinct from CD11C⁻CD123⁺ AS DCs. Since pDCs and AXL⁺SIGLEC6⁺CD123⁺CD1C⁻/ˡᵒ DCs co-expressed many genes (FIG. 5D-E, FIG. 6A), Applicants assessed whether these cell types also shared other functional properties. Importantly, Applicants found that the genes expressed by pDCs, but not AS DCs, were associated with biological functions of pDCs. This includes, for example, pathogen sensing and induction of type I IFNs (IRF7, TLR7, SLC15A4, PACSIN1), secretion (e.g. DERL3, LAMP5, and SCAMP5), and the pDC master regulator transcription factor TCF4, along with its binding targets (e.g. SLA2, PTCRA, PTPRCAP) (FIG. 7A; FIG. 6A) (Swiecki and Colonna; Cheng et al.). In contrast, CD11C⁻CD123⁺ AS DCs expressed cDC markers, including CD2, CX3CR1, CD33 (SIGLEC3), CD5 and SIGLEC1 both at protein and mRNA levels (FIG. 7A, FIG. 6A-B). pDCs were also morphologically distinct from AS DCs, with AS DCs possessing the same cerebriform nucleus and cytoplasmic features of cDCs (FIG. 7B). Applicants hypothesized that although AS DCs expressed pDC markers, including CD123/ILRA and CD303/CLEC4C (FIG. 5L, N), they are functionally distinct from pDCs.

Figure 7D:
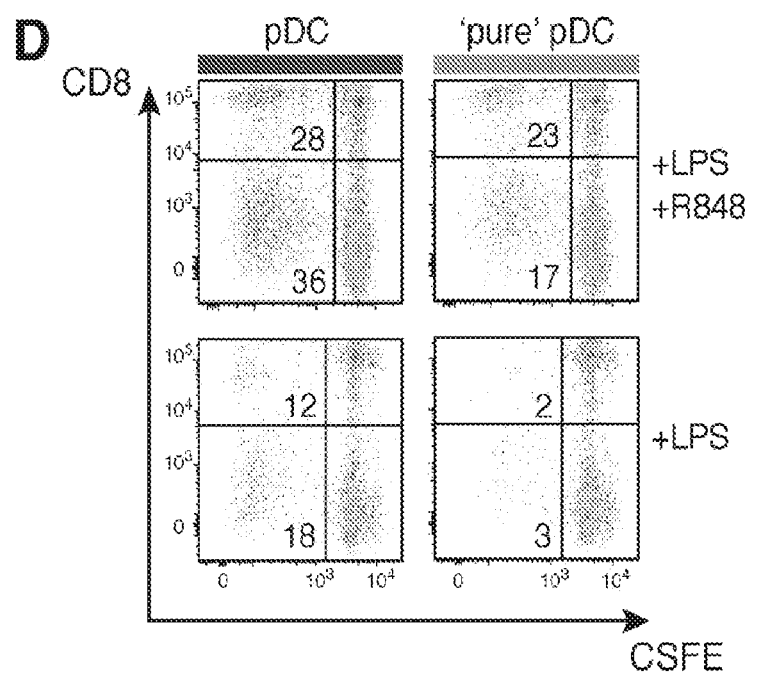
Figure 7D:
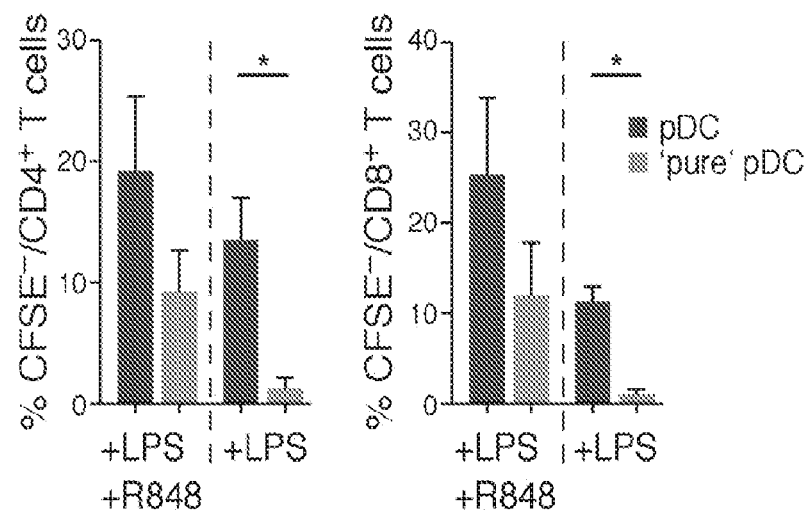

To compare the functional properties of pure pDCs to AS DCs and cDCs, Applicants used the markers identified in our studies to isolate pure pDCs by excluding AS DCs, CLEC9A⁺ DCs, CD1C⁺ DCs and monocytes. As expected, pDCs produced their hallmark cytokines, IFNα, while AS DCs produced negligible amounts of IFNα upon TLR9 stimulation (p<0.01; FIG. 7C). In contrast, both AS DC subsets secreted IL-12p70 to greater levels than other cDCs, while pure pDCs did not produce IL-12p70 (p<0.01; FIG. 7C). Finally, pure pDCs induced undetectable or reduced levels of T cell proliferation in response to LPS or LPS+R848, respectively (p<0.05; FIG. 7D). Applicants conclude that pure IFNα-producing pDCs (that lack AS DCs) do not induce IL-12 secretion, are diminished in their ability to induce of T cell proliferation, and that contamination of AS DCs within the traditionally defined pDC gate is likely responsible for IL-12 secretion/T cell stimulation activities measured in prior reports (Swiecki and Colonna; Cheng et al.; Matsui et al.).

Figure 6C:
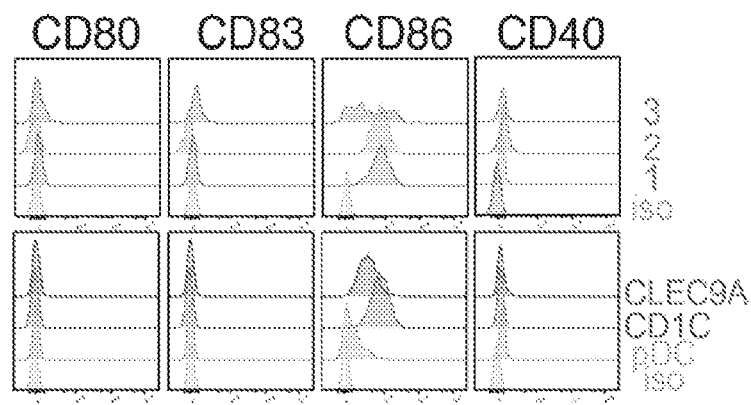
Figure 7E:
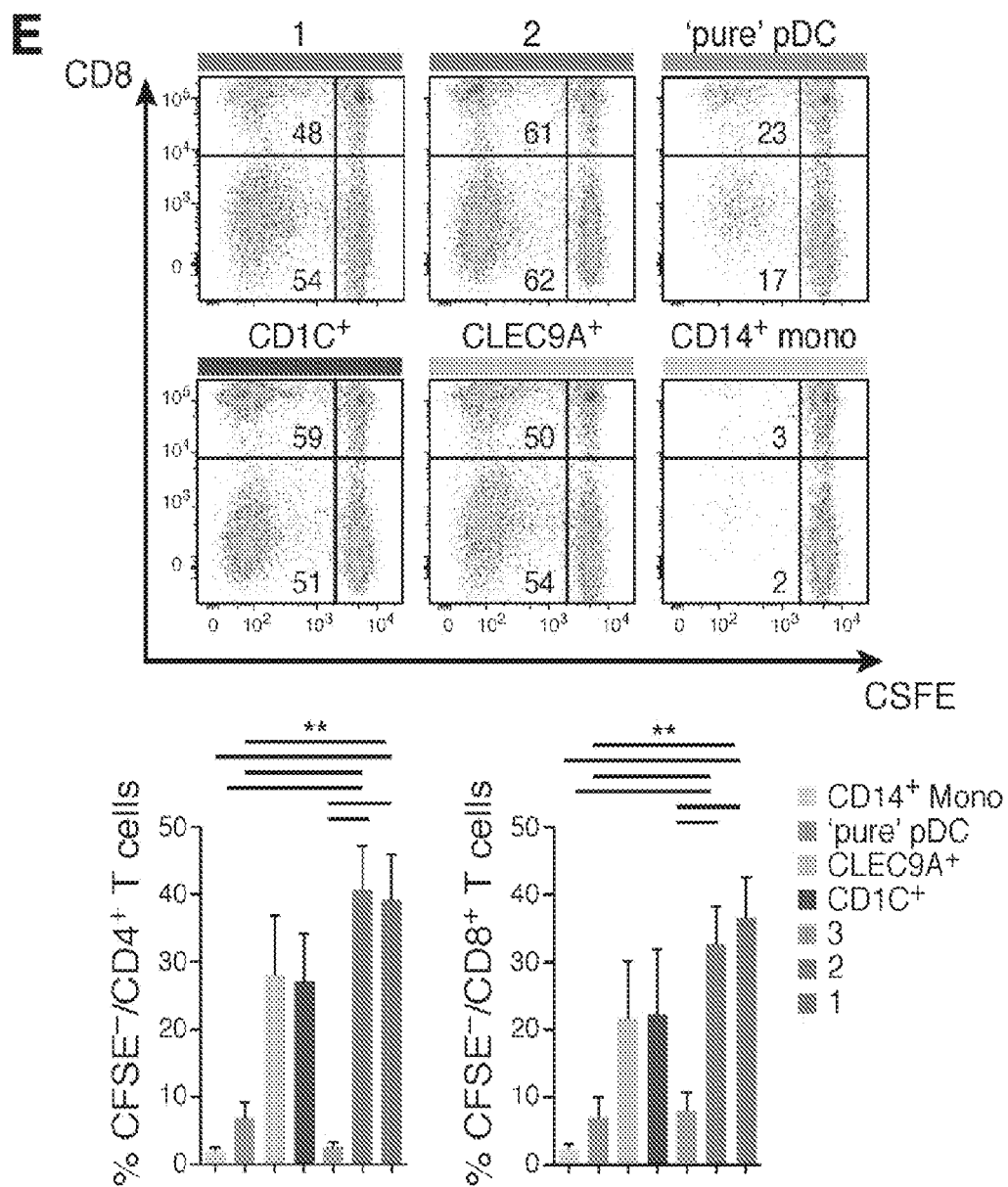

AS DCs produce IL-12, stimulate T cell proliferation, and are present in tonsils. To understand the potential for AS DCs to stimulate T cells, Applicants first considered their expression of costimulatory molecules and cytokines. While CD80 and CD83 were absent across all DCs, AS DCs expressed CD86 at comparable levels to CD1C$^+$ DCs and CLEC9A$^+$ DCs (FIG. 6C). Strikingly, both AS DC subtypes were potent stimulators of allogeneic CD4 and CD8$^+$ T cell proliferation, unlike pDCs (p<0.01), and were marginally superior to CD1C' and CLEC9A$^+$ DCs FIG. 7E). These latter results are consistent with IL-12 secretion being induced in both AS DC subsets upon stimulation (FIG. 7C), and with AS DCs expressing costimulatory molecule CD86 along with components of the antigen processing machinery (FIG. 6A).

Figure 6D:
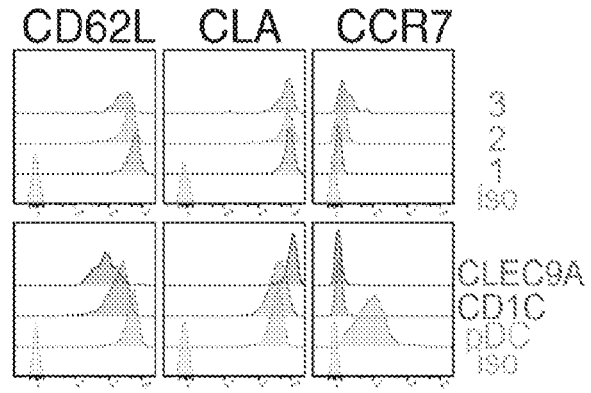
Figure 7F:
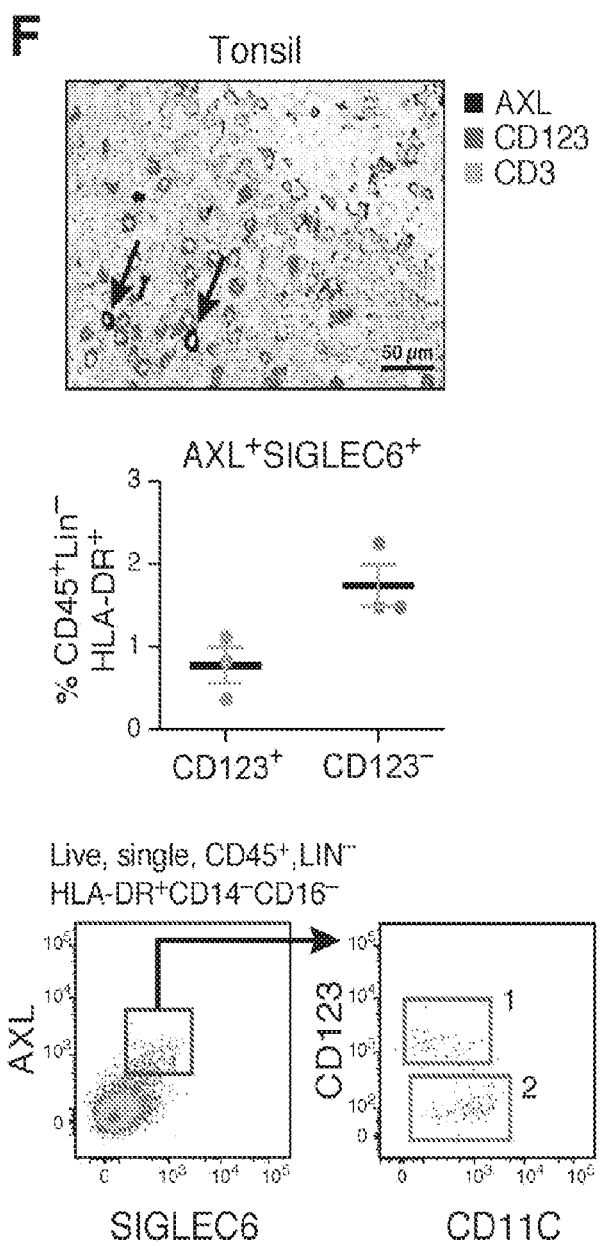

The AS DCs also expressed CLA and CD62L but not CCR7 protein, like other DCs (FIG. 6D), suggesting potential endowment to home to peripheral tissue such as skin and lymph node from the circulatory pool. Since CD123$^+$ pDCs were previously found in the T cell area of the human tonsil (Grouard et al.), Applicants evaluated whether CD123$^+$ AS DCs were also present by staining human tonsils with antibodies to CD123 and AXL. Indeed, AS DCs were found adjacent to CD3$^+$ T cells, admixed with CD123$^+$AXL$^-$ pDCs (FIG. 7F). Flow cytometry confirmed this finding, showing that the CD123$^+$CD11C$^{-/lo}$ AS DCs represented 0.7% and CD123$^-$CD11C$^+$ AS DCs represented 1.7% of the CD45$^+$ LIN$^-$HLA-DR$^+$ fraction (FIG. 7F). Thus, AS DCs are both able to stimulate T cells and are present in the T cell zones of tonsils.

Figure 9:
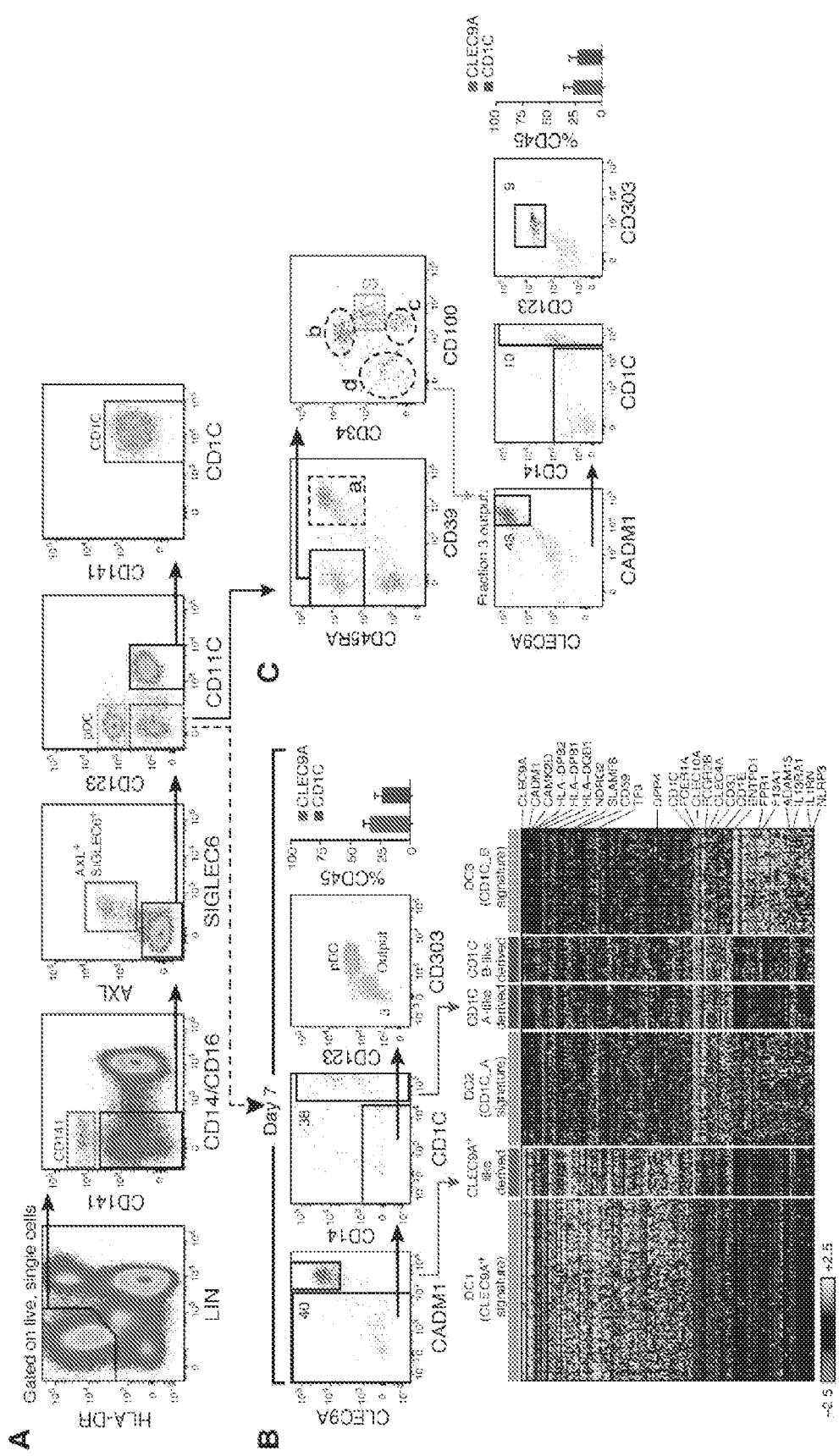
FIG. 9A-9Q illustrates identification and functional characterization of novel CD100$^{hi}$CD34$^{int}$ DC progenitors. (A) Flow cytometry gating strategy to isolate DC subsets: CLEC9A$^+$ DCs (red), CD1C$^+$ DCs (blue), pDCs (green), and AXL$^+$SIGLEC6$^+$ (purple), as well as CD123$^-$CD11C$^-$ cells (red gate) for differentiation assays (see FIG. 9K-M). Data shown is a representative analysis of at least ten healthy individuals. (B) Differentiation assays after seven days of co-culturing LIN(CD3, CD19, CD20, CD161)$^-$HLA-DR$^+$ CD14$^-$CD16$^-$AXL$^-$SIGLEC6$^-$CD123$^-$CD11C$^-$ cells with MS5 stromal cell line and the cytokines (GM-CSF, SCF and FLT3LG; see Methods). Readouts were done by flow cytometry for CLEC9A$^+$ DCs, CD1C$^+$ DCs and pDC, and by scRNA-seq profiling of isolated CD45$^+$ cells. Top panel shows representative overlay dot plots. Overlay of pDC (green), and output cells (grey) for CD123 and CD303 expression shown in the far right (in green). Population 3 (in beige) represents CD100$^{hi}$CD34$^{int}$ at day 0 (see panel C for characterization). Top right are composite bar graphs for CLEC9A$^+$ and CD1C$^+$ DCs differentiated from culture by flow cytometry analysis (n=4, mean±SEM). Heatmap in bottom panel reports scaled expression (log TPM values) signature from culture output by scRNA-seq (n=132), confirming differentiated CLEC9A$^+$ DC (red) and CD1C$^+$ DC (blue) transcriptional identities. Original transcriptional signatures from DC1 (CD141$^+$/CLEC9A$^+$ DC), DC2 (CD1C_A subset), and DC3 (CD1C_B subset) clusters (from FIG. 2) are used as reference to confirm distinct signatures observed through scRNA-seq analysis of differentiation assay output. (C) Top panel: flow cytometry gating strategy used to narrow down and identify the scRNA-seq-predicted CD100$^{hi}$CD34$^{int.}$ cells, highlighting all cell fractions (in dashed-gate) tested for differentiation potential (see FIG. 9H-M), and which contained cells that differentiated into CLEC9A$^+$ and CD1C$^+$ DC (beige squared gate, labeled '3'). (C, F) Representative culture outputs on day seven (Methods) and composite bar graphs. N=6 donors, bar graphs show mean±SEM. (C) Output from CD100$^{hi}$CD34$^{int}$ fraction (population 3, beige gate; see FIG. 9M for fractions a-d). (D) Frequency of CD100$^{hi}$CD34$^{int.}$ cells as 0.02% of LIN(CD3, CD19, CD20, CD161)⁻HLA-DR⁺ PBMCs. Scatter plot of data from nine healthy individuals is shown. Morphology of CD100$^{hi}$CD34$^{int.}$ cells by Giemsa-Wright stain. Scale bar=10 μm. (E) Proliferative capacity of peripheral blood Cell Trace Violet (CTV)-labeled CD34⁺ HSCs (purple), CD100$^{hi}$CD34$^{int.}$ (beige), AXL⁺SIGLEC6⁺CD123⁺CD11C⁻$^{/lo}$ (pink), and AXL⁺SIGLEC6⁺CD123$^{lo}$CD11C⁺ (blue), as measured by CTV dilution after five days in culture with MS5 stromal cell line supplemented with GM-CSF, SCF and FLT3LG; mean values reported above. Left panel shows representative overlay histogram; right panel shows composite bar graphs illustrating % of proliferated cells and number of proliferations undergone from three donors shown. *p<0.05, paired t-test. (F) Output from differentiation assays starting with CLEC9A⁺ DCs, CD1C⁺ DCs, pDCs, and AXL⁺SIGLEC6⁺ cells isolated using gating strategy in panel A. AXL⁺SIGLEC6⁺× 2=double FLT3LG concentration. (G) PCA analysis incorporating monocytes (n=339), DCs (n=742), and 4 BPDCN patient samples (n=174) using the R software package Seurat. PC1 vs. PC2 demonstrates the close transcriptional proximity between all 4 BPDCN samples and pDCs (dashed black circle), with overlapping cells (see black bracket in the legend). Each dot represents an individual cell and colored legend for each subset is shown on the right. (H) Flow cytometry gating strategy to isolate LIN(CD3, CD19, CD20, CD34)⁻HLA-DR⁺CD14⁻CD16⁻ CD141⁻AXL⁻SIGLEC6⁻CD123⁻CD11C⁻ blood mononuclear cells for scRNA-seq profiling. (I) Heatmap reporting scaled gene expression (log TPM values) signatures (AUC cutoff≥0.75) of 6 clusters uncovered through unbiased clustering of the single cell fraction profiled in panel A (n=110 cells; left side of heatmap). SEMA4D/CD100 (labeled in orange) is a surface marker uniquely expressed by single cells in cluster 6, which also expressed KIT, HLX, RUNX2 and ID2 suggestive of DC progenitor function. CD100 marker was subsequently used to isolate CD100$^{hi}$CD34$^{int}$ progenitors as detailed in FIG. 9J, and single cell profiling of this latter population (n=68; right side of the heatmap) shows strong transcriptional signature overlap with cluster 6, validating the gating strategy used to enrich for this progenitor population. Heatmap color scheme is based on z-score distribution, from −2.5 (yellow) to 2.5 (purple). (J) Flow cytometry gating strategy to identify and isolate the novel AXL⁺SIGLEC6⁺ DCs, the CD100⁺CD34$^{int}$ progenitor populations revealed by scRNA-seq, as well as know DC populations. (K) Workflow of the differentiation assay, depicting isolation of PBMC from fresh blood through ficoll gradient centrifugation, followed by sorting 5,000-10,000 cells using an antibody cocktail designed to enrich for fractions of interest in eppendorf tubes containing cell culture medium. Cells were then cultured in 96-well flat bottomed plate layered with 4×10⁴ murine MS5 stromal cells in the presence of FLT3L (100 ng/ml), SCF (20 ng/ml) and GM-CSF (10 ng/ml) for up to 7 days prior to harvesting, flow cytometry analysis and/or single cell index sorting on live CD45⁺ for single cell RNA-sequencing of culture output. (L) In vitro differentiation culture output analysed by flow cytometry showing CLEC9A⁺ and CD1C⁺ DC differentiation potential within LIN(CD3, CD19, CD20, CD34)⁻HLA-DR⁺CD14⁻CD16⁻CD141⁻ AXL⁻SIGLEC6⁻CD123⁻CD11C⁻ was restricted to CD45RA⁺ cells in this fraction (Output as % CD45⁺ cells; CD1C⁺ DC output: 36%; CLEC9A⁺ DC output: 40.5%). Data shown is a representative analysis from at least four independent experiments. (M) Top panel: gating strategy of all fractions analyzed for differentiation potential. Bottom panel: representative culture outputs (see Methods) on day seven. On the right are composite bar graphs from fractions a, b, c, d and CD100$^{hi}$CD34$^{int}$ (3; beige gate) cells. N=6 donors, bar graphs show mean±SEM. (N) Relative expression of growth factor receptors represented as overlay histograms comparing AXL⁺SIGLEC6⁺CD123⁺CD11C⁻$^{/lo}$ (pink), AXL⁺SIGLEC6⁺CD123$^{lo}$CD11C⁺ (blue), CD100$^{hi}$CD34$^{int}$ (beige) cells, CLEC9A⁺ DCs (red), CD1C⁺ (dark blue) and pDCs (green) and isotype control (grey). Representative data from at least three donors shown. (O) Purity assessment of FACS-sorted AXL⁺SIGLEC6⁺ new DC subsets and novel DC progenitor population at day 0 (from fresh blood), using the gating strategy (FIG. 9J) subsequently used in functional and in vitro differentiation assays. (P) Purity assessment of FACS-sorted known DC subsets population at day 0 (from fresh blood) using the gating strategy (FIG. 9J) subsequently used in functional and in vitro differentiation assays. (Q) Representative outputs on day six (see Methods) of AXL⁺SIGLEC6⁺CD123⁺CD11C⁻$^{/lo}$ (pink), AXL⁺SIGLEC6⁺CD123$^{lo}$CD11C⁺ (blue), initially isolated using gating strategy detailed on FIG. 9J (n=6).

Identification of rare CD100$^{hi}$CD34$^{int}$ cells with potential to generate CD1C$^+$ and CLEC9A$^+$ DCs. Applicants further interrogated CD11C$^-$CD123$^-$ cells that were contained within the HLA-DR$^+$CD14$^-$ gate used for isolating DCs but were not considered in the initial analysis since they were not previously thought to include DCs (see red dashed gate in FIG. 2B; and updated gate in FIG. 9A used for these experiments). Single cell RNA-seq of CD11C-CD123$^-$ cells identified 6 clusters in this gate (FIG. 9H-I). Cells in cluster 6 expressed genes associated with hematopoiesis, DC progenitors, and genes essential for DC development (e.g. SATB1, RUNX2, KIT, HLX, ID2) (Miller et al.; Satpathy et al.; Breton et al. J Exp Med 2015; Lee et al. 2015), and were marked by high expression of the cell surface protein SMA4D (CD100). Applicants therefore recognized that cluster 6 could represent a progenitor population.

To assess the progenitor potential of this compartment, Applicants cultured FACS-purified CD11C$^-$CD123$^-$ cells with MS5 stromal cells and cytokines that induce DC differentiation (Methods), based on a published human DC progenitor differentiation assay (Breton et al. Nat Protoc 2015). The cells in culture after several days were evaluated by: flow cytometry using a panel of antibodies that identify pDCs, CD1C$^+$ and CLEC9A$^+$ DCs (Methods) and scRNA-Seq profiling of CD45$^+$ immune cells for a more comprehensive assessment. For comparison, under the same conditions, Applicants monitored the differentiation potential of isolated pDCs, CD1C$^+$ and CLEC9A$^+$ DCs, as well as AS DCs and their 2 subtypes (see FIG. 9J-K).

After 7 days of culture, cells isolated from the CD11C$^-$CD123$^-$ gate gave rise to CLEC9A$^+$ and CD1C$^+$ DCs, based on flow cytometry and scRNA-seq analyses (FIG. 9B). While some day 7 cells expressed low CD303 or CD123 proteins, they did not express a bonafide pDC transcriptional signature by scRNA-seq. Applicants narrowed down the progenitor cells to CD45RA$^+$CD39$^-$CD100$^+$ cells based on the unique marker CD100/SEMA4D, expressed in cluster 6, along with candidate markers that Applicants tested (based on a marker of DC progenitors in the bone marrow (CD45RA) and of tissue DCs (CD39)), guided by iterative testing of differentiation potential for each sorted population (FIG. 9C and FIG. 9L-M). Applicants discovered that only the CD100$^{hi}$CD34$^{int}$ cells generated CLEC9A$^+$ and CD1C$^+$ DCs in the differentiation assay (FIG. 9C, FIG. 9M-O). scRNA-seq of CD100$^{hi}$CD34$^{int}$ cells mapped these cells to the originally observed cluster 6 and revealed the expression of the same genes associated with DC differentiation and progenitor function (FIG. 9I).

Figure 9D:
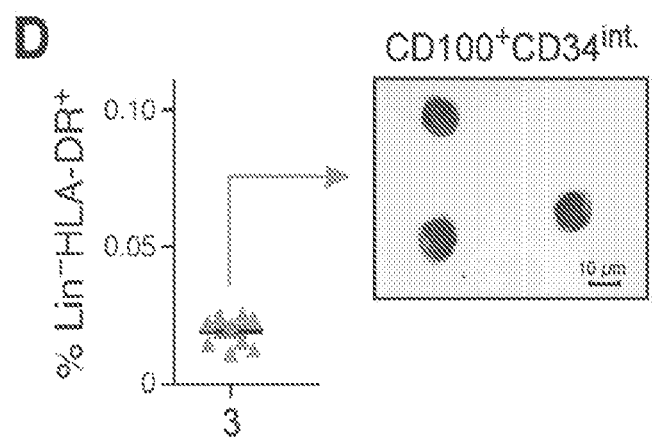
Figure 9E:
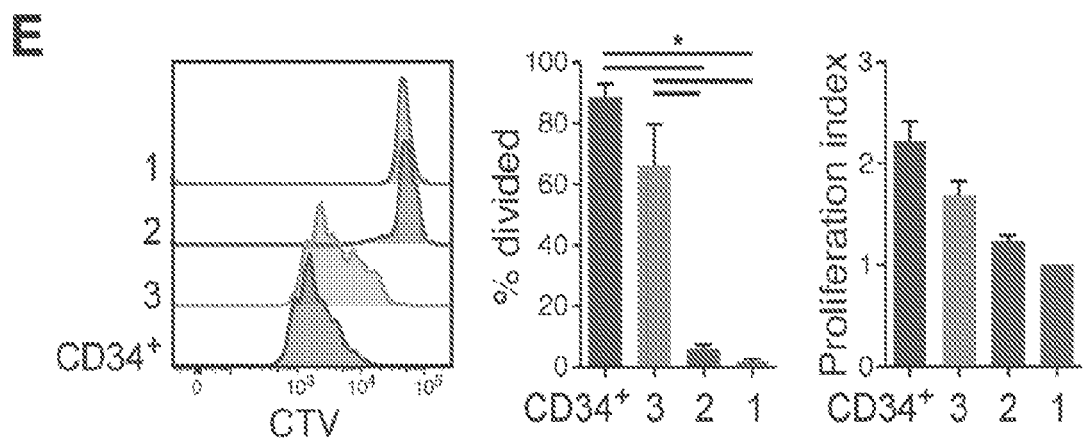

Applicants validated the existence of CD100$^{hi}$CD34$^{int}$ progenitors in 10 individuals, with a frequency of ~0.02% of the LIN$^-$HLA-DR$^+$ fraction of PBMCs (FIG. 9D). These cells were morphologically primitive, possessing high nuclear to cytoplasmic ratio and circular or indented nuclei (FIG. 9D), in contrast to AS DCs, pDCs, CD1C$^+$ and CLEC9A$^+$ DCs (FIG. 7B). Expression of cytokine receptors CD117/KIT, CD116/CSF2R and CD135/FLT3 (FIG. 9N) displayed by these cells has also been observed in the recently reported circulating human DC progenitor (Breton et al. J Exp Med 2015). Furthermore, only CD100$^{hi}$CD34$^{int}$ cells retained significant proliferative capacity among the cells tested (p<0.05; FIG. 9E), in accordance with their more primitive morphology, phenotype and expression profile.

While expressing some level of the co-stimulatory molecule CD86 (FIG. 6C), the CD100$^{hi}$CD34$^{int}$ cells have low T cell stimulatory potential (FIG. 7C). CD100$^{hi}$CD34$^{int}$ cells expressed CLA and CD62L at similar protein amounts to their more mature DC counterparts (FIG. 6D). Furthermore, while CCR7 was detected at the gene expression level in these cells (FIG. 9I), only modest protein level was detected (FIG. 6D). Both CD100$^{hi}$CD34$^{int}$ cells and AS DCs were CD45RA$^+$ and CD38$^+$ (FIG. 5L; FIG. 6B), consistent with the expression of these antigens on bone marrow DC progenitors (Notta et al.; Doulatov et al.).

Figure 9F:
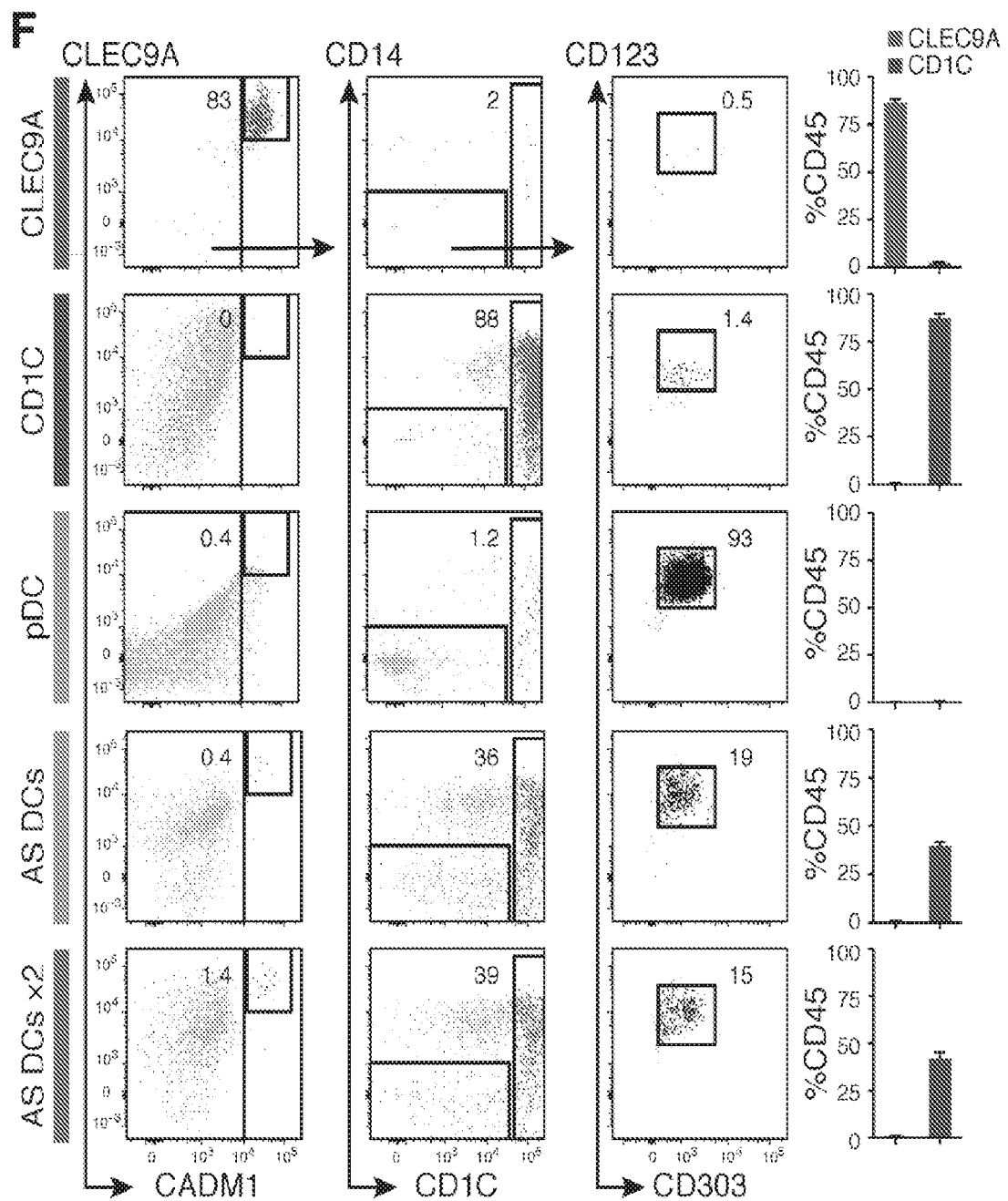
Figure 9G:
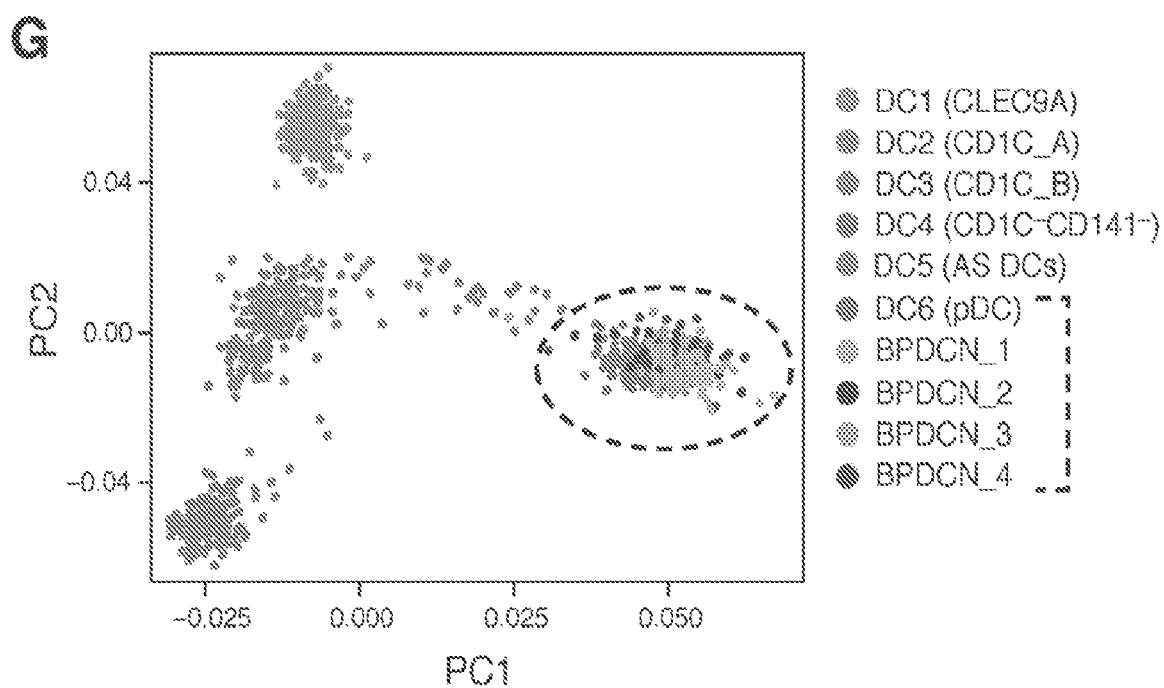
Figure 9H:
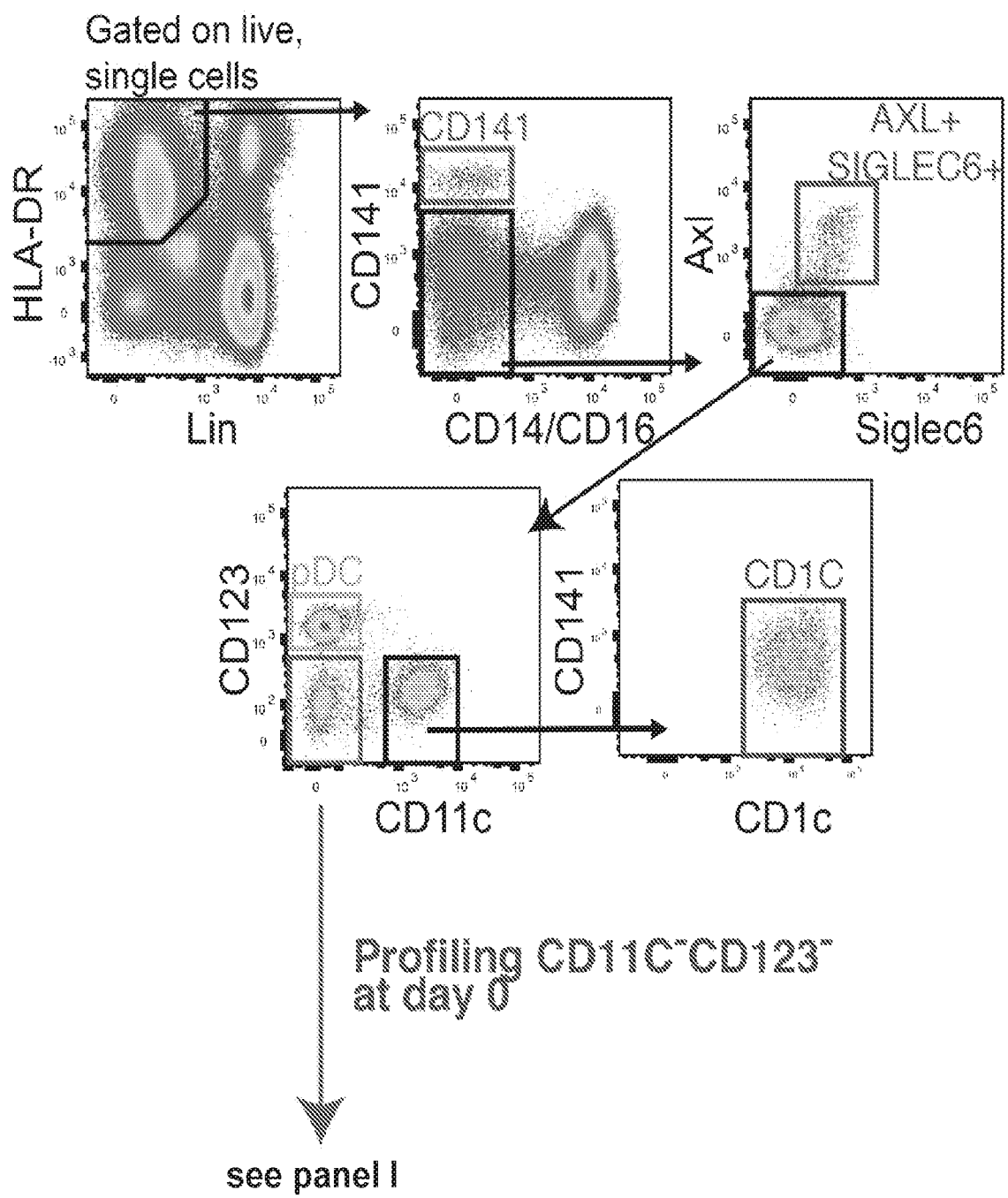
Figure 9I:
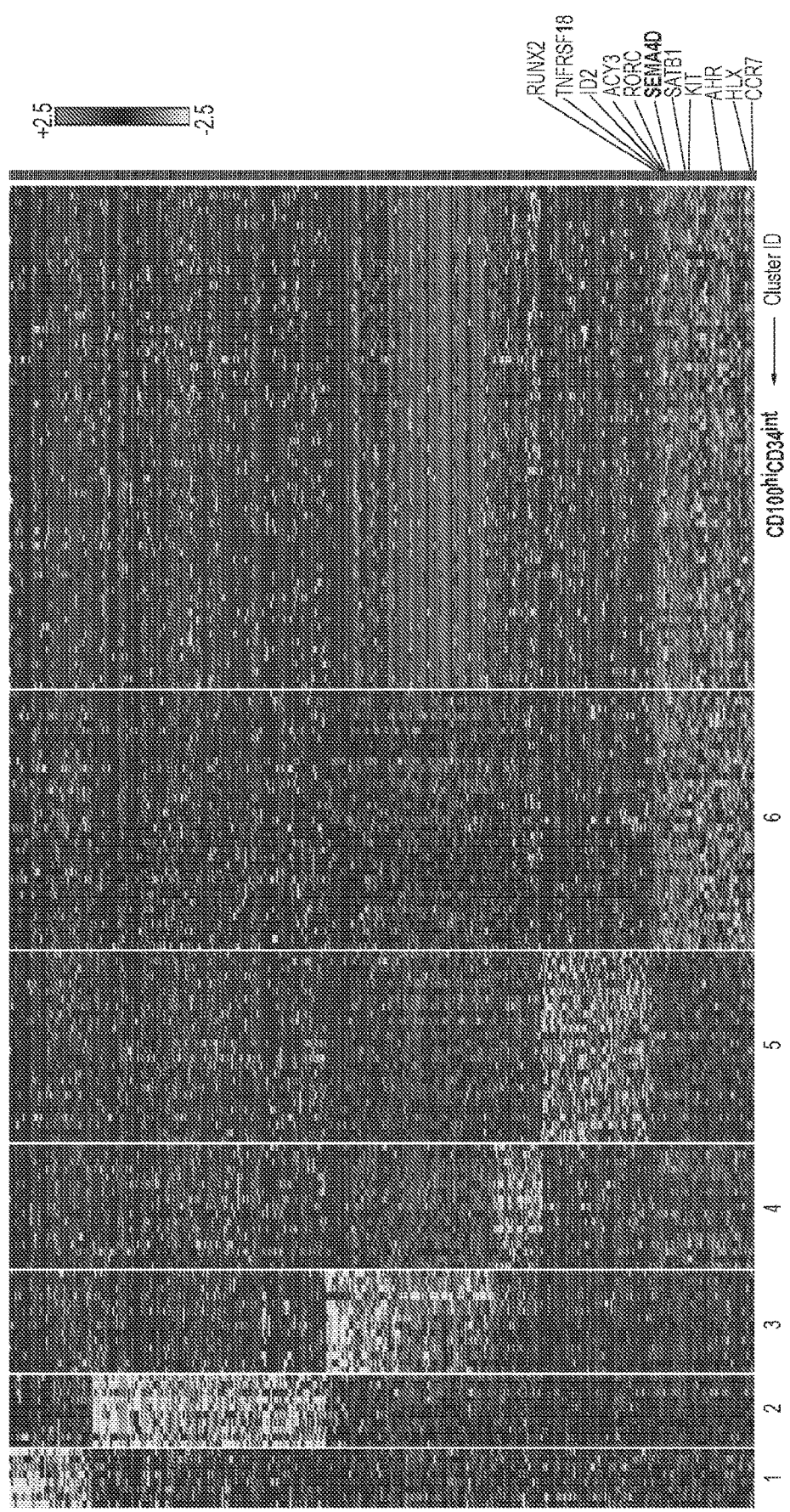
Figure 9K:
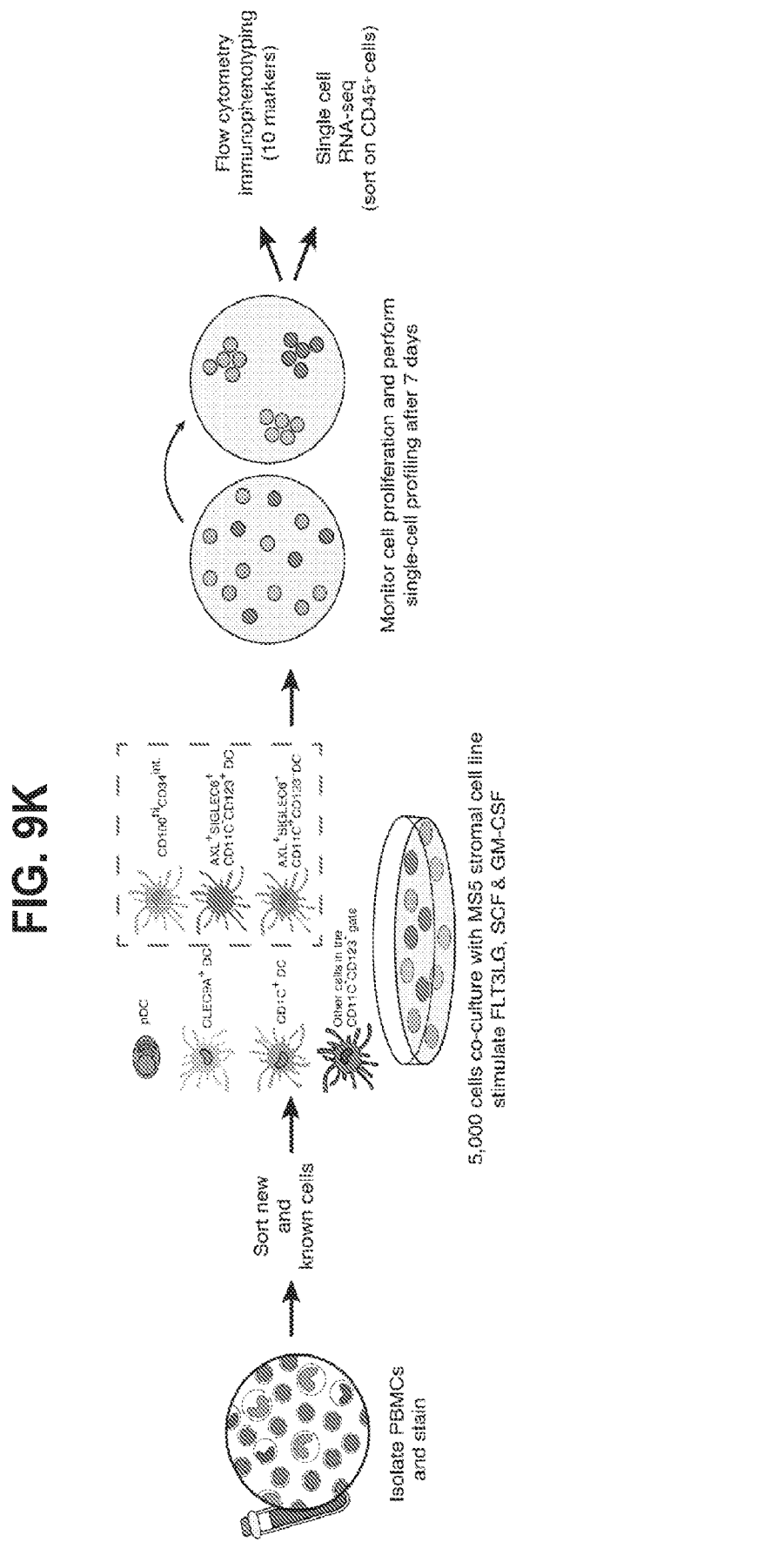
Figure 9L:
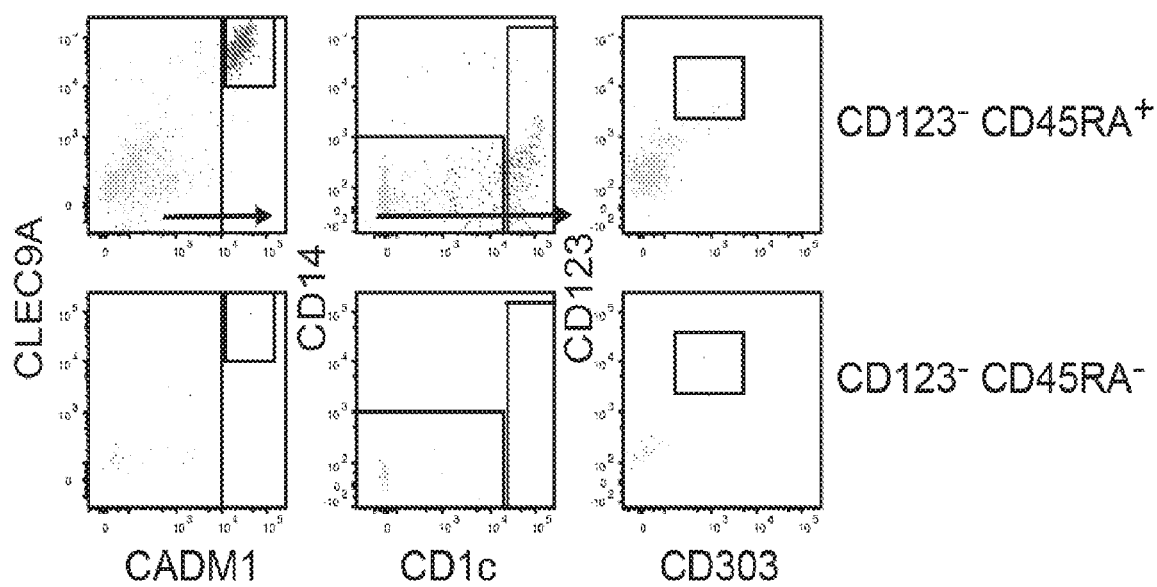
Figure 9M:
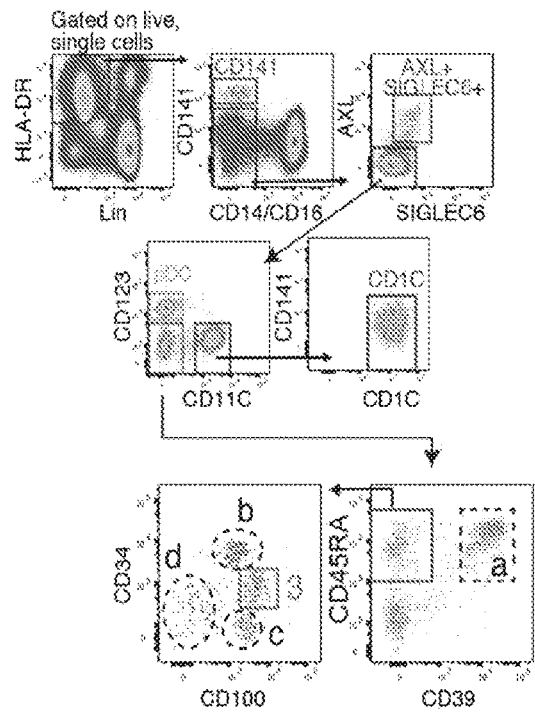
Figure 9M:
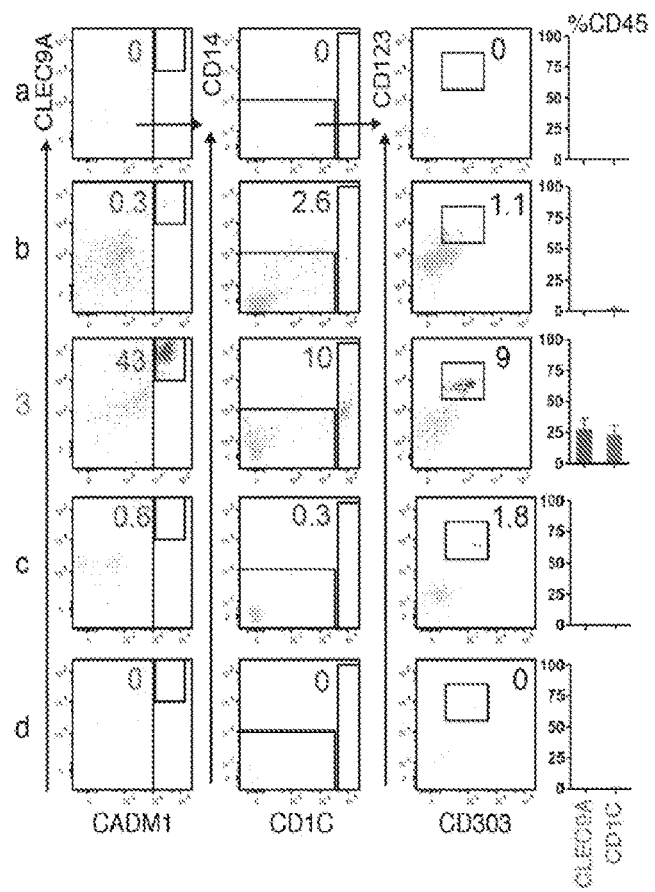
Figure 9N:
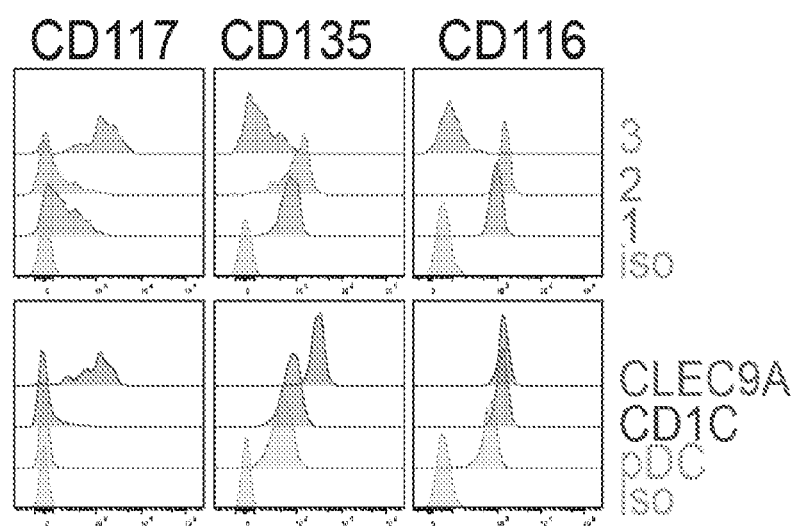
Figure 9O:
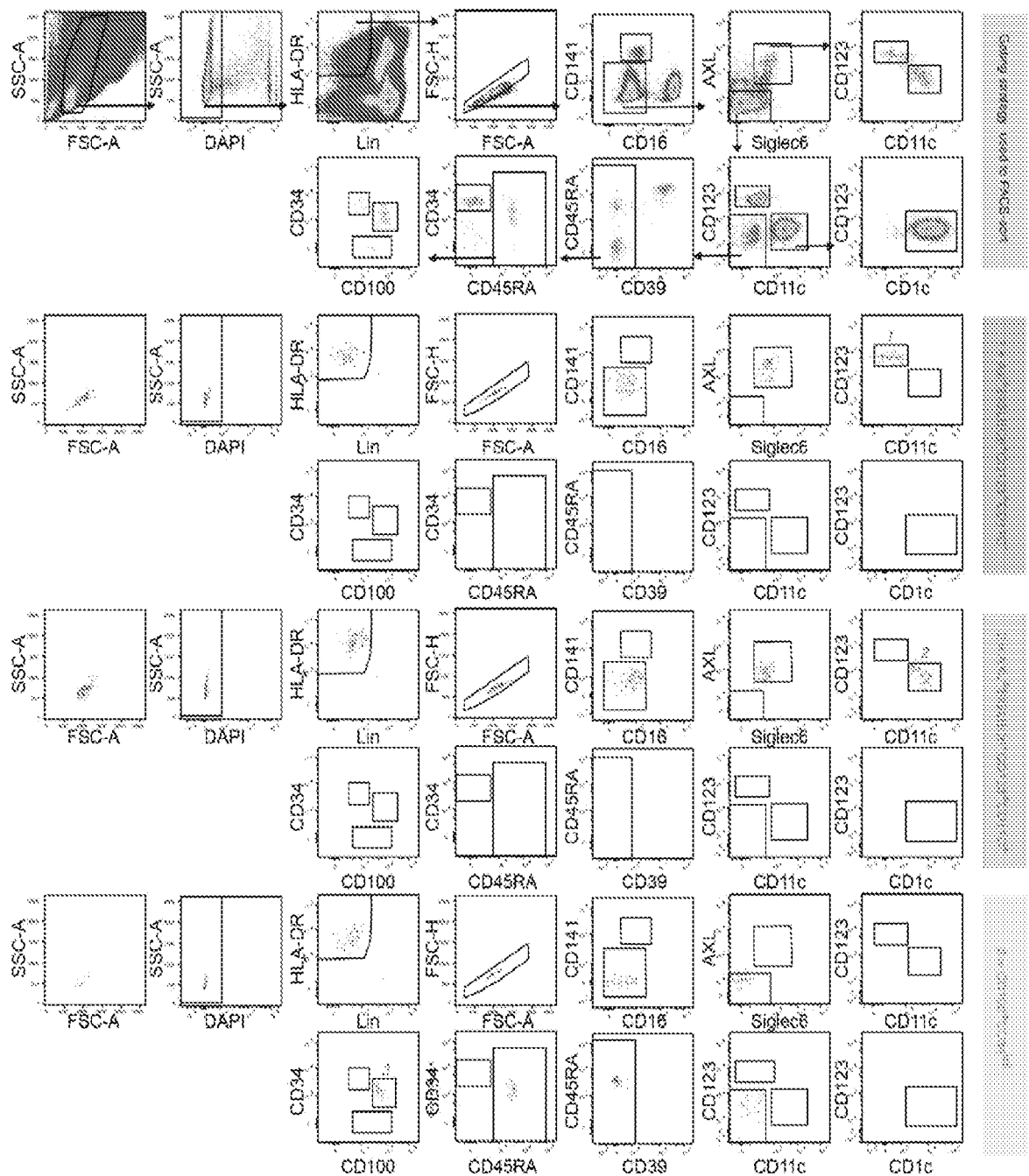
Figure 9P:
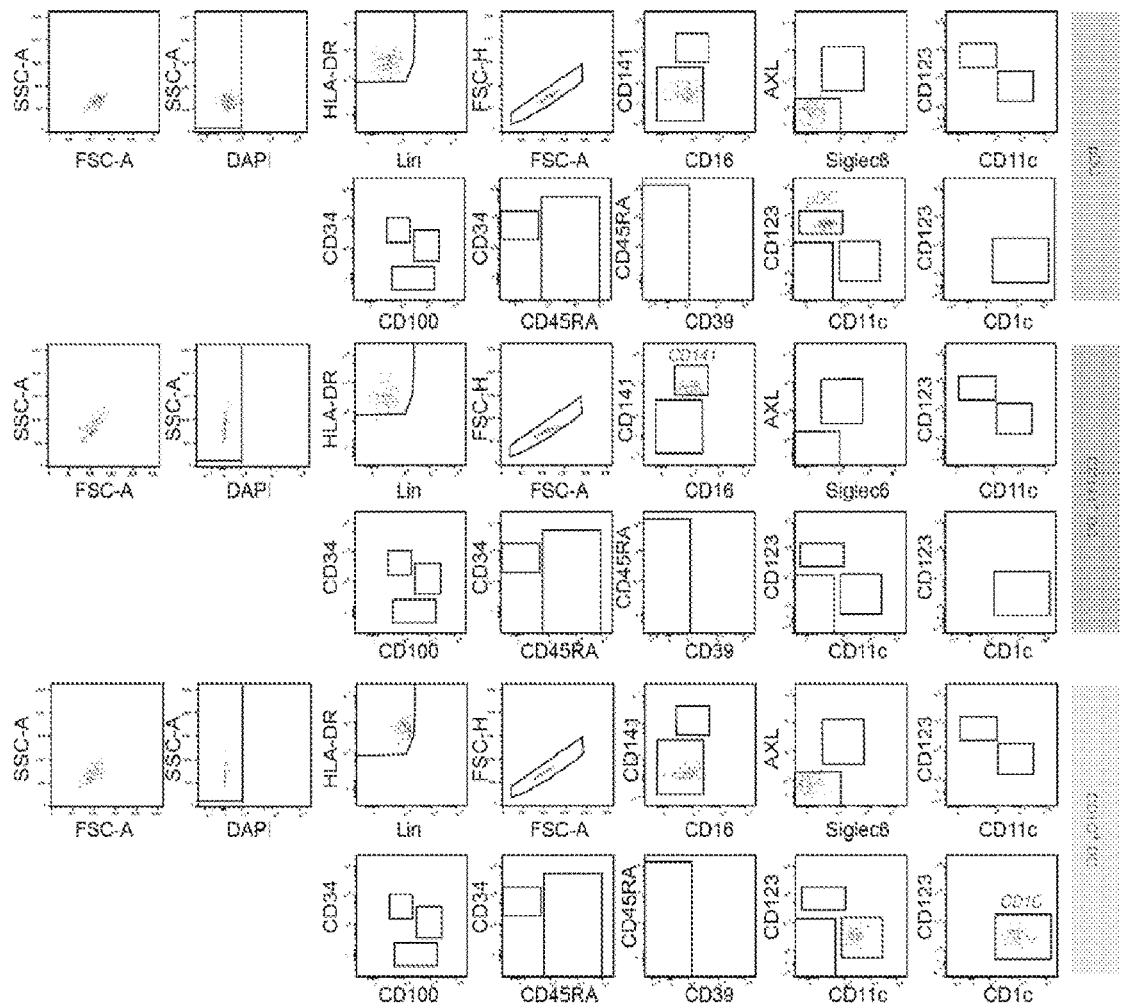
Figure 9Q:
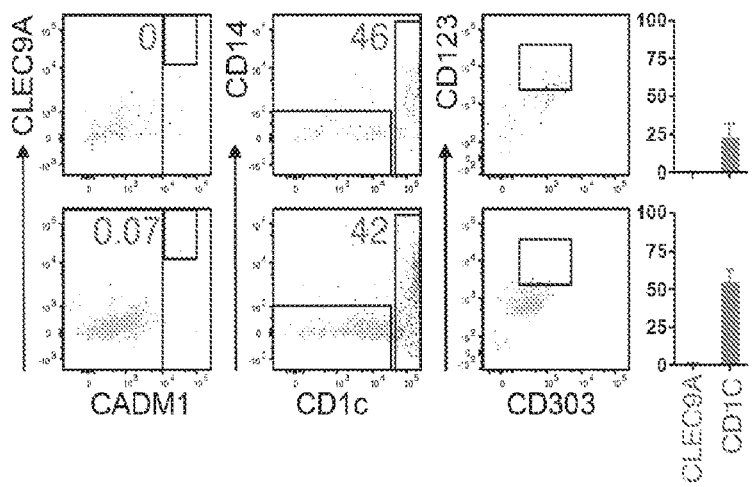
Figure 10A:
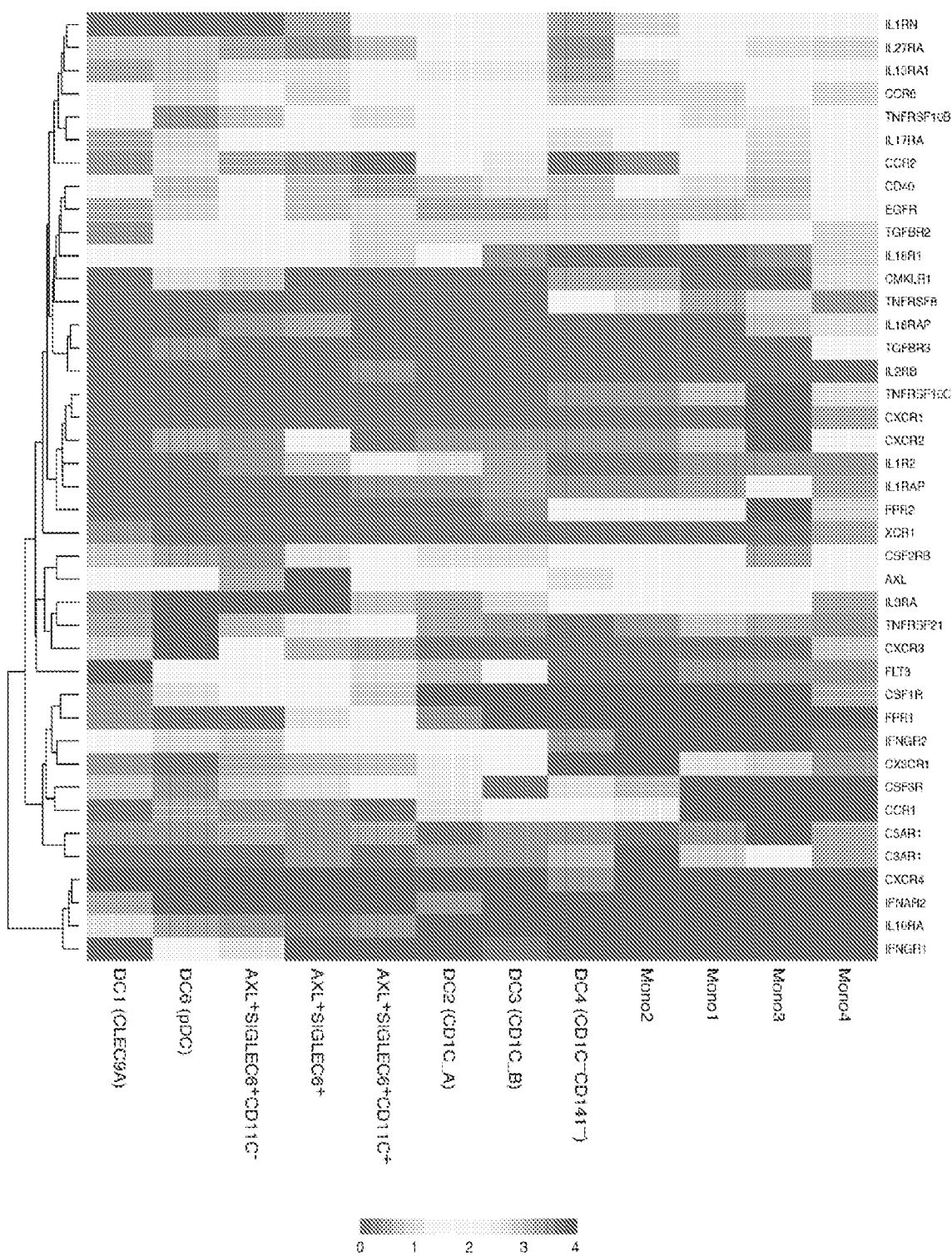
FIG. 10A-10F illustrates supervised analysis of immune-related gene sets across DC and monocyte subsets. Heatmaps reporting average gene expression across all DC and monocyte subsets defined in this study through unbiased clustering classification (i.e. 12 clusters; see Methods). A gene was included in the supervised analysis if it was expressed in at least 40% of the cells in any of the 12 clusters (based on the expression cutoff log(TPM+1)=2). Heatmaps in panels A-F report the average log-expression across all the cells within each cluster for (A) CD markers; (B) immune-related ligands; (C) immune-related receptors; (D) discriminative surface markers, looking at all predicted surface markers from the protein atlas (http://www.proteinatlas.org/search/protein_class:Predicted+membrane+proteins); (E) pathogen sensors; and (F) transcription factors. The average expression matrices used for each heatmap are available in Tables E9A-9F.
Figure 10B:
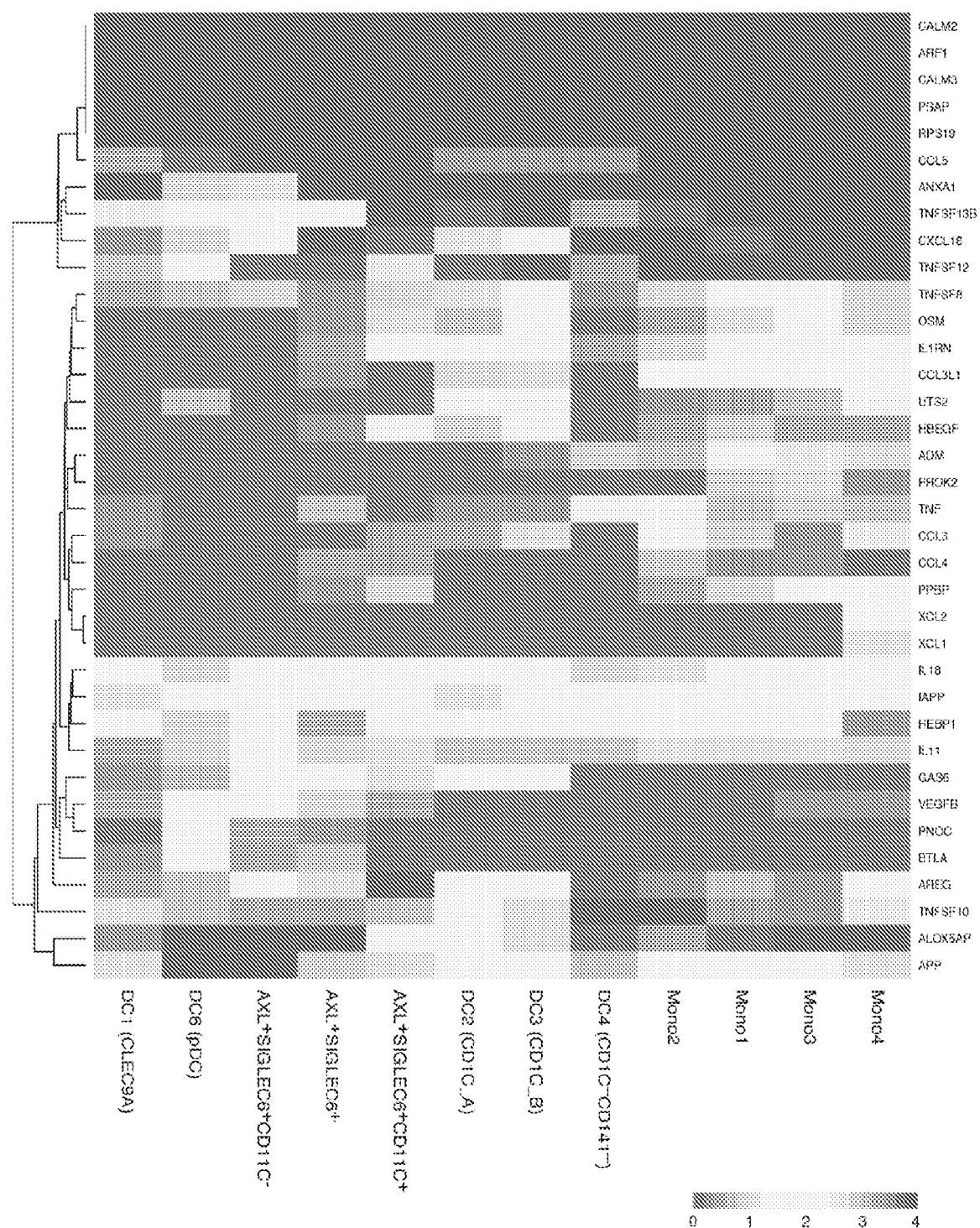
Figure 10C:
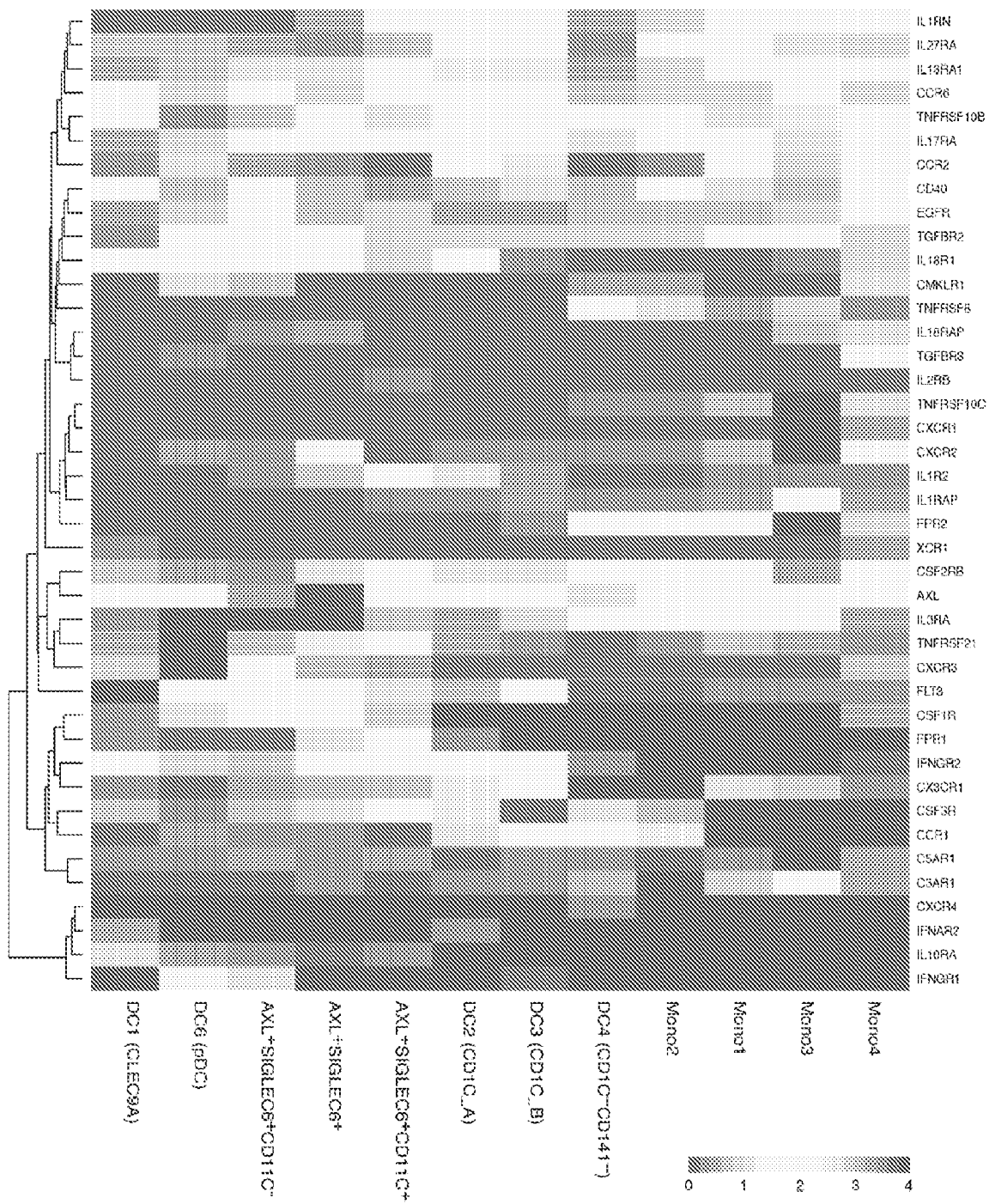
Figure 10D:
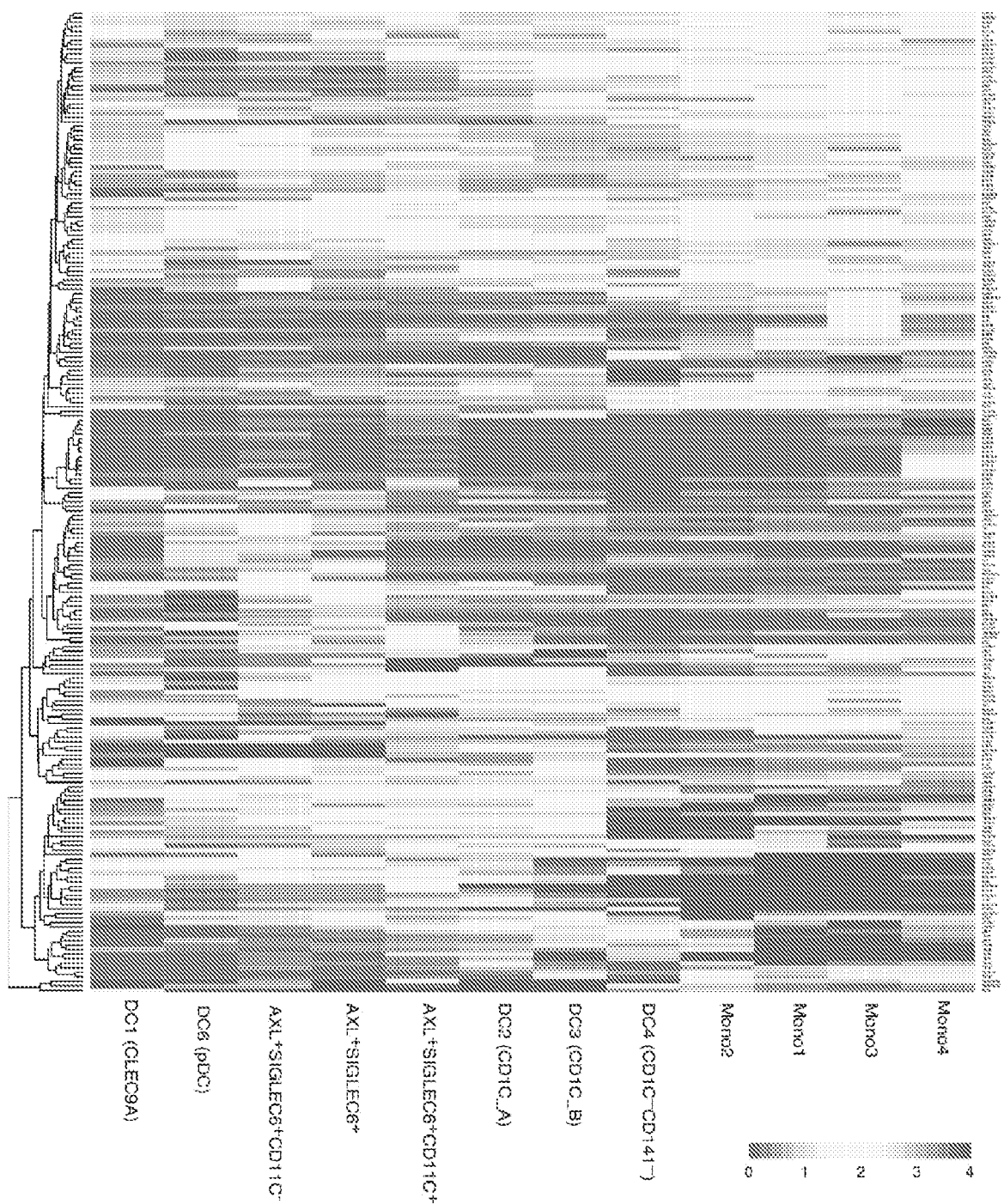
Figure 10E:
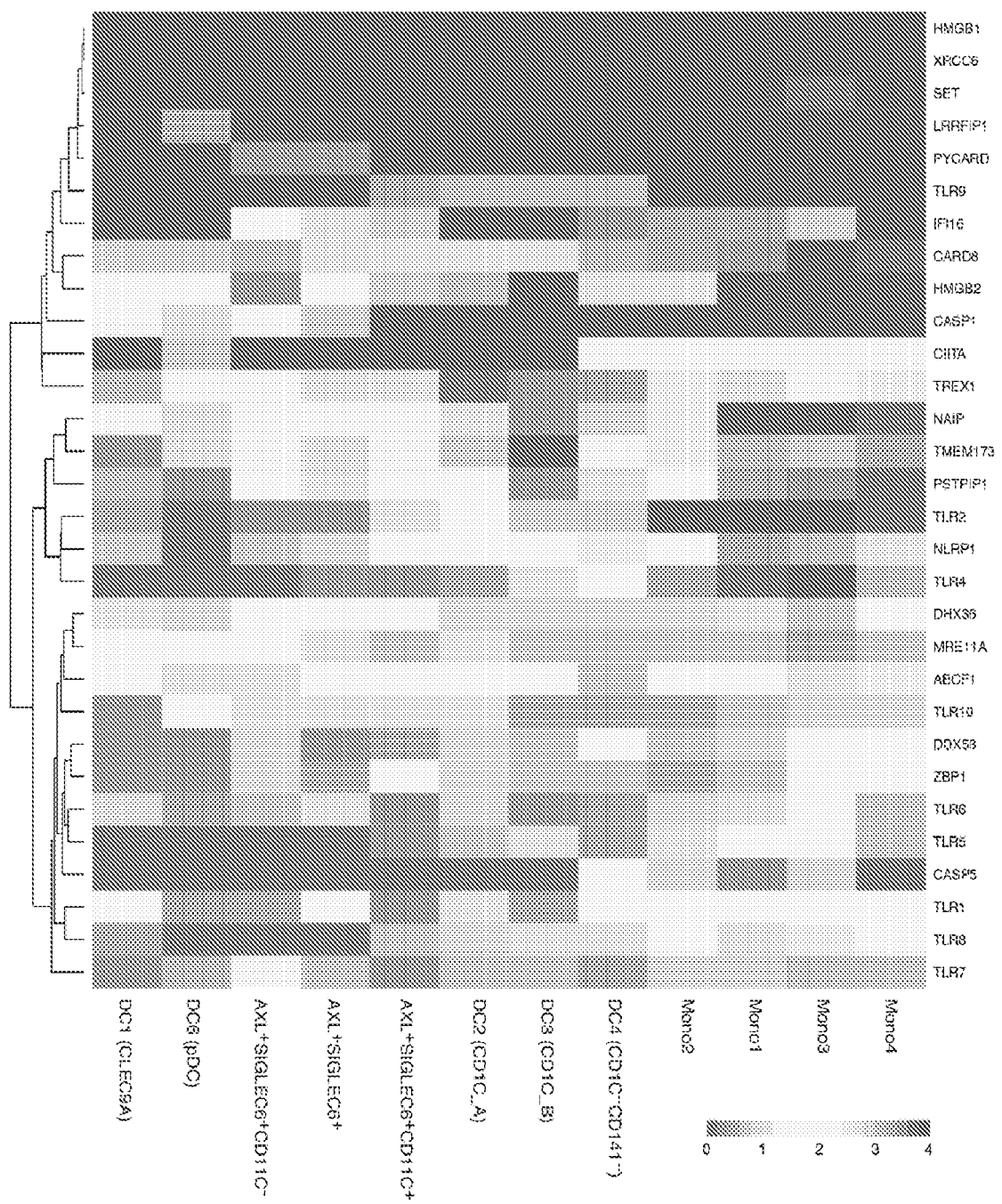
Figure 10F:
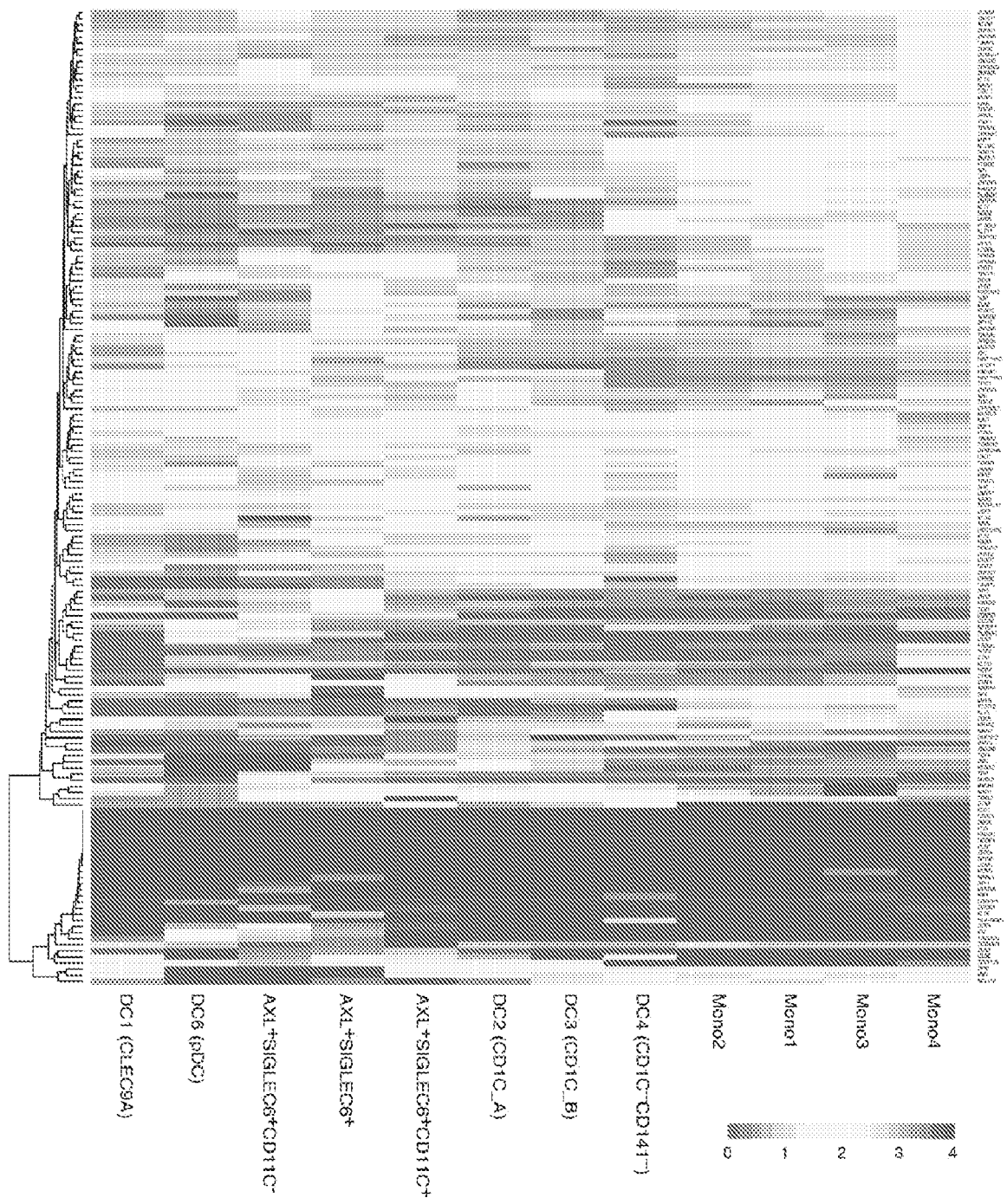

Differentiation of other cell types to DCs. As a control, Applicants seeded cultures with pDCs, CD1C$^+$ and CLEC9A$^+$ DCs and found that they generally retained the same phenotype throughout the differentiation assay (FIG. 9F, FIG. 9N-O). Consistent with AS DC expressing some genes commonly observed in CD1C$^+$ DCs at day 0 (FIG. 7A, FIG. 6A), Applicants detected CD1C$^+$ DCs (frequency 40%-50%, n=6 donors) and only small numbers of CLEC9A$^+$ DCs (0.5-0.8%) by flow cytometry at day 7 of culture (FIG. 9F), regardless of FLT3 ligand dose (FIG. 9F) or if the culture was seeded with either of the two AS DC subpopulations (FIG. 9Q). Notably, both AS DCs at day 0 and the CD1C$^+$ DCs generated from AS DC differentiation did not express BATF3 (transcription factor required for terminal differentiation of CLEC9A$^+$ DCs), CADM1 or XCR1, which are key CLEC9A$^+$ DCs discriminative markers (Satpathy et al.; Hildner et al.; Poulin et al. 2010; Crozat et al.; Jongbloed et al.; Haniffa et al. 2012). Importantly, since none of the CD100$^{hi}$CD34$^{int}$ cells expressed AU or SIGLEC6 genes at day 0 or during differentiation, CD100$^{hi}$CD34$^{int}$ differentiation into CD1C$^+$ DCs is likely independent of AS DC differentiation. While CD100$^{hi}$CD34$^{int}$ blood progenitors divide and differentiate into CLEC9A+ and CD1C+ DCs, AS DCs do not divide during the transition into CD1C+ DCs.

Figure 8A:
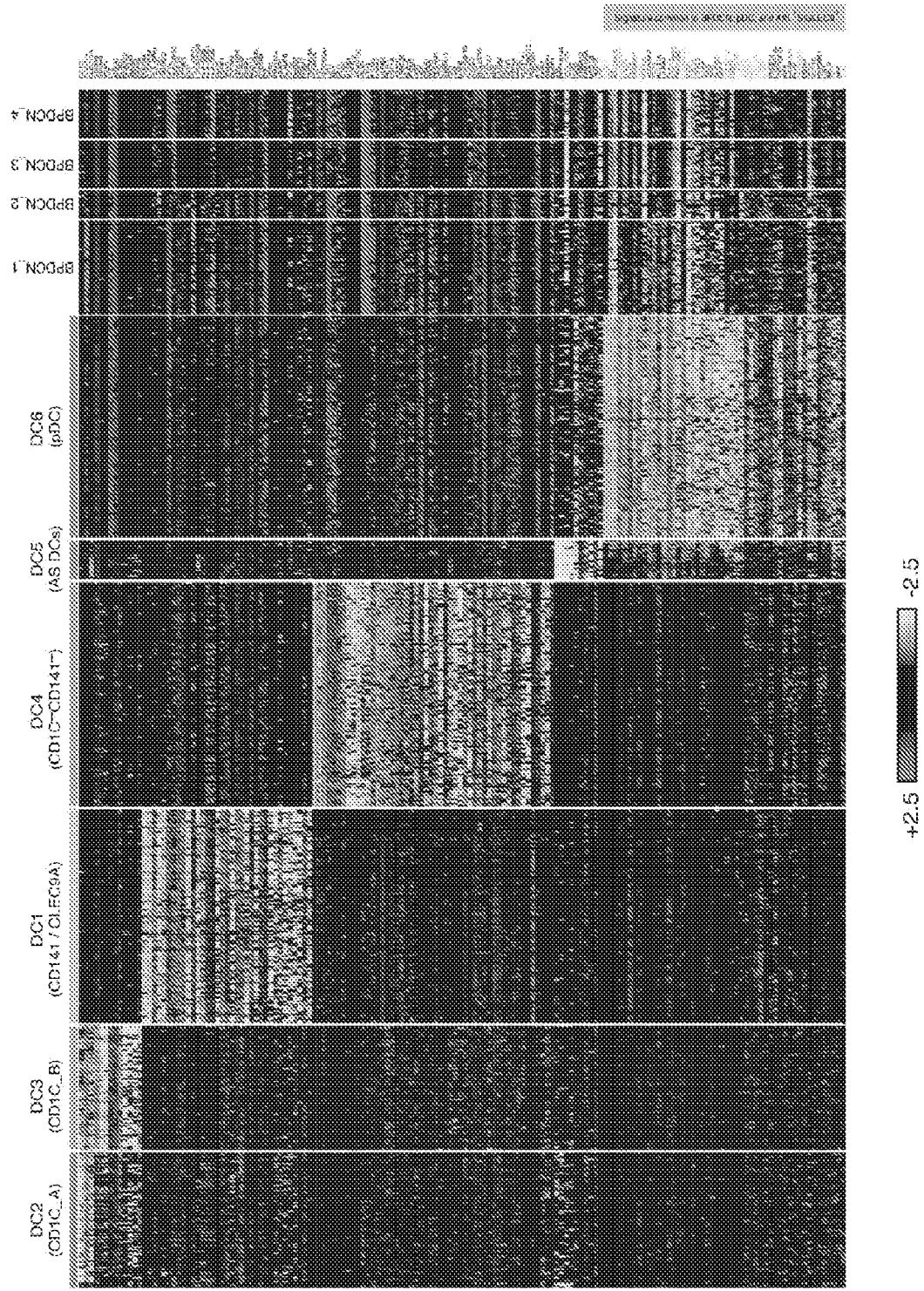

Mapping malignant cells from patients to the healthy DC atlas. Applicants leveraged the entire scRNAseq DC atlas to compare pathogenic cells driving blastic plasmacytoid dendritic cell neoplasm (BPDCN), a rare and aggressive hematological malignancy previously known as natural killer (NK) cell leukemia/lymphoma (Riaz et al.; Garnache-Ottou et al.), to healthy DC populations. Since the ontogeny of these cells remains unclear (Riaz et al.; Garnache-Ottou et al. Sapienza, et al.; Osaki, et al.; Yu et al.), Applicants performed scRNA-seq on CD451HLA-DR+CD123+ blasts from 4 BPDCN patients (n=174 cells; Methods). The first principal component highlighted gene sets clustering all 4 patients together along with healthy blood pDCs (FIG. 9G). Analysis for BPDCN gene expression overlap with healthy DC discriminatory gene sets showed highest overlap with pDC and AXL+SIGLEC6+ signatures (FIG. 8A). Since pure pDC and the AXL+SIGLEC6+ subsets co-express many genes, yet have distinct biological function, Applicants further analyzed the genes overlapping between BPDCN, pure pDCs and cDCs (FIG. 8B). Despite sharing some pDCs genes (e.g. NRP1, IL3RA, DERL3, LAMP5, PTCRA and PTPRCAP), several key genes essential for pDC function were missing or very lowly expressed in patient cells (e.g. GZMMB, IRF7, CLEC4C/CD303, IRF4, SLC15A4; FIG. 8B). Only a small number of cDC genes were expressed in patient cells, including SIGLEC6, LTK, FCER1A, CD59, CADM1, and TMEM14A. Noteworthy, all 4 patient samples shared a set of discriminative genes (FIG. 8B; Table E8) that included several genes expressed in B cells (e.g. FCRLA, IGLL1, TCL1A, IGLL5) or with hematopoietic progenitors (e.g. SOX4 and CLEC11A). The single cell profiles of malignant cells thus suggest BPDCN cells are most closely related to pDCs and B cells.

TABLE E8

Discriminative genes for BPDCN - commonly discriminative between the 4 BPDCN samples profiled and blood mononuclear phagnocytes (DCs and monocytes)

| Gene.ID | AUC value | Avg. Diff.[1] | Power[2] | Pct.1[3] | Pct.2[4] | Surface Marker[5] |
|---|---|---|---|---|---|---|
| IGLL1 | 0.97 | 7.65 | 0.94 | 0.94 | 0.00 | 0 |
| TCL1A | 0.95 | 2.42 | 0.91 | 0.99 | 0.18 | 0 |
| NUCB2 | 0.94 | 2.31 | 0.88 | 0.98 | 0.91 | 0 |
| LAMP5 | 0.93 | 2.43 | 0.85 | 0.96 | 0.24 | 1 |
| STMN1 | 0.92 | 2.19 | 0.83 | 0.97 | 0.64 | 0 |
| ARPP21 | 0.91 | 4.02 | 0.83 | 0.84 | 0.02 | 0 |
| SOX4 | 0.91 | 2.08 | 0.82 | 0.95 | 0.53 | 0 |
| PCDHGC5 | 0.90 | 3.45 | 0.81 | 0.85 | 0.09 | 1 |
| PLVAP | 0.89 | 3.56 | 0.77 | 0.82 | 0.08 | 1 |
| WASF1 | 0.88 | 3.82 | 0.76 | 0.78 | 0.04 | 0 |
| TPM2 | 0.87 | 2.30 | 0.74 | 0.85 | 0.20 | 0 |
| PDLIM1 | 0.87 | 2.63 | 0.74 | 0.83 | 0.25 | 0 |
| LOC100505678 | 0.87 | 2.57 | 0.74 | 0.82 | 0.18 | 0 |
| MYBPH | 0.86 | 4.88 | 0.73 | 0.74 | 0.01 | 0 |
| LOC728175 | 0.86 | 4.64 | 0.71 | 0.71 | 0.00 | 0 |
| CSMD1 | 0.85 | 4.04 | 0.70 | 0.71 | 0.01 | 1 |
| FCRLA | 0.84 | 3.53 | 0.68 | 0.71 | 0.05 | 1 |
| TNNI2 | 0.83 | 2.33 | 0.66 | 0.78 | 0.23 | 0 |
| SCN3A | 0.83 | 3.33 | 0.66 | 0.67 | 0.01 | 1 |
| SIRPG | 0.82 | 4.97 | 0.65 | 0.66 | 0.01 | 1 |
| C16ORF93 | 0.81 | 2.06 | 0.63 | 0.76 | 0.17 | 0 |
| DNTT | 0.81 | 6.19 | 0.63 | 0.63 | 0.00 | 0 |
| SERHL2 | 0.80 | 3.72 | 0.59 | 0.68 | 0.24 | 0 |
| CLEC11A | 0.80 | 3.77 | 0.59 | 0.62 | 0.07 | 0 |
| IGLL5 | 0.79 | 5.75 | 0.59 | 0.60 | 0.02 | 0 |
| SHQ1 | 0.79 | 2.14 | 0.57 | 0.71 | 0.24 | 0 |
| LOXL4 | 0.78 | 4.32 | 0.57 | 0.58 | 0.02 | 1 |
| C1ORF228 | 0.78 | 2.57 | 0.57 | 0.63 | 0.08 | 0 |
| LOC643529 | 0.78 | 2.23 | 0.56 | 0.64 | 0.10 | 0 |
| SERPINB2 | 0.77 | 6.53 | 0.54 | 0.55 | 0.00 | 1 |
| UHRF1 | 0.77 | 4.28 | 0.54 | 0.57 | 0.05 | 0 |
| CNTROB | 0.77 | 2.75 | 0.53 | 0.60 | 0.09 | 0 |
| LOC100507600 | 0.77 | 2.05 | 0.53 | 0.66 | 0.16 | 0 |
| CEP70 | 0.76 | 3.91 | 0.53 | 0.54 | 0.02 | 0 |
| RPS4Y1 | 0.76 | 5.70 | 0.53 | 0.53 | 0.00 | 0 |
| HMSD | 0.76 | 4.10 | 0.52 | 0.52 | 0.01 | 0 |
| MYB | 0.76 | 2.70 | 0.51 | 0.68 | 0.46 | 0 |

Footnotes in Table E8: 1—Value refers to average differential expression within one subset (log fold change); 2—Value refers to discriminatory power of each marker; 3—Percentage of cells, within the cluster ID for which the gene is a marker, that detect the gene; 4—Percentage of all the other cells, excluding the cluster ID for which the gene is a marker, that detect the gene; 5—"1" refers to predicted surface marker; "0" refers to predicted not a surface marker according to the Protein Atlas: Protein Atlas: http://www.proteinatlas.org/search/protein_class:Predicted+membrane+proteins.

Observations and Conclusions

Prior studies have defined subtypes of DCs and monocytes based on a combination of molecular markers and analyses of function and ontogeny. However, an open question is how accurately the expression of existing markers tracks with the complex internal cell type and states. To address this question, Applicants monitored the molecular states of cells through comprehensive profiling of gene expression at single cell resolution. Based on these data, Applicants empirically inferred cell subtypes within the MHC Class II+ compartment of healthy human blood, identified optimal markers that could be used for purifying the hypothesized cell subtypes, and validated the use of such markers by showing that prospectively purified cell types corresponded to the inferred subtypes using single cell RNA-sequencing profiling approach. This general strategy enabled us to propose a more accurate taxonomy of DCs and monocytes, which consists of 6 DC and 4 monocyte subtypes, along with a circulating, dividing precursor of cDCs.

Prior to our report, human blood DCs were classified into one pDC and two cDC populations (CD1C+ DCs and CD141+ DCs). Our study reveals far greater complexity in the organization of blood DC network and highlights the inadequacies of some commonly used antigens to define DCs, including CD303/BDCA-2, CD141/BDCA-3 and CD123. Applicants define six blood DC populations (DC1-6) based on unbiased clustering of single cell RNA expression: (1) DC1 corresponds best to the cross-presenting CD141/BDCA-3 DC and is marked with CLEC9A; (2) DC2 and DC3 correspond to new subdivisions of the CD1C/BDCA-1+ DCs; (3) DC4 corresponds to CD1C−CD141− CD11C+ DC, is marked by CD16 expression, and has some common signatures with monocytes; (4) DC5 captures the novel AXL+SIGLEC6+ cDC (AS DCs); (5) DC6 corresponds to the IFN-producing pDC. The exact functions and origins of cells in these clusters is investigated, with guidance from the expression of specific genes (e.g. transcription factors, cytokines, cytokine receptors, etc.; FIG. 10A-F; Tables E9A-9F). Our revised classification should lead to re-appraisal of the existing nomenclature proposed for human DCs (Guilliams et al.).

Our unbiased profiling and clustering strategy led to discovering the new AXL+SIGLEC6+ (AS) DC subtypes. In addition to expressing distinct markers, AS DCs are distributed across a spectrum of expression, with some cells sharing gene sets with pDCs and others co-expressing more cDC-like gene sets. Furthermore, although AS DCs fell into the established pDC gate, they exhibited only cDC-like functions ex vivo, and could transition towards CD1C+ DCs through in vitro differentiation assays. One possibility for why AS DCs express pDC genes is shared developmental origin, consistent with a recent publication (Xiao et al.) that shows cDC (e.g., SIGLEC6, (CLEC10A) and pDC (e.g., CLEC4C, IL3RA) markers co-expressed on cells that may include a common progenitor of cDCs and pDCs (Lee et al 2015). Applicants also expect AS DCs to have some unique functions relative to cDCs. For example, numerous lectins are expressed in AS DCs, implying a unique role in glycan recognition; the expression of AXL suggests potential interactions with apoptotic cells and, more recently, with Zika virus (Macauley et al.; Rothlin et al.; Nowakowski et al.); and the chemokine receptor profile and localization in peripheral lymphoid tissues suggest a role in tissue homeostasis and inflammation.

Importantly, the discovery of the AS DCs within the pDC gate led us to update the strategy for isolating pure pDCs. When Applicants removed AS DCs from pDCs isolated with standard markers (e.g. CD123 and CD303), the resulting pDCs were highly attenuated in their ability to induce T cell proliferation and produce T cell stimulatory ligands (e.g., IL-12), consistent with reports that found several markers splitting pDCs into those that stimulate or do not stimulate T cells (Swiecki and Colonna; Matsui et al.; Wilhelm et al.; Schwab et al.; Du et al.; Bryant et al.). Applicants thus propose that our purer pDC population corresponds more closely to the 'natural interferon-alpha producing cells' (Grouard et al.; Cella et al.). These cells also appear to share more properties with plasma B cells than DCs based on morphology, higher expression of ER/secretory machinery, known rearrangement at the Ig locus, and expression of B-cell related transcripts. Applicants also found that BPDCN cells share the pDC signature as well as additional B cell genes (e.g., IGLL1, IGLL5, TCL1A). Applicants conclude that while pure pDCs do fall into the MHC II-expressing gate, they have markers, gene signatures, and functions distinct from cDCs.

An unresolved question in the field is how DCs resemble monocytes. In the process of addressing this question, Applicants profiled the MHC II-expressing cells from the CD14+ gate and identified 4 monocyte subtypes—the 2 known ones, along with a novel monocyte killer subtype and one characterized by cell cycle-arrest and trafficking gene sets. Although CD1C+ and CD141−CD1C− DCs both globally shared substantial gene expression with monocytes, each was more closely related to a different monocyte subset. These common functional modules may potentially but without limitation arise from expression in a shared precursor, convergent programs induced during development, or interconversion between monocytes and DCs.

Our results have a number of impacts. For example, our new strategy for purifying pDCs from blood combined with the knowledge that AS DCs may have contaminated prior analyses of pDCs should lead to more accurate interpretation and characterization of pDC functions, as well as therapeutic application of pDCs in human trials (De Vries and Figdor; Tel et al. 2012; Tel et al. 2013). Further, with the identification of AS DCs, future studies of these highly potent DCs should lead to a more complete understanding of the role of DCs in tissues, inflammation and disease. Additionally, the two CD1C+ subsets are postulated to have distinct functions with implications for how Applicants understand the roles of cDCs. Moreover, the identification of circulating CD100$^{hi}$CD34$^{int}$ progenitors provides a novel blood-based cell type for developing vaccines or immunotherapies. Also, our use of the DC atlas to map cells associated with disease, such as BPDCN, illustrates the power of single cell analysis in pinpointing relationships to the healthy cell taxonomy. Further, some susceptibility genes identified in human genetics association studies are expressed in the DCs and monocytes subsets defined in this study, suggesting potential implications for their role in disease (FIG. 11A-B; Table E10A-C).

Single cell profiling is poised to overcome the constraints of traditional immune cell classification, enabling identification of cell types that are currently undetectable in bulk population analyses (either because they are rare, such as AS DCs, or are admixed with other cell types, such as the 'intermediate' monocytes), and examination of complex relationships between cell types, including deciphering continuous spectra within cell subsets. Our results with DCs and monocytes form a foundation towards building a comprehensive cell atlas of the immune system.

Notes and legends for Tables E9A-F. Columns (all tables): 1. DC1 (CLEC9A), 2. DC6 (pDC), 3. DC5 (AXL+SIGLEC6+CD11C−), 4. DC5 (AXL+SIGLEC6+), 5. DC5 (AXL+SIGLEC6+CD11C+), 6. DC2 (CD1C_A), 7. DC3 (CD1C_B), 8. DC4 (CD1C−CD141−), 9. Mono2 (non-classical CD16+Monocyte), 10. Mono1 (classical CD14+ Monocyte), 11. Mono3, 12. Mono4. Note (all tables): candidate genes were included if expressed in at least 40% of cells of at least 1 subset. Note (Table E9F): Supervised analysis included all transcription factors reported in supplementary Table 2 of Vaquerizas et al.

Notes and legends for Table E10A. Columns: 1. DC1 (CLEC9A), 2. DC6 (pDC), 3. DC5 (AXL+SIGLEC6+CD11C−), 4. DC5 (AXL+SIGLEC6+), 5. DC5 (AXL+SIGLEC6+CD11C+), 6. DC2 (CD1C_A), 7. DC3 (CD1C_B), 8. DC4 (CD1C−CD141−), 9. Mono2 (non-classical CD16+Monocyte), 10. Mono1 (classical CD14+ Monocyte), 11. Mono3, 12. Mono4. Note: candidate genes were included if expressed in at least 400/of cells of at least 1 subset and reported in 1 study. Average gene expression for the heatmap depicting 99 candidate GWAS susceptibility loci (FIG. 11B) were sampled from this table. Supervised analysis was performed on all immune-related susceptibility GWAS loci from the NHGRI-EBI Catalog of published genome-wide association studies (https://www.ebi.ac.uk/gwas/).

Notes and legends for Tables E10B-C. Candidate genes were included if expressed in at least 40% of cells of at least 1 subset and reported in 1 study. Table E10B accompanies FIG. 11A. Table E10C accompanies FIG. 11B. Supervised analysis was performed on all immune-related susceptibility GWAS loci from the NHGRI-EBI Catalog of published genome-wide association studies (https://www.ebi.ac.uk/gwas/).

TABLE E9A

Supervised analysis of CD markers - average expression values across DC and monocyte subsets

| Gene.ID | 1 | 2 | 3 | 4 | 5 | 6 | 7 | 8 | 9 | 10 | 11 | 12 |
|---|---|---|---|---|---|---|---|---|---|---|---|---|
| IL1RN | 0.09 | 0.01 | 0.06 | 0.55 | 1.24 | 1.69 | 2.39 | 0.58 | 0.98 | 1.85 | 1.64 | 2.05 |
| IL27RA | 0.64 | 0.68 | 0.41 | 0.28 | 0.69 | 1.55 | 2.18 | 0.37 | 1.31 | 1.68 | 1.07 | 0.99 |
| IL13RA1 | 0.45 | 0.66 | 1.01 | 1.02 | 2.06 | 2.42 | 2.56 | 0.43 | 0.84 | 1.69 | 1.71 | 2.14 |
| CCR6 | 1.37 | 0.94 | 1.78 | 0.86 | 1.46 | 2.31 | 1.97 | 0.63 | 0.85 | 0.97 | 1.22 | 0.97 |
| TNFRSF10B | 1.58 | 0.34 | 0.75 | 1.44 | 1.09 | 1.68 | 2.10 | 1.22 | 2.07 | 2.73 | 2.40 | 1.90 |
| IL17RA | 0.60 | 0.95 | 1.61 | 1.53 | 1.21 | 1.55 | 1.64 | 1.05 | 1.47 | 2.39 | 2.80 | 2.37 |
| CCR2 | 0.37 | 2.68 | 0.54 | 0.39 | 0.00 | 1.50 | 2.55 | 0.01 | 0.34 | 1.86 | 0.93 | 1.25 |
| CD40 | 2.14 | 0.67 | 1.21 | 0.71 | 0.54 | 0.73 | 1.08 | 0.74 | 1.36 | 1.06 | 0.72 | 1.41 |
| EGFR | 0.57 | 0.90 | 1.47 | 0.74 | 0.89 | 0.51 | 0.54 | 0.67 | 0.66 | 0.74 | 0.81 | 1.25 |
| TGFBR2 | 0.29 | 2.05 | 1.70 | 1.78 | 0.85 | 0.93 | 0.82 | 0.96 | 0.88 | 1.39 | 1.60 | 0.86 |
| IL18R1 | 1.77 | 1.90 | 1.91 | 1.62 | 0.86 | 1.46 | 0.40 | 0.02 | 0.03 | 0.12 | 0.21 | 0.84 |
| CMKLR1 | 0.00 | 2.65 | 0.62 | 0.14 | 0.03 | 0.11 | 0.14 | 0.43 | 0.52 | 0.19 | 0.16 | 1.06 |
| TNFRSF8 | 0.06 | 0.14 | 0.16 | 0.16 | 0.17 | 0.13 | 0.13 | 2.05 | 1.09 | 0.54 | 0.80 | 0.29 |
| IL18RAP | 0.04 | 0.15 | 0.39 | 0.46 | 0.10 | 0.04 | 0.05 | 0.04 | 0.04 | 0.01 | 0.64 | 2.68 |
| TGEBR3 | 0.03 | 0.21 | 0.10 | 0.15 | 0.14 | 0.02 | 0.05 | 0.05 | 0.03 | 0.08 | 0.01 | 1.73 |
| IL2RB | 0.03 | 0.01 | 0.14 | 0.10 | 0.26 | 0.00 | 0.00 | 0.00 | 0.07 | 0.02 | 0.11 | 3.68 |
| TNFRSF10C | 0.05 | 0.00 | 0.00 | 0.01 | 0.04 | 0.07 | 0.12 | 0.38 | 0.27 | 0.75 | 4.51 | 1.18 |
| CXCR1 | 0.00 | 0.01 | 0.00 | 0.16 | 0.00 | 0.00 | 0.00 | 0.02 | 0.09 | 0.02 | 3.95 | 0.55 |
| CXCR2 | 0.20 | 0.58 | 0.35 | 1.33 | 0.17 | 0.35 | 0.27 | 0.34 | 0.30 | 0.64 | 5.18 | 1.77 |
| IL1R2 | 0.12 | 0.08 | 0.29 | 0.78 | 1.55 | 1.12 | 0.43 | 0.00 | 0.02 | 0.34 | 3.46 | 0.31 |
| IL1RAP | 0.14 | 0.05 | 0.18 | 0.19 | 0.28 | 0.24 | 0.43 | 0.33 | 0.26 | 0.55 | 2.09 | 0.56 |
| FPR2 | 0.06 | 0.02 | 0.08 | 0.14 | 0.09 | 0.10 | 0.23 | 1.78 | 1.91 | 1.83 | 4.47 | 0.91 |
| XCR1 | 3.47 | 0.07 | 0.00 | 0.01 | 0.03 | 0.01 | 0.04 | 0.06 | 0.06 | 0.07 | 0.00 | 0.43 |
| CSF2RB | 0.77 | 3.30 | 3.50 | 2.75 | 1.80 | 1.14 | 1.16 | 1.24 | 1.98 | 2.30 | 3.38 | 2.00 |
| AXL | 1.25 | 1.40 | 3.30 | 5.43 | 2.17 | 2.15 | 1.39 | 1.14 | 1.66 | 1.74 | 2.03 | 1.57 |
| IL3RA | 0.26 | 6.38 | 4.69 | 4.58 | 0.69 | 0.42 | 0.80 | 1.38 | 1.44 | 1.50 | 1.31 | 0.49 |
| TNFRSF21 | 0.49 | 4.32 | 3.00 | 2.46 | 1.72 | 0.47 | 0.30 | 0.08 | 0.34 | 0.65 | 0.43 | 0.20 |
| CXCR3 | 2.97 | 4.57 | 2.08 | 3.01 | 0.55 | 0.18 | 0.10 | 0.03 | 0.01 | 0.16 | 0.00 | 0.79 |
| FLT3 | 4.47 | 1.74 | 2.13 | 1.35 | 2.63 | 3.07 | 1.85 | 0.04 | 0.05 | 0.24 | 0.30 | 0.36 |
| CSF1R | 0.31 | 1.06 | 1.91 | 1.63 | 2.95 | 3.83 | 4.86 | 6.49 | 6.10 | 4.68 | 3.88 | 3.21 |
| FPR1 | 0.28 | 0.17 | 0.19 | 1.06 | 1.74 | 3.59 | 5.59 | 4.49 | 6.08 | 7.11 | 7.61 | 6.45 |
| IFNGR2 | 2.23 | 0.95 | 0.61 | 1.98 | 1.40 | 2.11 | 2.02 | 3.46 | 3.98 | 3.87 | 4.25 | 3.65 |
| CX3CR1 | 0.35 | 0.13 | 0.49 | 3.03 | 0.71 | 2.51 | 2.37 | 4.59 | 4.43 | 2.66 | 2.97 | 3.52 |
| CSF3R | 0.77 | 0.21 | 0.61 | 1.02 | 2.15 | 2.42 | 3.73 | 1.04 | 3.11 | 5.26 | 5.93 | 4.35 |
| CCR1 | 0.04 | 0.58 | 0.27 | 0.27 | 0.14 | 1.03 | 1.84 | 1.21 | 2.49 | 3.97 | 4.05 | 4.03 |
| C5AR1 | 0.22 | 0.24 | 0.45 | 0.30 | 0.60 | 0.15 | 0.32 | 3.58 | 3.71 | 3.53 | 4.59 | 3.37 |
| C3AR1 | 0.10 | 0.12 | 0.11 | 0.39 | 0.00 | 0.23 | 0.27 | 3.19 | 4.13 | 2.94 | 2.30 | 3.30 |
| CXCR4 | 5.74 | 5.94 | 5.10 | 5.51 | 6.88 | 6.31 | 5.86 | 3.55 | 5.97 | 6.07 | 6.70 | 7.02 |
| IFNAR2 | 3.22 | 4.93 | 4.42 | 3.95 | 4.05 | 3.47 | 4.06 | 4.55 | 4.97 | 4.68 | 5.41 | 5.17 |
| IL10RA | 2.76 | 3.35 | 3.51 | 3.65 | 3.46 | 4.17 | 4.85 | 4.32 | 5.46 | 5.38 | 4.24 | 4.46 |
| IFNGR1 | 4.16 | 2.27 | 2.73 | 4.43 | 4.28 | 4.11 | 3.63 | 4.18 | 5.59 | 5.68 | 6.16 | 5.79 |

TABLE E9B

Supervised analysis of candidate ligands (e.g. cytokines, chemokines, growth factors) - average expression values across DC and monocyte subsets

| Gene.ID | 1 | 2 | 3 | 4 | 5 | 6 | 7 | 8 | 9 | 10 | 11 | 12 |
|---|---|---|---|---|---|---|---|---|---|---|---|---|
| CALM2 | 7.41 | 7.65 | 6.11 | 6.60 | 6.55 | 7.35 | 7.34 | 7.73 | 7.59 | 7.40 | 7.27 | 7.52 |
| ARF1 | 5.69 | 6.10 | 6.01 | 6.00 | 5.76 | 5.85 | 5.94 | 5.91 | 6.19 | 6.28 | 6.35 | 6.25 |
| CALM3 | 5.35 | 4.94 | 4.73 | 5.52 | 5.22 | 5.16 | 5.32 | 5.24 | 5.10 | 5.09 | 5.26 | 5.72 |
| PSAP | 7.56 | 7.92 | 7.09 | 6.85 | 7.20 | 7.39 | 7.92 | 9.03 | 9.25 | 8.94 | 8.62 | 8.47 |
| RPS19 | 6.66 | 7.16 | 7.12 | 6.72 | 7.05 | 6.85 | 6.81 | 7.41 | 6.81 | 6.17 | 5.82 | 6.40 |
| CCL5 | 3.23 | 3.65 | 4.89 | 3.84 | 4.26 | 3.54 | 3.55 | 3.45 | 3.94 | 4.28 | 4.67 | 6.83 |
| ANXA1 | 5.61 | 0.93 | 2.64 | 5.85 | 6.90 | 7.53 | 7.86 | 4.33 | 5.60 | 7.47 | 6.82 | 7.33 |
| TNFSF13B | 2.40 | 2.06 | 2.02 | 2.21 | 3.84 | 3.74 | 4.04 | 3.35 | 3.70 | 4.21 | 4.59 | 3.85 |
| CXCL16 | 3.44 | 0.87 | 2.37 | 4.19 | 3.71 | 2.62 | 1.37 | 4.56 | 4.36 | 3.66 | 4.68 | 3.96 |
| TNFSF12 | 0.65 | 2.03 | 3.65 | 3.75 | 2.57 | 3.73 | 4.77 | 3.40 | 4.71 | 5.35 | 4.76 | 4.69 |
| TNFSF8 | 0.43 | 0.64 | 0.84 | 0.27 | 0.96 | 1.18 | 1.39 | 0.27 | 0.94 | 1.59 | 1.86 | 0.99 |
| OSM | 0.04 | 0.12 | 0.13 | 0.20 | 1.00 | 0.68 | 1.87 | 0.08 | 0.49 | 1.18 | 1.74 | 0.96 |
| IL1RN | 0.09 | 0.01 | 0.06 | 0.55 | 1.24 | 1.69 | 2.39 | 0.58 | 0.98 | 1.85 | 1.64 | 2.05 |
| CCL3L1 | 0.17 | 0.04 | 0.11 | 0.21 | 0.18 | 0.82 | 1.11 | 0.17 | 1.62 | 1.52 | 2.16 | 2.08 |
| UTS2 | 0.07 | 0.61 | 0.07 | 0.16 | 0.00 | 1.28 | 1.59 | 0.07 | 0.21 | 0.54 | 0.78 | 1.67 |
| HBEGF | 0.06 | 0.07 | 0.13 | 0.30 | 2.31 | 0.88 | 1.99 | 0.19 | 0.43 | 0.80 | 0.52 | 0.58 |
| ADM | 0.02 | 0.00 | 0.10 | 0.04 | 0.12 | 0.00 | 0.21 | 0.82 | 0.78 | 1.62 | 2.49 | 1.14 |
| PROK2 | 0.02 | 0.00 | 0.14 | 0.04 | 0.13 | 0.00 | 0.00 | 0.01 | 0.07 | 1.00 | 2.74 | 0.28 |
| TNF | 0.39 | 0.13 | 0.00 | 0.66 | 0.11 | 0.20 | 0.38 | 1.35 | 1.47 | 0.71 | 0.91 | 0.61 |
| CCL3 | 0.25 | 0.10 | 0.13 | 0.16 | 0.48 | 0.55 | 1.06 | 0.12 | 1.44 | 1.00 | 0.35 | 2.43 |
| CCL4 | 0.07 | 0.11 | 0.20 | 0.49 | 0.59 | 0.03 | 0.06 | 0.06 | 0.76 | 0.30 | 0.39 | 3.63 |
| PPBP | 0.18 | 0.10 | 0.09 | 0.36 | 0.93 | 0.00 | 0.10 | 0.17 | 0.44 | 0.92 | 1.32 | 1.75 |
| XCL2 | 0.00 | 0.01 | 0.12 | 0.13 | 0.18 | 0.00 | 0.00 | 0.00 | 0.00 | 0.02 | 0.00 | 1.52 |

TABLE E9B-continued

Supervised analysis of candidate ligands (e.g. cytokines, chemokines, growth factors) - average expression values across DC and monocyte subsets

| Gene.ID | 1 | 2 | 3 | 4 | 5 | 6 | 7 | 8 | 9 | 10 | 11 | 12 |
|---|---|---|---|---|---|---|---|---|---|---|---|---|
| XCL1 | 0.00 | 0.02 | 0.10 | 0.07 | 0.02 | 0.00 | 0.00 | 0.02 | 0.00 | 0.00 | 0.00 | 1.18 |
| IL18 | 1.46 | 0.87 | 1.49 | 1.63 | 2.09 | 2.31 | 1.81 | 0.82 | 1.16 | 1.60 | 1.64 | 1.28 |
| IAPP | 1.16 | 1.36 | 2.03 | 1.41 | 1.60 | 1.05 | 1.30 | 1.23 | 1.64 | 1.84 | 2.09 | 1.30 |
| HEBP1 | 1.22 | 0.88 | 1.26 | 0.51 | 1.27 | 1.61 | 1.41 | 1.68 | 1.52 | 2.09 | 1.77 | 0.21 |
| IL11 | 0.60 | 1.00 | 1.70 | 0.90 | 1.15 | 0.63 | 0.68 | 0.67 | 1.05 | 1.07 | 1.18 | 0.89 |
| GAS6 | 0.31 | 3.11 | 1.77 | 1.52 | 1.00 | 1.61 | 1.33 | 0.05 | 0.19 | 0.15 | 0.07 | 0.10 |
| VEGFB | 0.46 | 2.20 | 1.94 | 0.82 | 0.44 | 0.10 | 0.09 | 0.03 | 0.03 | 0.11 | 0.23 | 0.21 |
| PNOC | 0.12 | 1.73 | 0.57 | 0.22 | 0.00 | 0.00 | 0.00 | 0.12 | 0.09 | 0.03 | 0.07 | 0.00 |
| BTLA | 3.47 | 1.55 | 0.58 | 0.71 | 0.19 | 0.14 | 0.01 | 0.03 | 0.00 | 0.09 | 0.07 | 0.00 |
| AREG | 0.42 | 0.69 | 1.71 | 1.14 | 4.16 | 2.02 | 1.66 | 0.00 | 0.34 | 0.72 | 0.26 | 1.40 |
| TNFSF10 | 1.02 | 0.61 | 0.60 | 0.58 | 0.79 | 2.02 | 2.63 | 5.18 | 3.84 | 3.30 | 3.47 | 2.42 |
| ALOX5AP | 0.22 | 7.65 | 6.07 | 5.72 | 1.72 | 1.86 | 2.63 | 0.04 | 0.56 | 3.63 | 5.39 | 4.10 |
| APP | 1.03 | 4.77 | 4.60 | 3.00 | 1.17 | 1.50 | 1.48 | 0.75 | 1.22 | 2.03 | 1.88 | 1.07 |

TABLE E9C

Supervised analysis of candidate receptors (i.e. cytokines, chemokines, growth factors) - average expression values across DC and monocyte subsets

| Gene.ID | 1 | 2 | 3 | 4 | 5 | 6 | 7 | 8 | 9 | 10 | 11 | 12 |
|---|---|---|---|---|---|---|---|---|---|---|---|---|
| IL1RN | 0.09 | 0.01 | 0.06 | 0.55 | 1.24 | 1.69 | 2.39 | 0.58 | 0.98 | 1.85 | 1.64 | 2.05 |
| IL27RA | 0.64 | 0.68 | 0.41 | 0.28 | 0.69 | 1.55 | 2.18 | 0.37 | 1.31 | 1.68 | 1.07 | 0.99 |
| IL13RA1 | 0.45 | 0.66 | 1.01 | 1.02 | 2.06 | 2.42 | 2.56 | 0.43 | 0.84 | 1.69 | 1.71 | 2.14 |
| CCR6 | 1.37 | 0.94 | 1.78 | 0.86 | 1.46 | 2.31 | 1.97 | 0.63 | 0.85 | 0.97 | 1.22 | 0.97 |
| TNFRSF10B | 1.58 | 0.34 | 0.75 | 1.44 | 1.09 | 1.68 | 2.10 | 1.22 | 2.07 | 2.73 | 2.40 | 1.90 |
| IL17RA | 0.60 | 0.95 | 1.61 | 1.53 | 1.21 | 1.55 | 1.64 | 1.05 | 1.47 | 2.39 | 2.80 | 2.37 |
| CCR2 | 0.37 | 2.68 | 0.54 | 0.39 | 0.00 | 1.50 | 2.55 | 0.01 | 0.34 | 1.86 | 0.93 | 1.25 |
| CD40 | 2.14 | 0.67 | 1.21 | 0.71 | 0.54 | 0.73 | 1.08 | 0.74 | 1.36 | 1.06 | 0.72 | 1.41 |
| EGFR | 0.57 | 0.90 | 1.47 | 0.74 | 0.89 | 0.51 | 0.54 | 0.67 | 0.66 | 0.74 | 0.81 | 1.25 |
| TGFBR2 | 0.29 | 2.05 | 1.70 | 1.78 | 0.85 | 0.93 | 0.82 | 0.96 | 0.88 | 1.39 | 1.60 | 0.86 |
| IL18R1 | 1.77 | 1.90 | 1.91 | 1.62 | 0.86 | 1.46 | 0.40 | 0.02 | 0.03 | 0.12 | 0.21 | 0.84 |
| CMKLR1 | 0.00 | 2.65 | 0.62 | 0.14 | 0.03 | 0.11 | 0.14 | 0.43 | 0.52 | 0.19 | 0.16 | 1.06 |
| TNFRSF8 | 0.06 | 0.14 | 0.16 | 0.16 | 0.17 | 0.13 | 0.13 | 2.05 | 1.09 | 0.54 | 0.80 | 0.29 |
| IL18RAP | 0.04 | 0.15 | 0.39 | 0.46 | 0.10 | 0.04 | 0.05 | 0.04 | 0.04 | 0.01 | 0.64 | 2.68 |
| TGFBR3 | 0.03 | 0.21 | 0.10 | 0.15 | 0.14 | 0.02 | 0.05 | 0.05 | 0.03 | 0.08 | 0.01 | 1.73 |
| IL2RB | 0.03 | 0.01 | 0.14 | 0.10 | 0.26 | 0.00 | 0.00 | 0.00 | 0.07 | 0.02 | 0.11 | 3.68 |
| TNFRSF10C | 0.05 | 0.00 | 0.00 | 0.01 | 0.04 | 0.07 | 0.12 | 0.38 | 0.27 | 0.75 | 4.51 | 1.18 |
| CXCR1 | 0.00 | 0.01 | 0.00 | 0.16 | 0.00 | 0.00 | 0.00 | 0.02 | 0.09 | 0.02 | 3.95 | 0.55 |
| CXCR2 | 0.20 | 0.58 | 0.35 | 1.33 | 0.17 | 0.35 | 0.27 | 0.34 | 0.30 | 0.64 | 5.18 | 1.77 |
| IL1R2 | 0.12 | 0.08 | 0.29 | 0.78 | 1.55 | 1.12 | 0.43 | 0.00 | 0.02 | 0.34 | 3.46 | 0.31 |
| IL1RAP | 0.14 | 0.05 | 0.18 | 0.19 | 0.28 | 0.24 | 0.43 | 0.33 | 0.26 | 0.55 | 2.09 | 0.56 |
| FPR2 | 0.06 | 0.02 | 0.08 | 0.14 | 0.09 | 0.10 | 0.23 | 1.78 | 1.91 | 1.83 | 4.47 | 0.91 |
| XCR1 | 3.47 | 0.07 | 0.00 | 0.01 | 0.03 | 0.01 | 0.04 | 0.06 | 0.06 | 0.07 | 0.00 | 0.43 |
| CSF2RB | 0.77 | 3.30 | 3.50 | 2.75 | 1.80 | 1.14 | 1.16 | 1.24 | 1.98 | 2.30 | 3.38 | 2.00 |
| AXL | 1.25 | 1.40 | 3.30 | 5.43 | 2.17 | 2.15 | 1.39 | 1.14 | 1.66 | 1.74 | 2.03 | 1.57 |
| IL3RA | 0.26 | 6.38 | 4.69 | 4.58 | 0.69 | 0.42 | 0.80 | 1.38 | 1.44 | 1.50 | 1.31 | 0.49 |
| TNFRSF21 | 0.49 | 4.32 | 3.00 | 2.46 | 1.72 | 0.47 | 0.30 | 0.08 | 0.34 | 0.65 | 0.43 | 0.20 |
| CXCR3 | 2.97 | 4.57 | 2.08 | 3.01 | 0.55 | 0.18 | 0.10 | 0.03 | 0.01 | 0.16 | 0.00 | 0.79 |
| FLT3 | 4.47 | 1.74 | 2.13 | 1.35 | 2.63 | 3.07 | 1.85 | 0.04 | 0.05 | 0.24 | 0.30 | 0.36 |
| CSF1R | 0.31 | 1.06 | 1.91 | 1.63 | 2.95 | 3.83 | 4.86 | 6.49 | 6.10 | 4.68 | 3.88 | 3.21 |
| FPR1 | 0.28 | 0.17 | 0.19 | 1.06 | 1.74 | 3.59 | 5.59 | 4.49 | 6.08 | 7.11 | 7.61 | 6.45 |
| IFNGR2 | 2.23 | 0.95 | 0.61 | 1.98 | 1.40 | 2.11 | 2.02 | 3.46 | 3.98 | 3.87 | 4.25 | 3.65 |
| CX3CR1 | 0.35 | 0.13 | 0.49 | 3.03 | 0.71 | 2.51 | 2.37 | 4.59 | 4.43 | 2.66 | 2.97 | 3.52 |
| CSF3R | 0.77 | 0.21 | 0.61 | 1.02 | 2.15 | 2.42 | 3.73 | 1.04 | 3.11 | 5.26 | 5.93 | 4.35 |
| CCR1 | 0.04 | 0.58 | 0.27 | 0.27 | 0.14 | 1.03 | 1.84 | 1.21 | 2.49 | 3.97 | 4.05 | 4.03 |
| C5AR1 | 0.22 | 0.24 | 0.45 | 0.30 | 0.60 | 0.15 | 0.32 | 3.58 | 3.71 | 3.53 | 4.59 | 3.37 |
| C3AR1 | 0.10 | 0.12 | 0.11 | 0.39 | 0.00 | 0.23 | 0.27 | 3.19 | 4.13 | 2.94 | 2.30 | 3.30 |
| CXCR4 | 5.74 | 5.94 | 5.10 | 5.51 | 6.88 | 6.31 | 5.86 | 3.55 | 5.97 | 6.07 | 6.70 | 7.02 |
| IFNAR2 | 3.22 | 4.93 | 4.42 | 3.95 | 4.05 | 3.47 | 4.06 | 4.55 | 4.97 | 4.68 | 5.41 | 5.17 |
| IL10RA | 2.76 | 3.35 | 3.51 | 3.65 | 3.46 | 4.17 | 4.85 | 4.32 | 5.46 | 5.38 | 4.24 | 4.46 |
| IFNGR1 | 4.16 | 2.27 | 2.73 | 4.43 | 4.28 | 4.11 | 3.63 | 4.18 | 5.59 | 5.68 | 6.16 | 5.79 |

TABLE E9D

Supervised analysis of candidate surface markers - average expression values across DC and monocyte subsets of surface markers that were most discriminative

| Gene.ID | 1 | 2 | 3 | 4 | 5 | 6 | 7 | 8 | 9 | 10 | 11 | 12 |
|---|---|---|---|---|---|---|---|---|---|---|---|---|
| LRP10 | 1.43 | 1.20 | 1.14 | 1.40 | 1.41 | 0.87 | 1.06 | 1.03 | 1.54 | 1.60 | 2.77 | 1.87 |
| MAN2B2 | 1.06 | 0.99 | 1.26 | 1.04 | 1.31 | 0.91 | 1.19 | 1.72 | 1.80 | 1.63 | 2.55 | 1.78 |
| ANO6 | 1.01 | 0.89 | 1.12 | 0.75 | 1.83 | 0.84 | 1.20 | 1.07 | 1.41 | 1.88 | 1.94 | 1.29 |
| GLA | 1.67 | 0.97 | 1.15 | 1.00 | 1.08 | 1.50 | 1.19 | 1.60 | 2.56 | 1.89 | 2.72 | 1.33 |
| SLC6A6 | 1.45 | 0.46 | 0.85 | 1.48 | 0.75 | 1.14 | 1.19 | 1.72 | 1.99 | 2.06 | 3.01 | 1.53 |
| TLR1 | 1.26 | 0.41 | 0.44 | 1.40 | 0.30 | 1.18 | 0.57 | 1.89 | 1.88 | 2.03 | 2.32 | 2.22 |
| ITPRIP | 0.73 | 0.64 | 0.53 | 0.90 | 1.41 | 1.17 | 1.21 | 1.06 | 1.65 | 1.87 | 2.22 | 3.28 |
| SEMA4D | 0.26 | 0.91 | 1.01 | 0.94 | 0.81 | 0.69 | 0.90 | 1.16 | 1.48 | 1.52 | 2.54 | 2.96 |
| P2RY8 | 1.09 | 0.37 | 1.23 | 1.12 | 1.27 | 0.80 | 0.92 | 0.40 | 1.17 | 1.68 | 2.91 | 2.42 |
| OSCAR | 0.98 | 0.08 | 0.31 | 0.52 | 1.42 | 1.60 | 1.48 | 1.56 | 1.78 | 2.61 | 1.63 | 2.60 |
| SLC8A1 | 0.95 | 0.05 | 0.28 | 0.58 | 1.55 | 1.48 | 1.58 | 1.38 | 2.54 | 1.79 | 2.33 | 1.56 |
| KCNE3 | 0.40 | 0.45 | 0.95 | 0.71 | 0.71 | 0.96 | 1.92 | 1.55 | 2.44 | 2.78 | 2.78 | 1.77 |
| SIGLEC7 | 0.65 | 0.10 | 0.22 | 0.19 | 0.65 | 1.23 | 1.50 | 1.20 | 1.74 | 2.04 | 1.45 | 2.64 |
| P2RX4 | 0.71 | 0.28 | 0.51 | 0.17 | 0.45 | 0.93 | 1.39 | 1.39 | 1.90 | 2.03 | 1.58 | 2.03 |
| PLOD1 | 0.95 | 0.22 | 0.21 | 0.25 | 0.46 | 1.25 | 1.31 | 0.72 | 1.69 | 1.82 | 1.50 | 1.90 |
| SLCO3A1 | 0.98 | 0.02 | 0.08 | 0.17 | 0.34 | 0.72 | 1.09 | 0.88 | 1.24 | 1.58 | 1.97 | 2.02 |
| ENG | 0.34 | 0.26 | 0.40 | 0.46 | 0.41 | 0.77 | 0.85 | 1.10 | 1.25 | 1.16 | 1.46 | 1.83 |
| SORT1 | 0.06 | 0.31 | 0.23 | 0.07 | 0.22 | 0.55 | 0.74 | 1.21 | 1.51 | 1.96 | 1.29 | 1.36 |
| PLXND1 | 0.88 | 0.17 | 0.89 | 0.31 | 0.76 | 0.44 | 1.27 | 0.88 | 1.38 | 1.69 | 2.06 | 1.09 |
| METTL9 | 0.62 | 0.70 | 0.39 | 0.72 | 0.57 | 1.18 | 1.78 | 0.44 | 0.49 | 1.87 | 1.26 | 2.04 |
| STIM1 | 1.34 | 0.86 | 0.88 | 0.90 | 1.08 | 0.82 | 1.43 | 1.64 | 1.79 | 1.43 | 1.43 | 2.38 |
| BTN2A1 | 1.03 | 1.06 | 0.44 | 1.22 | 0.75 | 0.89 | 1.11 | 0.75 | 1.38 | 1.54 | 1.81 | 2.06 |
| OSTM1 | 0.52 | 1.69 | 0.73 | 0.78 | 0.66 | 1.09 | 1.28 | 1.66 | 0.98 | 1.09 | 1.11 | 2.06 |
| PBXIP1 | 1.07 | 1.57 | 1.04 | 0.48 | 0.55 | 0.50 | 0.79 | 0.94 | 1.10 | 1.07 | 2.25 | 1.27 |
| PTGER2 | 0.65 | 0.03 | 0.09 | 0.01 | 0.22 | 0.18 | 0.60 | 1.97 | 2.33 | 2.23 | 1.55 | 2.31 |
| UGT8 | 0.69 | 0.89 | 2.40 | 1.26 | 1.69 | 0.85 | 0.80 | 0.79 | 1.32 | 1.37 | 1.49 | 1.25 |
| TMC7 | 0.63 | 0.95 | 1.70 | 0.95 | 1.36 | 0.73 | 0.66 | 0.80 | 1.07 | 1.29 | 1.57 | 1.49 |
| PTK7 | 0.76 | 1.75 | 2.25 | 0.92 | 0.99 | 0.70 | 0.70 | 0.65 | 0.95 | 1.03 | 0.91 | 1.61 |
| SDK2 | 0.63 | 1.42 | 1.89 | 1.42 | 1.22 | 0.64 | 0.54 | 0.69 | 0.92 | 0.87 | 1.14 | 1.22 |
| SLC23A2 | 1.04 | 1.84 | 1.16 | 1.00 | 1.07 | 1.22 | 0.67 | 0.65 | 0.86 | 1.13 | 0.90 | 1.82 |
| GLCE | 0.93 | 1.99 | 1.48 | 0.69 | 0.73 | 0.87 | 0.73 | 0.55 | 1.12 | 1.02 | 0.51 | 2.12 |
| CLEC2D | 0.82 | 1.36 | 1.24 | 0.93 | 1.76 | 0.89 | 0.86 | 0.67 | 0.93 | 1.13 | 1.25 | 2.15 |
| ABCA7 | 0.98 | 2.04 | 2.03 | 1.25 | 1.56 | 1.60 | 0.77 | 0.74 | 0.52 | 1.16 | 1.38 | 1.15 |
| TMX3 | 1.32 | 2.10 | 1.57 | 1.26 | 0.96 | 1.13 | 0.96 | 1.11 | 1.11 | 1.15 | 0.86 | 0.78 |
| TGFBR2 | 0.29 | 2.05 | 1.70 | 1.78 | 0.85 | 0.93 | 0.82 | 0.96 | 0.88 | 1.39 | 1.60 | 0.86 |
| TM2D3 | 0.94 | 0.58 | 0.88 | 0.85 | 1.46 | 0.92 | 0.80 | 0.86 | 1.06 | 1.08 | 1.14 | 1.61 |
| CLCN6 | 0.42 | 0.37 | 0.81 | 0.74 | 1.06 | 0.70 | 0.52 | 0.93 | 1.45 | 1.31 | 0.79 | 1.54 |
| EGFR | 0.57 | 0.90 | 1.47 | 0.74 | 0.89 | 0.51 | 0.54 | 0.67 | 0.66 | 0.74 | 0.81 | 1.25 |
| FKBP9 | 0.55 | 0.60 | 1.00 | 0.74 | 0.94 | 0.48 | 0.50 | 0.56 | 0.75 | 1.11 | 1.24 | 1.27 |
| TMEM2 | 0.15 | 0.08 | 0.49 | 0.57 | 1.10 | 0.59 | 1.11 | 0.99 | 0.85 | 1.18 | 0.76 | 2.04 |
| SIGLEC5 | 0.07 | 1.18 | 0.87 | 2.14 | 1.44 | 1.83 | 1.44 | 1.13 | 0.73 | 1.05 | 1.56 | 1.05 |
| HGSNAT | 0.85 | 0.28 | 0.56 | 1.90 | 1.46 | 1.17 | 1.07 | 0.50 | 0.94 | 1.16 | 1.18 | 0.91 |
| PIGS | 1.27 | 1.44 | 1.43 | 1.40 | 1.38 | 1.43 | 1.66 | 1.20 | 2.10 | 2.24 | 2.33 | 2.56 |
| IL17RA | 0.60 | 0.95 | 1.61 | 1.53 | 1.21 | 1.55 | 1.64 | 1.05 | 1.47 | 2.39 | 2.80 | 2.37 |
| SLC12A6 | 1.15 | 1.60 | 2.13 | 1.53 | 1.99 | 1.64 | 1.54 | 1.39 | 1.96 | 2.47 | 3.34 | 2.57 |
| CD82 | 1.14 | 1.83 | 2.04 | 1.52 | 1.10 | 0.98 | 0.72 | 1.00 | 1.85 | 2.89 | 2.57 | 2.68 |
| GNPTAB | 1.13 | 1.45 | 2.03 | 1.41 | 1.52 | 1.05 | 1.19 | 1.05 | 1.66 | 1.76 | 1.95 | 2.63 |
| CNNM3 | 0.97 | 1.40 | 1.91 | 1.40 | 1.51 | 0.96 | 0.95 | 1.26 | 1.33 | 1.73 | 1.85 | 2.34 |
| FCRL2 | 1.08 | 1.32 | 2.59 | 1.49 | 1.82 | 1.26 | 1.16 | 1.29 | 1.55 | 1.73 | 1.84 | 1.58 |
| DMTF1 | 1.39 | 1.83 | 2.52 | 2.33 | 1.52 | 1.38 | 1.45 | 1.37 | 1.57 | 1.64 | 1.26 | 1.48 |
| GMPS | 1.82 | 1.15 | 1.22 | 0.92 | 2.26 | 1.39 | 1.62 | 0.76 | 1.45 | 1.12 | 0.82 | 0.95 |
| TMEM206 | 2.25 | 1.09 | 0.97 | 1.22 | 1.58 | 1.23 | 1.42 | 0.80 | 1.13 | 0.85 | 0.33 | 0.67 |
| TRAP1 | 2.30 | 0.24 | 0.72 | 1.03 | 1.84 | 2.03 | 1.98 | 0.88 | 1.32 | 1.03 | 1.17 | 0.81 |
| ENPP1 | 3.03 | 0.86 | 1.47 | 0.88 | 0.97 | 0.58 | 0.52 | 0.69 | 0.83 | 1.06 | 1.23 | 1.30 |
| CD40 | 2.14 | 0.67 | 1.21 | 0.71 | 0.54 | 0.73 | 1.08 | 0.74 | 1.36 | 1.06 | 0.72 | 1.41 |
| SLC9A9 | 2.62 | 0.18 | 0.18 | 0.74 | 1.19 | 1.21 | 0.81 | 1.24 | 1.12 | 1.37 | 0.68 | 1.18 |
| CREG1 | 1.43 | 0.35 | 0.66 | 0.77 | 0.51 | 1.65 | 2.20 | 1.04 | 1.21 | 1.49 | 1.93 | 0.85 |
| IL27RA | 0.64 | 0.68 | 0.41 | 0.28 | 0.69 | 1.55 | 2.18 | 0.37 | 1.31 | 1.68 | 1.07 | 0.99 |
| ADAM15 | 1.75 | 0.24 | 0.46 | 0.25 | 1.57 | 1.62 | 2.78 | 0.48 | 1.37 | 1.69 | 1.58 | 1.23 |
| SCARB2 | 0.57 | 3.16 | 2.32 | 0.89 | 1.13 | 0.96 | 1.18 | 1.76 | 2.11 | 2.04 | 1.69 | 1.43 |
| ASPH | 0.79 | 3.18 | 1.90 | 0.71 | 0.97 | 0.64 | 1.61 | 0.51 | 0.89 | 1.63 | 2.27 | 0.78 |
| CYSLTR1 | 0.02 | 2.83 | 1.32 | 0.56 | 0.57 | 1.32 | 1.10 | 2.04 | 0.98 | 0.95 | 0.70 | 0.82 |
| EMR3 | 0.03 | 0.02 | 0.11 | 0.29 | 0.31 | 0.36 | 0.17 | 1.32 | 1.19 | 0.71 | 2.05 | 0.72 |
| ADAMTSL4 | 0.09 | 0.13 | 0.38 | 0.08 | 0.33 | 0.30 | 0.58 | 0.89 | 0.88 | 1.21 | 1.78 | 0.56 |
| ABCA1 | 0.06 | 0.02 | 0.41 | 0.50 | 0.14 | 0.00 | 0.02 | 0.50 | 1.15 | 1.02 | 1.76 | 0.88 |
| NOTCH1 | 0.25 | 0.47 | 0.35 | 0.52 | 0.37 | 0.40 | 0.65 | 0.46 | 0.69 | 0.88 | 1.59 | 1.39 |
| STC19A1 | 0.02 | 0.17 | 0.14 | 0.12 | 0.31 | 0.61 | 0.62 | 0.37 | 0.72 | 1.06 | 1.48 | 1.24 |
| MME | 0.01 | 0.24 | 0.22 | 0.07 | 0.09 | 0.01 | 0.00 | 0.01 | 0.03 | 0.11 | 1.91 | 0.34 |
| ALPL | 0.00 | 0.00 | 0.00 | 0.06 | 0.00 | 0.03 | 0.00 | 0.01 | 0.03 | 0.01 | 2.37 | 0.30 |
| IL1RAP | 0.14 | 0.05 | 0.18 | 0.19 | 0.28 | 0.24 | 0.47 | 0.43 | 0.26 | 0.55 | 2.09 | 0.56 |
| SLC2A9 | 0.45 | 0.68 | 0.41 | 0.37 | 0.83 | 0.69 | 1.11 | 0.17 | 0.35 | 1.22 | 1.82 | 0.27 |
| SIRPA | 0.00 | 0.02 | 0.18 | 0.18 | 0.66 | 1.00 | 1.19 | 0.14 | 0.51 | 1.45 | 1.91 | 0.74 |
| PTGS2 | 0.11 | 0.07 | 0.05 | 0.21 | 0.71 | 1.27 | 1.73 | 0.35 | 0.64 | 1.18 | 2.99 | 0.89 |
| CR1 | 0.12 | 0.19 | 0.38 | 0.23 | 0.26 | 0.27 | 0.43 | 0.70 | 0.95 | 2.15 | 2.63 | 1.46 |
| IGF2R | 0.23 | 0.81 | 0.82 | 0.36 | 0.27 | 0.09 | 0.13 | 0.20 | 0.88 | 1.41 | 2.28 | 1.90 |

TABLE E9D-continued

Supervised analysis of candidate surface markers - average expression values across DC and monocyte subsets of surface markers that were most discriminative

| Gene.ID | 1 | 2 | 3 | 4 | 5 | 6 | 7 | 8 | 9 | 10 | 11 | 12 |
|---|---|---|---|---|---|---|---|---|---|---|---|---|
| TNFRSF8 | 0.06 | 0.14 | 0.16 | 0.16 | 0.17 | 0.13 | 0.13 | 2.05 | 1.09 | 0.54 | 0.80 | 0.29 |
| FCGR3B | 0.12 | 0.09 | 0.22 | 0.17 | 0.06 | 0.02 | 0.04 | 1.78 | 0.79 | 0.44 | 5.78 | 0.71 |
| CXCR1 | 0.00 | 0.01 | 0.00 | 0.16 | 0.00 | 0.00 | 0.00 | 0.02 | 0.09 | 0.02 | 3.95 | 0.55 |
| IL1R2 | 0.12 | 0.08 | 0.29 | 0.78 | 1.55 | 1.12 | 0.43 | 0.00 | 0.02 | 0.34 | 3.46 | 0.31 |
| CD79B | 0.30 | 0.19 | 0.74 | 0.55 | 0.76 | 0.73 | 1.30 | 4.45 | 2.99 | 0.97 | 0.50 | 1.12 |
| CTSL1 | 0.37 | 0.14 | 0.33 | 0.46 | 0.08 | 0.36 | 0.68 | 5.52 | 3.66 | 1.26 | 1.04 | 1.36 |
| SIDT2 | 0.92 | 0.61 | 0.62 | 0.95 | 0.91 | 1.06 | 1.04 | 4.58 | 3.05 | 1.68 | 1.51 | 0.98 |
| VAMP5 | 0.92 | 0.93 | 1.60 | 0.77 | 0.40 | 1.06 | 0.66 | 3.33 | 2.15 | 1.68 | 1.51 | 1.93 |
| PNPLA6 | 0.97 | 0.49 | 0.64 | 0.85 | 1.83 | 1.42 | 1.12 | 2.09 | 2.18 | 1.50 | 0.66 | 1.25 |
| MYOF | 0.88 | 0.78 | 0.23 | 1.03 | 0.67 | 1.26 | 1.09 | 2.64 | 2.52 | 1.16 | 0.79 | 0.69 |
| TTYH3 | 0.28 | 0.22 | 0.58 | 0.47 | 0.84 | 0.75 | 0.63 | 2.03 | 2.43 | 1.88 | 1.27 | 0.76 |
| MARCKS | 0.72 | 0.04 | 0.08 | 0.16 | 0.58 | 0.86 | 0.72 | 2.57 | 2.05 | 1.26 | 1.64 | 1.05 |
| ECE1 | 2.18 | 0.57 | 1.20 | 3.15 | 0.83 | 0.25 | 0.28 | 1.32 | 1.75 | 1.85 | 2.48 | 1.73 |
| FCGR2B | 0.11 | 0.08 | 0.32 | 0.32 | 0.69 | 3.59 | 2.50 | 0.61 | 0.37 | 0.50 | 0.83 | 0.29 |
| CD200R1 | 0.15 | 0.07 | 0.00 | 0.11 | 0.53 | 1.88 | 1.23 | 0.05 | 0.03 | 0.10 | 0.15 | 0.34 |
| PRF1 | 0.03 | 0.03 | 0.34 | 0.33 | 0.33 | 0.00 | 0.02 | 0.06 | 0.08 | 0.14 | 0.32 | 6.54 |
| KLRF1 | 0.09 | 0.13 | 0.26 | 0.05 | 0.24 | 0.12 | 0.10 | 0.00 | 0.01 | 0.04 | 0.51 | 4.58 |
| IL2RB | 0.03 | 0.01 | 0.14 | 0.10 | 0.26 | 0.00 | 0.00 | 0.00 | 0.07 | 0.02 | 0.11 | 3.68 |
| GZMH | 0.03 | 0.41 | 0.70 | 0.10 | 0.46 | 0.00 | 0.00 | 0.00 | 0.01 | 0.05 | 0.00 | 5.27 |
| S1PR5 | 0.04 | 0.07 | 0.40 | 0.15 | 0.08 | 0.07 | 0.02 | 0.07 | 0.10 | 0.08 | 0.28 | 3.21 |
| GPR56 | 0.07 | 0.06 | 0.10 | 0.12 | 0.18 | 0.07 | 0.04 | 0.09 | 0.05 | 0.18 | 0.32 | 3.13 |
| NCR3 | 0.00 | 0.00 | 0.00 | 0.04 | 0.31 | 0.00 | 0.00 | 0.08 | 0.05 | 0.02 | 0.10 | 3.11 |
| KLRC1 | 0.02 | 0.02 | 0.22 | 0.03 | 0.17 | 0.00 | 0.00 | 0.01 | 0.04 | 0.05 | 0.00 | 2.84 |
| KIR2DS4 | 0.00 | 0.03 | 0.37 | 0.11 | 0.28 | 0.00 | 0.03 | 0.00 | 0.01 | 0.01 | 0.18 | 2.44 |
| K1R2DS1 | 0.00 | 0.01 | 0.12 | 0.04 | 0.08 | 0.00 | 0.00 | 0.03 | 0.02 | 0.04 | 0.07 | 2.19 |
| FCRL3 | 0.00 | 0.00 | 0.54 | 0.16 | 0.22 | 0.02 | 0.02 | 0.01 | 0.00 | 0.03 | 0.05 | 1.89 |
| TGFBR3 | 0.03 | 0.21 | 0.10 | 0.15 | 0.14 | 0.02 | 0.05 | 0.05 | 0.03 | 0.08 | 0.01 | 1.73 |
| KLRG1 | 0.27 | 0.21 | 0.06 | 0.20 | 0.21 | 0.15 | 0.29 | 0.11 | 0.15 | 0.13 | 0.37 | 2.24 |
| CD96 | 0.19 | 0.30 | 0.91 | 0.36 | 0.88 | 0.28 | 0.22 | 0.19 | 0.48 | 0.47 | 0.70 | 2.95 |
| KLRB1 | 0.01 | 0.00 | 1.79 | 0.02 | 1.12 | 0.00 | 0.00 | 0.01 | 0.10 | 0.11 | 0.24 | 3.26 |
| FCRL6 | 2.58 | 0.02 | 0.16 | 0.10 | 0.62 | 0.46 | 0.09 | 0.02 | 0.05 | 0.05 | 0.40 | 3.56 |
| CD38 | 2.37 | 0.92 | 0.79 | 0.81 | 0.39 | 0.68 | 0.52 | 0.06 | 0.45 | 0.26 | 0.53 | 1.14 |
| DPP4 | 2.06 | 0.54 | 1.07 | 0.63 | 0.30 | 0.19 | 0.03 | 0.00 | 0.00 | 0.14 | 0.00 | 0.19 |
| CD59 | 3.37 | 0.34 | 0.23 | 0.96 | 0.37 | 1.07 | 0.89 | 0.06 | 0.33 | 0.56 | 1.02 | 0.77 |
| BTLA | 3.47 | 1.55 | 0.58 | 0.71 | 0.19 | 0.14 | 0.01 | 0.03 | 0.00 | 0.09 | 0.07 | 0.00 |
| CADM1 | 4.84 | 0.04 | 0.17 | 0.11 | 0.00 | 0.09 | 0.08 | 0.02 | 0.08 | 0.12 | 0.00 | 0.48 |
| TMEM63A | 0.64 | 2.07 | 1.72 | 0.77 | 0.72 | 0.66 | 0.62 | 0.47 | 0.46 | 0.66 | 0.37 | 0.91 |
| HYOU1 | 0.74 | 1.69 | 1.45 | 1.00 | 0.90 | 0.33 | 0.66 | 0.24 | 0.17 | 0.41 | 0.52 | 0.17 |
| ST3GAL4 | 0.51 | 2.68 | 1.95 | 0.97 | 0.45 | 1.22 | 0.76 | 0.24 | 0.21 | 0.22 | 0.30 | 0.37 |
| LY9 | 0.62 | 2.99 | 2.10 | 0.95 | 0.55 | 0.49 | 0.33 | 0.16 | 0.11 | 0.22 | 0.26 | 1.30 |
| TMIGD2 | 0.28 | 3.02 | 1.40 | 0.33 | 0.63 | 0.41 | 0.43 | 0.32 | 0.39 | 0.64 | 0.61 | 1.04 |
| SUSD1 | 0.17 | 2.36 | 2.89 | 1.31 | 0.57 | 0.17 | 0.20 | 0.42 | 0.92 | 0.71 | 0.62 | 0.74 |
| GPM6B | 0.16 | 3.08 | 0.82 | 0.75 | 0.11 | 0.08 | 0.05 | 0.04 | 0.03 | 0.09 | 0.00 | 0.20 |
| PLXNA4 | 0.00 | 2.56 | 1.26 | 0.81 | 0.18 | 0.05 | 0.00 | 0.01 | 0.03 | 0.04 | 0.04 | 0.00 |
| IGFBP3 | 0.01 | 2.71 | 1.06 | 0.10 | 0.00 | 0.05 | 0.01 | 0.01 | 0.01 | 0.03 | 0.00 | 0.00 |
| CMKLR1 | 0.00 | 2.65 | 0.62 | 0.14 | 0.03 | 0.11 | 0.14 | 0.43 | 0.52 | 0.19 | 0.16 | 1.06 |
| LTB | 0.30 | 2.79 | 0.58 | 0.97 | 0.33 | 0.31 | 0.23 | 0.90 | 0.60 | 0.43 | 0.69 | 0.20 |
| SLC1A4 | 0.42 | 1.07 | 1.18 | 2.18 | 0.38 | 0.40 | 0.44 | 0.60 | 0.56 | 0.27 | 0.13 | 0.37 |
| CD22 | 0.28 | 0.22 | 0.79 | 1.47 | 0.46 | 0.44 | 0.45 | 0.08 | 0.09 | 0.07 | 0.15 | 0.00 |
| PCDHGC5 | 0.02 | 0.75 | 1.85 | 0.91 | 0.19 | 0.05 | 0.02 | 0.05 | 0.30 | 0.32 | 0.32 | 0.39 |
| KCNK17 | 0.00 | 0.23 | 2.35 | 0.31 | 0.00 | 0.01 | 0.02 | 0.00 | 0.00 | 0.00 | 0.00 | 0.00 |
| IL18R1 | 1.77 | 1.90 | 1.91 | 1.62 | 0.86 | 1.46 | 0.40 | 0.02 | 0.03 | 0.12 | 0.21 | 0.84 |
| ST14 | 1.35 | 1.62 | 1.34 | 1.90 | 1.19 | 0.90 | 1.14 | 0.13 | 0.11 | 0.32 | 0.08 | 0.00 |
| SLC2A1 | 1.85 | 3.53 | 1.56 | 2.19 | 2.07 | 1.50 | 1.39 | 0.03 | 0.11 | 0.22 | 0.08 | 1.32 |
| SLC15A4 | 0.35 | 4.36 | 2.86 | 2.29 | 0.60 | 0.49 | 0.57 | 0.75 | 0.70 | 0.79 | 0.81 | 1.66 |
| PTPRS | 0.31 | 3.77 | 3.31 | 1.58 | 0.76 | 0.36 | 0.28 | 0.45 | 0.53 | 0.84 | 1.12 | 0.72 |
| NPC1 | 0.44 | 4.60 | 2.31 | 0.98 | 0.51 | 0.46 | 0.74 | 0.99 | 1.20 | 1.14 | 0.98 | 1.43 |
| NRP1 | 0.12 | 5.02 | 3.28 | 0.88 | 0.33 | 0.25 | 0.41 | 0.15 | 0.24 | 0.35 | 0.52 | 0.33 |
| EPHB1 | 0.08 | 3.59 | 3.30 | 0.79 | 0.06 | 0.10 | 0.08 | 0.07 | 0.11 | 0.12 | 0.98 | 0.28 |
| TSPAN13 | 0.39 | 5.43 | 2.97 | 1.62 | 0.16 | 0.07 | 0.09 | 0.01 | 0.03 | 0.07 | 0.00 | 0.00 |
| SEL1L3 | 1.03 | 2.24 | 3.30 | 2.56 | 1.00 | 0.54 | 0.15 | 0.01 | 0.12 | 0.18 | 0.11 | 0.08 |
| SLC7A5 | 0.06 | 2.21 | 2.33 | 3.01 | 1.51 | 0.19 | 0.41 | 0.04 | 0.07 | 0.15 | 0.10 | 0.29 |
| TNFRSF21 | 0.49 | 4.32 | 3.00 | 2.46 | 1.72 | 0.47 | 0.30 | 0.08 | 0.34 | 0.65 | 0.43 | 0.20 |
| SIGLEC6 | 0.06 | 0.71 | 2.50 | 3.18 | 1.77 | 0.94 | 0.11 | 0.02 | 0.03 | 0.13 | 0.00 | 0.00 |
| CD5 | 0.08 | 0.02 | 1.52 | 3.57 | 2.02 | 0.64 | 0.02 | 0.01 | 0.08 | 0.10 | 0.09 | 0.28 |
| IL13RA1 | 0.45 | 0.66 | 1.01 | 1.02 | 2.06 | 2.42 | 2.56 | 0.43 | 0.84 | 1.69 | 1.71 | 2.14 |
| CES1 | 0.32 | 0.05 | 1.19 | 0.93 | 2.61 | 1.30 | 3.84 | 0.07 | 0.32 | 2.44 | 1.74 | 1.82 |
| CD1D | 0.44 | 0.24 | 0.22 | 0.24 | 2.65 | 3.50 | 4.00 | 0.79 | 1.89 | 3.20 | 2.40 | 2.35 |
| ADAM8 | 2.00 | 0.07 | 0.25 | 1.46 | 3.97 | 3.85 | 3.07 | 0.68 | 0.85 | 1.88 | 2.68 | 3.25 |
| CD1C | 0.34 | 0.12 | 0.25 | 0.51 | 4.80 | 6.17 | 4.54 | 0.15 | 0.49 | 0.47 | 0.54 | 0.91 |
| AREG | 0.42 | 0.69 | 1.71 | 1.14 | 4.16 | 2.02 | 1.66 | 0.00 | 0.34 | 0.72 | 0.26 | 1.40 |
| CD2 | 0.09 | 0.19 | 0.99 | 2.48 | 1.72 | 2.36 | 2.22 | 0.03 | 0.17 | 0.21 | 0.42 | 3.58 |
| TSPAN3 | 2.81 | 4.49 | 3.18 | 1.98 | 1.82 | 2.08 | 1.93 | 1.09 | 1.27 | 1.39 | 1.14 | 2.17 |
| STT3A | 2.63 | 3.37 | 2.24 | 1.49 | 1.85 | 1.67 | 1.96 | 0.97 | 1.18 | 1.13 | 1.19 | 2.34 |
| NOP56 | 2.18 | 3.82 | 1.90 | 1.98 | 2.25 | 1.98 | 2.22 | 1.95 | 1.80 | 1.82 | 2.00 | 2.30 |

TABLE E9D-continued

Supervised analysis of candidate surface markers - average expression values across DC and monocyte subsets of surface markers that were most discriminative

| Gene.ID | 1 | 2 | 3 | 4 | 5 | 6 | 7 | 8 | 9 | 10 | 11 | 12 |
|---|---|---|---|---|---|---|---|---|---|---|---|---|
| TRPV2 | 3.42 | 2.34 | 1.44 | 1.88 | 1.98 | 2.77 | 2.64 | 1.95 | 2.22 | 1.55 | 1.16 | 1.96 |
| SLC1A5 | 3.41 | 3.37 | 1.69 | 2.23 | 0.78 | 2.19 | 1.90 | 1.98 | 1.95 | 1.72 | 1.61 | 1.54 |
| CSF2RB | 0.77 | 3.30 | 3.50 | 2.75 | 1.80 | 1.14 | 1.16 | 1.24 | 1.98 | 2.30 | 3.38 | 2.00 |
| AXL | 1.25 | 1.40 | 3.30 | 5.43 | 2.17 | 2.15 | 1.39 | 1.14 | 1.66 | 1.74 | 2.03 | 1.57 |
| PDE4B | 2.08 | 2.02 | 3.14 | 1.46 | 3.24 | 1.17 | 1.29 | 0.36 | 1.30 | 1.50 | 3.02 | 1.23 |
| ZC3HAV1 | 2.51 | 2.80 | 3.62 | 3.51 | 4.96 | 2.95 | 3.18 | 3.14 | 2.54 | 2.80 | 2.87 | 2.94 |
| IDH2 | 4.92 | 2.26 | 3.33 | 2.90 | 3.04 | 3.22 | 3.30 | 2.88 | 2.66 | 2.27 | 2.04 | 2.56 |
| SLAMF7 | 6.17 | 5.28 | 4.21 | 4.10 | 2.43 | 2.20 | 0.96 | 2.30 | 2.37 | 1.51 | 1.80 | 2.94 |
| TUBB6 | 2.27 | 3.33 | 2.66 | 3.18 | 1.10 | 1.02 | 1.61 | 0.32 | 0.94 | 1.57 | 1.50 | 0.93 |
| ADAM19 | 2.56 | 3.66 | 3.30 | 2.73 | 0.81 | 1.08 | 0.66 | 0.03 | 0.09 | 1.26 | 1.18 | 1.06 |
| CXCR3 | 2.97 | 4.57 | 2.08 | 3.01 | 0.55 | 0.18 | 0.10 | 0.03 | 0.01 | 0.16 | 0.00 | 0.79 |
| THBD | 3.49 | 1.87 | 1.15 | 3.50 | 0.77 | 0.66 | 0.93 | 0.17 | 0.21 | 0.62 | 1.38 | 1.03 |
| LGMN | 4.91 | 5.44 | 4.66 | 5.51 | 2.83 | 2.18 | 1.06 | 0.38 | 0.44 | 0.37 | 0.22 | 0.60 |
| SERPINF1 | 4.26 | 7.20 | 5.30 | 4.11 | 1.05 | 1.69 | 1.59 | 0.12 | 0.29 | 0.57 | 0.31 | 0.76 |
| IL3RA | 0.26 | 6.38 | 4.69 | 4.58 | 0.69 | 0.42 | 0.80 | 1.38 | 1.44 | 1.50 | 1.31 | 0.49 |
| PON2 | 4.10 | 1.36 | 1.61 | 2.96 | 3.70 | 3.44 | 2.65 | 0.13 | 0.17 | 0.54 | 0.70 | 0.89 |
| FLT3 | 4.47 | 1.74 | 2.13 | 1.35 | 2.63 | 3.07 | 1.85 | 0.04 | 0.05 | 0.24 | 0.30 | 0.36 |
| ITGB7 | 2.85 | 0.74 | 1.67 | 2.76 | 2.45 | 2.12 | 2.12 | 0.02 | 0.21 | 0.34 | 0.34 | 1.64 |
| ALCAM | 1.50 | 2.35 | 2.04 | 2.68 | 2.05 | 3.07 | 2.34 | 0.22 | 0.56 | 0.79 | 0.91 | 0.76 |
| TOR3A | 1.98 | 1.89 | 0.87 | 2.14 | 0.98 | 2.54 | 2.40 | 1.08 | 0.75 | 0.90 | 1.12 | 0.77 |
| LMNA | 3.12 | 0.04 | 0.24 | 2.66 | 0.73 | 1.17 | 2.74 | 0.09 | 0.93 | 1.36 | 1.57 | 0.27 |
| ADAM10 | 1.04 | 1.49 | 2.16 | 1.34 | 1.34 | 1.85 | 1.99 | 2.69 | 3.61 | 3.77 | 3.53 | 3.52 |
| PTPRJ | 1.51 | 1.80 | 2.08 | 1.73 | 1.43 | 1.53 | 1.23 | 2.54 | 3.43 | 2.74 | 3.38 | 3.23 |
| FCAR | 1.47 | 1.94 | 2.69 | 1.83 | 2.05 | 1.39 | 1.40 | 2.30 | 2.49 | 3.84 | 3.64 | 4.00 |
| SIRPB1 | 0.17 | 2.50 | 2.49 | 1.33 | 1.03 | 1.10 | 1.63 | 3.06 | 3.19 | 4.07 | 4.87 | 3.67 |
| DMXL2 | 0.32 | 2.19 | 1.38 | 0.53 | 0.92 | 0.62 | 1.53 | 3.01 | 3.87 | 3.70 | 3.06 | 2.98 |
| LILRB1 | 0.28 | 3.10 | 2.46 | 2.30 | 1.59 | 1.72 | 2.33 | 4.85 | 4.89 | 3.47 | 3.50 | 2.67 |
| P2RX1 | 0.49 | 2.04 | 2.65 | 1.60 | 1.38 | 0.85 | 0.97 | 3.70 | 3.29 | 2.42 | 2.96 | 2.21 |
| TSPAN14 | 0.87 | 0.92 | 1.39 | 1.65 | 1.66 | 1.85 | 1.69 | 3.98 | 4.48 | 3.82 | 3.79 | 4.16 |
| LILRA5 | 0.24 | 1.17 | 1.34 | 2.73 | 1.28 | 1.35 | 2.09 | 4.73 | 4.61 | 3.97 | 4.25 | 2.70 |
| ICAM2 | 1.58 | 0.75 | 0.77 | 1.87 | 1.15 | 2.60 | 1.98 | 4.63 | 3.89 | 2.24 | 2.92 | 3.00 |
| EMR2 | 0.36 | 0.71 | 0.93 | 2.36 | 1.53 | 2.41 | 1.60 | 4.57 | 3.62 | 3.03 | 3.46 | 1.50 |
| FCGR3A | 0.63 | 0.51 | 0.43 | 0.46 | 0.54 | 0.73 | 0.64 | 8.86 | 7.14 | 2.55 | 4.51 | 6.10 |
| PGCP | 1.57 | 0.84 | 0.96 | 1.00 | 2.52 | 1.71 | 1.69 | 1.94 | 2.16 | 2.67 | 3.53 | 3.36 |
| TUBA4A | 1.57 | 0.13 | 0.32 | 0.95 | 1.37 | 0.98 | 0.70 | 2.38 | 1.98 | 2.53 | 3.74 | 2.19 |
| CLEC2B | 2.67 | 1.81 | 1.54 | 0.73 | 1.30 | 1.76 | 1.99 | 3.48 | 2.55 | 2.40 | 2.41 | 1.96 |
| SORL1 | 0.16 | 3.43 | 1.50 | 0.40 | 1.04 | 0.85 | 1.77 | 1.26 | 2.26 | 3.91 | 5.00 | 3.63 |
| ASAH1 | 2.45 | 1.65 | 1.27 | 2.38 | 3.42 | 2.81 | 3.82 | 6.45 | 6.60 | 6.07 | 6.10 | 5.34 |
| CTSA | 1.25 | 1.84 | 1.83 | 1.72 | 2.77 | 2.41 | 3.70 | 3.31 | 5.18 | 5.92 | 5.38 | 5.38 |
| SQRDL | 1.50 | 1.62 | 1.17 | 0.88 | 2.22 | 2.73 | 3.51 | 2.50 | 3.44 | 4.14 | 4.53 | 4.45 |
| PTAFR | 0.82 | 1.17 | 1.98 | 1.43 | 1.69 | 3.13 | 3.55 | 2.09 | 3.55 | 5.32 | 5.34 | 4.47 |
| PECAM1 | 2.40 | 3.38 | 2.19 | 1.09 | 2.49 | 2.33 | 2.62 | 5.36 | 4.59 | 4.22 | 4.36 | 3.46 |
| GNS | 1.54 | 2.87 | 2.23 | 1.55 | 1.50 | 2.00 | 2.96 | 4.53 | 4.88 | 4.89 | 4.42 | 4.09 |
| SERPINA1 | 1.40 | 0.48 | 0.47 | 0.42 | 1.78 | 3.81 | 5.18 | 7.99 | 7.62 | 7.29 | 7.50 | 6.74 |
| PILRA | 0.25 | 0.19 | 0.46 | 0.58 | 2.28 | 3.27 | 4.36 | 6.52 | 6.11 | 6.01 | 5.91 | 5.14 |
| FCGR2A | 0.24 | 0.28 | 0.58 | 0.52 | 0.58 | 2.86 | 3.47 | 4.00 | 4.66 | 5.70 | 6.47 | 4.99 |
| TLR2 | 0.46 | 0.05 | 0.26 | 0.24 | 1.17 | 1.76 | 2.84 | 2.83 | 4.19 | 4.45 | 5.00 | 3.71 |
| CLEC12A | 1.90 | 0.30 | 1.06 | 1.00 | 2.00 | 1.97 | 3.14 | 4.11 | 4.11 | 4.50 | 4.38 | 4.20 |
| PLBD1 | 2.63 | 0.17 | 0.36 | 0.78 | 3.44 | 4.09 | 6.09 | 2.09 | 4.23 | 6.29 | 6.01 | 6.23 |
| SIGLEC10 | 3.28 | 1.65 | 2.57 | 2.24 | 2.69 | 2.27 | 1.43 | 5.53 | 4.96 | 3.25 | 3.00 | 3.38 |
| CD83 | 3.76 | 0.74 | 1.01 | 1.83 | 3.22 | 2.85 | 2.01 | 2.90 | 4.39 | 2.57 | 1.77 | 2.42 |
| ACTN1 | 3.63 | 1.29 | 2.41 | 2.31 | 2.78 | 1.95 | 2.27 | 1.17 | 1.63 | 2.85 | 4.47 | 2.61 |
| ANPEP | 3.92 | 0.05 | 0.30 | 0.97 | 1.43 | 2.04 | 2.77 | 1.89 | 2.59 | 3.62 | 4.21 | 3.20 |
| LRP1 | 0.04 | 0.02 | 0.33 | 0.33 | 1.06 | 1.36 | 2.21 | 1.79 | 3.37 | 4.00 | 3.55 | 2.92 |
| TLR4 | 0.05 | 0.05 | 0.16 | 0.36 | 0.28 | 0.53 | 1.13 | 2.15 | 3.37 | 3.75 | 4.09 | 3.19 |
| BST1 | 0.09 | 0.90 | 0.36 | 0.17 | 0.44 | 0.42 | 2.63 | 1.15 | 2.43 | 4.73 | 4.74 | 3.50 |
| ITGAM | 0.01 | 0.23 | 0.37 | 0.43 | 0.66 | 0.91 | 1.29 | 0.41 | 2.93 | 4.52 | 4.10 | 4.30 |
| VNN2 | 0.77 | 0.29 | 0.14 | 0.41 | 0.48 | 0.71 | 0.49 | 1.07 | 1.70 | 5.16 | 6.18 | 3.94 |
| VCAN | 0.06 | 0.13 | 0.39 | 0.16 | 1.57 | 2.40 | 5.39 | 0.82 | 4.01 | 6.59 | 5.50 | 5.15 |
| CD14 | 0.05 | 0.08 | 0.23 | 0.16 | 0.30 | 0.69 | 4.30 | 0.88 | 5.64 | 8.16 | 7.23 | 6.84 |
| CD163 | 0.02 | 0.04 | 0.24 | 0.31 | 0.29 | 1.48 | 3.42 | 0.03 | 1.11 | 3.83 | 3.59 | 3.02 |
| F13A1 | 0.12 | 0.07 | 0.56 | 0.12 | 0.60 | 0.98 | 3.20 | 0.05 | 0.59 | 2.71 | 1.99 | 2.04 |
| FCGR1A | 0.04 | 0.05 | 0.08 | 0.00 | 0.00 | 0.37 | 1.09 | 0.48 | 1.96 | 2.83 | 2.51 | 2.45 |
| STAB1 | 0.00 | 0.02 | 0.17 | 0.00 | 0.24 | 0.09 | 1.43 | 0.06 | 1.69 | 3.00 | 2.37 | 2.17 |
| HLA-DRB4 | 7.90 | 5.91 | 0.48 | 6.39 | 1.64 | 7.81 | 7.53 | 5.94 | 1.58 | 1.09 | 0.93 | 1.75 |
| HLA-DQA2 | 5.53 | 3.06 | 0.78 | 4.20 | 3.67 | 5.50 | 4.49 | 2.19 | 0.83 | 0.31 | 0.07 | 0.58 |
| PLD4 | 1.73 | 7.30 | 5.81 | 4.80 | 3.82 | 4.52 | 4.48 | 3.49 | 0.93 | 0.60 | 0.29 | 0.31 |

TABLE E9E

Supervised analysis of candidate pathogen sensors (i.e. TLRs, NLRs, nucleic acid sensors) - average expression values across DC and monocyte subsets

| Gene.ID | 1 | 2 | 3 | 4 | 5 | 6 | 7 | 8 | 9 | 10 | 11 | 12 |
|---|---|---|---|---|---|---|---|---|---|---|---|---|
| HMGB1 | 5.59 | 5.61 | 5.70 | 5.47 | 5.61 | 5.39 | 5.16 | 4.90 | 4.90 | 5.34 | 5.38 | 6.01 |
| XRCC6 | 5.66 | 5.10 | 4.19 | 5.22 | 4.77 | 5.54 | 5.53 | 5.03 | 5.05 | 4.93 | 4.94 | 5.58 |
| SET | 4.88 | 4.63 | 4.20 | 4.15 | 4.78 | 4.71 | 4.78 | 4.08 | 4.18 | 4.12 | 3.76 | 4.62 |
| LRRFIP1 | 3.83 | 3.34 | 3.90 | 5.30 | 4.86 | 4.41 | 4.40 | 4.84 | 4.61 | 4.59 | 5.12 | 4.32 |
| PYCARD | 5.59 | 4.53 | 3.46 | 3.56 | 4.23 | 5.16 | 5.29 | 5.70 | 5.56 | 5.05 | 5.17 | 5.86 |
| TLR9 | 4.59 | 5.09 | 4.27 | 3.91 | 3.23 | 3.15 | 3.14 | 3.14 | 4.10 | 4.34 | 4.20 | 4.61 |
| IFI16 | 4.95 | 4.05 | 2.34 | 2.73 | 2.94 | 4.08 | 4.33 | 3.51 | 3.38 | 3.28 | 2.92 | 4.22 |
| CARD8 | 2.89 | 2.85 | 3.10 | 2.79 | 2.77 | 2.62 | 2.70 | 3.15 | 3.29 | 3.41 | 4.42 | 3.74 |
| HMGB2 | 2.38 | 2.39 | 3.40 | 1.28 | 2.89 | 3.11 | 4.00 | 2.70 | 2.78 | 4.74 | 4.42 | 4.52 |
| CASP1 | 1.67 | 1.09 | 1.63 | 2.89 | 6.05 | 6.21 | 6.35 | 7.11 | 6.74 | 6.35 | 6.60 | 6.11 |
| CIITA | 4.24 | 2.86 | 3.91 | 4.37 | 4.63 | 4.67 | 3.88 | 1.22 | 2.29 | 2.38 | 1.79 | 2.21 |
| TREX1 | 3.13 | 2.17 | 1.55 | 1.09 | 2.60 | 3.69 | 3.59 | 3.40 | 2.43 | 2.64 | 2.02 | 2.43 |
| NAIP | 1.20 | 1.03 | 1.96 | 1.62 | 2.34 | 2.76 | 3.57 | 0.88 | 2.45 | 4.24 | 4.27 | 3.68 |
| TMEM173 | 0.29 | 1.05 | 2.12 | 1.06 | 1.59 | 2.90 | 3.97 | 1.28 | 2.45 | 3.08 | 2.96 | 3.22 |
| PSTPIP1 | 3.16 | 0.29 | 1.25 | 2.77 | 2.18 | 1.90 | 3.53 | 1.06 | 1.40 | 3.34 | 3.52 | 3.70 |
| TLR2 | 0.46 | 0.05 | 0.26 | 0.24 | 1.17 | 1.76 | 2.84 | 2.83 | 4.19 | 4.45 | 5.00 | 3.71 |
| NLRP1 | 0.78 | 0.16 | 0.62 | 0.88 | 1.42 | 1.93 | 2.19 | 2.57 | 2.30 | 3.30 | 3.04 | 2.68 |
| TLR4 | 0.05 | 0.05 | 0.16 | 0.36 | 0.28 | 0.53 | 1.13 | 2.15 | 3.37 | 3.75 | 4.09 | 3.19 |
| DHX36 | 1.05 | 0.85 | 1.22 | 1.48 | 1.22 | 0.95 | 0.92 | 0.91 | 0.87 | 1.07 | 0.69 | 1.34 |
| MRE11A | 1.57 | 1.31 | 1.33 | 1.17 | 0.66 | 1.08 | 0.68 | 0.66 | 0.75 | 0.74 | 0.50 | 0.71 |
| ABCF1 | 1.30 | 1.17 | 1.16 | 1.39 | 1.59 | 1.56 | 1.43 | 0.75 | 1.89 | 1.62 | 1.13 | 2.41 |
| TLR10 | 3.40 | 1.46 | 1.05 | 1.09 | 1.18 | 1.18 | 0.48 | 0.54 | 0.60 | 0.60 | 0.86 | 0.92 |
| DDX58 | 0.25 | 0.26 | 0.82 | 0.29 | 0.41 | 0.83 | 0.78 | 1.73 | 0.65 | 0.82 | 1.24 | 1.93 |
| ZBP1 | 0.20 | 0.39 | 0.81 | 0.47 | 1.37 | 0.98 | 0.67 | 0.77 | 0.57 | 0.63 | 1.22 | 1.49 |
| TLR6 | 0.90 | 0.54 | 0.75 | 1.06 | 0.40 | 0.82 | 0.37 | 0.58 | 0.82 | 1.14 | 2.13 | 0.65 |
| TLR5 | 0.02 | 0.01 | 0.06 | 0.09 | 0.38 | 0.80 | 1.11 | 0.44 | 1.04 | 1.46 | 2.25 | 0.77 |
| CASP5 | 0.05 | 0.05 | 0.00 | 0.10 | 0.11 | 0.06 | 0.11 | 1.48 | 0.93 | 0.28 | 0.94 | 0.10 |
| TLR1 | 1.26 | 0.41 | 0.44 | 1.40 | 0.30 | 1.18 | 0.57 | 1.89 | 1.88 | 2.03 | 2.32 | 2.22 |
| TLR8 | 0.41 | 0.04 | 0.05 | 0.06 | 0.76 | 0.85 | 1.13 | 1.12 | 2.24 | 2.66 | 2.52 | 2.38 |
| TLR7 | 0.22 | 3.20 | 1.84 | 0.63 | 0.37 | 0.63 | 0.66 | 0.56 | 0.99 | 0.93 | 0.76 | 0.75 |

TABLE E9F

Supervised analysis of candidate transcription factors- average expression values across DC and monocyte subsets

| Gene.ID | 1 | 2 | 3 | 4 | 5 | 6 | 7 | 8 | 9 | 10 | 11 | 12 |
|---|---|---|---|---|---|---|---|---|---|---|---|---|
| SCML4 | 0.55 | 0.65 | 1.53 | 0.97 | 0.92 | 0.56 | 0.56 | 0.63 | 0.83 | 1.02 | 1.21 | 1.80 |
| ZNF571 | 0.53 | 0.75 | 1.39 | 0.81 | 0.97 | 0.50 | 0.53 | 0.46 | 0.71 | 0.76 | 0.91 | 1.88 |
| ATXN7 | 0.59 | 0.76 | 1.11 | 0.92 | 0.89 | 0.60 | 0.88 | 0.49 | 0.53 | 1.05 | 0.89 | 2.47 |
| ZNF611 | 0.63 | 0.76 | 0.95 | 0.77 | 0.65 | 0.54 | 0.69 | 0.46 | 0.60 | 0.60 | 0.88 | 2.01 |
| ZNF266 | 0.84 | 1.28 | 1.28 | 0.94 | 0.55 | 0.54 | 0.95 | 0.64 | 0.98 | 0.72 | 0.79 | 1.70 |
| CENPT | 0.63 | 0.94 | 0.74 | 0.79 | 0.54 | 0.51 | 1.04 | 0.65 | 0.91 | 1.04 | 0.76 | 1.65 |
| ZNF92 | 1.27 | 0.87 | 0.79 | 0.98 | 0.91 | 0.75 | 0.59 | 0.78 | 0.94 | 0.78 | 1.16 | 2.14 |
| SCAPER | 0.89 | 0.86 | 0.55 | 0.75 | 0.80 | 0.88 | 0.82 | 0.49 | 1.02 | 1.20 | 1.07 | 2.05 |
| ZNF335 | 0.72 | 0.78 | 1.25 | 0.98 | 1.07 | 0.90 | 1.05 | 0.96 | 1.09 | 1.17 | 1.11 | 1.95 |
| ZNF280D | 1.00 | 1.06 | 1.30 | 0.80 | 1.00 | 1.16 | 0.62 | 0.76 | 0.92 | 1.11 | 1.03 | 1.70 |
| ZNF605 | 0.79 | 0.93 | 1.50 | 0.87 | 1.19 | 0.85 | 0.83 | 0.77 | 0.94 | 1.26 | 1.69 | 1.66 |
| ELK4 | 1.11 | 1.25 | 1.43 | 1.31 | 1.46 | 0.96 | 1.03 | 0.53 | 1.26 | 1.31 | 1.29 | 2.12 |
| SATB1 | 1.17 | 0.99 | 1.00 | 1.76 | 1.48 | 1.18 | 1.08 | 0.54 | 0.50 | 0.89 | 0.92 | 1.82 |
| CBLL1 | 1.23 | 0.80 | 0.90 | 1.20 | 1.10 | 1.05 | 1.25 | 0.96 | 0.83 | 0.98 | 0.99 | 1.74 |
| MGMT | 1.50 | 1.11 | 0.87 | 0.76 | 0.40 | 1.00 | 1.48 | 1.10 | 1.30 | 1.01 | 0.83 | 1.85 |
| LYAR | 0.99 | 0.45 | 0.58 | 0.49 | 1.03 | 0.70 | 0.82 | 0.95 | 1.43 | 1.31 | 1.24 | 2.69 |
| ZNF281 | 0.75 | 0.74 | 0.52 | 0.77 | 0.54 | 0.65 | 0.92 | 0.65 | 1.39 | 1.86 | 1.53 | 2.08 |
| ARNTL | 0.63 | 0.25 | 0.28 | 0.64 | 0.92 | 0.57 | 0.79 | 0.98 | 0.95 | 1.21 | 1.54 | 1.82 |
| TGIF1 | 0.49 | 0.04 | 0.25 | 0.67 | 1.07 | 0.78 | 1.07 | 0.09 | 0.66 | 1.22 | 1.53 | 2.09 |
| ZNF516 | 1.78 | 0.50 | 0.31 | 0.54 | 0.81 | 0.55 | 0.72 | 0.63 | 0.88 | 1.12 | 1.42 | 1.86 |
| TRERF1 | 2.38 | 0.81 | 1.22 | 1.02 | 1.26 | 1.08 | 1.07 | 0.24 | 0.72 | 0.90 | 1.01 | 2.35 |
| MTF1 | 0.50 | 0.71 | 1.18 | 0.81 | 0.95 | 0.97 | 1.15 | 1.39 | 2.07 | 1.86 | 2.01 | 1.89 |
| NCOA2 | 0.75 | 0.60 | 0.72 | 0.50 | 0.92 | 0.74 | 0.95 | 1.50 | 1.94 | 1.90 | 1.90 | 2.02 |
| FOXO1 | 0.75 | 0.66 | 1.15 | 1.05 | 1.19 | 0.73 | 0.75 | 1.62 | 1.45 | 1.50 | 2.10 | 1.47 |
| ZNF217 | 0.60 | 0.97 | 1.02 | 1.02 | 1.07 | 0.92 | 0.82 | 1.45 | 1.28 | 1.46 | 1.87 | 1.17 |
| FOXO3 | 0.26 | 0.79 | 0.72 | 1.03 | 1.09 | 0.24 | 0.66 | 1.04 | 1.70 | 1.95 | 2.53 | 1.59 |
| SP1 | 1.40 | 0.47 | 0.82 | 0.77 | 1.06 | 0.79 | 0.93 | 1.01 | 1.47 | 1.81 | 1.62 | 1.60 |
| USF1 | 1.09 | 0.68 | 1.21 | 0.78 | 0.90 | 0.89 | 0.99 | 0.84 | 1.46 | 1.77 | 1.23 | 1.43 |
| ZBTB43 | 0.52 | 0.49 | 0.79 | 0.97 | 1.19 | 0.72 | 0.90 | 0.83 | 1.19 | 2.00 | 1.24 | 1.23 |
| PHF21A | 0.65 | 0.70 | 0.73 | 0.41 | 1.13 | 0.75 | 1.20 | 0.80 | 1.35 | 2.26 | 2.55 | 1.16 |
| PLXND1 | 0.88 | 0.17 | 0.89 | 0.31 | 0.76 | 0.44 | 1.27 | 0.88 | 1.38 | 1.69 | 2.06 | 1.09 |
| ZBTB16 | 0.26 | 0.44 | 0.90 | 0.53 | 0.65 | 0.26 | 0.26 | 0.59 | 1.18 | 2.05 | 2.42 | 1.99 |
| KLF7 | 0.55 | 0.29 | 0.20 | 0.21 | 0.24 | 0.20 | 0.51 | 0.88 | 1.49 | 1.57 | 2.39 | 2.16 |
| MBD2 | 0.54 | 0.31 | 0.54 | 0.60 | 0.67 | 0.29 | 0.27 | 1.60 | 1.64 | 1.34 | 0.96 | 1.39 |

TABLE E9F-continued

Supervised analysis of candidate transcription factors-
average expression values across DC and monocyte subsets

| Gene.ID | 1 | 2 | 3 | 4 | 5 | 6 | 7 | 8 | 9 | 10 | 11 | 12 |
|---|---|---|---|---|---|---|---|---|---|---|---|---|
| MXD3 | 0.35 | 0.23 | 0.45 | 0.46 | 0.68 | 0.66 | 0.57 | 1.86 | 1.06 | 0.98 | 1.20 | 1.21 |
| PLAGL2 | 0.22 | 0.17 | 0.64 | 0.31 | 0.06 | 0.34 | 0.42 | 1.27 | 1.57 | 1.08 | 1.38 | 0.65 |
| KLF11 | 0.80 | 0.23 | 0.13 | 0.24 | 0.78 | 0.98 | 0.92 | 2.04 | 1.71 | 1.55 | 1.47 | 1.17 |
| ZNF75D | 0.51 | 0.50 | 0.31 | 0.54 | 0.35 | 0.44 | 0.63 | 0.50 | 0.65 | 1.21 | 1.50 | 1.17 |
| NFIL3 | 0.09 | 0.11 | 0.40 | 0.09 | 0.45 | 0.40 | 0.60 | 0.48 | 0.65 | 2.00 | 1.77 | 0.94 |
| LCORL | 0.96 | 0.49 | 1.19 | 0.57 | 0.66 | 0.73 | 0.74 | 0.53 | 0.78 | 0.84 | 1.98 | 0.94 |
| PPARD | 0.66 | 0.80 | 1.65 | 1.88 | 1.37 | 0.80 | 0.85 | 0.66 | 1.06 | 1.22 | 1.80 | 0.88 |
| NFKBID | 0.62 | 0.58 | 1.23 | 2.09 | 1.51 | 0.82 | 0.64 | 0.22 | 1.22 | 1.14 | 1.70 | 1.15 |
| PHTF1 | 0.56 | 0.96 | 0.97 | 1.95 | 1.26 | 0.60 | 0.96 | 0.41 | 0.77 | 0.86 | 1.56 | 0.98 |
| ZNF791 | 0.25 | 1.30 | 0.96 | 2.72 | 1.20 | 1.03 | 0.63 | 0.55 | 1.25 | 1.07 | 1.11 | 1.38 |
| REST | 1.19 | 1.32 | 1.40 | 2.04 | 0.96 | 0.99 | 0.69 | 1.21 | 1.28 | 0.91 | 1.20 | 1.82 |
| TFEB | 0.91 | 0.40 | 0.67 | 1.91 | 0.84 | 1.44 | 1.05 | 0.63 | 1.10 | 1.14 | 1.33 | 1.58 |
| PPP1R10 | 1.03 | 0.90 | 0.34 | 2.12 | 0.70 | 1.10 | 1.09 | 0.61 | 0.82 | 0.79 | 1.12 | 0.77 |
| VDR | 1.03 | 0.18 | 0.39 | 2.28 | 1.44 | 0.86 | 0.82 | 0.93 | 1.06 | 0.67 | 0.35 | 0.33 |
| ELK3 | 0.64 | 0.50 | 0.83 | 1.98 | 1.17 | 0.51 | 0.94 | 0.51 | 0.57 | 1.03 | 0.68 | 0.97 |
| RUNX3 | 0.96 | 0.37 | 0.65 | 2.45 | 1.42 | 1.06 | 0.38 | 1.15 | 1.12 | 0.53 | 0.27 | 2.28 |
| ARID5B | 0.38 | 0.13 | 0.78 | 1.63 | 1.11 | 0.51 | 0.26 | 1.23 | 1.07 | 0.72 | 0.47 | 1.73 |
| SP140 | 1.65 | 0.05 | 0.45 | 1.80 | 1.38 | 1.24 | 0.77 | 0.71 | 0.58 | 0.33 | 0.62 | 2.04 |
| ZNF296 | 2.02 | 1.00 | 0.40 | 1.38 | 0.76 | 1.02 | 0.70 | 1.69 | 1.09 | 0.94 | 0.72 | 0.62 |
| ZNF595 | 1.13 | 1.65 | 2.00 | 1.20 | 1.52 | 1.00 | 0.88 | 0.83 | 0.86 | 0.94 | 0.59 | 1.05 |
| ARID1B | 1.15 | 1.76 | 1.69 | 1.05 | 0.92 | 0.67 | 0.69 | 0.65 | 0.73 | 1.16 | 0.65 | 1.54 |
| MEF2D | 0.44 | 1.48 | 1.86 | 1.32 | 1.64 | 0.65 | 0.61 | 0.41 | 0.69 | 0.96 | 0.91 | 1.20 |
| ZFY | 0.58 | 1.01 | 2.04 | 1.16 | 1.06 | 0.63 | 0.61 | 0.74 | 0.98 | 1.00 | 0.99 | 0.90 |
| HIST1H1C | 1.19 | 1.26 | 1.99 | 0.41 | 1.36 | 0.59 | 0.44 | 0.40 | 0.57 | 0.55 | 0.59 | 0.77 |
| HIVEP1 | 0.33 | 1.19 | 1.98 | 0.89 | 0.69 | 0.33 | 0.15 | 0.37 | 0.49 | 0.57 | 0.48 | 0.86 |
| HMGA1 | 2.11 | 1.26 | 1.15 | 1.05 | 1.39 | 1.22 | 1.26 | 0.30 | 0.44 | 0.62 | 0.50 | 0.49 |
| HIST1H1D | 1.80 | 1.22 | 1.63 | 0.68 | 1.44 | 0.74 | 0.93 | 0.29 | 0.21 | 0.22 | 0.26 | 0.75 |
| TRIT1 | 1.64 | 1.21 | 1.91 | 0.97 | 0.68 | 1.29 | 1.01 | 0.72 | 0.58 | 0.64 | 0.57 | 0.99 |
| ZBTB33 | 1.38 | 2.33 | 1.13 | 1.52 | 1.04 | 1.23 | 1.01 | 0.85 | 0.73 | 1.19 | 0.79 | 1.29 |
| XPA | 1.73 | 1.71 | 1.11 | 0.86 | 0.62 | 1.61 | 0.92 | 0.81 | 0.96 | 1.31 | 0.59 | 1.37 |
| ZNF22 | 1.92 | 2.33 | 1.10 | 1.78 | 1.09 | 1.42 | 0.78 | 0.53 | 0.78 | 0.58 | 1.44 | 0.93 |
| CREB3L2 | 0.64 | 2.87 | 1.67 | 1.20 | 1.17 | 1.12 | 1.22 | 0.75 | 1.18 | 1.44 | 0.64 | 2.15 |
| NFATC3 | 1.44 | 1.84 | 2.17 | 1.13 | 1.57 | 1.32 | 1.33 | 1.77 | 1.78 | 1.98 | 2.47 | 3.26 |
| KAT7 | 1.36 | 1.76 | 1.56 | 1.43 | 1.94 | 1.42 | 2.00 | 1.45 | 1.86 | 1.80 | 1.89 | 3.10 |
| BDP1 | 1.54 | 1.64 | 2.08 | 2.05 | 1.56 | 1.20 | 1.28 | 1.27 | 1.42 | 1.66 | 1.49 | 2.66 |
| FOXJ3 | 0.86 | 1.57 | 1.62 | 1.30 | 1.59 | 1.06 | 1.02 | 1.18 | 1.19 | 1.49 | 1.95 | 2.42 |
| ZNF622 | 1.96 | 0.98 | 1.59 | 1.58 | 1.53 | 1.64 | 1.52 | 1.74 | 1.89 | 1.59 | 1.27 | 2.84 |
| PSMD12 | 1.11 | 1.07 | 0.89 | 1.38 | 1.12 | 1.08 | 1.47 | 1.49 | 2.10 | 1.86 | 1.81 | 2.79 |
| GPATCH8 | 0.80 | 1.03 | 0.95 | 1.90 | 1.21 | 0.71 | 1.37 | 0.98 | 1.58 | 1.14 | 0.91 | 2.64 |
| CHD1 | 0.86 | 0.95 | 1.49 | 1.50 | 2.80 | 1.52 | 1.93 | 1.53 | 1.64 | 1.70 | 2.01 | 2.09 |
| FOXN3 | 1.00 | 0.58 | 1.21 | 0.94 | 1.70 | 1.93 | 2.18 | 1.19 | 1.87 | 2.01 | 1.46 | 2.74 |
| FARSA | 2.75 | 1.48 | 0.91 | 1.69 | 1.11 | 1.71 | 1.47 | 1.25 | 1.62 | 1.42 | 0.83 | 2.04 |
| RFX5 | 2.29 | 1.47 | 0.97 | 1.50 | 1.11 | 2.14 | 1.93 | 0.82 | 1.25 | 1.23 | 0.42 | 1.48 |
| TRMT1 | 2.08 | 1.28 | 0.80 | 0.76 | 1.28 | 2.13 | 2.36 | 1.01 | 1.31 | 1.62 | 1.58 | 1.52 |
| AHR | 2.34 | 0.86 | 0.97 | 1.21 | 1.62 | 3.04 | 2.22 | 0.85 | 1.45 | 2.21 | 1.98 | 2.61 |
| DMTF1 | 1.39 | 1.83 | 2.52 | 2.33 | 1.52 | 1.38 | 1.45 | 1.37 | 1.57 | 1.64 | 1.26 | 1.48 |
| SFPQ | 1.55 | 1.35 | 1.81 | 2.28 | 1.72 | 1.33 | 1.43 | 0.94 | 1.11 | 1.19 | 0.88 | 1.00 |
| ZCCHC11 | 0.78 | 2.69 | 2.88 | 2.48 | 1.71 | 0.91 | 0.94 | 0.79 | 0.95 | 1.46 | 1.28 | 1.69 |
| USF2 | 0.76 | 1.93 | 2.64 | 2.13 | 1.12 | 1.24 | 0.83 | 0.81 | 1.14 | 1.26 | 0.88 | 1.14 |
| SOX4 | 1.67 | 1.88 | 3.82 | 2.84 | 1.33 | 0.59 | 0.90 | 1.08 | 1.40 | 1.49 | 1.30 | 1.62 |
| AFF3 | 1.68 | 2.46 | 3.01 | 2.15 | 2.36 | 2.14 | 1.34 | 0.68 | 0.64 | 0.77 | 0.67 | 1.17 |
| HIST1H1E | 2.46 | 0.90 | 2.47 | 1.11 | 2.11 | 1.81 | 1.43 | 0.98 | 0.90 | 0.88 | 0.56 | 1.18 |
| KLF3 | 0.48 | 0.34 | 1.28 | 1.32 | 0.87 | 0.97 | 1.24 | 2.47 | 2.24 | 1.75 | 2.51 | 2.86 |
| RXRA | 0.42 | 0.23 | 0.44 | 1.56 | 0.86 | 0.81 | 1.42 | 2.57 | 2.64 | 2.28 | 1.98 | 2.44 |
| POU2F2 | 0.69 | 0.21 | 0.67 | 0.88 | 1.22 | 1.53 | 1.63 | 2.83 | 2.28 | 1.83 | 1.70 | 2.31 |
| PHTF2 | 0.87 | 0.80 | 1.21 | 0.80 | 0.81 | 0.95 | 0.84 | 3.38 | 2.66 | 1.78 | 2.33 | 1.59 |
| DRAP1 | 1.10 | 1.24 | 1.23 | 1.71 | 1.95 | 1.66 | 1.60 | 3.06 | 1.93 | 1.40 | 1.42 | 1.18 |
| DDIT3 | 1.39 | 0.22 | 0.44 | 0.69 | 1.32 | 1.55 | 1.22 | 1.38 | 1.98 | 2.33 | 2.38 | 2.31 |
| ZNF267 | 0.67 | 0.41 | 1.48 | 0.98 | 0.95 | 1.01 | 0.81 | 0.88 | 2.24 | 2.50 | 2.66 | 2.40 |
| CREB5 | 0.12 | 0.18 | 0.30 | 0.37 | 1.02 | 1.35 | 1.74 | 0.11 | 1.01 | 2.60 | 2.85 | 2.65 |
| CEBPD | 0.13 | 0.03 | 0.08 | 0.40 | 1.11 | 0.85 | 1.37 | 0.79 | 1.52 | 2.49 | 2.54 | 2.14 |
| ATF5 | 0.41 | 0.79 | 0.92 | 1.95 | 0.65 | 0.57 | 0.36 | 0.22 | 0.47 | 0.35 | 0.41 | 0.76 |
| ZHX2 | 0.16 | 0.77 | 1.07 | 2.21 | 0.39 | 0.17 | 0.13 | 0.30 | 0.19 | 0.33 | 0.51 | 0.35 |
| HIVEP2 | 0.61 | 0.20 | 0.66 | 1.64 | 0.54 | 0.72 | 0.59 | 0.34 | 0.22 | 0.19 | 0.26 | 0.57 |
| ZEB1 | 1.58 | 0.95 | 0.98 | 1.89 | 0.60 | 0.45 | 0.10 | 0.00 | 0.09 | 0.13 | 0.44 | 0.00 |
| KDM5D | 0.01 | 0.01 | 1.90 | 0.90 | 1.05 | 0.00 | 0.00 | 0.01 | 0.00 | 0.02 | 0.03 | 0.00 |
| CUL4B | 0.84 | 1.97 | 1.10 | 0.52 | 0.46 | 0.70 | 0.67 | 0.49 | 0.48 | 0.78 | 0.59 | 1.07 |
| SETBP1 | 0.54 | 1.73 | 1.13 | 0.22 | 0.22 | 0.17 | 0.01 | 1.19 | 0.86 | 0.27 | 0.13 | 0.85 |
| PLXNA4 | 0.00 | 2.56 | 1.26 | 0.81 | 0.18 | 0.05 | 0.00 | 0.01 | 0.03 | 0.04 | 0.04 | 0.00 |
| CUX2 | 0.00 | 1.64 | 0.93 | 0.05 | 0.04 | 0.00 | 0.00 | 0.01 | 0.03 | 0.09 | 0.07 | 0.00 |
| PRDM1 | 0.04 | 0.28 | 0.40 | 0.32 | 0.43 | 0.38 | 0.49 | 0.10 | 0.32 | 0.38 | 0.29 | 2.17 |
| IKZF3 | 0.00 | 0.02 | 0.20 | 0.25 | 0.11 | 0.00 | 0.00 | 0.00 | 0.01 | 0.08 | 0.27 | 2.82 |
| ETS1 | 0.08 | 0.95 | 0.50 | 0.27 | 0.10 | 0.04 | 0.00 | 0.13 | 0.06 | 0.21 | 0.28 | 1.65 |
| KLF12 | 0.10 | 0.69 | 1.05 | 0.91 | 0.55 | 0.39 | 0.68 | 0.70 | 0.42 | 0.26 | 0.00 | 2.27 |
| HOPX | 0.07 | 0.00 | 0.12 | 0.11 | 0.12 | 0.16 | 0.13 | 0.47 | 0.02 | 0.09 | 0.06 | 5.74 |

TABLE E9F-continued

Supervised analysis of candidate transcription factors-
average expression values across DC and monocyte subsets

| Gene.ID | 1 | 2 | 3 | 4 | 5 | 6 | 7 | 8 | 9 | 10 | 11 | 12 |
|---|---|---|---|---|---|---|---|---|---|---|---|---|
| CREM | 0.26 | 0.99 | 1.37 | 4.35 | 2.50 | 0.63 | 0.50 | 0.25 | 0.30 | 0.26 | 0.72 | 1.85 |
| STAT4 | 0.18 | 1.31 | 1.37 | 2.21 | 1.30 | 0.35 | 0.25 | 0.27 | 0.36 | 0.34 | 0.41 | 2.29 |
| ARID5A | 1.30 | 1.55 | 1.83 | 3.64 | 1.27 | 1.93 | 1.78 | 0.65 | 1.14 | 1.52 | 2.36 | 3.06 |
| SKIL | 0.67 | 0.49 | 1.11 | 4.04 | 1.40 | 1.35 | 1.11 | 1.48 | 1.60 | 1.32 | 1.64 | 0.86 |
| MAFB | 0.06 | 0.03 | 0.05 | 0.02 | 0.00 | 0.07 | 0.53 | 3.52 | 2.78 | 2.19 | 1.82 | 1.94 |
| TCF7L2 | 0.17 | 0.06 | 0.21 | 0.13 | 0.34 | 0.07 | 0.05 | 4.17 | 2.92 | 1.02 | 0.76 | 1.31 |
| KLF2 | 0.06 | 0.02 | 0.28 | 0.08 | 0.48 | 0.09 | 0.27 | 1.64 | 2.22 | 1.28 | 1.17 | 2.56 |
| FOSB | 1.89 | 1.12 | 2.65 | 1.08 | 4.11 | 3.05 | 3.32 | 1.47 | 0.95 | 2.05 | 2.41 | 1.19 |
| NR4A2 | 1.40 | 0.80 | 0.39 | 0.88 | 3.19 | 2.78 | 2.79 | 1.02 | 0.52 | 1.10 | 1.48 | 1.12 |
| NR4A1 | 0.59 | 0.30 | 1.19 | 1.56 | 3.57 | 0.97 | 1.69 | 2.45 | 2.06 | 0.66 | 0.28 | 0.28 |
| RNASE2 | 0.05 | 0.06 | 0.41 | 0.09 | 0.33 | 0.70 | 4.87 | 0.09 | 0.58 | 2.45 | 2.31 | 0.99 |
| BATF3 | 3.94 | 0.04 | 0.00 | 0.04 | 0.33 | 1.12 | 0.92 | 1.75 | 1.18 | 0.27 | 0.14 | 0.19 |
| ZNF366 | 3.74 | 0.03 | 0.11 | 0.25 | 0.34 | 1.15 | 0.41 | 0.02 | 0.00 | 0.06 | 0.00 | 0.51 |
| TCF4 | 1.07 | 5.75 | 5.16 | 3.80 | 1.37 | 1.00 | 1.16 | 0.74 | 0.54 | 0.48 | 0.31 | 1.01 |
| IRF4 | 0.17 | 4.49 | 5.59 | 2.99 | 3.17 | 1.70 | 0.99 | 0.27 | 0.28 | 0.32 | 0.49 | 0.49 |
| RUNX2 | 0.71 | 4.28 | 3.95 | 1.55 | 1.24 | 1.49 | 0.90 | 0.07 | 0.17 | 0.47 | 0.55 | 0.47 |
| ZFAT | 0.42 | 4.99 | 2.73 | 0.86 | 0.47 | 0.38 | 0.39 | 0.27 | 0.43 | 0.55 | 0.48 | 0.16 |
| MYBL2 | 0.04 | 3.64 | 2.01 | 0.21 | 0.12 | 0.02 | 0.02 | 0.01 | 0.02 | 0.14 | 0.00 | 0.00 |
| BACH1 | 1.78 | 0.51 | 1.03 | 1.31 | 1.78 | 1.11 | 1.80 | 2.71 | 3.30 | 3.27 | 4.06 | 3.34 |
| MXD1 | 1.07 | 0.50 | 1.69 | 1.73 | 2.02 | 1.50 | 2.06 | 1.64 | 2.59 | 3.28 | 5.00 | 2.79 |
| FOSL2 | 0.35 | 0.47 | 1.40 | 1.42 | 3.80 | 1.34 | 1.82 | 1.49 | 1.94 | 2.52 | 2.54 | 3.21 |
| ETS2 | 0.56 | 0.49 | 0.23 | 0.46 | 1.79 | 3.31 | 3.00 | 1.89 | 3.87 | 4.25 | 3.78 | 4.32 |
| EDF1 | 5.27 | 5.04 | 5.49 | 4.90 | 5.08 | 5.02 | 4.95 | 4.33 | 4.85 | 4.85 | 4.61 | 5.56 |
| CSDE1 | 4.83 | 4.38 | 4.53 | 4.77 | 4.62 | 4.54 | 4.71 | 4.28 | 5.08 | 5.04 | 4.92 | 4.45 |
| EIF3K | 5.82 | 5.16 | 5.41 | 5.70 | 5.95 | 6.04 | 6.13 | 5.67 | 5.64 | 5.60 | 5.10 | 5.70 |
| EOS | 8.08 | 4.89 | 4.84 | 4.76 | 7.70 | 8.34 | 8.77 | 7.35 | 6.43 | 8.24 | 8.15 | 7.61 |
| HMGB1 | 5.59 | 5.61 | 5.70 | 5.47 | 5.61 | 5.39 | 5.16 | 4.90 | 4.90 | 5.34 | 5.38 | 6.01 |
| NCOR1 | 4.35 | 4.34 | 4.94 | 4.46 | 4.71 | 4.32 | 4.66 | 4.20 | 4.61 | 4.94 | 4.98 | 4.88 |
| PLEK | 6.53 | 6.56 | 4.99 | 5.65 | 5.14 | 4.90 | 4.54 | 6.04 | 6.53 | 6.06 | 6.03 | 6.27 |
| ZFP36 | 4.54 | 5.62 | 4.68 | 5.03 | 5.37 | 5.41 | 5.69 | 5.71 | 5.23 | 5.31 | 5.14 | 5.09 |
| SP100 | 3.93 | 4.40 | 4.21 | 4.03 | 4.36 | 3.97 | 4.20 | 4.34 | 4.54 | 4.60 | 4.97 | 5.06 |
| U2AF1 | 4.58 | 4.65 | 4.16 | 5.15 | 4.63 | 4.25 | 4.53 | 3.82 | 4.04 | 4.26 | 4.17 | 4.48 |
| NONO | 4.75 | 4.75 | 4.29 | 4.53 | 4.55 | 4.46 | 4.59 | 4.37 | 4.60 | 4.55 | 3.50 | 4.51 |
| MBNL1 | 4.62 | 4.22 | 4.57 | 3.46 | 4.76 | 4.75 | 4.71 | 4.75 | 4.46 | 4.66 | 4.36 | 5.24 |
| ATF4 | 5.36 | 3.91 | 3.64 | 4.57 | 4.96 | 4.67 | 4.73 | 4.45 | 4.96 | 5.10 | 4.99 | 5.27 |
| NFKBIA | 5.34 | 4.22 | 3.27 | 4.76 | 4.61 | 5.64 | 5.93 | 5.65 | 6.74 | 6.69 | 6.58 | 6.50 |
| IRF8 | 8.04 | 8.46 | 7.63 | 5.98 | 4.98 | 4.54 | 4.70 | 3.45 | 4.26 | 4.47 | 3.77 | 4.25 |
| LRRFIP1 | 3.83 | 3.34 | 3.90 | 5.30 | 4.86 | 4.41 | 4.40 | 4.84 | 4.61 | 4.59 | 5.12 | 4.32 |
| EWSR1 | 4.36 | 4.18 | 3.18 | 4.33 | 3.60 | 3.87 | 4.09 | 4.48 | 4.29 | 3.95 | 3.80 | 3.74 |
| KLF6 | 5.17 | 5.37 | 4.43 | 2.84 | 3.95 | 4.10 | 4.81 | 5.65 | 4.92 | 5.09 | 5.03 | 5.24 |
| HLA-DQB1 | 8.03 | 4.85 | 3.94 | 6.74 | 6.82 | 7.60 | 6.51 | 2.73 | 5.58 | 5.18 | 4.85 | 5.67 |
| JUNB | 4.21 | 3.03 | 1.73 | 3.28 | 3.74 | 5.40 | 5.46 | 5.52 | 4.83 | 5.10 | 5.20 | 4.27 |
| ID2 | 6.94 | 1.82 | 1.17 | 3.01 | 4.31 | 4.93 | 5.62 | 5.23 | 6.11 | 4.82 | 4.83 | 6.30 |
| TSC22D3 | 3.43 | 2.11 | 2.93 | 3.58 | 4.57 | 5.28 | 5.51 | 6.96 | 6.69 | 6.27 | 6.79 | 6.76 |
| ZC3HAV1 | 2.51 | 2.80 | 3.62 | 3.51 | 4.96 | 2.95 | 3.18 | 3.14 | 2.54 | 2.80 | 2.87 | 2.94 |
| ZEB2 | 0.19 | 4.11 | 3.57 | 3.37 | 2.88 | 3.62 | 4.40 | 4.92 | 5.32 | 5.14 | 4.73 | 4.62 |
| CD36 | 1.33 | 4.73 | 3.36 | 1.67 | 2.57 | 3.09 | 5.16 | 1.55 | 4.71 | 6.63 | 5.63 | 5.23 |
| ZCCHC6 | 1.90 | 2.17 | 2.82 | 2.23 | 2.22 | 2.31 | 2.37 | 3.88 | 4.43 | 4.04 | 4.65 | 3.42 |
| SPIB | 1.42 | 5.33 | 4.46 | 4.74 | 2.32 | 2.19 | 1.59 | 1.35 | 1.59 | 1.81 | 2.24 | 2.33 |
| IRF7 | 2.21 | 6.92 | 4.73 | 3.95 | 1.64 | 2.15 | 2.64 | 2.26 | 1.20 | 1.74 | 1.20 | 1.81 |
| BCL11A | 3.23 | 5.86 | 5.81 | 3.49 | 3.86 | 3.51 | 2.54 | 1.31 | 1.21 | 1.01 | 1.56 | 1.43 |

TABLE E10A

Figure 11A:
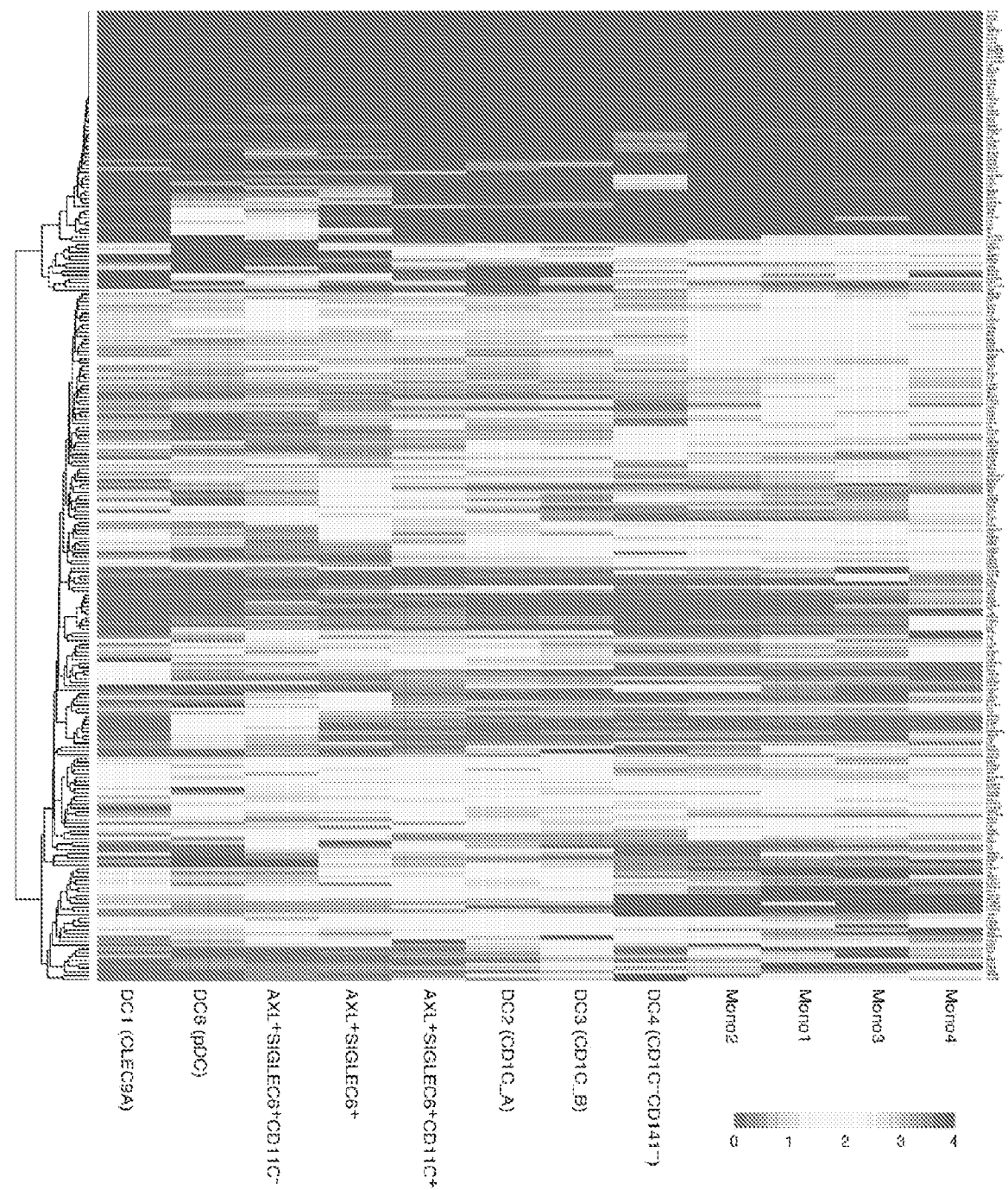
FIG. 11A-11B illustrates expression of GWAS loci in DC and monocyte subsets. Supervised analysis was performed on all immune-related susceptibility GWAS loci from the NHGRI-EBI Catalog of published genome-wide association studies (GWAS) (www.ebi.ac.uk/gwas/). Cross-referencing this cell atlas with the GWAS catalog of susceptibility loci contributing to immune disorders' risk should facilitate focus on the appropriate cell type for functional follow-up studies (panels A-B). (A, B) For both panels, a gene was included in the supervised analysis if it was expressed in at least 40% of the cells in any of the 12 clusters (Methods; based on the expression cutoff log(TPM+1)=2). Table E10A reports average expression matrix used to generate both heatmaps. (A) Heatmap illustrates supervised analysis of 255 candidate GWAS susceptibility loci that met the above criteria (Methods). A susceptibility gene was included in the analysis if it had been reported in at least one GWAS. Table E10B compiles the studies associated with genes reported in panel A. (B) Heatmap illustrates supervised analysis of 99 candidate GWAS susceptibility loci. A susceptibility gene was included in the analysis if it had been reported in at least two GWAS. Table E10C compiles the studies associated with genes reported in panel B.
Figure 11B:
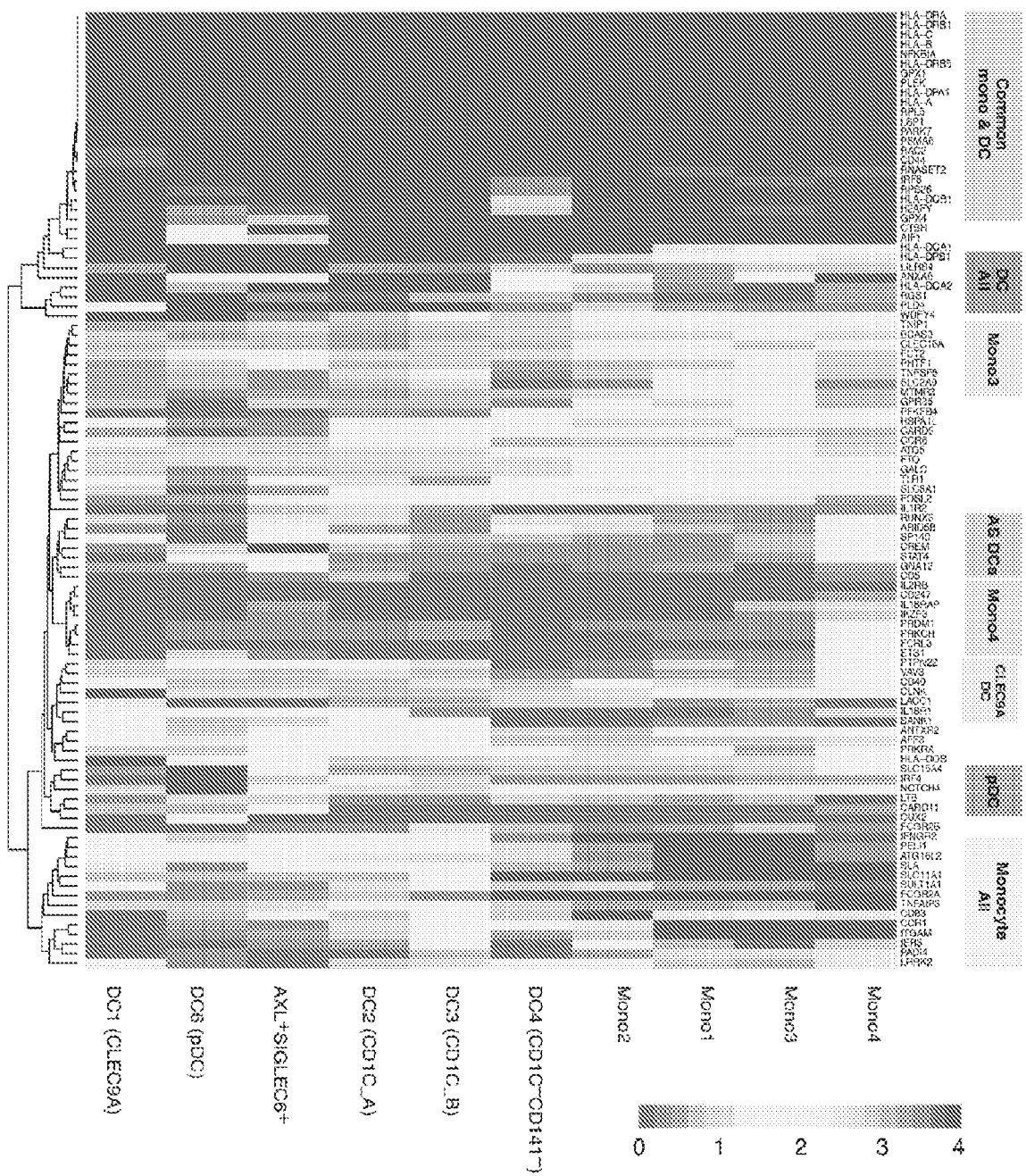

Supervised analysis of 255 candidate GWAS susceptibility loci - average
expression values across DC and monocyte subsets (see FIG. 11A-B)

| Gene.ID | 1 | 2 | 3 | 4 | 5 | 6 | 7 | 8 | 9 | 10 | 11 | 12 |
|---|---|---|---|---|---|---|---|---|---|---|---|---|
| CALM3 | 5.35 | 4.94 | 4.73 | 5.52 | 5.22 | 5.16 | 5.32 | 5.24 | 5.10 | 5.09 | 5.26 | 5.72 |
| ARPC2 | 7.58 | 6.95 | 6.42 | 7.00 | 7.01 | 7.31 | 7.16 | 7.62 | 7.28 | 7.07 | 7.23 | 7.17 |
| COX4I1 | 6.49 | 6.41 | 6.31 | 6.49 | 6.63 | 6.57 | 6.79 | 6.32 | 6.41 | 6.51 | 6.06 | 6.33 |
| FOS | 8.08 | 4.89 | 4.84 | 4.76 | 7.70 | 8.34 | 8.77 | 7.35 | 6.43 | 8.24 | 8.15 | 7.61 |
| GPX1 | 6.57 | 7.52 | 6.70 | 6.61 | 5.50 | 6.43 | 7.01 | 4.28 | 5.48 | 7.05 | 6.06 | 6.84 |
| HERPUD1 | 4.50 | 7.15 | 6.62 | 6.49 | 5.84 | 4.45 | 4.90 | 4.51 | 4.73 | 5.05 | 5.11 | 4.58 |
| HLA-A | 7.81 | 7.49 | 7.22 | 7.88 | 7.36 | 7.48 | 7.71 | 7.77 | 8.15 | 8.32 | 8.54 | 8.54 |
| HLA-B | 8.20 | 8.06 | 8.63 | 8.57 | 8.44 | 7.71 | 7.87 | 8.25 | 8.81 | 8.97 | 9.10 | 9.08 |
| HLA-C | 8.32 | 8.17 | 7.25 | 8.00 | 7.22 | 7.93 | 8.02 | 8.51 | 8.66 | 8.82 | 9.05 | 8.92 |
| HLA-DPA1 | 9.40 | 7.56 | 7.76 | 8.84 | 9.13 | 8.80 | 8.23 | 7.47 | 7.79 | 5.81 | 5.32 | 6.59 |
| HLA-DPB2 | 9.03 | 7.24 | 6.22 | 7.86 | 7.72 | 8.61 | 7.88 | 6.48 | 7.04 | 5.10 | 4.57 | 5.45 |
| HLA-DRA | 10.44 | 9.18 | 8.67 | 9.62 | 9.97 | 10.39 | 9.87 | 8.59 | 8.98 | 8.23 | 7.87 | 8.48 |
| HLA-DRB1 | 10.07 | 8.57 | 8.17 | 8.83 | 9.41 | 9.87 | 9.41 | 8.32 | 8.35 | 7.76 | 7.02 | 7.79 |

TABLE E10A-continued

Supervised analysis of 255 candidate GWAS susceptibility loci - average expression values across DC and monocyte subsets (see FIG. 11A-B)

| Gene.ID | 1 | 2 | 3 | 4 | 5 | 6 | 7 | 8 | 9 | 10 | 11 | 12 |
|---|---|---|---|---|---|---|---|---|---|---|---|---|
| HLA-DRB5 | 7.45 | 5.86 | 4.81 | 6.18 | 6.16 | 7.19 | 6.74 | 5.58 | 6.04 | 5.37 | 4.69 | 5.59 |
| LSP1 | 7.09 | 6.31 | 5.82 | 6.28 | 6.80 | 6.96 | 6.81 | 6.30 | 7.13 | 7.13 | 6.90 | 6.64 |
| MYL12B | 6.26 | 6.80 | 4.95 | 6.22 | 5.35 | 6.25 | 6.17 | 6.90 | 6.11 | 6.12 | 5.84 | 6.28 |
| PARK7 | 5.59 | 6.67 | 5.83 | 5.46 | 4.95 | 5.36 | 5.61 | 4.30 | 4.95 | 4.75 | 4.78 | 5.11 |
| PLEK | 6.53 | 6.56 | 4.99 | 5.65 | 5.14 | 4.90 | 4.54 | 6.04 | 6.53 | 6.06 | 6.03 | 6.27 |
| PSMB1 | 5.71 | 4.56 | 4.16 | 5.31 | 4.84 | 5.84 | 6.02 | 5.68 | 5.40 | 5.20 | 4.50 | 5.44 |
| PTPRC | 5.10 | 4.45 | 4.15 | 4.54 | 5.94 | 5.71 | 5.69 | 6.75 | 6.83 | 6.54 | 6.65 | 6.34 |
| RPL41 | 7.92 | 8.01 | 8.56 | 8.02 | 8.42 | 7.91 | 7.81 | 7.58 | 7.75 | 7.65 | 7.40 | 7.87 |
| RPL5 | 8.13 | 7.99 | 8.43 | 8.25 | 8.18 | 7.90 | 8.04 | 7.20 | 7.56 | 7.56 | 7.06 | 7.93 |
| RPL7 | 8.41 | 8.36 | 8.29 | 8.39 | 8.31 | 8.36 | 8.33 | 7.86 | 8.00 | 7.95 | 7.37 | 8.17 |
| TAGLN2 | 7.55 | 7.81 | 7.11 | 6.83 | 7.15 | 7.15 | 7.03 | 4.76 | 5.43 | 5.96 | 6.77 | 6.16 |
| CDC42 | 4.84 | 3.87 | 4.13 | 4.48 | 4.88 | 4.93 | 5.11 | 5.43 | 5.23 | 5.05 | 4.88 | 5.50 |
| ATF4 | 5.36 | 3.91 | 3.64 | 4.57 | 4.96 | 4.67 | 4.73 | 4.45 | 4.96 | 5.10 | 4.99 | 5.27 |
| PSMA6 | 5.52 | 5.06 | 3.73 | 4.18 | 5.17 | 4.88 | 5.19 | 4.20 | 4.29 | 4.12 | 3.81 | 4.53 |
| CSNK2B | 4.51 | 3.94 | 3.81 | 3.85 | 4.13 | 4.25 | 3.94 | 4.20 | 4.40 | 4.55 | 4.45 | 5.49 |
| RAC2 | 3.63 | 6.58 | 5.15 | 4.03 | 5.05 | 5.58 | 5.73 | 6.63 | 6.11 | 5.91 | 5.96 | 6.31 |
| CD44 | 3.64 | 3.87 | 4.35 | 5.08 | 4.91 | 4.67 | 5.00 | 5.30 | 5.76 | 6.25 | 5.91 | 5.53 |
| PSMA4 | 5.24 | 3.72 | 3.77 | 3.72 | 4.80 | 5.06 | 5.29 | 5.34 | 4.93 | 4.53 | 3.90 | 3.75 |
| RNASET2 | 4.69 | 6.27 | 4.48 | 4.12 | 4.11 | 4.41 | 4.18 | 4.65 | 4.02 | 3.64 | 4.61 | 3.62 |
| CXCR4 | 5.74 | 5.94 | 5.10 | 5.51 | 6.88 | 6.31 | 5.86 | 3.55 | 5.97 | 6.07 | 6.70 | 7.02 |
| IRF8 | 8.04 | 8.46 | 7.63 | 5.98 | 4.98 | 4.54 | 4.70 | 3.45 | 4.26 | 4.47 | 3.77 | 4.25 |
| DDX39B | 4.29 | 3.87 | 3.97 | 3.75 | 4.33 | 4.09 | 4.22 | 3.60 | 4.31 | 4.42 | 4.66 | 4.15 |
| RPS26 | 4.43 | 3.76 | 3.66 | 5.22 | 4.13 | 3.84 | 4.26 | 3.56 | 5.47 | 5.41 | 5.45 | 5.50 |
| CDC37 | 4.00 | 3.92 | 3.52 | 3.72 | 4.03 | 3.89 | 4.60 | 3.47 | 4.12 | 4.47 | 4.01 | 4.69 |
| NFKBIA | 5.34 | 4.22 | 3.27 | 4.76 | 4.61 | 5.64 | 5.93 | 5.65 | 6.74 | 6.69 | 6.58 | 6.50 |
| CAPZB | 4.86 | 3.99 | 3.44 | 3.58 | 4.30 | 4.58 | 4.83 | 5.35 | 4.75 | 4.38 | 3.91 | 4.92 |
| ASTN2 | 3.57 | 4.31 | 5.17 | 4.20 | 4.54 | 3.67 | 3.61 | 3.90 | 4.56 | 4.63 | 5.08 | 4.91 |
| CFLAR | 4.09 | 3.80 | 4.30 | 3.98 | 4.04 | 3.56 | 3.37 | 4.25 | 4.49 | 4.60 | 5.06 | 4.86 |
| IFNAR2 | 3.22 | 4.93 | 4.42 | 3.95 | 4.05 | 3.47 | 4.06 | 4.55 | 4.97 | 4.68 | 5.41 | 5.17 |
| PRDX5 | 4.63 | 3.78 | 3.49 | 3.54 | 3.07 | 4.01 | 4.08 | 3.95 | 4.05 | 4.17 | 4.36 | 5.00 |
| HLA-DQB1 | 8.03 | 4.85 | 3.94 | 6.74 | 6.82 | 7.60 | 6.51 | 2.73 | 5.58 | 5.18 | 4.85 | 5.67 |
| LITAF | 4.07 | 3.92 | 3.47 | 5.40 | 5.34 | 4.78 | 4.58 | 2.68 | 4.16 | 4.32 | 6.35 | 5.60 |
| H2AFY | 4.46 | 3.33 | 3.89 | 3.65 | 4.07 | 4.33 | 4.31 | 2.92 | 3.97 | 4.19 | 3.77 | 4.80 |
| SYK | 4.30 | 4.34 | 3.18 | 3.32 | 3.91 | 4.24 | 4.44 | 2.99 | 3.94 | 4.02 | 4.31 | 4.18 |
| PSMB9 | 6.09 | 3.82 | 3.79 | 3.06 | 4.02 | 4.76 | 4.42 | 5.56 | 5.15 | 4.13 | 4.53 | 5.19 |
| GPX4 | 3.90 | 3.46 | 3.43 | 2.83 | 3.92 | 4.46 | 4.83 | 4.29 | 4.25 | 4.94 | 4.33 | 4.56 |
| OSTF1 | 4.67 | 3.28 | 2.79 | 3.44 | 4.28 | 4.32 | 4.47 | 4.83 | 4.50 | 4.25 | 4.52 | 4.79 |
| ANKRD44 | 3.76 | 2.92 | 3.04 | 2.80 | 4.22 | 4.31 | 3.58 | 4.13 | 4.09 | 4.10 | 4.36 | 4.66 |
| HLA-F | 4.52 | 3.00 | 2.83 | 4.22 | 3.20 | 3.42 | 3.47 | 5.12 | 5.88 | 5.93 | 6.24 | 6.57 |
| CD48 | 5.97 | 1.73 | 3.44 | 4.75 | 5.49 | 5.67 | 5.47 | 6.23 | 6.13 | 5.62 | 5.14 | 6.01 |
| CTSH | 4.67 | 2.00 | 2.90 | 4.68 | 5.50 | 6.56 | 6.55 | 4.48 | 5.45 | 6.13 | 5.35 | 5.93 |
| LGALS9 | 4.72 | 1.92 | 2.57 | 3.65 | 4.08 | 4.11 | 4.51 | 4.61 | 4.50 | 3.97 | 3.17 | 4.06 |
| HCK | 5.43 | 0.97 | 2.38 | 4.10 | 4.25 | 4.99 | 5.41 | 7.02 | 7.01 | 6.23 | 6.33 | 6.17 |
| LST1 | 3.78 | 1.33 | 2.10 | 4.34 | 5.53 | 6.04 | 5.69 | 7.63 | 6.67 | 5.91 | 5.71 | 5.27 |
| AIF1 | 5.37 | 1.81 | 2.28 | 2.68 | 5.63 | 6.18 | 6.22 | 7.87 | 7.15 | 6.72 | 6.72 | 6.56 |
| ID2 | 6.94 | 1.82 | 1.17 | 3.01 | 4.31 | 4.93 | 5.62 | 5.23 | 6.11 | 4.82 | 4.83 | 6.30 |
| HLA-DQA1 | 8.32 | 6.22 | 2.75 | 6.07 | 7.56 | 8.32 | 7.47 | 4.96 | 4.73 | 2.44 | 2.06 | 2.38 |
| HLA-DPB1 | 7.09 | 4.81 | 6.66 | 6.84 | 8.11 | 6.69 | 5.76 | 3.73 | 2.66 | 1.40 | 1.61 | 2.53 |
| HIGD1A | 2.49 | 5.91 | 3.93 | 2.51 | 2.84 | 2.41 | 2.58 | 2.91 | 2.70 | 2.71 | 2.10 | 1.97 |
| SEC61G | 2.93 | 4.31 | 4.15 | 2.52 | 2.12 | 2.45 | 3.34 | 2.26 | 2.33 | 2.33 | 1.52 | 1.43 |
| IRF7 | 2.21 | 6.92 | 4.73 | 3.95 | 1.64 | 2.15 | 2.64 | 2.26 | 1.20 | 1.74 | 1.20 | 1.81 |
| SLAMF7 | 6.17 | 5.28 | 4.21 | 4.10 | 2.43 | 2.20 | 0.96 | 2.30 | 2.37 | 1.51 | 1.80 | 2.94 |
| WDFY4 | 6.07 | 4.10 | 3.68 | 3.58 | 3.21 | 2.82 | 1.79 | 0.89 | 1.34 | 1.55 | 1.79 | 1.76 |
| LILRB4 | 0.48 | 5.73 | 4.46 | 4.44 | 2.65 | 3.26 | 3.51 | 2.95 | 3.59 | 3.21 | 2.99 | 2.81 |
| LPXN | 1.15 | 4.22 | 2.75 | 4.66 | 3.33 | 4.32 | 3.83 | 1.73 | 2.13 | 2.77 | 2.58 | 1.64 |
| GPR183 | 4.57 | 7.36 | 4.93 | 6.55 | 5.68 | 5.21 | 5.89 | 0.57 | 1.93 | 2.73 | 2.70 | 3.46 |
| ANXA6 | 4.87 | 2.23 | 2.84 | 1.60 | 3.80 | 3.81 | 3.94 | 1.37 | 1.61 | 3.20 | 2.04 | 5.22 |
| HLA-DOA | 3.95 | 2.62 | 2.34 | 2.47 | 3.65 | 4.27 | 2.99 | 0.69 | 1.08 | 0.83 | 1.04 | 1.36 |
| RGS1 | 4.59 | 4.71 | 2.43 | 3.43 | 2.62 | 3.61 | 3.09 | 0.75 | 0.26 | 0.13 | 0.18 | 0.58 |
| HLA-DQA2 | 5.53 | 3.06 | 0.78 | 4.20 | 3.67 | 5.50 | 4.49 | 2.19 | 0.83 | 0.31 | 0.07 | 0.58 |
| PLD4 | 1.73 | 7.30 | 5.81 | 4.80 | 3.82 | 4.52 | 4.48 | 3.49 | 0.93 | 0.60 | 0.29 | 0.31 |
| CLEC16A | 0.78 | 0.87 | 0.82 | 0.74 | 1.31 | 0.54 | 0.87 | 0.73 | 1.24 | 1.31 | 0.82 | 1.64 |
| SCAPER | 0.89 | 0.86 | 0.55 | 0.75 | 0.80 | 0.88 | 0.82 | 0.49 | 1.02 | 1.20 | 1.07 | 2.05 |
| USF1 | 1.09 | 0.68 | 1.21 | 0.78 | 0.90 | 0.89 | 0.99 | 0.84 | 1.46 | 1.77 | 1.23 | 1.43 |
| DGKD | 0.41 | 0.97 | 1.37 | 1.22 | 1.07 | 0.73 | 1.14 | 0.40 | 0.70 | 1.26 | 1.52 | 2.04 |
| BCO2 | 0.61 | 0.78 | 2.01 | 0.90 | 1.33 | 0.72 | 0.67 | 0.66 | 0.94 | 1.31 | 1.29 | 1.20 |
| ATG5 | 0.99 | 1.02 | 1.22 | 0.92 | 0.90 | 1.01 | 1.15 | 1.41 | 1.54 | 1.46 | 1.31 | 2.65 |
| FTO | 1.18 | 1.03 | 1.33 | 1.15 | 1.33 | 1.14 | 1.19 | 1.03 | 1.28 | 1.24 | 1.47 | 2.19 |
| CENPC1 | 0.91 | 1.61 | 1.73 | 1.24 | 0.87 | 1.18 | 0.98 | 0.86 | 1.34 | 1.59 | 1.24 | 2.19 |
| FUT2 | 0.93 | 1.22 | 1.99 | 1.27 | 1.19 | 1.10 | 0.86 | 1.03 | 1.30 | 1.47 | 2.07 | 0.99 |
| ATXN2 | 0.98 | 1.04 | 1.31 | 0.90 | 1.10 | 1.09 | 1.01 | 1.03 | 1.27 | 1.29 | 1.84 | 0.90 |
| ANO6 | 1.01 | 0.89 | 1.12 | 0.75 | 1.83 | 0.84 | 1.20 | 1.07 | 1.41 | 1.88 | 1.94 | 1.29 |
| PIM3 | 0.96 | 1.75 | 0.90 | 0.75 | 1.20 | 0.93 | 0.97 | 0.50 | 1.89 | 1.92 | 2.11 | 1.48 |
| GALC | 0.94 | 0.39 | 0.70 | 0.79 | 0.96 | 0.97 | 0.92 | 1.07 | 1.95 | 1.60 | 1.97 | 2.23 |
| MFN2 | 0.88 | 0.52 | 0.61 | 0.98 | 0.81 | 0.70 | 1.04 | 1.06 | 1.74 | 2.00 | 1.73 | 1.87 |

TABLE E10A-continued

Supervised analysis of 255 candidate GWAS susceptibility loci - average
expression values across DC and monocyte subsets (see FIG. 11A-B)

| Gene.ID | 1 | 2 | 3 | 4 | 5 | 6 | 7 | 8 | 9 | 10 | 11 | 12 |
|---|---|---|---|---|---|---|---|---|---|---|---|---|
| MTF1 | 0.50 | 0.71 | 1.18 | 0.81 | 0.95 | 0.97 | 1.15 | 1.39 | 2.07 | 1.86 | 2.01 | 1.89 |
| RAP1GAP2 | 0.41 | 0.83 | 0.89 | 1.05 | 1.15 | 0.51 | 0.58 | 1.74 | 2.15 | 1.55 | 1.50 | 1.59 |
| FOXO3 | 0.26 | 0.79 | 0.72 | 1.03 | 1.09 | 0.24 | 0.66 | 1.04 | 1.70 | 1.95 | 2.53 | 1.59 |
| MGMT | 1.50 | 1.11 | 0.87 | 0.76 | 0.40 | 1.00 | 1.48 | 1.10 | 1.30 | 1.01 | 0.83 | 1.85 |
| CD40 | 2.14 | 0.67 | 1.21 | 0.71 | 0.54 | 0.73 | 1.08 | 0.74 | 1.36 | 1.06 | 0.72 | 1.41 |
| TNIP1 | 0.59 | 0.71 | 0.68 | 1.04 | 1.28 | 0.72 | 0.96 | 0.95 | 1.32 | 1.27 | 1.69 | 1.23 |
| RIT1 | 0.45 | 0.55 | 0.42 | 1.22 | 0.83 | 0.73 | 1.03 | 0.50 | 1.14 | 1.29 | 1.96 | 0.81 |
| BCAS3 | 0.81 | 0.54 | 1.08 | 0.79 | 0.65 | 0.45 | 0.66 | 0.85 | 1.00 | 1.09 | 1.58 | 1.19 |
| CLYBL | 0.54 | 0.75 | 0.90 | 0.71 | 0.86 | 0.57 | 0.65 | 0.86 | 0.72 | 0.89 | 1.43 | 0.98 |
| TLR6 | 0.90 | 0.54 | 0.75 | 1.06 | 0.40 | 0.82 | 0.37 | 0.58 | 0.82 | 1.14 | 2.13 | 0.65 |
| MTMR3 | 0.59 | 0.30 | 0.56 | 0.57 | 0.62 | 0.58 | 0.64 | 0.70 | 1.05 | 1.84 | 1.96 | 0.63 |
| ABHD5 | 0.45 | 0.32 | 0.36 | 0.56 | 0.53 | 0.47 | 0.51 | 0.71 | 0.92 | 1.46 | 2.44 | 1.22 |
| NFIL3 | 0.09 | 0.11 | 0.40 | 0.09 | 0.45 | 0.40 | 0.60 | 0.48 | 0.65 | 2.00 | 1.77 | 0.94 |
| ABCA1 | 0.06 | 0.02 | 0.41 | 0.50 | 0.14 | 0.00 | 0.02 | 0.50 | 1.15 | 1.02 | 1.76 | 0.88 |
| TNFSF8 | 0.43 | 0.64 | 0.84 | 0.27 | 0.96 | 1.18 | 1.39 | 0.27 | 0.94 | 1.59 | 1.86 | 0.99 |
| SLC2A9 | 0.45 | 0.68 | 0.41 | 0.37 | 0.83 | 0.69 | 1.11 | 0.17 | 0.35 | 1.22 | 1.82 | 0.27 |
| IGF2R | 0.23 | 0.81 | 0.82 | 0.36 | 0.27 | 0.09 | 0.13 | 0.20 | 0.88 | 1.41 | 2.28 | 1.90 |
| CCNY | 0.71 | 0.40 | 0.35 | 0.62 | 0.91 | 1.03 | 1.23 | 0.55 | 1.48 | 1.77 | 2.93 | 1.95 |
| TRIB1 | 0.20 | 0.06 | 0.29 | 0.86 | 0.54 | 1.30 | 0.82 | 0.71 | 1.07 | 1.54 | 2.51 | 1.83 |
| TGIF1 | 0.49 | 0.04 | 0.25 | 0.67 | 1.07 | 0.78 | 1.07 | 0.09 | 0.66 | 1.22 | 1.53 | 2.09 |
| GPR35 | 0.65 | 0.04 | 0.12 | 0.97 | 1.49 | 0.76 | 0.72 | 0.37 | 2.06 | 1.08 | 1.36 | 0.66 |
| SVIL | 0.63 | 0.11 | 0.25 | 0.39 | 1.25 | 0.57 | 0.73 | 1.92 | 1.32 | 1.13 | 1.40 | 1.50 |
| PFKFB4 | 0.20 | 0.03 | 0.10 | 0.04 | 0.40 | 0.43 | 0.34 | 1.56 | 1.51 | 1.68 | 1.62 | 1.66 |
| TTYH3 | 0.28 | 0.22 | 0.58 | 0.47 | 0.84 | 0.75 | 0.63 | 2.03 | 2.43 | 1.88 | 1.27 | 0.76 |
| GCH1 | 0.35 | 0.17 | 0.31 | 0.24 | 0.60 | 0.45 | 0.57 | 1.95 | 1.50 | 1.23 | 0.86 | 0.38 |
| SAMD9L | 0.93 | 1.12 | 0.27 | 0.74 | 0.73 | 2.17 | 1.18 | 2.06 | 1.13 | 0.86 | 0.82 | 1.51 |
| HSPA1L | 1.31 | 0.47 | 0.14 | 0.24 | 0.25 | 1.23 | 1.38 | 2.07 | 1.00 | 1.14 | 1.68 | 1.23 |
| CARD9 | 0.56 | 0.01 | 0.03 | 0.24 | 0.68 | 1.56 | 1.92 | 2.06 | 1.86 | 1.42 | 0.97 | 0.72 |
| GABBR1 | 0.45 | 0.41 | 0.67 | 0.30 | 1.66 | 1.26 | 1.61 | 1.42 | 0.99 | 0.90 | 0.21 | 0.48 |
| SAX18 | 0.18 | 1.29 | 1.13 | 0.50 | 0.58 | 0.69 | 0.47 | 1.68 | 1.05 | 0.59 | 0.25 | 0.93 |
| CCR6 | 1.37 | 0.94 | 1.78 | 0.86 | 1.46 | 2.31 | 1.97 | 0.63 | 0.85 | 0.97 | 1.22 | 0.97 |
| IL27RA | 0.64 | 0.68 | 0.41 | 0.28 | 0.69 | 1.55 | 2.18 | 0.37 | 1.31 | 1.68 | 1.07 | 0.99 |
| PPIL4 | 1.12 | 0.99 | 1.31 | 2.11 | 1.00 | 0.95 | 0.94 | 0.89 | 1.26 | 1.32 | 1.31 | 1.19 |
| PHTF1 | 0.56 | 0.96 | 0.97 | 1.95 | 1.26 | 0.60 | 0.96 | 0.41 | 0.77 | 0.86 | 1.56 | 0.98 |
| ARHGAP18 | 0.92 | 1.70 | 0.83 | 2.09 | 0.76 | 1.01 | 0.86 | 0.24 | 0.59 | 0.72 | 0.93 | 0.87 |
| SIGLEC5 | 0.07 | 1.18 | 0.87 | 2.14 | 1.44 | 1.83 | 1.44 | 1.13 | 0.73 | 1.05 | 1.56 | 1.05 |
| GNA12 | 0.58 | 0.59 | 0.92 | 1.70 | 0.98 | 0.42 | 0.36 | 0.20 | 0.29 | 0.45 | 0.11 | 0.53 |
| ZHX2 | 0.16 | 0.77 | 1.07 | 2.21 | 0.39 | 0.17 | 0.13 | 0.30 | 0.19 | 0.33 | 0.51 | 0.35 |
| VDR | 1.03 | 0.18 | 0.39 | 2.28 | 1.44 | 0.86 | 0.82 | 0.93 | 1.06 | 0.67 | 0.35 | 0.33 |
| RUNX3 | 0.96 | 0.37 | 0.65 | 2.45 | 1.42 | 1.06 | 0.38 | 1.15 | 1.12 | 0.53 | 0.27 | 2.28 |
| ARID5B | 0.38 | 0.13 | 0.78 | 1.63 | 1.11 | 0.51 | 0.26 | 1.23 | 1.07 | 0.72 | 0.47 | 1.73 |
| SP140 | 1.65 | 0.05 | 0.45 | 1.80 | 1.38 | 1.24 | 0.77 | 0.71 | 0.58 | 0.33 | 0.62 | 2.04 |
| CBLB | 0.82 | 1.42 | 1.65 | 0.99 | 0.70 | 0.72 | 0.18 | 0.40 | 0.81 | 0.85 | 0.66 | 2.54 |
| STAT4 | 0.18 | 1.31 | 1.37 | 2.21 | 1.30 | 0.35 | 0.25 | 0.27 | 0.36 | 0.34 | 0.41 | 2.29 |
| BIN1 | 1.77 | 1.01 | 1.69 | 2.97 | 1.43 | 1.22 | 0.59 | 0.08 | 0.21 | 0.44 | 0.47 | 1.16 |
| IL18R1 | 1.77 | 1.90 | 1.91 | 1.62 | 0.86 | 1.46 | 0.40 | 0.02 | 0.03 | 0.12 | 0.21 | 0.84 |
| KLF3 | 0.48 | 0.34 | 1.28 | 1.32 | 0.87 | 0.97 | 1.24 | 2.47 | 2.24 | 1.75 | 2.51 | 2.86 |
| RXRA | 0.42 | 0.23 | 0.44 | 1.56 | 0.86 | 0.81 | 1.42 | 2.57 | 2.64 | 2.28 | 1.98 | 2.44 |
| ARHGEF3 | 1.01 | 0.71 | 0.30 | 1.22 | 0.83 | 0.85 | 1.06 | 2.33 | 1.55 | 1.86 | 1.36 | 2.94 |
| TLR1 | 1.26 | 0.41 | 0.44 | 1.40 | 0.30 | 1.18 | 0.57 | 1.89 | 1.88 | 2.03 | 2.32 | 2.22 |
| TMBIM1 | 1.54 | 0.98 | 0.48 | 1.89 | 0.82 | 1.24 | 1.51 | 2.91 | 2.82 | 2.59 | 2.22 | 2.18 |
| UBE2D1 | 0.91 | 0.82 | 0.02 | 0.63 | 0.44 | 1.86 | 2.23 | 1.35 | 1.44 | 2.40 | 2.71 | 1.86 |
| ODF3B | 1.05 | 0.61 | 0.26 | 0.53 | 1.17 | 1.40 | 1.49 | 1.75 | 1.39 | 2.10 | 2.45 | 1.88 |
| SLC8A1 | 0.95 | 0.05 | 0.28 | 0.58 | 1.55 | 1.48 | 1.58 | 1.38 | 2.54 | 1.79 | 2.33 | 1.56 |
| CREB5 | 0.12 | 0.18 | 0.30 | 0.37 | 1.02 | 1.35 | 1.74 | 0.11 | 1.01 | 2.60 | 2.85 | 2.65 |
| TLR8 | 0.41 | 0.04 | 0.05 | 0.06 | 0.76 | 0.85 | 1.13 | 1.12 | 2.24 | 2.66 | 2.52 | 2.38 |
| LRRK2 | 2.40 | 0.31 | 0.22 | 0.20 | 0.95 | 0.95 | 1.09 | 2.15 | 2.19 | 2.89 | 3.07 | 2.52 |
| NEDD9 | 2.76 | 1.31 | 1.01 | 0.48 | 1.02 | 1.05 | 1.04 | 2.03 | 1.95 | 1.52 | 1.96 | 1.93 |
| CXCR2 | 0.20 | 0.58 | 0.35 | 1.33 | 0.17 | 0.35 | 0.27 | 0.34 | 0.30 | 0.64 | 5.18 | 1.77 |
| FCGR3B | 0.12 | 0.09 | 0.22 | 0.17 | 0.06 | 0.02 | 0.04 | 1.78 | 0.79 | 0.44 | 5.78 | 0.71 |
| TECPR2 | 0.31 | 0.19 | 0.36 | 0.06 | 0.07 | 0.24 | 0.26 | 0.35 | 0.42 | 0.67 | 2.11 | 0.40 |
| ALPL | 0.00 | 0.00 | 0.00 | 0.06 | 0.00 | 0.03 | 0.00 | 0.01 | 0.03 | 0.01 | 2.37 | 0.30 |
| CXCR1 | 0.00 | 0.01 | 0.00 | 0.16 | 0.00 | 0.00 | 0.00 | 0.02 | 0.09 | 0.02 | 3.95 | 0.55 |
| PTGS2 | 0.11 | 0.07 | 0.05 | 0.21 | 0.71 | 1.27 | 1.73 | 0.35 | 0.64 | 1.18 | 2.99 | 0.89 |
| IL1R2 | 0.12 | 0.08 | 0.29 | 0.78 | 1.55 | 1.12 | 0.43 | 0.00 | 0.02 | 0.34 | 3.46 | 0.31 |
| IKZF3 | 0.00 | 0.02 | 0.20 | 0.25 | 0.11 | 0.00 | 0.00 | 0.00 | 0.01 | 0.08 | 0.27 | 2.82 |
| NCR3 | 0.00 | 0.00 | 0.00 | 0.04 | 0.31 | 0.00 | 0.00 | 0.08 | 0.05 | 0.02 | 0.10 | 3.11 |
| CD247 | 0.00 | 0.03 | 0.63 | 0.15 | 0.19 | 0.00 | 0.00 | 0.02 | 0.01 | 0.11 | 0.15 | 3.29 |
| IL18RAP | 0.04 | 0.15 | 0.39 | 0.46 | 0.10 | 0.04 | 0.05 | 0.04 | 0.04 | 0.01 | 0.64 | 2.68 |
| TXK | 0.04 | 0.13 | 0.38 | 0.09 | 0.31 | 0.07 | 0.08 | 0.16 | 0.14 | 0.18 | 0.32 | 3.88 |
| IL2RB | 0.03 | 0.01 | 0.14 | 0.10 | 0.26 | 0.00 | 0.00 | 0.00 | 0.07 | 0.02 | 0.11 | 3.68 |
| PRKCH | 0.20 | 0.21 | 0.63 | 0.36 | 0.53 | 0.34 | 0.56 | 0.08 | 0.12 | 0.25 | 0.27 | 2.16 |
| PRDM1 | 0.04 | 0.28 | 0.40 | 0.32 | 0.43 | 0.38 | 0.49 | 0.10 | 0.32 | 0.38 | 0.29 | 2.17 |
| FCRL3 | 0.00 | 0.00 | 0.54 | 0.16 | 0.22 | 0.02 | 0.02 | 0.01 | 0.00 | 0.03 | 0.05 | 1.89 |
| ETS1 | 0.08 | 0.95 | 0.50 | 0.27 | 0.10 | 0.04 | 0.00 | 0.13 | 0.06 | 0.21 | 0.28 | 1.65 |

TABLE E10A-continued

Supervised analysis of 255 candidate GWAS susceptibility loci - average expression values across DC and monocyte subsets (see FIG. 11A-B)

| Gene.ID | 1 | 2 | 3 | 4 | 5 | 6 | 7 | 8 | 9 | 10 | 11 | 12 |
|---|---|---|---|---|---|---|---|---|---|---|---|---|
| CTSW | 0.10 | 0.97 | 2.03 | 1.38 | 1.10 | 1.25 | 1.47 | 0.08 | 0.16 | 0.12 | 0.22 | 6.23 |
| IL32 | 0.38 | 0.58 | 1.65 | 0.51 | 0.73 | 0.37 | 0.37 | 0.55 | 0.56 | 0.81 | 0.97 | 4.07 |
| FYN | 1.62 | 0.38 | 1.10 | 1.21 | 1.13 | 1.45 | 1.00 | 1.02 | 1.04 | 1.83 | 0.49 | 3.08 |
| TLR10 | 3.40 | 1.46 | 1.05 | 1.09 | 1.18 | 1.18 | 0.48 | 0.54 | 0.60 | 0.60 | 0.86 | 0.92 |
| VAV3 | 2.87 | 0.94 | 0.77 | 0.72 | 1.22 | 1.17 | 0.72 | 0.21 | 0.29 | 0.59 | 0.54 | 1.44 |
| PTPN22 | 2.92 | 1.79 | 0.58 | 1.23 | 1.01 | 1.58 | 1.14 | 0.13 | 0.30 | 0.83 | 0.49 | 2.29 |
| GYPC | 3.36 | 0.65 | 1.09 | 1.72 | 1.63 | 1.70 | 1.03 | 0.71 | 0.67 | 0.55 | 0.56 | 2.15 |
| CLNK | 4.13 | 1.03 | 1.60 | 1.04 | 1.32 | 0.74 | 0.73 | 0.86 | 1.09 | 1.33 | 1.44 | 1.40 |
| DENND1B | 2.32 | 0.40 | 0.57 | 1.09 | 1.65 | 1.09 | 0.73 | 0.27 | 0.57 | 0.46 | 0.35 | 0.17 |
| BANK1 | 1.84 | 0.80 | 0.68 | 0.90 | 1.32 | 1.57 | 1.33 | 0.04 | 0.11 | 0.22 | 0.24 | 0.00 |
| DPP4 | 2.06 | 0.54 | 1.07 | 0.63 | 0.30 | 0.19 | 0.03 | 0.00 | 0.00 | 0.14 | 0.00 | 0.19 |
| LRRC18 | 2.11 | 0.51 | 0.49 | 0.35 | 0.45 | 0.37 | 0.15 | 0.07 | 0.13 | 0.13 | 0.00 | 0.14 |
| LACC1 | 2.49 | 0.11 | 0.06 | 0.16 | 0.49 | 0.43 | 0.41 | 0.91 | 0.83 | 0.30 | 0.46 | 0.09 |
| MAP2K6 | 2.19 | 2.34 | 1.20 | 0.46 | 0.42 | 0.66 | 0.43 | 0.04 | 0.25 | 0.73 | 0.45 | 0.56 |
| BATF3 | 3.94 | 0.04 | 0.00 | 0.04 | 0.33 | 1.12 | 0.92 | 1.75 | 1.18 | 0.27 | 0.14 | 0.19 |
| CLEC4F | 0.07 | 0.00 | 0.11 | 0.02 | 0.33 | 0.29 | 0.14 | 2.45 | 1.25 | 0.28 | 0.00 | 0.00 |
| LIME1 | 0.22 | 5.10 | 2.95 | 2.01 | 0.19 | 0.17 | 0.02 | 0.15 | 0.15 | 0.20 | 0.06 | 1.17 |
| CARD11 | 0.75 | 3.11 | 2.85 | 1.67 | 0.35 | 0.09 | 0.02 | 0.01 | 0.08 | 0.04 | 0.00 | 0.51 |
| DAB2 | 0.13 | 3.44 | 2.02 | 2.33 | 0.59 | 0.67 | 0.40 | 0.18 | 0.47 | 0.21 | 0.19 | 0.51 |
| SLC15A4 | 0.35 | 4.36 | 2.86 | 2.29 | 0.60 | 0.49 | 0.57 | 0.75 | 0.70 | 0.79 | 0.81 | 1.66 |
| AHI1 | 0.79 | 2.38 | 2.11 | 1.22 | 1.00 | 0.36 | 0.50 | 0.35 | 0.59 | 0.71 | 0.43 | 1.37 |
| TLR7 | 0.22 | 3.20 | 1.84 | 0.63 | 0.37 | 0.63 | 0.66 | 0.56 | 0.99 | 0.93 | 0.76 | 0.75 |
| AHNAK2 | 0.07 | 1.71 | 1.51 | 0.50 | 0.42 | 0.19 | 0.23 | 0.03 | 0.04 | 0.11 | 0.02 | 0.00 |
| AMIGO3 | 0.14 | 1.46 | 1.43 | 0.46 | 0.23 | 0.21 | 0.09 | 0.15 | 0.11 | 0.24 | 0.00 | 0.00 |
| DUSP5 | 0.08 | 1.81 | 1.23 | 0.17 | 0.40 | 0.16 | 0.01 | 0.29 | 0.11 | 0.16 | 0.00 | 0.13 |
| CUX2 | 0.00 | 1.64 | 0.93 | 0.05 | 0.04 | 0.00 | 0.00 | 0.01 | 0.03 | 0.09 | 0.07 | 0.00 |
| MAPKAPK2 | 0.19 | 1.63 | 1.71 | 0.48 | 0.32 | 0.16 | 0.22 | 0.25 | 0.38 | 0.28 | 0.05 | 0.55 |
| CMKLR1 | 0.00 | 2.65 | 0.62 | 0.14 | 0.03 | 0.11 | 0.14 | 0.43 | 0.52 | 0.19 | 0.16 | 1.06 |
| PHEX | 0.00 | 2.41 | 0.66 | 0.10 | 0.09 | 0.03 | 0.00 | 0.03 | 0.07 | 0.10 | 0.09 | 0.66 |
| LTB | 0.30 | 2.79 | 0.58 | 0.97 | 0.33 | 0.31 | 0.23 | 0.90 | 0.60 | 0.43 | 0.69 | 0.20 |
| CCR2 | 0.37 | 2.68 | 0.54 | 0.39 | 0.00 | 1.50 | 2.55 | 0.01 | 0.34 | 1.86 | 0.93 | 1.25 |
| RNASE2 | 0.05 | 0.06 | 0.41 | 0.09 | 0.33 | 0.70 | 4.87 | 0.09 | 0.58 | 2.45 | 2.31 | 0.99 |
| FCGR2B | 0.11 | 0.08 | 0.32 | 0.32 | 0.69 | 3.59 | 2.50 | 0.61 | 0.37 | 0.50 | 0.83 | 0.29 |
| PRKRA | 2.89 | 2.84 | 2.23 | 2.22 | 2.35 | 1.39 | 1.69 | 1.21 | 1.16 | 1.31 | 0.46 | 1.53 |
| GNL3 | 2.74 | 2.51 | 1.67 | 2.22 | 1.45 | 2.04 | 2.15 | 0.89 | 1.02 | 1.05 | 0.58 | 1.24 |
| ANTXR2 | 1.73 | 2.83 | 1.41 | 2.38 | 1.52 | 2.15 | 2.04 | 0.93 | 0.72 | 1.38 | 1.43 | 1.58 |
| ALCAM | 1.50 | 2.35 | 2.04 | 2.68 | 2.05 | 3.07 | 2.34 | 0.22 | 0.56 | 0.79 | 0.91 | 0.76 |
| AFF3 | 1.68 | 2.46 | 3.01 | 2.15 | 2.36 | 2.14 | 1.34 | 0.68 | 0.64 | 0.77 | 0.67 | 1.17 |
| RNASEH2B | 1.46 | 2.81 | 1.65 | 1.23 | 1.23 | 1.70 | 1.92 | 1.32 | 1.03 | 0.91 | 0.73 | 2.20 |
| MTG1 | 1.89 | 2.23 | 1.81 | 0.85 | 1.03 | 1.01 | 0.87 | 1.34 | 1.45 | 1.31 | 0.95 | 1.97 |
| SCAMP3 | 2.00 | 1.89 | 2.50 | 1.50 | 1.48 | 1.42 | 1.65 | 1.31 | 1.46 | 1.48 | 1.55 | 2.70 |
| NOTCH4 | 0.86 | 4.07 | 2.50 | 1.26 | 1.38 | 1.03 | 0.98 | 1.70 | 1.70 | 1.74 | 1.73 | 1.22 |
| FCHSD2 | 1.61 | 3.58 | 2.63 | 1.62 | 1.48 | 1.24 | 0.91 | 0.66 | 0.77 | 1.45 | 1.43 | 1.73 |
| TNFAIP8 | 3.19 | 1.66 | 0.90 | 2.64 | 1.27 | 2.50 | 2.21 | 1.81 | 1.71 | 1.82 | 1.37 | 1.37 |
| FARSA | 2.75 | 1.48 | 0.91 | 1.69 | 1.11 | 1.71 | 1.47 | 1.25 | 1.62 | 1.42 | 0.83 | 2.04 |
| CAMK2G | 3.31 | 1.19 | 1.66 | 1.80 | 2.29 | 2.02 | 2.08 | 1.10 | 1.35 | 2.06 | 1.73 | 2.75 |
| HLA-DOB | 5.76 | 1.39 | 1.79 | 1.95 | 1.98 | 2.91 | 0.91 | 1.12 | 1.20 | 1.01 | 1.20 | 1.57 |
| HDAC9 | 3.52 | 1.70 | 0.99 | 0.99 | 1.77 | 2.83 | 2.64 | 1.23 | 0.70 | 1.01 | 0.79 | 1.27 |
| HLA-DRB6 | 3.18 | 1.32 | 0.81 | 1.82 | 1.79 | 2.87 | 2.39 | 1.18 | 0.58 | 0.36 | 0.06 | 0.38 |
| RGS14 | 2.48 | 1.03 | 0.32 | 0.53 | 1.30 | 2.58 | 2.74 | 1.04 | 1.30 | 2.15 | 2.34 | 1.47 |
| ASAP1 | 3.50 | 0.22 | 0.85 | 1.50 | 3.25 | 1.94 | 0.92 | 1.33 | 1.51 | 1.63 | 1.95 | 1.26 |
| PNP | 1.77 | 0.81 | 0.85 | 3.53 | 1.52 | 1.79 | 2.60 | 1.11 | 1.08 | 1.34 | 1.17 | 1.81 |
| CDH23 | 1.19 | 2.35 | 1.51 | 1.64 | 1.51 | 1.30 | 0.85 | 3.24 | 2.40 | 1.49 | 1.60 | 1.52 |
| DNASE2 | 0.36 | 1.72 | 1.71 | 1.70 | 0.43 | 0.48 | 0.58 | 3.22 | 2.14 | 2.13 | 2.29 | 2.88 |
| ADA | 1.27 | 3.54 | 1.85 | 1.07 | 0.34 | 0.47 | 0.53 | 3.32 | 2.23 | 0.79 | 0.73 | 0.43 |
| CREM | 0.26 | 0.99 | 1.37 | 4.35 | 2.50 | 0.63 | 0.50 | 0.25 | 0.30 | 0.26 | 0.72 | 1.85 |
| CDS | 0.08 | 0.02 | 1.52 | 3.57 | 2.02 | 0.64 | 0.02 | 0.01 | 0.08 | 0.10 | 0.09 | 0.28 |
| CD2 | 0.09 | 0.19 | 0.99 | 2.48 | 1.72 | 2.36 | 2.22 | 0.03 | 0.17 | 0.20 | 0.42 | 3.58 |
| ADAM19 | 2.56 | 3.66 | 3.30 | 2.73 | 0.81 | 1.08 | 0.66 | 0.03 | 0.09 | 1.26 | 1.18 | 1.06 |
| DNASE1L3 | 4.77 | 4.48 | 3.46 | 1.08 | 0.57 | 0.37 | 0.19 | 0.22 | 0.37 | 0.51 | 0.10 | 0.96 |
| GZMB | 0.42 | 9.01 | 4.42 | 2.11 | 0.64 | 0.56 | 0.71 | 0.23 | 0.20 | 0.27 | 0.30 | 6.27 |
| IRF4 | 0.17 | 4.49 | 5.59 | 2.99 | 3.17 | 1.70 | 0.99 | 0.27 | 0.28 | 0.32 | 0.49 | 0.49 |
| IFNGR2 | 2.23 | 0.95 | 0.61 | 1.98 | 1.40 | 2.11 | 2.02 | 3.46 | 3.98 | 3.87 | 4.25 | 3.65 |
| SLA | 2.45 | 0.27 | 0.23 | 1.54 | 1.05 | 1.49 | 2.23 | 3.13 | 3.24 | 3.82 | 4.33 | 4.63 |
| ARAP1 | 1.56 | 0.92 | 0.62 | 1.00 | 1.11 | 1.82 | 1.92 | 3.46 | 3.39 | 3.27 | 3.91 | 2.54 |
| CTDSP1 | 1.13 | 0.74 | 0.69 | 1.52 | 1.70 | 1.15 | 1.86 | 2.03 | 3.16 | 3.53 | 3.39 | 3.32 |
| SULT1A1 | 1.24 | 0.39 | 0.81 | 0.38 | 1.83 | 1.05 | 2.37 | 2.88 | 2.75 | 3.26 | 3.32 | 3.74 |
| ATG16L2 | 1.84 | 1.35 | 2.02 | 1.50 | 1.73 | 2.54 | 2.65 | 2.66 | 3.45 | 4.16 | 4.41 | 3.57 |
| PELI1 | 1.84 | 1.26 | 2.28 | 1.97 | 1.87 | 1.46 | 1.99 | 2.77 | 3.35 | 4.62 | 5.43 | 3.52 |
| TSPAN14 | 0.87 | 0.92 | 1.39 | 1.65 | 1.66 | 1.85 | 1.69 | 3.98 | 4.48 | 3.82 | 3.79 | 4.16 |
| SLC11A1 | 0.65 | 0.78 | 1.26 | 0.71 | 1.08 | 0.72 | 1.74 | 4.48 | 4.91 | 5.19 | 5.13 | 4.17 |
| FCGR3A | 0.63 | 0.51 | 0.43 | 0.46 | 0.54 | 0.73 | 0.64 | 8.86 | 7.14 | 2.55 | 4.51 | 6.10 |
| SERPINA1 | 1.40 | 0.48 | 0.47 | 0.42 | 1.78 | 3.81 | 5.18 | 7.99 | 7.62 | 7.29 | 7.50 | 6.74 |
| FCGR2A | 0.24 | 0.28 | 0.58 | 0.52 | 0.58 | 2.86 | 3.47 | 4.00 | 4.66 | 5.70 | 6.47 | 4.99 |
| LILRB1 | 0.28 | 3.10 | 2.46 | 2.30 | 1.59 | 1.72 | 2.33 | 4.85 | 4.89 | 3.47 | 3.50 | 2.67 |

TABLE E10A-continued

Supervised analysis of 255 candidate GWAS susceptibility loci - average expression values across DC and monocyte subsets (see FIG. 11A-B)

| Gene.ID | 1 | 2 | 3 | 4 | 5 | 6 | 7 | 8 | 9 | 10 | 11 | 12 |
|---|---|---|---|---|---|---|---|---|---|---|---|---|
| UIMC1 | 1.75 | 1.93 | 3.04 | 1.94 | 1.91 | 1.53 | 1.71 | 1.58 | 2.26 | 2.99 | 3.35 | 2.62 |
| FBXL20 | 1.60 | 1.61 | 2.24 | 1.71 | 1.56 | 1.65 | 1.37 | 1.57 | 2.01 | 2.49 | 2.89 | 2.37 |
| IFRD1 | 2.12 | 2.44 | 1.84 | 1.67 | 2.20 | 2.12 | 1.85 | 2.37 | 2.48 | 2.30 | 3.86 | 2.23 |
| TNFAIP3 | 0.98 | 2.88 | 2.14 | 1.01 | 2.44 | 2.02 | 2.23 | 0.96 | 3.24 | 3.39 | 3.06 | 4.31 |
| NCF4 | 2.38 | 3.00 | 0.84 | 0.34 | 1.25 | 1.97 | 2.33 | 1.78 | 2.07 | 3.49 | 4.73 | 4.08 |
| TMEM173 | 0.29 | 1.05 | 2.12 | 1.06 | 1.59 | 2.90 | 3.97 | 1.28 | 2.45 | 3.08 | 2.96 | 3.22 |
| FOSL2 | 0.35 | 0.47 | 1.40 | 1.42 | 3.80 | 1.34 | 1.82 | 1.49 | 1.94 | 2.52 | 2.54 | 3.21 |
| CD83 | 3.76 | 0.74 | 1.01 | 1.83 | 3.22 | 2.85 | 2.01 | 2.90 | 4.39 | 2.57 | 1.77 | 2.42 |
| QPCT | 0.56 | 0.02 | 0.19 | 0.04 | 0.03 | 0.88 | 2.13 | 0.11 | 1.11 | 4.49 | 4.05 | 3.16 |
| IER3 | 0.08 | 0.18 | 0.18 | 0.30 | 0.28 | 0.58 | 1.84 | 0.11 | 1.34 | 3.11 | 3.63 | 2.99 |
| IL8 | 0.62 | 0.00 | 0.16 | 0.05 | 0.48 | 0.45 | 0.87 | 0.71 | 1.18 | 2.71 | 5.24 | 3.25 |
| PADI4 | 0.17 | 0.27 | 0.11 | 0.08 | 0.15 | 0.19 | 0.67 | 0.11 | 0.42 | 2.77 | 2.71 | 2.49 |
| CCR1 | 0.04 | 0.58 | 0.27 | 0.27 | 0.14 | 1.03 | 1.84 | 1.21 | 2.49 | 3.97 | 4.05 | 4.03 |
| ITGAM | 0.01 | 0.23 | 0.37 | 0.43 | 0.66 | 0.91 | 1.29 | 0.41 | 2.93 | 4.52 | 4.10 | 4.30 |
| DOK3 | 0.02 | 0.07 | 0.36 | 0.28 | 0.00 | 0.05 | 0.43 | 2.32 | 2.84 | 3.52 | 3.41 | 2.36 |
| GPBAR1 | 0.15 | 0.06 | 0.29 | 0.20 | 0.38 | 1.21 | 2.41 | 4.42 | 3.78 | 2.32 | 2.19 | 1.57 |
| FCGR2C | 0.13 | 0.05 | 0.25 | 0.23 | 0.88 | 3.56 | 3.09 | 4.36 | 2.16 | 1.71 | 1.42 | 0.69 |

TABLE E10B

Supervised analysis of 255 candidate GWAS susceptibility loci - list of genes reported in heatmap (column B; see FIG. 11A) along with associated immune diseases from the GWAS catalog

| Heatmap. Rank | List of genes | DISEASE/TRAIT | PUBMEDID | REGION | SNPS |
|---|---|---|---|---|---|
| 1 | CALM3 | Ulcerative colitis | 23128233 | 19q13.32 | rs1126510 |
| 2 | ARPC2 | Inflammatory bowel disease | 23128233 | 2q35 | rs2382817 |
| 3 | COX4I1 | Leprosy | 25642632 | 16q24.1 | rs2733954 |
| 4 | FOS | Inflammatory bowel disease | 23128233 | 14q24.3 | rs4899554 |
| 5 | HLA-A | Vitiligo | 20410501 | 6p22.1 | rs3823355 |
| 6 | HLA-B | Clozapine-induced agranulocytosis | 25187353 | 6p21.33 | rs41549217 |
| 7 | HLA-B | CD4:CD8 lymphocyte ratio | 20045101 | 6p21.33 | rs2524054 |
| 8 | HLA-B | CD4:CD8 lymphocyte ratio | 20045101 | 6p21.33 | rs2524054 |
| 9 | HLA-B | Ankylosing spondylitis | 21743469 | 6p21.33 | rs4349859 |
| 10 | HLA-B | Graves' disease | 21841780 | 6p21.33 | rs1521 |
| 11 | HLA-B | Multiple sclerosis | 19525953 | 6p22.1 | rs2523393 |
| 12 | HLA-B | Multiple sclerosis | 22190364 | 6p22.1 | rs9260489 |
| 13 | HLA-C | Atopic dermatitis | 25574825 | 6p21.33 | rs148203517 |
| 14 | HLA-C | Vitiligo | 20526339 | 6p21.33 | rs11966200 |
| 15 | HLA-C | AIDS progression | 19115949 | 6p21.33 | rs10484554 |
| 16 | HLA-C | Psoriatic arthritis | 20953186 | 6p21.33 | rs13191343 |
| 17 | HLA-C | Psoriasis | 18369459 | 6p21.33 | rs10484554 |
| 18 | HLA-C | Psoriasis | 18369459 | 6p21.33 | rs2395029 |
| 19 | HLA-C | Psoriasis | 18364390 | 6p21.33 | rs3134792 |
| 20 | HLA-C | Psoriasis | 19169254 | 6p21.33 | rs12191877 |
| 21 | HLA-C | Atopic dermatitis | 23042114 | 6p21.33 | rs9368677 |
| 22 | HLA-C | Psoriasis | 20953188 | 6p21.33 | rs12191877 |
| 23 | HLA-C | Psoriasis | 20953190 | 6p21.33 | rs10484554 |
| 24 | HLA-DPA1 | Systemic sclerosis | 21779181 | 6p21.32 | rs987870 |
| 25 | HLA-DRA | Crohn's disease | 23850713 | 6p21.32 | rs9271366 |
| 26 | HLA-DRA | Ulcerative colitis | 21297633 | 6p21.32 | rs9268853 |
| 27 | HLA-DRA | Crohn's disease | 23850713 | 6p21.32 | rs10947261 |
| 28 | HLA-DRA | Vitiligo | 20410501 | 6p21.32 | rs3806156 |
| 29 | HLA-DRA | Vogt-Koyanagi-Harada syndrome | 25108386 | 6p21.32 | rs114800139 |
| 30 | HLA-DRA | Ulcerative colitis | 18836448 | 6p21.32 | rs9268877 |
| 31 | HLA-DRA | Multiple sclerosis | 17660530 | 6p21.32 | rs3135388 |
| 32 | HLA-DRA | Multiple sclerosis (OCB status) | 23472185 | 6p21.32 | rs3129871 |
| 33 | HLA-DRA | Systemic sclerosis | 21779181 | 6p21.32 | rs3129882 |
| 34 | HLA-DRA | Ulcerative colitis | 20228798 | 6p21.32 | rs9268923 |
| 35 | HLA-DRA | Multiple sclerosis (OCB status) | 23472185 | 6p21.32 | rs3129871 |
| 36 | HLA-DRB1 | Sj\'fögren's syndrome | 24097066 | 6p21.32 | rs9271588 |
| 37 | HLA-DRB1 | Myasthenia gravis | 25643325 | 6p21.32 | rs9270986 |
| 38 | HLA-DRB1 | Systemic sclerosis | 21779181 | 6p21.32 | rs3129763 |
| 39 | HLA-DRB1 | Immune response to anthrax vaccine | 22658931 | 6p21.32 | rs3104402 |
| 40 | HLA-DRB1 | Vogt-Koyanagi-Harada syndrome | 25108386 | 6p21.32 | rs3021304 |
| 41 | HLA-DRB1 | Rheumatoid arthritis (ACPA-negative) | 24532677 | 6p21.32 | rs9271348 |
| 42 | HLA-DRB1 | Ulcerative colitis | 23511034 | 6p21.32 | rs9271366 |
| 43 | HLA-DRB1 | Systemic lupus erythematosus | 24871463 | | HLA-DRB1*03:01, rs9275572 |
| 44 | HLA-DRB1 | Rheumatoid arthritis | 17554300 | 6p21.32 | rs615672 |

TABLE E10B-continued

Supervised analysis of 255 candidate GWAS susceptibility loci - list of genes reported in heatmap
(column B; see FIG. 11A) along with associated immune diseases from the GWAS catalog

| Heatmap. Rank | List of genes | DISEASE/TRAIT | PUBMEDID | REGION | SNPS |
|---|---|---|---|---|---|
| 45 | HLA-DRB1 | Arthritis (juvenile idiopathic) | 18576341 | 6p21.32 | rs2395148 |
| 46 | HLA-DRB1 | Rheumatoid arthritis | 17804836 | 6p21.32 | rs660895 |
| 47 | HLA-DRB1 | Rheumatoid arthritis | 18794853 | 6p21.32 | rs6457620 |
| 48 | HLA-DRB1 | Multiple sclerosis | 18941528 | 6p21.32 | rs3129934 |
| 49 | HLA-DRB1 | Multiple sclerosis | 19525955 | 6p21.32 | rs9271366 |
| 50 | HLA-DRB1 | Systemic lupus erythematosus | 23273568 | 6p21.32 | rs9270984 |
| 51 | HLA-DRB1 | Rheumatoid arthritis | 21452313 | 6p21.32 | rs7765379 |
| 52 | HLA-DRB1 | Multiple sclerosis | 22190364 | 6p21.32 | rs3129889 |
| 53 | HLA-DRB1 | Systemic lupus erythematosus | 19838193 | 6p21.32 | rs9271100 |
| 54 | HLA-DRB1 | Rheumatoid arthritis | 20453841 | 6p21.32 | rs13192471 |
| 55 | HLA-DRB1 | Rheumatoid arthritis | 20453842 | 6p21.32 | rs6910071 |
| 56 | HLA-DRB1 | Epstein-Barr virus immune response (EBNA-1) | 23326239 | 6p21.32 | rs477515 |
| 57 | HLA-DRB1 | Multiple sclerosis (OCB status) | 23472185 | 6p21.32 | rs3828840 |
| 58 | HLA-DRB1 | Type 1 diabetes | 17632545 | 6p21.32 | rs2647044 |
| 59 | HLA-DRB1 | Multiple sclerosis | 19525953 | 6p21.32 | rs3135388 |
| 60 | HLA-DRB1 | Rheumatoid arthritis | 24390342 | 6p21.32 | rs9268839 |
| 61 | HLA-DRB1 | Rheumatoid arthritis | 24390342 | 6p21.32 | rs9268839 |
| 62 | HLA-DRB1 | Rheumatoid arthritis | 24390342 | 6p21.32 | rs9268839 |
| 63 | LSP1 | Ulcerative colitis | 21297633 | 11p15.5 | rs907611 |
| 64 | PARK7 | Ulcerative colitis | 21297633 | 1p36.23 | rs35675666 |
| 65 | PARK7 | Celiac disease | 20190752 | 1p36.23 | rs12727642 |
| 66 | PLEK | Multiple sclerosis | 21833088 | 2p13.3 | rs7595037 |
| 67 | PLEK | Celiac disease | 20190752 | 2p14 | rs17035378 |
| 68 | PTPRC | Ulcerative colitis | 24837172 | 1q31.3 | rs2359952 |
| 69 | RPL41 | Systemic sclerosis | 21779181 | 12q13.2 | rs11171747 |
| 70 | RPL5 | Multiple sclerosis | 19525955 | 1p22.1 | rs6604026 |
| 71 | RPL5 | Multiple sclerosis | 17660530 | 1p22.1 | rs6604026 |
| 72 | TAGLN2 | Crohn's disease-related phenotypes | 25557950 | 1q23.2 | rs12122337 |
| 73 | CDC42 | Immune response to smallpox vaccine (IL-6) | 22610502 | 1p36.12 | rs2501276 |
| 74 | ATF4 | Inflammatory bowel disease | 23128233 | 22q13.1 | rs2413583 |
| 75 | PSMA6 | Psoriasis | 20953189 | 14q13.2 | rs12586317 |
| 76 | PSMA6 | Psoriasis | 25903422 | 14q13.2 | rs8016947 |
| 77 | PSMA6 | Psoriasis | 25903422 | 14q13.2 | rs8016947 |
| 78 | PSMA6 | Psoriasis | 25903422 | 14q13.2 | rs8016947 |
| 79 | CSNK2B | Cutaneous lupus erythematosus | 25827949 | 6p21.33 | rs9267531 |
| 80 | CD44 | Vitiligo | 22561518 | 11p13 | rs10768122 |
| 81 | CD44 | Systemic lupus erythematosus | 23273568 | 11p13 | rs2785197 |
| 82 | PSMA4 | Response to tocilizumab in rheumatoid arthritis | 22491018 | 15q25.1 | rs12901682 |
| 83 | RNASET2 | Crohn's disease | 23850713 | 6q27 | rs2149085 |
| 84 | RNASET2 | Vitiligo | 20526339 | 6q27 | rs2236313 |
| 85 | RNASET2 | Graves' disease | 21841780 | 6q27 | rs9355610 |
| 86 | CXCR4 | Multiple sclerosis | 19525953 | 2q22.1 | rs882300 |
| 87 | IRF8 | Multiple sclerosis | 21833088 | 16q24.1 | rs13333054 |
| 88 | IRF8 | Multiple sclerosis | 19525953 | 16q24.1 | rs17445836 |
| 89 | IRF8 | Systemic sclerosis | 21779181 | 16q24.1 | rs11642873 |
| 90 | IRF8 | Rheumatoid arthritis | 22446963 | 16q24.1 | rs2280381 |
| 91 | IRF8 | Ulcerative colitis | 23511034 | 16q24.1 | rs16940186 |
| 92 | IRF8 | Inflammatory bowel disease | 23128233 | 16q24.1 | rs10521318 |
| 93 | IRF8 | Systemic lupus erythematosus and Systemic sclerosis | 23740937 | 16q24.1 | rs12711490 |
| 94 | IRF8 | Rheumatoid arthritis | 24390342 | 16q24.1 | rs13330176 |
| 95 | IRF8 | Rheumatoid arthritis | 24390342 | 16q24.1 | rs13330176 |
| 96 | RPS26 | Psoriasis | 20953189 | 12q13.2 | rs12580100 |
| 97 | RPS26 | Psoriasis | 25574825 | 12q13.2 | rs12580100 |
| 98 | RPS26 | Inflammatory skin disease | 25574825 | 12q13.2 | rs1131017 |
| 99 | CDC37 | Multiple sclerosis | 21833088 | 19p13.2 | rs8112449 |
| 100 | NFKBIA | Psoriasis | 25574825 | 14q13.2 | rs12586317 |
| 101 | NFKBIA | Inflammatory skin disease | 25574825 | 14q13.2 | rs12884468 |
| 102 | NFKBIA | Psoriasis | 20953190 | 14q13.2 | rs8016947 |
| 103 | CAPZB | Crohn's disease and psoriasis | 22482804 | 1p36.13 | rs7667 |
| 104 | ASTN2 | Immune response to anthrax vaccine | 22658931 | 9q33.1 | rs6478282 |
| 105 | HLA-DQB1 | Ulcerative colitis | 19122664 | 6p21.32 | rs2395185 |
| 106 | HLA-DQB1 | Ulcerative colitis | 23128233 | 6p21.32 | rs6927022 |
| 107 | HLA-DQB1 | Ulcerative colitis | 24837172 | 6p21.32 | rs1063355 |
| 108 | HLA-DQB1 | Multiple sclerosis | 20453840 | 6p21.32 | rs2040406 |
| 109 | HLA-DQB1 | Celiac disease | 20190752 | 6p21.32 | rs2187668 |
| 110 | HLA-DQB1 | Self-reported allergy | 23817569 | 6p21.32 | rs6906021 |
| 111 | HLA-DQB1 | Systemic lupus erythematosus | 24871463 | | HLA-DQB1*02:01, rs558702 |
| 112 | HLA-DQB1 | Systemic sclerosis | 21779181 | 6p21.32 | rs9275390 |
| 113 | HLA-DQB1 | Systemic sclerosis | 21779181 | 6p21.32 | rs9275390 |

TABLE E10B-continued

Supervised analysis of 255 candidate GWAS susceptibility loci - list of genes reported in heatmap
(column B; see FIG. 11A) along with associated immune diseases from the GWAS catalog

| Heatmap. Rank | List of genes | DISEASE/TRAIT | PUBMEDID | REGION | SNPS |
|---|---|---|---|---|---|
| 114 | HLA-DQB1 | Systemic sclerosis | 20383147 | 6p21.32 | rs6457617 |
| 115 | HLA-DQB1 | Multiple sclerosis (OCB status) | 23472185 | 6p21.32 | rs3129720 |
| 116 | HLA-DQB1 | Asthma and hay fever | 24388013 | 6p21.32 | rs9273373 |
| 117 | LITAF | Inflammatory bowel disease | 23128233 | 16p13.13 | rs529866 |
| 118 | H2AFY | Immune response to anthrax vaccine | 22658931 | 5q31.1 | rs634308 |
| 119 | H2AFY | AIDS progression | 21502085 | 5q31.1 | rs477687 |
| 120 | SYK | Multiple sclerosis | 21833088 | 9q22.2 | rs290986 |
| 121 | GPX4 | Crohn's disease | 21102463 | 19p13.3 | rs740495 |
| 122 | GPX4 | Crohn's disease | 23128233 | 19p13.3 | rs2024092 |
| 123 | OSTF1 | Allergic rhinitis | 25085501 | 9q21.13 | rs1332366 |
| 124 | ANKRD44 | Interferon alpha levels in systemic lupus erythematosus | 25338677 | 2q33.1 | rs4850410 |
| 125 | ANKRD44 | Interferon alpha levels in systemic lupus erythematosus | 25338677 | 2q33.1 | rs1429411 |
| 126 | CTSH | Type 1 diabetes | 18978792 | 15q25.1 | rs3825932 |
| 127 | CTSH | Type 1 diabetes | 19430480 | 15q25.1 | rs3825932 |
| 128 | LGALS9 | Crohn's disease | 23128233 | 17q11.2 | rs2945412 |
| 129 | HCK | Inflammatory bowel disease | 23128233 | 20q11.21 | rs6142618 |
| 130 | AIF1 | Crohn's disease | 22936669 | 6p21.33 | rs9348876 |
| 131 | ID2 | Self-reported allergy | 23817569 | 2p25.1 | rs10174949 |
| 132 | HLA-DQA1 | Mixed cryoglobulinemia vasculitis in chronic hepatitis C infection | 25030430 | 6p21.32 | rs9461776 |
| 133 | HLA-DQA1 | Immunoglobulin G index levels in multiple sclerosis | 25616667 | 6p21.32 | rs9271640, rs6457617, rs3957148 |
| 134 | HLA-DQA1 | Systemic lupus erythematosus | 24871463 | | HLA-DQA1*05:01 |
| 135 | HLA-DQA1 | Inflammatory bowel disease | 18758464 | 6p21.32 | rs477515 |
| 136 | HLA-DQA1 | Systemic lupus erythematosus | 18204098 | 6p21.32 | rs2187668 |
| 137 | HLA-DQA1 | Autoimmune hepatitis type-1 | 24768677 | 6p21.32 | rs2187668 |
| 138 | HLA-DQA1 | Multiple sclerosis (OCB status) | 23472185 | 6p21.32 | rs9271640 |
| 139 | HLA-DQA1 | Immunoglobulin G index levels in multiple sclerosis | 25616667 | 6p21.32 | rs6457617 |
| 140 | HLA-DQA1 | Cutaneous lupus erythematosus | 25827949 | 6p21.32 | rs2187668 |
| 141 | HLA-DPB1 | Aspirin exacerbated respiratory disease in asthmatics | 23180272 | 6p21.32 | rs1042151 |
| 142 | SEC61G | Systemic lupus erythematosus | 24871463 | 7p11.2 | rs6946131 |
| 143 | IRF7 | Systemic lupus erythematosus and Systemic sclerosis | 23740937 | 11p15.5 | rs2396545 |
| 144 | WDFY4 | Systemic lupus erythematosus | 23273568 | 10q11.23 | rs877819 |
| 145 | WDFY4 | Systemic lupus erythematosus | 20169177 | 10q11.23 | rs7097397 |
| 146 | WDFY4 | Rheumatoid arthritis | 24390342 | 10q11.23 | rs2671692 |
| 147 | GPR183 | Inflammatory bowel disease | 23128233 | 13q32.3 | rs9557195 |
| 148 | ANXA6 | Psoriasis | 25574825 | 5q33.1 | rs2233278 |
| 149 | ANXA6 | Inflammatory skin disease | 25574825 | 5q33.1 | rs17728338 |
| 150 | HLA-DOA | Wegener's granulomatosis | 23740775 | 6p21.32 | rs9277554 |
| 151 | RGS1 | Multiple sclerosis | 21833088 | 1q31.2 | rs1323292 |
| 152 | RGS1 | Celiac disease | 18311140 | 1q31.2 | rs2816316 |
| 153 | RGS1 | Celiac disease | 20190752 | 1q31.2 | rs2816316 |
| 154 | HLA-DQA2 | Crohn's disease | 23266558 | 6p21.32 | rs7765379 |
| 155 | HLA-DQA2 | Crohn's disease | 21102463 | 6p21.33 | rs1799964 |
| 156 | HLA-DQA2 | Rheumatoid arthritis | 23918589 | 6p21.32 | rs9275406 |
| 157 | HLA-DQA2 | Knee osteoarthritis | 20305777 | 6p21.32 | rs10947262 |
| 158 | HLA-DQA2 | Rheumatoid arthritis | 24782177 | 6p21.32 | rs12525220 |
| 159 | HLA-DQA2 | Rheumatoid arthritis | 24782177 | 6p21.32 | rs12525220 |
| 160 | HLA-DQA2 | Rheumatoid arthritis | 24782177 | 6p21.32 | rs12525220 |
| 161 | HLA-DQA2 | Rheumatoid arthritis | 18668548 | 6p21.32 | rs6457617 |
| 162 | HLA-DQA2 | Systemic lupus erythematosus | 21408207 | 6p21.32 | rs2647012 |
| 163 | HLA-DQA2 | Systemic lupus erythematosus | 24871463 | 6p21.32 | rs9275572 |
| 164 | HLA-DQA2 | Multiple sclerosis (OCB status) | 23472185 | 6p21.32 | rs9275563 |
| 165 | HLA-DQA2 | Systemic lupus erythematosus | 23053960 | 6p21.32 | rs2051549 |
| 166 | HLA-DQA2 | Systemic lupus erythematosus | 21408207 | 6p21.32 | rs2301271 |
| 167 | PLD4 | Rheumatoid arthritis | 22446963 | 14q32.33 | rs2841277 |
| 168 | CLEC16A | Celiac disease | 20190752 | 16p13.13 | rs12928822 |
| 169 | CLEC16A | Multiple sclerosis | 21833088 | 16p13.13 | rs7200786 |
| 170 | CLEC16A | Self-reported allergy | 23817569 | 16p13.13 | rs7203459 |
| 171 | CLEC16A | Multiple sclerosis | 19525953 | 16p13.13 | rs11865121 |
| 172 | CLEC16A | Atopic dermatitis | 23042114 | 16p13.13 | rs9923856 |
| 173 | CLEC16A | Systemic lupus erythematosus | 23273568 | 16p13.13 | rs12599402 |
| 174 | CLEC16A | Allergic rhinitis | 22036096 | 16p13.13 | rs887864 |
| 175 | CLEC16A | Type 1 diabetes | 19430480 | 16p13.13 | rs12708716 |
| 176 | CLEC16A | Type 1 diabetes | 18978792 | 16p13.13 | rs12708716 |
| 177 | CLEC16A | Type 1 diabetes autoantibodies | 21829393 | 16p13.13 | rs12708716 |
| 178 | CLEC16A | Asthma and hay fever | 24388013 | 16p13.13 | rs62026376 |
| 179 | SCAPER | Recalcitrant atopic dermatitis | 25935106 | 15q24.3 | rs3099143 |

TABLE E10B-continued

Supervised analysis of 255 candidate GWAS susceptibility loci - list of genes reported in heatmap (column B; see FIG. 11A) along with associated immune diseases from the GWAS catalog

| Heatmap. Rank | List of genes | DISEASE/TRAIT | PUBMEDID | REGION | SNPS |
|---|---|---|---|---|---|
| 180 | BCO2 | Immune reponse to smallpox (secreted IL-12p40) | 22610502 | 11q23.1 | rs7105056 |
| 181 | ATG5 | Rheumatoid arthritis | 24390342 | 6q21 | rs9372120 |
| 182 | ATG5 | Systemic lupus erythematosus and Systemic sclerosis | 23740937 | 6q21 | rs3827644 |
| 183 | ATG5 | Rheumatoid arthritis | 24390342 | 6q21 | rs9372120 |
| 184 | FTO | Osteoarthritis | 22763110 | 16q12.2 | rs8044769 |
| 185 | FTO | Allergic rhinitis | 25085501 | 16q12.2 | rs7187423 |
| 186 | CENPC1 | Multiple sclerosis (severity) | 19010793 | 4q13.2 | rs10518025 |
| 187 | FUT2 | Crohn's disease | 23128233 | 19q13.33 | rs516246 |
| 188 | FUT2 | Crohn's disease | 21102463 | 19q13.33 | rs281379 |
| 189 | FUT2 | Crohn's disease | 20570966 | 19q13.33 | rs504963 |
| 190 | FUT2 | Psoriasis | 25574825 | 19q13.33 | rs1047781 |
| 191 | ANO6 | Ankylosing spondylitis | 22138694 | 12q12 | rs17095830 |
| 192 | GALC | Crohn's disease | 21102463 | 14q31.3 | rs8005161 |
| 193 | GALC | Inflammatory bowel disease | 23128233 | 14q31.3 | rs8005161 |
| 194 | MFN2 | Inflammatory skin disease | 25574825 | 1p36.22 | rs6686734 |
| 195 | MTF1 | Rheumatoid arthritis | 24390342 | 1p34.3 | rs28411352 |
| 196 | MTF1 | Rheumatoid arthritis | 24390342 | 1p34.3 | rs28411352 |
| 197 | RAP1GAP2 | Inflammatory skin disease | 25574825 | 17p13.3 | rs9902403 |
| 198 | FOXO3 | Normalized brain volume | 19010793 | 6q21 | rs9480865 |
| 199 | MGMT | Inflammatory skin disease | 25574825 | 10q26.3 | rs80312298 |
| 200 | CD40 | Inflammatory bowel disease | 23128233 | 20q13.12 | rs1569723 |
| 201 | CD40 | Rheumatoid arthritis | 18794853 | 20q13.12 | rs4810485 |
| 202 | CD40 | Multiple sclerosis | 19525955 | 20q13.12 | rs6074022 |
| 203 | CD40 | Multiple sclerosis | 22190364 | 20q13.12 | rs6074022 |
| 204 | CD40 | Kawasaki disease | 22446962 | 20q13.12 | rs4813003 |
| 205 | CD40 | Kawasaki disease | 22446961 | 20q13.12 | rs1569723 |
| 206 | CD40 | Rheumatoid arthritis | 20453842 | 20q13.12 | rs4810485 |
| 207 | CD40 | Rheumatoid arthritis | 24390342 | 20q13.12 | rs4239702 |
| 208 | CD40 | Rheumatoid arthritis | 24390342 | 20q13.12 | rs4239702 |
| 209 | TNIP1 | Inflammatory bowel disease | 23128233 | 5q33.1 | rs11741861 |
| 210 | TNIP1 | Psoriasis | 25903422 | 5q33.1 | rs17728338 |
| 211 | TNIP1 | Psoriasis | 25903422 | 5q33.1 | rs17728338 |
| 212 | TNIP1 | Myasthenia gravis | 23055271 | 5q33.1 | rs4958881 |
| 213 | TNIP1 | Psoriasis | 19169254 | 5q33.1 | rs17728338 |
| 214 | TNIP1 | Systemic lupus erythematosus | 23273568 | 5q33.1 | rs10036748 |
| 215 | TNIP1 | Systemic sclerosis | 21750679 | 5q33.1 | rs2233287 |
| 216 | TNIP1 | Systemic lupus erythematosus | 19838193 | 5q33.1 | rs10036748 |
| 217 | TNIP1 | Systemic lupus erythematosus and Systemic sclerosis | 23740937 | 5q33.1 | rs960709 |
| 218 | RIT1 | Inflammatory bowel disease | 23128233 | 1q22 | rs670523 |
| 219 | BCAS3 | Immune reponse to smallpox (secreted IL-2) | 22610502 | 17q23.2 | rs7224438 |
| 220 | BCAS3 | Gout | 25967671 | 17q23.2 | rs11653176 |
| 221 | CLYBL | Rheumatoid arthritis (ACPA-negative) | 24532677 | 13q32.3 | rs9557321 |
| 222 | MTMR3 | Crohn's disease | 21102463 | 22q12.2 | rs713875 |
| 223 | ABHD5 | Inflammatory skin disease | 25574825 | 3p21.33 | rs75594032 |
| 224 | NFIL3 | Inflammatory bowel disease | 23128233 | 9q22.2 | rs4743820 |
| 225 | ABCA1 | Allergic rhinitis | 25085501 | 9q31.1 | rs2472448 |
| 226 | TNFSF8 | Ulcerative colitis | 21297633 | 9q32 | rs4246905 |
| 227 | TNFSF8 | Crohn's disease | 21102463 | 9q32 | rs3810936 |
| 228 | SLC2A9 | Gout | 21983786 | 4p16.1 | rs734553 |
| 229 | SLC2A9 | Gout | 23263486 | 4p16.1 | rs4475146 |
| 230 | SLC2A9 | Urate levels | 20884846 | 4p16.1 | rs13129697 |
| 231 | SLC2A9 | Gout | 25646370 | 4p16.1 | rs3775948 |
| 232 | IGF2R | Brain lesion load | 19010793 | 6q25.3 | rs6917747 |
| 233 | CCNY | Ulcerative colitis | 21297633 | 10p11.21 | rs12261843 |
| 234 | TRIB1 | Inflammatory bowel disease | 23128233 | 8q24.13 | rs921720 |
| 235 | TGIF1 | Response to methotrexate in juvenile idiopathic arthritis | 24709693 | 18p11.31 | rs6506122 |
| 236 | GPR35 | Ulcerative colitis | 21297633 | 2q37.3 | rs4676406 |
| 237 | GPR35 | Inflammatory bowel disease | 23128233 | 2q37.3 | rs3749171 |
| 238 | SVIL | Normalized brain volume | 19010793 | 10p11.23 | rs1927457 |
| 239 | PFKFB4 | Inflammatory bowel disease | 23128233 | 3p21.31 | rs3197999 |
| 240 | PFKFB4 | Ulcerative colitis | 25082827 | 3p21.31 | rs3197999 |
| 241 | GCH1 | Rheumatoid arthritis | 22446963 | 14q22.2 | rs3783637 |
| 242 | SAMD9L | Systemic lupus erythematosus and Systemic sclerosis | 23740937 | 7q21.2 | rs1133906 |
| 243 | CARD9 | Crohn's disease | 22936669 | 9q34.3 | rs4077515 |
| 244 | CARD9 | Crohn's disease | 21102463 | 9q34.3 | rs4077515 |
| 245 | CARD9 | Ankylosing spondylitis | 21743469 | 9q34.3 | rs10781500 |
| 246 | CARD9 | Ulcerative colitis | 19915572 | 9q34.3 | rs10781500 |
| 247 | CARD9 | Ulcerative colitis | 20228799 | 9q34.3 | rs4077515 |

TABLE E10B-continued

Supervised analysis of 255 candidate GWAS susceptibility loci - list of genes reported in heatmap
(column B; see FIG. 11A) along with associated immune diseases from the GWAS catalog

| Heatmap. Rank | List of genes | DISEASE/TRAIT | PUBMEDID | REGION | SNPS |
|---|---|---|---|---|---|
| 248 | SNX18 | Immune response to smallpox vaccine (IL-6) | 22542470 | 5q11.2 | rs2548621 |
| 249 | CCR6 | Crohn's disease | 18587394 | 6q27 | rs2301436 |
| 250 | CCR6 | Rheumatoid arthritis | 20453841 | 6q27 | rs3093024 |
| 251 | CCR6 | Rheumatoid arthritis | 20453842 | 6q27 | rs3093023 |
| 252 | CCR6 | Crohn's disease | 21102463 | 6q27 | rs415890 |
| 253 | CCR6 | Rheumatoid arthritis | 24782177 | 6q27 | rs3093023 |
| 254 | CCR6 | Rheumatoid arthritis | 24782177 | 6q27 | rs1854853 |
| 255 | CCR6 | Rheumatoid arthritis | 24782177 | 6q27 | rs1854853 |
| 256 | CCR6 | Rheumatoid arthritis | 24390342 | 6q27 | rs1571878 |
| 257 | CCR6 | Rheumatoid arthritis | 24390342 | 6q27 | rs1571878 |
| 258 | CCR6 | Rheumatoid arthritis | 24390342 | 6q27 | rs1571878 |
| 259 | IL27RA | Immune response to measles-mumps-rubella vaccine | 24811271 | | kgp4580976 |
| 260 | PPIL4 | Rheumatoid arthritis | 24390342 | 6q25.1 | rs9373594 |
| 261 | PPIL4 | Rheumatoid arthritis | 24390342 | 6q25.1 | rs9373594 |
| 262 | PHTF1 | Type 1 diabetes | 17554260 | 1p13.2 | rs6679677 |
| 263 | PHTF1 | Type 1 diabetes and autoimmune thyroid diseases | 25936594 | 1p13.2 | rs2476601 |
| 264 | ARHGAP18 | Antineutrophil cytoplasmic antibody-associated vasculitis | 22808956 | 6q22.33 | rs17057678 |
| 265 | SIGLEC5 | Leprosy | 25642632 | 19q13.41 | rs10414149 |
| 266 | GNA12 | Ulcerative colitis | 23128233 | 7p22.3 | rs798502 |
| 267 | GNA12 | Ulcerative colitis | 21297633 | 7p22.3 | rs798502 |
| 268 | ZHX2 | Immune response to smallpox vaccine (IL-6) | 22542470 | 8q24.13 | rs10108684 |
| 269 | VDR | Inflammatory bowel disease | 23128233 | 12q13.11 | rs11168249 |
| 270 | RUNX3 | Celiac disease | 20190752 | 1p36.11 | rs10903122 |
| 271 | RUNX3 | Crohn's disease | 23266558 | 1p36.11 | rs7551188 |
| 272 | RUNX3 | Ankylosing spondylitis | 21743469 | 1p36.11 | rs11249215 |
| 273 | ARID5B | Systemic lupus erythematosus | 23273568 | 10q21.2 | rs4948496 |
| 274 | ARID5B | Rheumatoid arthritis | 22446963 | 10q21.2 | rs10821944 |
| 275 | ARID5B | Rheumatoid arthritis | 24390342 | 10q21.2 | rs71508903 |
| 276 | ARID5B | Rheumatoid arthritis | 24390342 | 10q21.2 | rs71508903 |
| 277 | ARID5B | Rheumatoid arthritis | 24390342 | 10q21.2 | rs71508903 |
| 278 | SP140 | Multiple sclerosis | 21833088 | 2q37.1 | rs10201872 |
| 279 | SP140 | Crohn's disease | 23128233 | 2q37.1 | rs6716753 |
| 280 | SP140 | Crohn's disease | 21102463 | 2q37.1 | rs7423615 |
| 281 | CBLB | Multiple sclerosis | 20453840 | 3q13.11 | rs9657904 |
| 282 | STAT4 | Celiac disease or Rheumatoid arthritis | 21383967 | 2q32.2 | rs7574865 |
| 283 | STAT4 | Systemic lupus erythematosus | 19165918 | 2q32.2 | rs3821236 |
| 284 | STAT4 | Systemic lupus erythematosus | 18204098 | 2q32.2 | rs7574865 |
| 285 | STAT4 | Behcet's disease | 23001997 | 2q32.3 | rs897200 |
| 286 | STAT4 | Systemic lupus erythematosus | 23053960 | 2q32.2 | rs7574865 |
| 287 | STAT4 | Behcet's disease | 23001997 | 2q32.3 | rs897200, rs7572482, rs7574070 |
| 288 | STAT4 | Systemic lupus erythematosus | 23273568 | 2q32.2 | rs7574865 |
| 289 | STAT4 | Systemic lupus erythematosus | 21408207 | 2q32.2 | rs7574865 |
| 290 | STAT4 | Systemic lupus erythematosus | 21408207 | 2q32.2 | rs7574865 |
| 291 | STAT4 | Systemic sclerosis | 21750679 | 2q32.2 | rs7574865 |
| 292 | STAT4 | Systemic sclerosis | 21779181 | 2q32.2 | rs3821236 |
| 293 | STAT4 | Systemic lupus erythematosus | 19838193 | 2q32.2 | rs7574865 |
| 294 | STAT4 | Systemic sclerosis | 20383147 | 2q32.2 | rs3821236 |
| 295 | STAT4 | Rheumatoid arthritis | 20453841 | 2q32.2 | rs7574865 |
| 296 | STAT4 | Rheumatoid arthritis | 20453842 | 2q32.2 | rs7574865 |
| 297 | STAT4 | Sj\'f6gren's syndrome | 24097066 | 2q32.2 | rs10168266 |
| 298 | STAT4 | Systemic lupus erythematosus | 24871463 | 2q32.2 | rs7574865 |
| 299 | STAT4 | Behcet's disease | 23291587 | 2q32.3 | rs7574070 |
| 300 | STAT4 | Systemic lupus erythematosus and Systemic sclerosis | 23740937 | 2q32.2 | rs7601754 |
| 301 | STAT4 | Rheumatoid arthritis | 24390342 | 2q32.2 | rs11889341 |
| 302 | STAT4 | Rheumatoid arthritis | 24390342 | 2q32.2 | rs11889341 |
| 303 | STAT4 | Rheumatoid arthritis | 24390342 | 2q32.2 | rs11889341 |
| 304 | BIN1 | Systemic lupus erythematosus | 24871463 | 2q14.3 | rs12993006 |
| 305 | IL18R1 | Inflammatory bowel disease | 23128233 | 2q12.1 | rs917997 |
| 306 | IL18R1 | Celiac disease | 18311140 | 2q12.1 | rs13015714 |
| 307 | IL18R1 | Celiac disease | 20190752 | 2q12.1 | rs917997 |
| 308 | IL18R1 | Atopic dermatitis | 23042114 | 2q12.1 | rs13015714 |
| 309 | IL18R1 | Leprosy | 25642632 | 2q12.1 | rs76886731 |
| 310 | KLF3 | Crohn's disease | 23850713 | 4p14 | rs6856616 |
| 311 | ARHGEF3 | Rheumatoid arthritis | 21452313 | 3p14.3 | rs2062583 |
| 312 | TLR1 | Asthma and hay fever | 24388013 | 4p14 | rs4833095 |
| 313 | UBE2D1 | Crohn's disease | 21102463 | 10q21.1 | rs1819658 |

TABLE E10B-continued

Supervised analysis of 255 candidate GWAS susceptibility loci - list of genes reported in heatmap (column B; see FIG. 11A) along with associated immune diseases from the GWAS catalog

| Heatmap. Rank | List of genes | DISEASE/TRAIT | PUBMEDID | REGION | SNPS |
|---|---|---|---|---|---|
| 314 | ODF3B | Multiple sclerosis | 21833088 | 22q13.33 | rs140522 |
| 315 | SLC8A1 | HIV-associated dementia | 22628157 | 2p22.1 | rs404005 |
| 316 | LRRK2 | Leprosy | 25642632 | 12q12 | rs11174812 |
| 317 | NEDD9 | HIV-1 susceptibility | 22174851 | 6p24.2 | rs4437462 |
| 318 | TECPR2 | Birdshot chorioretinopathy | 24957906 | 14q32.31 | rs150571175 |
| 319 | ALPL | Response to TNF-alpha inhibitors in rheumatoid arthritis | 22569225 | 1p36.12 | rs885814 |
| 320 | PTGS2 | Knee osteoarthritis | 18471798 | 1q31.1 | rs4140564 |
| 321 | IL1R2 | Ulcerative colitis | 21297633 | 2q11.2 | rs2310173 |
| 322 | IL1R2 | Ankylosing spondylitis | 20062062 | 2q11.2 | rs2310173 |
| 323 | IKZF3 | Crohn's disease | 21102463 | 17q21.1 | rs2872507 |
| 324 | IKZF3 | Rheumatoid arthritis | 20453842 | 17q21.1 | rs2872507 |
| 325 | IKZF3 | Systemic lupus erythematosus and Systemic sclerosis | 23740937 | 17q21.1 | rs9303277 |
| 326 | IKZF3 | Asthma and hay fever | 24388013 | 17q21.1 | rs12450323 |
| 327 | CD247 | Celiac disease or Rheumatoid arthritis | 21383967 | 1q24.2 | rs864537 |
| 328 | CD247 | Celiac disease | 20190752 | 1q24.2 | rs864537 |
| 329 | CD247 | Systemic sclerosis | 21750679 | 1q24.2 | rs2056626 |
| 330 | CD247 | Systemic sclerosis | 21779181 | 1q24.2 | rs2056626 |
| 331 | CD247 | Systemic sclerosis | 20383147 | 1q24.2 | rs2056626 |
| 332 | CD247 | Rheumatoid arthritis | 20453842 | 1q24.2 | rs840016 |
| 333 | TXK | Crohn's disease | 23128233 | 4p11 | rs6837335 |
| 334 | IL2RB | Rheumatoid arthritis | 24390342 | 22q12.3 | rs3218251 |
| 335 | IL2RB | Type 1 diabetes autoantibodies | 21829393 | 22q12.3 | rs743777 |
| 336 | PRKCH | Rheumatoid arthritis | 22446963 | 14q23.1 | rs1957895 |
| 337 | PRKCH | Rheumatoid arthritis | 24390342 | 14q23.1 | rs3783782 |
| 338 | PRKCH | Rheumatoid arthritis | 24390342 | 14q23.1 | rs3783782 |
| 339 | PRDM1 | Systemic lupus erythematosus | 23273568 | 6q21 | rs742108 |
| 340 | PRDM1 | Systemic lupus erythematosus | 19838193 | 6q21 | rs548234 |
| 341 | PRDM1 | Crohn's disease | 21102463 | 6q21 | rs6568421 |
| 342 | FCRL3 | Multiple sclerosis | 21833088 | 1q23.1 | rs3761959 |
| 343 | FCRL3 | Graves' disease | 21841780 | 1q23.1 | rs3761959 |
| 344 | FCRL3 | Rheumatoid arthritis | 24390342 | 1q23.1 | rs2317230 |
| 345 | FCRL3 | Type 1 diabetes autoantibodies | 21829393 | 1q23.1 | rs7528684 |
| 346 | ETS1 | Rheumatoid arthritis | 22446963 | 11q24.3 | rs4937362 |
| 347 | ETS1 | Self-reported allergy | 23817569 | 11q24.3 | rs10893845 |
| 348 | ETS1 | Celiac disease | 20190752 | 11q24.3 | rs11221332 |
| 349 | ETS1 | Systemic lupus erythematosus | 23273568 | 11q24.3 | rs6590330 |
| 350 | ETS1 | Systemic lupus erythematosus | 19838193 | 11q24.3 | rs6590330 |
| 351 | ETS1 | Systemic lupus erythematosus | 20169177 | 11q24.3 | rs1128334 |
| 352 | ETS1 | Rheumatoid arthritis | 24390342 | 11q24.3 | rs73013527 |
| 353 | ETS1 | Rheumatoid arthritis | 24390342 | 11q24.3 | rs73013527 |
| 354 | ETS1 | Rheumatoid arthritis | 24390342 | 11q24.3 | rs73013527 |
| 355 | ETS1 | Psoriasis | 25903422 | 11q24.3 | rs6590334 |
| 356 | ETS1 | Psoriasis | 25903422 | 11q24.3 | rs6590334 |
| 357 | ETS1 | Psoriasis | 25903422 | 11q24.3 | rs7933433 |
| 358 | ETS1 | Psoriasis | 25903422 | 11q24.3 | rs7933433 |
| 359 | ETS1 | Psoriasis | 25903422 | 11q24.3 | rs55974252 |
| 360 | IL32 | HIV-1 susceptibility | 22174851 | 16p13.3 | rs4349147 |
| 361 | TLR10 | Self-reported allergy | 23817569 | 4p14 | rs2101521 |
| 362 | VAV3 | Hashimoto thyroiditis versus Graves' disease | 25429627 | 1p13.3 | rs7537605 |
| 363 | VAV3 | Asthma and hay fever | 24388013 | 1p13.3 | rs7521681 |
| 364 | PTPN22 | Myasthenia gravis | 23055271 | 1p13.2 | rs2476601 |
| 365 | PTPN22 | Crohn's disease | 18587394 | 1p13.2 | rs2476601 |
| 366 | PTPN22 | Rheumatoid arthritis | 17554300 | 1p13.2 | rs6679677 |
| 367 | PTPN22 | Rheumatoid arthritis | 17804836 | 1p13.2 | rs2476601 |
| 368 | PTPN22 | Rheumatoid arthritis | 18794853 | 1p13.2 | rs6679677 |
| 369 | PTPN22 | Rheumatoid arthritis | 19503088 | 1p13.2 | rs2476601 |
| 370 | PTPN22 | Vitiligo | 20410501 | 1p13.2 | rs2476601 |
| 371 | PTPN22 | Rheumatoid arthritis | 20453842 | 1p13.2 | rs2476601 |
| 372 | PTPN22 | Rheumatoid arthritis | 21156761 | 1p13.2 | rs2476601 |
| 373 | PTPN22 | Rheumatoid arthritis | 24449572 | 1p13.2 | rs2476601 |
| 374 | PTPN22 | Type 1 diabetes | 17554300 | 1p13.2 | rs6679677 |
| 375 | PTPN22 | Crohn's disease | 21102463 | 1p13.2 | rs2476601 |
| 376 | PTPN22 | Rheumatoid arthritis | 24390342 | 1p13.2 | rs2476601 |
| 377 | PTPN22 | Type 1 diabetes | 17632545 | 1p13.2 | rs2476601 |
| 378 | PTPN22 | Type 1 diabetes | 17554260 | 1p13.2 | rs2476601 |
| 379 | PTPN22 | Type 1 diabetes | 18978792 | 1p13.2 | rs6679677 |
| 380 | PTPN22 | Type 1 diabetes | 19430480 | 1p13.2 | rs2476601 |
| 381 | PTPN22 | Type 1 diabetes autoantibodies | 21829393 | 1p13.2 | rs2476601 |
| 382 | GYPC | Pyoderma gangrenosum in inflammatory bowel disease | 24487271 | 2q14.3 | rs10184704 |
| 383 | CLNK | Vitiligo | 22561518 | 4p16.1 | rs16872571 |

TABLE E10B-continued

Supervised analysis of 255 candidate GWAS susceptibility loci - list of genes reported in heatmap (column B; see FIG. 11A) along with associated immune diseases from the GWAS catalog

| Heatmap. Rank | List of genes | DISEASE/TRAIT | PUBMEDID | REGION | SNPS |
|---|---|---|---|---|---|
| 384 | CLNK | Rheumatoid arthritis | 24390342 | 4p16.1 | rs13142500 |
| 385 | CLNK | Rheumatoid arthritis | 24390342 | 4p16.1 | rs13142500 |
| 386 | DENND1B | Crohn's disease | 21102463 | 1q31.3 | rs1998598 |
| 387 | BANK1 | Systemic lupus erythematosus | 18204447 | 4q24 | rs10516487 |
| 388 | BANK1 | Systemic lupus erythematosus | 23273568 | 4q24 | rs4522865 |
| 389 | DPP4 | Rheumatoid arthritis | 24782177 | 2q24.2 | rs12617656 |
| 390 | DPP4 | Rheumatoid arthritis | 24782177 | 2q24.2 | rs12617656 |
| 391 | LRRC18 | Systemic lupus erythematosus | 19838193 | 10q11.23 | rs1913517 |
| 392 | LACC1 | Crohn's disease | 23128233 | 13q14.11 | rs3764147 |
| 393 | LACC1 | Leprosy | 25642632 | 13q14.11 | rs8002861 |
| 394 | LACC1 | Leprosy | 25642632 | 13q14.11 | rs9567307 |
| 395 | MAP2K6 | Response to TNF-alpha inhibitors in rheumatoid arthritis | 22569225 | 17q24.3 | rs11870477 |
| 396 | BATF3 | Leprosy | 25642632 | 1q32.3 | rs2221593 |
| 397 | LIME1 | Inflammatory bowel disease | 23128233 | 20q13.33 | rs6062504 |
| 398 | CARD11 | Atopic dermatitis | 23042114 | 7p22.2 | rs4722404 |
| 399 | DAB2 | Self-reported allergy | 23817569 | 5p13.1 | rs7720838 |
| 400 | SLC15A4 | Systemic lupus erythematosus | 23273568 | 12q24.33 | rs1385374 |
| 401 | SLC15A4 | Systemic lupus erythematosus | 19838193 | 12q24.33 | rs1385374 |
| 402 | AHI1 | Multiple sclerosis | 21833088 | 6q23.3 | rs11154801 |
| 403 | TLR7 | Celiac disease | 20190752 | Xp22.2 | rs5979785 |
| 404 | AHNAK2 | Rheumatoid arthritis | 24390342 | 14q32.33 | rs2582532 |
| 405 | AHNAK2 | Rheumatoid arthritis | 24390342 | 14q32.33 | rs2582532 |
| 406 | CUX2 | Type 1 diabetes | 22293688 | 12q24.11 | rs1265564 |
| 407 | PHEX | Immune reponse to smallpox (secreted IFN-alpha) | 22610502 | Xp22.11 | rs1540283 |
| 408 | PRKRA | Inflammatory skin disease | 25574825 | 2q31.2 | rs62176107 |
| 409 | PRKRA | Multiple sclerosis (OCB status) | 23472185 | 2q31.2 | rs9283487 |
| 410 | GNL3 | Osteoarthritis | 22763110 | 3p21.1 | rs11177 |
| 411 | ANTXR2 | Ankylosing spondylitis | 21743469 | 4q21.21 | rs4389526 |
| 412 | ANTXR2 | Ankylosing spondylitis | 20062062 | 4q21.21 | rs4333130 |
| 413 | ALCAM | Erectile dysfunction in type 1 diabetes | 22704111 | 3q13.11 | rs9810233 |
| 414 | AFF3 | Type 1 diabetes | 17554260 | 2q11.2 | rs9653442 |
| 415 | AFF3 | Rheumatoid arthritis | 20453842 | 2q11.2 | rs11676922 |
| 416 | AFF3 | Rheumatoid arthritis | 20453842 | 2q11.2 | rs10865035 |
| 417 | AFF3 | Rheumatoid arthritis | 24390342 | 2q11.2 | rs9653442 |
| 418 | AFF3 | Rheumatoid arthritis | 24782177 | 2q11.2 | rs11676922 |
| 419 | AFF3 | Rheumatoid arthritis | 24390342 | 2q11.2 | rs9653442 |
| 420 | RNASEH2B | Rheumatoid arthritis (ACPA-negative) | 24532677 | 13q14.3 | rs3790022 |
| 421 | MTG1 | Systemic lupus erythematosus | 24871463 | 10q26.3 | rs10857712 |
| 422 | SCAMP3 | Crohn's disease | 21102463 | 1q22 | rs3180018 |
| 423 | NOTCH4 | Systemic lupus erythematosus | 21408207 | 6p21.32 | rs3130320 |
| 424 | NOTCH4 | Systemic sclerosis | 21779181 | 6p21.32 | rs443198 |
| 425 | NOTCH4 | Mixed cryoglobulinemia vasculitis in chronic hepatitis C infection | 25030430 | 6p21.32 | rs2071286 |
| 426 | NOTCH4 | Ulcerative colitis | 24837172 | 6p21.32 | rs549182 |
| 427 | NOTCH4 | Systemic sclerosis | 21779181 | 6p21.32 | rs9296015 |
| 428 | TNFAIP8 | Pyoderma gangrenosum in inflammatory bowel disease | 24487271 | 5q23.1 | rs161857 |
| 429 | CAMK2G | Psoriasis | 25939698 | 10q22.2 | rs2675662 |
| 430 | HLA-DOB | Kawasaki disease | 22446962 | 6p21.32 | rs2857151 |
| 431 | HDAC9 | Ulcerative colitis | 20848476 | 7p21.1 | rs11764116 |
| 432 | RGS14 | Multiple sclerosis | 21833088 | 5q35.3 | rs4075958 |
| 433 | ASAP1 | Multiple sclerosis | 19525955 | 8q24.21 | rs6984045 |
| 434 | PNP | Interferon alpha levels in systemic lupus erythematosus | 25338677 | 14q11.2 | rs1049564 |
| 435 | DXASE2 | Clozapine-induced agranulocytosis | 25187353 | 19p13.13 | rs45495792 |
| 436 | CREM | Crohn's disease | 21102463 | 10p11.21 | rs12242110 |
| 437 | CREM | Inflammatory bowel disease | 23128233 | 10p11.21 | rs11010067 |
| 438 | CD5 | Inflammatory bowel disease | 23128233 | 11q12.2 | rs11230563 |
| 439 | CD5 | Multiple sclerosis | 21833088 | 11q12.2 | rs650258 |
| 440 | CD5 | Rheumatoid arthritis | 24390342 | 11q12.2 | rs508970 |
| 441 | CD2 | Rheumatoid arthritis | 24390342 | 1p13.1 | rs624988 |
| 442 | ADAM19 | Inflammatory skin disease | 25574825 | 5q33.3 | rs6860540 |
| 443 | GZMB | Vitiligo | 20410501 | 14q12 | rs8192917 |
| 444 | IRF4 | Celiac disease | 20190752 | 6p25.3 | rs1033180 |
| 445 | IRF4 | Rheumatoid arthritis | 24390342 | 6p25.3 | rs9378815 |
| 446 | IRF4 | Rheumatoid arthritis | 24390342 | 6p25.3 | rs9378815 |
| 447 | IFNGR2 | Crohn's disease | 23128233 | 21q22.11 | rs2284553 |
| 448 | IFNGR2 | Crohn's disease | 22936669 | 21q22.11 | rs2834215 |
| 449 | IFNGR2 | Rheumatoid arthritis | 24390342 | 21q22.11 | rs73194058 |
| 450 | IFNGR2 | Rheumatoid arthritis | 24390342 | 21q22.11 | rs73194058 |
| 451 | SLA | Graves' disease | 23612905 | 8q24.22 | rs2294025 |

TABLE E10B-continued

Supervised analysis of 255 candidate GWAS susceptibility loci - list of genes reported in heatmap (column B; see FIG. 11A) along with associated immune diseases from the GWAS catalog

| Heatmap. Rank | List of genes | DISEASE/TRAIT | PUBMEDID | REGION | SNPS |
|---|---|---|---|---|---|
| 452 | SLA | Vitiligo | 22561518 | 8q24.22 | rs853308 |
| 453 | ATG16L2 | Crohn's disease | 23266558 | 11q13.4 | rs72981516 |
| 454 | PELI1 | Kawasaki disease | 21221998 | 2p14 | rs7604693 |
| 455 | PELI1 | Allergic dermatitis (nickel) | 23921680 | 2p14 | rs6733160 |
| 456 | TSPAN14 | Inflammatory bowel disease | 23128233 | 10q23.1 | rs6586030 |
| 457 | FCGR2A | Inflammatory bowel disease | 23128233 | 1q23.3 | rs1801274 |
| 458 | FCGR2A | Ulcerative colitis | 21297633 | 1q23.3 | rs1801274 |
| 459 | FCGR2A | Ulcerative colitis | 20228799 | 1q23.3 | rs10800309 |
| 460 | FCGR2A | Kawasaki disease | 22081228 | 1q23.3 | rs1801274 |
| 461 | FCGR2A | Ulcerative colitis | 19915573 | 1q23.3 | rs1801274 |
| 462 | FCGR2A | Systemic lupus erythematosus | 24871463 | 1q23.3 | rs1801274 |
| 463 | FCGR2A | Rheumatoid arthritis | 24390342 | 1q23.3 | rs72717009 |
| 464 | FCGR2A | Rheumatoid arthritis | 24390342 | 1q23.3 | rs72717009 |
| 465 | LILRB1 | Clozapine-induced agranulocytosis | 25187353 | 19q13.42 | rs425283 |
| 466 | UIMC1 | Menopause (age at onset) | 22267201 | 5q35.2 | rs365132 |
| 467 | IFRD1 | Osteoarthritis (hip) | 23989986 | 7q31.1 | rs5009270 |
| 468 | TNFAIP3 | Rheumatoid arthritis | 17982456 | 6q23.3 | rs10499194 |
| 469 | TNFAIP3 | Rheumatoid arthritis | 17982456 | 6q23.3 | rs6920220 |
| 470 | TNFAIP3 | Rheumatoid arthritis | 20453841 | 6q23.3 | rs2230926 |
| 471 | TNFAIP3 | Celiac disease | 20190752 | 6q23.3 | rs2327832 |
| 472 | TNFAIP3 | Systemic lupus erythematosus | 19165918 | 6q23.3 | rs5029939 |
| 473 | TNFAIP3 | Psoriasis | 19169254 | 6q23.3 | rs610604 |
| 474 | TNFAIP3 | Systemic lupus erythematosus | 23273568 | 6q23.3 | rs2230926 |
| 475 | TNFAIP3 | Systemic lupus erythematosus | 19838193 | 6q23.3 | rs2230926 |
| 476 | TNFAIP3 | Rheumatoid arthritis | 20453842 | 6q23.3 | rs6920220 |
| 477 | TNFAIP3 | Sj\'f6gren's syndrome | 24097066 | 6q23.3 | rs5029939 |
| 478 | TNFAIP3 | Rheumatoid arthritis | 24449572 | 6q23.3 | rs6920220 |
| 479 | TNFAIP3 | Psoriasis | 25574825 | 6q23.3 | rs582757 |
| 480 | TNFAIP3 | Inflammatory skin disease | 25574825 | 6q23.3 | rs643177 |
| 481 | TNFAIP3 | Inflammatory skin disease | 25574825 | 6q23.3 | rs681323 |
| 482 | TNFAIP3 | Inflammatory bowel disease | 23128233 | 6q23.3 | rs6920220 |
| 483 | TNFAIP3 | Psoriasis | 20953190 | 6q23.3 | rs610604 |
| 484 | TNFAIP3 | Systemic lupus erythematosus and Systemic sclerosis | 23740937 | 6q23.3 | rs10499197 |
| 485 | TNFAIP3 | Rheumatoid arthritis | 24390342 | 6q23.3 | rs7752903 |
| 486 | TNFAIP3 | Rheumatoid arthritis | 24390342 | 6q23.3 | rs7752903 |
| 487 | TNFAIP3 | Rheumatoid arthritis | 24390342 | 6q23.3 | rs7752903 |
| 488 | TNFAIP3 | Psoriasis | 25903422 | 6q23.3 | rs643177 |
| 489 | TNFAIP3 | Psoriasis | 25903422 | 6q23.3 | rs643177 |
| 490 | NCF4 | Atopic dermatitis | 22197932 | 22q12.3 | rs4821544 |
| 491 | FOSL2 | Inflammatory bowel disease | 23128233 | 2p23.2 | rs925255 |
| 492 | FOSL2 | Type 1 diabetes | 21980299 | 2p23.2 | rs6547853 |
| 493 | CD83 | Rheumatoid arthritis | 22446963 | 6p23 | rs12529514 |
| 494 | CD83 | Rheumatoid arthritis | 24390342 | | chr6:14103212 |
| 495 | CD83 | Rheumatoid arthritis | 24390342 | | chr6:14103212 |
| 496 | QPCT | Response to TNF-alpha inhibitors in rheumatoid arthritis | 22569225 | 2p22.2 | rs960902 |
| 497 | IER3 | Ulcerative colitis | 20848476 | 6p21.33 | rs9501030 |
| 498 | IER3 | Type 1 diabetes and autoimmune thyroid diseases | 25936594 | 6p21.33 | rs886424 |
| 499 | PADI4 | Rheumatoid arthritis | 21505073 | 1p36.13 | rs2240335 |
| 500 | PADI4 | Rheumatoid arthritis | 21452313 | 1p36.13 | rs2240335 |
| 501 | PADI4 | Rheumatoid arthritis | 24390342 | 1p36.13 | rs2301888 |
| 502 | PADI4 | Rheumatoid arthritis | 24390342 | 1p36.13 | rs2301888 |
| 503 | PADI4 | Rheumatoid arthritis | 24390342 | 1p36.13 | rs2301888 |
| 504 | CCR1 | Celiac disease | 18311140 | 3p21.31 | rs6441961 |
| 505 | CCR1 | Behcet's disease | 23291587 | 3p21.31 | rs7616215 |
| 506 | ITGAM | Systemic lupus erythematosus | 18204446 | 16p11.2 | rs11574637 |
| 507 | ITGAM | Systemic lupus erythematosus | 18204446 | 16p11.2 | rs9888739 |
| 508 | ITGAM | Systemic lupus erythematosus | 19165918 | 16p11.2 | rs11150610 |
| 509 | ITGAM | Systemic lupus erythematosus | 23273568 | 16p11.2 | rs9937837 |
| 510 | ITGAM | Systemic lupus erythematosus | 21408207 | 16p11.2 | rs9888739 |
| 511 | ITGAM | Systemic lupus erythematosus | 24871463 | 16p11.2 | rs9888739 |
| 512 | ITGAM | Systemic lupus erythematosus and Systemic sclerosis | 23740937 | 16p11.2 | rs11860650 |
| 513 | DOK3 | Inflammatory bowel disease | 23128233 | 5q35.3 | rs12654812 |
| 514 | GPX1 | Crohn's disease | 21102463 | 3p21.31 | rs3197999 |
| 515 | HLA-A | Crohn's disease | 22412388 | 6p22.1 | rs9258260 |
| 516 | HLA-B | Atopic dermatitis | 25574825 | 6p21.33 | rs148203517 |
| 517 | HLA-B | Vitiligo | 20526339 | 6p21.33 | rs11966200 |
| 518 | HLA-B | Rheumatoid arthritis (ACPA-negative) | 24532677 | 6p21.33 | rs2596565 |
| 519 | HLA-C | Self-reported allergy | 23817569 | 6p21.33 | rs9266772 |
| 520 | HLA-DRA | Ulcerative colitis | 19122664 | 6p21.32 | rs2395185 |
| 521 | HLA-DRA | Ulcerative colitis | 23128233 | 6p21.32 | rs6927022 |

TABLE E10B-continued

Supervised analysis of 255 candidate GWAS susceptibility loci - list of genes reported in heatmap (column B; see FIG. 11A) along with associated immune diseases from the GWAS catalog

| Heatmap. Rank | List of genes | DISEASE/TRAIT | PUBMEDID | REGION | SNPS |
|---|---|---|---|---|---|
| 522 | HLA-DRA | Ulcerative colitis | 24837172 | 6p21.32 | rs1063355 |
| 523 | HLA-DRB1 | Mixed cryoglobulinemia vasculitis in chronic hepatitis C infection | 25030430 | 6p21.32 | rs9461776 |
| 524 | HLA-DRB1 | Immunoglobulin G index levels in multiple sclerosis | 25616667 | 6p21.32 | rs9271640, rs6457617, rs3957148 |
| 525 | HLA-DRB1 | Ulcerative colitis or Crohn's disease | 21699788 | 6p21.32 | rs9271366 |
| 526 | HLA-DRB5 | Crohn's disease | 23850713 | 6p21.32 | rs9271366 |
| 527 | HLA-DRB5 | Ulcerative colitis | 21297633 | 6p21.32 | rs9268853 |
| 528 | HLA-DRB5 | Crohn's disease | 23850713 | 6p21.32 | rs10947261 |
| 529 | HLA-DRB5 | Vogt-Koyanagi-Harada syndrome | 25108386 | 6p21.32 | rs114800139 |
| 530 | LSP1 | Inflammatory bowel disease | 23128233 | 11p15.5 | rs907611 |
| 531 | MYL12B | Response to methotrexate in juvenile idiopathic arthritis | 24709693 | 18p11.31 | rs6506122 |
| 532 | RAC2 | Response to methotrexate in juvenile idiopathic arthritis | 24709693 | 22q13.1 | rs10084630 |
| 533 | RAC2 | Graves' disease | 23612905 | 22q12.3 | rs229527 |
| 534 | RNASET2 | Inflammatory bowel disease | 23128233 | 6q27 | rs1819333 |
| 535 | NFKBIA | Psoriasis | 20953189 | 14q13.2 | rs12586317 |
| 536 | NFKBIA | Psoriasis | 25903422 | 14q13.2 | rs8016947 |
| 537 | NFKBIA | Psoriasis | 25903422 | 14q13.2 | rs8016947 |
| 538 | NFKBIA | Psoriasis | 25903422 | 14q13.2 | rs8016947 |
| 539 | CFLAR | Rheumatoid arthritis | 24390342 | 2q33.1 | rs6715284 |
| 540 | CFLAR | Rheumatoid arthritis | 24390342 | 2q33.1 | rs6715284 |
| 541 | PRDX5 | Crohn's disease | 21102463 | 11q13.1 | rs694739 |
| 542 | HLA-DQB1 | Rheumatoid arthritis | 23918589 | 6p21.32 | rs9275406 |
| 543 | HLA-DQB1 | Knee osteoarthritis | 20305777 | 6p21.32 | rs10947262 |
| 544 | HLA-DQA1 | Sj\'f6gren's syndrome | 24097066 | 6p21.32 | rs9271588 |
| 545 | HLA-DQA1 | Myasthenia gravis | 25643325 | 6p21.32 | rs9270986 |
| 546 | HLA-DQA1 | Systemic sclerosis | 21779181 | 6p21.32 | rs3129763 |
| 547 | HLA-DQA1 | Immune response to anthrax vaccine | 22658931 | 6p21.32 | rs3104402 |
| 548 | HLA-DQA1 | Vogt-Koyanagi-Harada syndrome | 25108386 | 6p21.32 | rs3021304 |
| 549 | HLA-DQA1 | Rheumatoid arthritis (ACPA-negative) | 24532677 | 6p21.32 | rs9271348 |
| 550 | HLA-DQA1 | Ulcerative colitis | 23511034 | 6p21.32 | rs9271366 |
| 551 | HLA-DQA1 | Celiac disease | 20190752 | 6p21.32 | rs2187668 |
| 552 | HLA-DQA1 | Self-reported allergy | 23817569 | 6p21.32 | rs6906021 |
| 553 | HLA-DQA1 | Rheumatoid arthritis | 18668548 | 6p21.32 | rs6457617 |
| 554 | HLA-DQA1 | Systemic lupus erythematosus | 21408207 | 6p21.32 | rs2647012 |
| 555 | HLA-DPB1 | Systemic sclerosis | 21779181 | 6p21.32 | rs987870 |
| 556 | HLA-DPB1 | Sj\'f6gren's syndrome | 24097066 | 6p21.32 | rs4282438 |
| 557 | HIGD1A | Clozapine-induced agranulocytosis | 25187353 | 3p22.1 | rs10865924 |
| 558 | WDFY4 | Systemic lupus erythematosus | 19838193 | 10q11.23 | rs1913517 |
| 559 | LILRB4 | Clozapine-induced agranulocytosis | 25187353 | 19q13.42 | rs425283 |
| 560 | LILRB4 | Inflammatory bowel disease | 23128233 | 19q13.42 | rs11672983 |
| 561 | LPXN | Inflammatory bowel disease | 23128233 | 11q12.1 | rs10896794 |
| 562 | ANXA6 | Psoriasis | 25903422 | 5q33.1 | rs17728338 |
| 563 | ANXA6 | Psoriasis | 25903422 | 5q33.1 | rs17728338 |
| 564 | ANXA6 | Psoriasis | 25903422 | 5q33.1 | rs17728338 |
| 565 | PLD4 | Rheumatoid arthritis | 24390342 | 14q32.33 | rs2582532 |
| 566 | PLD4 | Rheumatoid arthritis | 24390342 | 14q32.33 | rs2582532 |
| 567 | DGKD | Crohn's disease | 22412388 | 2q37.1 | rs2241880 |
| 568 | ATG5 | Systemic lupus erythematosus | 23273508 | 6q21 | rs742108 |
| 569 | ATG5 | Systemic lupus erythematosus | 19838193 | 6q21 | rs548234 |
| 570 | ATXN2 | Celiac disease | 18311140 | 12q24.12 | rs653178 |
| 571 | PIM3 | Ulcerative colitis | 21297633 | 22q13.33 | rs5771069 |
| 572 | CD40 | Multiple sclerosis | 21833088 | 20q13.12 | rs2425752 |
| 573 | TNIP1 | Psoriasis | 25574825 | 5q33.1 | rs2233278 |
| 574 | TNIP1 | Inflammatory skin disease | 25574825 | 5q33.1 | rs17728338 |
| 575 | MTMR3 | Inflammatory bowel disease | 23128233 | 22q12.2 | rs2412970 |
| 576 | TNFSF8 | Inflammatory bowel disease | 23128233 | 9q32 | rs4246905 |
| 577 | HSPA1L | Type 1 diabetes and autoimmune thyroid diseases | 25936594 | 6p21.33 | rs1270942 |
| 578 | STAT4 | Inflammatory bowel disease | 23128233 | 2q32.2 | rs1517352 |
| 579 | IL18R1 | Crohn's disease | 21102463 | 2q12.1 | rs2058660 |
| 580 | RXRA | Crohn's disease (need for surgery) | 23665963 | 9q34.3 | rs11103429 |
| 581 | TLR1 | Self-reported allergy | 23817569 | 4p14 | rs2101521 |
| 582 | TMBIM1 | Inflammatory bowel disease | 23128233 | 2q35 | rs2382817 |
| 583 | SLC8A1 | Immune response to measles-mumps-rubella vaccine | 24811271 | 2p22.1 | rs4140752 |
| 584 | CREB5 | Crohn's disease | 23128233 | 7p15.1 | rs864745 |
| 585 | TLR8 | Celiac disease | 20190752 | Xp22.2 | rs5979785 |
| 586 | LRRK2 | Crohn's disease | 18587394 | 12q12 | rs11175593 |
| 587 | LRRK2 | Crohn's disease | 21102463 | 12q12 | rs11564258 |
| 588 | LRRK2 | Inflammatory bowel disease | 23128233 | 12q12 | rs11564258 |

TABLE E10B-continued

Supervised analysis of 255 candidate GWAS susceptibility loci - list of genes reported in heatmap (column B; see FIG. 11A) along with associated immune diseases from the GWAS catalog

| Heatmap. Rank | List of genes | DISEASE/TRAIT | PUBMEDID | REGION | SNPS |
|---|---|---|---|---|---|
| 589 | IKZF3 | Inflammatory bowel disease | 23128233 | 17q12 | rs12946510 |
| 590 | IKZF3 | Ulcerative colitis | 21297633 | 17q21.1 | rs2872507 |
| 591 | IKZF3 | Self-reported allergy | 23817569 | 17q21.1 | rs9303280 |
| 592 | IKZF3 | Rheumatoid arthritis | 24390342 | | chr17:38031857 |
| 593 | IKZF3 | Rheumatoid arthritis | 24390342 | | chr17:38031857 |
| 594 | IL18RAP | Leprosy | 25642632 | 2q12.1 | rs76886731 |
| 595 | FYN | Inflammatory bowel disease | 23128233 | 6q21 | rs3851228 |
| 596 | PTPN22 | Type 1 diabetes | 17554260 | 1p13.2 | rs6679677 |
| 597 | PTPN22 | Type 1 diabetes and autoimmune thyroid diseases | 25936594 | 1p13.2 | rs2476601 |
| 598 | PTPN22 | Crohn's disease | 23128233 | 1p13.2 | rs6679677 |
| 599 | CARD11 | Ulcerative colitis | 23128233 | 7p22.3 | rs798502 |
| 600 | DUSP5 | Crohn's disease | 23850713 | 10q25.2 | rs11195128 |
| 601 | CUX2 | Gout | 25646370 | 12q24.11 | rs2188380 |
| 602 | RNASE2 | Crohn's disease | 20570966 | 6q27 | rs2301436 |
| 603 | FCGR2B | Ulcerative colitis | 21297633 | 1q23.3 | rs1801274 |
| 604 | NOTCh4 | Lupus nephritis in systemic lupus erythematosus | 24925725 | 6p21.32 | rs9267972 |
| 605 | NOTCH4 | Crohn's disease | 23266558 | 6p21.32 | rs9267911 |
| 606 | FCHSD2 | Crohn's disease | 23266558 | 11q13.4 | rs72981516 |
| 607 | HLA-DOB | Crohn's disease | 23266558 | 6p21.32 | rs7765379 |
| 608 | CDH23 | Vitiligo | 22951725 | 10q22.1 | rs1417210 |
| 609 | ADA | Ulcerative colitis | 23128233 | 20q13.12 | rs6017342 |
| 610 | IRF4 | Psoriasis | 25574825 | 6p25.3 | rs9504361 |
| 611 | IRF4 | Psoriasis | 25903422 | 6p25.3 | rs3799296 |
| 612 | ARAP1 | Rheumatoid arthritis | 22446963 | 11q13.4 | rs3781913 |
| 613 | SULT1A1 | Inflammatory bowel disease | 23128233 | 16p11.2 | rs26528 |
| 614 | ATG16L2 | Crohn's disease | 23850713 | 11q13.4 | rs11235667 |
| 615 | SLC11A1 | Ulcerative colitis | 21297633 | 2q35 | rs11676348 |
| 616 | FCGR3A | Inflammatory bowel disease | 23128233 | 1q23.3 | rs1801274 |
| 617 | SERPINA1 | Anti neutrophil cytoplasmic antibody-associated vasculitis | 22808956 | 14q32.13 | rs7151526 |
| 618 | TMEM173 | Immune reponse to smallpox (secreted IFN-alpha) | 22610502 | 5q31.2 | rs13181561 |
| 619 | IL8 | Inflammatory bowel disease | 23128233 | 4q13.3 | rs2472649 |
| 620 | GPBAR1 | Pyoderma gangrenosum in inflammatory bowel disease | 24487271 | 2q35 | rs13392177 |
| 621 | FCGR2C | Ulcerative colitis | 20228799 | 1q23.3 | rs10800309 |
| 622 | HLA-C | Crohn's disease | 23128233 | 6p21.33 | rs9264942 |
| 623 | HLA-DPA1 | Sj\'fógren's syndrome | 24097066 | 6p21.32 | rs4282438 |
| 624 | HLA-DRB1 | Ulcerative colitis | 23128233 | 6p21.32 | rs6927022 |
| 625 | PLEK | Multiple sclerosis | 22190364 | 2p13.3 | rs7592330 |
| 626 | RPL7 | Crohn's disease | 22412388 | 8q21.11 | rs12677663 |
| 627 | IFNAR2 | Crohn's disease | 23128233 | 21q22.11 | rs2284553 |
| 628 | HLA-DQB1 | Crohn's disease | 23266558 | 6p21.32 | rs7765379 |
| 629 | HLA-DQB1 | Rheumatoid arthritis | 24782177 | 6p21.32 | rs12525220 |
| 630 | HLA-DQB1 | Rheumatoid arthritis | 24782177 | 6p21.32 | rs12525220 |
| 631 | HLA-DQB1 | Rheumatoid arthritis | 24782177 | 6p21.32 | rs12525220 |
| 632 | CD48 | Inflammatory bowel disease | 23128233 | 1q23.3 | rs4656958 |
| 633 | AIF1 | Neonatal lupus | 20662065 | 6p21.33 | rs3099844 |
| 634 | HLA-DQA1 | Ulcerative colitis | 24837172 | 6p21.32 | rs1063355 |
| 635 | HLA-DQA1 | Vitiligo | 20410501 | 6p21.32 | rs3806156 |
| 636 | TLR6 | Self-reported allergy | 23817569 | 4p14 | rs2101521 |
| 637 | MTMR3 | Inflammatory bowel disease (early onset) | 19915574 | 22q12.2 | rs2412973 |
| 638 | TNFSF8 | Crohn's disease | 23266558 | 9q32 | rs6478106 |
| 639 | TTYH3 | Ulcerative colitis | 23128233 | 7p22.3 | rs798502 |
| 640 | CARD9 | Inflammatory bowel disease | 23128233 | 9q34.3 | rs10781499 |
| 641 | CCR6 | Inflammatory bowel disease | 23128233 | 6q27 | rs1819333 |
| 642 | CCR6 | Crohn's disease | 20570966 | 6q27 | rs2301436 |
| 643 | CCR6 | Crohn's disease | 23850713 | 6q27 | rs2149085 |
| 644 | CCR6 | Vitiligo | 20526339 | 6q27 | rs2236313 |
| 645 | NCR3 | Type 1 diabetes and autoimmune thyroid diseases | 25936594 | 6p21.33 | rs2857595 |
| 646 | IL18RAP | Atopic dermatitis | 23042114 | 2q12.1 | rs13015714 |
| 647 | CLEC4F | Erythema nodosum in inflammatory bowel disease | 24487271 | 2p13.3 | rs390966 |
| 648 | FCGR2B | Inflammatory bowel disease | 23128233 | 1q23.3 | rs1801274 |
| 649 | FCHSD2 | Crohn's disease | 23850713 | 11q13.4 | rs11235667 |
| 650 | DNASE1L3 | Rheumatoid arthritis | 24390342 | 3p14.3 | rs73081554 |
| 651 | CTDSP1 | Inflammatory bowel disease | 23128233 | 2q35 | rs2382817 |
| 652 | SULT1A1 | Inflammatory bowel disease (early onset) | 19915574 | 16p11.2 | rs8049439 |
| 653 | GPX1 | Ulcerative colitis | 25082827 | 3p21.31 | rs3197999 |
| 654 | HLA-DRB1 | Crohn's disease | 23850713 | 6p21.32 | rs9271366 |

TABLE E10B-continued

Supervised analysis of 255 candidate GWAS susceptibility loci - list of genes reported in heatmap (column B; see FIG. 11A) along with associated immune diseases from the GWAS catalog

| Heatmap. Rank | List of genes | DISEASE/TRAIT | PUBMEDID | REGION | SNPS |
|---|---|---|---|---|---|
| 655 | HLA-DRB1 | Ulcerative colitis | 21297633 | 6p21.32 | rs9268853 |
| 656 | HLA-DRB1 | Crohn's disease | 23850713 | 6p21.32 | rs10947261 |
| 657 | HLA-DRB5 | Ulcerative colitis | 19122664 | 6p21.32 | rs2395185 |
| 658 | HLA-DQB1 | Epstein-Barr virus immune response (EBNA-1) | 23326239 | 6p21.32 | rs2854275 |
| 659 | PSMB9 | Crohn's disease | 23266558 | 6p21.32 | rs7765379 |
| 660 | HLA-F | Crohn's disease | 22412388 | 6p22.1 | rs9258260 |
| 661 | LST1 | Crohn's disease | 21102463 | 6p21.33 | rs1799964 |
| 662 | HLA-DQA1 | Ulcerative colitis | 23128233 | 6p21.32 | rs6927022 |
| 663 | HLA-DQA1 | Rheumatoid arthritis | 23918589 | 6p21.32 | rs9275406 |
| 664 | HSPA1L | Ulcerative colitis | 24837172 | 6p21.33 | rs4151657 |
| 665 | CARD9 | Ulcerative colitis | 21297633 | 9q34.3 | rs10781499 |
| 666 | IL18RAP | Crohn's disease | 21102463 | 2q12.1 | rs2058660 |
| 667 | IL18RAP | Celiac disease | 18311140 | 2q12.1 | rs13015714 |
| 668 | IL18RAP | Celiac disease | 20190752 | 2q12.1 | rs917997 |
| 669 | CTSW | Inflammatory bowel disease | 23128233 | 11q13.1 | rs2231884 |
| 670 | AMIGO3 | Ulcerative colitis | 21297633 | 3p21.31 | rs9822268 |
| 671 | CMKLR1 | Response to methotrexate in juvenile idiopathic arthritis | 24709693 | 12q23.3 | rs11113818 |
| 672 | LTB | AIDS progression | 19115949 | 6p21.33 | rs2395029 |
| 673 | SLC11A1 | Inflammatory bowel disease | 23128233 | 2q35 | rs2382817 |
| 674 | FBXL20 | Ulcerative colitis | 20228799 | 17q21.1 | rs2305480 |
| 675 | CCR1 | Celiac disease | 20190752 | 3p21.31 | rs13098911 |
| 676 | HLA-DRA | Sj\'fögren's syndrome | 24097066 | 6p21.32 | rs9271588 |
| 677 | HLA-DRB1 | Ulcerative colitis | 19122664 | 6p21.32 | rs2395185 |
| 678 | HLA-DRB1 | Crohn's disease | 23266558 | 6p21.32 | rs7765379 |
| 679 | HLA-DQA1 | Crohn's disease | 23850713 | 6p21.32 | rs9271366 |
| 680 | HLA-DQA1 | Ulcerative colitis | 21297633 | 6p21.32 | rs9268853 |
| 681 | HLA-DQA1 | Crohn's disease | 23850713 | 6p21.32 | rs10947261 |
| 682 | CXCR2 | Inflammatory bowel disease | 23128233 | 2q35 | rs2382817 |
| 683 | FCGR3B | Inflammatory bowel disease | 23128233 | 1q23.3 | rs1801274 |
| 684 | IL18RAP | Inflammatory bowel disease | 23128233 | 2q12.1 | rs917997 |
| 685 | LTB | Crohn's disease | 21102463 | 6p21.33 | rs1799964 |
| 686 | LTB | Neonatal lupus | 20662065 | 6p21.33 | rs3099844 |
| 687 | CCR2 | Celiac disease | 20190752 | 3p21.31 | rs13098911 |
| 688 | NOTCH4 | Type 1 diabetes and autoimmune thyroid diseases | 25936594 | 6p21.33 | rs1270942 |
| 689 | FARSA | Clozapine-induced agranulocytosis | 25187353 | 19p13.13 | rs45495792 |
| 690 | HLA-DRB5 | Sj\'fögren's syndrome | 24097066 | 6p21.32 | rs9271588 |
| 691 | HLA-DQA1 | Ulcerative colitis | 19122664 | 6p21.32 | rs2395185 |
| 692 | HLA-DQA1 | Crohn's disease | 23266558 | 6p21.32 | rs7765379 |
| 693 | USF1 | Inflammatory bowel disease | 23128233 | 1q23.3 | rs4656958 |
| 694 | GABBR1 | Crohn's disease | 22412388 | 6p22.1 | rs9258260 |
| 695 | CXCR1 | Inflammatory bowel disease | 23128233 | 2q35 | rs2382817 |
| 696 | IL1R2 | Inflammatory bowel disease | 23128233 | 2q12.1 | rs917997 |
| 697 | MAPKAPK2 | Inflammatory bowel disease | 23128233 | 1q32.1 | rs3024505 |
| 698 | GPX1 | Inflammatory bowel disease | 23128233 | 3p21.31 | rs3197999 |
| 699 | HLA-DPB1 | Wegener's granulomatosis | 23740775 | 6p21.32 | rs9277554 |
| 700 | SLAMF7 | Inflammatory bowel disease | 23128233 | 1q23.3 | rs4656958 |
| 701 | NOTCH4 | Epstein-Barr virus immune response (EBNA-1) | 23326239 | 6p21.32 | rs2854275 |
| 702 | HLA-DRB6 | Sj\'fögren's syndrome | 24097066 | 6p21.32 | rs9271588 |
| 703 | HLA-DPB2 | Wegener's granulomatosis | 23740775 | 6p21.32 | rs9277554 |
| 704 | RPS26 | Vitiligo | 22951725 | 12q13.2 | rs10876864 |
| 705 | HLA-B | Epstein-Barr virus immune response (EBNA-1) | 23326239 | 6p21.32 | rs2854275 |
| 706 | PSMB1 | Type 1 diabetes | 21980299 | 6q27 | rs924043 |
| 707 | IKZF3 | Ulcerative colitis | 20228799 | 17q21.1 | rs2305480 |

TABLE E10C

Supervised analysis of 99 candidate GWAS susceptibility loci-list of genes reported in heatmap (column B; (see heatmap FIG. 11B) along with associated immune diseases from the GWAS catalog

| Heatmap.Rank | List of genes | DISEASE/TRAIT | PUBMEDID | REGION | SNPS |
|---|---|---|---|---|---|
| 1 | HLA-DRA | Crohn's disease | 23850713 | 6p21.32 | rs9271366 |
| 2 | HLA-DRA | Ulcerative colitis | 21297633 | 6p21.32 | rs9268853 |
| 3 | HLA-DRA | Crohn's disease | 23850713 | 6p21.32 | rs10947261 |
| 4 | HLA-DRA | Vitiligo | 20410501 | 6p21.32 | rs3806156 |
| 5 | HLA-DRA | Vogt-Koyanagi-Harada syndrome | 25108386 | 6p21.32 | rs114800139 |
| 6 | HLA-DRA | Ulcerative colitis | 18836448 | 6p21.32 | rs9268877 |

TABLE E10C-continued

Supervised analysis of 99 candidate GWAS susceptibility loci-list of genes reported in heatmap
(column B; (see heatmap FIG. 11B) along with associated immune diseases from the GWAS catalog

| Heatmap.Rank | List of genes | DISEASE/TRAIT | PUBMEDID | REGION | SNPS |
|---|---|---|---|---|---|
| 7 | HLA-DRA | Multiple sclerosis | 17660530 | 6p21.32 | rs3135388 |
| 8 | HLA-DRA | Multiple sclerosis (OCB status) | 23472185 | 6p21.32 | rs3129871 |
| 9 | HLA-DRA | Systemic sclerosis | 21779181 | 6p21.32 | rs3129882 |
| 10 | HLA-DRA | Ulcerative colitis | 20228798 | 6p21.32 | rs9268923 |
| 11 | HLA-DRA | Multiple sclerosis (OCB status) | 23472185 | 6p21.32 | rs3129871 |
| 12 | HLA-DRA | Ulcerative colitis | 19122664 | 6p21.32 | rs2395185 |
| 13 | HLA-DRA | Ulcerative colitis | 23128233 | 6p21.32 | rs6927022 |
| 14 | HLA-DRA | Ulcerative colitis | 24837172 | 6p21.32 | rs1063355 |
| 15 | HILA-DRA | Sjogren's syndrome | 24097066 | 6p21.32 | rs9271588 |
| 16 | HLA-DRB1 | Sjogren's syndrome | 24097066 | 6p21.32 | rs9271588 |
| 17 | HLA-DRB1 | Myasthenia gravis | 25643325 | 6p21.32 | rs9270986 |
| 18 | HLA-DRB1 | Systemic sclerosis | 21779181 | 6p21.32 | rs9129763 |
| 19 | HLA-DRB1 | Immune response to anthrax vaccine | 22658931 | 6p21.32 | rs3104402 |
| 20 | HLA-DRB1 | Vogt-Koyanagi-Harada syndrome | 25108386 | 6p21.32 | rs3021304 |
| 21 | HLA-DRB1 | Rheumatoid arthritis (ACPA negative) | 24532677 | 6p21.32 | rs9271348 |
| 22 | HLA-DRB1 | Ulcerative colitis | 23511034 | 6p21.32 | rs9271366 |
| 23 | HLA-DRB1 | Systemic lupus etythematostis | 24871463 | | HLA-DRB1*03:01, rs9275572 |
| 24 | HLA-DRB1 | Rheumatoid arthritis | 17554300 | 6p21.32 | rs615672 |
| 25 | HLA-DRB1 | Arthritis (juvenile idiopathic) | 18576341 | 6p21.32 | rs2395148 |
| 26 | HLA-DRB1 | Rheumatoid arthritis | 17804836 | 6p21.32 | rs660895 |
| 27 | HLA-DRB1 | Rheumatoid arthritis | 18794853 | 6p21.32 | rs6457620 |
| 28 | HLA-DRB1 | Multiple sclerosis | 18941528 | 6p21.32 | rs3129934 |
| 29 | HLA-DRB1 | Multiple sclerosis | 19525955 | 6p21.32 | rs9271366 |
| 30 | HLA-DRB1 | Systemic lupus erythematosus | 23273568 | 6p21.32 | rs9270984 |
| 31 | HLA-DRB1 | Rheumatoid arthritis | 21452313 | 6p21.32 | rs7765379 |
| 32 | HLA-DRB1 | Multiple sclerosis | 22190364 | 6p21.32 | rs3129889 |
| 33 | HLA-DRB1 | Systemic lupus erythematosus | 19838193 | 6p21.32 | rs9271100 |
| 34 | HLA-DRB1 | Rheumatoid arthritis | 20453841 | 6p21.32 | rs13192471 |
| 35 | HLA-DRB1 | Rheumatoid arthritis | 20453842 | 6p21.32 | rs6910071 |
| 36 | HLA-DRB1 | Epstein-Barr virus immune response (EBNA-1) | 23326239 | 6p21.32 | rs477515 |
| 37 | HLA-DRB1 | Multiple sclerosis (OCB status) | 23472185 | 6p21.32 | rs3828840 |
| 38 | HLA-DRB1 | Type 1 diabetes | 17632545 | 6p21.32 | rs2647044 |
| 39 | HLA-DRB1 | Multiple sclerosis | 19525953 | 6p21.32 | rs3135388 |
| 40 | HLA-DRB1 | Rheumatoid arthritis | 24390342 | 6p21.32 | rs9268839 |
| 41 | HLA-DRB1 | Rheumatoid arthritis | 24390342 | 6p21.32 | rs9268839 |
| 42 | HLA-DRB1 | Rheumatoid arthritis | 24390342 | 6p21.32 | rs9268839 |
| 43 | HLA-DRB1 | Mixed cryoglobulinemia vasculitis in chronic hepatitis infection | 25030430 | 6p21.32 | rs9461776 |
| 44 | HILA-DRB1 | Immunoglobulin G index levels in multiple sclerosis | 25616667 | 6p21.32 | rs9271640, rs6457617, rs3957148 |
| 45 | HLA-DRB1 | Ulcerative colitis or Crohn's disease | 21699788 | 6p21.32 | rs9271366 |
| 46 | HLA-DRB1 | Ulcerative colitis | 23128233 | 6p21.32 | rs6927022 |
| 47 | HLA-DRB1 | Crohn's disease | 23850713 | 6p21.32 | rs9271366 |
| 48 | HLA-DRB1 | Ulcerative colitis | 21297633 | 6p21.32 | rs9268853 |
| 49 | HLA-DRB1 | Crohn's disease | 23850713 | 6p21.32 | rs10947261 |
| 50 | HLA-DRB1 | Ulcerative colitis | 19122664 | 6p21.32 | rs2395185 |
| 51 | HLA-DRB1 | Crohn's disease | 23266558 | 6p21.32 | rs7765379 |
| 52 | HLA-C | Atopic dermatitis | 25574825 | 6p21.33 | rs148203517 |
| 53 | HLA-C | Vitiligo | 20526339 | 6p21.33 | rs11966200 |
| 54 | HLA-C | AIDS progression | 19115949 | 6p21.33 | rs10484554 |
| 55 | HLA-C | Psoriatic arthritis | 20953186 | 6p21.33 | rs13191343 |
| 56 | HLA-C | Psoriasis | 18369459 | 6p21.33 | rs10484554 |
| 57 | HLA-C | Psoriasis | 18369459 | 6p21.33 | rs2395029 |
| 58 | HLA-C | Psoriasis | 18364390 | 6p21.33 | rs3134792 |
| 59 | HLA-C | Psoriasis | 19169254 | 6p21.33 | rs12191877 |
| 60 | HLA-C | Atopic dermatitis | 23042114 | 6p21.33 | rs9368677 |
| 61 | HLA-C | Psoriasis | 20953188 | 6p21.33 | rs12191877 |
| 62 | HLA-C | Psoriasis | 20953190 | 6p21.33 | rs10484554 |
| 63 | HLA-C | Self-reported allergy | 23817569 | 6p21.33 | rs9266772 |
| 64 | HLA-C | Crohn's disease | 23128233 | 6p21.33 | rs9264942 |
| 65 | HLA-B | Clozapine-induced agranulocytosis | 25187353 | 6p21.33 | rs41549217 |
| 66 | HLA-B | CD4:CD8 lymphocyte ratio | 20045101 | 6p21.33 | rs2524054 |
| 67 | HLA-B | CD4:CD8 lymphocyte ratio | 20045101 | 6p21.33 | rs2524054 |
| 68 | HLA-B | Ankylosing spondylitis | 21743469 | 6p21.33 | rs4349859 |
| 69 | HLA-B | Graves disease | 21841780 | 6p21.33 | rs1521 |
| 70 | HLA-B | Multiple sclerosis | 19525953 | 6p22.1 | rs2523393 |
| 71 | HLA-B | Multiple sclerosis | 22190364 | 6p22.1 | rs9260489 |
| 72 | HLA-B | Atopic dermatitis | 25574825 | 6p21.33 | rs148203517 |

TABLE E10C-continued

Supervised analysis of 99 candidate GWAS susceptibility loci-list of genes reported in heatmap
(column B; (see heatmap FIG. 11B) along with associated immune diseases from the GWAS catalog

| Heatmap.Rank | List of genes | DISEASE/TRAIT | PUBMEDID | REGION | SNPS |
|---|---|---|---|---|---|
| 73 | HLA-B | Vitiligo | 20526339 | 6p21.33 | rs11966200 |
| 74 | HLA-B | Rheumatoid arthritis (ACPA-negative) | 24532677 | 6p21.33 | rs2596565 |
| 75 | HLA-B | Epstein-Barr virus immune response (EBNA-1) | 23316239 | 6p21.32 | rs2854275 |
| 76 | NFKBIA | Psoriasis | 25574825 | 14q13.2 | rs12586317 |
| 77 | NFKBIA | Inflammatory skin disease | 25574825 | 14q13.2 | rs12884468 |
| 78 | NFKBIA | Psoriasis | 20953190 | 14q13.2 | rs8016947 |
| 79 | NFKBIA | Psoriasis | 20953189 | 14q13.2 | rs12586317 |
| 80 | NFKBIA | Psoriasis | 25903422 | 14q13.2 | rs8016947 |
| 81 | NFKBIA | Psoriasis | 25903422 | 14q13.2 | rs8016947 |
| 82 | NFKBIA | Psotiasis | 25903422 | 14q13.2 | rs8016947 |
| 83 | HLA-DRB5 | Crohn's disease | 23850713 | 6p21.32 | rs9271366 |
| 84 | HLA-DRB5 | Ulcerative colitis | 21297633 | 6p21.32 | rs9268853 |
| 85 | HLA-DRB5 | Crohn's disease | 23850713 | 6p21.32 | rs10947261 |
| 86 | HLA-DRB5 | Vogt-Koyanagi-E arada syndrome | 25108386 | 6p21.32 | rs114800139 |
| 87 | HLA-DRB5 | Ulcerative colitis | 19122664 | 6p21.32 | rs2395185 |
| 88 | HLA-DRB5 | Sj\'f6gren's syndrome | 24097066 | 6p21.32 | rs9271588 |
| 89 | GPX1 | Crohn's disease | 21102463 | 3p21.31 | rs3197999 |
| 90 | GPX1 | Ulcerative colitis | 25082827 | 3p21.31 | rs3197999 |
| 91 | GPX1 | Inflammatory bowel disease | 23128233 | 3p21.31 | rs3197999 |
| 92 | PLEK | Multiple sclerosis | 21833088 | 2p13.3 | rs7595037 |
| 93 | PLEK | Celiac disease | 20190752 | 2p14 | rs17035378 |
| 94 | PLEK | Multiple sclerosis | 22190364 | 2p13.3 | rs7592330 |
| 95 | HLA-DPA1 | Systemic sclerosis | 21779181 | 6p21.32 | rs987870 |
| 96 | HLA-DPA1 | Sj\'f6gren's syndrome | 24097066 | 6p21.32 | rs4282438 |
| 97 | HLA-A | Vitiligo | 20410501 | 6p22.1 | rs3823355 |
| 98 | HLA-A | Crohn's disease | 22412388 | 6p22.1 | rs9258260 |
| 99 | RPL5 | Multiple sclerosis | 19525955 | 1p22.1 | rs6604026 |
| 100 | RPL5 | Multiple sclerosis | 17660530 | 1p22.1 | rs6604026 |
| 101 | LSP1 | Ulcerative colitis | 21297633 | 11p15.5 | rs907611 |
| 102 | LSP1 | Inflammatory bowel disease | 23128233 | 11p15.5 | rs907611 |
| 103 | PARK7 | Ulcerative colitis | 21797633 | 1p36.23 | rs35675666 |
| 104 | PARK7 | Celiac disease | 20190752 | 1p36.23 | rs12727642 |
| 105 | PSMA6 | Psoriasis | 20953189 | 14q13.2 | rs12586317 |
| 106 | PSMA6 | Psoriasis | 25903422 | 14q13.2 | rs8016947 |
| 107 | PSMA6 | Psoriasis | 25903422 | 14q13.2 | rs8016947 |
| 108 | PSMA6 | Psoriasis | 25903422 | 14q13.2 | rs8016947 |
| 109 | RAC2 | Response to methotrexate in juvenile idiopathic arthritis | 24709693 | 22q13.1 | rs10084630 |
| 110 | RAC2 | Graves' disease | 23612905 | 22q12.3 | rs229527 |
| 111 | CD44 | Vitiligo | 22561518 | 11p13 | rs10768122 |
| 112 | CD44 | Systemic lupus erythematosus | 23273568 | 11p13 | rs2785197 |
| 113 | RNASET2 | Crohn's disease | 23850713 | 6q27 | rs2149085 |
| 114 | RNASET2 | Vitiligo | 20526339 | 6q27 | rs2236313 |
| 115 | RNASET2 | Graves' disease | 21841780 | 6q27 | rs9355610 |
| 116 | RNASET2 | Inflammatoty bowel disease | 23128233 | 6q27 | rs1819333 |
| 117 | IRF8 | Multiple sclerosis | 21833088 | 16q24.1 | rs13333054 |
| 118 | IRF8 | Multiple sclerosis | 19575953 | 16q24.1 | rs17445836 |
| 119 | IRF8 | Systemic sclerosis | 21779181 | 16q24.1 | rs11642873 |
| 120 | IRF8 | Rheumatoid arthritis | 22446963 | 16q24.1 | rs2280381 |
| 121 | IRF8 | Ulcerative colitis | 23511034 | 16q24.1 | rs16940186 |
| 122 | IRF8 | Inflammatory bowel disease | 23128233 | 16q24.1 | rs10521318 |
| 123 | IRF8 | Systemic lupus erythematosus and Systemic sclerosis | 23740937 | 16q24.1 | rs12711490 |
| 124 | IRF8 | Rheumatoid arthritis | 24390342 | 16q24.1 | rs13330176 |
| 125 | IRF8 | Rheumatoid arthritis | 24390342 | 16q24.1 | rs13330176 |
| 126 | RPS26 | Psoriasis | 20953189 | 12q13.2 | rs12580100 |
| 127 | RPS26 | Psoriasis | 25574825 | 12q13.2 | rs12580100 |
| 128 | RPS26 | Inflammatory skin disease | 25574825 | 12q13.2 | rs1131017 |
| 129 | RPS26 | Vitiligo | 22951725 | 12q13.2 | rs10876864 |
| 130 | HLA-DQB1 | Ulcerative colitis | 19122664 | 6p21.32 | rs2395185 |
| 131 | HLA-DQB1 | Ulcerative colitis | 23128233 | 6p21.32 | rs6927022 |
| 132 | HLA-DQB1 | Ulcerative colitis | 24837172 | 6p21.32 | rs1063355 |
| 133 | HLA-DQB1 | Multiple sclerosis | 20453840 | 6p21.32 | rs2040406 |
| 134 | HLA-DQB1 | Celiac disease | 20190752 | 6p21.32 | rs2187668 |
| 135 | HLA-DQB1 | Self-reported allergy | 23817569 | 6p21.32 | rs6906021 |
| 136 | HLA-DQB1 | Systemic lupus erythematosus | 24871463 | | HLA-DQB1*02:01, rs558702 |
| 137 | HLA-DQB1 | Systemic sclerosis | 21779181 | 6p21.32 | rs9275390 |
| 138 | HLA-DQB1 | Systemic sclerosis | 21779181 | 6p21.32 | rs9275390 |
| 139 | HLA-DQB1 | Systemic sclerosis | 20383147 | 6p21.32 | rs6457617 |
| 140 | III-A-DOB1 | Multiple sclerosis (OCB status) | 23472185 | 6p21.32 | rs3129720 |
| 141 | HLA-DQB1 | Asthma and hay fever | 24388013 | 6p21.32 | rs9273373 |

TABLE E10C-continued

Supervised analysis of 99 candidate GWAS susceptibility loci-list of genes reported in heatmap
(column B; (see heatmap FIG. 11B) along with associated immune diseases from the GWAS catalog

| Heatmap.Rank | List of genes | DISEASE/TRAIT | PUBMEDID | REGION | SNPS |
|---|---|---|---|---|---|
| 142 | HLA-DQB1 | Rheumatoid arthritis | 23918589 | 6p21.32 | rs9275406 |
| 143 | HLA-DQB1 | Knee osteo arthritis | 20305777 | 6p21,32 | rs10947262 |
| 144 | HLA-DQB1 | Crohn's disease | 23266558 | 6p21.32 | rs7765379 |
| 145 | HLA-DQB1 | Rheumatoid arthritis | 24782177 | 6p21.32 | rs12525220 |
| 146 | HLA-DQB1 | Rheumatoid arthritis | 24782177 | 6p21.32 | rs12525220 |
| 147 | HLA-DQB1 | Rheumatoid arthritis | 24782177 | 6p21.32 | rs12525220 |
| 148 | HLA-DQB1 | Epstein-Barr virus immune response (EBNA-1) | 21326239 | 6p21.32 | rs2854275 |
| 149 | H2AFY | Immune response to anthrax vaccine | 22658931 | 5q31.1 | rs634308 |
| 150 | H2AFY | AIDS progression | 21502085 | 5q31.1 | rs477687 |
| 151 | GPX4 | Crohn's disease | 21102463 | 19p13.3 | rs740495 |
| 152 | GPX4 | Crohn's disease | 23128233 | 19p13.3 | rs2024092 |
| 153 | CTSH | Type 1 diabetes | 18978792 | 15q25.1 | rs3825932 |
| 154 | CTSH | Type 1 diabetes | 19430480 | 15q25.1 | rs3825932 |
| 155 | AIF1 | Crohn's disease | 22936669 | 6p21.33 | rs9348876 |
| 156 | AIF1 | Neonatal lupus | 20662065 | 6p21.33 | rs3099844 |
| 157 | HLA-DQA1 | Mixed cryoglohulinemia vasculitis in chronic hepatitis C infection | 25030430 | 6p21.32 | rs9461776 |
| 158 | HLA-DQA1 | Immunoglobulin G index levels in multiple sclerosis | 25616667 | 6p21.32 | rs9271640, rs6457617, rs3957148 |
| 159 | HLA-DQA1 | Systemic lupus etythematostis | 24871463 | | HLA-DQA1*05:01 |
| 160 | HLA-DQA1 | Inflammatory bowel disease | 18758464 | 6p21.32 | rs477515 |
| 161 | HLA-DQA1 | Systemic lupus erythematosus | 18204098 | 6p21.32 | rs2187668 |
| 162 | HLA-DQA1 | Autoimmune hepatitis type-1 | 24768677 | 6p21.32 | rs2187668 |
| 163 | HLA-DQA1 | Multiple sclerosis (OCB status) | 23472185 | 6p21.32 | rs9271640 |
| 164 | HLA-DQA1 | Immunoglobulin G index levels in multiple sclerosis | 25616667 | 6p21.32 | rs6457617 |
| 165 | HLA-DQA1 | Cutaneous lupus erythematosus | 25827949 | 6p21.32 | rs2187668 |
| 166 | HLA-DQA1 | Sj\'f6gren's syndrome | 24097066 | 6p21.32 | rs9271588 |
| 167 | HLA-DQA1 | Myasthenia gravis | 25643325 | 6p21.32 | rs9270986 |
| 168 | HLA-DQA1 | Systemic sclerosis | 21779181 | 6p21.32 | rs3129763 |
| 169 | HLA-DQA1 | Immune response to anthrax vaccine | 22658931 | 6p21.32 | rs3104402 |
| 170 | HLA-DQA1 | Vogt-Koyanagi-Harada syndrome | 25108386 | 6p21.32 | rs3021304 |
| 171 | HLA-DQA1 | Rheumatoid arthritis (ACPA-negative) | 24532677 | 6p21.32 | rs9271348 |
| 172 | HLA-DQA1 | Ulcerative colitis | 23511034 | 6p21.32 | rs9271366 |
| 173 | HLA-DQA1 | Celiac disease | 20190752 | 6p21.32 | rs2187668 |
| 174 | HLA-DQA1 | Self-reported allergy | 23817569 | 6p21.32 | rs6906021 |
| 175 | HLA-DQA1 | Rheumatoid arthritis | 18668548 | 6p21.32 | rs6457617 |
| 176 | HLA-DQA1 | Systemic lupus erythematosus | 21408207 | 6p21.32 | rs2647012 |
| 177 | HLA-DQA1 | Ulcerative colitis | 24837172 | 6p21.32 | rs1063355 |
| 178 | HLA-DQA1 | Vitiligo | 20410501 | 6p21.32 | rs3806156 |
| 179 | HLA-DQA1 | Ulcerative colitis | 23128233 | 6p21.32 | rs6927022 |
| 180 | HLA-DQA1 | Rheumatoid arthritis | 23918589 | 6p21.32 | rs9275406 |
| 181 | HLA-DQA1 | Crohn's disease | 23850713 | 6p21.32 | rs9271366 |
| 182 | HLA-DQA1 | Ulcerative colitis | 21297633 | 6p21.32 | rs9268853 |
| 183 | HLA-DQA1 | Crohn's disease | 23850713 | 6p21.32 | rs10947261 |
| 184 | HLA-DQA1 | Ulcerative colitis | 19122664 | 6p21.32 | rs2395185 |
| 185 | HLA-DQA1 | Crohn's disease | 23266558 | 6p21.32 | rs7765379 |
| 186 | HLA-DPB1 | Aspirin exacerbated respiratory disease in asthmatics | 23180272 | 6p21.32 | rs1042151 |
| 187 | HLA-DPB1 | Systemic sclerosis | 21779181 | 6p21.32 | rs987870 |
| 188 | HLA-DPB1 | Sj\'f6gren's syndrome | 24097066 | 6p21.32 | rs4282438 |
| 189 | HLA-DPB1 | Wegener's granulomatosis | 23740775 | 6p21.32 | rs9277554 |
| 190 | LILRB4 | Clozapine-induced agranulocytosis | 25187353 | 19q13.42 | rs425283 |
| 191 | LILRB4 | Inflammatory bowel disease | 23128233 | 19q13.42 | rs11672983 |
| 192 | ANXA6 | Psoriasis | 25574825 | 5q33.1 | rs2233278 |
| 193 | ANXA6 | Inflammatory skin disease | 25574825 | 5q33.1 | rs17728338 |
| 194 | ANXA6 | Psoriasis | 25903422 | 5q33.1 | rs17728338 |
| 195 | ANXA6 | Psoriasis | 25903422 | 5q33.1 | rs17728338 |
| 196 | ANXA6 | Psoriasis | 25903422 | 5q33.1 | rs17728338 |
| 197 | HLA-DQA2 | Crohn's disease | 23266558 | 6p21.32 | rs7765379 |
| 198 | HLA-DQA2 | Crohn's disease | 21102463 | 6p21.33 | rs1799964 |
| 199 | HLA-DOA2 | Rheumatoid arthritis | 23918589 | 6p21.32 | rs9275406 |
| 200 | HLA-DQA2 | Knee osteoarthritis | 20305777 | 6p21.32 | rs10947262 |
| 201 | HLA-DQA2 | Rheumatoid arthritis | 24782177 | 6p21.32 | rs12525220 |
| 202 | HLA-DQA2 | Rheumatoid arthritis | 24782177 | 6p21.32 | rs12525220 |
| 203 | HLA-DQA2 | Rheumatoid arthritis | 24782177 | 6p21.32 | rs12525220 |
| 204 | HLA-DQA2 | Rheumatoid arthritis | 18668548 | 6p21.32 | rs6457617 |
| 205 | HLA-DQA2 | Systemic lupus erythematosus | 21408207 | 6p21.32 | rs2647012 |
| 206 | HLA-DQA2 | Systemic lupus erythematosus | 24871463 | 6p21.32 | rs9275572 |
| 207 | HLA-DQA2 | Multiple sclerosis (OCB status) | 23472185 | 6p21.32 | rs9275563 |
| 208 | HLA-DQA2 | Systemic lupus erythematosus | 23053960 | 6p21.32 | rs2051549 |

TABLE E10C-continued

Supervised analysis of 99 candidate GWAS susceptibility loci-list of genes reported in heatmap
(column B; (see heatmap FIG. 11B) along with associated immune diseases from the GWAS catalog

| Heatmap.Rank | List of genes | DISEASE/TRAIT | PUBMEDID | REGION | SNPS |
|---|---|---|---|---|---|
| 209 | HLA-DQA2 | Systemic lupus erythematosus | 21408207 | 6p21.32 | rs2301271 |
| 210 | RGS1 | Multiple sclerosis | 21833088 | 1q31.2 | rs1323292 |
| 211 | RGS1 | Celiac disease | 18311140 | 1q31.2 | rs2816316 |
| 212 | RGS1 | Celiac disease | 20190752 | 1q31.2 | rs2816316 |
| 213 | PLD4 | Rheumatoid arthritis | 22446963 | 14q32.33 | rs2841277 |
| 214 | PLD4 | Rheumatoid arthritis | 24390342 | 14q32.33 | rs2582532 |
| 215 | PLD4 | Rheumatoid arthritis | 24390342 | 14q32.33 | rs2582532 |
| 216 | WDFY4 | Systemic lupus erythematosus | 23273568 | 10q11.23 | rs877819 |
| 217 | WDFY4 | Systemic lupus erythematosus | 20169177 | 10q11.23 | rs7097397 |
| 218 | WDFY4 | Rheumatoid arthritis | 24390342 | 10q11.23 | rs2671692 |
| 219 | WDFY4 | Systemic lupus erythematosus | 19838193 | 10q11.23 | rs1913517 |
| 220 | TNIP1 | Inflammatory bowel disease | 23128233 | 5q33.1 | rs11741861 |
| 221 | TNIP1 | Psoriasis | 25903422 | 5q33.1 | rs17728338 |
| 222 | TNIP1 | Psoriasis | 25903422 | 5q33.1 | rs17728338 |
| 223 | TNIP1 | Myasthenia gravis | 23055271 | 5q33.1 | rs4958881 |
| 224 | TNIP1 | Psoriasis | 19169254 | 5q33.1 | rs17728338 |
| 225 | TNIP1 | Systemic lupus erythematosus | 23273568 | 5q33.1 | rs10036748 |
| 226 | TNIP1 | Systemic sclerosis | 21750679 | 5q33.1 | rs2233287 |
| 227 | TNIP1 | Systemic lupus erythematosus | 19838193 | 5q33.1 | rs10036748 |
| 228 | TNIP1 | Systemic lupus erythematosus and Systemic sclerosis | 23740937 | 5q33.1 | rs960709 |
| 229 | TNIP1 | Psoriasis | 25574825 | 5q33.1 | rs2233278 |
| 230 | TNIP1 | Inflammatoty skin disease | 25574825 | 5q33.1 | rs17728338 |
| 231 | BCAS3 | Immune reponse to smallpox (secreted IL-2) | 22610502 | 17q23.2 | rs7224438 |
| 232 | BCAS3 | Gout | 25967671 | 17q23.2 | rs11653176 |
| 233 | CLEC16A | Celiac disease | 20190752 | 16p13.13 | rs12928822 |
| 234 | CLEC16A | Multiple sclerosis | 21833088 | 16p13.13 | rs7200786 |
| 235 | CLEC16A | Self-reported allergy | 23817569 | 16p13.13 | rs7203459 |
| 236 | CLEC16A | Multiple sclerosis | 19525953 | 16p13.13 | rs11865121 |
| 237 | CLEC16A | Atopic dermatitis | 23042114 | 16p13.13 | rs9923856 |
| 238 | CLEC16A | Systemic lupus erythematosus | 23273568 | 16p13.13 | rs12599402 |
| 239 | CLEC16A | Allergic rhinitis | 22036096 | 16p13.13 | rs887864 |
| 240 | CLEC16A | Type 1 diabetes | 19430480 | 16p13.13 | rs12708716 |
| 241 | CLEC16A | Type 1 diabetes | 18978792 | 16p13.13 | rs12708716 |
| 242 | CLEC16A | Type 1 diabetes autoantibodies | 21829393 | 16p13.13 | rs12708716 |
| 243 | CLEC16A | Asthma and hay fever | 24388013 | 16p13.13 | rs62026376 |
| 244 | FUT2 | Crohn's disease | 23128233 | 16q13.33 | rs516246 |
| 245 | FUT2 | Crohn's disease | 21102463 | 19q13.33 | rs281379 |
| 246 | FUT2 | Crohn's disease | 20570966 | 19q13.33 | rs504963 |
| 247 | FUT2 | Psoriasis | 25574825 | 19q13.33 | rs1047781 |
| 248 | PHTF1 | Type 1 diabetes | 17554260 | 1p13.2 | rs6679677 |
| 249 | PHTF1 | Type 1 diabetes and autoimmune thyroid diseases | 25936594 | 1p13.2 | rs2476601 |
| 250 | TNFSF8 | Ulcerative colitis | 21297633 | 9q32 | rs4246905 |
| 251 | TNTSF8 | Crohn's disease | 21102463 | 9q32 | rs3810936 |
| 252 | TNFSF8 | Inflammatory bowel disease | 23128233 | 9q32 | rs4246905 |
| 253 | TNTSF8 | Crohn's disease | 23266558 | 9q32 | rs6478106 |
| 254 | SLC2A9 | Gout | 21983786 | 4p16.1 | rs734553 |
| 255 | SLC2A9 | Gout | 23263486 | 4p16.1 | rs4475146 |
| 256 | SLC2A9 | Urate levels | 20884846 | 4p16.1 | rs13129697 |
| 257 | SLC2A9 | Gout | 25646370 | 4p16.1 | rs3775948 |
| 258 | MTMR3 | Crohn's disease | 21102463 | 22q12.2 | rs713875 |
| 259 | MTMR3 | Inflammatory bowel disease | 23128233 | 22q12.2 | rs2412970 |
| 260 | MTMR3 | Inflammatory bowel disease (early onset) | 19915574 | 22q12.2 | rs2412973 |
| 261 | GPR35 | Ulcerative colitis | 21297633 | 2q37.3 | rs4676406 |
| 262 | GPR35 | Inflammatory bowel disease | 23128233 | 2q37.3 | rs3749171 |
| 263 | PFKFB4 | Inflammatory bowel disease | 23128233 | 3p21.31 | rs3197999 |
| 264 | PFKFB4 | Ulcerative colitis | 25082827 | 3p21.31 | rs3197999 |
| 265 | HSPA1L | Type 1 diabetes and autoimmune thyroid diseases | 25936594 | 6p21.33 | rs1270942 |
| 266 | HSPA1L | Ulcerative colitis | 24837172 | 6p21.33 | rs4151657 |
| 267 | CARD9 | Crohn's disease | 22936669 | 9q34.3 | rs4077515 |
| 268 | CARD9 | Crohn's disease | 21102463 | 9q34.3 | rs4077515 |
| 269 | CARD9 | Ankylosing spondylitis | 21743469 | 9q34.3 | rs10781500 |
| 270 | CARD9 | Ulcerative colitis | 19915572 | 9q34.3 | rs10781500 |
| 271 | CARD9 | Ulcerative colitis | 20228799 | 9q34.3 | rs4077515 |
| 272 | CARD9 | Inflammatory bowel disease | 23128233 | 9q34.3 | rs10781499 |
| 273 | CARD9 | Ulcerative colitis | 21297633 | 9q34.3 | rs10781499 |
| 274 | CCR6 | Crohn's disease | 18587394 | 6q27 | rs2301436 |
| 275 | CCR6 | Rheumatoid arthritis | 20453841 | 6q27 | rs3093024 |
| 276 | CCR6 | Rheumatoid arthritis | 20453842 | 6q27 | rs3093023 |
| 277 | CCR6 | Crohn's disease | 21102463 | 6q27 | rs415890 |
| 278 | CCR6 | Rheumatoid arthritis | 24782177 | 6q27 | rs3093023 |

TABLE E10C-continued

Supervised analysis of 99 candidate GWAS susceptibility loci-list of genes reported in heatmap
(column B; (see heatmap FIG. 11B) along with associated immune diseases from the GWAS catalog

| Heatmap.Rank | List of genes | DISEASE/TRAIT | PUBMEDID | REGION | SNPS |
|---|---|---|---|---|---|
| 279 | CCR6 | Rheumatoid arthritis | 24782177 | 6q27 | rs1854853 |
| 280 | CCR6 | Rheumatoid arthritis | 24782177 | 6q27 | rs1854853 |
| 281 | CCR6 | Rheumatoid arthritis | 24390342 | 6q27 | rs1571878 |
| 282 | CCR6 | Rheumatoid arthritis | 24390342 | 6q27 | rs1571878 |
| 283 | CCR6 | Rheumatoid arthritis | 24390342 | 6q27 | rs1571878 |
| 284 | CCR6 | Inflammatory bowel disease | 23128233 | 6q27 | rs1819333 |
| 285 | CCR6 | Crohn's disease | 20570966 | 6q27 | rs2301436 |
| 286 | CCR6 | Crohn's disease | 23850713 | 6q27 | rs2149085 |
| 287 | CCR6 | Vitiligo | 20526339 | 6q27 | rs2236313 |
| 288 | ATG5 | Rheumatoid arthritis | 24390342 | 6q21 | rs9372120 |
| 289 | ATG5 | Systemic lupus erythematosus and Systemic sclerosis | 23740937 | 6q21 | rs3827644 |
| 290 | ATG5 | Rheumatoid arthritis | 24390342 | 6q21 | rs9372120 |
| 291 | ATG5 | Systemic lupus erythematosus | 23273568 | 6q21 | rs742108 |
| 292 | ATG5 | Systemic lupus erythematosus | 19838193 | 6q21 | rs548234 |
| 293 | FTO | Osteoarthritis | 22763110 | 16q12.2 | rs8044769 |
| 294 | FTO | Allergic rhinitis | 25085501 | 16q12.2 | rs7187423 |
| 295 | GALC | Crohn's disease | 21102463 | 14q31.3 | rs8005161 |
| 296 | GALC | Inflammatory bowel disease | 23128233 | 14q31.3 | rs8005161 |
| 297 | TLR1 | Asthma and hay fever | 24388013 | 4p14 | rs4833095 |
| 298 | TLR1 | Self-reported allergy | 23817569 | 4p14 | rs2101521 |
| 299 | SLC8A1 | HIV-associated dementia | 22628157 | 2p22.1 | rs404005 |
| 300 | SLC8A1 | Immune response to measles-mumps-rubella vaccine | 24811271 | 2p22.1 | rs4140752 |
| 301 | FOSL2 | Inflammatory bowel disease | 23128233 | 2p23.2 | rs925255 |
| 302 | FOSL2 | Type 1 diabetes | 21980299 | 2p23.2 | rs6547853 |
| 303 | IL1R2 | Ulcerative colitis | 21297633 | 2q11.2 | rs2310173 |
| 304 | IL1R2 | Ankylosing spondylitis | 20062062 | 2q11.2 | rs2310173 |
| 305 | IL1R2 | Inflammatory bowel disease | 23128233 | 2q12.1 | rs917997 |
| 306 | RUNX3 | Celiac disease | 20190752 | 1p36.11 | rs10903122 |
| 307 | RUNX3 | Crohn's disease | 23266558 | 1p36.11 | rs7551188 |
| 308 | RUNX3 | Ankylosing spondylitis | 21743469 | 1p36.11 | rs11249215 |
| 309 | ARID5B | Systemic lupus erythematosus | 23273568 | 10q21.2 | rs4948496 |
| 310 | ARID5B | Rheumatoid arthritis | 22446963 | 10q21.2 | rs10821944 |
| 311 | ARID5B | Rheumatoid arthritis | 24390342 | 10q21.2 | rs71508903 |
| 312 | ARID5B | Rheumatoid arthritis | 24390342 | 10q21.2 | rs71508903 |
| 313 | ARID5B | Rheumatoid arthritis | 24390342 | 10q21.2 | rs71508903 |
| 314 | SP140 | Multiple sclerosis | 21833088 | 2q37.1 | rs10201872 |
| 315 | SP140 | Crohn's disease | 23128233 | 2q37.1 | rs6716753 |
| 316 | SP140 | Crohn's disease | 21102463 | 2q37.1 | rs7423615 |
| 317 | CREM | Crohn's disease | 21102463 | 10p11.21 | rs12242110 |
| 318 | CREM | Inflammatory bowel disease | 23128233 | 10p11.21 | rs11010067 |
| 319 | STAT4 | Celiac disease or Rheumatoid arthritis | 21383967 | 2q32.2 | rs7574865 |
| 320 | STAT4 | Systemic lupus erythematosus | 19165918 | 2q32.2 | rs3821236 |
| 321 | STAT4 | Systemic lupus erythematosus | 18204098 | 2q32.2 | rs7574865 |
| 322 | STAT4 | Behcet's disease | 23001997 | 2q32.3 | rs897200 |
| 323 | STAT4 | Systemic lupus erythematosus | 23053960 | 2q32.2 | rs7574865 |
| 324 | STAT4 | Behcet's disease | 23001997 | 2q32.3 | rs897200, rs7572482, rs7574070 |
| 325 | STAT4 | Systemic lupus erythematosus | 23273568 | 2q32.2 | rs7574865 |
| 326 | STAT4 | Systemic lupus erythematosus | 21408207 | 2q32.2 | rs7574865 |
| 327 | STAT4 | Systemic lupus erythematosus | 21408207 | 2q32.2 | rs7574865 |
| 328 | STAT4 | Systemic sclerosis | 21750679 | 2q32.2 | rs7574865 |
| 329 | STAT4 | Systemic sclerosis | 21779181 | 2q32.2 | rs3821236 |
| 330 | STAT4 | Systemic lupus erythematosus | 19838193 | 2q32.2 | rs7574865 |
| 331 | STAT4 | Systemic sclerosis | 20383147 | 2q32.2 | rs3821236 |
| 332 | STAT4 | Rheumatoid arthritis | 20453841 | 2q32.2 | rs7574865 |
| 333 | STAT4 | Rheumatoid arthritis | 20453842 | 2q32.2 | rs7574865 |
| 334 | STAT4 | Sj\'f6gren's syndrome | 24097066 | 2q32.2 | rs10168266 |
| 335 | STAT4 | Systemic lupus erythematosus | 24871463 | 2q32.2 | rs7574865 |
| 336 | STAT4 | Behcet's disease | 23291587 | 2q32.2 | rs7574070 |
| 337 | STAT4 | Systemic lupus erythematosus and Systemic sclerosis | 23740937 | 2q32.2 | rs7601754 |
| 338 | STAT4 | Rheumatoid arthritis | 24390342 | 2q32.2 | rs11889341 |
| 339 | STAT4 | Rheumatoid arthritis | 24390342 | 2q32.2 | rs11889341 |
| 340 | STAT4 | Rheumatoid arthritis | 24390342 | 2q32.2 | rs11889341 |
| 341 | STAT4 | Inflammatory bowel disease | 23128233 | 2q32.2 | rs1517352 |
| 342 | GNA12 | Ulcerative colitis | 23128233 | 7p22.3 | rs798502 |
| 343 | GNA12 | Ulcerative colitis | 21297633 | 7p22.3 | rs798502 |
| 344 | CD5 | Inflammatoty bowel disease | 23128233 | 11q12.2 | rs11230563 |
| 345 | CD5 | Multiple sclerosis | 21833088 | 11q12.2 | rs650258 |
| 346 | CD5 | Rheumatoid arthritis | 24390342 | 11q12.2 | rs508970 |
| 347 | IL2RB | Rheumatoid arthritis | 24390342 | 22q12.3 | rs3218251 |

TABLE E10C-continued

Supervised analysis of 99 candidate GWAS susceptibility loci-list of genes reported in heatmap (column B; (see heatmap FIG. 11B) along with associated immune diseases from the GWAS catalog

| Heatmap.Rank | List of genes | DISEASE/TRAIT | PUBMEDID | REGION | SNPS |
|---|---|---|---|---|---|
| 348 | IL2RB | Type 1 diabetes autoantibodies | 21829393 | 22q12.3 | rs743777 |
| 349 | CD247 | Celiac disease or Rheumatoid arthritis | 21383967 | 1q24.2 | rs864537 |
| 350 | CD247 | Celiac disease | 20190752 | 1q24.2 | rs864537 |
| 351 | CD247 | Systemic sclerosis | 21750679 | 1q24.2 | rs2056626 |
| 352 | CD247 | Systemic sclerosis | 21779181 | 1q24.2 | rs2056626 |
| 353 | CD247 | Systemic sclerosis | 20383147 | 1q24.2 | rs2056626 |
| 354 | CD247 | Rheumatoid arthritis | 20453842 | 1q24.2 | rs840016 |
| 355 | IL18RAP | Leprosy | 25642632 | 2q12.1 | rs76886731 |
| 356 | IL18RAP | Atopic dermatitis | 23042114 | 2q12.1 | rs13015714 |
| 357 | IL18RAP | Crohn's disease | 21102463 | 2q12.1 | rs2058660 |
| 358 | IL18RAP | Celiac disease | 18311140 | 2q12.1 | rs13015714 |
| 359 | IL18RAP | Celiac disease | 20190752 | 2q12.1 | rs917997 |
| 360 | IL18RAP | Inflammatory bowel disease | 23128233 | 2q12.1 | rs917997 |
| 361 | IKZF3 | Crohn's disease | 21102463 | 17q21.1 | rs2872507 |
| 362 | IKZF3 | Rheumatoid arthritis | 20453842 | 17q21.1 | rs2872507 |
| 363 | IKZF3 | Systemic lupus erythematosus and Systemic sclerosis | 23740937 | 17q21.1 | rs9303277 |
| 364 | IKZF3 | Asthma and hay fever | 24388013 | 17q21.1 | rs12450323 |
| 365 | IKZF3 | Inflammatory bowel disease | 23128233 | 17q12 | rs12946510 |
| 366 | IKZF3 | Ulcerative colitis | 21297633 | 17q21.1 | rs2872507 |
| 367 | IKZF3 | Self-reported allergy | 23817569 | 17q21.1 | rs9303280 |
| 368 | IKZF3 | Rheumatoid arthritis | 24390342 | | chr17:38031857 |
| 369 | IKZF3 | Rheumatoid arthritis | 24390342 | | chr17:38031857 |
| 370 | IKZF3 | Ulcerative colitis | 20228799 | 17q21.1 | rs2305480 |
| 371 | PRDM1 | Systemic lupus erythematosus | 23273568 | 6q21 | rs742108 |
| 372 | PRDM1 | Systemic lupus erythematosus | 19838193 | 6q21 | rs548234 |
| 373 | PRDM1 | Cronn's disease | 21102463 | 6q21 | rs6568421 |
| 374 | PRKCH | Rheumatoid arthritis | 22446963 | 14q23.1 | rs1957895 |
| 375 | PRKCH | Rheumatoid arthritis | 24390342 | 14q23.1 | rs3783782 |
| 376 | PRKCH | Rheumatoid arthritis | 24390342 | 14q23.1 | rs3783782 |
| 377 | FCRL3 | Multiple sclerosis | 21833088 | 1q23.1 | rs3761959 |
| 378 | FCRL3 | Graves' disease | 21841780 | 1q23.1 | rs3761959 |
| 379 | FCRL3 | Rheumatoid arthritis | 24390342 | 1q23.1 | rs2317230 |
| 380 | FCRL3 | Type 1 diabetes autoantibodies | 21829393 | 1q23.1 | rs7528684 |
| 381 | ETS1 | Rheumatoid arthritis | 22446963 | 11q24.3 | rs4937362 |
| 382 | ETS1 | Self-reported allergy | 23817569 | 11q24.3 | rs10893845 |
| 383 | ETS1 | Celiac disease | 20190752 | 11q24.3 | rs11221332 |
| 384 | ETS1 | Systemic lupus erythematosus | 23273568 | 11q24.3 | rs6590330 |
| 385 | ETS1 | Systemic lupus erythematosus | 19838193 | 11q24.3 | rs6590330 |
| 386 | ETS1 | Systemic lupus erythematosus | 20169177 | 11q24.3 | rs1128334 |
| 387 | ETS1 | Rheumatoid arthritis | 24390342 | 11q24.3 | rs73013527 |
| 388 | ETS1 | Rheumatoid arthritis | 24390342 | 11q24.3 | rs73013527 |
| 389 | ETS1 | Rheumatoid arthritis | 24390342 | 11q24.3 | rs73013527 |
| 390 | ETS1 | Psoriasis | 25903422 | 11q24.3 | rs6590334 |
| 391 | ETS1 | Psoriasis | 25903422 | 11q24.3 | rs6590334 |
| 392 | ETS1 | Psoriasis | 25903422 | 11q24.3 | rs7933433 |
| 393 | ETS1 | Psoriasis | 25903422 | 11q24.3 | rs7933433 |
| 394 | ETS1 | Psoriasis | 25903422 | 11q24.3 | rs55974252 |
| 395 | PTPN22 | Myasthenia gravis | 23055271 | 1p13.2 | rs2476601 |
| 396 | PTPN22 | Crohn's disease | 18587394 | 1p13.2 | rs2476601 |
| 397 | PTPN22 | Rheumatoid arthritis | 17554300 | 1p13.2 | rs6679677 |
| 398 | PTPN22 | Rheumatoid arthritis | 17804836 | 1p13.2 | rs2476601 |
| 399 | PTPN22 | Rheumatoid arthritis | 18794853 | 1p13.2 | rs6679677 |
| 400 | PTPN22 | Rheumatoid arthritis | 19503088 | 1p13.2 | rs2476601 |
| 401 | PTPN22 | Vitiligo | 20410501 | 1p13.2 | rs2476601 |
| 402 | PTPN22 | Rheumatoid arthritis | 20453842 | 1p13.2 | rs2476601 |
| 403 | PTPN22 | Rheumatoid arthritis | 21156761 | 1p13.2 | rs2476601 |
| 404 | PTPN22 | Rheumatoid arthritis | 24449572 | 1p13.2 | rs2476601 |
| 405 | PTPN22 | Type 1 diabetes | 17554300 | 1p13.2 | rs6679677 |
| 406 | PTPN22 | Crohn's disease | 21102463 | 1p13.2 | rs2476601 |
| 407 | PTPN22 | Rheumatoid arthritis | 24390342 | 1p13.2 | rs2476601 |
| 408 | PTPN22 | Type 1 diabetes | 17632545 | 1p13.2 | rs2476601 |
| 409 | PTPN22 | Type 1 diabetes | 17554260 | 1p13.2 | rs2476601 |
| 410 | PTPN22 | Type 1 diabetes | 18978792 | 1p13.2 | rs6679677 |
| 411 | PTPN22 | Type 1 diabetes | 19430480 | 1p13.2 | rs2476601 |
| 412 | PTPN22 | Type 1 diabetes autoantibodies | 21829393 | 1p13.2 | rs2476601 |
| 413 | PTPN22 | Type 1 diabetes | 17554260 | 1p13.2 | rs6679677 |
| 414 | PTPN22 | Type 1 diabetes and autoimmune thyroid diseases | 25936594 | 1p13.2 | rs2476601 |
| 415 | PTPN22 | Crohn's disease | 23128233 | 1p13.2 | rs6679677 |
| 416 | VAV3 | Hashimoto thyroiditis versus Graves' disease | 25479627 | 1p13.3 | rs7537605 |
| 417 | VAV3 | Asthma and hay fever | 24388013 | 1p13.3 | rs7521681 |
| 418 | CD40 | Inflammatory bowel disease | 23128233 | 20q13.12 | rs1569723 |

TABLE E10C-continued

Supervised analysis of 99 candidate GWAS susceptibility loci-list of genes reported in heatmap (column B; (see heatmap FIG. 11B) along with associated immune diseases from the GWAS catalog

| Heatmap.Rank | List of genes | DISEASE/TRAIT | PUBMEDID | REGION | SNPS |
|---|---|---|---|---|---|
| 419 | CD40 | Rheumatoid arthritis | 18794853 | 20q13.12 | rs4810485 |
| 420 | CD40 | Multiple sclerosis | 19525955 | 20q13.12 | rs6074022 |
| 421 | CD40 | Multiple sclerosis | 22190364 | 20q13.12 | rs6074022 |
| 422 | CD40 | Kawasaki disease | 22446962 | 20q13.12 | rs4813003 |
| 423 | CD40 | Kawasaki disease | 22446961 | 20q13.12 | rs1569723 |
| 424 | CD40 | Rheumatoid arthritis | 20453842 | 20q13.12 | rs4810485 |
| 425 | CD40 | Rheumatoid arthritis | 24390342 | 20q13.12 | rs4239702 |
| 426 | CD40 | Rheumatoid arthritis | 24390342 | 20q13.12 | rs4239702 |
| 427 | CD40 | Multiple sclerosis | 21833088 | 20q13.12 | rs2425752 |
| 428 | CLNK | Vitiligo | 22561518 | 4p16.1 | rs16872571 |
| 429 | CLNK | Rheumatoid arthritis | 24390342 | 4p16.1 | rs13142500 |
| 430 | CLNK | Rheumatoid arthritis | 24390342 | 4p16.1 | rs13142500 |
| 431 | LACC1 | Crohn's disease | 23128233 | 13q14.11 | rs3764147 |
| 432 | LACC1 | Leprosy | 25642632 | 13q14.11 | rs8002861 |
| 433 | LACC1 | Leprosy | 25642632 | 13q14.11 | rs9567307 |
| 434 | IL18R1 | Inflammatory bowel disease | 23128233 | 2q12.1 | rs917997 |
| 435 | IL18R1 | Celiac disease | 18311140 | 2q12.1 | rs13015714 |
| 436 | IL18R1 | Celiac disease | 20190752 | 2q12.1 | rs917997 |
| 437 | IL18R1 | Atopic dermatitis | 23042114 | 2q12.1 | rs13015714 |
| 438 | IL18R1 | Leprosy | 25642632 | 2q12.1 | rs76886731 |
| 439 | IL18R1 | Crohn's disease | 21102463 | 2q12.1 | rs2058660 |
| 440 | BANK1 | Systemic lupus erythematosus | 18204447 | 4q24 | rs10516487 |
| 441 | BANK1 | Systemic lupus erythematosus | 23273568 | 4q24 | rs4522865 |
| 442 | ANTXR2 | Ankylosing spondylitis | 21743469 | 4q21.21 | rs4389526 |
| 443 | ANTXR2 | Ankylosing spondylitis | 20062062 | 4q21.21 | rs4333130 |
| 444 | AFF3 | Type 1 diabetes | 17554260 | 2q11.2 | rs9653442 |
| 445 | AFF3 | Rheumatoid arthritis | 20453842 | 2q11.2 | rs11676922 |
| 446 | AFF3 | Rheumatoid arthritis | 20453842 | 2q11.2 | rs10865035 |
| 447 | AFF3 | Rheumatoid arthritis | 24390342 | 2q11.2 | rs9653442 |
| 448 | AFF3 | Rheumatoid arthritis | 24782177 | 2q11.2 | rs11676922 |
| 449 | AFF3 | Rheumatoid arthritis | 24390342 | 2q11.2 | rs9653442 |
| 450 | PRKRA | Inflammatory skin disease | 25574825 | 2q31.2 | rs62176107 |
| 451 | PRKRA | Multiple sclerosis (OCB status) | 23472185 | 2q31.2 | rs9283487 |
| 452 | HLA-DOB | Kawasaki disease | 22446962 | 6p21.32 | rs2857151 |
| 453 | HLA-DOB | Crohn's disease | 23266558 | 6p213.2 | rs7765379 |
| 454 | SLC15A4 | Systemic lupus erythematosus | 23273568 | 12q24.33 | rs1385374 |
| 455 | SLC15A4 | Systemic lupus erythematosus | 19838913 | 12q24.33 | rs1385374 |
| 456 | IRF4 | Celiac disease | 20190752 | 6p25.3 | rs1033180 |
| 457 | IRF4 | Rheumatoid arthritis | 24390342 | 6p25.3 | rs9378815 |
| 458 | IRF4 | Rheumatoid arthritis | 24390342 | 6p25.3 | rs9378815 |
| 459 | IRF4 | Psoriasis | 25574825 | 6p25.3 | rs9504361 |
| 460 | IRF4 | Psoriasis | 25903422 | 6p25.3 | rs3799296 |
| 461 | NOTCH4 | Systemic lupus erythematosus | 21408207 | 6p21.32 | rs3130320 |
| 462 | NOTCH4 | Systemic sclerosis | 21779181 | 6p21.32 | rs443198 |
| 463 | NOTCH4 | Mixed cryoglobulinemia vasculitis in chronic hepatitis C infection | 25030430 | 6p21.32 | rs2071286 |
| 464 | NOTCH4 | Ulcerative colitis | 24837172 | 6p21.32 | rs549182 |
| 465 | NOTCH4 | Systemic sclerosis | 21779181 | 6p21.32 | rs9296015 |
| 466 | NOTCh4 | Lupus nephritis in systemic lupus erythematosus | 24925725 | 6p21.32 | rs9267972 |
| 467 | NOTCH4 | Crohn's disease | 23266558 | 6p21.32 | rs9267911 |
| 468 | NOTCH4 | Type 1 diabetes and autoimmune thyroid diseases | 25936594 | 6p21.33 | rs1270942 |
| 469 | NOTCH4 | Epstein-Barr virus immune response (EBNA-1) | 23326239 | 6p21.32 | rs2854275 |
| 470 | LTB | AIDS progression | 19115949 | 6p21.33 | rs2395029 |
| 471 | LTB | Crohn's disease | 21102463 | 6p21.33 | rs1799964 |
| 472 | LTB | Neonatal lupus | 20662065 | 6p21.33 | rs3099844 |
| 473 | CARD11 | Atopic dermatitis | 23042114 | 7p22.2 | rs4722404 |
| 474 | CARD11 | Ulcerative colitis | 23128233 | 7p22.3 | rs798502 |
| 475 | CUX2 | Type 1 diabetes | 22293688 | 12q24.11 | rs1265564 |
| 476 | CUX2 | Gout | 25646370 | 12q24.11 | rs2188380 |
| 477 | FCGR2B | Ulcerative colitis | 21297633 | 1q23.3 | rs1801274 |
| 478 | FCGR2B | Inflammatory bowel disease | 23128233 | 1q23.3 | rs1801274 |
| 479 | IFNGR2 | Crohn's disease | 23128233 | 21q22.11 | rs2284553 |
| 480 | IFNGR2 | Crohn's disease | 22936669 | 21q22.11 | rs2834215 |
| 481 | IFNGR2 | Rheumatoid arthritis | 24390342 | 21q22.11 | rs73194058 |
| 482 | IFNGR2 | Rheumatoid arthritis | 24390342 | 21q22.11 | rs73194058 |
| 483 | PELI1 | Kawasaki disease | 21221998 | 2p14 | rs7604693 |
| 484 | PELI1 | Allergic dermatitis (nickel) | 23921680 | 2p14 | rs6733160 |
| 485 | ATG16L2 | Crohn's disease | 23266558 | 11q13.4 | rs72981516 |
| 486 | ATG16L2 | Crohn's disease | 23850713 | 11q13.4 | rs11235667 |
| 487 | SLA | Graves' disease | 23612905 | 8q24.22 | rs2294025 |
| 488 | SLA | Vitiligo | 22561518 | 8q24.22 | rs853308 |
| 489 | SLC11A1 | Ulcerative colitis | 21297633 | 2q35 | rs11676348 |

TABLE E10C-continued

Supervised analysis of 99 candidate GWAS susceptibility loci-list of genes reported in heatmap (column B; (see heatmap FIG. 11B) along with associated immune diseases from the GWAS catalog

| Heatmap.Rank | List of genes | DISEASE/TRAIT | PUBMEDID | REGION | SNPS |
|---|---|---|---|---|---|
| 490 | SLC11A1 | Inflammatory bowel disease | 23128233 | 2q35 | rs2382817 |
| 491 | SULT1A1 | Inflammatory bowel disease | 23128233 | 16p11.2 | rs26528 |
| 492 | SULT1A1 | Inflammatory bowel disease (early onset) | 19915574 | 16p11.2 | rs8049439 |
| 493 | FCGR2A | Inflammatory bowel disease | 23128233 | 1q23.3 | rs1801274 |
| 494 | FCGR2A | Ulcerative colitis | 21297633 | 1q23.3 | rs1801274 |
| 495 | FCGR2A | Ulcerative colitis | 20228799 | 1q23.3 | rs10800309 |
| 496 | FCGR2A | Kawasaki disease | 22081228 | 1q23.3 | rs1801274 |
| 497 | FCGR2A | Ulcerative colitis | 19915573 | 1q23.3 | rs1801274 |
| 498 | FCGR2A | Systemic lupus erythematosus | 24871463 | 1q23.3 | rs1801274 |
| 499 | FCGR2A | Rheumatoid arthritis | 24390342 | 1q23.3 | rs72717009 |
| 500 | FCGR2A | Rheumatoid arthritis | 24390342 | 1q23.3 | rs72717009 |
| 501 | TNFAIP3 | Rheumatoid arthritis | 17982456 | 6q23.3 | rs10499194 |
| 502 | TNFAIP3 | Rheumatoid arthritis | 17982456 | 6q23.3 | rs6920220 |
| 503 | TNFAIP3 | Rheumatoid arthritis | 20453841 | 6q23.3 | rs2230926 |
| 504 | TNFAIP3 | Celiac disease | 20190752 | 6q23.3 | rs2327832 |
| 505 | TNFAIP3 | Systemic lupus erythematosus | 19165918 | 6q23.3 | rs5029939 |
| 506 | TNFAIP3 | Psoriasis | 19169254 | 6q23.3 | rs610604 |
| 507 | TNFAIP3 | Systemic lupus erythematosus | 23273568 | 6q23.3 | rs2230926 |
| 508 | TNFAIP3 | Systemic lupus etythematostis | 19838193 | 6q23.3 | rs2230926 |
| 509 | TNFAIP3 | Rheumatoid arthritis | 20453842 | 6q23.3 | rs6920220 |
| 510 | TNFAIP3 | Sj\'f6gren's syndrome | 24097066 | 6q23.3 | rs5029939 |
| 511 | TNFAIP3 | Rheumatoid arthritis | 24449572 | 6q23.3 | rs6920220 |
| 512 | TNFAIP3 | Psoriasis | 25574825 | 6q23.3 | rs582757 |
| 513 | TNFAIP3 | Inflammatory skin disease | 25574825 | 6q23.3 | rs643177 |
| 514 | TNFAIP3 | Inflammatory skin disease | 25574825 | 6q23.3 | rs681323 |
| 515 | TNFAIP3 | Inflammatory bowel disease | 23128233 | 6q23.3 | rs6920220 |
| 516 | TNFAIP3 | Psoriasis | 20953190 | 6q23.3 | rs610604 |
| 517 | TNFAIP3 | Systemic lupus erythematosus and Systemic sclerosis | 23740937 | 6q23.3 | rs10499197 |
| 518 | TNFAIP3 | Rheumatoid arthritis | 24390342 | 6q23.3 | rs7752903 |
| 519 | TNFAIP3 | Rheumatoid arthritis | 24390342 | 6q23.3 | rs7752903 |
| 520 | TNFAIP3 | Rheumatoid arthritis | 24390342 | 6q23.3 | rs7752903 |
| 521 | TNFAIP3 | Psoriasis | 25903422 | 6q23.3 | rs643177 |
| 522 | TNFAIP3 | Psoriasis | 25903422 | 6q23.3 | rs643177 |
| 523 | CD83 | Rheumatoid arthritis | 22446963 | 6p23 | rs12529514 |
| 524 | CD83 | Rheumatoid arthritis | 24390342 | | chr6:14103212 |
| 525 | CD83 | Rheumatoid arthritis | 24390342 | | chr6:14103212 |
| 526 | CCR1 | Celiac disease | 18311140 | 3p21.31 | rs6441961 |
| 527 | CCR1 | Behcet's disease | 23291587 | 3p21.31 | rs7616215 |
| 528 | CCR1 | Celiac disease | 20190752 | 3p21.31 | rs13098911 |
| 529 | ITGAM | Systemic lupus erythematosus | 18204098 | 16p11.2 | rs11574637 |
| 530 | ITGAM | Systemic lupus erythematosus | 18204446 | 16p11.2 | rs9888739 |
| 531 | ITGAM | Systemic lupus erythematosus | 19165918 | 16p11.2 | rs11150610 |
| 532 | ITGAM | Systemic lupus erythematosus | 23273568 | 16p11.2 | rs9937837 |
| 533 | 1TGAM | Systemic lupus erythematosus | 21408207 | 16p11.2 | rs9888739 |
| 534 | ITGAM | Systemic lupus erythematosus | 24871463 | 16p11.2 | rs9888739 |
| 535 | ITGAM | Systemic lupus erythematosus and Systemic sclerosis | 23740937 | 16p11.2 | rs11860650 |
| 536 | IER3 | Ulcerative colitis | 20848476 | 6p21.33 | rs9501030 |
| 537 | IER3 | Type 1 diabetes and autoimmune thyroid diseases | 25936594 | 6p21.33 | rs886424 |
| 538 | PADI4 | Rheumatoid arthritis | 21505073 | 1p36.13 | rs2240335 |
| 539 | PADI4 | Rheumatoid arthritis | 21452313 | 1p36.13 | rs2240335 |
| 540 | PADI4 | Rheumatoid arthritis | 24390342 | 1p36.13 | rs2301888 |
| 541 | PADI4 | Rheumatoid arthritis | 24390342 | 1p36.13 | rs2301888 |
| 542 | PADI4 | Rheumatoid arthritis | 24390342 | 1p36.13 | rs2301888 |
| 543 | LRRK2 | Leprosy | 25642632 | 12q12 | rs11174812 |
| 544 | LRRK2 | Crohn's disease | 18587394 | 12q12 | rs11175593 |
| 545 | LRRK2 | Crohn's disease | 21102463 | 12q12 | rs11564258 |
| 546 | LRRK2 | Inflammatory bowel disease | 23128233 | 12q12 | rs11564258 |

Experimental Procedures Used in the Examples

The study was performed in accordance with protocols approved by the relevant institutional review boards at. All patients provided written informed consent for the genetic research studies and molecular testing. Healthy donors were recruited from the Boston based PhenoGenetic project, a resource of healthy subjects that are re-contactable by genotype (Xia et al.), and the Newcastle community. Individuals were excluded if they had a history of cancer, allergies, inflammatory disease, autoimmune disease, chronic metabolic disorders or infectious disorders. All healthy donors were non-smoker, had a normal BMI and normal blood pressure, and were between 25-40 years of age.

Cell solation, flow cytometry staining, and cell sorting. For profiling of healthy cells, peripheral blood mononuclear cells (PBMCs) were isolated from fresh blood within 2 hrs of collection, using Ficoll-Paque density gradient centrifugation as previously described (Lee et al. 2014). Single-cell suspensions were stained per manufacturer recommendations with different panels of antibodies (see Table E11)

designed to enrich for certain population for single cell sorting and single cell RNA-sequencing (scRNA-seq) profiling.

TABLE E11

List of antibodies used

DC single cell sort (FIG. 2)

| Antigen | Fluorochrome | Clone | Manufacturer |
|---|---|---|---|
| CD3 | FITC | HIT3a | BD |
| CD19 | FITC | HIB19 | Biolegend |
| CD56 | FITC | HCD56 | Biolegend |
| HLA-DR | eFluor ® 605NC | LN3 | eBioscience |
| CD11c | V450 | B-ly6 | BD |
| CD14 | APC-Cy ™ 7 | MφP9 | BD |
| CD1c | PerCP-eFluor 710 | L161 | eBioscience |
| CD141 | APC | AD5-14H12 | Miltenyi Biotec |
| CD123 | BV711 | 9F5 | BD |

CD1C subsets enrichment sort (FIG. 3)

| Antigen | Fluorochrome | Clone | Manufacturer |
|---|---|---|---|
| CD3 | FITC | HIT3a | BD |
| CD19 | FITC | HIB19 | Biolegend |
| CD56 | FITC | HCD56 | Biolegend |
| HLA-DR | eFluor ® 605NC | LN3 | eBioscience |
| CD11C | V450 | B-ly6 | BD |
| CD14 | APC-Cy ™ 7 | MφP9 | BD |
| CD1C | PerCP-eFluor 710 | L161 | eBioscience |
| CD32B | PE | #190723 | R&D Systems |
| CD36 | APC | 5-271 | Biolegend |
| CD163 | BV711 | GHI/61 | BD |

Monocyte single cell sort (FIG. 4)

| Antigen | Fluorochrome | Clone | Vendor |
|---|---|---|---|
| CD3 | FITC | HIT3a | BD |
| CD19 | FITC | HIB19 | Biolegend |
| CD56 | FITC | HCD56 | Biolegend |
| CD14 | PE-Cy7 | M5E2 | BD |
| CD16 | APC-Cy ™ 7 | 3G8 | BD |

AXL⁺SIGLEC6⁺ enrichment sorting panel (FIG. 5)

| Antigen | Fluorochrome | Clone | Manufacturer |
|---|---|---|---|
| CD3 | FITC | HIT3a | BD |
| CD19 | FITC | HIB19 | Biolegend |
| CD56 | FITC | HCD56 | Biolegend |
| HLA-DR | eFluor ® 605NC | LN3 | eBiosciencee |
| CD141 | APC | AD5-14H12 | Miltenyi Biotec |
| CD14 | APC-Cy ™ 7 | MφP9 | BD |
| CD16 | APC-Cy ™ 7 | 3G8 | BD |
| AXL | A700 | # 108724 | R&D |
| SIGLEC6 | APC | # 767329 | R&D |
| CD11C | V450 | B-ly6 | BD |
| CD123 | BV711 | 9F5 | BD |

Differentiation assay input sort (FIG. 9)

| Antigen | Fluorochrome | Clone | Manufacturer |
|---|---|---|---|
| CD3 | FITC | SK7 | BD |
| CD19 | FITC | 4G7 | BD |
| CD20 | FITC | L27 | BD |
| CD161 | FITC | 191B8 | Miltenyi Biotec |
| CD141 | PerCP/Cy5.5 | M80 | Biolegend |
| CD1c | PE/Cy7 | L161 | Biolegend |
| CD39 | PE/Cy7 | A1 | Biolegend |
| CD100 | PE | A8 | Biolegend |
| CD34 | APC | 563 | BD |
| CD14 | APC/Cy7 | MφP9 | BD |
| CD11c | BV421 | B-ly6 | BD |
| CD16 | V500 | 3G8 | BD |
| CD45RA | evolve 605 | HI100 | eBioscience |
| CD123 | BUV395 | 7G3 | BD |

TABLE E11-continued

List of antibodies used

| HLA-DR | BV785 | L243 | Biolegend |
|---|---|---|---|
| AXL | APC | # 108724 | R&D |
| SIGLEC6 | A700 | # 767329 | R&D |

Differentiation assay output sort (FIG. 9)

| Antigen | Fluorochrome | Clone | Manufacturer |
|---|---|---|---|
| CD141 | FITC | AD5-14H12 | Miltenyi Biotec |
| CLEC9A | PE | 8F9 | Biolegend |
| CD303 | PerCP/Cy5.5 | 201A | Biolegend |
| CD1c | PE/Cy7 | L161 | Biolegend |
| CADM1 | AF647 | 3E1 | MBL |
| CD14 | APC/Cy7 | MφP9 | BD |
| CD11c | BV421 | B-ly6 | BD |
| CD45 | V500 | H130 | BD |
| HLA-DR | BV785 | L243 | Biolegend |
| CD123 | BUV395 | 7G3 | BD |

Phenotyping (FIG. 5-9)

| Antigen | Fluorochrome | Clone | Manufacturer |
|---|---|---|---|
| CD62L | PE | DREG-56 | BD |
| CD117 | PE and BV605 | YB5.B8 and 104D2 | BD (both) |
| CD86 | PE | 2331 | BD |
| CD116 | BV421 | hGMCSFR-M1 | BD |
| FcER1 | PE | AER-37 | eBioscience |
| CCR2 | PE | K036C2 | Biolegend |
| CD5 | PE | UCHT2 | Biolegend |
| CD33 | PE and PerCP/Cy5.5 | WM53 (both) | Biolegend (both) |
| CD115 | PE | 9-4D2-1E4 | Biolegend |
| IRF4 | PE | 3E4 | eBioscience |
| IRF8 | PE | V3GYWCH | eBioscience |
| CD26 | PE | BA5b | Biolegend |
| CD85j | PE | GHI/75 | Biolegend |
| CD135 | PE | BV10A4H2 | eBioscience |
| CD83 | PE | HB15E | BD |
| CLA | PE | HECA-452 | BD |
| CCR7 | PE | 1050503 | BD |
| CD45RA | BV510 | HI100 | Biolegend |
| CD34 | BV605 | 581 | Biolegend |
| CD100 | Biotin | REA316 | Miltenyi Biotec |
| CD304 | PerCP/Cy5.5 | 12C2 | Biolegend |
| CD303 | Bv605 and Biotin | 201A and AC144 | Biolegend and Miltenyi Biotec |
| CD163 | APC | 215927 | R&D Systems |
| CD22 | PE | S-HCL-1 | BD |
| CD40 | PE | 5C3 | BD |
| CD80 | PE | L307.4 | BD |
| SIGLEC1 | PE | 7-239 | Biolegend |
| CX3CR1 | PE | 2A9-1 | Biolegend |
| Streptavidin | BUV737 | N/A | BD |

For dendritic cell (DC) characterization, PBMCs cell suspension was first immunostained with an antibody cocktail (CD3, CD19, CD56, CD14) to exclude other blood lineages (LIN), and with antibodies for known DC markers (HLA-DR, CD11C, CD1C, CD141, CD123; Table E11). Since CD14⁻CD16⁺ cells within human LIN⁻HLA-DR⁺ fraction have been classified as both monocytes and DCs, Applicants only excluded CD14⁺ monocytes using a stringent gate. For the DC single-cell sorting (FIG. 2B), Applicants isolated 24 single cells from 4 loosely gated populations (i.e. LIN⁻CD14⁻HLA-DR⁺CD11C⁻CD123⁺, LIN⁻CD14⁻HLA-DR⁺CD11C⁺CD141⁺, LIN⁻CD14⁻HLA-DR⁺CD11C⁺CD1C⁺, LIN⁻CD14⁻HLA-DR⁺CD11C⁻CD141⁻CD1C⁻) per 96-well plate containing 5 ul of lysis buffer (FIG. 2A-B). For the CD1C⁺ DC subsets single-cell sorting, 48 cells were sorted from the two gates defined in FIG. 3B (Table E11 for antibodies). For the monocyte single-cell sorting, Applicants isolated 32 single cells from 3 loosely gated populations defined in FIG. 4A (i.e. classical' CD14++ CD16− monocyte (yellow gate), 'intermediate' CD14++ CD16− monocyte (purple gate), and 'non-classical' CD14+ CD16++ monocytes (blue gate) per 96-well plate.

BPDCN patient samples (FIG. 9G) came from two sources. Single cells from two BPDCN primary samples (BPDCN_1 and BPDCN_2) were isolated by flow sorting on live single CD45+HLA-DR+CD123+ cells from bone marrow aspirates obtained from patient tissues with >50% BPDCN involvement. Since BPDCN blasts are pathologically characterized by overexpression of the interleukin-3 receptor, Applicants used CD123 as a marker to enrich for the blasts, capturing indeed the majority of them (Riaz et al., Garnache-Ottou et al., Sapienza et al., Osaki et al., Yu et al.). Two additional BPDCN samples were patient derived xenografts (BPDCN_3 and BPDCN 4) that Applicants also isolated by flow sorting single CD45+HLA-DR+CD123+ cells from passage 1 xenografts, harvested from immunodeficient NSG (NOD scid gamma) mouse spleens containing >80% involvement with human BPDCN as described in Townsend et al. Note that regardless of the source of the BPDCN samples (direct from patients or patient-derived xenografts), all 4 samples clustered together (FIG. 9G) and a shared unique expression signature (FIG. 8B).

All antibody panels for different gating strategies are compiled in Table E11. Flow cytometry and FACS-sorting of PBMC was performed on a BD Fortessa or BD FACS Fusion instrument, and data analysed using FlowJov10.1 (Treestar™). Single-cells were sorted in 96-well full-skirted eppendorf plate chilled to 4° C., pre-prepared with 5 µl TCL buffer (Qiagen) supplemented with 1% beta-mercaptoethanol (lysis buffer). Single-cell lysates were sealed, vortexed, spun down at 300 g at 4° C. for 1 minute, immediately placed on dry ice and transferred for storage at ~80° C. Tonsil was mechanically disrupted to obtain single-cell suspension.

Single-cell RNA-sea: Reverse transcription. Smart-Seq2 protocol was performed on single sorted cells as described (Picelli et al.; Trombetta et al.), with some modifications. For DCs, a total of 8 96-well plates (768 single DCs) were initially profiled from the same blood draw and sort from the index volunteer and subsequent validation performed on an additional ten healthy individuals. For monocytes, a total of 4 plates were profiled (384 single monocytes). An additional 774 single cells were successfully profiled to further characterize the CD1C DC subsets (n=95), AXL+SIGLEC6+ cells (n=195), CD11C−CD123-compartment (n=110), differentiation assay outputs (n=132), CD100$^{hi}$CD34$^{int}$ cells (n=68), and BPDCN patient samples (n=174). Single-cells lysates were thawed on ice for 2 minutes, then centrifuged at 2,500 rpm at 4° C. for 1 minute. Lysates were mixed with 11 µL (2.2×) of Agencourt RNAClean XP SPRI beads (Beckman-Coulter) and incubated at room temperature for 10 min. The lysate plate was transferred to a magnet (DynaMag-96 Side Skirted Magnet, Life Technologies), the supernatant was removed, and the beads were washed three times in 100 µL of 80% ethanol, with care being taken to avoid loss of beads during the washes. Ethanol was removed, and the beads were left to dry at room temperature for 10 min. Beads were resuspended in 4 µL of Elution Mix (1 µL 10 µM RT primer [5'AGACGTGTGCTCTTCC-GATCT(T)30VN-3', IDT], (SEQ ID NO:19) 1 µL 10 mM dNTP [Agilent], 0.1 µL SUPERase•In RNase-Inhibitor [20 U/µL, Life Technologies], and 1.9 µL nuclease-free water). The samples were denatured at 72° C. for 3 min and placed immediately on ice afterwards. 7 µL of the Reverse Transcription Mix was subsequently added (2 µL 5×RT buffer [Thermo Scientific], 2 µL 5 M Betaine [Sigma-Aldrich], 0.9 µL 100 mM MgCl2 [Sigma-Aldrich], 1 µL 10 µM TSO [5'-AGACGTGTGCTCTTCCGATCTNNNNNrGrGrG-3', Exiqon], (SEQ ID NO. 20) 0.25 µL SUPERase•In RNase-Inhibitor [20U/µL, Life Technologies], 0.1 µL Maxima H Minus Reverse Transcriptase [200 U/µL, Thermo Scientific], and 0.75 µL nuclease-free water). Every well was mixed with the resuspended beads. Reverse transcription was carried out by incubating the plate at 50° C. for 90 min, followed by heat inactivation at 70° C. for 10 min.

Single-cell RNA-seq: PCR pre-amplification. 14 µL of PCR Mix was added for a final PCR reaction volume of 25 µL (0.5 µL 10 µM PCR primer [5'AGACGTGTGCTCTTCCGATCT-3', IDT], (SEQ ID NO: 21) 12.5 µL 2×KAPA HiFi HotStart ReadyMix [KAPA Biosystems], 1 µL nuclease-free water). The reaction was carried out with an initial incubation at 98° C. for 3 min, followed by 22 cycles at (98° C. for 15 sec, 67° C. for 20 sec, and 72° C. for 6 min) and a final extension at 72° C. for 5 min. PCR products were purified by mixing with 20 µL (0.8×) Agencourt AMPureXP SPRI beads (Beckman-Coulter), followed by incubation for 6 minutes at room temperature. The plate was placed on a magnet for 6 minutes, the supernatant was removed, and the beads were washed twice with 100 µL of 70% ethanol, with care being taken to avoid loss of beads during the washes. Ethanol was removed, and the beads were left to dry at room temperature for 10 min. The beads were resuspended in 20 µL TE buffer (Teknova). The plate was placed on the magnet and supernatant containing the amplified cDNA was transferred to a new 96-well PCR plate. The cDNA SPRI clean-up was repeated a second time to remove all residual primer dimers following the same approach. The concentration of amplified cDNA was measured on the Synergy Hi Hybrid Microplate Reader (BioTek) using High-Sensitivity Qubit reagent (Life Technologies), and the size distribution of select wells was checked on a High-Sensitivity Bioanalyzer Chip (Agilent). Expected quantification was around 0.5-2 ng/µL with size distribution sharply peaking around 2 kb.

Single-cell RNA-sea: Library preparation. Library preparation was carried out using the Nextera XT DNA Sample Kit (Illumina) with custom indexing adapters, allowing 384 libraries to be simultaneously generated in a 384-well PCR plate. For each library, the amplified cDNA was normalized to 0.15-0.20 ng/µL. The tagmentation reaction consisted of 0.625 µL of cDNA mixed with 1.25 µL Tagment DNA Buffer and 0.625 µL Tagment DNA enzyme mix. The 2.5 µL reaction was incubated at 55° C. for 10 min and placed immediately on ice afterwards. The reaction was quenched with 0.625 µL Neutralize Tagment Buffer and incubated at room temperature for 10 min. The libraries were amplified by adding 1.875 µL Nextera PCR Master Mix, 0.625 µL of 10 µM i5 adapter (5'-AATGATACGGCGAC-CACCGAGATCTACAC[i5]TCGTCGGCAGCGTC-3', (SEQ ID NO: 22) IDT, where [i5] signifies the 8 bp i5 barcode sequence (see below for sequences), and 0.625 µL of 10 µM i7 adapter (5'CAAGCAGAAGACGGCAT-ACGAGAT[i7]GTGACTGGAGTTCA-GACGTGTGCTCTTCC GATCTGGG-3', (SEQ ID NO: 23) IDT, where [i7] signifies the reverse-complement of the 8 bp i7 barcode sequence (see below for sequences). The PCR was carried out at an initial incubation at 72° C. for 3 min, 95° C. for 30 sec, followed by 12 cycles of (95° C. for 10 sec, 55° C. for 30 sec, 72° C. for 1 min), and a final extension at 72° C. for 5 min. Following PCR amplification, 2.5 µL of each library were pooled in a 2.0 mL microcentrifuge tube. The pool was mixed with 864 µL (0.9× for 2.5 ul of 384 cells pooled together) Agencourt AMPureXP SPRI beads (Beckman-Coulter) and incubated at room temperature for 5 min. The pool was placed on a magnet (DynaMag-2, Life Technologies) and incubated for 5 min. The supernatant was removed and the beads were washed twice in 1 mL of 70% ethanol. The ethanol was removed and the beads left to dry at room temperature for 10 min. The beads were resuspended in 50 µL of nuclease-free water. The tube was returned to the magnet, and the supernatant was transferred to a new 1.5 mL microcentrifuge tube. The SPRI clean-up of the library was repeated a second time to remove all residual primer dimers. The concentration of the pooled libraries was measured using the High-Sensitivity DNA Qubit (Life Technologies), and the size distribution measured on a High-Sensitivity Bioanalyzer Chip (Agilent). Expected concentration of the pooled libraries was 10-30 ng/µL with size distribution of 300-700 bp.

i5 barcodes: AAGTAGAG, ACACGATC, TGTTCCGA, CATGATCG, CGTTACCA, TCCTTGGT, AACGCATT, ACAGGTAT, AGGTAAGG, AACAATGG, ACTGTATC, AGGTCGCA, GGTCCAGA, CATGCTTA, AGGATCTA, TCTGGCGA, AGGTTATC, GTCTGATG, CCAACATT, CAACTCTC, ATTCCTCT, CTAACTCG, CTGCGGAT, CTACCAGG i7 barcodes: CTACCAGG, CATGCTTA, GCACATCT, TGCTCGAC, AGCAATTC, AGTTGCTT, CCAGTTAG, TTGAGCCT, ACCAACTG, GGTCCAGA, GTATAACA, TTCGCTGA, AACTTGAC, CACATCCT, TCGGAATG, AAGGATGT 384-pooled cells were sequenced as paired-end 25 base reads on a HiSeq2500 (Illumina).

Single-Cell RNA Sequencing Analyses

Raw data processing. Raw sequencing data were processed as previously described (Shalek et al.). Briefly, short sequencing reads were aligned to the UCSC hg19 transcriptome. These alignments were used to estimate transcriptomic alignment rates, and were also used as input in RSEM v 1.2.1 to quantify gene expression levels (transcripts per million; TPM) for all UCSC hg19 genes in all samples. Applicants filtered out low-quality cells from our dataset based on a threshold for the # of genes detected (a minimum of 3000 unique genes/cell for cells sequenced at HiSeq depth, 2000 unique genes/cell for cells sequenced at MiSeq depth). All genes that were not detected in at least 0.5% of all our single cells were discarded, leaving 21,581 genes for all further analyses. Data were log transformed (log(TPM+1)) for all downstream analyses.

Regressing out latent technical effects. Data in FIG. 2 (742 dendritic cells composing four gated populations) were processed in two experimental batches: 369 cells in batch 1, 373 cells in batch 2. All gated populations were evenly split between both batches. Applicants observed a weak batch effect in our data corresponding to this experimental design (representing PC5 in a PCA of uncorrected data). Applicants conservatively removed this batch effect using a 'latent-variable' approach similar to Buettner et al. Briefly, Applicants fit a linear model to predict the expression value of each gene based on a batch indicator variable, as well as the total number of unique genes detected in that cell. Applicants considered the residual expression from this model as a 'corrected' gene expression value, and used these values as input to the downstream clustering analyses. Additional follow-up single cell experiments were performed in a single batch per condition, and therefore Applicants did not use batch correction for these analyses.

Figure 12A:
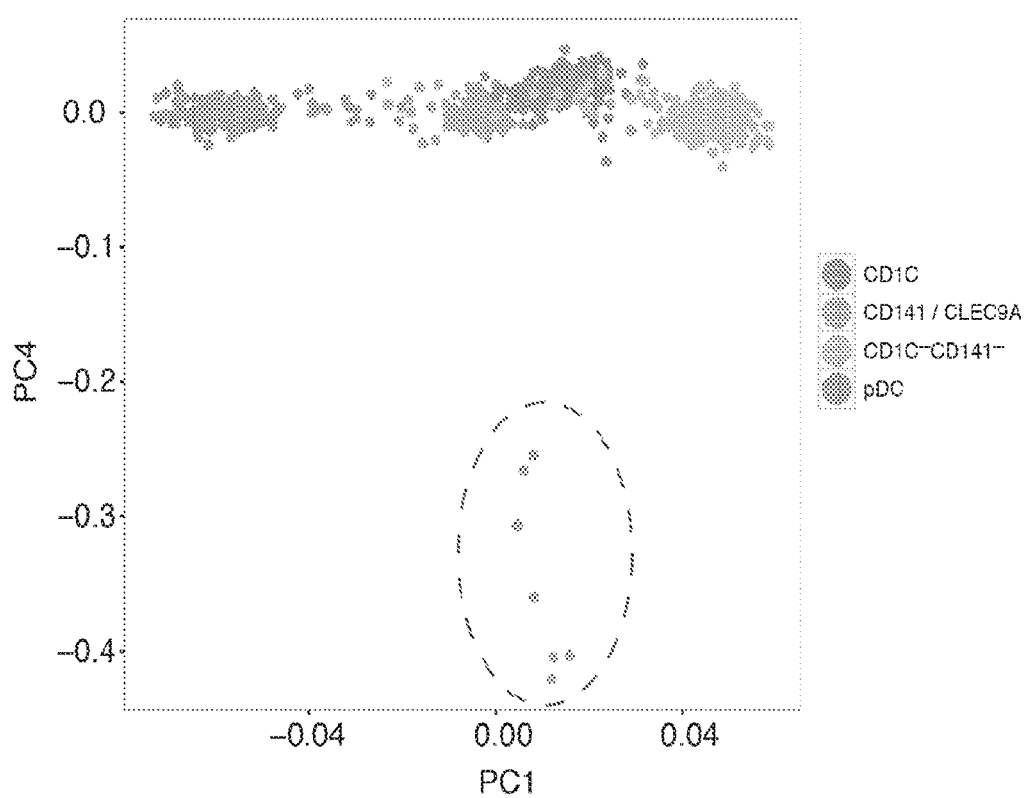
FIG. 12A-12B illustrates identifying contaminating non-DC and non-monocyte subpopulations (basophils). In our initial analysis of four DC subsets (FIG. 2), Applicants observed a contaminating subpopulation of seven basophils, which were removed from the dataset prior to proceeding with the clustering analysis (see Methods). (A) These basophils, delimited by the red-dashed circle, were clearly separated along PC4 in an unbiased principal components analysis. Note that most of the contaminating basophils came from the loosely defined pDC gate. (B) These basophils were also easily distinguished by their strong expression of Charcot-Leyden Crystal Galectin (CLC) and MS4A2, as illustrated in the feature plot where only putative contaminating cells express these two genes (highlighted in red). Each dot represents an individual cell.
Figure 12B:
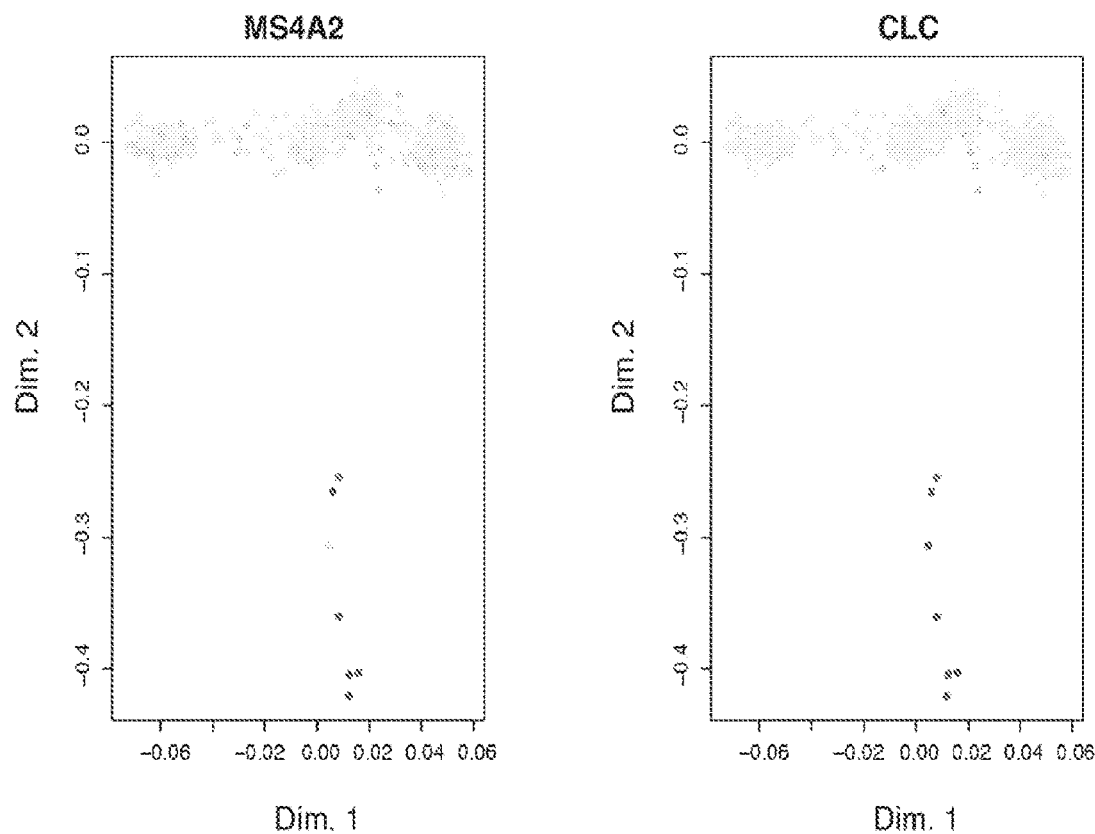

Removing contaminating subpopulations (basophils). In our initial analysis of four dendritic cell subsets, Applicants observed a contaminating subpopulation of seven basophils, which were easily distinguished by their strong expression of Charcot-Leyden Crystal Galectin (CLC). These cells also clearly separated along PC4 in an unbiased principal components analysis (FIG. 12). Applicants removed these cells from the dataset and proceeded with the clustering analysis described below.

Graph-based clustering of single cell data. For all single cell-clustering analyses, Applicants used an approach similar to our recently proposed clustering strategy for Drop-seq data. Briefly, as in Macosko et al., Applicants first identified the set of genes that was most variable across our dataset, after controlling for the relationship in single cell RNA-seq data that inherently exists between mean expression and variability by binning genes into 20 bins based on their average expression level, and z-scoring dispersion (mean/variance) estimates within a bin. Applicants excluded all genes which were very lowly expressed on average, (log (TPM+1)<1) and used a Z-score cutoff of 1 to select variable genes, resulting in the selection of 595 variable genes across the 742 DCs.

Applicants next reduced the dimensionality of our dataset, using principal components analysis. As previously described in Macosko et al., Applicants ran PCA using the prcomp function in R, and then utilized a modified a randomization approach ('jack straw') proposed by Chung and Storey to identify 'statistically significant' principal components in the dataset. Briefly, Applicants performed 1,000 PCAs on the input data, but in each analysis, Applicants randomly 'scrambled' 1% of the genes to empirically estimate a null distribution of scores for every gene. Applicants used the joint-null criterion (Leek and Storey) to identify PCs that had gene scores significantly different from the respective null distributions ($p<0.01$, Bonferroni corrected). For the 742 DCs, Applicants identified five PCs that passed this criterion. As expected, markers for distinct DCs types were highly represented among the genes with the largest scores along these PCs. Applicants then applied t-distributed stochastic neighbor embedding (tSNE) (van der Maaten et al.), using cell loadings for the significant principal components as input, to visualize the structure of our data in two dimensions.

While Applicants had previously used density clustering to enable unbiased clustering of the cells, here Applicants utilized graph-based clustering methods, similar to those that have been recently proposed for both single cell RNA-seq and mass cytometry data (Xu and Su; Levine et al.). Applicants first construct a Euclidean distance matrix on the loadings for the significant principal components as described above, and use this to construct a k-nearest neighbor graph (KNN, k=30). Our goal was to identify 'quasi-cliques' (Xu and Su), or 'communities' (Levine et al.) of cells that were highly interconnected across this graph. Therefore Applicants first converted the KNN graph into a weighted shared nearest neighbor (SNN) graph, where the weight between any two cells was represented by the percent overlap in their respective K-nearest neighborhoods (Jaccard distance). Finally, to group the cells into clusters, Applicants used a recently developed method for modularity optimization (Waltman and Van Eck), which aims to optimize a function describing the density of connections within a cluster versus connections between clusters, essentially to identify highly interconnected nodes within the SNN graph. Here, Applicants applied the smart local moving algorithm, which is similar to the widely used 'Louvain' algorithm for community detection, but implements a local moving heuristic that enables communities to be split up and iteratively re-organized in an attempt to improve the overall partition modularity. This grants the SLM algorithm additional freedom to identify an optimal clustering solution, and Applicants empirically observed increased sensitivity and consistency applying this approach to single cell data.

Identifying cluster markers. To identify genes that were enriched in individual single cell clusters, Applicants used the same approach as in in Macosko et al., aiming to identify genes whose expression values could individually serve as a binary classifier for cell identity. For each gene, the AUC value corresponds to the area under the receiver-operating curve. An AUC value of 1 implies that the gene is a perfect classifier for a given cluster (i.e., that the expression value of the gene alone is sufficient to predict if the cell is a member of that cluster). An AUC value of 0.5 implies that the gene has no predictive value of cluster identity.

To identify AXL-SIGLEC6 'purity scores' (FIG. 5D-E), Applicants used a signature scoring system described in Shalek et al. Briefly, Applicants assign a quantitative score to each cell based on the overall expression of a supervised signature gene set, after correcting for 'drop-out' effects that commonly characterize single cell data (Shalek et al.).

Supervised Analysis. Applicants examined the expression patterns of various curated gene sets across our clusters of single cells. Applicants assembled different gene sets consisting of: (i) transcription factors previously validated in humans (Vaquerizas et al.), (ii) predicted cell surface markers as reported in the Protein Atlas (Uhlén et al.; Bausch-Fluck et al.) (www.proteinatlas.org), (iii) immune-disorders related susceptibility loci compiled in the genome wide association study catalog (Hindorff et al.) (https://www.ebi.ac.uk/gwas/), (iv) immune-related cellular receptors and ligands (Kanehisa et al.; Kanehisa and Goto), as well as (v) pathogen sensors genes (Kanehisa et al.; Kanehisa and Goto) were assembled.

Each gene set was first filtered to exclude genes that were expressed in fewer than 40% of the cells in any of the 12 clusters (based on the expression cutoff log (TPM+1)=2). For each retained gene, Applicants calculated its average log-expression across all the cells within each cluster. The average expression matrix (genes x clusters) was then hierarchically clustered along its rows (euclidean distance, average linkage), and represented as a heatmap.

Get Set Enrichment Analysis. Enriched Gene Ontology (GO) terms (p<10^-5) across differentially expressed genes were calculated using GOrilla (Eden et al.). The enrichment was calculated against the background of all appreciably expressed genes in the data.

DC differentiation assay on MS5 stromal cells. DC differentiation assay was performed as previously described (Breton et al., J Exp Med. 2015; Lee et al. 2015; Breton et al. Nat Protoc. 2015) with minor adaptation. Briefly, $1\times10^4$ purified progenitors, DC and monocyte subsets were cultured in 96-well flat bottomed plate layered with $4\times10^4$ murine MS5 stromal cells (DSMZ, Germany) in the presence of human FLT3-ligand (FL; 100 ng/ml; Miltenyi Biotec), recombinant human SCF (20 ng/ml; R&D Systems) and recombinant human GM-CSF (10 ng/ml; Peprotech). MS5 stromal cells were seeded 24 hours prior to co-culture. Growth factors were replenished on day 3 of culture. Cells were in culture for up to 7 days prior to harvesting by physical dissociation on ice. Cells were then stained on ice either for flow cytometry analysis (see output panel in Table E11) or single cell index sorting of $CD45^+$ cells for single cell RNA-sequencing of culture output analysis.

Cytokine production measurements. Purified subsets were cultured at $5\times10$; cells/well in 96 well round bottom plates in the presence of LPS (100 ng/ml; Invivogen) and ODN2395 (1 µM; Invivogen) or ODN5328 (ODN2395 control, 1 µM; Invivogen). Culture supernatants were harvested after 24 hours and analyzed using a multiplexed cytokine assay (ProcartaPlex, eBioscience).

Assessing T cell stimulatory potential. DC, monocyte and progenitor subsets were purified from peripheral blood of healthy donors by FACS sorting (BD FACS Fusion; see Table E1 for sorting panels and antibodies). For T cell stimulatory potential, purified DCs, monocytes, $AXL^+SI$-$GLEC6'$ subsets, and progenitor subset were cultured at $5\times10^4$/well cell density and matured with LPS (100 ng/ml, Sigma) and R848 (2.5 ug/ml, Invivogen), or just LPS (100 ng/ml, Sigma), for 24 hours prior to co-culture with $5\times10^5$ CFSE-labelled allogeneic unfractionated $CD3^+$ T cells at a 1:10 DC:T cell ratio. T cell proliferation was assessed by measuring CFSE dilution on day 5 of culture.

Cytospin & Immunostaining. Cytospin of FACS-purified cells were prepared as previously described (Haniffa et al. 2009) using Shandon Cytospin 4 (Thermo Scientific), Giemsa-Wright staining was performed using Advia S60 (Siemens) and imaged using Axioimager.Z2 microscope with Axiovision software v4.8 (Carl Zeiss, Germany). Human tonsil paraffin sections were immunostained with the following antibodies (clone: manufacturer); anti-AXL (MM0098-2N33: Abcam), CD123 (BR4MS: Leica Biosystems) and CD3 (LN10: Leica Biosystems) using a Ventana Benchmark XT instrument.

Monitoring Cell Proliferation. PBMCs were labeled with Cell Trace Violet (CTV, Life Technologies) according to manufacturer's protocol. CTV-labeled FACS-purified progenitors and DC subsets were cultured on murine MS5 stromal cells as described above and analyzed on day 5 to assess proliferation measured by CTV dilution.

REFERENCES

D. Bausch-Fluck et al., A Mass Spectrometric-Derived Cell Surface Protein Atlas. PLoS One. 10, e0121314 (2015).
G. Breton et al., Circulating precursors of human CD1c+ and CD141+ dendritic cells. J Exp Med. 212 (3), 401-413 (2015).
G. Breton, J. Lee, K. Liu, M. C. Nussenzweig, Defining human dendritic cell progenitors by multiparametric flow cytometry. Nat Protoc. 10 (9), 1407-1422 (2015).
C. Bryant et al., A CD2 high-expressing stress-resistant human plasmacytoid dendritic-cell subset. Immunol Cell Biol. 94 (5), 447-57 (2016).
F. Buettner et al., Computational analysis of cell-to-cell heterogeneity in single-cell RNA-sequencing data reveals hidden subpopulations of cells. Nat Biotechnol. 33(2), 155-160 (2015).
M. Cella et al., Plasmacytoid monocytes migrate to inflamed lymph nodes and produce large amounts of type I interferon. Nat Med 5 (8), 919-923 (1999).
C. W. Chan et al. Interferon-producing killer dendritic cells provide a link between innate and adaptive immunity. Nat Med. 12(2), 207-113 (2006).
M. Cheng et al., Characterization of species-specific genes regulated by E2-2 in human plasmacytoid dendritic cells. Sci Rep. 5, 10752 (2015).
N. C. Chung, J. D. Storey, Statistical significance of variables driving systematic variation in high-dimensional data. Bioinformatics. 31(4), 545-554 (2015).

K. Crozat et al., The XC chemokine receptor 1 is a conserved selective marker of mammalian cells homologous to mouse CD8alpha+ dendritic cells. J Exp Med. 207 (6), 1283-1292 (2010).

J. De Vries, C. Figdor. Immunotherapy: Cancer vaccine triggers antiviral-type defences. Nature. 534 (7607), 329-331 (2016).

S. Doulatov, F. Notta, E. Laurenti, J. E. Dick, Hematopoiesis: a human perspective. Cell Stem Cell. 10 (2), 120-136 (2012).

Q. Du et al., Preferential depletion of CD2(low) plasmacytoid dendritic cells in HIV-infected subjects. Cell Mol Immunol. 8 (5), 441-444 (2011).

E. Eden et al., GOrilla: a tool for discovery and visualization of enriched GO terms in ranked gene lists. BMC Bioinformatics. 10, 48 (2009).

F. Garnache-Ottou, J. Feuillard, P. Saas, Plasmacytoid dendritic cell leukaemia/lymphoma: towards a well defined entity? Br J Haematol. 136 (4), 539-548 (2007).

G. Grouard et al., The enigmatic plasmacytoid T cells develop into dendritic cells with interleukin (IL)-3 and CD40-ligand. J Exp Med. 185(6), 1101-1111 (1997).

D. Grun, A. van Oudenaarden, Design and Analysis of Single-Cell Sequencing Experiments. Cell. 163(4), 799-810 (2015).

M. Guilliams et al., Dendritic cells, monocytes and macrophages: a unified nomenclature based on ontogeny. Nat Rev Immunol. 14 (8), 571-578 (2014).

M. Haniffa et al., Differential rates of replacement of human dermal dendritic cells and macrophages during hematopoietic stem cell transplantation. J Exp Med. 206 (2), 371-385 (2009).

Haniffa M, et al., Human tissues contain CD141hi cross-presenting dendritic cells with functional homology to mouse CD103+ nonlymphoid dendritic cells. Immunity 37(1), 60-73 (2012).

M. Haniffa, V. Bigley, M. Collin, Human mononuclear phagocyte system reunited. Semin Cell Dev Biol. 41, 59-69 (2015).

K. Hildner et al., Batf3 deficiency reveals a critical role for CD8alpha+ dendritic cells in cytotoxic T cell immunity. Science. 322 (5904), 1097-1100 (2008).

L. A. Hindorff et al., A Catalog of Published Genome-Wide Association Studies. Available at: www.genome.gov/gwastudies. Accessed [June 2016].

S. L. Jongbloed et al., Human CD141+ (BDCA-3)+ dendritic cells (DCs) represent a unique myeloid DC subset that cross-presents necrotic cell antigens. J Exp Med. 207 (6), 1247-1260 (2010).

M. Kanehisa, S. Goto. KEGG: Kyoto encyclopedia of genes and genomes. Nucleic Acids Res. 28 (1), 27-30 (2000).

M. Kanehisa et al. KEGG as a reference resource for gene and protein annotation. Nucleic Acids Res. 44 (D1), D457-462 (2016).

M. N. Lee et al., Common genetic variants modulate pathogen-sensing responses in human dendritic cells. Science. 343(6175), 1246980 (2014).

J. Lee et al., Restricted dendritic cell and monocyte progenitors in human cord blood and bone marrow. J Exp Med. 212 (3), 385-399 (2015).

J. T. Leek, J. D. Storey. "The joint null criterion for multiple hypothesis tests." Statistical Applications in Genetics and Molecular Biology 10.1 (2011).

J. H. Levine et al. Data-Driven Phenotypic Dissection of AML Reveals Progenitor-like Cells that Correlate with Prognosis. Cell. 162(1), 184-197 (2015).

H. Liu, et al., Gene signature-based mapping of immunological systems and diseases. BMC Bioinformatics. 17, 171 (2016).

M. S. Macauley, P. R. Crocker, J. C. Paulson, Siglec-mediated regulation of immune cell function in disease. Nat Rev Immunol. 14(10), 653-666 (2014).

E. Z. Macosko et al., Highly Parallel Genome-wide Expression Profiling of Individual Cells Using Nanoliter Droplets. Cell. 161 (5), 1202-1214 (2015).

Matsui T, et al., CD2 distinguishes two subsets of human plasmacytoid dendritic cells with distinct phenotype and functions. J Immunol. 182 (11), 6815-6823 (2009).

B. Mesko, S. Poliska, L. Nagy. Gene expression profiles in peripheral blood for the diagnosis of autoimmune diseases. Trends Mol Med. 17(4), 223-233 (2011).

A. Mildner, S. Jung, Development and function of dendritic cell subsets. Immunity. 40(5), 642-656 (2014).

J. C. Miller J C et al., Deciphering the transcriptional network of the dendritic cell lineage. Nat Immunol. 13(9), 888-899 (2012).

F. Notta et al., Distinct routes of lineage development reshape the human blood hierarchy across ontogeny. Science. 351 (6269), aab2116 (2016).

T. J. Nowakowski et al., Expression Analysis Highlights AXL as a Candidate Zika Virus Entry Receptor in Neural Stem Cells. Cell Stem Cell. 18 (5), 591-596 (2016).

Y. Osaki, et al., Characterization of CD56+ dendritic-like cells: a normal counterpart of blastic plasmacytoid dendritic cell neoplasm? PLoS One. 8 (11), e81722 (2013).

V. Pascual, D. Chaussabel, J. Banchereau, A genomic approach to human autoimmune diseases. Annu Rev Immunol. 28, 535-571 (2010).

S. Picelli et al., Smart-seq2 for sensitive full-length transcriptome profiling in single cells. Nat. Methods. 10, 1096-1098 (2013).

L. F. Poulin et al., Characterization of human DNGR-1+ BDCA3+ leukocytes as putative equivalents of mouse CD8alpha+ dendritic cells. J Exp Med. 207 (6), 1261-1271 (2010).

W. Riaz, L. Zhang, P. Horna, L. Sokol, Blastic plasmacytoid dendritic cell neoplasm: update on molecular biology, diagnosis, and therapy. Cancer Control. 21 (4), 279-289 (2014).

C. V. Rothlin, E. A. Carrera-Silva, L. Bosurgi, S. Ghosh. TAM receptor signaling in immune homeostasis. Annu Rev Immunol. 33, 355-391 (2015).

M. R. Sapienza, et al., Molecular profiling of blastic plasmacytoid dendritic cell neoplasm reveals a unique pattern and suggests selective sensitivity to NF-kB pathway inhibition. Leukemia. 28 (8), 1606-1616 (2014).

A. T. Satpathy, X. Wu, J. C. Albring, K. M. Murphy. Re(de)fining the dendritic cell lineage. Nat Immunol. 13(12), 1145-54 (2012).

B. U. Schraml, C. Reis e Sousa, Defining dendritic cells. Curr Opin Immunol. 32, 13-20 (2015).

N. Schwab et al., An imbalance of two functionally and phenotypically different subsets of plasmacytoid dendritic cells characterizes the dysfunctional immune regulation in multiple sclerosis. J Immunol. 184 (9), 5368-5374 (2010).

A. K. Shalek et al., Single-cell RNA-seq reveals dynamic paracrine control of cellular variation. Nature. 510 (7505), 363-369 (2014).

M. Swiecki, M. Colonna, The multifaceted biology of plasmacytoid dendritic cells. Nat Rev Immunol. 15(8), 471-485 (2015).

J. Taieb et al., A novel dendritic cell subset involved in tumor immunosurveillance. Nat Med. 12(2), 214-219 (2006).

J. Tel et al., Human plasmacytoid dendritic cells are equipped with antigen-presenting and tumoricidal capacities. Blood. 120 (19), 3936-3944 (2012), J. Tel et al., Natural human plasmacytoid dendritic cells induce antigen-specific T-cell responses in melanoma patients. Cancer Res. 73 (3), 1063-1075 (2013).

E. C. Townsend, et al., The Public Repository of Xenografts Enables Discovery and Randomized Phase II-like Trials in Mice. Cancer Cell. 29 (4), 574-586 (2016).

C. Trapnell, Defining cell types and states with single-cell genomics. Genome Res. 25(10), 1491-1498 (2015).

J. J. Trombetta et al., Preparation of Single-Cell RNA-Seq Libraries for Next Generation Sequencing. Curr. Protoc. Mol. Biol. Ed. Frederick M Ausubel Al. 107, 4.22.1-4.22.17 (2014).

M. Uhlén et al., Proteomics. Tissue-based map of the human proteome. Science. 347 (6220), 1260419 (2015).

L. van der Maaten, G. Hinton, Visualizing Data using t-SNE. 9, 2579-2605 (2008).

J. M. Vaquerizas, S. K. Kummerfeld, S. A. Teichmann, N. M. Luscombe, A census of human transcription factors: function, expression and evolution. Nat Rev Genet. 10 (4), 252-263 (2009).

L. Waltman, N. J. Van Eck, A smart local moving algorithm for large-scale modularity-based community detection. European Physical Journal B. 86 (11), 471 (2013).

R. S. Welner et al., Interferon-producing killer dendritic cells (IKDCs) arise via a unique differentiation pathway from primitive c-kitHiCD62L+ lymphoid progenitors. Blood. 109 (11), 4825-4931 (2007).

T. R. Wilhelm et al., Siglec-1-positive plasmacytoid dendritic cells (pDCs) in human peripheral blood: A semimature and myeloid-like subset imbalanced during protective and autoimmune responses. Clin Immunol. 163, 42-51 (2016).

Z. Xia et al., A 17q12 allele is associated with altered NK cell subsets and function. J Immunol. 188 (7), 3315-3322 (2012).

Y. Xiao et al., Identification of the Common Origins of Osteoclasts, Macrophages, and Dendritic Cells in Human Hematopoiesis. Stem Cell Reports. 4 (6), 984-994 (2015).

C. Xu, Z. Su, Identification of cell types from single-cell transcriptomes using a novel clustering method. Bioinformatics. 31(12), 1974-1980 (2015).

H. Yu et al., Human BDCA2+CD123+CD56+ dendritic cells (DCs) related to blastic plasmacytoid dendritic cell neoplasm represents a unique myeloid DC subset. Protein Cell. 6 (4), 297-306 (2015).

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An isolated dendritic cell comprising a recombinant nucleic acid encoding an antigen, wherein the dendritic cell is selected from the group consisting of:
   e1) a dendritic cell characterized in that the dendritic cell comprises expression of HLA-DR, does not express CD3, CD56, CD19 and CD14, and comprises expression of one or more genes or gene products selected from the group consisting of AXL (AXL Receptor Tyrosine Kinase), SIGLEC6, SIGLEC1, PPP1R14A, CD22, CD5, and GPR146;
   e2) a dendritic cell which is HLA-DR positive, CD3 negative, CD56 negative, CD19 negative and CD14 negative, and positive for one or more genes or gene products selected from the group consisting of AXL, SIGLEC6, SIGLEC1, PPP1R14A, CD22, CD5, and GPR146;
   e3) a dendritic cell characterized in that the dendritic cell comprises expression of HLA-DR, does not express CD3, CD56, CD19 and CD14, and comprises a gene or gene product signature, the signature comprising one or more genes or gene products selected from AXL, PPP1R14A, SIGLEC6, CD22, DAB2, S100A10, FAM105A, MED12L, ALDH2, LTK, DPYSL2, LGMN, IRF4, SEPT6, PLAC8, CCND3, MYO1E, SLC41A2, SCN9A, SIGLEC1, CX3CR1, NDRG1, VASH1, CD5, BHLHE40, SNRNP25, USF2, SLC20A1, ATF5, FAM129A, KLF4, RUNX2, ARHGAP18, APEX1, ENTPD7, SLC35C2, CDH1, GPR146, BAIAP2, CDKN1A, UPK3A, GNAQ, THBD, TNFSF12, SOX4, CXCR2, HIP1, STX18, CTSW, ATP2B4, CD72, MGLL, SUSD1, RNF141, TNNI2, GGTA1P, C5ORF25, PTGDS, TSEN54, KLF12, MYH11, TXN, AK125727, CD300LB, SUCLA2, BIN1, MRPS6, ZNF789, RAD1, PIM2, PLA2G16, TBC1D9, ADAM33, ZEB1, CD300LG, SLC4A3, STAG3L4, MECR, COQ7, RBL1, CEP95, RNASEL, ACPP, SP4, or LAX1;
   the dendritic cell as defined in e1) comprises expression of two or more, three or more, four or more, five or more, six or more, or all genes or gene products selected from the group consisting of AXL, SIGLEC6, SIGLEC1, PPP1R14A, CD22, CD5, and GPR146;
   the dendritic cell as defined in e1) comprises expression of AXL and SIGLEC6;
   the dendritic cell as defined in e2) is positive for two or more, three or more, four or more, five or more, six or more, or all genes or gene products selected from the group consisting of AXL, SIGLEC6, SIGLEC1, PPP1R14A, CD22, CD5, and GPR146;
   the dendritic cell as defined in e2) is AXL positive and SIGLEC6 positive;
   the dendritic cell as defined in any one of e1), e2), or e3) does not express CD141, or CD16, or CD141 and CD16;

the dendritic cell as defined in any one of e1), e2), or e3) is CD141 negative, or CD16 negative, or CD141 negative and CD16 negative;

the dendritic cell as defined in any one of e1), e2), or e3) comprises expression of CD123 and does not express CD11C;

the dendritic cell as defined in any one of e1), e2), or e3) is CD123 positive and CD11C negative (CD123$^+$ CD11C$^-$);

the dendritic cell as defined in any one of e1), e2), or e3) comprises a gene or gene product signature, the signature comprising one or more genes or gene products selected from the group consisting of PROC, IRF8, FMNL3, APP, SERPINF1, C1ORF186, CYBASC3, PLAC8, NRP1, CCDC50, TSPAN13, UGCG, LILRA4, MZB1, PTPRS, AK128525, IGJ, and IL3RA;

the dendritic cell as defined in any one of e1), e2), or e3) does not express ITGAX;

the dendritic cell as defined in any one of e1), e2), or e3) does not express CD123 and comprises expression of CD11C;

the dendritic cell as defined in any one of e1), e2), or e3) is CD123 negative and CD11C positive (CD123$^-$ CD11C$^+$);

the dendritic cell as defined in any one of e1), e2), or e3) comprises a gene or gene product signature, the signature comprising one or more genes or gene products selected from the group consisting of ITGAX, IFI30, LGALS2, FGR, LY86, GLIPR2, TIMP1, LST1, AGPAT9, IFITM3, DUSP23, ENTPD1, LOC645638, and IL1RN; or the dendritic cell as defined in any one of e1), e2), or e3) comprises expression of ITGAX.

2. The isolated dendritic cell according to claim 1, wherein the dendritic cell is a progenitor or precursor of a dendritic cell; and/or
wherein the dendritic cell is a human cell.

3. A method for detecting or quantifying dendritic cells in a biological sample of a subject, or for isolating dendritic cells from a biological sample of a subject, the method comprising:
   a) providing a biological sample of a subject; and
   b) detecting or quantifying in the biological sample dendritic cells that express HLA-DR, do not express CD3, CD56, CD19 and CD14, and comprises expression of one or more genes or gene products selected from AXL, SIGLEC6, SIGLEC1, PPP1R14A, CD22, CD5, and GPR146, or isolating from the biological sample dendritic cells that express HLA-DR, do not express CD3, CD56, CD19 and CD14, and comprises expression of one or more genes or gene products selected from the group consisting of AXL, SIGLEC6, SIGLEC1, PPP1R14A, CD22, CD5, or GPR146,
optionally, wherein the dendritic cells are detected, quantified or isolated using a technique selected from the group consisting of flow cytometry, mass cytometry, fluorescence activated cell sorting, fluorescence microscopy, affinity separation, magnetic cell separation, microfluidic separation, and combinations thereof, optionally, wherein the technique employs one or more agents capable of specifically binding to one or more gene products expressed or not expressed by the immune cells, optionally, on the cell surface of the immune cells, optionally, wherein the one or more agents are one or more antibodies.

4. A population of dendritic cells as defined in claim 1.

5. A composition, pharmaceutical composition or vaccine comprising the dendritic cell as defined in claim 1.

6. The composition, pharmaceutical composition or vaccine according to claim 5, wherein the antigen is an allergen, autoimmune antigen, tumor antigen, or pathogen antigen, optionally, wherein the pathogen is a bacterial, fungal, protozoal, parasitic, or viral pathogen.

7. A method for preparing the isolated dendritic cell of claim 1 comprising:
   a) isolating from a biological sample of a subject a dendritic cell as defined in claim 1;
   b) optionally in vitro expanding the dendritic cell of a);
   c) transducing said dendritic cell or expanded dendritic cell population with a recombinant nucleic acid encoding an antigen; and
   d) isolating the dendritic cell or dendritic cell population, optionally, wherein the antigen is an allergen, autoimmune antigen, tumor antigen, or pathogen antigen, optionally, wherein the pathogen is a bacterial, fungal, protozoal, parasitic, or viral pathogen.

8. A method for eliciting an immune response or immune tolerance to an antigen in a subject comprising administering to the subject the dendritic cell or population of dendritic cells as defined in claim 1, wherein the dendritic cell or dendritic cell population comprises a recombinant nucleic acid encoding said antigen, optionally, wherein the dendritic cell or dendritic cell population is autologous to said subject.

9. A method for preparing a composition comprising activated T cells, the method comprising isolating T cells from a biological sample of a subject and contacting said T cells in vitro with a dendritic cell according to claim 1, optionally,
   wherein the dendritic cell or dendritic cell population is autologous to said subject.

10. A method for adoptive immunotherapy in a subject in need thereof comprising administering to said subject a composition comprising activated T cells prepared with a method according to claim 9, optionally, wherein said T cells are CD8+ T cells and said subject is suffering from a proliferative disease.

* * * * *

UNITED STATES PATENT AND TRADEMARK OFFICE
CERTIFICATE OF CORRECTION

PATENT NO. : 11,630,103 B2
APPLICATION NO. : 16/325807
DATED : April 18, 2023
INVENTOR(S) : Alexandra-Chloé Villani et al.

It is certified that error appears in the above-identified patent and that said Letters Patent is hereby corrected as shown below:

On the Title Page

On page 3, in Column 1, item [56] under "Other Publications", Line 34, delete "Dell" and insert -- Cell --.

On page 3, in Column 1, item [56] under "Other Publications", Line 41, delete "Dancer" and insert -- Cancer --.

On page 3, in Column 2, item [56] under "Other Publications", Line 10, delete "Dells" and insert -- Cells --.

In the Specification

In Column 1, Line 66, delete "2015," and insert -- 2015; --.

In Column 3, Line 7, delete "DC." and insert -- 'DC1' --.

In Column 3, Line 34, delete "S100A12:" and insert -- S100A12; --.

In Column 12, Line 33, delete "types:" and insert -- types; --.

In Column 12, Line 55, delete "in" and insert -- n --.

In Column 13, Line 2, delete "3:" and insert -- 3; --.

In Column 13, Line 3, delete "in" and insert -- n --.

In Column 13, Line 66, delete "CD1C'" and insert -- CD1C$^+$ --.

Signed and Sealed this
Ninth Day of April, 2024

Katherine Kelly Vidal
*Director of the United States Patent and Trademark Office*

CERTIFICATE OF CORRECTION (continued)
U.S. Pat. No. 11,630,103 B2

In Column 14, Line 3, delete "CD1C'" and insert -- $CD1C^+$ --.

In Column 14, Line 21, delete "$CD14^+CD16^-$" and insert -- $CD14^{++}CD16^-$ --.

In Column 14, Line 32, delete "137:" and insert -- 137; --.

In Column 15, Line 52, delete "t" and insert -- ± --.

In Column 16, Line 36, delete "$AXL^+$" and insert -- $AXL^-$ --.

In Column 16, Line 45, delete "CD123" and insert -- $CD123^+$ --.

In Column 17, Line 5, delete "doK means" and insert -- doKmeans --.

In Column 17, Line 11, delete "IF130" and insert -- IFl30 --.

In Column 17, Line 30, delete "doK means" and insert -- doKmeans --.

In Column 17, Line 67, delete "$CD123^{lo/-}$." and insert -- $CD123^{lo/-}$: --.

In Column 18, Line 8, delete "20.85;" and insert -- 0.85; --.

In Column 18, Line 47, delete "$CD34^{int}$" and insert -- $CD34^{int.}$ --.

In Column 25, Line 57, delete "$CD11C^{lo}$);" and insert -- $CD11C^{lo/-}$); --.

In Column 35, Line 43, delete "vis-A-vis" and insert -- vis-à-vis --.

In Column 36, Line 37, delete "2'-0,4'" and insert -- 2'-O,4' --.

In Column 36, Line 37, delete "2'-0,4'" and insert -- 2'-O,4' --.

In Column 36, Line 38, delete "2'-0,4'" and insert -- 2'-O,4' --.

In Column 39, Line 18, delete "for" and insert -- f or --.

In Column 40, Line 53, delete "200%," and insert -- 20%, --.

In Column 41, Line 59, delete "600%," and insert -- 60%, --.

In Column 42, Line 28, delete "200%," and insert -- 20%, --.

In Column 44, Line 32, delete "9/c," and insert -- 9%, --.

In Column 44, Line 34, delete "400%," and insert -- 40%, --.

CERTIFICATE OF CORRECTION (continued)
U.S. Pat. No. 11,630,103 B2

In Column 53, Line 60, delete "60%6," and insert -- 60%, --.

In Column 58, Lines 3-4, delete "Antibodies." and insert -- Antibodies: --.

In Column 73, Line 50, delete "archaeabacteria" and insert -- archaebacteria --.

In Column 74, Line 19, delete "Plasnodium" and insert -- Plasmodium --.

In Column 74, Line 21, delete "lambia," and insert -- lamblia, --.

In Column 74, Line 30, delete "Strongvloides" and insert -- Strongyloides --.

In Column 77, Lines 60-61, delete "population:" and insert -- population; --.

In Column 85, Line 60, delete "a CD8a" and insert -- a CD8α --.

In Column 85, Line 60, delete "CD8a" and insert -- CD8α --.

In Column 86, Line 4, delete "1a-" and insert -- la- --.

In Column 88, Line 37, delete "a and R," and insert -- α and β, --.

In Column 88, Line 44, delete "a and D" and insert -- α and β --.

In Column 100, Line 30, delete "Nature 12466." and insert -- Nature12466. --.

In Column 105, Line 43, delete "32(6);" and insert -- 32(6): --.

In Column 111, Line 26, delete "alpha," and insert -- alpha; --.

In Column 113, Line 61, delete "L P T" and insert -- L R T --.

In Column 114, Line 4, delete "G P P" and insert -- G R P --.

In Column 114, Line 5, delete "S H P" and insert -- S H R --.

In Column 114, Line 7, delete "R P V" and insert -- R R V --.

In Column 114, Line 7, delete "A P S" and insert -- A R S --.

In Column 114, Line 10, delete "T A S" and insert -- T R A S --.

In Column 116, Line 65, delete "m Sin" and insert -- mSin --.

In Column 119, Line 44, delete "$^{198}$Re," and insert -- $^{188}$Re, --.

In Column 123, Line 36, delete "hi." and insert -- h1. --.

In Column 124, Line 7, delete "'DCV'" and insert -- 'DC1' --.

In Column 128, Line 12, delete "more," and insert -- more; --.

In Column 129, Line 61, delete "400%," and insert -- 40%, --.

In Column 130, Line 30, delete "400%," and insert -- 40%, --.

In Column 133, Line 58, delete "400/a," and insert -- 40%, --.

In Column 142, Line 45, delete "500%," and insert -- 50%, --.

In Column 142, Line 55, delete "200%," and insert -- 20%, --.

In Column 148, Line 29, delete "(77):" and insert -- (77); --.

In Column 148, Line 67, delete "anyone" and insert -- any one --.

In Column 149, Line 24, delete "h i)" and insert -- h1) --.

In Column 150, Line 1, delete "2015," and insert -- 2015; --.

In Column 150, Line 18, delete "CD123-cells." and insert -- CD123+ cells. --.

In Column 151, Line 3, delete "hood" and insert -- blood --.

In Column 151, Line 11, delete "CD141$^{lo/+}$" and insert -- CD14$^{lo/+}$ --.

In Column 182, Line 35, delete "subpopulation." and insert -- subpopulations. --.

In Column 190, Line 53, delete "CD1C'" and insert -- CD1C$^+$ --.

In Columns 245-246 (TABLE E5-continued), Line 44, delete "http:/" and insert -- http:// --.

In Column 265, Line 36, delete "DCs." and insert -- pDCs. --.

In Column 265, Line 54, delete "ENIPD1)." and insert -- ENTPD1). --.

In Column 265, Line 56, delete "IL3R4" and insert -- IL3RA --.

In Column 266, Line 36, delete "CD1C$^{-/lo}$" and insert -- CD11C$^{-/lo}$ --.

In Column 267, Line 16, delete "CD4" and insert -- CD4$^+$ --.

CERTIFICATE OF CORRECTION (continued)
U.S. Pat. No. 11,630,103 B2

In Column 267, Line 18, delete "CD1C"" and insert -- $CD1C^+$ --.

In Column 267, Line 53, delete "SMA4D" and insert -- SEMA4D --.

In Column 268, Line 5, delete "bonafide" and insert -- bona fide --.

In Column 268, Line 63, delete "AU" and insert -- AXL --.

In Column 269, Line 12, delete "CD451HLA" and insert -- $CD45^+HLA$ --.

In Column 269, Line 26, delete "GZMMB," and insert -- GZMB, --.

In Column 270, Line 53, delete "BDCA-3" and insert -- $BDCA-3^+$ --.

In Column 271, Line 14, delete "(CLEC10A)" and insert -- CLEC10A) --.

In Column 272, Line 51, delete "400/of" and insert -- 40% of --.

In Column 332, Line 61, delete "solation," and insert -- isolation, --.

In Column 332, Line 61, before "and" insert -- analysis --.

In Column 334, Line 62, delete "CD11C⁻" and insert -- $CD11C^+$ --.

In Column 335, Line 3, delete "CD16⁻" and insert -- $CD16^+$ --.

In Column 335, Line 37, delete "RNA-sea:" and insert -- RNA-seq: --.

In Column 335, Line 46, delete "CD1C" and insert -- $CD1C^+$ --.

In Column 335, Line 47, delete "CD123-compartment" and insert -- $CD123^-$ compartment --.

In Column 335, Line 48, delete "$CD34^{int}$"" and insert -- $CD34^{int.}$ --.

In Column 336, Line 34, delete "Hi" and insert -- H1 --.

In Column 336, Line 40, delete "RNA-sea:" and insert -- RNA-seq: --.

In Column 339, Line 67, delete "5×10;" and insert -- $5 \times 10^3$ --.

In Column 340, Line 9, delete "E1" and insert -- E11 --.

In Column 340, Lines 11-12, delete "$AXL^+SIGLEC6$"" and insert -- $AXL^+SIGLEC6^+$ --.

In the Claims

In Column 354, Lines 61-62, in Claim 1, delete "PPP1 R14A," and insert -- PPP1R14A, --.